(12) United States Patent
Lowman et al.

(10) Patent No.: US 7,101,851 B2
(45) Date of Patent: Sep. 5, 2006

(54) IGE RECEPTOR ANTAGONISTS

(75) Inventors: Henry B. Lowman, El Granada, CA (US); Gerald R. Nakamura, San Francisco, CA (US); Mark E. Reynolds, Millbrae, CA (US); Melissa A. Starovasnik, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 199 days.

(21) Appl. No.: 10/381,112

(22) PCT Filed: Sep. 26, 2001

(86) PCT No.: PCT/US01/30289

§ 371 (c)(1),
(2), (4) Date: Mar. 20, 2003

(87) PCT Pub. No.: WO02/26781

PCT Pub. Date: Apr. 4, 2002

(65) Prior Publication Data

US 2004/0086942 A1  May 6, 2004

Related U.S. Application Data

(60) Provisional application No. 60/278,540, filed on Mar. 23, 2001, provisional application No. 60/235,353, filed on Sep. 26, 2000.

(51) Int. Cl.
*A61K 38/03* (2006.01)
*A61K 38/16* (2006.01)
*C07K 4/00* (2006.01)
*C07K 14/00* (2006.01)

(52) U.S. Cl. .................... 514/12; 436/513; 514/13; 514/14; 530/324; 530/325; 530/326

(58) Field of Classification Search ............... 530/324, 530/325, 326, 327; 514/12, 13, 14; 436/501, 436/513
See application file for complete search history.

(56) References Cited

U.S. PATENT DOCUMENTS

| 5,116,964 | A | 5/1992 | Capon et al. ............... 536/27 |
| 5,336,603 | A | 8/1994 | Capon et al. ............... 435/69.7 |
| 5,627,263 | A | 5/1997 | Ruoslahti et al. ........... 530/327 |
| 5,714,147 | A | 2/1998 | Capon et al. ............... 424/178.1 |
| 5,731,168 | A | 3/1998 | Carter et al. ............... 435/69.1 |
| 5,821,047 | A | 10/1998 | Garrard et al. ............... 435/5 |
| 5,962,634 | A | 10/1999 | Jameson et al. ............ 530/324 |

FOREIGN PATENT DOCUMENTS

WO    WO 89/02922    6/1989

WO    WO 99/05271    4/1999

OTHER PUBLICATIONS

Arap et al., "Cancer Treatment by Targeted Drug Delivery to Tumor Vasculature in a Mouse Model" *Science* 279:377-380 (1998).
Aruffo et al., "CD44 is the Principal Cell Surface Receptor for Hyaluronate" *Cell* 61:1303-1313 (1990).
Bass et al., "Hormone Phage: An Enrichment Method for Variant Proteins with Altered Binding Properties" *Proteins: Structure, Function, and Genetics* 8 (4) :309-314 (1990).
Chen et al., "Selection and Analysis of an Optimized Anti-VEGF Antibody: Crystal Structure of an Affinity-matured Fab in Complex with Antigen" *Journal of Molecular Biology* 293(4) :865-881 (1999).
Clackson and Wells, "In Vitro Selection from Protein and Peptide Libraries." *Trends Biotechnol.* 12:173-184 (1994).
Creighton, Thomas E. *Proteins: Structure and Molecular Properties*, 2nd ed., W.H. Freeman and Company (1984) (table of contents only).
Cunningham et al., "Production of an Atrial Natriuretic Peptide Variant that is Specific for Type A Receptor" *EMBO Journal* 13(11):2508-2515 (1994).
Cwirla et al., "Peptide Agonist of the Thrombopoientin Receptor as Potent as the Natural Cytokine" *Science* 276:1696-1699 (1997).
Cwirla et al., "Peptides on phage: a vast library of peptides for identifying ligands" *Proc. Natl. Acad. Sci. USA* 87(16) :6378-6382 (1990).
Dennis et al., "Kunitz Domain Inhibitors of Tissue-Factor VIIa" *Journal of Biological Chemistry* 269:22137-22144 (1994).
Dennis et al., "Peptide Exosite Inhibitors of Factor VIIa as Anticoagulants." *Nature* 404:465-470 (Mar. 2000).
Devlin et al., "Random peptide libraries: a source of specific protein binding molecules" *Science* 249:404-406 (1990).
Garman et al., "Crystal Structure of the Human High-Affinity IgE Receptor" *Cell* 95:951-961 (1998).
Garman et al., "Structure of the Fc fragment of human IgE bound to its high-affinity receptor FCERIα" *Nature* 406:259-266 (2000).
Hakimi et al., "The α subunit of the human IgE receptor (FCERI) is sufficient for high affinity IgE binding" *Journal of Biological Chemistry* 265(36) :22079-22081 (1990).
Ishizaka et al., "Biologic Function of the Fc Fragment of E Myeloma" *Immunochemistry* 7:687-702 (1970).
Jardieu and Fick, "IgE Inhibition as a therapy for Allergic Disease" *Intl. Arch. Allergy Immunol.* 118:112-115 (1999).
Kinet J.P., "The High-Affinity IgE Receptor (FCERI) : From Physiology to Pathology" *Ann. Rev. Immunol* 17:931-972 (1999).
Kolbinger et al., "A Humanized Antibody for the Treatment of Allergy" *Protein Engineering* (Abstract, top left), Oxford, GB 6(Suppl.):90 (1993).

(Continued)

Primary Examiner—Jeffrey E. Russel
(74) Attorney, Agent, or Firm—Craig G. Svoboda

(57) ABSTRACT

The invention provides novel compounds which bind to the high affinity receptor for immunoglobulin E (IgE) designated FcεRI and methods for identifying and preparing such compounds. In particular aspects, the invention provides to the treatment of disorders mediated by IgE utilizing the novel compounds of the invention. The invention also provides composition, such as pharmaceutical compositions, comprising the novel compounds, as well as for their use in research, diagnostic, therapeutic, and prophylactic methods.

24 Claims, 25 Drawing Sheets

OTHER PUBLICATIONS

Kunkel et al., "Efficient site-directed mutagenesis using uracil-containing DNA" *Methods in Enzymology* 204:125-139 (1991).

Lowe et al., "Allergen-induced Histamine Release in Rat Mast Cells Transfected with the α Subunits of FCERI" *J. Immunological Methods* 184:113-122 (1995).

Lowman and Wells, "Affinity Maturation of Human Growth Hormone by Monovalent Phage Display" *J. Mol. Biol.* 234:564-578 (1993).

Lowman and Wells, "Monovalent Phage Display: A Method for Selecting Variant Proteins from Random Libraries" *Methods: Comp. to Methods Enzymol.* 3:205-216 (1991).

Lowman et al., "Molecular Mimics of Insulin-Like Growth Factor 1 (IGF-1) for Inhibiting IGF-1: IGF-Binding Protein Interactions." *Biochemistry* 37 (25) :8870-8878 (1998).

Lowman et al., "Selecting High-Affinity Binding Proteins by Monovalent Phage Display" *Biochemistry* 30 (45):10832-10838 (1991).

Lowman, H., "Bacteriophage display and discovery of peptide leads for drug development" *Annual Review of Biophysics and Biomolecular Structure* 26:401-424 (1997).

Lowman, H., "Phage display of peptide libraries on protein scaffolds" *Methods in Molecular Biology*, Chapter 24, 87:249-264 (1998).

McDonnell et al., "Structure Based Design and Characterization of Peptides that Inhibit IgE Binding to Its High-affinity Receptor" *Nature Structural Biology* 3 (5) :419-426 (May 1996).

McDonnell et al., "Structure-based design of peptides that inhibit IgE binding to its high-affinity receptor FCERI" *Biochem Soc. Trans* 25:387-392 (1997).

Metzger et al., "The Receptor with High Affinity for Immunoglobulin E" *Ann. Rev. Immunol* 4:419-470 (1986).

Nechansky et al., "The membrane-proximal part of FCERIα contributes to human IgE and antibody binding—implications for a general structural motif in Fc receptors" *FEBS Letters* 441:225-230 (1998).

Nilsson et al., "Integrated production of human insulin and its C-peptide" *Journal of Biotechnology* 48:241-250 (1996).

Nissim et al., "Mapping of the high affinity Fce receptor binding site to the third constant region domain of IgE" *EMBO Journal* 10 (1) :101-107 (Jan. 1991).

Olivera et al., "Combinatorial peptide libraries in drug design: lessons from venomous cone snails" *Trends BioTech* 13:422-426 (1995).

Pasqualini and Ruoslahti, "Organ Targeting In Vivo Using Phage Display Peptide Libraries." *Nature* 380:364-366 (1996).

Pelton et al., "Design and Synthesis of Conformationally Constrained Somatostatin Analogues with High Potency and Specificity for µ Opoid Receptors" *J. Med. Chem.* 29:2370-2375 (1986).

Presta et al., "Humanization of Antibody Directed Against IgE" *J. Immunol.* 151(5) :2623-2632 (Sep. 1, 1993).

Saini et al., "Down-Regulation of Human Basophil IgE and FCERIα Surface Densities and Mediator Release by Anti-IgE-Infusions Is Reversible In Vitro and In Vivo" *J. Immunol* 162:5624-5630 (1999).

Sawyer, T.K., "Peptidomimetic Design and Chemical Approaches to Peptide Metabolism" *Peptide-Based Drug Design: Controlling Transport and Metabolism*, Taylor and Amidon, Washington, DC:American Chemical Society pp. 387-422 (1995).

Sidhu et al., "Phage Display for Selection of Novel Binding Peptides" *Methods Enzymology* 328:333-363 (2000).

Smith B.J., "Enzymatic Methods for Cleaving Proteins" *Methods Mol. Biol.* 32:289-296 (1994).

Stamenkovic et al., "The B Lymphocyte Adhesion Molecule CD22 Interacts with Leukocyte Common Antigen CD45RO on T Cells and α2-6 Sialyltransferase, CD75, on B Cells" *Cell* 66:1133-1144 (1991).

Van Wezenbeek and Schoenmakers, "Nucleotide sequence of the genes III, VI, and I of bacteriophage M13" *Nucleic Acids Research* 6:2799-2818 (1979).

Wells and Lowman, "Rapid Evolution of Peptide and Protein Binding Properties in Vitro" *Curr. Opin. Struct. Biol.* 2:597-604 (1992).

Wrighton et al., "Small Peptides as Potent Mimetics of the Protein Hormone Erythropoietin." *Science* 273:458-463 (1996).

Yanofsky et al., "High Affinity Type I Interleukin 1 Receptor Antagonists Discovered by Screening Recombinant Peptide Libraries." *Proc. Natl. Acad. Sci. USA* 93:7381-7386 (1996).

Takahashi et al., "Design of Peptides Derived from Anti-IgE Antibody for Allergic Treatment" *Bioorg. Med. Chem. Lett.* 9:2185-2188 (1999).

| (Library) Clone name | R | N | 1 | 2 | 3 | 4 | 5 | 6 | 7 | 8 | 9 | 10 | 11 | 12 | 13 | 14 | 15 | 16 | 17 | 18 | 19 | 20 | 21 | $IC_{50}/IC_{50}(wt)$ | wt |
|---|---|---|---|---|---|---|---|---|---|---|---|---|---|---|---|---|---|---|---|---|---|---|---|---|---|
| IGE83 library | | | | | | | | | | | | | | | | | | | | | | | | | |
| NB0836-584K (SEQ ID NO: 236) | 3 | 13 | L | Y | C | P | R | L | C | Y | V | G | G | K | A | L | C | P | D | V | C | Y | V | 1.0 | IGE120 |
| NB0848-584G (SEQ ID NO: 237) | 3 | 12 | Y | Y | C | P | H | L | C | Y | V | G | G | K | A | L | C | P | D | V | C | Y | V | 0.54 | |
| NB0836-584A (SEQ ID NO: 238) | 3 | 8 | H | R | C | P | A | E | C | Y | V | G | G | K | A | L | C | P | D | V | C | Y | V | | |
| NB0848-584B (SEQ ID NO: 239) | 3 | 7 | K | Y | C | P | L | L | C | Y | V | G | G | K | A | L | C | P | D | V | C | Y | V | | |
| NB0836-584D (SEQ ID NO: 240) | 3 | 6 | R | S | C | P | I | W | C | Y | V | G | G | K | A | L | C | P | D | V | C | Y | V | | |
| NB0848-584P (SEQ ID NO: 241) | 3 | 3 | N | Y | C | P | G | W | C | Y | V | G | G | K | A | L | C | P | D | V | C | Y | V | | |
| NB0836-584B (SEQ ID NO: 242) | 3 | 3 | Y | B | C | P | N | M | C | Y | V | G | G | K | A | L | C | P | D | V | C | Y | V | 4.4 | |
| NB0836-584S (SEQ ID NO: 243) | 3 | 2 | K | L | C | P | R | W | C | Y | V | G | G | K | A | L | C | P | D | V | C | Y | V | | |
| NB0848-584-21 (SEQ ID NO: 244) | 3 | 2 | L | P | C | P | M | M | C | Y | V | G | G | K | A | L | C | P | D | V | C | Y | V | | |
| NB0836-584T (SEQ ID NO: 245) | 3 | 2 | M | M | C | P | R | W | C | Y | V | G | G | K | A | L | C | P | D | V | C | Y | V | 2.3 | |
| NB0836-584J (SEQ ID NO: 246) | 3 | 2 | N | G | C | P | E | M | C | Y | V | G | G | K | A | L | C | P | D | V | C | Y | V | | |
| NB0848-584Z4 (SEQ ID NO: 247) | 3 | 2 | S | Y | C | P | R | L | C | Y | V | G | G | K | A | L | C | P | D | V | C | Y | V | | |
| NB0836-584H (SEQ ID NO: 248) | 3 | 1 | Y | A | C | P | E | W | C | Y | V | G | G | K | A | L | C | P | D | V | C | Y | V | 0.73 | |
| NB0848-584-32 (SEQ ID NO: 249) | 3 | 1 | A | A | C | P | D | W | C | Y | V | G | G | K | A | L | C | P | D | V | C | Y | V | | |
| NB0848-584C (SEQ ID NO: 250) | 3 | 1 | G | G | C | P | S | M | C | Y | V | G | G | K | A | L | C | P | D | V | C | Y | V | | |
| NB0848-584A (SEQ ID NO: 251) | 3 | 1 | G | G | C | P | G | L | C | Y | V | G | G | K | A | L | C | P | D | V | C | Y | V | | |
| NB0848-584-5 (SEQ ID NO: 252) | 3 | 1 | G | H | C | P | Q | M | C | Y | V | G | G | K | A | L | C | P | D | V | C | Y | V | | |
| NB0848-584-38 (SEQ ID NO: 253) | 3 | 1 | I | B | C | P | Q | L | C | Y | V | G | G | K | A | L | C | P | D | V | C | Y | V | | |
| NB0848-584-39 (SEQ ID NO: 254) | 3 | 1 | K | S | C | P | P | Q | C | Y | V | G | G | K | A | L | C | P | D | V | C | Y | V | | |

| SEQ ID NO | Name | | | Sequence |
|---|---|---|---|---|
| 255 | NB0836-584E | 3 | 1 | L L C P W L C Y V G G K A L C P D V C Y V |
| 256 | NB0848-584T | 3 | 1 | L Y C P R M C Y V G G K A L C P D V C Y V |
| 257 | NB0848-584I | 3 | 1 | M M C P I L C Y V G G K A L C P D V C Y V |
| 258 | NB0836-584P | 3 | 1 | M R C P L L C Y V G G K A L C P D V C Y V |
| 259 | NB0848-584U | 3 | 1 | R E C P Q M C Y V G G K A L C P D V C Y V |
| 260 | NB0836-584R | 3 | 1 | R I C P L L C Y V G G K A L C P D V C Y V |
| 261 | NB0848-584K | 3 | 1 | S Y C P Q L C Y V G G K A L C P D V C Y V |
| 262 | NB0848-584Z7 | 3 | 1 | S A C P S M C Y V G G K A L C P D V C Y V |
| 263 | NB0848-584-3 | 3 | 1 | S K C P E L C Y V G G K A L C P D V C Y V |
| 264 | NB0848-584-6 | 3 | 1 | S K C P E L C Y V G G K A L C P D V C Y V |
| 265 | NB0848-584-36 | 3 | 1 | S K C P W L C Y V G G K A L C P D V C Y V |
| 266 | NB0836-584O | 3 | 1 | S P C P A L C Y V G G K A L C P D V C Y V |
| 267 | NB0848-584-27 | 3 | 1 | H P C P R L C Y V G G K A L C P D V C Y V |
| 268 | NB0848-584F | 3 | 1 | V L C P G L C Y V G G K A L C P D V C Y V |
| 269 | NB0848-584Z6 | 3 | 1 | V A C P A L C Y V G G K A L C P D V C Y V |
| 270 | NB0848-584-28 | 3 | 1 | V A C P E L C Y V G G K A L C P D V C Y V |
| 271 | NB0848-584-9 | 3 | 1 | V A C P R L C Y V G G K A L C P D V C Y V |
| 272 | NB0836-584C | 3 | 1 | V L C P S L C Y V G G K A L C P D V C Y V |
| 273 | NB0836-584G | 3 | 1 | V M C P R L C Y V G G K A L C P D V C Y V |
| 274 | NB0848-584W | 3 | 1 | V P C P H E C Y V G G K A L C P D V C Y V |
| 275 | NB0836-584F | 3 | 1 | V Q C P W L C Y V G G K A L C P D V C Y V |
| 276 | NB0836-584O | 3 | 1 | V R C P R L C Y V G G K A L C P D V C Y V |
| 277 | NB0836-584N | 3 | 1 | Y K C P H L C Y V G G K A L C P D V C Y V |
| 278 | NB0848-584-7 | 3 | 1 | Y S C P B L C Y V G G K A L C P D V C Y V |
| 279 | NB0848-584R | 3 | 1 | Y S C P B L C Y V G G K A L C P D V C Y V |

| | | | | | | | | | | | | | | | | | | | | | | | |
|---|---|---|---|---|---|---|---|---|---|---|---|---|---|---|---|---|---|---|---|---|---|---|---|---|
| (SEQ ID NO: 280) | NB0849-584-14 | 4* | 5 | S | K | C | P | W | L | C | Y | V | G | G | K | A | L | C | P | D | V | C | Y | V |
| (SEQ ID NO: 281) | NB0849-584-9 | 4* | 4 | L | Y | C | P | B | L | C | Y | V | G | G | K | A | L | C | P | D | V | C | Y | V |
| (SEQ ID NO: 282) | NB0849-584-1 | 4* | 4 | Y | Q | C | P | H | E | C | Y | V | G | G | K | A | L | C | P | D | V | C | Y | V |
| (SEQ ID NO: 283) | NB0849-584-6 | 4* | 4 | L | W | C | P | B | I | C | Y | V | G | G | K | A | L | C | P | D | V | C | Y | V |
| (SEQ ID NO: 284) | NB0849-584-19 | 4* | 3 | M | M | C | P | B | W | C | Y | V | G | G | K | A | L | C | P | D | V | C | Y | V |
| (SEQ ID NO: 285) | NB0849-584-5 | 4* | 1 | B | W | C | P | B | E | C | Y | V | G | G | K | A | L | C | P | D | V | C | Y | V |
| (SEQ ID NO: 286) | NB0849-584-13 | 4* | 1 | Y | R | C | P | S | L | C | Y | V | G | G | K | A | L | C | P | D | V | C | Y | V |
| (SEQ ID NO: 287) | NB0849-584-20 | 4* | 1 | V | I | C | P | B | W | C | Y | V | G | G | K | A | L | C | P | D | V | C | Y | V |

4* = 2x FcERI, 1x hGHr, 2x FcERI

| | | | | | | | | | | | | | | | | | | | | | | |
|---|---|---|---|---|---|---|---|---|---|---|---|---|---|---|---|---|---|---|---|---|---|---|
| | IGE83 library | 3 | - | A | L | C | P | A | V | C | Y | V | G | G | K | A | L | C | P | D | V | C | Y | V |
| (SEQ ID NO: 288) | HL585 No enrichment | | | | | | | | | | | | | | | | | | | | | | | |

| | | | | | | | | | | | | | | | | | | | | | | |
|---|---|---|---|---|---|---|---|---|---|---|---|---|---|---|---|---|---|---|---|---|---|---|
| | IGE83 library | 3 | - | A | L | C | P | A | V | C | Y | V | G | G | K | A | L | C | P | D | V | C | Y | K |
| (SEQ ID NO: 289) | HL586 No enrichment | | | | | | | | | | | | | | | | | | | | | | | |

| | (Library)<br>Clone name | R | N | 1 | 2 | 3 | 4 | 5 | 6 | 7 | 8 | 9 | 10 | 11 | 12 | 13 | 14 | 15 | 16 | 17 | 18 | 19 | 20 | 21 | $IC_{50}/$<br>$IC_{50}(wt)$ | wt |
|---|---|---|---|---|---|---|---|---|---|---|---|---|---|---|---|---|---|---|---|---|---|---|---|---|---|---|
| | IGE120 library | | | | | | | | | | | | | | | | | | | | | | | | | IGE120 |
| (SEQ ID NO: 290) | HL615<br>No enrichment | 3 | – | I | V | Q | P | R | L | C | Y | V | G | G | K | A | L | C | P | D | V | C | Y | V | | |
| | IGE120 library | | | | | | | | | | | | | | | | | | | | | | | | | |
| (SEQ ID NO: 291) | HL617<br>No enrichment | 3 | – | I | V | C | P | R | L | C | Y | V | G | G | K | A | L | C | P | D | V | C | Y | V | | |
| | IGE120 library | | | | | | | | | | | | | | | | | | | | | | | | | |
| (SEQ ID NO: 292) | NB0862-619M | 3 | 1 | – | V | C | P | R | L | C | Y | A | S | L | Q | Q | L | C | P | D | V | C | Y | V | | |
| (SEQ ID NO: 293) | NB0862-619H | 3 | 1 | – | V | C | P | R | L | C | Y | Y | E | L | L | E | L | C | P | D | V | C | Y | V | | |
| (SEQ ID NO: 294) | NB0862-619A | 3 | 1 | – | V | C | P | R | L | C | Y | Y | E | A | G | W | G | C | P | D | V | C | Y | V | | |
| (SEQ ID NO: 295) | NB0862-619K | 3 | 1 | – | V | C | P | R | L | C | Y | Y | G | G | A | K | E | C | P | D | V | C | Y | V | | |
| (SEQ ID NO: 296) | NB0862-619G | 3 | 1 | – | V | C | P | R | L | C | Y | Y | E | P | D | A | G | C | P | D | V | C | Y | V | | |
| (SEQ ID NO: 297) | NB0862-619S | 3 | 1 | – | V | C | P | R | L | C | Y | Y | G | S | G | D | A | C | P | D | V | C | Y | V | | |
| (SEQ ID NO: 298) | NB0862-619F | 3 | 1 | – | V | C | P | R | L | C | Y | Y | G | E | M | G | G | C | P | D | V | C | Y | V | | |
| (SEQ ID NO: 299) | NB0862-619O | 3 | 1 | – | V | C | P | R | L | C | Y | Y | S | Y | Y | W | Y | C | P | D | V | C | Y | V | | |
| (SEQ ID NO: 300) | NB0862-619E | 3 | 1 | – | V | C | P | R | L | C | Y | Y | V | S | L | L | S | C | P | D | V | C | Y | V | 0.42 | |
| (SEQ ID NO: 301) | NB0862-619R | 3 | 1 | – | V | C | P | R | L | C | Y | Y | W | W | A | P | W | C | P | D | V | C | Y | V | | |
| (SEQ ID NO: 302) | NB0862-619C | 3 | 1 | – | V | C | P | R | L | C | Y | Y | I | A | P | E | E | C | P | D | V | C | Y | V | | |
| (SEQ ID NO: 303) | NB0862-619D | 3 | 1 | – | V | C | P | R | L | C | Y | L | K | L | W | G | Q | C | P | D | V | C | Y | V | | |

FIG._2B

| | | | | | | | | | | | | | | | | | | | | | | | | | | |
|---|---|---|---|---|---|---|---|---|---|---|---|---|---|---|---|---|---|---|---|---|---|---|---|---|---|---|
| NB0862-619L | (SEQ ID NO: 304) | 3 | 1 | - | V | C | P | R | L | C | Y | L | W | E | D | S | L | C | P | D | V | C | Y | V | | |
| NB0862-619P | (SEQ ID NO: 305) | 3 | 1 | - | V | C | P | R | L | C | Y | M | E | S | S | L | C | P | D | V | C | Y | V | | |
| NB0862-619T | (SEQ ID NO: 306) | 3 | 1 | - | V | C | P | R | L | C | Y | N | D | D | E | L | C | P | D | V | C | Y | V | | |
| NB0862-619I | (SEQ ID NO: 307) | 3 | 1 | - | V | C | P | R | L | C | Y | V | S | Y | G | L | C | P | D | V | C | Y | V | | |
| NB0862-619Q | (SEQ ID NO: 308) | 3 | 1 | - | V | C | P | R | L | C | Y | W | M | D | H | L | C | P | D | V | C | Y | V | | |
| NB0862-619N | (SEQ ID NO: 309) | 3 | 1 | - | V | C | P | R | L | C | Y | W | E | G | S | L | C | P | D | V | C | Y | V | | |
| NB0862-619J | (SEQ ID NO: 310) | 3 | 1 | - | V | C | P | R | L | C | Y | Y | F | G | G | L | C | P | D | V | C | Y | V | | |
| NB0862-619B | (SEQ ID NO: 311) | 3 | 1 | - | V | C | P | R | L | C | Y | A | E | D | A | L | C | P | D | V | C | Y | V | | |
| NB0895-619D | (SEQ ID NO: 312) | 4 | 6 | - | V | C | P | R | L | C | Y | L | D | Y | E | L | C | P | D | V | C | Y | V | 0.58 | IGE120 |
| NB0895-619I | (SEQ ID NO: 313) | 4 | 2 | - | V | C | P | R | L | C | Y | D | D | B | G | L | C | P | D | V | C | Y | V | | |
| NB0891-619A | (SEQ ID NO: 314) | 4 | 1 | - | V | C | P | R | L | C | Y | Q | Q | W | Q | L | C | P | D | V | C | Y | V | | |
| NB0895-619H | (SEQ ID NO: 315) | 4 | 1 | - | V | C | P | R | L | C | Y | Y | F | Q | Q | L | C | P | D | V | C | Y | V | | |
| NB0895-619C | (SEQ ID NO: 316) | 4 | 1 | - | V | C | P | R | L | C | Y | E | L | L | A | L | C | P | D | V | C | Y | V | | |
| NB0895-619B | (SEQ ID NO: 317) | 4 | 1 | - | V | C | P | R | L | C | Y | V | D | L | G | L | C | P | D | V | C | Y | V | | |
| NB0869-619L | (SEQ ID NO: 318) | 5 | 1 | - | V | C | P | R | L | C | Y | A | W | G | G | L | C | P | D | V | C | Y | V | | |
| NB0869-619H | (SEQ ID NO: 319) | 5 | 1 | - | V | C | P | R | L | C | Y | D | G | S | Y | L | C | P | D | V | C | Y | V | | |
| NB0869-619T | (SEQ ID NO: 320) | 5 | 1 | - | V | C | P | R | L | C | Y | Q | G | E | H | L | C | P | D | V | C | Y | V | | |
| NB0869-619R | (SEQ ID NO: 321) | 5 | 1 | - | V | C | P | R | L | C | Y | E | G | A | E | L | C | P | D | V | C | Y | V | | |
| NB0869-619O | (SEQ ID NO: 322) | 5 | 1 | - | V | C | P | R | L | C | Y | E | L | P | D | L | C | P | D | V | C | Y | V | | |
| NB0869-619B | (SEQ ID NO: 323) | 5 | 1 | - | V | C | P | R | L | C | Y | L | L | L | R | L | C | P | D | V | C | Y | V | | |
| NB0869-619E | (SEQ ID NO: 324) | 5 | 1 | - | V | C | P | R | L | C | Y | G | L | — | G | L | C | P | D | V | C | Y | V | | |
| NB0869-619F | (SEQ ID NO: 325) | 5 | 1 | - | V | C | P | R | L | C | Y | L | S | W | E | L | C | P | D | V | C | Y | V | | |
| NB0869-619P | (SEQ ID NO: 326) | 5 | 1 | - | V | C | P | R | L | C | Y | L | G | E | P | L | C | P | D | V | C | Y | V | | |

| SEQ ID NO | Name | | | | | | | | | | | | | | | | | | | | | | |
|---|---|---|---|---|---|---|---|---|---|---|---|---|---|---|---|---|---|---|---|---|---|---|---|
| (SEQ ID NO: 327) | NB0869-619A | 5 | 1 | – | V | C | P | R | L | C | Y | L | Y | G | P | G | L | C | P | D | V | C | Y | V |
| (SEQ ID NO: 328) | NB0869-619J | 5 | 1 | – | V | C | P | R | L | C | Y | M | G | D | S | E | L | C | P | D | V | C | Y | V |
| (SEQ ID NO: 329) | NB0869-619C | 5 | 1 | – | V | C | P | R | L | C | Y | N | S | L | Q | F | L | C | P | D | V | C | Y | V |
| (SEQ ID NO: 330) | NB0869-619I | 5 | 1 | – | V | C | P | R | L | C | Y | S | D | L | W | L | L | C | P | D | V | C | Y | V |
| (SEQ ID NO: 331) | NB0869-619G | 5 | 1 | – | V | C | P | R | L | C | Y | H | G | L | S | Q | L | C | P | D | V | C | Y | V |
| (SEQ ID NO: 332) | NB0869-619K | 5 | 1 | – | V | C | P | R | L | C | Y | V | I | S | L | G | L | C | P | D | V | C | Y | V |
| (SEQ ID NO: 333) | NB0869-619D | 5 | 1 | – | V | C | P | R | L | C | Y | W | G | S | H | D | L | C | P | D | V | C | Y | V |
| (SEQ ID NO: 334) | NB0869-619S | 5 | 1 | – | V | C | P | R | L | C | Y | W | G | G | I | G | L | C | P | D | V | C | Y | V |
| (SEQ ID NO: 335) | NB0869-619N | 5 | 1 | – | V | C | P | R | L | C | Y | Y | A | A | A | L | L | C | P | D | V | C | Y | V |
| (SEQ ID NO: 336) | NB0869-619Q | 5 | 1 | V | V | C | P | R | L | C | Y | Y | G | A | S | G | L | C | P | D | V | C | Y | V |
| (SEQ ID NO: 337) | NB1112-619 | 3* | 1 | V | V | C | P | R | L | C | Y | W | Y | P | S | L | L | C | P | D | V | C | Y | V |

3* = 1x FcERI, 2x hGHr, 2x FcERI

IgE122 library (soft randomized)

| SEQ ID NO | Name | | | | | | | | | | | | | | | | | | | | | | |
|---|---|---|---|---|---|---|---|---|---|---|---|---|---|---|---|---|---|---|---|---|---|---|---|
| (SEQ ID NO: 338) | NB1112-167B | 3* | 2 | V | Q | C | C | P | E | L | F | C | Y | G | G | P | E | L | C | P | D | S | Y | G |
| (SEQ ID NO: 339) | NB1112-167C | 3* | 1 | V | Q | C | C | P | D | L | F | C | Y | Y | G | G | A | A | L | C | P | D | V | C | Y |
| (SEQ ID NO: 340) | NB1112-167D | 3* | 1 | V | R | C | C | P | E | L | F | C | Y | D | G | I | A | L | C | P | D | V | C | Y |

*FIG._2C*

| | | | | | | | | | | | | | | | | | | | | | | |
|---|---|---|---|---|---|---|---|---|---|---|---|---|---|---|---|---|---|---|---|---|---|---|
| (SEQ ID NO: 341) | NB1112-167G | 3* | 1 | V | P | C | P | H | F | C | Y | D | G | D | K | E | L | C | P | E | V | C | H | V | 0.56 | IGE122 |
| (SEQ ID NO: 342) | NB1112-167F | 3* | 1 | V | Q | C | P | H | F | C | Y | Y | G | G | K | E | L | C | P | D | V | C | Y | V |
| (SEQ ID NO: 343) | NB1112-167A | 3* | 1 | G | Q | C | P | Q | F | C | Y | L | G | G | H | G | L | C | P | D | V | C | Y | V |
| (SEQ ID NO: 344) | NB1112-167E | 3* | 1 | V | Q | C | P | L | F | C | Y | E | G | G | E | G | L | C | P | D | V | C | Y | V |
| (SEQ ID NO: 345) | NB1112-167I | 3* | 1 | V | Q | C | P | D | F | C | Y | Q | G | G | N | S | L | C | P | D | V | C | Y | V |
| (SEQ ID NO: 346) | NB0891-167C | 4 | 5 | V | Q | C | P | S | E | C | Y | D | G | G | K | A | L | C | P | D | V | C | Y | V | 0.58 | IGE122 |
| (SEQ ID NO: 347) | NB0891-167D | 4 | 2 | V | Q | C | P | H | F | C | Y | L | G | G | V | G | L | C | P | D | V | C | Y | V |
| (SEQ ID NO: 348) | NB0891-167J | 4 | 1 | V | K | C | P | D | F | C | Y | E | G | G | P | I | S | C | P | D | V | C | Y | K |

IGE122 library (soft randomized)

| | | | | | | | | | | | | | | | | | | | | | | |
|---|---|---|---|---|---|---|---|---|---|---|---|---|---|---|---|---|---|---|---|---|---|---|
| (SEQ ID NO: 349) | NB1112-168G | 3* | 1 | V | Q | C | P | H | F | C | Y | R | G | G | D | E | A | L | C | P | D | V | C | Y | V | 0.46 | IGE122 |
| (SEQ ID NO: 350) | NB1112-168F | 3* | 1 | V | Q | C | P | Q | F | C | Y | Q | G | G | G | N | E | L | C | P | D | V | C | Y | V |
| (SEQ ID NO: 351) | NB1112-168A | 3* | 1 | V | V | C | P | S | F | C | Y | V | G | G | C | Q | N | L | C | P | D | L | C | I | S |
| (SEQ ID NO: 352) | NB1112-168C | 3* | 1 | V | P | C | P | H | F | C | Y | V | G | G | E | N | G | L | C | P | D | V | C | Y | V |
| (SEQ ID NO: 353) | NB1112-168D | 3* | 1 | V | Q | C | P | Q | F | C | Y | V | G | G | V | K | S | L | C | P | D | V | C | Y | V |
| (SEQ ID NO: 354) | NB1112-168E | 3* | 1 | V | L | C | P | S | F | C | Y | Y | G | G | G | H | S | L | C | P | D | V | C | Y | E |
| (SEQ ID NO: 355) | NB1112-168H | 3* | 1 | V | Q | C | P | H | F | C | Y | Y | G | G | D | K | I | L | C | P | D | Q | C | Y | V |
| (SEQ ID NO: 356) | NB1112-168B | 3* | 1 | V | B | C | P | Y | F | C | Y | A | G | G | G | K | S | L | C | P | D | V | C | Y | V |
| (SEQ ID NO: 357) | NB0896-168B | 4 | 10 | V | K | C | P | H | F | C | Y | E | G | G | G | K | E | L | C | P | G | V | C | Y | A | 0.65 | IGE122 |
| | | | | | | | | | | | | | | | | | | | | | | | | | 0.54 | IGE122 |
| | | | | | | | | | | | | | | | | | | | | | | | | | 0.85 | IGE122 |
| (SEQ ID NO: 358) | NB0896-168A | 4 | 1 | V | B | C | P | H | F | C | Y | Y | G | G | Q | D | I | L | C | P | D | V | C | Y | V | 1.2 | IGE122 |

3* = 1x FcERI, 2x hGHr, 2x FcERI

| | | Start | Sequence | End |
|---|---|---|---|---|
| IGE120library | (SEQ ID NO: 359) | 5 | VCPRLCYVGGKHECPSRCYV | |
| NB0869-621C | (SEQ ID NO: 360) | 5 | VCPRLCYVGGKQLCPDGCYV | |
| NB0869-621K | (SEQ ID NO: 361) | 5 | VCPRLCYVGGKGWCPDKCYV | |
| NB0869-621G | (SEQ ID NO: 362) | 5 | VCPRLCYVGGKLWCPALCYV | |
| NB0869-621H | (SEQ ID NO: 363) | 5 | VCPRLCYVGGKAWCPHECYV | |
| NB0869-621F | (SEQ ID NO: 364) | 5 | VCPRLCYVGGKAWCPSLCYV | |
| NB0869-621O | (SEQ ID NO: 365) | 5 | VCPRLCYVGGKAWCPGECYV | |
| NB0869-621A | (SEQ ID NO: 366) | 5 | VCPRLCYVGGKAWCPLSCYV | |
| NB0869-621R | (SEQ ID NO: 367) | 5 | VCPRLCYVGGKDWCPNMCYV | |
| NB0869-621E | (SEQ ID NO: 368) | 5 | VCPRLCYVGGKHWCPSVCYV | |
| NB0869-621T | (SEQ ID NO: 369) | 5 | VCPRLCYVGGKHWCPWSCYV | |
| NB0869-621J | (SEQ ID NO: 370) | 5 | VCPRLCYVGGKHWCPSECYV | |
| NB0869-621S | (SEQ ID NO: 371) | 5 | VCPRLCYVGGKHWCPMMCYV | |
| NB0869-621D | (SEQ ID NO: 372) | 5 | VCPRLCYVGGKLWCPSLCYV | |
| NB0869-621P | (SEQ ID NO: 373) | 5 | VCPRLCYVGGKLPCPAACYV | |
| NB0869-621I | (SEQ ID NO: 374) | 5 | VCPRLCYVGGKQWCPGECYV | |
| NB0869-621M | (SEQ ID NO: 375) | 5 | VCPRLCYVGGKIWCPSMCYV | |
| NB0869-621Q | (SEQ ID NO: 376) | 5 | VCPRLCYVGGKIWCPAWCYV | |
| NB0869-621N | (SEQ ID NO: 377) | 5 | VCPRLCYVGGKWWCPQMCYV | |

| | | | | | | | | | | | | | | | | | | | | | | | | | | |
|---|---|---|---|---|---|---|---|---|---|---|---|---|---|---|---|---|---|---|---|---|---|---|---|---|---|---|
| | IGE122 library | | | | | | | | | | | | | | | | | | | | | | | | | |
| (SEQ ID NO: 378) | NB1112-166D | 3* | 2 | V | Q | C | P | H | F | C | Y | V | G | G | K | R | E | C | P | D | K | C | Y | V | 0.56 | IGE122 |
| (SEQ ID NO: 379) | NB1112-166E | 3* | 1 | V | Q | C | P | H | F | C | Y | V | G | G | K | H | D | C | P | D | R | C | Y | V | >10 | IGE122 |
| (SEQ ID NO: 380) | NB1112-166A | 3* | 1 | V | Q | C | P | H | F | C | Y | V | G | G | K | R | E | C | P | D | S | C | Y | V | 1.3 | IGE122 |
| (SEQ ID NO: 381) | NB1112-166I | 3* | 1 | V | Q | C | P | H | F | C | Y | V | G | G | K | Q | L | C | P | D | L | C | Y | V | 1.1 | IGE122 |
| (SEQ ID NO: 382) | NB1112-166F | 3* | 1 | V | Q | C | P | H | F | C | Y | V | G | G | K | H | L | C | P | D | G | C | Y | V | 1.2 | IGE122 |
| (SEQ ID NO: 383) | NB1112-166J | 3* | 1 | V | Q | C | P | H | F | C | Y | V | G | G | K | Q | P | C | P | D | Y | C | Y | V | 1.4 | IGE122 |
| (SEQ ID NO: 384) | NB1112-166G | 3* | 1 | V | Q | C | P | H | F | C | Y | V | G | G | K | N | Q | C | P | D | K | C | Y | V | 1.4 | IGE122 |
| (SEQ ID NO: 385) | NB1112-166H | 3* | 1 | V | Q | C | P | H | F | C | Y | V | G | G | K | G | V | C | P | D | I | C | Y | V | 1.7 | IGE122 |
| (SEQ ID NO: 386) | NB0892-166A | 5 | 4 | V | Q | C | P | H | F | C | Y | V | G | G | K | G | L | C | P | D | I | C | Y | V | 0.85 | IGE122 |
| (SEQ ID NO: 387) | NB0892-166B | 5 | 2 | V | Q | C | P | H | F | C | Y | V | G | G | K | S | M | C | P | D | P | C | Y | V | 0.99 | IGE122 |
| (SEQ ID NO: 388) | NB0892-166C | 5 | 1 | V | Q | C | P | H | F | C | Y | V | G | G | K | L | L | C | P | D | L | C | Y | V | | |
| (SEQ ID NO: 389) | NB0892-166J | 5 | 1 | V | Q | C | P | H | F | C | Y | V | G | G | K | S | L | C | P | D | R | C | Y | V | | |
| (SEQ ID NO: 390) | NB0892-166H | 5 | 1 | V | Q | C | P | H | F | C | Y | V | G | G | K | L | V | C | P | D | A | C | Y | V | | |
| 3* = 1x FcER, 2x hGHr, 2x FcER | | | | | | | | | | | | | | | | | | | | | | | | | | |
| | IGE122 library | | | | | | | | | | | | | | | | | | | | | | | | | |
| (SEQ ID NO: 391) | NB1138-172A | 4* | 9 | V | Q | C | P | H | F | C | Y | V | G | G | K | A | L | C | P | D | R | C | Y | I | | |
| (SEQ ID NO: 392) | NB1138-172E | 4* | 1 | V | Q | C | P | H | F | C | Y | V | G | G | K | A | L | C | P | D | B | C | Y | S | | |
| (SEQ ID NO: 393) | NB1138-172H | 4* | 1 | V | Q | C | P | H | F | C | Y | V | G | G | K | A | V | C | P | D | Y | C | Y | H | | |
| 4* = 1x FcER, 2x hGHr, 3x FcER | | | | | | | | | | | | | | | | | | | | | | | | | | |

FIG._2F

IGE122 library

| | | | | | | | | | | | | | | | | |
|---|---|---|---|---|---|---|---|---|---|---|---|---|---|---|---|---|
| (SEQ ID NO: 394) | NB1139-174B | 4* | 11 | V | B | C | P | H | F | C | Y | V | G | G | K | A | L | C | P | D | Y | C | Y | Y |
| (SEQ ID NO: 395) | NB1139-174A | 4* | 6 | V | Y | C | P | H | F | C | Y | V | G | G | K | A | L | C | P | D | K | C | Y | Y |
| (SEQ ID NO: 396) | NB1139-174G | 4* | 1 | V | E | C | P | H | F | C | Y | V | G | G | K | A | L | C | P | D | L | C | Y | Y |

4* = 1x FcER, 2x hGHr, 3x FcER

IGE122 library

| | | | | | | | | | | | | | | | | |
|---|---|---|---|---|---|---|---|---|---|---|---|---|---|---|---|---|
| (SEQ ID NO: 397) | NB1140-175F | 4* | 5 | V | B | C | P | H | F | C | Y | V | G | G | K | A | L | C | P | D | Y | C | Y | Y |
| (SEQ ID NO: 398) | NB1140-175C | 4* | 4 | V | B | C | P | H | F | C | Y | V | G | G | K | A | L | C | P | D | P | C | Y | Y |
| (SEQ ID NO: 399) | NB1140-175A | 4* | 4 | V | K | C | P | H | F | C | Y | V | G | G | K | A | L | C | P | D | B | C | Y | Y |
| (SEQ ID NO: 400) | NB1140-175Q | 4* | 1 | V | M | C | P | H | F | C | Y | V | G | G | K | G | L | C | P | D | K | C | Y | Y |
| (SEQ ID NO: 401) | NB1140-175E | 4* | 1 | V | M | C | P | H | F | C | Y | V | G | G | K | A | L | C | P | D | K | C | Y | Y |
| (SEQ ID NO: 402) | NB1140-175D | 4* | 1 | V | B | C | P | H | F | C | Y | V | G | G | K | A | L | C | P | D | Y | C | Y | Y |
| (SEQ ID NO: 403) | NB1140-175I | 4* | 1 | V | Y | C | P | H | F | C | Y | V | G | G | K | T | L | C | P | D | Q | C | Y | Y |
| (SEQ ID NO: 404) | NB1140-175M | 4* | 1 | V | Y | C | P | H | F | C | Y | V | G | G | K | A | L | C | P | D | Y | C | Y | Y |

4* = 1x FcER, 2x hGHr, 3x FcER

IGE122 library

| | | | | | | | | | | | | | | | | |
|---|---|---|---|---|---|---|---|---|---|---|---|---|---|---|---|---|
| (SEQ ID NO: 405) | NB1141-177F | 4* | 1 | V | Q | C | P | H | F | C | E | V | G | G | K | A | L | C | P | D | V | C | Y | V |

FIG._2G

| | | | | | | | | | | | | | | | | | | | | | | |
|---|---|---|---|---|---|---|---|---|---|---|---|---|---|---|---|---|---|---|---|---|---|---|
| (SEQ ID NO: 406) | IGE122 library NB1142-179B | 4* | 1 | V | Q | Q | P | H | F | C | F | V | G | D | K | A | L | C | P | D | V | G | Y | V |
| (SEQ ID NO: 407) | NB1142-179D | 4* | 1 | V | Q | Q | P | H | F | C | F | V | G | E | | A | L | C | P | D | V | G | Y | V |
| (SEQ ID NO: 408) | IGE122 library NB1143-180A | 4* | 1 | V | Q | C | P | H | F | C | Y | V | G | G | K | A | L | C | P | D | V | C | D | V |
| (SEQ ID NO: 409) | IGE122 library YC165 | 5 | 10 | V | Q | C | P | H | F | C | Y | V | G | G | K | A | L | C | P | D | V | C | Y | V |
| (SEQ ID NO: 410) | IGE122 library YC177 | 6 | 12 | V | Q | C | P | H | F | C | Y | V | G | G | K | A | L | C | P | D | V | C | Y | V |
| (SEQ ID NO: 411) | IGE122 library YC179 | 6 | 12 | V | Q | Q | P | H | F | C | Y | V | G | G | K | A | L | C | P | D | V | G | Y | V |
| (SEQ ID NO: 412) | IGE122 library YC180 | 6 | 12 | V | Q | Q | P | H | F | C | Y | V | G | G | K | A | L | C | P | D | V | C | Y | V |

4* = 1x FcER, 2x hGHr, 3x FcER

FIG._2H

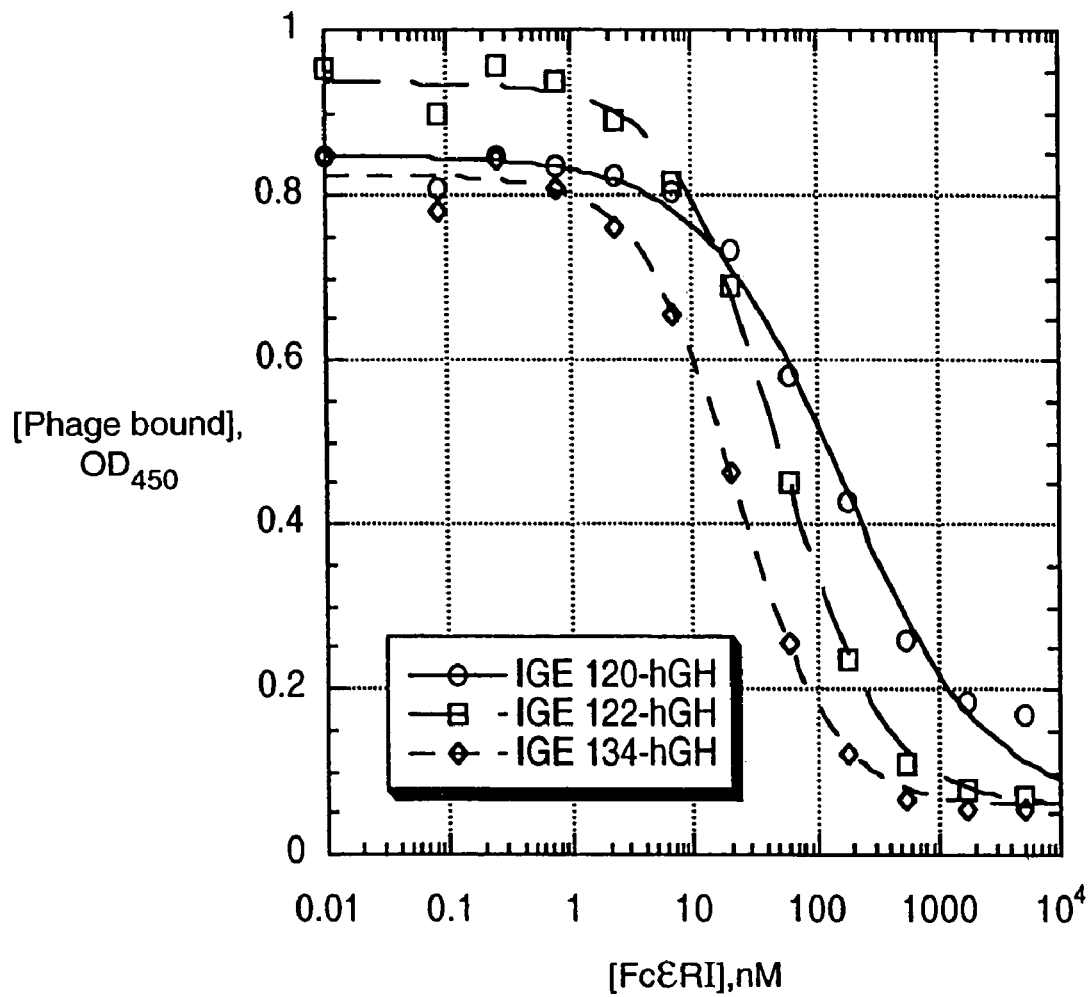
FIG._3

FIG. 4A

| | Clone name (Library) | R | N | Sequence | IC₅₀/IC₅₀(wt) | wt |
|---|---|---|---|---|---|---|
| | IGE134 library | | | | | |
| (SEQ ID NO: 413) | NB1161-682L | 3 | 8 | L L C P L F C Y E L D Y E L C P D V C Y V | | IGE134 |
| (SEQ ID NO: 414) | NB1161-682C | 3 | 5 | Q L C P L F C Y E L D Y E L C P D V C Y V | 1.9 | IGE134 |
| (SEQ ID NO: 415) | NB1161-682A | 3 | 4 | A L C P L F C Y E L D Y E L C P D V C Y V | 2.2 | IGE134 |
| (SEQ ID NO: 416) | NB1161-682J | 3 | 2 | A G C P L F C Y E L D Y E L C P D V C Y V | 2.4 | IGE134 |
| (SEQ ID NO: 417) | NB1161-682S | 3 | 1 | Y E C P L F C Y E L D Y E L C P D V C Y V | 1.8 | IGE134 |
| (SEQ ID NO: 418) | NB1161-682E | 3 | 1 | K L C P Q F C Y E L D Y E L C P D V C Y V | | |
| | IGE134 library | | | | | |
| (SEQ ID NO: 419) | NB1162-684M | 3 | 1 | V Q C P H W C Y E L D G E L C P D V C Y V | | |
| (SEQ ID NO: 420) | NB1162-684A | 3 | 1 | V Q C P H M C Y E L D E E L C P D V C Y V | | |
| (SEQ ID NO: 421) | NB1162-684C | 3 | 1 | V Q C P H L C Y E L D G E Y C P D V C Y V | | |
| (SEQ ID NO: 422) | NB1162-684N | 3 | 1 | V Q C P H L C Y E L D L E E C P D V C Y V | | |
| (SEQ ID NO: 423) | NB1162-684L | 3 | 1 | V Q C P H L C Y E L D D E L C P D V C Y V | | |
| (SEQ ID NO: 424) | NB1162-684P | 3 | 1 | V Q C P H L C Y E L D P E L C P D V C Y V | | |
| (SEQ ID NO: 425) | NB1162-684F | 3 | 1 | V Q C P H L C Y E L D I E P C P D V C Y V | | |
| (SEQ ID NO: 426) | NB1162-684D | 3 | 1 | V Q C P H I C Y E L D E E Y C P D V C Y V | | |

FIG. 4B

Left panel:

| Seq | Name | SEQ ID |
|---|---|---|
| V Y C V D P C P E D G D L E Y C F H P C Q V ... 1 3 | NB1162-684J | (SEQ ID NO: 427) |
| V Y C V D P C Q E G L D L E Y C F H P C Q V ... 1 3 | NB1162-684K | (SEQ ID NO: 428) |
| V Y C V D P C L E R D L E Y C F H P C Q V ... 1 3 | NB1162-684I | (SEQ ID NO: 429) |
| V Y C V D P C P E P D D L E Y C F H P C Q V ... 1 3 | NB1162-684G | (SEQ ID NO: 430) |
| V Y C V D P C M E S D D L E Y C F H P C Q V ... 1 3 | NB1162-684B | (SEQ ID NO: 431) |
| V Y C V D P C V E V D D L E Y C F H P C Q V ... 1 3 | NB1162-684E | (SEQ ID NO: 432) |
| V Y C V D P C L E Y D D L E Y C F H P C Q V ... 1 3 | NB1162-684Q | (SEQ ID NO: 433) |

IGE134 library

| Seq | Name | SEQ ID |
|---|---|---|
| V Y C V D P C L E Y S Y G G Y E L C F H P C Q V ... 9 3 | NB1163-686B | (SEQ ID NO: 434) |
| V Y C V D P C L E Y G A G G Y E L C F H P C Q V ... 1 3 | NB1163-686J | (SEQ ID NO: 435) |
| V Y C V D P C L E Y Q E G Q Y E L C F H P C Q V ... 1 3 | NB1163-686A | (SEQ ID NO: 436) |
| V Y C V D P C L E Y Q G D Q Y E L C F H P C Q V ... 1 3 | NB1163-686L | (SEQ ID NO: 437) |
| V Y C V D P C L E Y Q G G P Y E L C F H P C Q V ... 1 3 | NB1163-686N | (SEQ ID NO: 438) |
| V Y C V D P C L E Y E G D G Y E L C F H P C Q V ... 1 3 | NB1163-686K | (SEQ ID NO: 439) |
| V Y C V D P C L E Y G G Q H Y E L C F H P C Q V ... 1 3 | NB1163-686H | (SEQ ID NO: 440) |
| V Y C V D P C L E Y G W G I Y E L C F H P C Q V ... 1 3 | NB1163-686D | (SEQ ID NO: 441) |
| V Y C V D P C L E Y R L G G Y E L C F H P C Q V ... 1 3 | NB1163-686P | (SEQ ID NO: 442) |
| V Y C V D P C L E Y B W G A Y E L C F H P C Q V ... 1 3 | NB1163-686S | (SEQ ID NO: 443) |
| V Y C V D P C L E Y S Y G G Y E L C F H P C Q V ... 1 3 | NB1163-686G | (SEQ ID NO: 444) |
| V Y C V D P C L E Y G V A Y E L C F H P C Q V ... 1 3 | NB1163-686T | (SEQ ID NO: 445) |
| V Y C V D P C L E Y G G G C Y E L C F H P C Q V ... 1 3 | NB1163-686M | (SEQ ID NO: 446) |

FIG._4C

| Sequence | Pos | V | Q | C | P | H | F | C | Y | E | L | L | X | X | X | L | C | P | D | V | C | Y | Pos |
|---|---|---|---|---|---|---|---|---|---|---|---|---|---|---|---|---|---|---|---|---|---|---|---|
| IGE134library (SEQ ID NO: 447) | 3 | V | Q | C | P | H | F | C | Y | E | L | L | E | A | R | L | C | P | D | V | C | Y | 2 |
| NB1164-687I (SEQ ID NO: 448) | 3 | V | Q | C | P | H | F | C | Y | E | L | L | D | L | B | L | C | P | D | V | C | Y | 1 |
| NB1164-687Q (SEQ ID NO: 449) | 3 | V | Q | C | P | H | F | C | Y | E | L | L | S | H | A | L | C | P | D | V | C | Y | 1 |
| NB1164-687O (SEQ ID NO: 450) | 3 | V | Q | C | P | H | F | C | Y | E | L | L | A | G | D | L | C | P | D | V | C | Y | 1 |
| NB1164-687N (SEQ ID NO: 451) | 3 | V | Q | C | P | H | F | C | Y | E | L | L | L | Q | P | L | C | P | D | V | C | Y | 1 |
| NB1164-687F (SEQ ID NO: 452) | 3 | V | Q | C | P | H | F | C | Y | E | L | L | Y | K | H | L | C | P | D | V | C | Y | 1 |
| NB1164-687A (SEQ ID NO: 453) | 3 | V | Q | C | P | H | F | C | Y | E | L | L | Q | N | I | L | C | P | D | V | C | Y | 1 |
| NB1164-687L (SEQ ID NO: 454) | 3 | V | Q | C | P | H | F | C | Y | E | L | L | D | K | G | L | C | P | D | V | C | Y | 1 |
| NB1164-687R (SEQ ID NO: 455) | 3 | V | Q | C | P | H | F | C | Y | E | L | L | E | Q | V | L | C | P | D | V | C | Y | 1 |
| NB1164-687C (SEQ ID NO: 456) | 3 | V | Q | C | P | H | F | C | Y | E | L | L | G | E | E | L | C | P | D | V | C | Y | 1 |
| NB1164-687G (SEQ ID NO: 457) | 3 | V | Q | C | P | H | F | C | Y | E | L | L | P | D | A | L | C | P | D | V | C | Y | 1 |
| NB1164-687M (SEQ ID NO: 458) | 3 | V | Q | C | P | H | F | C | Y | E | L | L | P | G | N | L | C | P | D | V | C | Y | 1 |
| NB1164-687D (SEQ ID NO: 459) | 3 | V | Q | C | P | H | F | C | Y | E | L | L | Q | A | Z | L | C | P | D | V | C | Y | 1 |
| NB1164-687K (SEQ ID NO: 460) | 3 | V | Q | C | P | H | F | C | Y | E | L | L | A | K | N | L | C | P | D | V | C | Y | 1 |
| NB1164-687H (SEQ ID NO: 461) | 3 | V | Q | C | P | H | F | C | Y | E | L | L | P | S | R | L | C | P | D | V | C | Y | 1 |
| NB1164-687P (SEQ ID NO: 462) | 3 | V | Q | C | P | H | F | C | Y | E | L | L | Q | R | S | L | C | P | D | V | C | Y | 1 |
| NB1164-687E | 3 | V | Q | C | P | H | F | C | Y | E | L | L | V | L | G | L | C | P | D | V | C | Y | 1 |

FIG. 4D

IGE134 library

| SEQ ID NO | Clone | # | n | Sequence | Affinity | |
|---|---|---|---|---|---|---|
| 463 | NB1165-692A | 3 | 3 | V Q C P H F C Y E L D Y E L C P D V C Y V | | |
| 464 | NB1165-692B | 3 | 5 | V Q C P H F C Y E L D Y E L C P D V C D V | 4 | IGE134 |
| 465 | NB1165-692M | 3 | 3 | V Q C P H F C Y E L D Y E L C P D V C H V | 2.5 | IGE134 |
| 466 | NB1165-692I | 3 | 2 | V Q C P H F C Y E L D Y E L C P D V C D V | | |
| 467 | NB1165-692H | 3 | 1 | V Q C P H F C A E L D Y E L C P D V C A V | | |
| 468 | NB1165-692G | 3 | 1 | V Q C P H F C Y E L D Y E L C P D V C G V | 8.7 | IGE134 |
| 469 | NB1165-692F | 3 | 1 | V Q C P H F C Y E L D Y E L C P D V C S V | | |

IGE134 library

| SEQ ID NO | Clone | # | n | Sequence | | |
|---|---|---|---|---|---|---|
| 470 | NB1174-682A | 4* | 22 | L I C P L F C Y E L D Y E L C P D V C Y V | | |
| 471 | NB1174-682D | 4* | 12 | Q A C P L F C Y E L D Y E L C P D V C Y V | | |
| 472 | NB1174-682C | 4* | 4 | A G C P L F C Y E L D Y E L C P D V C Y V | | |
| 473 | NB1174-682X | 4* | 4 | I R C P L F C Y E L D Y E L C P D V C Y V | | |
| 474 | NB1175-682A23 | 4* | 1 | L L C P G F C Y E L D Y E L C P D V C Y V | | |
| 475 | NB1175-682A19 | 4* | 1 | K S C P G F C Y E L D Y E L C P D V C Y V | | |
| 476 | NB1174-682O | 4* | 1 | L D C P G F C Y E L D Y E L C P D V C Y V | | |
| 477 | NB1174-682N | 4* | 1 | S I C P G F C Y E L D Y E L C P D V C Y V | | |
| 478 | NB1174-682T | 4* | 1 | Y K C P G F C Y E L D Y E L C P D V C Y V | | |
| 479 | NB1175-682A24 | 4* | 1 | Y H C P L F C Y E L D Y E L C P D V C Y V | | |
| 480 | NB1175-682A15 | 4* | 1 | A L C P L F C Y E L D Y E L C P D V C Y V | | |
| 481 | NB1175-682A25 | 4* | 1 | K E C P L F C Y E L D Y E L C P D V C Y V | | |
| 482 | NB1175-682A13 | 4* | 1 | L P C P L F C Y E L D Y E L C P D V C Y V | | |
| 483 | NB1175-682A7 | 4* | 1 | S A C P S F C Y E L D Y E L C P D V C Y V | | |
| 484 | NB1175-682A27 | 4* | 1 | I L C P Y F C Y E L D Y E L C P D V C Y V | | |

4* = 3x FcER, 1x hGHr, 1x FcER

FIG._4E

IGE134 library

| | | | | | | | | | | | | | | | | | | | | | | | | |
|---|---|---|---|---|---|---|---|---|---|---|---|---|---|---|---|---|---|---|---|---|---|---|---|---|
| (SEQ ID NO: 485) | NB1176-684A | 4* | 6 | V | Q | C | P | H | E | C | Y | E | L | D | L | E | E | L | C | P | D | V | C | Y | V |
| (SEQ ID NO: 486) | NB1176-684C | 4* | 1 | V | Q | C | P | H | E | C | Y | E | L | D | D | E | E | I | C | P | D | V | C | Y | V |
| (SEQ ID NO: 487) | NB1176-684B | 4* | 1 | V | Q | C | P | H | E | C | Y | E | L | D | D | E | E | V | C | P | D | V | C | Y | V |
| (SEQ ID NO: 488) | NB1176-684J | 4* | 1 | V | Q | C | P | H | E | C | Y | E | L | D | D | E | E | E | C | P | D | V | C | Y | V |
| (SEQ ID NO: 489) | NB1176-684N | 4* | 1 | V | Q | C | P | H | E | C | Y | E | L | D | G | E | E | L | C | P | D | V | C | Y | V |
| (SEQ ID NO: 490) | NB1176-684R | 4* | 1 | V | Q | C | P | H | E | C | Y | E | L | D | G | E | E | L | C | P | D | V | C | Y | V |
| (SEQ ID NO: 491) | NB1176-684F | 4* | 1 | V | Q | C | P | H | E | C | Y | E | L | D | D | E | E | P | C | P | D | V | C | Y | V |
| (SEQ ID NO: 492) | NB1176-684S | 4* | 1 | V | Q | C | P | H | E | C | Y | E | L | D | G | E | E | V | C | P | D | V | C | Y | V |
| (SEQ ID NO: 493) | NB1176-684E | 4* | 1 | V | Q | C | P | H | E | C | Y | E | L | D | D | E | E | L | C | P | D | V | C | Y | V |
| (SEQ ID NO: 494) | NB1176-684G | 4* | 1 | V | Q | C | P | H | E | C | Y | E | L | D | R | E | E | L | C | P | D | V | C | Y | V |
| (SEQ ID NO: 495) | NB1176-684O | 4* | 1 | V | Q | C | P | H | E | C | Y | E | L | D | E | E | E | M | C | P | D | V | C | Y | V |
| (SEQ ID NO: 496) | NB1176-684D | 4* | 1 | V | Q | C | P | H | E | C | Y | E | L | D | R | E | L | V | C | P | D | V | C | Y | V |
| (SEQ ID NO: 497) | NB1176-684T | 4* | 1 | V | Q | C | P | H | L | C | Y | E | L | D | D | E | P | L | C | P | D | V | C | Y | V |
| (SEQ ID NO: 498) | NB1176-684L | 4* | 1 | V | Q | C | P | H | M | C | Y | E | L | D | D | E | P | P | C | P | D | V | C | Y | V |

4* = 3x FcER, 1x hGHr, 1x FcER

IGE134 library

| | | | | | | | | | | | | | | | | | | | | | | | | |
|---|---|---|---|---|---|---|---|---|---|---|---|---|---|---|---|---|---|---|---|---|---|---|---|---|
| (SEQ ID NO: 499) | NB1177-686B | 4* | 11 | V | Q | C | P | H | F | C | Y | E | Y | G | S | E | Y | L | C | P | D | V | C | Y | V |
| (SEQ ID NO: 500) | NB1177-686H | 4* | 2 | V | Q | C | P | H | F | C | Y | E | Y | G | G | E | Y | L | C | P | D | V | C | Y | V |
| (SEQ ID NO: 501) | NB1177-686A | 4* | 1 | V | Q | C | P | H | F | C | Y | E | A | G | A | E | C | L | C | P | D | V | C | Y | V |

|  |  |  |  | Sequence |
|---|---|---|---|---|
| (SEQ ID NO: 502) | NB1177-686M | 4* | 1 | V Q C P H F C Y A L P Y E L C P D V C Y V |
| (SEQ ID NO: 503) | NB1177-686P | 4* | 1 | V Q C P H F C Y A D P Y E L C P D V C Y V |
| (SEQ ID NO: 504) | NB1177-686R | 4* | 1 | V Q C P H F C Y Q G E Y E L C P D V C Y V |
| (SEQ ID NO: 505) | NB1177-686T | 4* | 1 | V Q C P H F C Y G G D Y E L C P D V C Y V |
| (SEQ ID NO: 506) | NB1177-686E | 4* | 1 | V Q C P H F C Y E L H Y E L C P D V C Y V |
| (SEQ ID NO: 507) | NB1177-686O | 4* | 1 | V Q C P H F C Y G I S Y E L C P D V C Y V |

4* = 3x FcER, 1x hGHr, 1x FcER

LGE134 library

|  |  |  |  | Sequence |
|---|---|---|---|---|
| (SEQ ID NO: 508) | NB1178-687C | 4 | 12 | V Q C P H F C Y E L G Y K E L C P D V C Y V |
| (SEQ ID NO: 509) | NB1178-687B | 4 | 2 | V Q C P H F C Y E L G Q H E L C P D V C Y V |
| (SEQ ID NO: 510) | NB1178-687P | 4 | 1 | V Q C P H F C Y E L E G G E L C P D V C Y V |
| (SEQ ID NO: 511) | NB1178-687A | 4 | 1 | V Q C P H F C Y E L F S R E L C P D V C Y V |
| (SEQ ID NO: 512) | NB1178-687R | 4 | 1 | V Q C P H F C Y E L G D Q E L C P D V C Y V |
| (SEQ ID NO: 513) | NB1178-687E | 4 | 1 | V Q C P H F C Y E L G V A E L C P D V C Y V |
| (SEQ ID NO: 514) | NB1178-687L | 4 | 1 | V Q C P H F C Y E L G Y R E L C P D V C Y V |
| (SEQ ID NO: 515) | NB1178-687Q | 4 | 1 | V Q C P H F C Y E L M Q E E L C P D V C Y V |
| (SEQ ID NO: 516) | NB1178-687U | 4 | 1 | V Q C P H F C Y E L N P I V E L C P D V C Y V |

LGE134 library

|  |  |  |  | Sequence |
|---|---|---|---|---|
| (SEQ ID NO: 517) | NB1179-692A | 4 | 22 | V Q C P H F C Y E L D Y E L C P D V C Y V |
| (SEQ ID NO: 518) | NB1179-692W | 4 | 1 | V Q C P H F C Y E L D Y E L C P D V C D Y V |

IGE134 library

| | | | | | | | | | | | | | | | | | | | | | | | | | | |
|---|---|---|---|---|---|---|---|---|---|---|---|---|---|---|---|---|---|---|---|---|---|---|---|---|---|---|
| NB1195-700E | (SEQ ID NO: 519) | 3 | 2 | V | Q | G | C | P | H | F | C | Y | E | L | D | Y | E | L | C | P | D | K | C | Y | V | |
| NB1195-700C | (SEQ ID NO: 520) | 3 | 1 | V | Q | G | C | P | H | F | C | Y | E | L | D | Y | E | L | C | P | D | A | C | Y | V | |
| NB1195-700H | (SEQ ID NO: 521) | 3 | 1 | V | Q | G | C | P | H | F | C | Y | E | L | D | Y | E | L | C | P | D | P | C | Y | V | |
| NB1195-700D | (SEQ ID NO: 522) | 3 | 1 | V | Q | G | C | P | H | F | C | Y | E | L | D | Y | E | L | C | P | D | A | C | Y | V | |
| NB1195-700G | (SEQ ID NO: 523) | 3 | 1 | V | Q | G | C | P | H | F | C | Y | E | L | D | Y | E | L | C | P | D | R | C | Y | V | |
| NB1195-700J | (SEQ ID NO: 524) | 3 | 1 | V | Q | G | C | P | H | F | C | Y | E | L | D | Y | E | L | C | P | D | R | C | Y | V | |
| NB1195-700I | (SEQ ID NO: 525) | 3 | 1 | V | Q | G | C | P | H | F | C | Y | E | L | D | Y | E | L | C | P | D | S | C | Y | V | |

IGE134 library

| | | | | | | | | | | | | | | | | | | | | | | | | | | |
|---|---|---|---|---|---|---|---|---|---|---|---|---|---|---|---|---|---|---|---|---|---|---|---|---|---|---|
| NB1219-689H | (SEQ ID NO: 526) | 3 | 4 | V | Q | G | C | P | H | F | C | Y | E | L | D | Y | E | L | C | P | G | V | C | Y | V | |
| NB1219-689J | (SEQ ID NO: 527) | 3 | 2 | V | Q | G | C | P | H | F | C | Y | E | L | D | Y | E | L | C | P | R | V | C | Y | V | |
| NB1219-689B | (SEQ ID NO: 528) | 3 | 1 | V | Q | G | C | P | H | F | C | Y | E | L | D | Y | E | L | C | P | A | V | C | Y | V | 2.3 IGE134 |
| NB1219-689F | (SEQ ID NO: 529) | 3 | 1 | V | Q | G | C | P | H | F | C | Y | E | L | D | Y | E | L | C | P | W | V | C | Y | V | 1.7 IGE134 |

IGE134 library

| | | | | | | | | | | | | | | | | | | | | | | | | | | |
|---|---|---|---|---|---|---|---|---|---|---|---|---|---|---|---|---|---|---|---|---|---|---|---|---|---|---|
| NB1219-690B | (SEQ ID NO: 530) | 3 | 2 | V | Q | G | C | P | H | F | C | Y | E | L | D | Y | E | L | C | P | D | Y | C | Y | G | |
| NB1219-690F | (SEQ ID NO: 531) | 3 | 1 | V | Q | G | C | P | H | F | C | Y | E | L | D | Y | E | L | C | P | D | K | C | Y | A | |
| NB1219-690I | (SEQ ID NO: 532) | 3 | 1 | V | Q | G | C | P | H | F | C | Y | E | L | D | Y | E | L | C | P | D | L | C | Y | G | |
| NB1219-690K | (SEQ ID NO: 533) | 3 | 1 | V | Q | G | C | P | H | F | C | Y | E | L | D | Y | E | L | C | P | D | M | C | Y | H | |
| NB1219-690D | (SEQ ID NO: 534) | 3 | 1 | V | Q | G | C | P | H | F | C | Y | E | L | D | Y | E | L | C | P | D | B | C | Y | S | |
| NB1219-690E | (SEQ ID NO: 535) | 3 | 1 | V | Q | G | C | P | H | F | C | Y | E | L | D | Y | E | L | C | P | D | S | C | Y | G | |
| NB1219-690A | (SEQ ID NO: 536) | 3 | 1 | V | Q | G | C | P | H | F | C | Y | E | L | D | Y | E | L | C | P | D | H | C | Y | G | |
| NB1219-690H | (SEQ ID NO: 537) | 3 | 1 | V | Q | G | C | P | H | F | C | Y | E | L | D | Y | E | L | C | P | D | Y | C | Y | Q | |
| NB1219-690L | (SEQ ID NO: 538) | 3 | 1 | V | Q | G | C | P | H | F | C | Y | E | L | D | Y | E | L | C | P | D | Y | C | Y | L | |
| NB1219-690C | (SEQ ID NO: 539) | 3 | 1 | V | Q | G | C | P | H | F | C | Y | E | L | D | Y | E | L | C | P | D | V | C | Y | N | |

Linker insertion and deletion variants of IGE134

| | Name | 1 | 2 | 3 | 4 | 5 | 6 | 7 | 8 | 9 | 10 | 11 | 12 | 13 | a | b | c | d | e | 14 | 15 | 16 | 17 | 18 | 19 | 20 | 21 | Relative IC50 |
|---|---|---|---|---|---|---|---|---|---|---|---|---|---|---|---|---|---|---|---|---|---|---|---|---|---|---|---|---|
| (SEQ ID NO: 540) | IGE134 | V | Q | C | P | H | F | C | Y | E | L | D | Y | E | | | | | | L | C | P | D | V | C | Y | V | -1- |
| (SEQ ID NO: 541) | 718-1 | V | Q | C | P | H | F | C | Y | E | L | D | Y | E | T | | | | | L | C | P | D | V | C | Y | V | 1.3 |
| (SEQ ID NO: 542) | 719-12 | V | Q | C | P | H | F | C | Y | E | L | D | Y | E | R | E | T | | | L | C | P | D | V | C | Y | V | 0.88 |
| (SEQ ID NO: 543) | 718-9 | V | Q | C | P | H | F | C | Y | E | L | D | Y | E | K | E | H | | | L | C | P | D | V | C | Y | V | 0.71 |
| (SEQ ID NO: 544) | 718-3 | V | Q | C | P | H | F | C | Y | E | L | D | Y | E | R | E | G | | | L | C | P | D | V | C | Y | V | |
| (SEQ ID NO: 545) | 718-2 | V | Q | C | P | H | F | C | Y | E | L | D | Y | E | S | E | S | | | L | C | P | D | V | C | Y | V | 0.60 |
| (SEQ ID NO: 546) | 718-4 | V | Q | C | P | H | F | C | Y | E | L | D | Y | E | A | D | R | | | L | C | P | D | V | C | Y | V | 2.0 |
| (SEQ ID NO: 547) | 718-5 | V | Q | C | P | H | F | C | Y | E | L | D | Y | E | E | V | W | | | L | C | P | D | V | C | Y | V | 1.2 |
| (SEQ ID NO: 548) | 718-6 | V | Q | C | P | H | F | C | Y | E | L | D | Y | E | G | R | P | | | L | C | P | D | V | C | Y | V | 0.50 |
| (SEQ ID NO: 549) | 718-8 | V | Q | C | P | H | F | C | Y | E | L | D | Y | E | L | T | G | | | L | C | P | D | V | C | Y | V | |
| (SEQ ID NO: 550) | 718-10 | V | Q | C | P | H | F | C | Y | E | L | D | Y | E | M | L | G | | | L | C | P | D | V | C | Y | V | 1.1 |
| (SEQ ID NO: 551) | 719-11 | V | Q | C | P | H | F | C | Y | E | L | D | Y | E | M | D | G | Q | L | L | C | P | D | V | C | Y | V | 0.83 |
| (SEQ ID NO: 552) | 719-13 | V | Q | C | P | H | F | C | Y | E | L | D | Y | E | P | G | K | L | K | L | C | P | D | V | C | Y | V | 3.3 |
| (SEQ ID NO: 553) | 719-14 | V | Q | C | P | H | F | C | Y | E | L | D | Y | E | A | G | D | E | R | L | C | P | D | V | C | Y | V | 0.62 |
| (SEQ ID NO: 554) | 719-15 | V | Q | C | P | H | F | C | Y | E | L | D | Y | E | P | D | S | V | G | L | C | P | D | V | C | Y | V | |
| (SEQ ID NO: 555) | 719-16 | V | Q | C | P | H | F | C | Y | E | L | D | Y | E | V | E | D | A | P | L | C | P | D | V | C | Y | V | |

FIG._5A

Linker insertion and deletion variants of IGE134

| | | | | | | | | | | | | | | | | | | |
|---|---|---|---|---|---|---|---|---|---|---|---|---|---|---|---|---|---|---|
| (SEQ ID NO: 556) | 720-5 | V | Q | C | P | H | F | C | Y | G | A | L | E | L | C | P | D | V | C | Y | V | 1.3 |
| (SEQ ID NO: 557) | 720-6 | V | Q | C | P | H | F | C | Y | V | H | M | E | L | C | P | D | V | C | Y | V | 0.9 |
| (SEQ ID NO: 558) | 720-2 | V | Q | C | P | H | F | C | Y | L | V | M | E | L | C | P | D | V | C | Y | V | 6.3 |
| (SEQ ID NO: 559) | 720-7 | V | Q | C | P | H | F | C | Y | L | E | C | G | L | C | P | D | V | C | Y | V | 1.0 |
| (SEQ ID NO: 560) | 720-4 | V | Q | C | P | H | F | C | Y | G | C | R | L | L | C | P | D | V | C | Y | V | 1.9 |
| (SEQ ID NO: 561) | 720-1 | V | Q | C | P | H | F | C | Y | K | D | R | N | L | C | P | D | V | C | Y | V | |
| (SEQ ID NO: 562) | 720-3 | V | Q | C | P | H | F | C | Y | D | A | S | R | L | C | P | D | V | C | Y | V | 0.5 |
| (SEQ ID NO: 563) | 721-9 | V | Q | C | P | H | F | C | Y | V | E | E | L | C | P | D | V | C | Y | V | | 3.5 |
| (SEQ ID NO: 564) | 721-8 | V | Q | C | P | H | F | C | Y | M | G | E | L | C | P | D | V | C | Y | V | | 3.4 |
| (SEQ ID NO: 565) | 721-14 | V | Q | C | P | H | F | C | Y | S | G | E | L | C | P | D | V | C | Y | V | | 3.7 |
| (SEQ ID NO: 566) | 721-11 | V | Q | C | P | H | F | C | Y | F | S | E | L | C | P | D | V | C | Y | V | | 1.8 |
| (SEQ ID NO: 567) | 721-12 | V | Q | C | P | H | F | C | Y | A | E | P | L | C | P | D | V | C | Y | V | | 1.4 |
| (SEQ ID NO: 568) | 721-10 | V | Q | C | P | H | F | C | Y | V | R | P | L | C | P | D | V | C | Y | V | | 2.0 |
| (SEQ ID NO: 569) | 721-13 | V | Q | C | P | H | F | C | Y | L | T | R | L | C | P | D | V | C | Y | V | | 3.1 |

Alanine scanning of IGE134-Phage
Peptide-phage sequence

| | 1 | 2 | 3 | 4 | 5 | 6 | 7 | 8 | 9 | 10 | 11 | 12 | 13 | 14 | 15 | 16 | 17 | 18 | 19 | 20 | 21 | Relative IC50 |
|---|---|---|---|---|---|---|---|---|---|---|---|---|---|---|---|---|---|---|---|---|---|---|
| (SEQ ID NO: 570) | V | Q | C | P | H | F | C | Y | E | L | D | Y | E | L | C | P | D | V | C | Y | V | -1- |
| (SEQ ID NO: 571) | V | Q | C | P | H | F | C | Y | E | L | D | Y | E | L | C | P | D | V | C | Y | V | 0.9 |
| (SEQ ID NO: 572) | V | Q | C | P | H | F | C | A | E | L | D | Y | E | L | C | P | D | V | C | Y | V | 56.0 |
| (SEQ ID NO: 573) | V | Q | C | P | H | F | C | Y | E | L | D | A | E | L | C | P | D | V | C | A | V | 4.0 |
| (SEQ ID NO: 574) | V | Q | C | P | H | F | C | Y | E | L | D | Y | E | L | C | P | D | V | C | Y | V | 1.9 |
| (SEQ ID NO: 575) | V | Q | C | P | H | F | C | Y | E | L | D | Y | E | L | C | P | D | V | C | Y | V | 1.4 |
| (SEQ ID NO: 576) | V | Q | C | P | H | F | C | Y | E | L | D | Y | E | L | C | P | D | V | C | Y | V | 1.0 |
| (SEQ ID NO: 577) | V | Q | C | P | H | F | C | Y | E | L | D | Y | E | L | C | P | D | V | C | Y | A | 1.0 |
| (SEQ ID NO: 578) | V | Q | C | P | H | F | C | Y | E | L | D | Y | E | L | C | P | D | A | C | Y | V | 1.0 |
| (SEQ ID NO: 579) | A | Q | C | P | H | F | C | Y | A | L | D | Y | E | L | C | P | D | V | C | Y | V | 0.5 |
| (SEQ ID NO: 580) | V | A | C | P | H | A | C | Y | E | A | A | Y | E | A | C | P | A | A | C | Y | A | 13.0 |
| (SEQ ID NO: 581) | A | Q | C | P | H | F | C | Y | E | L | D | Y | E | L | C | P | D | V | C | Y | V | 2.5 |
| (SEQ ID NO: 582) | V | A | C | P | H | F | C | Y | E | L | A | Y | E | L | C | P | A | V | C | Y | V | 1.3 |
| (SEQ ID NO: 583) | V | Q | C | P | H | F | C | Y | E | L | D | Y | A | L | C | P | D | V | C | Y | V | 1.0 |
| (SEQ ID NO: 584) | V | Q | C | P | H | F | C | Y | E | L | D | A | A | L | C | P | A | V | C | Y | V | 0.8 |
| (SEQ ID NO: 585) | V | Q | C | P | H | F | C | Y | E | L | A | Y | A | L | C | P | D | V | C | Y | V | 10.0 |
| (SEQ ID NO: 586) | V | Q | C | P | H | F | C | Y | E | L | A | Y | A | L | C | P | A | V | C | Y | V | >20.0 |
| (SEQ ID NO: 587) | V | Q | C | P | H | F | C | Y | E | L | D | Y | A | L | C | P | D | V | C | Y | V | >10 |
| (SEQ ID NO: 588) | V | Q | C | A | H | F | C | Y | E | L | D | Y | E | L | C | A | D | V | C | Y | V | 2.3 |
| (SEQ ID NO: 589) | V | Q | C | P | H | F | C | Y | E | L | D | Y | E | L | C | P | D | V | C | Y | V | >80 |
| (SEQ ID NO: 590) | V | Q | C | P | H | F | C | Y | E | L | D | Y | E | L | C | P | D | V | C | Y | V | NDB |
| (SEQ ID NO: 591) | V | Q | C | P | H | F | C | Y | E | L | D | Y | E | L | C | P | D | V | C | Y | V | NDB |
| (SEQ ID NO: 592) | V | Q | C | P | H | F | C | Y | E | L | D | Y | E | L | C | P | D | V | C | Y | V | |
| (SEQ ID NO: 593) | V | Q | A | P | H | F | A | Y | E | L | D | Y | E | L | A | P | D | V | A | Y | V | NDB |
| (SEQ ID NO: 594) | V | Q | C | P | H | F | C | Y | E | L | D | Y | E | L | C | P | D | V | C | Y | V | NDB |
| (SEQ ID NO: 595) | V | Q | C | P | H | F | C | Y | E | L | D | Y | E | L | C | P | D | V | C | Y | A | |

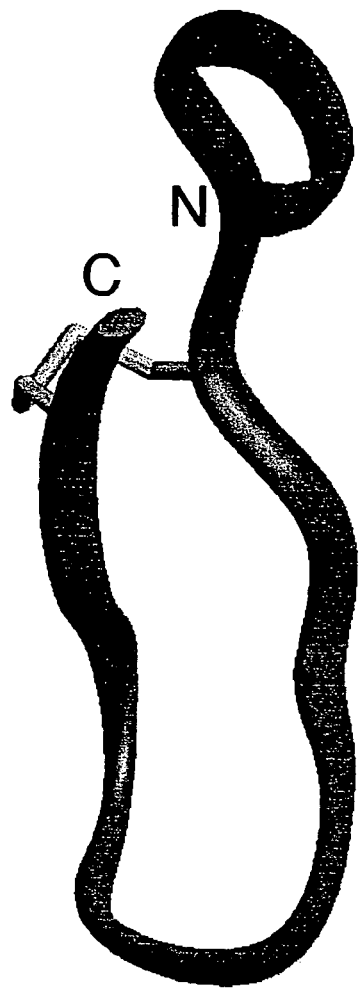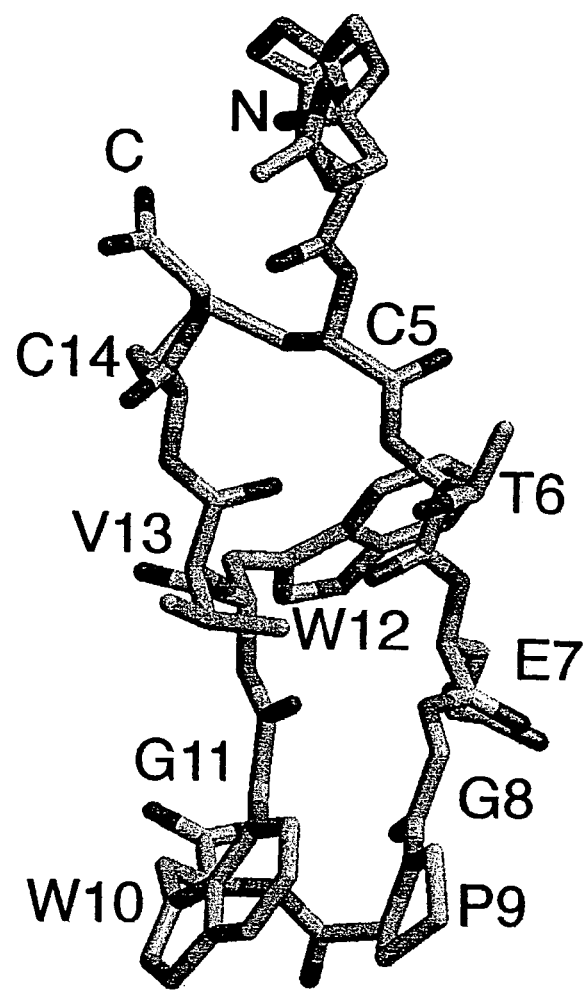
FIG._7A    FIG._7B

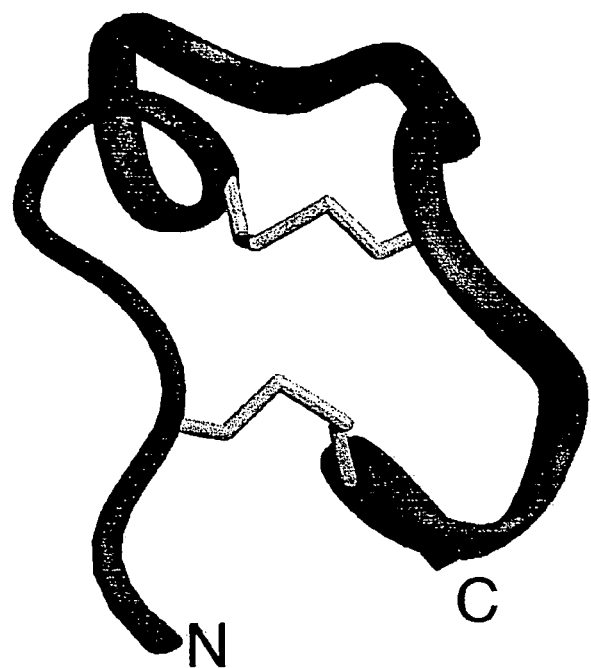
FIG._8A
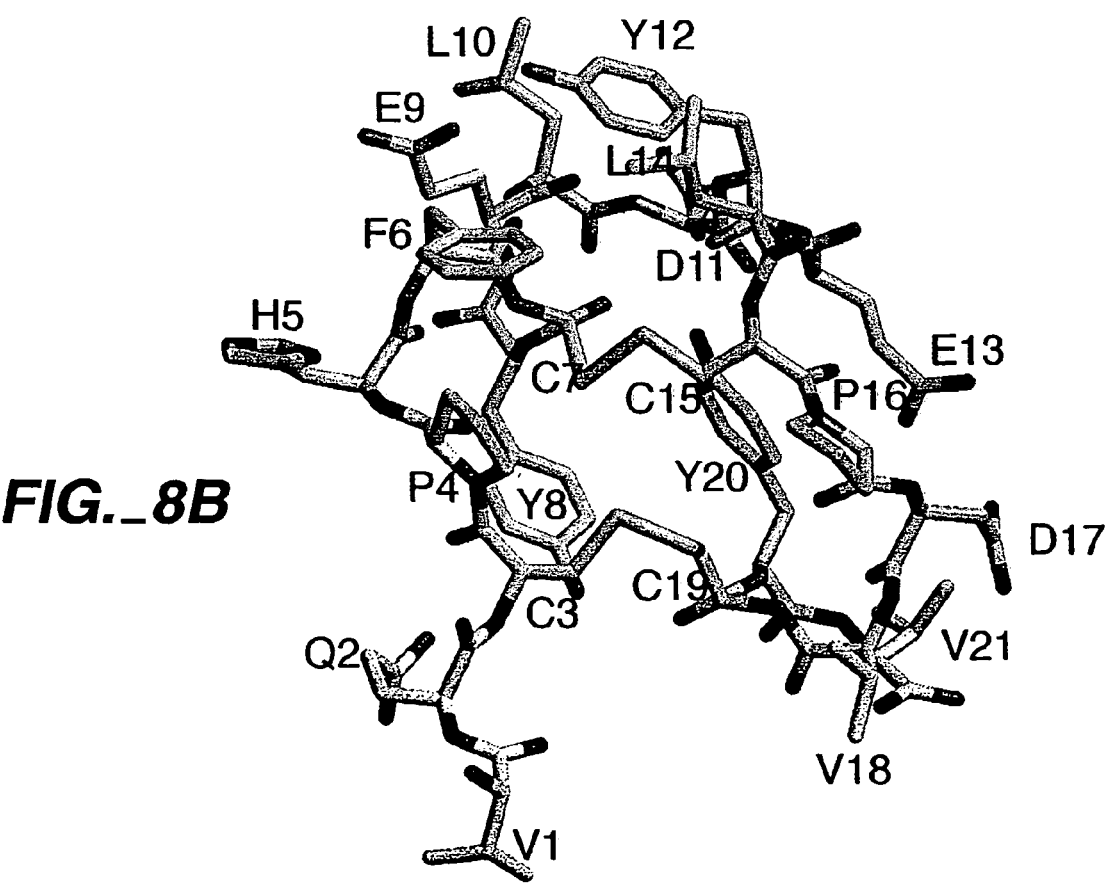
FIG._8B

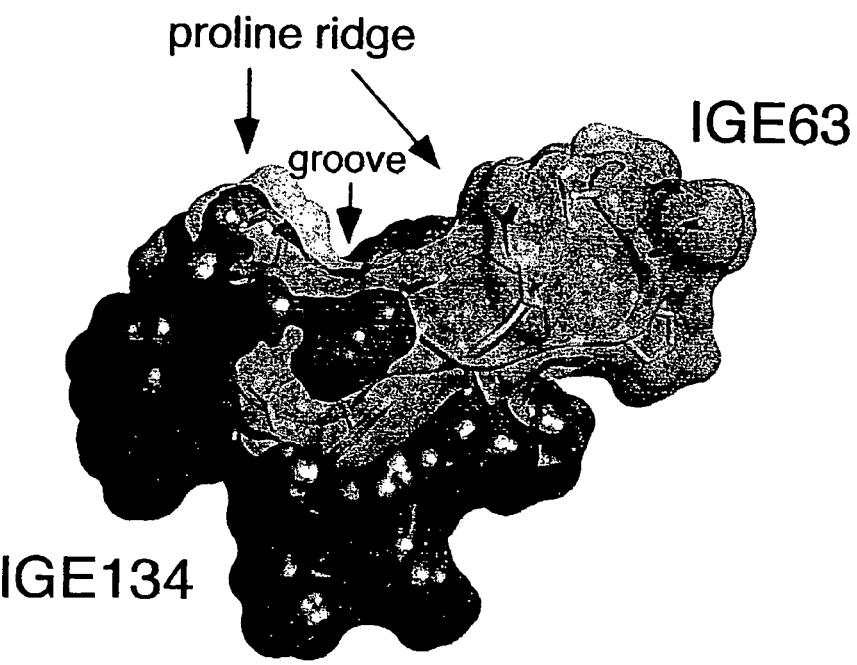
FIG._9A
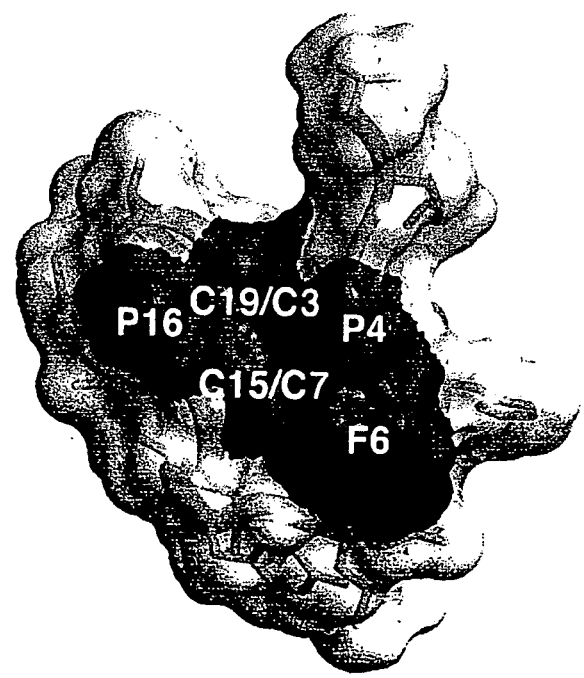
FIG._9B

IGE RECEPTOR ANTAGONISTS

FIELD OF THE INVENTION

This invention relates to novel compounds which bind to the high affinity receptor for immunoglobulin E (IgE) designated FcεRI and methods for identifying and preparing such compounds. In particular aspects, the invention relates to the treatment of disorders mediated by IgE utilizing the novel compounds of the invention. The invention also relates to compositions, such as pharmaceutical compositions, comprising the novel compounds, as well as their use in research, diagnostic, therapeutic, and prophylactic methods for the treatment of IgE-mediated disorders.

BACKGROUND OF THE INVENTION

IgE plays a central role in allergic disorders. IgE high affinity receptors (FcεRI) are located on mast cells and basophils, which serve as antigenic targets stimulating the further release of inflammatory mediators producing many of the manifestations of allergic disease.

IgE-mediated inflammation occurs when antigen binds to the IgE antibodies that occupy the FcεRI receptor on mast cells. Within minutes, this binding causes the mast cell to degranulate releasing certain preformed mediators. Subsequently, the degranulated cell begins to synthesize and release additional mediators de novo. The result is a two-phase response: an initial immediate effect on blood vessels, smooth muscle, and glandular secretion (immediate hypersensitivity), followed up a few hours later by cellular infiltration of the involved site.

IgE antibodies bind to mast cells via the numerous high-affinity Fc receptors on the surface of each cell. The binding is noncovalent and reversible, so that bound antibodies are in constant equilibrium with the pool of circulating IgE. As a result, each mast cell can bind many different antigens. A response is initiated when a multivalent antigen binds two or more IgE antibodies occupying FcεRI receptors. The cross-linking transmits a signal that activates the mast cell, resulting in activation of protein tyrosine kinases and increasing the intracellular free calcium levels. Soon after, cytoplasmic granules fuse with one another and with the surface membrane, discharging their contents to the exterior. Basophils also express FcεRI receptors, but their effect on immediate hypersensitivity reactions is unknown.

This immediate phase of the inflammatory response results mainly from preformed mediators (especially histamine) that are stored in mast cell granules, as well as certain rapidly synthesized arachidonate derivatives. Maximal intensity of the response results after about 15 minutes after the initial antigen contact. Characteristics of this phase are erythema, localized edema in the form of a wheal and pruritus (itching). However, the granule contents also induce local expression of the vascular addressin VCAM-1 (Vascular Cell Adhesion Molecule) which assists in vascular permeability. Additional mast cell granule contents include RANTES and other chemokines, which are molecules having chemoattractant activity for leukocytes and fibroblasts, ultimately resulting in inflammation of the site.

Manifestations of the late phase are due in part to presynthesized TNF-α and in part to other mediators (e.g., PAF, IL-4 and arachidonate metabolites), the synthesis of which begins after mast cell degranulation. The effects of these mediators becomes apparent about six hours after antigen contact and are marked by an infiltrate of eosinophils and neutrophils. Clinical features of the late phase include erythema, induration, warmth, pruritus, and a burning sensation at the affected site. Mast cell-derived IL-4 promotes the production of $T_H2$ cells. TNF-α not only functions in the short term as a leukocyte chemoattractant, but can also stimulate local angiogenesis, fibroblast proliferation, and scar formation during prolonged hypersensitivity reactions.

IgE-mediated inflammation is the mechanism underlying atopic allergy (such as hay fever, asthma and atopic dermatitis), systemic anaphylactic reactions and allergic urticaria (hives). It may normally play a role as a first line of immunologic defense, since it causes rapid vasodilation, facilitating entry of circulating soluble factors and cells to the site of antigen contact. Many of the most destructive attributes of allergic disease are due to the actions of the chemoattracted leukocytes, rather than from the mast cells themselves.

The use of bacteriophage particles for display of diverse peptide libraries (phage display) has been described (Lowman, (1997) *Ann. Rev. Biophys. Biomol. Struct.* 26:401–424). Phage display technology provides a means for generating both structurally constrained and unconstrained peptide libraries (Devin et al., (1990) *Science* 249:404–406; Cwirla et al., (1990) *Proc. Natl. Acad. Sci. USA* 87:6378–6382; Lowman and Wells (1991) *Methods: Comp. to Methods Enzymol.* 3:205–216; Lowman (1997) *Ann. Rev. Biophys. Biomol. Struct.* 26:401–424). These libraries can be used in the identification and selection of peptide ligands that bind a predetermined target molecule (Lowman (1997), supra); Clackson and Wells (1994) *Trends Biotechnol.* 12:173–184; Devlin et al., (1990) supra). Phage display has been used to identify peptide motifs that home to a cellular target (Arap et al., (1998) *Science* 279:377–380); bind the human type I interleukin 1 (IL-1) receptor and block the binding of IL-1 (Yanofsky et al., (1996) *Proc. Natl. Acad. Sci. USA,* 93:7381–7386); bind to and activate the receptor for the cytokine erythropoietin (EPO)(Wrighton et al., (1996) *Science* 273:458–463); bind the human thrombopoietin receptor and compete with the binding of the natural ligand thrombopoietin (TPO)(Cwirla et al., (1997) *Science,* 276:1696–1699), bind and inhibit Factor VIIa (Dennis et al. (2000) *Nature* 404:465) or to generate affinity improved or matured peptide ligands from native protein binding ligands (Lowman et al., (1991) *Biochemistry* 30: 10832–10838).

Using structurally constrained peptide libraries generated by monovalent phage display, 14 amino acid peptides that bind to insulin-like growth factor 1 binding proteins (IG-FBPs) have been isolated (Lowman et al., (1998) *Biochemistry,* 37:8870–8878). The peptides contain a helix structure and bind IGFBPs in vitro liberating insulin like growth factor-a (IGF-1) activity (Lowman et al., (1998) supra). Utilizing in vivo phage selection, the technique has been used to identify and isolate peptides capable of mediating selective localization to various organs such as brain and kidney (Pasqualini and Ruoslohti (1996) *Nature* 380:364–366) as well as to identify peptides that home to particular tumor types bearing αvβ3 or αvβ5 integrins (Arap et al., (1998) *Science* 279:377–380). U.S. Pat. No. 5,627,263 describes peptides that are recognized by and selectively bind the α5β1 integrin. Examples of affinity or specificity improved proteins include human growth hormone, zinc fingers, protease inhibitors, ANP, and antibodies (Wells, J. and Lowman H. (1992) *Curr. Opin. Struct. Biol.* 2:597–604; Clackson, T. and Wells, J. (1994) *Trends Biotechnol.* 12:173–184; Lowman et al., (1991) *Biochemistry* 30(10): 832–838; Lowman et al. and Wells J. (1993) *J. Mol. Biol.*

234:564–578; Dennis M. and Lazarus R. (1994) *J Biol. Chem.* 269(22):22137–22144.

The allergic response, when mediated by immunoglobulins of the E classification (IgE), is associated with disease states such as asthma and allergic rhinitis. The interaction between IgE and its high affinity receptor is a key step this allergic response. IgE immunoglobulins, specific for particular allergens, bind through their Fc region to specific high affinity receptors, FcεRI, on mast cells, basophils, and other cells (Ishizaka et al., (1970) *Immunochemistry* 7:687–702; Metzger et al., (1986) *Ann. Rev. Immunol.* 4:419–470; Kinet (1999) *Ann. Rev. Immunol.* 17:931–972). Antigen crosslinking of IgE bound FcεRI initiates an allergic cascade that results in mast cell degranulation and release of mediators of the allergic response such as histamine, leukotrienes and prostaglandins. Release of these mediators in turn leads to increased vascular permeability and the infiltration of platelets, eosinophils and neutrophils into surrounding tissue.

The FcεRI is present on cells as either a trimeric αγ2 or tetrameric αβ2 structure with the extracellular domains of the a chain conferring high affinity IgE binding. The crystal structure of the α chain has recently been solved (Garman S. C., et al. (1998) *Cell* 95:951–961). Mutagenesis studies have been performed to identify residues which contribute to IgE-Fc/FcεRI complex formation (Nissim et al., (1991) *EMBO J.* 10:101–107). Reports of the crystal structure of a complex of human FcεRI with bound IgE-Fc suggest two distinct binding sites for IgE-Fc in the IgE-Fc/FcεRI structure (Garman et al., (2000) *Nature* 406:259–266).

The binding of antibodies to the Fc portion of IgE can inhibit binding of IgE to receptor (Presta et al., (1993) *J. Immunol.* 151:2623–2632; Kolbinger et al., (1993) *Protein Engineering* 6:971–980) and can reduce free IgE levels in vivo (Saini et al., (1999) *J. Immunol.* 162:5624–5630). It has also been reported that certain peptides, designed to mimic a portion of the FcεRI receptor, can bind to the Fc portion of IgE and inhibit IgE binding to receptor (McDonnell et al., *Nature Struct. Biol.* 3:419425; McDonnell et al., (1997) *Biochem. Soc. Trans.* 25:387–392).

Presta et al. (1993) *J. Immunol.* 151:2623–2632 disclose a humanized anti-IgE antibody that prevents the binding of free IgE to FcεRI but does not bind to FcεRI-bound IgE. Clinical studies of allergic individuals using an anti-IgE monoclonal antibody have been reported (Jardieu and Fick (1999) *Intl. Arch. Allergy Immunol.* 118:112–115).

As a result, molecules which block the binding of IgE to FcεRI, the IgE high affinity receptor would also be expected to have efficacy in the treatment of IgE-mediated disorders.

SUMMARY OF THE INVENTION

The present invention provides compounds and compositions which block or prevent the association of immunoglobulin E (IgE) to the IgE high affinity receptor for IgE (FcεRI). In a particular aspect, the compounds of the invention block, prevent or attenuate the IgE mediated activation of the FcεRI. Therefore, particular embodiments of the present invention are useful in therapeutic and prophylactic methods for inhibiting IgE mediated or associated processes such as the IgE-dependent activation and degranulation of mast cells and basophils as well as the consequent release of inflammatory mediators such as histamine. Advantageously, the compositions allow for a potent inhibition of IgE mediated activation of FcεRI providing, in preferred embodiments, for low dose pharmaceutical formulations.

The compounds of the present invention bind FcεRI and block or prevent the binding of IgE. Preferred compounds are peptides or peptide derivatives such as peptide mimetics which bind FcεRI with a Kd less than about 100 μM, alternatively less than about 100 nM, alternatively less than 1 nm. Specific examples of such compounds include linear or cyclic peptides and combinations thereof, preferably between about 10 and 100 amino acid residues in length, optionally modified at the N-terminus or C-terminus or both, as well as salts, derivatives, and functional analogues thereof and pharmaceutically-acceptable compositions thereof.

In a particular embodiment, compounds according to the present invention are peptides or mimetics thereof having or derived from the general Formula I or which compete with a compound of general Formula I for binding FcεRI:

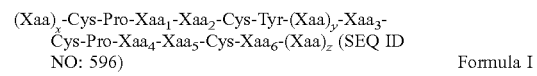

Formula I wherein Xaa is an amino acid and x, y and z are whole numbers greater or equal to 0, and x is generally less than 50, alternatively less than 20, alternatively less than 10, alternatively 0, 1 or 2; y is generally any integer between 3 and 10, inclusive, and z is generally an integer less than 50, alternatively less than 20, alternatively less than 10, alternatively 0, 1 or 3.

In an alternative embodiment, compound according to the present invention are peptide or mimetics thereof having or derived from the general Formula XI or which compete with a compound of general Formula XI for binding FcεRI:

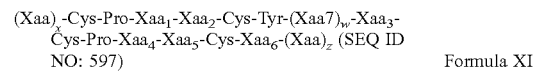

Formula XI wherein $Xaa_{1-6}$ are natural amino acids, Xaa7 is a non-natural amino acid and x, y and z are whole numbers greater than or equal to 0, and x is generally less than 50, alternatively less than 20, alternatively less than 10, alternatively 0, 1 or 2; w is generally 1, 10 or any integer therebetween, and z is generally an integer less than 50, alternatively less than 20, alternatively 10, alternatively 0, 1 or 3.

Further examples of compounds according to the present inventions are isolated based on the general formula IX:

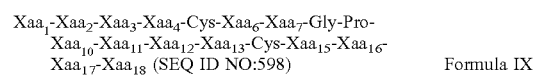

Formula IX

The present invention provides compounds, including peptides, peptide mimetics and the like, having general Formula I or which compete with compounds of general Formula I for binding FcεRI.

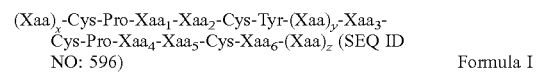

Formula I

Preferred are peptide compounds of general Formula I wherein Xaa is an amino acid and x is a whole number greater or equal to 0 (zero), generally less than 50, alternatively less than 20, alternatively less than 10, alternatively 0, 1 or 2; y is alternatively between 3 and 10, alternatively 3, 4 or 5 and z is a whole number greater or equal to zero, generally less than 50, alternatively less than 20, alternatively less than 10, alternatively 0, 1 or 3. For example, when x and z are 0, the invention provides for compounds having the general Formula II.

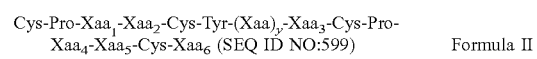

Formula II

Peptide compounds of general Formulas I and II contain an amino acid domain designated (Xaa)$_y$ in the formula of between 3 and 10 amino acid residues. Particular peptide compounds contain an amino acid domain (Xaa)$_y$ wherein y is 3, 4, 5, 8, or 10, alternatively 3, 4 or 5, alternatively 5. For example, in the context of peptide compounds of general Formula I, the invention provides peptide compounds having any one of the following general formulas:

(Xaa)$_x$-Cys-Pro-Xaa$_1$-Xaa$_2$-Cys-Tyr-Xaa$_a$-Xaa$_b$-Xaa$_c$-Xaa$_3$-Cys-Pro-Xaa$_4$-Xaa$_5$-Cys-Xaa$_6$-(Xaa)$_z$
(SEQ ID NO:600)  Formula III (Xaa)$_x$-Cys-Pro-Xaa$_1$-Xaa$_2$-Cys-Tyr-Xaa$_a$-Xaa$_b$-Xaa$_c$-Xaa$_d$-Xaa$_3$-Cys-Pro-Xaa$_4$-Xaa$_5$-Cys-Xaa$_6$-(Xaa)$_z$
(SEQ ID NO:601)  Formula IV (Xaa)$_x$-Cys-Pro-Xaa$_1$-Xaa$_2$-Cys-Tyr-Xaa$_a$-Xaa$_b$-Xaa$_c$-Xaa$_d$-Xaa$_e$-Xaa$_3$-Cys-Pro-Xaa$_4$-Xaa$_5$-Cys-Xaa$_6$-(Xaa)$_z$ (SEQ ID NO:602)  Formula V For compounds of general Formulas I through V, Xaa$_6$ is Tyr, providing for compounds of the general Formula VI:

(Xaa)$_x$-Cys-Pro-Xaa$_1$-Xaa$_2$-Cys-Tyr-(Xaa)$_y$-Xaa$_3$-Cys-Pro-Xaa$_4$-Xaa$_5$-Cys-Tyr-(Xaa)$_z$ (SEQ ID NO:603)  Formula VI wherein x is 0, 1 or 2, y is 3, 4 or 5, alternatively 5 and z is 0, 1 or 3.

According to certain embodiments, Xaa$_4$ is Asp, providing compounds of general Formula VII:

(Xaa)$_x$-Cys-Pro-Xaa$_1$-Xaa$_2$-Cys-Tyr-(Xaa)$_y$-Xaa$_3$-Cys-Pro-Asp-Xaa$_5$-Cys-Tyr-(Xaa)$_z$ (SEQ ID NO:604)  Formula VII wherein x is 0, 1 or 2, y is 3, 4 or 5, alternatively 5 and z is 0, 1 or 2.

According to certain embodiments Xaa$_2$ and Xaa$_3$ are large hydrophobic amino acids providing for compounds of the general Formula VIII:

(Xaa)$_x$-Cys-Pro-Xaa$_1$-LHR-Cys-Tyr-(Xaa)$_y$-LHR-Cys-Pro-Xaa$_4$-Xaa$_5$-Cys-Tyr-(Xaa)$_z$ (SEQ ID NO:605)  Formula VIII wherein LHR is a large hydrophobic amino acid, e.g., Phe or Leu, Xaa$_4$ is Asp and wherein x is 0, 1 or 2, y is 3, 4 or 5, alternatively 5 and z is 0, 1 or 3.

Further preferred compounds of the invention include compounds of general Formula IX:

Xaa$_1$-Xaa$_2$-Xaa$_3$-Xaa$_4$-Cys-Xaa$_6$-Xaa$_7$-Gly-Pro-Xaa$_{10}$-Xaa$_{11}$-Xaa$_{12}$-Xaa$_{13}$-Cys-Xaa$_{15}$-Xaa$_{16}$-Xaa$_{17}$-Xaa$_{18}$ (SEQ ID NO:598)  Formula IX Particular compounds of this group are peptide compounds such as those described in detail in Example sections 1–6, especially those described in Table 5. Examples include the peptides of Formula IX where Xaa$_{10}$ is Trp, Xaa$_{11}$ is Gly and Xaa$_{12}$ is Trp:

Xaa$_1$-Xaa$_2$-Xaa$_3$-Xaa$_4$-Cys-Xaa$_6$-Xaa$_7$-Gly-Pro-Trp-Gly-Trp-Xaa$_{13}$-Cys-Xaa$_{15}$-Xaa$_{16}$-Xaa$_{17}$-Xaa$_{18}$
(SEQ ID NO:606)  Formula X According to this aspect of the invention, peptides of the general Formulas IX and XI having N and C-terminal deletions are also preferred, for example, compounds of general Formula IX and X where Xaa$_1$ is optionally absent are preferred compounds within the context of the invention. As well, deletion of one to three amino acids from C-terminal end of the peptide results in preferred compounds of the invention.

In an alternative embodiment, compounds according to the present invention are peptide or mimetics thereof having or derived from the general Formula XI or which compete with a compound of general Formula XI for binding FcεRI:

(Xaa)$_x$-Cys-Pro-Xaa$_1$-Xaa$_2$-Cys-Tyr-(Xaa7)$_w$-Xaa$_3$-Cys-Pro-Xaa$_4$-Xaa$_5$-Cys-Xaa$_6$-(Xaa)$_z$ (SEQ ID NO:597)  Formula XI wherein Xaa$_{1-6}$ are natural amino acids, Xaa7 is a non-natural amino acid and x, y and z are whole numbers greater than or equal to 0, and x is generally less than 50, alternatively less than 20, alternatively less than 10, alternatively 0, 1 or 2; w is generally 1, 10 or any integer therebetween, and z is generally an integer less than 50, alternatively less than 20, alternatively 10, alternatively 0, 1 or 3.

In a particular aspect, the invention provides for the peptides of the invention which are dimerized or cyclized. The dimer or multimer can be between two like or dissimilar peptides, and the peptide components can be joined in either a parallel or anti-parallel manner.

The invention provides a method of inhibiting the binding of IgE to the high affinity IgE receptor (FcεRI) comprising the step of:

a) contacting the FcεRI with a composition comprising a compound of the invention, optionally in the presence of IgE, under conditions which allow binding of the compound to FcεRI to occur; and b) determining the amount of IgE binding to FcεRI in the presence and absence of a compound of the invention, wherein a reduction of IgE binding in the presence of the compound relative to its absence is indicative of inhibition.

The invention further provides a method for identifying a compound which blocks IgE mediated activation of FcεRI comprising the steps of:

(a) contacting a candidate compound with FcεRI in the presence and absence of a peptide compound of the invention under conditions which allow specific binding of the peptide compound of the invention to FcεRI to occur;

(b) detecting the amount of specific binding of the peptide compound of the invention to FcεRI that occurs in the presence and absence of the candidate compound, wherein a decrease in the amount of binding of the peptide compound in the presence of the candidate compound relative to the amount of binding in the absence of the candidate compound is indicative of the ability of the candidate compound to block IgE mediated activation of FcεRI.

In a further aspect, the invention provides a 3 dimensional solution structure of the peptides of the invention. A preferred 3 dimensional solution structure is provided by the NMR data provided herein. A further aspect provides a crystal formed by the complex of IGE134 (SEQ ID NOS: 155, 171) bound to FcεRI that diffracts x-ray radiation to produce a diffraction pattern representing the three-dimensional structure of the protein peptide complex. The invention also provides a composition comprising the above crystal.

The invention also provides a method of crystallizing FcεRI comprising the steps of:

(a) mixing an aqueous solution comprising FcεRI and a peptide of the invention with a reservoir solution comprising a precipitant to form a mixed volume; and (b) crystallizing the mixed volume.

The invention also provides crystalline FcεRI/peptide complex produced by the above method.

Additionally, the invention provides a method for determining a three-dimensional structure of FcεRI in complex with a peptide of the invention comprising:

(a) crystallizing the FcεRI/peptide complex;

(b) irradiating the crystalline FcεRI peptide complex to obtain a diffraction pattern characteristic of the crystalline FcεRI/peptide complex; and (c) transforming the diffraction pattern into the three-dimensional structure of the FcεRI/peptide complex.

Further, the invention provides a machine-readable data storage medium comprising a data storage material encoded with machine-readable data that, when read by an appropriate machine, displays a three-dimensional representation of a crystal of a molecular complex comprising FcεRI and a peptide of the invention. In further aspects, the invention provides, an FcεRI/peptide crystal with the structural coordinates shown in Appendix 1.

Additionally, the invention provides a method of using a three-dimensional structure of a peptide and/or complex of a peptide and FcεRI wherein the three-dimensional structure of FcεRI includes an FcεRI peptide binding region, the method comprising identifying compounds having structures that interact with the peptide binding region of the three-dimensional structure of FcεRI and function as an FcεRI agonist or antagonist. Preferably in such method the three-dimensional structure of FcεRI includes alpha-carbon coordinates substantially the same as those of the structural information presented in Appendix 1.

In another aspect, the invention provides a method of identifying FcεRI agonists or antagonists comprising the steps of:

(a) crystallizing FcεRI/peptide complex to form an FcεRI/peptide complex crystal, the FcεRI containing a group of amino acid residues defining a peptide binding region;

(b) irradiating the FcεRI/peptide complex crystals, from step (a) to obtain a diffraction pattern of the FcεRI/peptide complex crystals;

(c) determining the three-dimensional structure of FcεRI/peptide complex from the diffraction pattern, the structure including a peptide binding region; and (d) identifying an FcεRI agonist or antagonist compound, or chemical entity, having a three-dimensional structure that functionally duplicates essential FcεRI binding residues presenting the three-dimensional structure of the peptide residues that make contact with FcεRI.

According to certain further aspects, the invention includes a method of designing a compound or chemical entity, such as a peptidomimetic, that mimics the 3-dimensional surface structure of IgE 134 (SEQ ID NOS:155, 171) or other peptide of the invention comprising the steps of:

(a) determining the 3-dimensional structure of the FcεRI/peptide complex;

(b) determining the 3-dimensional structure of a peptide of the invention; and (c) designing a compound or chemical entity that mimics the 3-dimensional surface structure of the region of the peptide that makes contact with the FcεRI.

According to a further embodiment, the invention provides a method for identifying a peptidomimetic that binds FcεRI and blocks binding of an IgE comprising the steps of:

(a) searching a molecular structure database with the structural parameters or structural coordinates provided in Appendix 1; and (b) selecting a molecule from the database that mimics the structural parameters or structural coordinates of the peptide.

The invention also provides a method for determining at least a portion of a three-dimensional structure of a molecular complex, said complex comprising FcεRI and peptide and said method comprising the steps of:

(a) crystallizing a complex (b) collecting diffraction data (c) calculating an electron density map, using phases from any suitable source (d) identifying at least a portion of the complex based on said electron density.

The invention also provides a chemical entity identified by the above method wherein it can interfere with the in vivo or in vitro association between IgE and its receptor or can associate with a binding site on FcεRI.

In particular aspects, the invention is directed to combinations of the compounds with other compounds of the invention or with other proteins, especially serum proteins or peptides. The combinations are prepared with various objectives in mind, including; increasing the affinity or avidity of the peptide compound for FcεRI, as for example, by the use of various multimerization domains as described herein; increasing the stability of the peptide compound or facilitating its recovery and purification, as for example, by expressing the peptide compound as a Z protein fusion; and improving the therapeutic efficacy of the peptide compound in aspects of the invention involving in vivo use of the peptide compound, by for example, increasing or decreasing the serum half life, by for example, fusing the peptide compound to a plasma protein such as serum albumin, an immunoglobulin, apolipoproteins or transferrin such fusion being made conveniently in recombinant host cells or by the use of bifunctional crosslinking agents.

The invention includes compositions, including pharmaceutical compositions, comprising compounds such as peptides for the treatment of an IgE mediated disease or disorder as well as kits and articles of manufacture. Kits and articles of manufacture preferably include:

(a) a container;

(b) an instruction on or associated with said container; and (c) a composition comprising a compound of the present invention contained within said container; wherein the composition is effective for treating an IgE mediated disorder. Preferably, the label on said container indicates that the composition can be used for treating an IgE mediated disorders. The kits optionally include accessory components such as a second container comprising pharmaceutically-acceptable excipients and instructions for using the composition to treat a disorder.

Also disclosed are methods useful in the treatment of allergic reactions or responses, especially those characterized by the involvement of IgE or the FcεRI complex. Therefore, the invention provides a method of treating an IgE mediated disease or disorder in a host in need thereof comprising administering to the host a therapeutically effective amount of a compound of the invention. The methods are useful in preventing, blocking or inhibiting a IgE associated activation event. In preferred embodiments, the methods of the present invention are employed to reduce or prevent the severity of or the degree of tissue injury associated with allergic response.

The present invention further provides various dosage forms of the compounds of the present invention, including but not limited to, those suitable for parenteral, oral, rectal and pulmonary administration of a compound. In preferred aspects of the present invention a therapeutic dosage form is provided suitable for inhalation and the invention provides for the therapeutic treatment of diseases or disorders involving a IgE mediated or associated process or event, such as the activation of FcεRI, via pulmonary administration of a compound of the invention. More particularly, the invention is directed to pulmonary administration of the compounds of the invention, especially the peptide compounds, by inhalation. Thus, the present invention provides an aerosol formulation comprising an amount of a compound of the invention, more particularly a peptide compound of the invention, effective to block or prevent a IgE mediated or associated process or event and a dispersant. In one embodiment, the compound of the invention, particularly the peptide compound of the invention, can be provided in a liquid aerosol formulation. Alternatively, the compound can be provided as a dry powder aerosol formulation. Therefore, according to the present invention, formulations are provided which provide an effective noninvasive alternative to other parenteral routes of administration of the compounds of the present invention for the treatment of IgE mediated or associated events.

In yet another embodiment, the invention provides for the method of treating an IgE-mediated disorder in a patient suffering therefrom, comprising the administration to the patient of a composition comprising a therapeutically-effective amount of a compound of the invention. In a specific aspect, the IgE-mediated disorder is selected from the groups consisting of allergic rhinitis, asthma (e.g., allergic asthma), atopic dermatitis, urticaria-angioedema, parasitic infection, IgE myeloma, IgE-mediated gastrointestinal inflammatory disease and graft-versus-host reaction. In another specific aspect, the method of administration can be an injection or infusion via subcutaneous, intravenous, intraperitoneal, intramuscular, intraarterial, intralesional or intraarticular routes, by topical adminstration or by a sustained-release means.

BRIEF DESCRIPTION OF THE DRAWINGS

FIG. 1. Clones selected for binding FcεRI from libraries of IGE083-Phage. Underlined residues were randomized. R, the round number, indicates how many cycles of binding selection were used. N, the number of clones, represents the numbers of clones identified with the same amino acid sequence. Relative binding affinities ($IC_{50}/IC_{50}(wt)$) were measured in comparison to the wild-type (wt) control indicated.

FIG. 2. Clones selected for binding FcεRI from libraries of IGE120- and IGE122-Phage. Underlined residues were randomized. R, the round number, indicates how many cycles of binding selection were used. N, the number of clones, represents the numbers of clones identified with the same amino acid sequence. Relative binding affinities ($IC_{50}/IC_{50}(wt)$) were measured in comparison to the wild-type (wt) control indicated.

FIG. 3. Affinity of IGE120 (SEQ ID NOS:131, 159), IGE122 (SEQ ID NOS:132, 161) and IGE134 (SEQ ID NOS:155, 171). Relative affinities were measured in a competitive phage ELISA assay (Lowman, (1998) supra).

FIG. 4. Clones selected for binding FcεRI from libraries of IGE134-Phage. Underlined residues were randomized. R, the round number, indicates how many cycles of binding selection were used. N, the number of clones, represents the numbers of clones identified with the same amino acid sequence. Relative binding affinities ($IC_{50}/IC_{50}(wt)$) were measured in comparison to the wild-type (wt) control indicated.

FIG. 5. A set of monovalently displayed IGE134 peptide-phage libraries were constructed with variable lengths of the "linker region" [residues ELDYE (SEQ ID NO:154)] to test for improved affinity and for the peptide's ability to accommodate alternative sequences. Insertions of 3 or 5 random residues were designed to follow the ELDYE (SEQ ID NO:154) sequence in 2 libraries, HL718 and HL719. Shorter linker regions were constructed by substituting 3 or 4 random residues for the ELDYE (SEQ ID NO:154) sequence in libraries HL720 and HL721. Clones were shown from round 3 of selection.

FIG. 6. Alanine scanning of IGE134-Phage. Relative affinities were measured in a competitive phage ELISA assay.

FIGS. 7A and 7B. Three-dimensional structure of IGE063 (SEQ ID NO:49). One representative member of the ensemble of 20 structures that was calculated based on NMR-derived distance and dihedral angle restraints is shown. A. Ribbon diagram showing the backbone fold. B. All heavy atoms of IGE063 (SEQ ID NO:49), with the exception of those from the side chains of residues 1–4 and 15 which are not shown for clarity. IGE063 (SEQ ID NO:49) adopts a stable beta-hairpin conformation with a type-I turn; the N-terminal four residues are disordered in solution.

FIGS. 8A and 8B. Three-dimensional structure of IGE134 (SEQ ID NOS:155, 171). One representative member of the ensemble of 20 structures that was calculated based on NMR-derived distance and dihedral angle restraints is shown. A. Ribbon diagram showing the backbone fold. B. All heavy atoms of IGE134 (SEQ ID NOS:155, 171). IGE134 (SEQ ID NOS:155, 171) adopts a helical "zeta" conformation with the two disulfide bonds and tyrosine rings forming the core of the structure. The backbone conformation of residues at the N-terminus (Val 1, Gln2) and in the linker (Leu10, Asp11, Tyr12) are less well-defined by the NMR data than the rest of the molecule and are presumably more flexible in solution.

FIGS. 9A and 9B. A. Overlay of the structures of IGE063 (SEQ ID NO:49) (light grey) and IGE134 (SEQ ID NOS: 155, 171)(dark). Despite the vastly different secondary structures of the hairpin and knot peptide classes, an overlay of the three-dimensional surface structures reveals a potentially common mode of binding to FcεRI. In both cases there is a hydrophobic groove bordered by two hydrophobic and/or proline-containing ridges. Pro16 of IGE134 (SEQ ID NOS:155, 171) was optimally aligned on Pro9 of IGE063 (SEQ ID NO:49) such that the hydrophobic ridge defined by Pro4 and Phe6 of IGE134 (SEQ ID NOS:155, 171) superpose roughly on Val13 and Thr6 of IGE063 (SEQ ID NO:49), respectively, to reveal the common surface characteristics. B. Surface representation of IGE134 (SEQ ID NOS:155, 171). This view represents a 90° rotation from that shown in A such that the viewer is looking down on the proline face of the knot peptide. The solvent accessible surface of the side chains for residues Cys3, Pro4, Phe6, Cys7, Cys15, Pro16, and Cys19 is shown in dark grey and encompasses the essential structural and functional elements for high affinity FcεRI binding.

DETAILED DESCRIPTION OF THE PREFERRED EMBODIMENTS

I. Definitions

Terms used in the claims and specification have the conventional definition as is understood by one of ordinary skill in the art. Other terms are defined as set forth below unless otherwise specified.

As used herein, the term "aerosol" refers to suspension in the air. In particular, aerosol refers to the particlization of a formulation of the invention and its suspension in the air. According to the present invention, an aerosol formulation is a formulation comprising a compound of the present invention that is suitable for aerosolization, i.e., particlization and suspension in the air, for inhalation or pulmonary administration.

The expressions "agent" and "compound" are used within the scope of the present invention interchangeably and are meant to include any molecule or substance which blocks or prevents the interaction between FcεRI and a peptide compound of the present invention. Such molecules include small organic and bioorganic molecules, e.g. peptide mimetics and peptide analogs, antibodies, immunoadhesins, proteins, peptides, glycoproteins, glycopeptides, glycolipids, polysaccharides, oligosaccharides, nucleic acids, pharmacological agents and their metabolites, and the like.

Preferred compounds of the present invention include peptide analogs, mimetics or variants of the peptide compounds of the present invention. These include, for example, peptides containing non-naturally occurring amino acids provided the compound retains the ability to bind and prevent or block binding of IgE to the FcεRI. Similarly, peptide mimetics and analogs may include non-amino acid chemical structures that mimic the structure of the peptide compounds of the present invention and retain the ability to bind and prevent or block binding of IgE to the FcεRI as described herein. Such compounds are characterized generally as exhibiting similar physical characteristics such as size, charge or hydrophobicity that is present in the appropriate spatial orientation as found in the peptide compound counterparts. A specific example of a peptide mimetic compound is a compound in which the amide bond between one or more of the amino acids is replaced, for example, by a carbon—carbon bond or other bond as is well known in the art (see, for example Sawyer, in Peptide Based Drug Design pp. 378–422 (ACS, Washington D.C. 1995).

The term "IgE mediated" or "associated" disease or disorder means a condition resulting from or associated with the binding of IgE to FcεRI. An IgE mediated or associated disease or disorder includes, for example, allergic disease caused by IgE antibodies and mast cell mediators including but not limited to atopic diseases such as allergic rhinitis, allergic asthma, including asthma associated with specific antigenic factors such as seasonal pollens (grass: rye, timothy, ragweed) and tree (birch), perennial allergens such as dust mite, animal danders, feathers and fungal spores and occupational antigens such as detergents and metals as well as asthma associated with non-antigen specific factors such as infection, irritants such as smoke, fumes, diesel exhaust particles and sulphur dioxide, asthma associated with airway cooling (exercise, cold air temperatures) and emotional stress; atopic dermatitis and allergic gastroenteropathy as well as anaphylactic diseases including systemic anaphylaxis and reactions to proteins in foods, venom, vaccines, hormones, antiserum, enzymes and latex, reactions to haptens including antibiotics, muscle relaxants, vitamins, cytotoxins and opiates and reactions to polysaccharides such as dextran, iron dextran and polygeline and other anaphylactic diseases or disorders such as urticaria-angioedema.

"IgE-mediated gastro-intestinal inflammatory disorders" can be broadly defined as intractable chronic responses to a broad range of host reaction to a variety of insults, such as those caused by injury or infection which are characterized by, or results from pathology affected by IgE. Particular disorders included within the scope of the term includes inflammatory bowel disease (e.g., Crohn's disease, ulcerative colitis, indeterminate colitis and infectious colitis), gastroenteropathy, enteritis, mucositis (e.g., oral mucositis, gastrointestinal mucositis, nasal mucositis and proctitis), necrotizing enterocolitis and esophagitis.

The term "multimerization domain" as used in particular aspects of the present invention, is meant to refer to the portion of the molecule to which the compound, especially the peptide compound, is joined, either directly or through a "linker domain." The multimerization domain is an amino acid domain which, according to preferred embodiments, facilitates the interaction of two or more multimerization domains. While the multimerization domain promotes the interaction between two or more multimerization domains, there is no requirement within the context of the present invention that the peptide joined to a multimerization domain be present as a portion of a multimer.

According to preferred aspects of the present invention the multimerization domain is a polypeptide which promotes the stable interaction of two or more multimerization domains. By way of example and not limitation, a multimerization domain may be an immunoglobulin sequence, such as an immunoglobulin constant region, a leucine zipper, a hydrophobic region, a hydrophilic region, a polypeptide comprising a free thiol which forms an intermolecular disulfide bond between two or more multimerization domains or, for example a "protuberance-into-cavity" domain described in U.S. Pat. No. 5,731,168. In that patent, protuberances are constructed by replacing small amino acid side chains from the interface of a first polypeptide with a larger side chain (for example a tyrosine or tryptophan). Compensatory cavities of identical or similar size to the protuberances are optionally created on the interface of a second polypeptide by replacing large amino acid side chains with smaller ones (for example alanine or threonine).

Therefore, in a preferred aspect, the multimerization domain provides that portion of the molecule which promotes or allows stable interaction of two or more multimerization domains and promotes or allows the formation of dimers and other multimers from monomeric multimerization domains. Preferably, according to this aspect of the invention, multimerization domains are immunoglobulin constant region domains. Immunoglobulin constant domains provide the advantage of improving in vivo circulating half-life of the compounds of the invention and optionally allow the skilled artisan to incorporate an "effector function" as described herein below into certain aspects of the invention.

Throughout the present specification and claims, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

As used herein, the term "parenteral" refers to introduction of a compound of the invention into the body by other than the intestines, and in particular, intravenous (i.v.), intraarterial (i.a.), intraperitoneal (i.p.), intramuscular (i.m.), intraventricular, and subcutaneous (s.c.) routes.

The term "peptide" is used herein to refer to constrained (that is, having some element of structure as, for example, the presence of amino acids which initiate a β-turn or β-pleated sheet, or for example, cyclized by the presence of disulfide bonded Cys residues) or unconstrained (e.g., linear) amino acid sequences of less than about 50 amino acid residues, and preferably less than about 40 amino acid residues, including multimers, such as dimers thereof or there between. Of the peptides of less than about 40 amino acid residues, preferred are the peptides of between about 10 and about 30 amino acid residues and especially the peptides of about 20 amino acid residues. However, upon reading the instant disclosure, the skilled artisan will recognize that it is not the length of a particular peptide but its ability to bind and prevent or block binding of IgE to the FcεRI and compete with the binding of a peptide compound described herein that distinguishes the peptide of the invention. For example, amino acid sequences of 5, 6, 7, 8, 9, 10, 11, 12, 13, 14, 15, 16, 17, 18, 19, 20, 21, 22, 23, 24 and 25 amino acid residues, for example, are equally likely to be peptide compounds within the context of the present invention.

Other peptide compounds include peptides which have their N- and C-terminal residues joined, the fusion to the N- or C-terminus of the compounds described herein of immunogenic polypeptides, e.g., bacterial polypeptides such as beta lactamase or an enzyme encoded by *E. coli* Trp locus or yeast protein, other polypeptides such as the Z-domain of protein-A, and C-terminal fusion with proteins having a long half-life such as immunoglobulin constant region or other immunoglobulin regions, albumin, or ferritin as described in WO 89/02922 published 6 Apr. 1989. Further, free functional groups on the side chains of the amino acid residues can also be modified within the peptide compounds of the invention by amidation, acylation or other substitution, which can, for example, change the solubility of the compounds without affecting their activity. "Ac—" for example denotes a $CH_3CO$— modified N terminus and A-nh$_2$" or "—NH$_2$" a —NH$_2$ modified C-terminus.

Specific peptides within the context of the present invention comprise both naturally and non-naturally occurring amino acid sequences. By non-naturally occurring is meant that the amino acid sequence is not found in nature. Example non-naturally occurring amino acid sequences have between about 10 and 30 amino acid residues, alternatively about 20 amino acid residues. These include peptides, peptide analogs and mimetics containing naturally as well as non-naturally occurring amino acids. In a specific aspect, the peptides of the invention comprises amino acid residues consisting of only naturally occurring amino acids.

Examples of non-natural amino acids include $C_{1-10}$ alkyl, $C_{1-10}$ cycloalkyl and aromatic amino acids. Particular alkyl non-natural amino acids include β-alanine, 4-aminobutyric acid, 5-aminovaleric acid, 6-aminocaproic acid, 7-aminoheptanoic acid, 8-amino caprylic acid, etc. and isomers thereof. Particular cycloalkyl non-natural amino acids include 1-amino-cyclopropane carboxylic acid, 1-amino-cyclobutane carboxylic acid, 1-amino-cyclopentane carboxylic acid, 1-amino-cyclohexane carboxylic acid, cis-4-aminocyclohexane carboxylic acid, trans-4-aminocyclohexane carboxylic acid, cis-4-aminomethylcyclohexane carboxylic acid, trans-4-aminomethylcyclohexane carboxylic acid etc., and optical and chemical isomers thereof. Particular aromatic non-natural amino acids include 2-aminobenzoic acid, 3-aminobenzoic acid and 4-aminobenzoic acid, etc.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "control sequence" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, the term "pulmonary administration" refers to administration of a formulation of the invention through the lungs by inhalation. As used herein, the term "inhalation" refers to intake of air to the alveoli. In specific examples, intake can occur by self-administration of a formulation of the invention while inhaling, or by administration via a respirator, e.g., to a patient on a respirator. The term "inhalation" used with respect to a formulation of the invention is synonymous with "pulmonary administration."

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. For example, the extent of the release of inflammatory mediator(s) (e.g., cytokines) release from mast cells or basophils, tissue injury, inflammation or the amount leukocyte trafficking. Another manner in which to measure "treatment" of an IgE-mediated disorder to measure the extent to which IgE is inhibited from binding to the high affinity IgE receptor (such as those present on mast cells or basophils). Those "in need of treatment" include mammals, such as humans, already having the disease or disorder, including those in which the disease or disorder is to be prevented.

An "effective amount" is at least the minimum concentration of IgE receptor antagonist peptide which prevents, lessens or causes to lessen the ability of said peptide to bind to the high afinity IgE receptor (FcεRI). A "therapeutically effective amount" is at least the minimum concentration of IgE receptor antagonist peptide which attenuates or eliminates a pathological symptom or improves a pathological condition associated with an IgE-mediated disorder. For example, quantitative levels of inflammatory mediator(s) (e.g., histamine), free IgE, IgE bound to the high affinity receptor, inflammation, tissue injury or the amount of leukocyte trafficking.

"Chronic" administration refers to administration in a continuous mode as opposed to an acute mode, so as to maintain the initial therapeutic effect (activity) for an extended period of time. "Intermittent" administration is treatment that is done not consecutively without interruption, but rather is cyclic in nature.

"Active" means that the prospective compound of the invention binds to FcεRI Moreover, a compound which is active also inhibits or attenuates the binding of IgE to FcεRI. The inhibition of the binding of IgE to FcεRI can be measured by examining the reduction in cellular mediators resulting from the activation of FcεRI by IgE on mast cells or basophils (e.g., release of histamine).

The term "immunoadhesin" designates antibody-like molecules which combine the binding specificity of a heterologous protein (an "adhesin") with the effector functions of immunoglobulin constant domains. Structurally, the immunoadhesions comprise a fusion of an amino acid sequence with the desired binding specificity (e.g., a peptide of the invention), and an immunoglobulin constant domain sequence. The adhesin part of an immunoadhesin molecule typically is a continuous amino acid sequence comprising at least the binding site of a receptor or a ligand. The immunoglobulin, such as IgG1, IgG2, IgG3, or IgG4 subtypes, IgA (including IgA1 and IgA2), IgE, IgD or IgM.

The term "mammal" as used herein refers to any animal classified as a mammal, including human, domestic and farm animals, and zoo, sports or pet animals, such as cattle (e.g., cows), horses, dogs, sheep, pigs, rabbits, goats, cats, etc. In a specific aspect of the invention, the mammal is a human.

Administration "in combination with" one or more further therapeutic agents includes simultaneous (concurrent) and consecutive administration in any order.

"Carriers" as used herein include pharmaceutically-acceptable carriers, excipients, or stabilizers which are nontoxic to the cell or mammal being exposed thereto at the dosages and concentrations employed. Often the physiologically-acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulin; hydrophilic polymers such as polyvinylpyrrolidone; amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), PLURONICS® and hyaluronic acid (HA).

A "liposome" is a small vesicle composed of various types of lipids, phospholipids and/or surfactant which is useful for delivery of a drug (such as an IgE receptor antagonist polypeptide of the invention) to a mammal. The components of the liposome are commonly arranged in a bilayer formation, similar to the lipid arrangement of biological membranes.

A "small molecule" is defined herein to have a molecular weight below about 500 Daltons.

A "large hydrophobic amino acid" is an amino acid (including natural and non-natural) which is a molecule which is both an amino acid and is hydrophobic, as these terms are readily understood by one of ordinary skill in the art. The characterization "large" further describes the side chain as being of greater physical size relative to the side chains of other amino acids, which are of smaller physical size. It is common to group amino acid residues on the basis of the physical properties of the side chain (e.g., hydrophobicity, polarity, charge, acidic or basic character, etc.). The common feature of the amino acids falling under this definition are those which share the property of being hydrophobic and which have a side chain of larger physical size. Non-limiting examples of amino acids which fall under this definition are tryptophan, phenylalanine, napthylalanine, leucine, isoleucine, octahydroindole, tetrahydroisoquinoline and the like.

II. Modes for Carrying out the Invention

The present invention provides compounds, including peptides, peptide mimetics and the like, having general Formula I or which compete with compounds of general Formula I for binding FcεRI.

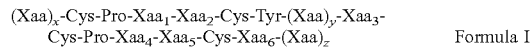
(Xaa)$_x$-Cys-Pro-Xaa$_1$-Xaa$_2$-Cys-Tyr-(Xaa)$_y$-Xaa$_3$-Cys-Pro-Xaa$_4$-Xaa$_5$-Cys-Xaa$_6$-(Xaa)$_z$    Formula I Preferred are peptide compounds of general Formula I wherein Xaa is an amino acid and x is a whole number greater or equal to 0 (zero), generally less than 50, alternatively less than 20, alternatively less than 10, alternatively 0, 1 or 2; y is alternatively between 3 and 10, alternatively 3, 4 or 5 and z is a whole number greater or equal to zero, generally less than 50, alternatively less than 20, alternatively less than 10, alternatively 0, 1 or 3. For example, when x and z are 0, the invention provides for compounds having the general Formula II.

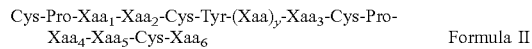
Cys-Pro-Xaa$_1$-Xaa$_2$-Cys-Tyr-(Xaa)$_y$-Xaa$_3$-Cys-Pro-Xaa$_4$-Xaa$_5$-Cys-Xaa$_6$    Formula II Peptide compounds of general Formulas I and II contain an amino acid domain designated (Xaa)$_y$ in the formula of between 3 and 10 amino acid residues. Particular peptide compounds contain an amino acid domain (Xaa)$_y$ wherein y is 3, 4, 5, 8, or 10, alternatively 3, 4 or 5, alternatively 5. For example, in the context of peptide compounds of general Formula I, the invention provides peptide compounds having any one of the following general formulas:

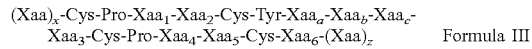
(Xaa)$_x$-Cys-Pro-Xaa$_1$-Xaa$_2$-Cys-Tyr-Xaa$_a$-Xaa$_b$-Xaa$_c$-Xaa$_3$-Cys-Pro-Xaa$_4$-Xaa$_5$-Cys-Xaa$_6$-(Xaa)$_z$    Formula III

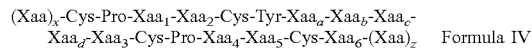
(Xaa)$_x$-Cys-Pro-Xaa$_1$-Xaa$_2$-Cys-Tyr-Xaa$_a$-Xaa$_b$-Xaa$_c$-Xaa$_d$-Xaa$_3$-Cys-Pro-Xaa$_4$-Xaa$_5$-Cys-Xaa$_6$-(Xaa)$_z$    Formula IV

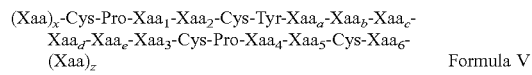
(Xaa)$_x$-Cys-Pro-Xaa$_1$-Xaa$_2$-Cys-Tyr-Xaa$_a$-Xaa$_b$-Xaa$_c$-Xaa$_d$-Xaa$_e$-Xaa$_3$-Cys-Pro-Xaa$_4$-Xaa$_5$-Cys-Xaa$_6$-(Xaa)$_z$    Formula V For compounds of general Formulas I through V, Xaa$_6$ is Tyr, providing for compounds of the general Formula VI:

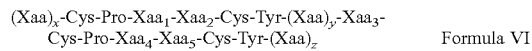
(Xaa)$_x$-Cys-Pro-Xaa$_1$-Xaa$_2$-Cys-Tyr-(Xaa)$_y$-Xaa$_3$-Cys-Pro-Xaa$_4$-Xaa$_5$-Cys-Tyr-(Xaa)$_z$    Formula VI wherein x is 0, 1 or 2, y is 3, 4 or 5, alternatively 5 and z is 0, 1 or 3.

According to certain embodiments, Xaa$_4$ is Asp, providing compounds of general Formula Formula VII:

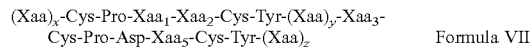
(Xaa)$_x$-Cys-Pro-Xaa$_1$-Xaa$_2$-Cys-Tyr-(Xaa)$_y$-Xaa$_3$-Cys-Pro-Asp-Xaa$_5$-Cys-Tyr-(Xaa)$_z$    Formula VII wherein x is 0, 1 or 2, y is 3, 4 or 5, alternatively 5 and z is 0, 1 or 2.

According to certain embodiments Xaa$_2$ and Xaa$_3$ are large hydrophobic amino acids providing for compounds of the general Formula VIII:

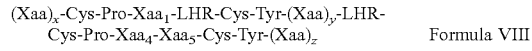
(Xaa)$_x$-Cys-Pro-Xaa$_1$-LHR-Cys-Tyr-(Xaa)$_y$-LHR-Cys-Pro-Xaa$_4$-Xaa$_5$-Cys-Tyr-(Xaa)$_z$    Formula VIII wherein LHR is a large hydrophobic amino acid, e.g., Phe or Leu, Xaa$_4$ is Asp and wherein x is 0, 1 or 2, y is 3, 4 or 5, alternatively 5 and z is 0, 1 or 3.

Further preferred compounds of the invention include compounds of general Formula IX:

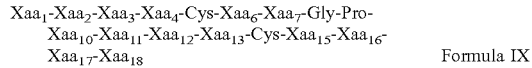
Xaa$_1$-Xaa$_2$-Xaa$_3$-Xaa$_4$-Cys-Xaa$_6$-Xaa$_7$-Gly-Pro-Xaa$_{10}$-Xaa$_{11}$-Xaa$_{12}$-Xaa$_{13}$-Cys-Xaa$_{15}$-Xaa$_{16}$-Xaa$_{17}$-Xaa$_{18}$    Formula IX Particular compounds of this group are peptide compounds such as those described in detail in Example sections 1–6, especially those described in Table 5. Examples include the peptides of Formula IX where $Xaa_{10}$ is Trp, $Xaa_{11}$ is Gly and $Xaa_{12}$ is Trp:

$Xaa_1$-$Xaa_2$-$Xaa_3$-$Xaa_4$-Cys-$Xaa_6$-$Xaa_7$-Gly-Pro-Trp-Gly-Trp-$Xaa_{13}$-Cys-$Xaa_{15}$-$Xaa_{16}$-$Xaa_{17}$-$Xaa_{18}$     Formula X According to this aspect of the invention, peptides of the general Formulas IX and XI having N and C-terminal deletions are also preferred, for example, compounds of general Formula IX and X where $Xaa_1$ is optionally absent are preferred compounds within the context of the invention. As well, deletion of 1 to three amino acids from C-terminal end of the peptide result in preferred compounds of the invention.

In an alternative embodiment, compounds according to the present invention are peptide or mimetics thereof having or derived from the general Formula XI or which compete with a compound of general Formula XI for binding FcεRI:

$(Xaa)_x$-Cys-Pro-$Xaa_1$-$Xaa_2$-Cys-Tyr-$(Xaa_7)_w$-$Xaa_3$-Cys-Pro-$Xaa_4$-$Xaa_5$-Cys-$Xaa_6$-$(Xaa)_z$     Formula XI wherein $Xaa_{1-6}$ are natural amino acids, Xaa7 is a non-natural amino acid and x, y and z are whole numbers greater than or equal to 0, and x is generally less than 50, alternatively less than 20, alternatively less than 10, alternatively 0, 1 or 2; w is generally 1, 10 or any integer therebetween, and z is generally an integer less than 50, alternatively less than 20, alternatively 10, alternatively 0, 1 or 3.

While compounds of general Formulas I through XI are illustrative of the peptide compounds of the invention, the invention includes compositions wherein the compounds make up a portion of a larger compound or composition. For example, peptide compounds of general Formula I may make up a part of a fusion protein wherein the compounds are linked or fused via their N— or C terminus or both or through a side chain to other peptide compounds or with other proteins or polypeptides.

According to this aspect of the invention, compounds are prepared with various objectives in mind, including, for example, increasing the affinity or avidity of the peptide compound for FcεRI, as for example, by the use of various multimerization domains as described herein. According to this aspect of the invention compounds are fused or linked, preferably via their N- or C-terminus to other proteins or peptides, such as immunoglobulins. Accordingly, the invention provides for hybrid immunoglobulin proteins containing compounds of general Formula I through XI fused or linked to immunoglobulin domains such as immunoglobulin constant regions. According to a further aspect, compounds of general Formulas I through XI may be fused or linked to other proteins with the objective of increasing the stability of the peptide compound or facilitating its recovery and purification, as for example, by expressing the peptide compound as a Z protein fusion as described herein. Further aspects of the invention include compounds or compositions wherein compounds of general Formulas I through XI are constructed with the objective of improving the therapeutic efficacy of the compound in aspects of the invention involving in vivo use of the peptide compound. For example, the serum half life of the compound may be modulated by, for example, fusing or linking the peptide compound to a plasma protein such as serum albumin, an immunoglobulin, apolipoproteins or transferrin. Alternatively, compounds of general formulas I through X may be fused or lined to other small organic or bioorganic molecules such as peptides which in turn bind a serum protein such as albumin or an immunoglobulin.

In general the compounds compete with a peptide having the sequence:

Val-Gln-Cys-Pro-His-Phe-Cys-Tyr-Glu-Leu-Asp-Tyr-Glu-Leu-Cys-Pro-Asp-Val-Cys-Tyr-Val (SEQ ID NOS: 155, 171; IgE134) for binding the high affinity IgE receptor (FcεRI) in an in vitro assay.

The invention includes a method of inhibiting the binding of an IgE to the high affinity IgE receptor (FcεRI) comprising the step of:

a) contacting the FcεRI with a composition comprising a peptide compound of the invention, optionally in the presence of IgE, under conditions which allow binding of the peptide to FcεRI to occur; and b) determining the amount of IgE binding to FcεRI in the presence and absence of a compound of the invention, wherein a lower level of IgE binding in the presence of the compound relative to its absence is indicative of inhibition.

The invention further includes a method of inhibiting the binding of an IgE to the high affinity IgE receptor (FcεRI) comprising contacting the FcεRI with a peptide comprising the following amino acid sequence wherein Xaa is an amino acid:

$(Xaa)_x$-Cys-Pro-$Xaa_1$-$Xaa_2$-Cys-Tyr-$(Xaa)_y$-$Xaa_3$-Cys-Pro-$Xaa_4$-$Xaa_5$-Cys-$Xaa_6$-$(Xaa)_z$ (SEQ ID NO:596)

and wherein x is a whole number greater or equal to 0 (zero), generally less than 50, alternatively less than 20, alternatively less than 10, alternatively 0, 1 or 2; y is between 3 and 10, alternatively 3, 4 or 5 and z is a whole number greater or equal to zero, generally less than 50, alternatively less than 20, alternatively less than 10, alternatively 0, 1 or 3.

Therefore, according to certain aspects, the invention includes a method of designing a compound such as a peptide mimetic that mimics the three-dimensional surface structure of a peptide compound of the invention, for example a peptide compound of general Formula I:

$(Xaa)_x$-Cys-Pro-$Xaa_1$-$Xaa_2$-Cys-Tyr-$(Xaa)_y$-$Xaa_3$-Cys-Pro-$Xaa_4$-$Xaa_5$-Cys-$Xaa_6$-$(Xaa)_z$ (SEQ ID NO:596)

comprising the steps of:

(a) preparing a peptide of general Formula I:

(b) determining the three-dimensional structure of the peptide; and (c) designing a compound that mimics the 3-dimensional surface structure of the peptide.

In a further aspect of the invention the invention includes a method for selecting a molecule which blocks the interaction of IgE with the high affinity IgE receptor (FcεRI) comprising the steps of:

(1) contacting the FcεRI with IgE134 (SEQ ID NOS:155, 171) in the presence and absence of a candidate molecule under conditions which allow specific binding of IgE134 to FcεRI to occur;

(2) determining the amount of specific binding of IgE134 (SEQ ID NOS:155, 171) to FcεRI that occurs in the presence and absence of the candidate molecule, wherein a lower level of binding in the presence of the candidate compound is indicative of the ability to block the binding of IgE to FcεRI.

A. Structural Analysis of Peptides and Analogs

Three-dimensional structures of peptide compounds can be determined using nuclear magnetic resonance spectroscopy (NMR) or X-ray crystallography. Structural information derived from an NMR or peptide crystal structure can be used for the identification of small organic and bioorganic molecules such as peptidomimetics and synthetic organic molecules which bind the FcεRI and preferably block or prevent an IgE mediated or associated process or event. An exemplary approach to such a structure based compound design is described in ("Structure Based Drug Design" Pandi Veerapandian, ed. Marcell Dekker, New York 1997).

According to this aspect, the invention provides compounds which present a 3-dimensional surface which mimics the solvent accessible surface presented by, for example, the compounds of general Formulas I and XI. By way of example, having determined the three-dimensional structure of the peptide of the invention, the skilled artisan constructs a model of the peptide such as those depicted in FIGS. 7 and 8. Since every atom of a peptide can be depicted as a sphere of the appropriate van der Waals radius, a detailed surface map of the folded peptide can be constructed. The surface that results is known as the van der Waals surface. The "solvent accessible surface" is the surface that is accessible to a chemical probe, a water molecule herein, and is constructed by rolling a water molecule of appropriate radius on the outside of the peptide maintaining contact with the van der Waals surface. Those parts of the van der Waals surface that contact the surface of the water molecule define a continuous surface known as the "solvent accessible surface." (Creighton, Thomas E., *Proteins: Structure and Molecular Properties*, 2nd. ed. W.H. Freeman and Company, 1984, pp227–229). Accordingly, the invention provides compounds which present a solvent accessible surface that mimics the solvent accessible surface described by peptides of general Formulas I and XI, especially the solvent accessible surface presented by peptides having IGE134 (SEQ ID NOS:155, 171) and IGE063 (SEQ ID NO:49), for example.

Such compounds which present a solvent accessible surface which mimics the solvent accessible surface of the peptide compounds can be constructed by those skilled in the art. By way of example, the skilled artisan, can search three-dimensional structural databases of compounds to identify those compounds that position appropriate functional groups in similar three-dimensional structural arrangement, then build combinatorial chemistry libraries around such compounds to identify and optimize those with high affinity.

Representative 3-dimensional structures of compounds of the general Formulas I and XI are provided in FIGS. 7 (Formula X) and 8 (Formula I). Despite the vastly different secondary structures of IGE063 (SEQ ID NO:49) and IGE134 (SEQ ID NOS:155, 171), an overlay of the 3-dimensional structures (FIG. 9) shows conserved surface features consisting of a hydrophobic groove bordered by two hydrophobic and/or proline-containing ridges. In the case of peptides of general Formula I, for example IGE 134 (SEQ ID NOS:155, 171), the disulfide bonds of Cys3/Cys 19 and Cys7/Cys15 line the bottom of a groove that is bordered on one side by a ridge formed by Pro4 and Phe6 and on the other side by the protrusion of Pro16. These features are known to be essential for the high affinity FcεRI binding by IGE134 (SEQ ID NOS:155, 171)(see Example 12) and shown to directly contact the receptor in the peptide FcεRI complex (see Example 13) thus providing the necessary information for the design of small synthetic organic molecules that mimic the ridge/groove/ridge solvent accessible surface presented by the peptides. For example, the skilled artisan will recognize that small molecules based upon the solvent accessible surface of IGE134 (SEQ ID NOS:155, 171) will present a surface that mimics the hydrophobic groove lined by a proline shaped protrusion and a hydrophobic ridge (FIG. 9B). Accordingly, the invention provides compounds having a solvent accessible surface which mimics that of, for example the peptide IGE134 (SEQ ID NOS:155, 171), especially the solvent accessible surface described by residues Cys3, Pro4, Phe6, Cys7, Cys15, Pro16 and Cys19 of IGE134 (SEQ ID NOS:155, 171).

Therefore, according to certain aspects, the invention includes a method of designing a compound such as a peptide mimetic that mimics the three-dimensional surface structure of a peptide compound of the invention, for example a peptide compound of general Formula I:

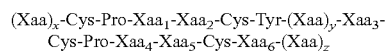

comprising the steps of:

(a) preparing a peptide of general Formula I:

(b) determining the three-dimensional structure of the peptide; and (c) designing a compound that mimics the 3-dimensional surface structure of the peptide.

According to a further embodiment, the invention provides a method for identifying a peptide mimetic which binds FcεRI and which blocks binding of IgE comprising the steps of:

(a) searching a molecular structure database with the structural parameters of a peptide prepared according to the instant invention, for example the structural coordinates provided here in IGE063 (SEQ ID NO:49) or IGE134 (SEQ ID NOS:155, 171) provided in Tables 6 and 8; and (b) selecting a molecule from the database which mimics the structural parameters of the peptide.

The peptide analogs identified using the peptide compounds of the present invention are useful in the therapeutic methods described herein and as pharmaceutical compositions.

Crystals of FcεRI in combination with a peptide of the invention of a size and quality to allow performance of x-ray diffraction studies enable those of skill in the art to conduct studies relating to the binding properties of FcεRI, as well as the binding properties of molecules which bind the FcεRI.

One approach enabled by this invention is the use of the structural coordinates of FcεRI to design chemical entities that bind to or associate with FcεRI and to alter the physical properties of the chemical entities in different ways. Thus, properties such as, for example, solubility, affinity, specificity, potency, on/off rates or other binding characteristics may all be altered and/or optimized.

One may design desired chemical entities by probing the FcεRI crystal structure with a library of different entities to determine optimal sites for interaction between candidate chemical entities and FcεRI utilizing the three-dimensional structure of the peptides of the present invention as well. For example, high-resolution x-ray diffraction data collected from crystals saturated with solvent allows the determination of where each type of solvent molecule adheres. Small molecules that bind tightly to those sites can then be designed and synthesized and tested for the desired activity. Once the desired activity is obtained, the molecules can be further optimized.

In various embodiments, the claimed invention relates to methods of preparing crystalline forms of FcεRI in complex with a peptide of the invention by first providing an aqueous solution comprising FcεRI and the peptide. A reservoir solution comprising a precipitant is then mixed with a volume of the FcεRI solution and the resultant mixed volume is then crystallized. The crystals are typically dissolved with this reagent in a small amount to minimize dilution effects of the other reagents and left to regrow for a period of time. In a further step, the crystalline complex is isolated from the mixed volume.

The concentration of FcεRI and peptide in the aqueous solution may vary, but is preferably about 1 to 50 mg/ml, more preferably about 5 to 15 mg/ml. Similarly, precipitants used in the invention may vary, and may be selected from any precipitant known in the art. Preferably, the precipitant is selected from the group consisting of sodium citrate, ammonium sulfate, polyethylene glycol, sodium acetate, or a mixture thereof. More preferably the precipitant is polyethylene glycol buffered with sodium citrate or sodium acetate. Any concentration of precipitant may be used in the reservoir solution; however, it is preferred that the concentration be about 20 to 25% if polyethylene glycol, and about 10 mM to 1 M if sodium citrate, ammonium sulfate, or sodium acetate. The pH of the reservoir solution may also be varied, generally between about 4 to 10, more specifically about 4.5.

One skilled in the art will understand that each of these parameters can be varied without undue experimentation and acceptable crystals will still be obtained. In practice, once the appropriate precipitating agents, buffers, or other experimental variables are determined for any given growth method, any of these methods or any other methods can be used to grow the claimed crystals. One skilled in the art can determine the variables depending upon one's particular needs.

Various methods of crystallization can be used in the claimed invention, including vapor diffusion, batch, liquid bridge, or dialysis crystallization. Vapor diffusion crystallization is preferred. See, e.g., McPherson et al., *Preparation and Analysis of Protein Crystals*, Glick, ed. (John Wiley & Co., 1982), pp. 82–159; Jancarik et al., *J. Appl. Cryst.*, 24: 409–411 (1991). In vapor diffusion crystallization, a small volume (i.e., a few milliliters) of protein solution is mixed with a solution containing a precipitant. This mixed volume is suspended over a well containing a small amount, i.e. about 1 ml, of precipitant. Vapor diffusion from the drop to the well will result in crystal formation in the drop.

The dialysis method of crystallization utilizes a semipermeable size-exclusion membrane that retains the protein but allows small molecules (i.e. buffers and precipitants) to diffuse in and out. In dialysis, rather than concentrating the protein and the precipitant by evaporation, the precipitant is allowed to slowly diffuse through the membrane and reduce the solubility of the protein while keeping the protein concentration fixed. The batch methods generally involve the slow addition of a precipitant to an aqueous solution of protein until the solution just becomes turbid; at this point the container can be sealed and left undisturbed for a period of time until crystallization occurs.

Thus, applicants intend that the claimed invention encompass any and all methods of crystallization. One skilled in the art can choose any of such methods and vary the parameters such that the chosen method results in the desired crystals.

The invention also contemplates computational screening of small-molecule databases or designing of chemical entities that can bind in whole or in part to FcεRI.

The information obtained can thus be used to optimize potential inhibitors or agonists of FcεRI. The design of chemical entities that inhibit or agonize FcεRI generally involves consideration of at least two factors. First, the chemical entity must be capable of physically or structurally associating with FcεRI. The association may be any physical, structural, or chemical association, such as, for example, covalent or noncovalent bonding, van der Waals, interactions, hydrophobic or electrostatic interactions.

Second, the chemical entity must be able to assume a conformation that allows it to associate with FcεRI. Although not all portions of the chemical entity will necessarily participate in the association with FcεRI, those non-participating portions may still influence the overall conformation of the molecule. This in turn may have a significant impact on the desirability of the chemical entity. Such conformational requirements include the overall three-dimensional structure and orientation of the chemical entity in relation to all or a portion of the binding site.

The potential inhibitory or binding effect of a chemical entity on FcεRI may be analyzed prior to its actual synthesis and testing by the use of computer-modeling techniques. If the theoretical structure of the given chemical entity suggests insufficient interaction and association between it and FcεRI, the need for synthesis and testing of the chemical entity is obviated.

However, if computer modeling indicates a strong interaction, the molecule may then be synthesized and tested for its ability to bind to FcεRI. Thus, expensive and time-consuming synthesis of inoperative compounds may be avoided.

An inhibitory or other binding compound of FcεRI may be computationally evaluated and designed by means of a series of steps in which chemical entities or fragments are screened and selected for their ability to associate with the individual binding sites of FcεRI.

Thus, one skilled in the art may use one of several methods to screen chemical entities or fragments for their ability to associate with FcεRI. This process may begin by visual inspection of, for example, the binding site on a computer screen based on the FcεRI coordinates in Appendix 1. Selected fragments or chemical entities may then be positioned in a variety of orientations, or "docked," within an individual binding pocket of FcεRI. Docking may be accomplished using software such as Quanta and Sybyl, followed by energy minimization and molecular dynamics with standard molecular mechanics force fields, such as CHARMM and AMBER.

Specialized computer programs may be of use for selecting interesting fragments or chemical entities. These programs include, for example, GRID, available from Oxford University, Oxford, UK; MCSS or CATALYST, available from Molecular Simulations, Burlington, Mass.; AUTODOCK, available from Scripps Research Institute, La Jolla, Calif.; DOCK, available from University of California, San Francisco, Calif., and XSITE, available from University College of London, UK.

Once suitable chemical entities or fragments have been selected, they can be assembled into an inhibitor or agonist. Assembly may be by visual inspection of the relationship of the fragments to each other on the three-dimensional image displayed on a computer screen, in relation to the structural coordinates disclosed herein.

Alternatively, one may design the desired chemical entities de novo, experimentally, using either an empty binding site or optionally including a portion of a molecule with desired activity. Thus, for example, one may use solid-phase screening techniques where either FcεRI or a fragment thereof, or candidate chemical entities to be evaluated, are attached to a solid phase, thereby identifying potential binders for further study or optimization.

In the design of FcεRI antagonists, any molecular modeling techniques may be employed in accordance with the invention; these techniques are known, or readily available to those skilled in the art. It will be understood that the methods, compounds and compositions disclosed herein can be used to identify, design, or characterize not only entities that will associate or bind to FcεRI, but alternatively such entities that will bind to the receptor thereby disrupting native FcεRI-IgE interaction.

Once a compound has been designed or selected by the above methods, the efficiency with which that compound may bind to FcεRI may be tested and optimized using computational or experimental evaluation. Various parameters can be optimized depending on the desired result. These include, but are not limited to, specificity, affinity, on/off rates, hydrophobicity, solubility, and other characteristics readily identifiable by the skilled artisan.

Additionally, the invention is useful for the optimization of potential small-molecule drug candidates. Thus, the crystal structures may be also used to obtain information about the crystal structures of complexes of FcεRI and small molecule inhibitors. For example, if the small molecule inhibitor is co-crystallized with FcεRI, then the crystal structure of the complex can be solved by molecular replacement using the known coordinates of FcεRI for the calculation of phases. Such information is useful, for example, for determining the nature of the interaction between the FcεRI and the small molecule inhibitor, and thus may suggest modifications that would improve binding characteristics such as affinity, specificity, and kinetics.

B. Peptide Combinations

1. Multimerization Domains

According to a preferred embodiment of the invention, the peptide compounds are combined with a multimerization domain. According to this aspect of the invention, hybrid molecules are provided which comprise at least two distinct domains. Each molecule comprises a peptide domain and a multimerization domain. According to the present invention, the peptide domain is joined to a multimerization domain such as an immunoglobulin Fc region, optionally via a flexible linker domain.

The hybrid molecules of the present invention are constructed by combining the peptide with a suitable multimerization domain. Ordinarily, when preparing the hybrid molecules of the present invention, nucleic acid encoding the peptide will be operably linked to nucleic acid encoding the multimerization domain sequence. Typically the construct encodes a fusion protein wherein the C-terminus of the peptide is joined to the N-terminus of the multimerization domain. However, fusions where, for example, the N-terminus of the peptide is joined to the C-terminus of the multimerization domain are also possible.

Preferred multimerization domains are immunoglobulin constant region sequences. Typically, in such fusions the encoded hybrid molecule will retain at least functionally active hinge, CH2 and CH3 domains of the constant region of an immunoglobulin heavy chain. Fusions are also made, for example, to the C-terminus of the Fc portion of a constant domain, or immediately N-terminal to the CH1 of the heavy chain or the corresponding region of the light chain.

The precise amino acid site at which the fusion of the peptide to the immunoglobulin constant domain is made is not critical; particular sites are well known and may be selected in order to optimize the biological activity, secretion, or binding characteristics. However, the attachment site should be chosen to best retain the binding properties of the fused molecule possess by the unfused one. In this regard, the skilled artisan may reference the construction of various immunoadhesins described in the literature (U.S. Pat. Nos. 5,116,964; 5,714,147 and 5,336,603; Capon et al., (1989) *Nature* 337:525–531; Traunecker et al., (1989) *Nature* 339: 68–70; and Byrn et al., (1990) *Nature* 344:667–670; Watson et al., (1990) *J. Cell. Biol.* 110:2221–2229; Watson et al., (1991) *Nature* 349:164–167; Aruffo et al., (1990) *Cell* 61:1303–1313; Linsley et al., (1991) *J. Exp. Med.* 173: 721–730; Linsley et al., *J. Exp. Med.* 174:561–569; Stamenkovic et al., *Cell* 66:1133–1144; Ashkenazi et al., (1991) *Proc. Natl. Acad. Sci. USA* 88:10535–10539; Lesslauer et al., (1991) *Eur. J. Immunol.* 27:2883–2886; and Peppel et al., (1991) *J. Exp. Med.* 174:1483–1489; Mohler et al., (1993) *J. Immunol.* 151:1548–1561); Bennett et al., (1991) *J. Biol. Chem.* 266:23060–23067; Kurschner et al., (1992) *J. Biol. Chem.* 267:9354–9360; Chalupny et al., (1992) *Proc. Natl. Acad. Sci USA* 89:10360–10364; Ridgway and Gorman, (1991) *J. Cell. Biol.* 115, Abstract No. 1448). According to a particular aspect, an immunoglobulin type multimerization domain is selected to provide a multimer such as a dimer having an immunoglobulin Fc region. Therefore, the peptide is joined, in particular aspects, to an immunoglobulin heavy chain constant domain to provide a multimer comprising a functional Fc domain. In this case, DNA encoding an immunoglobulin chain-peptide sequence is typically coexpressed with the DNA encoding a second peptide-immunoglobulin heavy chain fusion protein. Upon secretion, the hybrid heavy chain will be covalently associated to provide an immunoglobulin-like structure comprising two disulfide-linked immunoglobulin heavy chains.

In a particular embodiment, the Fc region is a human Fc region, e.g. a native sequence human Fc region human IgG1 (A and non-A allotypes), IgG2, IgG3 or IgG4 Fc region.

In another particular embodiment, the peptide sequence is fused to the N-terminus of the Fc region of immunoglobulin G1 (IgG1). It is possible to fuse the entire heavy chain constant region to the peptide sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the peptide amino acid sequence is fused to (a) the hinge region and CH2 and CH3 or (b) the CH1, hinge, CH2 and CH3 domains, of an IgG heavy chain. In a preferred embodiment the peptide ligand amino acid sequence is fused to (a) the hinge region and (b) the CH3 domain of IgG1.

According to a particular aspect of this embodiment, hybrid molecules comprising a peptide and a multimerization domain are assembled as multimers, for example homodimers, or heterodimers or even heterotetramers. Homodimers result from the pairing or crosslinking of two monomers comprising a peptide and a multimerization domain. However, it is not essential that two identical monomers pair. According to a particular aspect of the invention a hybrid molecule as defined herein comprising a peptide and a multimerization domain such as an immunoglobulin constant domain may pair with a companion immunoglobulin chain comprising one arm of an immunoglobulin. Various exemplary assembled hybrid molecules within the scope of the present invention are schematically diagramed below:

(a) A-CH (b) A-CH-ACH (c) A-CH-VHCH-VLCL (d) A-CH-VHCH wherein each A independently represents a peptide of the invention;

VL is an immunoglobulin light chain variable domain;

VH is an immunoglobulin heavy chain variable domain;

CL is an immunoglobulin light chain constant domain; and

CH is an immunoglobulin heavy chain constant domain.

The hybrid molecules described herein are most conveniently constructed by fusing the cDNA sequence encoding the peptide portion in-frame to an immunoglobulin cDNA sequence. However, fusion to genomic immunoglobulin fragments can also be used (see, e.g. Aruffo et al., (1990), *Cell* 61:1303–1313; and Stamenkovic et al. (1991), *Cell* 66:1133–1144). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the peptides and the immunoglobulin parts of the hybrid molecule are inserted in tandem into a plasmid vector that directs efficient expression in the chosen host cells.

Alternatively, and especially in embodiments where the peptide is synthesized by, for example standard solid phase synthesis techniques, the peptide may be linked to the multimerization domain by any of a variety of means familiar to those of skill in the art. Covalent attachment is typically the most convenient, but other forms of attachment may be employed depending upon the application. Examples of suitable forms of covalent attachment include the bonds resulting from the reaction of molecules bearing activated chemical groups with amino acid side chains in the multimerization domain and can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

2. Peptide Fusions

According to the present invention, the peptide is optionally linked to, for example, another peptide either directly or via a flexible peptide linker. According to the present invention, the linker domain, is any group of molecules that provides a spatial bridge between two or more peptide domains as described in more detail herein below. According to this aspect of the invention, peptides are linked together, as for example in a fusion protein.

3. Linker Domains

According to the present invention, the peptide domain is optionally linked to, for example, another peptide domain or a multimerization domain via a flexible peptide linker. The linker component of the hybrid molecule of the invention does not necessarily participate in but may contribute to the function of the hybrid molecule. Therefore, according to the present invention, the linker domain, is any group of molecules that provides a spatial bridge between two or more peptide domains or a peptide domain and a multimerization domain.

The linker domain can be of variable length and makeup. It is generally, the length of the linker domain and not its structure that is important. The linker domain preferably allows for the peptide domain of the hybrid molecule to bind, substantially free of spacial/conformational restrictions to a coordinating FcεRI molecule. Therefore, the length of the linker domain is dependent upon the character of the two functional, e.g., the peptide and the multimerization domains of the hybrid molecule.

One skilled in the art will recognize that various combinations of atoms provide for variable length molecules based upon known distances between various bonds (Morrison, and Boyd, Organic Chemistry, 3rd Ed, Allyn and Bacon, Inc., Boston, Mass. (1977)). For example, the linker domain may be a polypeptide of variable length. The amino acid composition of the polypeptide determines the character and length of the linker. Exemplary linker domains comprise one or more Gly and or Ser/Arg residues.

C. Variant molecules

Variants of the IgE receptor peptide antagonist molecules disclosed herein are contemplated to be within the scope of the present invention. Whereas changes in the formulation may be done to also affect a desirable change in the peptide's activity, the term "variants" is explicitly intended to cover changes and/or modifications to the peptide sequence. A discussion of the modifications in the formulation appears under section "G. Pharmaceutical Compositions and dosages". Such changes in the peptide sequence and/or formulation, could, at least in theory, alter the cellular processing of IgE signalling, improve binding to FcεRI, improve the peptide stability, lengthen the half-life in the body, etc. Such changes could thus ultimately improve the therapeutic potential of the IgE receptor peptide antagonist molecule.

The term "amino acid" is used in its broadest sense and is meant to include both the naturally occurring L α-amino acids or residues, as well as the corresponding D optical isomer. The commonly used one and three letter abbreviations for naturally occurring amino acids are used herein (Lehninger, A. L., *Biochemistry*, 2d ed., pp. 71–92, (1975), Worth Publishers, New York). The convention used here is an upper case letter for the L-optical isomer and a lower case letter for the D-form. The term includes D-amino acids as well as chemically modified amino acids such as amino acid analogs, naturally occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio (*The Peptides: Analysis, Synthesis, Biology,*) Eds. Gross and Meiehofer, Vol. 5 p 341, Academic Press, Inc, N.Y. 1983, which is incorporated herein by reference.

Suitable variants in the amino acid sequence of the peptides described herein, can be made, for example, using any of the techniques and guidelines for conservative and non-conservative mutations set forth, for instance, in U.S. Pat. No. 5,364,934. Variations may be a substitution, deletion or insertion of one or more nucleotides encoding the peptide that results in a change in the amino acid sequence of the peptide as compared with the unmodified form. Optionally, the variation results in substitution of at least one amino acid with any other amino acid in one or more of the domains of the peptide. Guidance in determining which amino acid residue may be inserted, substituted or deleted without adversely affecting the desired activity may be found by comparing the activity of the various peptides identified herein. Amino acid substitutions can be the result of replacing one amino acid with another amino acid having similar structural and/or chemical properties, such as the replacement of a leucine with a serine, i.e., conservative amino acid replacements. Insertions, deletions or substitutions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

The term "conservative" amino acid substitution as used within this invention is meant to refer to amino acid substitutions which substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. In general, substitutions within a group may be considered conservative with respect to structure and function. However, the skilled artisan will recognize that the role of a particular residue is determined by its context within the three-dimensional structure of the molecule in which it occurs. For example, Cys residues may occur in the oxidized (disulfide) form, which is less polar than the reduced (thiol) form. The long aliphatic portion of the Arg side chain may constitute a critical feature of its structural or functional role, and this may be best conserved by substitution of a nonpolar, rather than another basic residue. Also, it will be recognized that side chains containing aromatic groups (Trp, Tyr, and Phe) can participate in ionic-aromatic or "cation-pi" interactions. In these cases, substitution of one of these side chains with a member of the acidic or uncharged polar group may be conservative with respect to structure and function. Residues such as Pro, Gly, and Cys (disulfide form) can have direct effects on the main chain conformation, and often may not be substituted without structural distortions.

Examples of conservative substitutions are shown in Table I, under the heading of preferred substitutions. If such substitutions do not result in a change in the peptide's activity, then more substantial changes, called exemplary substitutions in Table I, or as further described below in reference to amino acid classes, may also be introduced prior to screening the resultant protein products.

TABLE I

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the peptides of the invention polypeptide are accomplished by selecting substitutions that alter the (a) structure of the polypeptide backbone in the area of the substitution, for example, as a sheet or helical conformation, (b) charge or hydrophobicity of the molecule at the target site, or (c) bulk of the side chain. Naturally occurring residues may be divided into groups based on common side-chain properties:

(1) hydrophobic: norleucine, met, ala, val, leu, ile;

(2) neutral hydrophilic: cys, ser, thr;

(3) nonpoloar: ala, val, leu, ile, pro, phe, trp, met;

(4) uncharged polar: gly, ser, thr, cys, tyr, asn, gln;

(5) acidic: asp, glu;

(6) basic: asn, gln, his, lys, arg;

(7) residues that influence chain orientation: gly, pro; and (8) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis, Carter et al., *Nucl. Acids Res.,* 13:4331 (1986); Zoller et al., *Nucl. Acids Res.,* 10:6487 (1987), cassette mutagenesis, Wells et al., *Gene,* 34:315 (1985), restriction selection mutagenesis, Wells et al., *Philos. Trans. R. Soc. London SerA,* 317:415 (1986) or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Cunningham and Wells, *Science,* 244: 1081–1085 (1989). Alanine is also typically preferred because it is the most common amino acid. Further, it is frequently found in both buried and exposed positions. Creighton, *The Proteins,* (W.H. Freeman & Co., N.Y.); Chothia, *J. Mol. Biol.,* 150:1 (1976). If alanine substitution does not yield adequate amounts of variant, an isosteric amino acid may be used.

Amino acid substitutions are not limited to amino acids encoded by genes. Commonly encountered amino acids which are not encoded by the genetic code, include, for example, those described in International Publication No. WO 90/01940 and described in Table I below, as well as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxyllysine (Hyl) for Lys; allohydroxyllysine (AHyl) for Lys; 3-(and 4)hydoxyproline (3Hyp, 4Hyp) for Pro, Ser, and Thr; alloisoleucine (AIle) for ile, Leu, and Val; N-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn or Or) for Lys, Arg and His; Citrulline (Cit) and methionine sulfoxide (MSO) for Thr, Asn and Gln; methylphenylalanine (MePhe), trimethylphenylalanine, halo (F, Cl, Br, and I) phenylalanine, triflourylphenylalanine, for Phe.

D. Covalent modifications

Covalent modifications of the peptides of the invention are included within the scope of this invention. One type of covalent modification includes reacting targeted amino acid residues of an peptide of the invention with an organic derivatizing agent that is capable of reacting with selected side chains or the N- or C-terminal residues of the molecule. Derivatization with bifunctional agents is useful, for instance, for crosslinking the molecule to a water-insoluble support matrix or surface for use in the method for purifying anti-(peptide of the invention) antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group. T. E. Creighton, *Proteins: Structure and Molecular Properties*, W.H. Freeman & Co., San Francisco, pp. 79–86 (1983)], Another type of covalent modification of the invention polypeptide included within the scope of this invention comprises altering or adding a glycosylation pattern to the polypeptide. Addition of glycosylation sites to the polypeptide may be accomplished by altering the amino acid sequence. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on the peptides of the invention is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.,* pp. 259–306 (1981).

Removal of carbohydrate moieties present on the peptides of the invention may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification comprises linking the invention polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The peptides of the present invention may also be modified in a way to form a chimeric molecule comprising the invention polypeptide fused to another, heterologous polypeptide or amino acid sequence.

In one embodiment, such a chimeric molecule comprises a fusion of the invention polypeptide with a tag polypeptide which provides an epitope to which an anti-tag antibody can selectively bind. The epitope tag is generally placed at the amino- or carboxyl-terminus of the polypeptide of the invention. The presence of such epitope-tagged forms of the polypeptide of the invention can be detected using an antibody against the tag polypeptide. Also, provision of the epitope tag enables the polypeptide of the invention to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5, Field et al., *Mol. Cell Biol.,* 8:2159–2165 (1988); the c-myc tag and the 8F9, 3C7, 6E10, G4, B7 and 9E10 antibodies thereto, Evan et al., *Molecular and Cellular Biology,* 5:3610–3616 (1985); and the Herpes Simplex virus glycoprotein D (gD) tag and its antibody, Paborsky et al., *Protein Engineering,* 3(6):547–553 (1990). Other tag polypeptides include the Flag-peptide, Hopp et al., *BioTechnology,* 6:1204–1210 (1988); the KT3 epitope peptide, Martin et al., *Science,* 255:192–194 (1992); an α-tubulin epitope peptide, Skinner et al., *J. Biol. Chem.,* 266:15163–15166 (1991); and the T7 gene 10 protein peptide tag, Lutz-Freyermuth et al., *Proc. Natl. Acad. Sci. USA,* 87:6393–6397 (1990).

In an alternative embodiment, the chimeric molecule may comprise a fusion of the polypeptide of the invention with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an invention polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

The peptide compounds of the invention can be modified at the N-terminus or the C-terminus using an amino-protecting group or carboxy protecting group, respectively. Numerous such modifications will be apparent to those skilled in the art. For example, the N-terminus of a peptide or peptide analog can be chemically modified such that the N-terminal amino group is substituted for example by an acetyl, cyclopentylcarboxy, isoquinolylcarboxy, furoyl, tosyl, picolyl, pyrazinecarboxy, tert-butylacetyl, tert-butyloxycarbonyl, benzyloxycarbonyl, benzoyl groups, including for example a benzyloxime such as a 2-aryl-2-o-benzyloxime as well as an amino acyl residue which itself can be modified by an amino-protecting group. Other amino-protecting groups are described for example in *The Peptides*, eds. Gross and Meienhofer, Vol. 3 (Academic Press, Inc. N.Y. 1981) and Greene and Wuts, in *Protective groups in Organic Synthesis* 2d ed., pages 309–405 (John Wiley & sons, New York (1991), each of which is incorporated herein by reference.

The N-terminal amino group also can be substituted, for example, with a reverse amide bond. Such modifications of amino groups can protect an otherwise reactive amino group against undesirable side reactions as can occur during a synthetic procedure or due to exopeptidase activity on a final compound. It should be recognized that the term amino group is used broadly herein to refer to any free amino group, including a primary, secondary, or tertiary amino group, present in a peptide. By contrast the term N-terminus refers to the α-amino group of the first amino acid present in a peptide written in the conventional manner. The product of any such modification of the N-terminus amino group of a peptide or peptide analog of the invention is referred to herein as an "N-terminal derivative".

Modification of an amino group also can provide additional advantages, including, for example, increasing the solubility or the activity of the compound. Compounds having these modifications are meant to be included within the compounds of the present invention since their construction is within the ability of the skilled artisan given the present disclosure. Various amino protecting groups are known in the art and include, for example, acyl groups such as an acetyl, picolyl, tert-butylacetyl, tert-butyloxycarbonyl, benzyloxycarbonyl, benzoyl groups, including for example a benzyloxime such as a 2-aryl-2-O-benzyloxime as well as an amino acyl residue which itself can be modified by an amino-protecting group. Other amino-protecting groups are described for example in *The Peptides*, eds. Gross and Meienhofer, Vol. 3 (Academic Press, Inc. N.Y. 1981) and Greene and Wuts, in *Protective groups in Organic Synthesis* 2d ed., pages 309405 (John Wiley & Sons, New York (1991), each of which is incorporated herein by reference.

Similarly, a carboxy group such as the carboxy group present at the C-terminus of a peptide can be chemically modified using a carboxy-protecting group. The terms "carboxy group" and "C-terminus" refer to the α-carboxy group present at the C-terminus of a peptide of the invention. A carboxy group such as that present at the C-terminus of a peptide can be modified by reduction of the C-terminal carboxy-group to an alcohol or aldehyde, by formation of an ester or by substitution of the carboxy-group with a substituent such as a thiazolyl, cyclohexyl, or other group. Suitable esters are well known in the art and include, for example, alkoxymethyl groups such as methoxymethyl, ethoxymethyl, propoxymethyl, isopropoxy methyl, and the like. Additionally, the carboxy group can be protected by reaction with an amine to form an amide.

E. Synthesis of Peptides

1. Chemical Synthesis

One method of producing the compounds of the invention involves chemical synthesis. This can be accomplished by using methodologies well known in the art (see Kelley, R. F. & Winkler, M. E. in *Genetic Engineering Principles and Methods*, Setlow, J. K, ed., Plenum Press, N.Y., vol. 12, pp 1–19 (1990), Stewart, J. M. Young, J. D., *Solid Phase Peptide Synthesis*, Pierce Chemical Co., Rockford, Ill. (1984); see also U.S. Pat. Nos. 4,105,603; 3,972,859; 3,842,067; and 3,862,925).

Peptides of the invention can be conveniently prepared using solid phase peptide synthesis (Merrifield, (1964) *J. Am. Chem. Soc.*, 85:2149; Houghten, (1985) *Proc. Natl. Acad. Sci. USA*, 82:5132. Solid phase synthesis begins at the carboxy terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g., a polyamide or polystyrene resin) as shown in FIGS. 1-1 and 1-2, on pages 2 and 4 of Stewart and Young, supra. In one embodiment, the C-terminal amino acid is coupled to a polystyrene resin to form a benzyl ester. A macromolecular support is selected such that the peptide anchor link is stable under the conditions used to deprotect the α-amino group of the blocked amino acids in peptide synthesis. If a base-labile α-protecting group is used, then it is desirable to use an acid-labile link between the peptide and the solid support. For example, an acid-labile ether resin is effective for base-labile Fmoc-amino acid peptide synthesis as described on page 16 of Stewart and Young, supra. Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis as described on pages 11–12 of Stewart and Young, supra.

After the initial amino acid is coupled to an inert solid support, the α-amino protecting group of the initial amino acid is removed with, for example, trifluoroacetic acid (TFA) in methylene chloride and neutralizing in, for example, triethylamine (TEA). Following deprotection of the initial amino acid's α-amino group, the next α-amino and sidechain protected amino acid in the synthesis is added. The remaining α-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris[dimethylamino]phosphonium hexafluorophosphate) method, N-hydroxysuccinic acid imido ester method, etc, and Woodward reagent K method, as is known in the art.

It is common in the chemical syntheses of peptides to protect any reactive side-chain groups of the amino acids with suitable protecting groups. Ultimately, these protecting groups are removed after the desired polypeptide chain has been sequentially assembled. Also common is the protection of the $\alpha$-amino group on an amino acid or peptide fragment while the C-terminal carboxy group of the amino acid or peptide fragment reacts with the free N-terminal amino group of the growing solid phase polypeptide chain, followed by the selective removal of the $\alpha$-amino group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

$\alpha$- and $\epsilon$-amino side chains can be protected with benzyloxycarbonyl (abbreviated Z), isonicotinyloxycarbonyl (iNOC), o-chlorobenzyloxycarbonyl [Z(2Cl)], p-nitrobenzyloxycarbonyl [Z(NO2)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulphenyl (NPS), diphenylphosphinothioyl (Ppt), and dimethylphosphinothioyl (Mpt) groups, and the like.

Protective groups for the carboxy functional group are exemplified by benzyl ester (OBzl), cyclohexyl ester (Chx), 4-nitrobenzyl ester (ONb), t-butyl ester (OtBu), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6-dimethylbenzenesulfonyl (Nds), 1,3,5-trimethylphenysulfonyl (Mts), and the like. The thiol group of cysteine can be protected with p-methoxybenzyl, trityl, and the like.

Many of the blocked amino acids described above can be obtained from commercial sources such as Novabiochem (San Diego, Calif.), Bachem CA (Torrence, Calif.) or Peninsula Labs (Belmont, Calif.).

Stewart and Young, supra, provide detailed information regarding procedures for preparing peptides. Protection of $\alpha$-amino groups is described on pages 14–18, and side chain blockage is described on pages 18–28. A table of protecting groups for amine, hydroxyl and sulfhydryl functions is provided on pages 149–151.

After the desired amino acid sequence has been completed, the peptide can be cleaved away from the solid support, recovered and purified. The peptide is removed from the solid support by a reagent capable of disrupting the peptide-solid phase link, and optionally deprotects blocked side chain functional groups on the peptide. In one embodiment, the peptide is cleaved away from the solid phase by acidolysis with liquid hydrofluoric acid (HF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the solid phase with sequential washes of acetic acid solutions. The combined washes are lyophilized, and the peptide is purified.

a. Disulfide Linked Peptides

As described above, some embodiments of the invention are cyclized by formation of a disulfide bond between cysteine residues. Such peptides can be made by chemical synthesis as described above and then cyclized by any convenient method used in the formation of disulfide linkages. For example, peptides can be recovered from solid phase synthesis with sulfhydryls in reduced form, dissolved in a dilute solution wherein the intramolecular cysteine concentration exceeds the intermolecular cysteine concentration in order to optimize intramolecular disulfide bond formation, such as a peptide concentration of 25 mM to 1 $\mu$M, and preferably 500 $\mu$M to 1 $\mu$M, and more preferably 25 $\mu$M to 1 $\mu$M, and then oxidized by exposing the free sulfhydryl groups to a mild oxidizing agent that is sufficient to generate intramolecular disulfide bonds, e.g. molecular oxygen with or without catalysts such as metal cations, potassium ferricyanide, sodium tetrathionate, etc. Alternatively, the peptides can be cyclized as described in Pelton et al., (1986) *J. Med. Chem.*, 29:2370–2375.

Cyclization can be achieved by the formation for example of a disulfide bond or a lactam bond between Cys residues. Residues capable of forming a disulfide bond include for example Cys, Pen, Mpr, and Mpp and its 2-amino group-containing equivalents. Residues capable of forming a lactam bridge include for example, Asp, Glu, Lys, Orn, $\alpha\beta$-diaminobutyric acid, diaminoacetic acid, aminobenzoic acid and mercaptobenzoic acid. The compounds herein can be cyclized for example via a lactam bond which can utilize the side chain group of a non-adjacent residue to form a covalent attachment to the N-terminus amino group of Cys or other amino acid. Alternative bridge structures also can be used to cyclize the compounds of the invention, including for example, peptides and peptidomimetics, which can cyclize via S—S, $CH_2$—S, $CH_2$—O—$CH_2$, lactam ester or other linkages.

Particular examples of peptides of the present invention which have been linked by disulfide binding include IgE088 (SEQ ID NOS:128, 128) (IgE037 linked in parallel manner) and IgE089 (SEQ ID NOS:128, 157)(IgE037 linked in antiparallel manner). However, disulfide bonding can also happen spontaneously, upon or after creation of the monomeric form.

2. Recombinant Synthesis a. Creation of Nucleic Acid Encoding the Peptides of the Invention In a further embodiment, the present invention encompasses a composition of matter comprising isolated nucleic acid, preferably DNA, encoding a peptide described herein. DNAs encoding the peptides of the invention can be prepared by a variety of methods known in the art. These methods include, but are not limited to, chemical synthesis such as that described herein, or by any of the methods described in Engels et al., (1989) *Agnew. Chem. Int. Ed. Engl.*, 28:716–734, the entire disclosure of which is incorporated herein by reference, such as the triester, phosphite, phosphoramidite and H-phosphonate methods. In one embodiment, codons preferred by the expression host cell are used in the design of the encoding DNA. Alternatively, DNA encoding the peptide can be altered to encode one or more variants by using recombinant DNA techniques, such as site specific mutagenesis (Kunkel et al., (1991) *Methods Enzymol.* 204:125–139; Carter, P., et al., (1986) *Nucl. Acids. Res.* 13:4331; Zoller, M. J. et al., (1982) *Nucl. Acids Res.* 10:6487), cassette mutagenesis (Wells, J. A., et al., (1985) *Gene* 34:315), restriction selection mutagenesis (Wells, J. A., et al., (1986) *Philos. Trans, R. Soc. London SerA* 317, 415), and the like.

b. Selection and Use of a Replicable Vector

The nucleic acid (e.g., cDNA or genomic DNA) encoding the peptides of the invention may be inserted into a replicable vector for cloning (amplification of the DNA) or for expression. Various vectors are publicly available. The vector may, for example, be in the form of a plasmid, cosmid, viral particle, phagemid or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Recombinant expression of the nucleic acid encoding the peptides of the invention typically requires an expression control sequence operably linked to such nucleic, and an expression vector, such as a plasmid, comprising the DNA molecule, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells.

The peptides of the invention may be produced recombinantly not only directly, but also as a fusion polypeptide with a heterologous polypeptide, which may be a signal sequence or other polypeptide having a specific cleavage site at the N-terminus of the mature peptide. In general, the signal sequence may be a component of the vector, or it may be a part of the peptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010, 182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Additional examples of secretory sequences which are operably linked so as to result in secretion of the expression product by the host cell into the culture medium, include stII, ecotin, lamB, herpes GD, lpp, alkaline phosphatase, invertase, MIP.5 and alpha factor. Also suitable for use herein is the 36 amino acid leader sequence of protein A (Abrahmsen et al., (1985) *EMBO J.,* 4:3901).

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding the peptides of the invention, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7. Stinchcomb et al., *Nature,* 282:39 (1979); Kingsman et al., *Gene,* 7:141 (1979); Tschemper et al., *Gene,* 10:157 (1980). The trp1 gene provides a selection marker for a mutant strain of yeast lacking the ability to grow in tryptophan, for example, ATCC No. 44076 or PEP4-1. Jones, *Genetics,* 85:12 (1977).

Expression and cloning vectors usually contain a promoter operably linked to the nucleic acid sequence encoding the peptides of the invention in order to direct mRNA synthesis. Promoters recognized by a variety of potential host cells are well known. Promoters suitable for use with prokaryotic hosts include the β-lactamase and lactose promoter systems; Chang et al., *Nature,* 275:615 (1978); Goeddel et al., *Nature,* 281:544 (1979); alkaline phosphatase, a tryptophan (trp) promoter system, Goeddel, *Nucleic Acids Res.,* 8:4057 (1980); EP 36,776; and hybrid promoters such as the tac promoter, deBoer et al., *Proc. Natl. Acad. Sci. USA,* 80:21–25 (1983). Promoters for use in bacterial systems also will contain a Shine-Dalgarno (S.D.) sequence operably linked to the DNA encoding a peptide of the invention.

Examples of suitable promoting sequences for use with yeast hosts include the promoters for 3-phosphoglycerate kinase, Hitzeman et al., *J. Biol. Chem.,* 255:2073 (1980) or other glycolytic enzymes, Hess et al., *J. Adv. Enzyme Reg.,* 7:149 (1968); Holland, *Biochemistry,* 17:4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Expression from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the polypeptides employable with the invention by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the coding sequence of a peptide of the invention, but is preferably located at a site 5' from the promoter. Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptides of the invention.

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen, (1990) Meth. Enzymol, 185:144–161), pRIT2T, pKK233-2, pDR540 and pPL-lambda. Prokaryotic host cells containing the expression vectors of the present invention include E. coli K12 strain 294 (ATCC NO. 31446), E. coli strain JM101 (Messing et al., (1981) Nucl. Acid Res., 9:309), E. coli strain B, E. coli strain 1776 (ATCC No. 31537), E. coli c600 (Appleyard, Genetics, 39: 440 (1954)), E. coli W3110 (F—, gamma-, prototrophic, ATCC No. 27325), E. coli strain 27C7 (W3110, tonA, phoA E15, (argF-lac)169, ptr3, degP41, ompT, kanr) (U.S. Pat. No. 5,288,931, ATCC No. 55,244), Bacillus subtilis, Salmonella typhimurium, Serratia marcesans, and Pseudomonas species.

For expression in yeast host cells, such as common baker's yeast or Saccharomyces cerevisiae, suitable vectors include episomally replicating vectors based on the 2-micron plasmid, integration vectors, and yeast artificial chromosome (YAC) vectors. Suitable host cells for expression also are derived from multicellular organisms.

For expression in insect host cells, such as Sf9 or hi five cells, suitable vectors include baculoviral vectors. For expression in plant host cells, particularly dicotyledonous plant hosts, such as tobacco, suitable expression vectors include vectors derived from the Ti plasmid of Agrobacterium tumefaciens.

Other preferred vectors can be constructed using standard techniques by combining the relevant traits of the vectors described above. Relevant traits include the promoter, the ribosome binding site, the gene of interest or gene fusion (the Z domain of protein A and gene of interest and a linker), the antibiotic resistance markers, and the appropriate origins of replication.

Still other methods, vectors, and host cells suitable for adaptation to the synthesis of the polypeptides of the invention in recombinant vertebrate cell culture are described in Gething et al., Nature, 293:620–625 (1981); Mantei et al., Nature, 281:40–46 (1979); EP 117,060; and EP 117,058.

C. Selection and Transformation of Host Cells

Host cells are transfected or transformed with the above-described expression or cloning vectors and cultured in conventional nutrient media modified as appropriate for inducing promoters, selecting transformants, or amplifying the genes encoding the desired sequences. General principles, protocols and practical techniques for maximizing the productivity of cell cultures can be found in Mammalian Cell Biotechnology: A Practical Approach, M. Butler, ed. (IRL Press, 1991) and Sambrook et al., infra.

Transfection refers to the taking up of an expression vector by a host cell whether or not any coding sequences are in fact expressed. Numerous methods of transfection are known to the ordinarily skilled artisan, for example, $CaCl_2$ or $CaPO_4$ precipitation, liposome-mediated and electroporation. Successful transfection is generally recognized when any indication of the operation of the vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, for example as described in section 1.82 of Sambrook et al., Molecular Cloning (2nd ed.), Cold Spring Harbor Laboratory, NY (1989), is generally used for prokaryotes or other cells that contain substantial cell-wall barriers. Infection with Agrobacterium tumefaciens is used for transformation of certain plant cells, as described by Shaw et al., (1983) Gene, 23:315 and WO 89/05859 published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., (1977) J. Bact., 130:946 and Hsiao et al., (1979) Proc. Natl. Acad. Sci. (USA), 76:3829. However, other methods for introducing DNA into cells such as by nuclear injection, electroporation, or by protoplast fusion may also be used.

The choice between transfection or transformation depends largely on the type of host cell used, using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456–457 (1978) can be employed. General aspects of mammalian cell host system transformations have been described in U.S. Pat. No. 4,399,216. Transformations into yeast are typically carried out according to the method of Van Solingen et al., J. Bact., 130: 946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, polycations, e.g., polybrene, polyornithine, or use of recombinant viral vectors, may also be used. For various techniques for transforming mammalian cells, see Keown et al., *Methods in Enzymology*, 185:527–537 (1990) and Mansour et al., *Nature*, 336:348–352 (1988).

Suitable host cells for expressing the DNA include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli* K12 strain MM294 (ATCC 31,446); *E. coli* X1776 (ATCC 31,537); *E. coli* strain W3110 (ATCC 27,325) and K5 772 (ATCC 53,635), *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may readily modified to turn of its endogenous genes in favor of expression of the heterologous sequence. For example, *E. coli* W3110 strain 1A2, which has the complete genotype tonA; *E. coli* W3110 strain 9E4, which has the complete genotype tonA ptr3; *E coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac)169 degP ompT rbs7 ilvG kan; *E. coli* W3110 strain 40B4, which is strain 37D6 with a non-kanamycin resistant degP deletion mutation; and an *E. coli* strain having mutant periplasmic protease disclosed in U.S. Pat. No. 4,946,83 issued 7 Aug. 1990.

In addition to prokaryotes, eukaryotic microbes such as filamentous fungi or yeast are suitable cloning or expression hosts for the vectors containing nucleic acid encoding the peptides of the invention. *Saccharomyces cerevisiae* is a commonly used lower eukaryotic host microorganism. Others include *Schizosaccharomyces pombe* (Beach and Nurse, *Nature* 290: 140 (1981); EP 139,383 published 2 May 1985); *Kluveromyces* hosts (U.S. Pat. No. 4,943,529; Fleer et al., *Bio/Technology* 2: 968–975 (1991)) such as, e.g., *K. lactis* (MW98-8C, CBS683, CBS4574; Louvencourt et al., *J. Bacteriol.* 154(2): 737 (1983); *K. fragilis* (ATCC 12,424), *K. bulgaricus* (ATCC 16,045), *K. wicheramii* (ATCC 24,178), *K. waltii* (ATCC 56,500), *K. drosopharum* (ATCC 36,906); Van den Berg et al., *Bio/Technology* 8: 135 (1990)), *K. thermotolerans*, and *K. marxianus; yarrowia* (EP 402,226); *Pichia pastoris* (EP 183,070); Sreekrishna et al., *J. Basic Microbiol.* 28: 265–278 (1988); *Candida; Trichoderma reesia* (EP 244,234); *Neurospora crassa* (Case et al., *Proc. Natl. Acad. Sci. USA*, 76:5259–5263 (1979); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.* 112: 284–289(1983); Tilburn et al., *Gene*, 26: 205–221 (1983); Yelton et al., *Proc. Natl. Acad. Sci. USA* 81: 1470–1474 (1984)) and *A. niger* (Kelly and Hynes, *EMBO J.* 4: 475–479 (1985)). Methylotropic yeasts are suitable herein and include, but are not limited to, yeast capable of growth on methanol selected from the genera consisting of *Hansenula, Cadida, Kloeckera, Pichia, Saccharomyces, Torulopsis*, and *Rhodotorula*. A list of specific species that are exemplary of this class of yeasts may be found in C. Anthony, *The Biochemistry of Methylotrophs* 269 (1982).

In addition to prokaryotes, filamentous fungi and yeasts, cells derived from multicellular organisms can be used as host cells. Examples of invertebrate cells include insect cells such as *Drosophila* S2 and *Spodoptera* Sf9 and hi five, as well as plant cells.

Examples of useful mammalian host cells include monkey kidney CV1 line transformed by SV40 (COS-7, ATCC CRL 1651); human embryonic kidney line (293 or 293 cells subcloned for growth in suspension culture, Graham et al., (1977) *J. Gen Virol.*, 36:59); baby hamster kidney cells (BHK, ATCC CCL 10); Chinese hamster ovary cells/-DHFR (CHO, Urlaub and Chasin, (1980) *Proc. Natl. Acad. Sci. USA*, 77:4216); mouse sertoli cells (TM4, Mather, (1980) *Biol. Reprod.*, 23:243–251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., (1982) *Annals N.Y. Acad. Sci.*, 383:44–68); MRC 5 cells; FS4 cells; and a human hepatoma cell line (Hep G2).

For expression in mammalian host cells, useful vectors include vectors derived from SV40, vectors derived from cytomegalovirus such as the pRK vectors, including pRK5 and pRK7 (Suva et al., (1987) *Science*, 237:893–896; EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

d. Detecting Gene Amplifciation/Expression

Gene amplification or expression may be measured in a sample directly, for example, by conventional Southern blotting or Northern blotting or RT-PCR (Taqman) to quantitate the transcription of mRNA, Thomas, *Proc. Natl. Acad. Sci. USA*, 77:5201–5205 (1980), dot blotting (DNA or RNA analysis), or in situ hybridization, using an appropriately labeled probe, based on the sequences provided herein.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a peptide of the invention or against a synthetic peptide based on the DNA sequences provided herein or against exogenous sequence fused to DNA encoding the peptide of the invention and encoding a specific antibody epitope.

e. Purification

Forms of the polypeptides employable with the present invention may be recovered from culture medium or from host cell lysates. If membrane-bound, they can be released from the membrane using a suitable detergent solution (e.g.

Triton®-X 100) or by enzymatic cleavage. Cells employed in expression of the polypeptide employable with the invention can be disrupted by various physical or chemical means, such as freeze-thaw cycling, sonication, mechanical disruption, or cell lysing agents. It may be desireable to purify a recombinantly produced peptide of the invention. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the polypeptide of the invention. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular peptide produced.

A variation on the above expression and purification procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide which can be secreted by the cell, making it possible to isolate and purify the desired peptide from the culture medium and eliminating the necessity of destroying the host cells which arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in insect cells as well as the subsequent purification of those gene products. Protein A fusions are often used because the binding of protein A, or more specifically the Z domain of protein A, to IgG provides an "affinity handle" for the purification of the fused protein. For example, a DNA sequence encoding the desired peptide ligand can be fused by site directed mutagenesis to the gene for a consensus domain of protein A known as the Z domain (Nilsson et al., (1987) *Protein Engineering* 1:107–113). After expression and secretion the fusion protein can be enzymatically cleaved to yield free peptide which can be purified from the enzymatic mix (see, e.g., Varadarajan et al., (1985) *Proc. Natl. Acad. Sci USA* 82:5681–5684; Castellanos-Serra et al., (1996) *FEBS Letters* 378:171–176; Nilsson et al., (1996) *J. Biotechnol.* 48:241–250).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein. Carter, in *Protein Purification: From Molecular Mechanisms to Large-Scale Processes*, Ladisch et al., eds. (American Chemical Society Symposium Series No. 427, 1990), Ch 13, pages 181–193.

Proteases such as Factor Xa, thrombin, and subtilisin or its mutants, and a number of others have been successfully used to cleave fusion proteins. Preferred according to the present invention for the production of peptide ligands of less than about 30 amino acids is the protease trypsin which is highly specific for Arg and Lys residues. Trypsin cleavage is discussed generally in Nilsson et al. (1996) *J. Biotech.* 48:241 and Smith et al., *Methods Mol. Biol.* 32:289. Typically, a peptide linker that is amenable to cleavage by the protease used is inserted between the "other" protein (e.g., the Z domain of protein A) and the desired peptide. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

The host cells referred to in this disclosure encompass cells in in vitro culture as well as cells that are within a host animal.

In cyclized embodiments of the invention, the recombinantly produced peptide can be cyclized by formation of an intramolecular disulfide bond as described above.

F. Research and Diagnostic Compositions

In a preferred embodiment, the peptides of the invention are non-covalently adsorbed or covalently bound to a macromolecule, such as a solid support. It will be appreciated that the invention encompasses both macromolecules complexed with the peptides. In general, the solid support is an inert matrix, such as a polymeric gel, comprising a three-dimensional structure, lattice or network of a material. Almost any macromolecule, synthetic or natural, can form a gel in a suitable liquid when suitably cross-linked with a bifunctional reagent. Preferably, the macromolecule selected is convenient for use in affinity chromatography. Most chromatographic matrices used for affinity chromatography are xerogels. Such gels shrink on drying to a compact solid comprising only the gel matrix. When the dried xerogel is resuspended in the liquid, the gel matrix imbibes liquid, swells and returns to the gel state. Xerogels suitable for use herein include polymeric gels, such as cellulose, cross-linked dextrans (e.g. Sepharose), agarose, cross-linked agarose, polyacrylamide gels, and polyacrylamide-agarose gels.

Alternatively, aerogels can be used for affinity chromatography. These gels do not shrink on drying but merely allow penetration of the surrounding air. When the dry gel is exposed to liquid, the latter displaces the air in the gel. Aerogels suitable for use herein include porous glass and ceramic gels.

Also encompassed herein are the peptides of the invention coupled to derivatized gels wherein the derivative moieties facilitate the coupling of the peptide ligands to the gel matrix and avoid steric hindrance of the peptide-ligand interaction in affinity chromatography. Alternatively, spacer arms can be interposed between the gel matrix and the peptide ligand for similar benefits.

In another embodiment, the invention provides fusion proteins in which a selected or desired polypeptide is fused at its N-terminus or its C-terminus, or at both termini, to one or more of the present peptides.

G. Pharmaceutical Compositions and Dosages

The peptides of the invention can be adminstered for the treatment of IgE-mediated disorders in the form of a pharmaceutical composition. Additionally, lipofections or liposomes can be used as a delivery vehicle.

Therapeutic formulations are prepared for storage by mixing the active ingredient having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

In order for the formulations to be used for in vivo administration, they must be sterile. The formulation may be rendered sterile by filtration through sterile filtration membranes, prior to or following lyophilization and reconstitution. The therapeutic compositions herein generally are placed into a container having a sterile access port, for example, an intravenous solution bag or vial having a stopper pierceable by a hypodermic injection needle.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The route of administration is in accordance with known and accepted methods, e.g., injection or infusion by intravenous, intraperitoneal, subcutaneous, intramuscular, intraarterial, intralesional or intraarticular routes, topical administration, by sustained release or extended-release means.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 4246.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. Microencapsulation of recombinant proteins for sustained release has been successfully performed with human growth hormone (rhGH), interferon-(rhIFN-), interleukin-2, and MN rpg 120. Johnson et al., *Nat. Med.* 2: 795–799 (1996); Yasuda et al., *Biomed. Ther.* 27: 1221–1223 (1993); Hora et al., *Bio/Technology* 8: 755–758 (1990); Cleland, "Design and Production of Single Immunization Vaccines Using Polylactide Polyglycolide Microsphere Systems," in *Vaccine Design: The Subunit and Adjuvant Approach*, Powell and Newman, eds., (Penum Press: New York, 1995), pp. 439–462; WO 97/03692; WO 96/40072; WO 96/07399; and U.S. Pat. No. 5,654,010.

The sustained-release formulations of these proteins may be developed using poly lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer", in *Biodegradable Polymers as Drug Delivery Systems* (Marcel Dekker; New York, 1990), M. Chasin and R. Langer (Eds.) pp. 141.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

When in vivo administration of the peptide of the invention are used, normal dosage amounts may vary from about 10 ng/kg up to about 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

H. Pulmonary Delivery

A particular route of administration of the present invention is in the aerosol or inhaled form. The compounds of the present invention, combined with a dispersing agent, or dispersant, can be administered in an aerosol formulation as a dry powder or in a solution or suspension with a diluent.

As used herein, the term "dispersant" refers to an agent that assists aerosolization of the compound or absorption of the protein in lung tissue, or both. Preferably the dispersant is pharmaceutically acceptable. As used herein, the term "pharmaceutically acceptable" means approved by a regulatory agency of the Federal or a state government or listed in the U.S. Pharmacopeia or other generally recognized pharmacopeia for use in animals, and more particularly in humans. Suitable dispersing agents are well known in the art, and include but are not limited to surfactants and the like. For example, surfactants that are generally used in the art to reduce surface induced aggregation of the compound, especially the peptide compound, caused by atomization of the solution forming the liquid aerosol may be used. Nonlimiting examples of such surfactants include polyoxyethylene fatty acid esters and alcohols, and polyoxyethylene sorbitan fatty acid esters. Amounts of surfactants used will vary, being generally within the range or 0.001 and 4% by weight of the formulation. In a specific aspect, the surfactant is polyoxyethylene sorbitan monooleate or sorbitan trioleate. Suitable surfactants are well known in the art, and can be selected on the basis of desired properties, depending on the specific formulation, concentration of the compound, diluent (in a liquid formulation) or form of powder (in a dry powder formulation), etc.

Moreover, depending on the choice of the compound, the desired therapeutic effect, the quality of the lung tissue (e.g., diseased or healthy lungs), and numerous other factors, the liquid or dry formulations can comprise additional components, as discussed further below.

The liquid aerosol formulations generally contain the compound and a dispersing agent in a physiologically acceptable diluent. The dry powder aerosol formulations of the present invention consist of a finely divided solid form of the compound and a dispersing agent. With either the liquid or dry powder aerosol formulation, the formulation must be aerosolized. That is, it must be broken down into liquid or solid particles in order to ensure that the aerosolized dose actually reaches the alveoli. In general the mass median dynamic diameter will be 5 micrometers or less in order to ensure that the drug particles reach the lung alveoli (Wearley, L. L., 1991, Crit. Rev. in *Ther. Drug Carrier Systems* 8:333). The term "aerosol particle" is used herein to describe the liquid or solid particle suitable for pulmonary administration, i.e., that will reach the alveoli. Other considerations such as construction of the delivery device, additional components in the formulation and particle characteristics are important. These aspects of pulmonary administration of a drug are well known in the art, and manipulation of formulations, aerosolization means and construction of a delivery device require at most routine experimentation by one of ordinary skill in the art.

With regard to construction of the delivery device, any form of aerosolization known in the art, including but not limited to nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellent. The propellent may be any propellant generally used in the art. Specific nonlimiting examples of such useful propellants are a chloroflourocarbon, a hydrofluorocarbon, a hydochlorofluorocarbon, or a hydrocarbon, including triflouromethane, dichlorodiflouromethane, dichlorotetraflouroethanol, and 1,1,1,2-tetraflouroethane, or combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the compound reaches the lung, a number of formulation-dependent factors effect the drug absorption. It will be appreciated that in treating a disease or disorder that requires circulatory levels of the compound, such factors as aerosol particle size, aerosol particle shape, the presence or absence of infection, lung disease or emboli may affect the absorption of the compounds. For each of the formulations described herein, certain lubricators, absorption enhancers, protein stabilizers or suspending agents may be appropriate. The choice of these additional agents will vary depending on the goal. It will be appreciated that in instances where local delivery of the compounds is desired or sought, such variables as absorption enhancement will be less critical.

1. Liquid Aerosol Formulations

The liquid aerosol formulations of the present invention will typically be used with a nebulizer. The nebulizer can be either compressed air driven or ultrasonic. Any nebulizer known in the art can be used in conjunction with the present invention such as but not limited to: Ultravent, Mallinckrodt, Inc. (St. Louis, Mo.); the Acorn II nebulizer (Marquest Medical Products, Englewood Colo.). Other nebulizers useful in conjunction with the present invention are described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for protein stabilization or for the regulation of osmotic pressure. Examples of the agents include but are not limited to salts, such as sodium chloride, or potassium chloride, and carbohydrates, such as glucose, galactose or mannose, and the like.

2. Aerosol Dry Powder Formulations

It is also contemplated that the present pharmaceutical formulation will be used as a dry powder inhaler formulation comprising a finely divided powder form of the compound and a dispersant. The form of the compound will generally be a lyophilized powder. Lyophilized forms of peptide compounds can be obtained through standard techniques.

In another embodiment, the dry powder formulation will comprise a finely divided dry powder containing one or more compounds of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

I. Methods of Treatment

1. IgE Mediated Disorders

Allergy refers to certain diseases in which immune responses to environmental antigens cause tissue inflammation and organ dysfunction. An allergen is any antigen that causes allergy. As such, it can be either the antigenic molecule itself or its source, such as pollen grain, animal dander, insect venom, or food product. Described below are various IgE-mediated disorders.

Atopic Diseases:

Atopy refers to an inherited propensity to respond immunologically to many common naturally occuring inhaled and ingested antigens with the continual production of IgE antibodies. Allergic rhinitis and allergic asthma are the most common manifestations of clinical disease following exposure to environmental antigens. Atopic dermatitis is less common. Allergic gastroenteropathy is rarer still and may be transient. Two or more of these clinical diseases can coexist in the same patient at the same time or at different times during the course of the illness. Atopy can also be asymptomatic. IgE antibodies can also cause the nonatopic allergic diseases anaphylaxis and urticaria-angioedema—discussed further below.

Other disorders believed to be IgE-mediated include allergic bronchopulmonary aspergillosis, parasitic infection, hyper-IgE syndrome, ataxia-telangiectasia, Wiskott-Aldrich syndrome, thymic alymphoplasia, IgE myeloma and graft-versus-host reaction.

Both mast cells and basophils have high-affinity IgE cell membrane receptors for IgE (FcεRI). Mast cells are abundant in the mucosa of the respiratory and gastrointestinal tract as well as the skin, where atopic reactions localize. The physiologic effects of the mediators released or activated immunologically by these cells are responsible for the functional and pathologic features of the immediate and late phases of atopic diseases. The important mediators of IgE allergy are histamine, chemotactic factors, prostaglandins, leukotrienes, and platelet-activating factor.

The site of antigen-antibody contact can vary. For example, in allergic rhinoconjunctivitis, the reaction occurs at the local tissue level. Contact with allergenic particles, such as pollen grains, fungus spores, dust or skin scales from a pet is followed promptly by absorption of soluble allergenic protein at the mucosal surface. At this location, the allergen-specific IgE antibody on the mucosal mast cell reacts with allergen, causing prompt mediator release and clinical symptoms. In asthma, it is not clear whether the bronchial reaction is caused by the inhalation of smaller particles capable of reaching the lower respiratory airways, or whether allergic asthma is initiated by soluble allergen reaching the bronchial mucosa through the circulation. In atopic dermatitis, ingestion of allergenic food can flare the skin lesions, in which case exposure to the allergen must be via the circulation. The dermatitis can also be activated by direct topical exposure in instances of house dust mite allergy.

Atopic patients typically have multiple allergies; they have IgE antibodies to and symptoms from many environmental allergens. While the total serum IgE level is higher on the average in the atopic population than in a comparable nonatopic population, there is sufficient overlap between the two that a normal IgE level does not rule out the diagnosis of atopy. In general, total serum IgE is higher in patients with allergic asthma than in those with allergic rhinitis and higher still in those with atopic dermatitis. Diseases associated with elevated levels of IgE include allergic rhinitis, allergic asthma, atopic dermatitis, allergic bronchopulmonary aspergillosis, parasitic diseases, hyper-IgE syndrome, ataxia-telangiectasia, Wilkott-Aldrich syndrome, thymic alymphoplasia, IgE myeloma, graft-versus-host reaction.

Allergens responsible for atopic disease are derived primarily from natural airborne organic particles, especially plant pollens, fungal spores, and animal and insect debris as well as ingested food. The ability of various pollens, molds or foods to sensitize IgE various, such that some environmental allergens are intrinsically more sensitizing than others.

Typical allergenic pollens are from wind-pollinated (anemophilous) flower plants rather than insect-pollinated (entomophilous) plants. Allergenic pollen grains are mostly spherical and 15–50 μm in diameter. Representative examples include club moss, ferns, conifers, flowering plants, grasses, sedges, palms, cattails, needles, beeches, chemopods, sorrels, willows, poplars, maples, ashes, ragweeds and sages.

Molds growth is proportional to temperature and humidity. Mold can reproduce sexually or asexually, producing airborne spores, some of which are allergenic. While fungal spores are important cause of allergy in atopic patients, it is often under recognized because of the confusing taxometry and the enormous biologic complexity of fungi in their morphologic, reproductive and ecological behavior. Common fungal aeroallergens include: Basidiomycetes (e.g., *Ustilgo, Ganoderma, Alternaria, Cladosporium, Aspergillus, Sporobolomyces, Penicillium, Epicoccum, Fusarium, Phoma, Botrytis, Helminthosporium, Stemphylium, Cephalosporium*), Phycomycetes (e.g., *Mucor, Rhizopus*) and Ascomycetes (e.g., *Eurotium, Chaetomium*).

Dust and house mites are also significant atopic allergens. While there are more than 50,000 species of mites, the dust mites *Dermatophagoides pteronyssinus* and *D. farinae* are the most common. These tiny arachnids are barely visible to the naked eye, and are found in house dust samples throughout the world, but are more prevalent in warm, humid climates. They are especially abundant in bedding, upholstery and blankets, where desquamated human skin cells are most likely to be found. IgE levels and environmental exposure to these allergens is highly correlative with atopic asthma and dermatitis because exposure occurs by inhalation and dermal contact, respectively.

Other allergenic mites include *Euroglyphus maynei, Lepidoglyphus destructor* and *Acarus siro*, all of which are storage mites that infest grains—and may cause occupational allergy in grain handlers. Additionally, atopy can be caused by cockroaches which can be prevalent in homes and restaurants, especially those where there is overcrowding and poor hygiene. Additional endemic causes of respiratory allergy include the emanations and debris from seasonal swarms of insects such as mayflies, caddis fly and Lepidoptera. Animals or pets (e.g., dogs, cats, horses, rats, mice) can also be the cause of allergy through dander, saliva, urine or feces.

Allergenic components of food can induce IgE antibodies responsible for either atopic or nonatopic reactions. IgE antibodies to foods frequently exist in atopic patients without causing any reaction when the food is eaten. The factors which operate to convert asymptomatic activity to symptomatic activity are currently unknown. While any food is capable of causing allergy, certain foods are more likely to be allergenic than others. For example, fish, crustaceans and mollusks are an important cause of anaphylaxis and anaphylactoid reactions. The allergenicity of a particular food can be changed by heating or cooking.

Anaphylaxis and Urticaria

While atopic diseases are characterized by a genetic predisposition to the production of IgE antibodies common to environmental allergens, IgE can also cause the nongenetic allergic disorders analphylaxis and urticaria. While the immunologic pathogenesis of all IgE-mediated diseases is the same, the differences between atopic and nonatopic disease are directed around the mode of allergen exposure, genetic factors influencing etiology, diagnostic methods, prognosis and treatment.

Anaphylaxis:

Anaphylaxis is an acute, generalized allergic reaction with simultaneous involvement of several organ systems, usually cardiovascular, respiratory, cutaneous and gastrointestinal. The reaction is immunologically mediated, and it occurs on exposure to an allergen to which the subject had been previously sensitized. Anaphylactic shock refers to anaphylaxis in which hypotension, with or without loss of consciousness occurs. Anaphylactoid reaction is a condition in which the symptoms and signs of anaphylaxis occur in the absence of an allergen-antibody mechanism. In this case, the endogenous mediators of anaphylaxis are released in vivo through a nonimmunologic mechanism.

The immunologic pathogenesis of anaphylaxis requires the presence of both IgE and exposure to the allergen. Anaphylaxis is the sudden, systemic result of the allergen-IgE mast cell-mediator release, which results in a sudden profound and life-threatening alteration in the functioning of the various vital organs. Vascular collapse, acute airway obstruction, cutaneous vasodilation and edema and gastrointestinal and genitourinary muscle spasm occur almost simultaneously.

In anaphylactic shock, the hypotension and shock result from generalized vasodilation of arterioles and increased vascular permeability with rapid transudation of plasma through postcapillary venules. This shift of fluid from intravascular to extravascular spaces produces hypovolemic shock with edema (angioedema) in skin and various visceral organ, pooling of venous blood (especially in the splanchnic bed), hemoconcentration, and increased blood viscosity. Low cardiac output diminishes cardiac return and produces inadequate coronary artery perfusion. Low peripheral vascular resistance can lead to myocardial hypoxia, dysrhythmias, and secondary cardiogenic shock. Stimulation of histamine $H_1$ receptors in coronary arteries may cause coronary artery spasm. Some patients may even experience anginal chest pain and occasionally, myocardial infarction during anaphylaxis. After a prolonged period of shock, organ failure elsewhere may ensue, particularly the kidneys and central nervous system.

The bronchial muscle spasm, edema and eosinophilic inflammation of the bronchial mucosa, and hypersecretion of mucus into the airway lumen occur in some patients with anaphylaxis, and are indistinguishable from an acute asthma attack. The primary bronchoconstrictors are histamine, which preferentially affects the larger proximal airways and leukotrienes, which affect the peripheral airways. Airway obstruction leads to impairment of gas exchange with hypoxia, further compounding the vascular effects of anaphylaxis. If left untreated, acute cor pulonale and respiratory failure may occur. Histamine also acts upon gastrointestinal and uterine smooth muscle, causing painful spasm.

The allergens responsible for anaphylaxis are different from those commonly associated with atopy. They are usually encountered in a food, a drug or insect sting. Since food and insect venoms are complex mixtures of many potential allergens, only a few of these allergens have been identified chemically. Moreover, the same allergen of allergenic epitope may exist naturally in more than one food, drug or venom, resulting in cross-reactivity. Foods which are known to cause analphylaxis include: lobster, shrimp, crab, clams, fish, peanuts, peas, beans, licorice, sesame, cottonseed, caraway, mustard, flaxseed, sunflower, nuts, berries, egg white (albumin), buckwheat and milk.

Drugs associated with anaphylaxis include hormones (e.g., insulin, parathormone, adrenocorticotropic hormone, vasopressin, relaxin), enzymes (e.g., trypsin, chymotrypsin, chymopapain, penicillinase, asparaginase), vaccines, toxoids, allergy extracts, polysaccharides (e.g., dextran, iron-dextran and acacia) and various haptenic drugs, including certain antibiotics (e.g., penicillin, streptomycin, cephalosporin, tetracycline, amphotericin B, nitrofurantoin), diagnostic agents (e.g., sulfobromophthalein, sodium dehydrocholate), vitamins (e.g., thiamine, folic acid), and barbituates, diazepan, phenyloin, protamine, aminopyrine, and acetylcysteine).

Insect venoms associated with anaphylaxid include honeybee (*Apis mellifera*), yellow jacket (*Vespula*), hornet (*Dolichovespula*), wasp (*Polistes*) and fire ant (*Solenopsis*). Additional allergens include semen and latex.

Urticaria and Angioedema:

Urticaria (also known as hives) and angioedema (also known as angioneurotic edema) can be considered a single illness characterized by vasodilation and increased vascular permeability of the skin (urticaria) or subcutaneous tissue (angioedema). It is a localized cutaneous form of anaphylaxis and is one of the manifestations of systemic anaphylaxis. IgE operates in a manner similar in the pathogenesis of urticaria as with systemic anaphylaxis, and the causative allergens are very similar. Idiopathic (nonallergic) urticaria-angioedema is analogous to the anaphylactoid reaction. In contrast to anaphylaxis, urticaria is a benign condition and is much more common.

Urticaria and angioedema are the visible manifestations of localized cutaneous or subcutaneous edema from the increased permeability of blood vessels, probably postcapillary venules. Acute urticaria and angioedema likely have an allergic cause. In these cases, allergen-specific IgE antibody fixed to local mast cells triggers meditor release or activate when allergen is encountered. Idiopathic urticaria-angioedema and various physical urticaria lack and allergen-antibody etiology. The precise means by which cutaneous mast cells are stimulated under these circumstances is unknown.

Urticaria appears as multiple areas of well-demarcated edematous plaques that are intensely pruritic. They are either white with surrounding erythema or red with blanching when stretched. Individual lesions vary in diameter from a few millimeters to many centimeters and are circular or serpiginous. Angioedema appears as diffuse areas of nondependent, nonpitting swelling without pruritis, with predilection for the face, especially the periorbital and perioral areas. Swelling can occur in the mouth and pharynx as well.

Ingested allergens are more frequently the cause of urticaria than are those which are inhaled. Any food or drug can cause hives. Occult sources of drugs including proprietary medications, such as laxatives, headache remedies and vitamin preparations can be allergenic. Urticaria can also be caused by cold, heat, exercise or emotional distress.

Gastrointestinal Diseases

The gastrointestinal tract is a location of intense immunological activity. The gastrointestinal lumen contains a complex mixture of harmless and necessary microbial flora, potential pathogens, and large quantities of complex macromolecules capable of eliciting immune responses. The mucosal immune system has evolved mechanisms to downregulate immune responses to harmless flora and food antigens while eliciting protective responses to pathogens.

Gluten-sensitive enteropathy (Celiac disease) is a disease of the small intestine that is characterized by villous atrophy and malabsorption caused by hypersensitivity to cereal grain storage proteins (gluten or gliadin) found in wheat, barley and rye. The inflammatory lesions are restricted primarily to the small-intestine mucosa, with the most severe changes being in the area most often in contact with ingested gluten, the proximal small intestine. The disease usually begins with subepithelial edema and thickening of the basement membrane followed by an influx of inflammatory cells. These inflammatory cells are typically polymorphonuclear leukocytes, which are soon replaced by lymphocytes and plasma cells. Although IgE plasma cells increase in number and continue to predominate, there is a disproportionate increase in IgG plasma cells. In contrast, few of any IgE plasma cells appear.

In contrast, non-gluten sensitive food hypersensitivity is an IgE-mediated hypersensitivity with symptoms very similar to those of the gluten-sensitive variety. In one type of IgE-mediated food hypersensitivity, a localized allergic reaction in the gastrointestinal tract is associated with generalized allergic symptoms. Exposure to the food allergen increases mucosal IgE plasma cells and mast cell degranulation, leading to severe protein-losing enteropathy. Elimination of the offensive food from the diet effectively remediates the disease.

In a second type of hypersensitivity, clinical symptoms are virtually identical to those observed in the gluten-sensitive food hypersensitivity: villous atrophy and malabsorption. This condition is more or less limited to young children and is most frequently caused by cow's milk. However, soy, egg and wheat proteins have also been implicated. The condition frequently occurs after a gastrointestinal infection and resolves spontaneously after the age of three years.

Inflammatory Bowel Disease (IBD) is the term generally applied to diseases of the bowel that cause inflammation and/or ulceration. For example, Crohn's disease, ulcerative colitis, indeterminate colitis and infectious colitis.

Crohn's disease (also known as regional enteritis or ulcerative colitis) is also a chronic inflammatory disease of unknown etiology, but unlike ulcerative colitis, it can affect any part of the bowel. The most prominent feature of this disease is the granular, reddish-purple edmatous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of the disease may be continuous or relapsing, mild or severe, but unlike ulcerative colitis, it is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

Anti-inflammatory drugs sulfasalazine and 5-aminosalisylic acid (5-ASA) are useful for treating mildly active colonic Crohn's disease and is commonly prescribed to maintain remission of the disease. Metroidazole and ciprofloxacin are similar in efficacy to sulfasalazine and appear to be particularly useful for treating perianal disease. In more severe cases, corticosteroids are effective in treating acute exacerbations and can even maintain remission. Azathioprine and 6-mercaptopurine have also shown success in patients who require chronic administration of cortico steroids. It is also possible that these drugs may play a role in the long-term prophylaxis. Unfortunately, there can be a very long delay (up to six months) before onset of action in some patients.

Antidiarrheal drugs can also provide symptomatic relief in some patients. Nutritional therapy or elemental diet can improve the nutritional status of patients and induce symtomatic improvement of acute disease, it does not induce sustained clinical remissions. Antibiotics are used in treating secondary small bowel bacterial overgrowth and in treatment of pyogenic complications. Ulcerative colitis (UC) is a chronic inflammatory disease of unknown etiology afflicting the large intestine. The course of the disease may be continuous or relapsing, mild or severe. The earliest lesion is an inflammatory infiltration with abscess formation at the base of the crypts of Lieberkühn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical feature of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

Treatment for UC includes sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

Mucositus is characterized by ulcerative breakdown of the mucosal epithelial tissue, and is literally defined as inflammation of the mucous membrane. The pathophysiology of mucositis is complex and involves a cascade of interactions among cells, cytokines and the oral microflora. The underlying premise for susceptibility of the mucosa of the oropharynx and gastrointestinal tract to chemotherapy or radiation damage is related to rapid epithelial stem cell turnover. Mucositis can be described as occurring in four phases: (1) Early inflammatory phase characterized by the release of inflammatory cytokines in response to local tissue damage caused by cytotoxic agent(s); (2) Epithelial phase characterized by the death of basal cells, to an extent which hinders the repopulation of the epithelium; (3) Infectious phase characterized by local invasion of microflora resulting in an inflammatory response to the local infection. This inflammation results in additional local tissue damage and possibly erosive ulceration; and (4) Healing phase characterized by resolution of the infection and regeneration of the epithelium.

Oral mucositis produces the following clinical signs and symptoms resulting from cellular damage: (1) sensation of dryness; (2) asymptomatic redness and erythema; (3) solitary white elevated desquamative patches which are painful to the touch; (4) large, painful, contiguous pseudomembranous lesions associated with dysphagia and decreased oral intake. These spontaneously painful lesions histopathologically show loss of epithelial cells to the basement membrane, which exposes the connective tissue stroma with its associated innervation.

Gastroinestinal mucositis results with the clinical signs and symptoms of tenesmus (painful ineffectual straining during defecation), pain, bleeding, diarrhea, telangectasia (neovascularization), and progression to ulceration. Early signs of diarrhea include increased stool frequency, loose or watery stool, food aversion, increased bowel sounds, abdominal pain, and some loss of skin turgo indicative of dehydration. When the diarrhea is severs it may be associated with mucosal ulceration, bleeding, intestinal performation and proctitis. Stool exam may reveal occult blood and fecal leukocytes.

Necrotizing enterocolitis is an inflammatory disease of unknown etiology that afflicts between 1–5% of all infants admitted to neonatal intensive care units, most of whom are premature infants. Signs and symptoms include abdominal distention, gastrointestinal hemorrhage, and feeding intolerance. The disease most often involves the ileium and colon, and is characterized by loss of epithelium and submucosal edema, ulcerations, and in severe cases, transmural necrosis.

2. Additional Immune Related Disorders

It is contemplated that the peptides of the present invention may be used to treat various other immune-related disorders. Exemplary other immune-related conditions or disorders contemplated herein include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, immunologic diseases of the lung such as eosinophilic pneumonias, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. These antibodies either directly or indirectly mediate tissue injury. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that affects the synovial membrane of multiple joints and which results in injury to the articular cartilage. The pathogenesis is associated with the production of rheumatoid factors, auto-antibodies directed against endogenous proteins, with the resultant formation of immune complexes that attain high levels in joint fluid and blood. These complexes may induce infiltration by lymphocytes, monocytes, and neutrophils into the synovial compartment. Tissues affected are primarily the joints, often in symmetrical pattern. However, disease outside the joints occurs in two major forms. In one form, typical lesions are pulmonary fibrosis, vasculitis, and cutaneous ulcers. The second form is the so-called Felty's syndrome which occurs late in the RA disease course, sometimes after joint disease has become quiescent, and involves the presence of neutropenia, thrombocytopenia and splenomegaly. This can be accompanied by vasculitis in multiple organs and occurrence of infarcts, skin ulcers and gangrene. Patients often also develop rheumatoid nodules in the subcutis tissue overlying affected joints; in late stages, the nodules have necrotic centers surrounded by a mixed inflammatory cellular infiltrate. Other manifestations which can occur in RA include: pericarditis, pleuritis, coronary arteritis, intestitial pneumonitis with pulmonary fibrosis, keratoconjunctivitis sicca, and rheumatoid nodules.

Juvenile chronic arthritis is a chronic idiopathic inflammatory disease which begins often at less than 16 years of age and which has some similarities to RA. Some patients which are rheumatoid factor positive are classified as juvenile rheumatoid arthritis. The disease is sub-classified into three major categories: pauciarticular, polyarticular, and systemic. The arthritis can be severe and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin which is likely induced by an active inflammatory process. Scleroderma can be localized or systemic. Vascular lesions are common, and endothelial cell injury in the microvasculature is an early and important event in the development of systemic sclerosis. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs may also be involved. In the gastrointestinal tract, smooth muscle atrophy and fibrosis can result in abnormal peristalsis/motility. In the kidney, concentric subendothelial intimal proliferation affecting small arcuate and interlobular arteries can result in reduced renal cortical blood flow and thus proteinuria, azotemia and hypertension. In skeletal and cardiac muscle, atrophy, interstitial fibrosis/scarring, and necrosis can occur. Finally, the lung can have interstitial pneumonitis and interstitial fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components involved in protein synthesis.

Sjögren's syndrome is the result of immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc, particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or Fc-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Diabetes mellitus is a genetic disorder of metabolism of carbohydrate, protein and fat associated with a relative or absolute insufficiency of insulin secretion and with various degrees of insulin resistance. In its fully developed clinical expression, it is characterized by fasting hyperglycemia and in the majority of long-standing patients by atherosclerotic and microangiopathic vascular disease and neuropathy. Differences between various forms of the disease are expressed in terms of cause and pathogenesis, natural history, and response to treatment. Thus, diabetes is not a single disease but a syndrome.

Type I, or insulin-dependent diabetes mellitus (IDDM) occurs in approximately 10 percent of all diabetic patients in the Western world. Type I diabetes mellitus or insulin-dependent diabetes is the autoimmune destruction of pancreatic islet β-cells; this destruction is mediated by auto-antibodies and auto-reactive T cells. Antibodies to insulin or the insulin receptor can also produce the phenotype of insulin-non-responsiveness.

Classically, this type of disease occurs most commonly in childhood and adolescence; however, it can be recognized and become symptomatic at any age. In the most common type of IDDM (Type IA), it has been postulated that environmental (acquired) factors such as certain viral infections, and possibly chemical agents, superimposed on genetic factors, may lead to cell-mediated autoimmune destruction of β cells. Thus, genetically determined abnormal immune responses (linked to HLA associations) characterized by cell mediated and humoral autoimmunity are thought to play a pathogenetic role after evocation by an environmental factor. A second type of IDDM (Type IB) is believed to be due to primary autoimmunity. These patients have associated autoimmune endocrine diseases such as Hashimoto's thyroiditis, Graves' disease, Addison's disease, primary gonadal failure, and associated nonendocrine autoimmune diseases such as pernicious anemia, connective tissue diseases, celiac disease and myasthenia gravis. Insulin dependency implies that administration of insulin is essential to prevent spontaneous ketosis, coma, and death. However, even with insulin treatment, diabetic patients can still have many of the additional problems associated with diabetes, i.e. connective tissue disorders, neuropathy, etc.

The second type of diabetes, Type II or non-insulin-dependent diabetes mellitus (NIDDM), present in approximately 90% of all diabetics, also has a genetic basis. Patients with type II diabetes may have a body weight that ranges from normal to excessive. Obesity and pathological insulin resistance are by no means essential in the evolution of NIDDM. In the majority of patients with NIDDM, a diagnosis is made in middle age. Patients with NIDDM are non-insulin-dependent for prevention of ketosis, but they may require insulin for correction of symptomatic or non-symptomatic persistent fasting hyperglycemia if this cannot bye achieved with the use of diet or oral agents. Thus, therapeutic administration of insulin does not distinguish between IDDM and NIDDM. In some NIDDM families, the insulin secretory responses to glucose are so low that they may resemble those of early Type I diabetes at any point in time. Early in its natural history, the insulin secretory defect and insulin resistance may be reversible by treatment (i.e., weight reduction) with normalization of glucose tolerance. The typical chronic complications of diabetes, namely macroangiopathy, microangiopathy, neuropathy, and cataracts seen in IDDM are seen in NIDDM as well.

Other types of diabetes include entities secondary to or associated with certain other conditions or syndromes. Diabetes may be secondary to pancreatic disease or removal of pancreatic tissue; endocrine diseases such as acromegaly, Cushing's syndrome, pheochromocytoma, glucagonoma, somatostatinoma, or primary aldosteronism; the administration of hormones, causing hyperglycemia; and the administration of certain drugs (i.e. antihypertensive drugs, thiazide diuretics, preparations containing estrogen, psychoactive drugs, sympathomimetic agents). Diabetes may be associated with a large number of genetic syndromes. Finally, diabetes may be associated with genetic defects of the insulin receptor or due to antibodies to the insulin receptor with or without associated immune disorders.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus, other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including multiple sclerosis; idiopathic demyelinating polyneuropathy or Guillain-Barre syndrome; and Chronic Inflammatory Demyelinating Polyneuropathy, are believed to have an autoimmune basis and result in nerve demyelination as a result of damage caused to oligodendrocytes or to myelin directly. Multiple sclerosis is a demyelinating disease that involves T lymphocytes, and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions.

Inflammatory and fibrotic lung disease, including eosinophilic pneumonias, idiopathic pulmonary fibrosis, and hypersensitivity pneumonitis may involve a disregulated immune-inflammatory response. Inhibition of that response would be of therapeutic benefit and within the scope of the invention.

Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e., as from chemotherapy) immunodeficiency, and neoplasia.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatis.

The compounds of the present invention, e.g. polypeptides or antibodies, are administered to a mammal, preferably a human, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation (intranasal, intrapulmonary) routes.

It may be desirable to also administer antibodies against other immune disease associated or tumor associated antigens, such as antibodies which bind to CD20, CD11a, CD 40, CD18, ErbB2, EGFR, ErbB3, ErbB4, or vascular endothelial growth factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the polypeptides of the invention are coadministered with a growth inhibitory agent. For example, the growth inhibitory agent may be administered first, followed by a polypeptide of the invention. However, simultaneous administration or administration first is also contemplated. Suitable dosages for the growth inhibitory agent are those presently used and may be lowered due to the combined action (synergy) of the growth inhibitory agent and the polypeptide of the invention.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

J. Articles of Manufacture

In another embodiment of the invention, an article of manufacture containing materials useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition comprises a peptide of the invention. The composition can further comprise any or multipe ingredients disclosed herein. The instruction on, or associated with, the container indicates that the composition is used for diagnosing or treating the condition of choice. For example, the instruction could indicate that the composition is effective for the treatment of an IgE-mediated disorder. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, (e.g., such as those described herein) filters, needles, syringes, and package inserts with instructions for use.

EXAMPLES

Example 1

IgE Receptor Binding Selection with Phase Displayed Peptide-g8 Libraries

A series of peptide libraries were assembled for display on M13 filamentous phage. Each peptide library consisted of random sequences, 18–20 residues in length and fused to the N-terminus of gene-8 protein (g8p), the major coat protein of M13 filamentous phage. Phagemid construction which allows for polyvalent display of the peptide libraries as g8p polypeptide fusions is described in Lowman et al., (1998) *Biochemistry* 37, 8870–8878 (1998) and Sidhu et al., (2000) *Methods Enzymol.* 328:333–363. Nine of the ten libraries contained a fixed pair of cysteine residues, with the form $X_iCX_jCX_k$, with i, j, and k varying. Two of these libraries also contained a fixed Gly-Pro sequence within the cysteine pair. One library contained only 20 randomized residues and no fixed cysteine pair. The diversity of the libraries based on the number of transformants into XL-1 Blue *E. coli* was on the order of $10^8$.

These libraries were pooled into four groups prior to selection. Group 1 consisted of library 300 (SGTACX$_2$GPX$_4$CSLAGSP) (SEQ ID NO:93); group 2 consisted of library 301 ($X_4CX_2GPX_4CX_4$) (SEQ ID NO:17); group 3 consisted of library 302 ($X_{20}$)(SEQ ID NO:101); and group 4 consisted of libraries 303–309 ($X_7CX_4CX_7$, $X_7CX_5CX_6$, $X_6CX_6CX_6$, $X_6CX_7CX_5$, $X_5CX_8CX_5$, $X_5CX_9CX_4$, $X_4CX_{10}CX_4$)(SEQ ID NOs: 94–100), respectively. Phage particles were purified twice by PEG precipitation and resuspended in 1.0 mL of phosphate buffer saline (PBS).

Binding selections were carried out with a bivalent fusion protein, FcεRI-IgG (Genentech, Inc.), consisting of the extracellular domain of FcεR Ifused to the Fc domain of IgG and produced from CHO cells. For phage binding selections, 96-well immunosorbant plates were coated with FcεRI-IgG and blocked with PBS containing 0.5% BSA. The coating was performed by passive absorption with a 2 ug/mL solution of FcεRI-IgG in PBS. For binding selections, the phage concentration was determined by OD 268 (1 OD=$1.13 \times 10^{13}$ phage/mL) and then diluted to as concentration of $1 \times 10^{11}$ phage/mL in phage selection buffer (PBTT): PBS with 0.5% bovine serum albumin (BSA), 0.05% Tween 20 and 0.005% Triton X-1.00. 100 ul of the diluted phage was added to 8 wells of a 96 well microtiter Maxisorp plate, coated as described above. In order to reduce the number of phage peptides binding to the IgG-Fc region of the FcεRI-IgG, a 25 ug/mL solution of an IgG1 humanized monoclonal antibody was also added to the phage selection buffer. The plate was incubated at room temperature for 2–3 hours. Each well was washed 10 times with PBS containing 0.05% Tween 20 (PBT) to remove non-binding phage particles. The bound phage was eluted with 0.2 M Glycine pH 2.0 for 7 minutes and neutralized with 1 M Tris Base. Half of the eluted pool was used to re-infect XL-1 *E. coli* cells for subsequent rounds of selection. Several rounds of binding selection and propagation were performed, with monitoring of selection by colony counting to determine enrichment factors at each round. Following the third, fourth and fifth round of panning, the pools were assessed for enrichment ratios (see e.g., Lowman, *Methods Mol. Biol.* 87, 249–264 (1998)), that is, the ratio of clones which specifically bind receptor versus those which bind the non-specific blocking agent, bovine serum albumin (BSA). Only pool 2 (#301, $X_4CX_2GPX_4CX_4$) (SEQ ID NO:17) showed a higher FcεRI-IgG receptor to BSA binding ratio with values of 15, 666 and 325 in the 3rd, 4th and 5th rounds, respectively. The others, pool 1 (#300), pool 3 (#302), and pool 4 (#303–309), showed no significant increase in the binding ratio of clones binding to FcεRI versus those binding to BSA and therefore were not considered as a source of possible candidates for further analysis.

a) Sequence of Selected Peptide Phage Clones.

To determine the sequences of selected peptide-phage clones, log-phase XL-1 Blue *E. coli* (Stratagene) was infected by phage and grown overnight in 5.0 mL of 2YT broth, carbenicillin and VCSM helper phage. The phage containing supernatant was purified by PEG precipitation and resuspended in 100 uL of PBS. The phage were heated for 5 minutes at 95° C. and centrifuged. Single stranded DNA template was isolated from the supernatant and used for sequencing using the standard SequenaseJ (USB) procedure. Oligonucleotide 687 which anneals ~80 bp upstream of the peptide encoding region was used as the sequencing primer.

Single stranded DNA was isolated from the positive binding clones and sequenced to determine the phage displayed peptide sequence and also the frequency of each clone. Clones following three rounds of selection had sequences (see Table 1) MGTLCLEGPEGWFCIESA (SEQ ID NO:1), QEWTCVEGPRGWECIAVL (SEQ ID NO:2), DGSLCFEGPWGWICQSDG (SEQ ID NO:3) and TGEACVEGPGAWVCCLEP (SEQ ID NO:4) representing 55, 23, 18 and 4 percent of the clones respectively (22 sequenced). Highly conserved among the sequences were a Glu at position 7, Trp at position 12 as well as a hydrophobic residue (Leu, Val, Phe) at position 6. All of the clones contained a Gly-Pro at position 8 and 9 respectively and cysteine residues at position 4 and 11 all of which had been initially designed into the naive library. One clone contained an extra (unpaired) cysteine residue at position 17. Seventeen clones from the 5th round of selection were also sequenced. Eight clones had the sequence MGTLCLEGPEGWFCIESA (SEQ ID NO:1), another 8 were TGEACVEGPGAWVCCLEP (SEQ ID NO:4) and 1 was QEWTCVEGPRGWECIAVL (SEQ ID NO:2). All of these 5th round clones were also present in the 3rd round group of sequenced clones.

b) Selecting for Additional Peptides on Gene 8 Phage.

In order to select for additional peptides from the $X_4CX_2GPX_4CX_4$ (SEQ ID NO:17) library, selections were repeated on immobilized FcεRI-IgG but maintained during the binding selection a 5–10 uM concentration of a synthetic peptide, corresponding to the previously selected g8a.37 clone (Table 1). Although this concentration was well below the dissociation constant for the peptide binding to the receptor (see below), including it in the incubation buffer as a competitor might aid in the selection of a tighter binding peptide. As well, the peptide could serve as an inhibitor and thereby direct selection to other sites on the receptor. Four consecutive rounds of panning were performed, and the level of binding enrichment was determined after each round. We observed a 6 fold, 18 fold, 1466 fold and 2500 fold increase after rounds 1, 2, 3, and 4, respectively. Clones were isolated and sequenced (Table 2).

TABLE 1

Sequences of g8 Phage Clones

| Seq. I.D. | Sequence | Selection Round | Number of Clones |
|---|---|---|---|
| g8a.37 (SEQ ID NO:1) | MGTLCLEGPEGWFCIESA | 3 | 12 |
| g8a.18 (SEQ ID NO:2) | QEWTCVEGPRGWECIAVL | 3 | 5 |
| g8a.19 (SEQ ID NO:3) | DGSLCFEGPWGDICQSDG | 3 | 4 |
| g8a.20 (SEQ ID NO:4) | TGEACVEGPGAWVCCLEP | 3 | 1 |
| g8a.37 (SEQ ID NO:1) | MGTLCLEGPEGWFCIESA | 5 | 8 |
| g8a.18 (SEQ ID NO:2) | QEWTCVEGPRGWECIAVL | 5 | 1 |
| g8a.20 (SEQ ID NO:4) | TGEACVEGPGAWVCCLEP | 5 | 8 |

TABLE 2

Sequences of Additional g8 Phage Clones

| Seq. I.D. | Sequence | Selection Rd. | Number of Clones |
|---|---|---|---|
| g8b.3 (SEQ ID NO:5) | GTDVCVEGPWGEVC | 2 | 1 |
| g8b.22 (SEQ ID NO:6) | NYEECVMGPDGVWCLIPT | 2 | 1 |
| g8b.23 (SEQ ID NO:7) | GRPSCIEGPSGLWCLIE | 2 | 1 |
| g8b.11 (SEQ ID NO:8) | EIQECTEGPWGWFCVGSG | 2 | 2 |
| g8b.35 (SEQ ID NO:9) | AEATCTEGPWGWVCMAAD | 2 | 2 |
| g8b.22 (SEQ ID NO:6) | NYEECVMGPDGVWCLIPT | 3 | 1 |
| g8b.23 (SEQ ID NO 7) | GRPSCIEGPSGLWCLIE | 3 | 1 |
| g8b.11 (SEQ ID NO:8) | EIQECTEGPWGWFCVGSG | 3 | 15 |
| g8b.35 (SEQ ID NO:9) | AEATCTEGPWGWVCMAAD | 3 | 3 |
| g8b.11 (SEQ ID NO:8) | EIQECTEGPWGWFCVGSG | 4 | 18 |
| g8b.35 (SEQ ID NO:9) | AEATCTEGPWGWVCMAAD | 4 | 15 |

At round 3, 15 of 20 clones had the sequence EIQECTEGPWGWFCVGSG (SEQ ID NO:8), 3 of 20 were AEATCTEGPWGWVCMAAD (SEQ ID NO:9), and 2 of 20 were either NYEECVMGPDGVWCLIPT (SEQ ID NO:6) or GRPSCIEGPSGLWCLIE (SEQ ID NO:7). Additional clones were sequenced from round 4. Of 33 clones sequenced, only 2 dominant sequences remained with 15 of 33 clones being AEATCTEGPWGWVCMAAD (SEQ ID NO:9), and 18 of 33 being EIQECTEGPWGWFCVGSG (SEQ ID NO:8).

Example 2 g8p and g3p Phage Display Based Assays of FcεRI-Binding Peptides

After several rounds of panning on FcεRI-IgG, phage clones were assayed for specific binding to receptor and inhibition by IgE.XL-1 Blue *E. coli* cells were infected by phage library pools and plated onto LB/carbenicillin agar plates. Individual colonies were picked and grown overnight in 5 mL of 2YT broth containing antibiotics (carbenicillin and tetracycline), and $10^{10}$/mL of VCSM13 helper phage (Stratagene). The cultures were centrifuged and 1.0 mL of a solution containing 20% PEG and 2.5 M NaCl was added to the supernatant. After 10 minutes, the mixture was centrifuged at 10K RPM for 10 minutes. The supernatant was aspirated, and the remaining phage pellet was solubilized in 100 uL of PBS. A 1/100 dilution of the solubilized phage was incubated on FcεRI-IgG immobilized Maxisorp 96 microtiter plates for 1 hour in the presence and absence of human IgE (2 ug/mL). The plates were washed 5 times in PBT and a 1/5000 dilution of a horseradish peroxidase conjugated anti M13 phage antibody (Pharmacia) was added for 30 minutes at room temperature. Plates were washed again 5 times with PBT and 100 uL of an OPD (o-phenylenediamine) substrate was added. After 15 minutes the reaction was stopped by the addition of 50 uL of 2.5 M $H_2SO_4$. The OD of each well was determined using an SLT plate reader at a wavelength of 492 nm.

Greater than 95% of the clones from pool 2 specifically bound FcεRI-IgG and not bovine serum albumin nor 4D5, a humanized IgG1 antibody. In addition, when tested for inhibition of binding by IgE, greater than 95% of the positive clones were prevented from binding when IgE was present in the incubation buffer.

Example 3

Optimization of Peptides Using Monovalent Phage Display

Peptides EIQECTEGPWGWFCVGSG (SEQ ID NO:8) and AEATCTEGPWGWVCMAAD (SEQ ID NO:9) were selected for optimization as fusions to gene 3 on phage. Here additional libraries based on these peptides were constructed in the g3 phage display background to select for stronger binding peptides. In the g3 phage display format, the level of display is generally monovalent and therefore the selection is dependent on the affinity of the binding interaction of the individual molecules. In the g8 phage format, the display of the peptides is polyvalent and selection benefits from the binding avidity effect which allows for the selection of peptides with weaker binding interactions. Libraries were designed in the background of both peptides randomizing residues 1–4, 5–15 and 17–20. After 5 rounds of panning against immobilized FcεRI-IgG only the AEATCTEGPWGWVCMAAD (SEQ ID NO:9) based library which contained randomized residues at positions 1–4, had significant enrichment. Seven clones were picked for sequencing and determination of $IC_{50}$ values by a phage binding ELISA assay. All seven contained different N-terminal sequences with no overall consensus except for a Pro at position 3 in 50% of the clones (Table 3). The N-terminal sequences were as follows: NLPR, NLPT, VMPT, AMAQ, GRAQ, DLPA and GRTE, (SEQ ID NOs:10–16), respectively.

TABLE 3 g3 Phage Selection Optimization

| Sequence No. | Phage Sequence | Phage $IC_{50}$ (nM) |
|---|---|---|
| g3b.1 (SEQ ID NO:18) | NLPRCTEGPWGWVCMAAD | 13 |
| g3b.3 (SEQ ID NO:19) | NLPTCTEGPWGWVCMAAD | 7 |
| g3b.4 (SEQ ID NO:20) | VMPTCTEGPWGWVCMAAD | 7 |
| g3b.5 (SEQ ID NO:21) | AMAQCTEGPWGWVCMAAD | 10 |
| g3b.6 (SEQ ID NO:22) | GRAQCTEGPWGWVCMAAD | 16 |
| g3b.7 (SEQ ID NO:23) | DLPACTEGPWGWVCMAAD | 9 |
| g3b.8 (SEQ ID NO:24) | GRTECTEGPWGWVCMAAD | 14 |

A phage based competitive binding ELISA for immobilized FcεRI-IgG in the presence of titrated amounts of soluble FcεRI-IgG was performed on each of the clones. $IC_{50}$ values ranged from 7–16 nM values for the clones with the NLPR (SEQ ID NO:10) clone having a value of 13 nM.

The NLPRCTEGPWGWVCMAAD (SEQ ID NO:18) peptide was synthesized and assayed in the cell based $I^{125}$-IgE binding inhibition assay (see Example 4). An $IC_{50}$ value of 1 uM was determined for this peptide. This represented a greater than 160 fold improvement over the initial MGTLCLEGPEGWFCIESA (SEQ ID NO:1) peptide and a 40 fold improvement over the EIQECTEGPWGWFCVGSG (SEQ ID NO:8) peptide. The fold improvement over the parent AEATCTEGPWGWVCMAAD (SEQ ID NO:9) peptide was not determined because the peptide was not soluble in the assay buffer. This $IC_{50}$ value of 1 uM for peptide NLPRCTEGPWGWVCMAAD (SEQ ID NO:18) differed significantly from the value of 13 nM determined in the phage binding ELISA. Although these results might be expected to differ slightly because the assay formats and reagents differ, we believe the differences are more likely due to monovalency in the FcεRI-IgG or in the g3 phage display of this peptide. It is possible for the display of up to five copies on gene 3 phage thereby increasing the binding through avidity and giving a lower $IC_{50}$ value (Lowman, *Ann. Rev. Biophys. Biomol. Struct.* 26, 401–424 (1997)).

Peptide sequences from g8p-fused phage clones that specifically bound FcεRI-IgG were transferred onto a g3p-display format for monovalent phage display (Bass et al., *Proteins* 8, 309–314 (1990); Lowman et al., *Biochemistry* 30, 10832–10838 (1991)). An oligonucleotide encoding for each desired peptide with additional 5' and 3' base pair that overlapped with g3 was synthesized. This oligonucleotide was annealed with a g3 single stranded DNA phagemid template. The mutagenesis reaction was transformed into XL-1 Blue *E. coli* and plated on LB-carb+ agar plates. Individual colonies were propagated in 5 mL of 2YT broth, tetracycline, carbenicillin and VCSM13 helper phage (Stratagene). Single stranded DNA was isolated from the purified phage particles and sequenced to confirm the insertion of the phage peptide sequence. 25 mL preparations of g3 phage clones were propagated overnight and purified by PEG precipitation. After resuspension of the phage pellet in 1.0 mL of PBS, it was serially diluted 1/3 and incubated with immobilized FcεRI-IgG 2 ug/mL in a 96 well Maxisorp microtiter plate for 1 hour at room temperature. The wells were washed 10× with PBST then incubated with 100 uL of anti M13 phage HRP as described above. An OD(492) value corresponding to less than 50% binding was selected and the purified phage clones were diluted to yield this normalized level of signal. For relative affinity ($IC_{50}$) determinations, FcεRI-IgG was serially diluted in PBTT and preincubated for 15 minutes with the diluted phage. The mixture was then transferred to 96 well microtiter dishes containing immobilized FcεRI-IgG. After a 1-hour incubation period, the plates were washed 10 times, incubated with anti M13-HRP conjugated antibody and developed with OPD as described above. The data was plotted, and 4-parameter fits (KaleidaGraph 3.0) used for calculation of $IC_{50}$ values.

Alanine substitutions were made at various positions throughout the peptide sequence for monovalent (g3p) phage display using site directed mutagenesis as described (Kunkel et al., *Methods Enzymol.* 204, 125–139 (1991)). In addition, stepwise N-terminal and C-terminal truncations of the peptide sequence were constructed. All constructs were made by designing oligonucleotides corresponding to the desired substitution or truncation, with an additional 18 bp of DNA overlapping the peptide or g3 phage DNA sequence. The phage clones were propagated overnight following infection in XL-1 Blue *E. coli*. Purified phage preparations were titered and assayed for binding to immobilized receptor. FcεRI-IgG competition assays were performed as described above.

The observed $IC_{50}$ values are reported in Table 4:

etry. IGE133 was expressed as a fusion protein in *E. coli* and cleaved by cyanogen bromide reaction (see Example 12).

Several peptides based on early phage selectants were synthesized. In addition, analogs of the optimized peptide (NLPRCTEGPWGWVCMAAD) (SEQ ID NO:28) were synthesized to assess the possibility of minimizing the size of the peptide and also to ascertain which residues contribute to receptor binding. Additional analogs were made to determine the contribution of peptide residue side chains to binding FcεRI (Hakimi et al., (1990) *J. Biol. Chem.* 265: 22079–81). Substitutions were primarily limited to the residues (T6-W12) within the cysteine loop. Several non-natural amino acid analogs were used to probe the nature of the binding interaction by the peptide Pro residue.

To determine the ability of peptides to inhibit IgE binding to FcεRI, a cell-based binding assay was used with radiolabeled IgE. Chinese hamster ovary cells expressing the alpha subunit of the human FcεRI receptor were cultured overnight in Falcon 96 well microtiter plates at a concentration of $5 \times 10^4$ cells per well. The following day the cells were rinsed three times with PBS and then once with F12/DMEM. Peptide stocks were reconstituted in 100 mM Hepes buffered water, pH 7.2, at a concentration of 5 mg/mL. Working concentrations of the peptide were diluted in assay buffer (see below). 75 uL of a desired concentration of peptide was added to the top row of a separate 96 well microtiter plate and serially diluted 1:3 in 50 uL of the assay buffer (F12/DMEM, 1% BSA, 0.05% $NaN_3$ and 0.025 mM Hepes pH 7.2). Starting concentrations ranged from 50–500 uM. Next, 50 uL of the diluted peptide was transferred to the 96 microtiter well plate containing a monolayer of CHO FcεRI+ cells. After a 1 hour incubation at room temperature, 50 uL of $^{125}$I-IgE (1.5 nM) was added to each well and incubated for an additional 45–60 minutes at 4° C. followed by 5 washes with 200 uL of assay buffer. Cells were

TABLE 4

FcεRI g3 Phage ELISA Binding of Truncated Peptides on Phage

| Phage No. | Phage Peptide Sequence | $IC_{50}$ | Relative ($IC_{50}$) (fold weaker) |
|---|---|---|---|
| g3c.42 (SEQ ID NO:28) | NLPRCTEGPWGWVCMAAD | 5.6 nM | 1X |
| g3c.29 (SEQ ID NO:25) | NLPRCTEGPWGWVCMAA | 5.0 nM | 1X |
| g3c.31 (SEQ ID NO:26) | NLPRCTEGPWGWVCMA | 6.1 nM | 1X |
| g3c.34 (SEQ ID NO:37) | NLPRCTEGPWGWVCM | 14.6 nM | 3X |
| g3c.42 (SEQ ID NO:28) | NLPRCTEGPWGWVCMAAD | 3.1 nM | 1X |
| g3c.1 (SEQ ID NO:29) | LPRCTEGPWGWVCMAAD | 3.0 nM | 1X |
| g3c.17 (SEQ ID NO:30) | RCTEGPWGWVCMAAD | — | NDB |
| g3c.21 (SEQ ID NO:31) | CTEGPWGWVCMAAD | — | NDB |

(NDB = no detectable binding)

Example 4

Design and Activity of Synthetic Peptides

A number of peptides corresponding to peptide-phage clones and analogs were synthesized. Except as noted, all peptides were oxidized to the cyclic disulfide form, and composition was confirmed by HPLC and mass spectromsolubilized with 200 uL of 1 N NaOH and transferred to a 96 microtiter tube for counting in a gamma counter to determine counts bound. The data were plotted using KaleidaGraph 3.0 and fitted using 4-parameter fits. $IC_{50}$ values were determined for each peptide.

The $IC_{50}$ of peptide MGTLCLEGPEGWFCIESA (SEQ ID NO:1) was found to be >160 uM. The $IC_{50}$ of peptide EIQECTEGPWGWFCVGSG (SEQ ID NO:8) was determined to be 37 uM, a >4 fold improvement in activity over the MGTLCLEGPEGWFCIESA (SEQ ID NO:1) peptide. Peptide AEATCTEGPWGWVCMAAD (SEQ ID NO:9) was insoluble in the binding buffer, and therefore a reliable $IC_{50}$ value could not be determined.

Peptide IGE063 (SEQ ID NO:49) (Table 5) had an $IC_{50}$ of about 1 uM, and was used as the basis for further structure-activity studies. Elimination of the residue 1 (Asn) had a minimal effect with a 3 fold reduction whereas eliminating the first 2 residues (Asn, Leu) resulted in a 34 fold reduction in inhibition. A truncation to residue 5 (Cys) resulted in a >400 fold reduction in inhibition. Thus residues 24 of the N-terminus were essential for receptor binding although whether the interactions involve sidechain or mainchain interactions is not clear. At the C-terminal end a truncation to residue 15 (Met) had little effect on binding whereas truncation to residue 14 (Cys) resulted in a >400-fold reduction in binding. In all, truncations of 1 residue from the N-terminus and 3 residues from the C-terminus had a minimal impact on inhibiting in the $^{125}$I-IgE cell binding inhibition assay.

Alanine substitutions in IGE063 (SEQ ID NO:49) were used to assess sidechain contributions. The P9A (IGE070, SEQ ID NO:52) substitution had the largest impact with a >500× reduction in binding. Also active, but less potent, were the G8A (IGE079, SEQ ID NO:61) and W12A (IGE073, SEQ ID NO:55) variants which resulted in 256× and 65× reduction respectively. The effect of W10A (IGE074, SEQ ID NO:56) was a 30-fold reduction and G11A was 53-fold reduction. The E7A (IGE059, SEQ ID NO:46) analog had a smaller, 6-fold reduction in binding. Clearly the alanine substitutions at G8, P9, W10, G11 and W12 all had major impacts on binding FcεRI.

Peptides were evaluated by 2D NMR spectroscopy to assess the effect of substitutions on the three-dimensional structure of the peptide analog. All peptides with a structural score indicated in Table 5 were analyzed by 2D NMR spectroscopy; backbone $^1$H resonances were assigned and $^3J_{HN\text{-}H\alpha}$ coupling constants were measured and compared to the reference peptide (IGE063, SEQ ID NO:49; see Example 5). Peptides are defined to be of similar structure to the reference peptide provided chemical shifts, coupling constants, and NOEs are consistent with that structure. Peptides are defined to be less stable when $^3J_{HN\text{-}H\alpha}$ coupling constants are less extreme than the reference (e.g., go from being >8.5 or <6 Hz to values between 6 and 8.5 Hz) and/or when chemical shifts of backbone resonances are closer to random coil values in the peptide relative to the reference.

Table 5

Inhibition of Labeled IgE-Binding to CHO FcεRI+ Cells

Peptides were evaluated for their ability to inhibit IgE binding and their three-dimensional structure. +++ indicates the peptide is structured similarly to IGE063 (SEQ ID NO:49)+indicates the peptide is structured similarly to IGE063 (SEQ ID NO:49), but is less stable, −/+ indicates the peptide has some elements of stable structure, but the conformation differs from the reference structure (e.g., a different turn type is evident).—indicates the peptide is predominantly unstructured in aqueous solution.

| Peptide No. SEQ ID NO: | Peptide Sequence | Mean $IC_{50}$(uM) ± S.D. | Struct. Score |
|---|---|---|---|
| IGE031 (SEQ ID NO:32) | Ac-NLPRCTEGPWGWVCMADD-nh2 | 1.1 ± 0.7 | +++ |
| IGE032 (SEQ ID NO:33) | Ac-NLPRCTEGPKGWVCMADD-nh2 | 10.8 ± 6.9 | +++ |
| IGE042 (SEQ ID NO:34) | Ac-NLPRCTEGPWGWVCMAAD-nh2 | 1.5 ± 1.0 | |
| IGE043 (SEQ ID NO:35) | NLPRCTEGPWGWVCMAAD-nh2 | 1.4 ± 1.0 | |
| IGE044 (SEQ ID NO:36) | Ac-CLEGPWGWFCI-nh2 | 194 | |
| IGE045 (SEQ ID NO:37) | CLEGPWGWFCI-nh2 | 300 ± 269 | |
| IGE046 (SEQ ID NO:38) | Ac-CTEGPWGWFCI-nh2 | 549 | |
| IGE047 (SEQ ID NO:39) | CTEGPWGWFCI-nh2 | 741 | |
| IGE050 (SEQ ID NO:40) | Ac-NLPRCTEGPNGWVCMAAD-nh2 | 19.4 ± 12.6 | |
| IGE051 (SEQ ID NO:41) | NLPRCTEGPNGWVCMAAD-nh2 | 23.7 ± 9.8 | |
| IGE055 (SEQ ID NO:42) | CTEGPWGWVCI-nh2 | >500 | |
| IGE056 (SEQ ID NO:43) | Ac-CTEGPWGWVCI-nh2 | >500 | |
| IGE057 (SEQ ID NO:44) | NLPRCTEGPWGWVCM-nh2 | 0.8 ± 0.3 | |
| IGE058 (SEQ ID NO:45) | Ac-NLPRCTEGPWGWVCM-nh2 | 1.8 ± 1.3 | |
| IGE059 (SEQ ID NO:46) | AC-NLPRCTAGPWGWVCMAAD-nh2 | 10.5 ± 2.6 | |
| IGE060 (SEQ ID NO:47) | Ac-NLPCTAGPWGWVCMAAD-nh2 | >500 | |
| IGE062 (SEQ ID NO:48) | NLPRCTEGPWGWVCM | 1.0 ± 0.6 | +++ |
| IGE063 | Ac-NLPRCTEGPWGWVCM | 1.8 ± 0.7 | +++ |

-continued

| Peptide No. SEQ ID NO: | Peptide Sequence | Mean IC$_{50}$(uM) ± S.D. | Struct. Score |
|---|---|---|---|
| IGE068 (SEQ ID NO:49) | LPRCTEGPWGWVCM-nh2 | 3.3 | |
| IGE069 (SEQ ID NO:50) | PRCTEGPWGWVCM-nh2 | 34 | |
| IGE070 (SEQ ID NO:51) | NLPRCTEGAWGWVCM | >500 | +++ |
| IGE071 (SEQ ID NO:52) | NLPRCTEGpWGWVCM | >500 | -/+ |
| IGE072 (SEQ ID NO:53) | NLPRCTEGPAGWVCM | 81.5 ± 4.9 | +++ |
| IGE073 (SEQ ID NO:54) | NLPRCTEGPWGAVCM | 118 ± 12.7 | + |
| IGE074 (SEQ ID NO:55) | NLPRCTEGPWAWVCM | 43.0 ± 27.6 | + |
| IGE075 (SEQ ID NO:56) | NLPRCTEGPWGWVCI | 1.4 ± 1.1 | |
| IGE076 (SEQ ID NO:57) | NLPRCTEGPWGWVCMAY | 2.0 ± 1.8 | |
| IGE077 (SEQ ID NO:58) | NLPRCTEGPWGWYCM | 126 ± 3.5 | +++ |
| IGE078 (SEQ ID NO:59) | Bt-NLPRCTEGPWGWVCM | 3.4 ± 3.1 | |
| IGE079 (SEQ ID NO:60) | NLPRCTEAPWGWVCM | 462 ± 425 | +++ |
| IGE080 (SEQ ID NO:61) | Ac-CLEGPWGWVCI-nh2 | 410 | |
| IGE082 (SEQ ID NO:62) | Ac-NLPRCTEGPWGWVC | >400 | |
| IGE085 (SEQ ID NO:63) | Ac-NLPRCTEG(Pip)WGWVCM-nh2 | 38.5 ± 19.1 | |
| IGE086 (SEQ ID NO:64) | Ac-NLPRCTEG(N-Me-A)WGWVCM-nh2 | 60 ± 7.1 | |
| IGE087 (SEQ ID NO:65) | Ac-NLPRCTEG(N-Me-G)WGWVCM-nh2 | 136 ± 19.1 | |
| IGE090 (SEQ ID NO:66) | Ac-EIQECTEGPWGWVCM-nh2 | 7.6 | |
| IGE091 (SEQ ID NO:67) | NLPRCTEGPWGWVC-nh2 | 12.8 | +++ |
| IGE092 (SEQ ID NO:68) | Ac-NLPRCTEGPWGWVC-nh2 | 20 | |
| IGE095 (SEQ ID NO:69) | Ac-NLPRCTEG(Pip)WGWVCM | 23 | +++ |
| IGE096 (SEQ ID NO:70) | Ac-NLPRCTEG(N-Me-A)WGWVCM | 44 | +++ |
| IGE097 (SEQ ID NO:71) | Ac-NLPRCTEG(N-Me-G)WGWVCM | 84 | -/+ |
| IGE098 (SEQ ID NO:72) | Ac-NLPRCTEG(pip)WGWVCM-nh2 | 315 | |
| IGE099 (SEQ ID NO:73) | Ac-NLPRCTEG(pip)WGWVCM | 219 | |
| IGE100 (SEQ ID NO:74) | Ac-NLPRCTEG(Oic)WGWVCM | 364 ± 84.85 | |
| IGE101 (SEQ ID NO:75) | Ac-NLPRCTEG(hyP)WGWVCM | 580 | +++ |
| IGE102 (SEQ ID NO:76) | Ac-NLPRCTEG(hyP-OBn)WGWVCM | >500 | |
| IGE103 (SEQ ID NO:77) | Ac-NLPRCTEGP(npA)GWVCM | 1.2 ± 0.6 | +++ |
| IGE104 (SEQ ID NO:78) | Ac-NLPRCTEGPWGWVcM | 121 ± 9.9 | - |
| IGE105 (SEQ ID NO:79) | Ac-NLPRCTEGPWaWVCM | 8.6 | +++ |
| IGE106 (SEQ ID NO:80) | Ac-NLPRCTEGPVGWVCM | 84 | +++ |
| IGE107 (SEQ ID NO:81) | Ac-NLPCTEGPWGWVCM | 28 | + |
| IGE108 (SEQ ID NO:82) | Ac-NLPRCTEGPWGWVCM | 20 | + |
| IGE109 (SEQ ID NO:83) | Ac-NLPRCTEGPWGLVCM | 10.6 | +++ |
| IGE114 (SEQ ID NO:84) | Ac-NLPRCTEGPWeWVCM | 1.7 | +++ |
| IGE115 (SEQ ID NO:85) | AC-NLPRCTEG(tP)WGWVCM | 1.4 ± 0.3 | |
| (SEQ ID NO:86) | | | |

-continued

| Peptide No. SEQ ID NO: | Peptide Sequence | Mean IC$_{50}$(uM) ± S.D. | Struct. Score |
|---|---|---|---|
| IGE116 (SEQ ID NO:87) | Ac-NLPRWTCGPWGCVEM | >500 | |
| IGE118 (SEQ ID NO:88) | Ac-NLCTLTEGPWGWVLTCAD | >500 | |
| IGE125 (SEQ ID NO:89) | Ac-NLPRCTEGPAWGWVCM | 259 | |
| IGE133 (SEQ ID NO:90) | Ac-NLPRCTEGPWGWVC-hS-lactone | 2.5 ± 1.0 | |
| IGE208 (SEQ ID NO:214) | Ac-NLPRCAEGPWGWVCM | 6.85 ± 0.78 | |
| IGE209 (SEQ ID NO:215) | Ac-NLPRCTEGPWGWACM | 14.35 ± 1.48 | |

(Bt = biotin; *hS = homoSerine; tP = thioProline; Ac = acetyl; hP = hydroxyProline; Oic = octahydroindole; pip = L-pipecolic acid; npA = 2-naphthyl-2-Alanine; lower case = "D" optical isomer; upper case = "L" optical isomer; M-Me-G = N-methylglycine; N-Me-A = N-methylalanine)

Example 5

Determination of Peptide Structure by NMR

NMR Analysis of Peptide IGE063 (SEQ ID NO:49)

An NMR sample of IGE063 (SEQ ID NO:49) was prepared by dissolving 3 mg of peptide in 500 mL 92% (v/v) H$_2$O/8% D$_2$O, then adjusting the pH to 5.7 by addition of 0.1 N NaOH. Two-dimensional double-quantum-filtered correlation spectroscopy (2QF-COSY), total correlation spectra (TOCSY), nuclear Overhauser effect spectra (NOESY), and rotating-frame Overhauser effect spectra (ROESY) were collected on a Bruker AMX-500 spectrometer equipped with a 5-mm triple axis pulsed-field gradient probe at 288K. The experiments were recorded as described by Cavanagh et al. in "Protein NMR Spectroscopy, Principles and Practice" (Academic Press, San Diego: ISBN 0-12-164490-1, 1995). After lyophilization and dissolution of the peptide in D$_2$O, a 2D NOESY and a COSY-35 spectrum, acquired with a 35° C. mixing pulse, were obtained. Complete $^1$H resonance assignments were derived from these data by standard methods (Wüthrich, in "NMR of proteins and nucleic acids", John Wiley & Sons, New York: ISBN 0-471-82893-9, 1986.)

Evidence for a well-defined three-dimensional structure for IGE063 (SEQ ID NO:49) was obtained from the following: (1) the $^1$H resonance positions are significantly different from those expected in an unstructured peptide. (2) Scalar coupling constants between amide and alpha protons (obtained from the 2QF-COSY spectrum) are distinct from the averaged values observed in unstructured peptides. The values are greater than 8.5 Hz for residues Cys5, Thr6, Trp10, Val13, and Cys14 indicating an extended backbone conformation for these residues. Scalar coupling constants were also measured between alpha and beta protons in the COSY-35 spectrum. These data indicate that the side chains of residues Cys5, Thr6, Trp10, and Cys14 have fixed chi-1 angles, i.e., these side chains do not sample the range of chi-1 rotamers that are populated in unstructured peptides. (3) Peaks in the NOESY and ROESY spectra indicate that there are many proton—proton contacts (<5 Å) between residues that are not adjacent in the primary sequence. These can only occur if the peptide folds up into a well-defined structure. Strong cross-strand NOEs between alpha protons of Cys5 and Cys14 and Glu7 and Trp12 indicate that IGE063 (SEQ ID NO:49) adopts a beta-hairpin conformation with the disulfide occurring at non-hydrogen-bonded positions within the two-stranded beta-sheet. Furthermore, local NOEs and coupling constants involving residues Gly8, Pro9, Trp10, and Gly11 indicate these residues adopt a type I beta-turn with Gly11 adopting a positive phi angle.

The NMR data were used to derive restraints that could be used to determine a three-dimensional model of the IGE063 (SEQ ID NO:49) structure. Dihedral angle restraints were derived from the amide-alpha and alpha-beta scalar coupling constants via an appropriate Karplus relationship (Karplus, J. Phys. Chem., 30: 11–15 (1959)). Distance restraints were introduced between protons which exhibited a through-space interaction in the ROESY or NOESY spectra; the size of the upper bound, and corrections to the upper bound because of peak overlap or resonance degeneracy were as described by Starovasnik et al., Biochemistry, 35: 15558–69 (1996). These restraints were used to generate a family of structures using the program DGH (Havel, Prog. Biophys. Mol. Biol., 56:43–78 (1991)) which were subsequently refined by restrained molecular dynamics with the program Discover (MSI, San Diego) using the AMBER all atom force field (Weiner et al., J. Comput. Chem., 7: 230–252 (1986)). The resulting structures converged to a single global fold (average root-mean-squared deviation from the mean structure of 0.24±0.06 Å for N, C-alpha, and carbonyl carbons of residues 5–14). The best twenty models (least violation of the input data) agreed with the input data very well (no distance restraint violations greater than 0.1 Å and no dihedral angle violations greater than 1°), and had good covalent geometry as judged by the program PROCHECK™ (Laskowski et al., J. Appl. Cryst., 26: 283–291 (1993)).

A representative member of the ensemble (the model that is closest to the mean coordinates) is shown in FIG. 7. According to the Kabsch and Sander secondary structure algorithm within the INSIGHT program (MSI, San Diego) IGE063 (SEQ ID NO:49) is composed of two beta strands comprised of residues 5–7 and 12–14, connected by a reverse turn centered at residues Pro9 and Trp10 (Type 1); Asn4 and Met15 extend the two beta-strands in some of the models. The N-terminal three residues (Asn1, Leu2, and Pro3) are not well-defined by the NMR data and appear to be more flexible in solution than residues Cys5–Cys14. The structure shows that the sidechain of Trp12 packs against the disulfide bond formed by Cys5 and Cys14 and contributes to the stability of the peptide as evidenced by comparison of NMR data obtained from a peptide with Trp12 substituted by Ala (IGE073, SEQ ID NO:55; see above). The disulfide bond is essential for stabilizing the hairpin conformation; there is no evidence of stable structure when excess reductant DTT (dithiothreitol) is added to the NMR sample. Gly11 (in position 4 of the type I beta-turn) adopts a positive phi angle. This backbone conformation can only be readily obtained by glycine which explains why the structure of a peptide with Gly11 replaced by alanine is significantly less stable (IGE074, SEQ ID NO:56). However, D-amino acids would readily adopt this conformation as was found for peptides with Gly11 replaced by D-Ala (IGE105, SEQ ID NO:80) or D-Glu (IGE114, SEQ ID NO:85).

TABLE 6

Structural Coordinates of IGE063 (SEQ ID NO: 49)

| | | | | | | | | | |
|---|---|---|---|---|---|---|---|---|---|
| ATOM | 1 | CA | ACE | 0 | 12.505 | −8.569 | −0.219 | 1.00 | 0.00 |
| ATOM | 2 | C | ACE | 0 | 12.214 | −7.244 | −0.912 | 1.00 | 0.00 |
| ATOM | 3 | O | ACE | 0 | 13.075 | −6.701 | −1.603 | 1.00 | 0.00 |
| ATOM | 4 | 2HA | ACE | 0 | 11.802 | −9.326 | −0.567 | 1.00 | 0.00 |
| ATOM | 5 | 3HA | ACE | 0 | 13.521 | −8.893 | −0.447 | 1.00 | 0.00 |
| ATOM | 6 | 1HA | ACE | 0 | 12.403 | −8.449 | 0.860 | 1.00 | 0.00 |
| ATOM | 7 | N | ASN | 1 | 10.996 | −6.725 | −0.721 | 1.00 | 0.00 |
| ATOM | 8 | CA | ASN | 1 | 10.564 | −5.465 | −1.311 | 1.00 | 0.00 |
| ATOM | 9 | C | ASN | 1 | 11.298 | −4.295 | −0.654 | 1.00 | 0.00 |
| ATOM | 10 | O | ASN | 1 | 11.576 | −4.323 | 0.544 | 1.00 | 0.00 |
| ATOM | 11 | CB | ASN | 1 | 9.049 | −5.288 | −1.142 | 1.00 | 0.00 |
| ATOM | 12 | CG | ASN | 1 | 8.216 | −6.315 | −1.909 | 1.00 | 0.00 |
| ATOM | 13 | OD1 | ASN | 1 | 8.742 | −7.138 | −2.655 | 1.00 | 0.00 |
| ATOM | 14 | ND2 | ASN | 1 | 6.895 | −6.266 | −1.724 | 1.00 | 0.00 |
| ATOM | 15 | H | ASN | 1 | 10.340 | −7.222 | −0.137 | 1.00 | 0.00 |
| ATOM | 16 | HA | ASN | 1 | 10.798 | −5.475 | −2.377 | 1.00 | 0.00 |
| ATOM | 17 | 1HB | ASN | 1 | 8.799 | −5.348 | −0.082 | 1.00 | 0.00 |
| ATOM | 18 | 2HB | ASN | 1 | 8.774 | −4.299 | −1.510 | 1.00 | 0.00 |
| ATOM | 19 | 1HD2 | ASN | 1 | 6.299 | −6.922 | −2.207 | 1.00 | 0.00 |
| ATOM | 20 | 2HD2 | ASN | 1 | 6.497 | −5.576 | −1.104 | 1.00 | 0.00 |
| ATOM | 21 | N | LEU | 2 | 11.601 | −3.262 | −1.448 | 1.00 | 0.00 |
| ATOM | 22 | CA | LEU | 2 | 12.247 | −2.047 | −0.970 | 1.00 | 0.00 |
| ATOM | 23 | C | LEU | 2 | 11.271 | −1.265 | −0.081 | 1.00 | 0.00 |
| ATOM | 24 | O | LEU | 2 | 10.065 | −1.320 | −0.319 | 1.00 | 0.00 |
| ATOM | 25 | CB | LEU | 2 | 12.682 | −1.191 | −2.170 | 1.00 | 0.00 |
| ATOM | 26 | CG | LEU | 2 | 13.651 | −1.902 | −3.132 | 1.00 | 0.00 |
| ATOM | 27 | CD1 | LEU | 2 | 13.968 | −0.966 | −4.303 | 1.00 | 0.00 |
| ATOM | 28 | CD2 | LEU | 2 | 14.960 | −2.308 | −2.441 | 1.00 | 0.00 |
| ATOM | 29 | H | LEU | 2 | 11.339 | −3.302 | −2.421 | 1.00 | 0.00 |
| ATOM | 30 | HA | LEU | 2 | 13.121 | −2.336 | −0.388 | 1.00 | 0.00 |
| ATOM | 31 | 1HB | LEU | 2 | 11.789 | −0.906 | −2.728 | 1.00 | 0.00 |
| ATOM | 32 | 2HB | LEU | 2 | 13.156 | −0.280 | −1.806 | 1.00 | 0.00 |
| ATOM | 33 | HG | LEU | 2 | 13.179 | −2.797 | −3.539 | 1.00 | 0.00 |
| ATOM | 34 | 1HD1 | LEU | 2 | 14.626 | −1.469 | −5.012 | 1.00 | 0.00 |
| ATOM | 35 | 2HD1 | LEU | 2 | 13.046 | −0.690 | −4.816 | 1.00 | 0.00 |
| ATOM | 36 | 3HD1 | LEU | 2 | 14.459 | −0.063 | −3.939 | 1.00 | 0.00 |
| ATOM | 37 | 1HD2 | LEU | 2 | 14.775 | −3.088 | −1.704 | 1.00 | 0.00 |
| ATOM | 38 | 2HD2 | LEU | 2 | 15.658 | −2.699 | −3.181 | 1.00 | 0.00 |
| ATOM | 39 | 3HD2 | LEU | 2 | 15.408 | −1.444 | −1.950 | 1.00 | 0.00 |
| ATOM | 40 | N | PRO | 3 | 11.761 | −0.539 | 0.939 | 1.00 | 0.00 |
| ATOM | 41 | CA | PRO | 3 | 10.917 | 0.229 | 1.842 | 1.00 | 0.00 |
| ATOM | 42 | C | PRO | 3 | 10.242 | 1.375 | 1.083 | 1.00 | 0.00 |
| ATOM | 43 | O | PRO | 3 | 10.912 | 2.201 | 0.467 | 1.00 | 0.00 |
| ATOM | 44 | CB | PRO | 3 | 11.849 | 0.734 | 2.948 | 1.00 | 0.00 |
| ATOM | 45 | CG | PRO | 3 | 13.215 | 0.788 | 2.267 | 1.00 | 0.00 |
| ATOM | 46 | CD | PRO | 3 | 13.162 | −0.395 | 1.301 | 1.00 | 0.00 |
| ATOM | 47 | HA | PRO | 3 | 10.161 | −0.421 | 2.286 | 1.00 | 0.00 |
| ATOM | 48 | 1HB | PRO | 3 | 11.545 | 1.702 | 3.349 | 1.00 | 0.00 |
| ATOM | 49 | 2HB | PRO | 3 | 11.884 | −0.005 | 3.750 | 1.00 | 0.00 |
| ATOM | 50 | 1HG | PRO | 3 | 13.303 | 1.717 | 1.701 | 1.00 | 0.00 |
| ATOM | 51 | 2HG | PRO | 3 | 14.037 | 0.705 | 2.979 | 1.00 | 0.00 |
| ATOM | 52 | 1HD | PRO | 3 | 13.798 | −0.197 | 0.440 | 1.00 | 0.00 |
| ATOM | 53 | 2HD | PRO | 3 | 13.493 | −1.300 | 1.813 | 1.00 | 0.00 |
| ATOM | 54 | N | ARG | 4 | 8.907 | 1.405 | 1.122 | 1.00 | 0.00 |
| ATOM | 55 | CA | ARG | 4 | 8.094 | 2.348 | 0.375 | 1.00 | 0.00 |
| ATOM | 56 | C | ARG | 4 | 6.627 | 2.074 | 0.704 | 1.00 | 0.00 |
| ATOM | 57 | O | ARG | 4 | 6.272 | 0.936 | 1.008 | 1.00 | 0.00 |
| ATOM | 58 | CB | ARG | 4 | 8.401 | 2.186 | −1.121 | 1.00 | 0.00 |
| ATOM | 59 | CG | ARG | 4 | 7.487 | 3.025 | −2.021 | 1.00 | 0.00 |
| ATOM | 60 | CD | ARG | 4 | 7.978 | 2.966 | −3.471 | 1.00 | 0.00 |
| ATOM | 61 | NE | ARG | 4 | 7.014 | 3.593 | −4.386 | 1.00 | 0.00 |
| ATOM | 62 | CZ | ARG | 4 | 5.928 | 2.990 | −4.898 | 1.00 | 0.00 |
| ATOM | 63 | NH1 | ARG | 4 | 5.631 | 1.719 | −4.589 | 1.00 | 0.00 |
| ATOM | 64 | NH2 | ARG | 4 | 5.128 | 3.669 | −5.730 | 1.00 | 0.00 |
| ATOM | 65 | H | ARG | 4 | 8.413 | 0.695 | 1.645 | 1.00 | 0.00 |
| ATOM | 66 | HA | ARG | 4 | 8.348 | 3.362 | 0.688 | 1.00 | 0.00 |
| ATOM | 67 | 1HB | ARG | 4 | 9.437 | 2.482 | −1.291 | 1.00 | 0.00 |

TABLE 6-continued

Structural Coordinates of IGE063 (SEQ ID NO: 49)

| ATOM | 68 | 2HB | ARG | 4 | 8.290 | 1.137 | −1.398 | 1.00 | 0.00 |
|---|---|---|---|---|---|---|---|---|---|
| ATOM | 69 | 1HG | ARG | 4 | 6.471 | 2.631 | −1.975 | 1.00 | 0.00 |
| ATOM | 70 | 2HG | ARG | 4 | 7.484 | 4.063 | −1.686 | 1.00 | 0.00 |
| ATOM | 71 | 1HD | ARG | 4 | 8.924 | 3.503 | −3.544 | 1.00 | 0.00 |
| ATOM | 72 | 2HD | ARG | 4 | 8.155 | 1.931 | −3.764 | 1.00 | 0.00 |
| ATOM | 73 | HE | ARG | 4 | 7.196 | 4.553 | −4.642 | 1.00 | 0.00 |
| ATOM | 74 | 2HH1 | ARG | 4 | 4.816 | 1.277 | −4.986 | 1.00 | 0.00 |
| ATOM | 75 | 1HH1 | ARG | 4 | 6.218 | 1.204 | −3.948 | 1.00 | 0.00 |
| ATOM | 76 | 1HH2 | ARG | 4 | 5.341 | 4.627 | −5.969 | 1.00 | 0.00 |
| ATOM | 77 | 2HH2 | ARG | 4 | 4.309 | 3.226 | −6.121 | 1.00 | 0.00 |
| ATOM | 78 | N | CYS | 5 | 5.783 | 3.113 | 0.652 | 1.00 | 0.00 |
| ATOM | 79 | CA | CYS | 5 | 4.357 | 3.012 | 0.937 | 1.00 | 0.00 |
| ATOM | 80 | C | CYS | 5 | 3.542 | 3.587 | −0.216 | 1.00 | 0.00 |
| ATOM | 81 | O | CYS | 5 | 4.017 | 4.451 | −0.953 | 1.00 | 0.00 |
| ATOM | 82 | CB | CYS | 5 | 4.019 | 3.723 | 2.253 | 1.00 | 0.00 |
| ATOM | 83 | SG | CYS | 5 | 4.952 | 3.205 | 3.721 | 1.00 | 0.00 |
| ATOM | 84 | H | CYS | 5 | 6.135 | 4.019 | 0.380 | 1.00 | 0.00 |
| ATOM | 85 | HA | CYS | 5 | 4.075 | 1.968 | 1.022 | 1.00 | 0.00 |
| ATOM | 86 | 1HB | CYS | 5 | 4.204 | 4.789 | 2.116 | 1.00 | 0.00 |
| ATOM | 87 | 2HB | CYS | 5 | 2.957 | 3.593 | 2.464 | 1.00 | 0.00 |
| ATOM | 90 | N | THR | 6 | 2.310 | 3.087 | −0.359 | 1.00 | 0.00 |
| ATOM | 91 | CA | THR | 6 | 1.362 | 3.472 | −1.394 | 1.00 | 0.00 |
| ATOM | 92 | C | THR | 6 | −0.033 | 3.567 | −0.778 | 1.00 | 0.00 |
| ATOM | 93 | O | THR | 6 | −0.377 | 2.766 | 0.091 | 1.00 | 0.00 |
| ATOM | 94 | CB | THR | 6 | 1.372 | 2.433 | −2.525 | 1.00 | 0.00 |
| ATOM | 95 | OG1 | THR | 6 | 1.159 | 1.136 | −2.001 | 1.00 | 0.00 |
| ATOM | 96 | CG2 | THR | 6 | 2.693 | 2.445 | −3.299 | 1.00 | 0.00 |
| ATOM | 97 | H | THR | 6 | 2.006 | 2.374 | 0.292 | 1.00 | 0.00 |
| ATOM | 98 | HA | THR | 6 | 1.627 | 4.447 | −1.806 | 1.00 | 0.00 |
| ATOM | 99 | HB | THR | 6 | 0.566 | 2.666 | −3.222 | 1.00 | 0.00 |
| ATOM | 100 | HG1 | THR | 6 | 0.380 | 1.155 | −1.439 | 1.00 | 0.00 |
| ATOM | 101 | 1HG2 | THR | 6 | 2.893 | 3.449 | −3.675 | 1.00 | 0.00 |
| ATOM | 102 | 2HG2 | THR | 6 | 3.514 | 2.129 | −2.657 | 1.00 | 0.00 |
| ATOM | 103* | 3HG2 | THR | 6 | 2.622 | 1.758 | −4.143 | 1.00 | 0.00 |
| ATOM | 104 | N | GLU | 7 | −0.837 | 4.533 | −1.240 | 1.00 | 0.00 |
| ATOM | 105 | CA | GLU | 7 | −2.221 | 4.686 | −0.821 | 1.00 | 0.00 |
| ATOM | 106 | C | GLU | 7 | −3.021 | 3.476 | −1.306 | 1.00 | 0.00 |
| ATOM | 107 | O | GLU | 7 | −3.248 | 3.334 | −2.507 | 1.00 | 0.00 |
| ATOM | 108 | CB | GLU | 7 | −2.785 | 6.002 | −1.379 | 1.00 | 0.00 |
| ATOM | 109 | CG | GLU | 7 | −4.249 | 6.245 | −0.983 | 1.00 | 0.00 |
| ATOM | 110 | CD | GLU | 7 | −4.429 | 6.413 | 0.524 | 1.00 | 0.00 |
| ATOM | 111 | OE1 | GLU | 7 | −4.566 | 5.373 | 1.204 | 1.00 | 0.00 |
| ATOM | 112 | OE2 | GLU | 7 | −4.430 | 7.581 | 0.970 | 1.00 | 0.00 |
| ATOM | 113 | H | GLU | 7 | −0.487 | 5.167 | −1.943 | 1.00 | 0.00 |
| ATOM | 114 | HA | GLU | 7 | −2.242 | 4.742 | 0.266 | 1.00 | 0.00 |
| ATOM | 115 | 1HB | GLU | 7 | −2.181 | 6.833 | −1.014 | 1.00 | 0.00 |
| ATOM | 116 | 2HB | GLU | 7 | −2.722 | 5.985 | −2.468 | 1.00 | 0.00 |
| ATOM | 117 | 1HG | GLU | 7 | −4.588 | 7.157 | −1.475 | 1.00 | 0.00 |
| ATOM | 118 | 2HG | GLU | 7 | −4.878 | 5.426 | −1.332 | 1.00 | 0.00 |
| ATOM | 119 | N | GLY | 8 | −3.437 | 2.609 | −0.376 | 1.00 | 0.00 |
| ATOM | 120 | CA | GLY | 8 | −4.198 | 1.402 | −0.664 | 1.00 | 0.00 |
| ATOM | 121 | C | GLY | 8 | −5.674 | 1.581 | −0.300 | 1.00 | 0.00 |
| ATOM | 122 | O | GLY | 8 | −6.064 | 2.640 | 0.193 | 1.00 | 0.00 |
| ATOM | 123 | H | GLY | 8 | −3.243 | 2.802 | 0.598 | 1.00 | 0.00 |
| ATOM | 124 | 1HA | GLY | 8 | −4.101 | 1.142 | −1.718 | 1.00 | 0.00 |
| ATOM | 125 | 2HA | GLY | 8 | −3.788 | 0.588 | −0.066 | 1.00 | 0.00 |
| ATOM | 126 | N | PRO | 9 | −6.506 | 0.550 | −0.531 | 1.00 | 0.00 |
| ATOM | 127 | CA | PRO | 9 | −7.924 | 0.559 | −0.193 | 1.00 | 0.00 |
| ATOM | 128 | C | PRO | 9 | −8.158 | 0.839 | 1.294 | 1.00 | 0.00 |
| ATOM | 129 | O | PRO | 9 | −9.029 | 1.632 | 1.644 | 1.00 | 0.00 |
| ATOM | 130 | CB | PRO | 9 | −8.460 | −0.823 | −0.588 | 1.00 | 0.00 |
| ATOM | 131 | CG | PRO | 9 | −7.469 | −1.306 | −1.644 | 1.00 | 0.00 |
| ATOM | 132 | CD | PRO | 9 | −6.147 | −0.703 | −1.173 | 1.00 | 0.00 |
| ATOM | 133 | HA | PRO | 9 | −8.419 | 1.320 | −0.798 | 1.00 | 0.00 |
| ATOM | 134 | 1HB | PRO | 9 | −8.425 | −1.504 | 0.260 | 1.00 | 0.00 |
| ATOM | 135 | 2HB | PRO | 9 | −9.478 | −0.771 | −0.976 | 1.00 | 0.00 |
| ATOM | 136 | 1HG | PRO | 9 | −7.430 | −2.394 | −1.710 | 1.00 | 0.00 |
| ATOM | 137 | 2HG | PRO | 9 | −7.738 | −0.879 | −2.611 | 1.00 | 0.00 |
| ATOM | 138 | 1HD | PRO | 9 | −5.677 | −1.360 | −0.441 | 1.00 | 0.00 |
| ATOM | 139 | 2HD | PRO | 9 | −5.489 | −0.568 | −2.031 | 1.00 | 0.00 |
| ATOM | 140 | N | TRP | 10 | −7.371 | 0.187 | 2.159 | 1.00 | 0.00 |
| ATOM | 141 | CA | TRP | 10 | −7.497 | 0.262 | 3.608 | 1.00 | 0.00 |
| ATOM | 142 | C | TRP | 10 | −6.464 | 1.246 | 4.162 | 1.00 | 0.00 |
| ATOM | 143 | O | TRP | 10 | −5.745 | 0.935 | 5.110 | 1.00 | 0.00 |
| ATOM | 144 | CB | TRP | 10 | −7.311 | −1.148 | 4.185 | 1.00 | 0.00 |
| ATOM | 145 | CG | TRP | 10 | −8.161 | −2.202 | 3.549 | 1.00 | 0.00 |
| ATOM | 146 | CD1 | TRP | 10 | −9.459 | −2.459 | 3.824 | 1.00 | 0.00 |

TABLE 6-continued

Structural Coordinates of IGE063 (SEQ ID NO: 49)

| ATOM | 147 | CD2 | TRP | 10 | −7.793 | −3.117 | 2.479 | 1.00 | 0.00 |
|---|---|---|---|---|---|---|---|---|---|
| ATOM | 148 | NE1 | TRP | 10 | −9.919 | −3.471 | 3.005 | 1.00 | 0.00 |
| ATOM | 149 | CE2 | TRP | 10 | −8.931 | −3.906 | 2.144 | 1.00 | 0.00 |
| ATOM | 150 | CE3 | TRP | 10 | −6.610 | −3.344 | 1.748 | 1.00 | 0.00 |
| ATOM | 151 | CZ2 | TRP | 10 | −8.895 | −4.873 | 1.128 | 1.00 | 0.00 |
| ATOM | 152 | CZ3 | TRP | 10 | −6.564 | −4.306 | 0.722 | 1.00 | 0.00 |
| ATOM | 153 | CH2 | TRP | 10 | −7.703 | −5.070 | 0.411 | 1.00 | 0.00 |
| ATOM | 154 | H | TRP | 10 | −6.664 | −0.433 | 1.791 | 1.00 | 0.00 |
| ATOM | 155 | HA | TRP | 10 | −8.493 | 0.610 | 3.885 | 1.00 | 0.00 |
| ATOM | 156 | 1HB | TRP | 10 | −6.270 | −1.443 | 4.049 | 1.00 | 0.00 |
| ATOM | 157 | 2HB | TRP | 10 | −7.513 | −1.137 | 5.253 | 1.00 | 0.00 |
| ATOM | 158 | HD1 | TRP | 10 | −10.052 | −1.941 | 4.563 | 1.00 | 0.00 |
| ATOM | 159 | HE1 | TRP | 10 | −10.856 | −3.849 | 3.009 | 1.00 | 0.00 |
| ATOM | 160 | HE3 | TRP | 10 | −5.735 | −2.760 | 1.991 | 1.00 | 0.00 |
| ATOM | 161 | HZ2 | TRP | 10 | −9.775 | −5.456 | 0.897 | 1.00 | 0.00 |
| ATOM | 162 | HZ3 | TRP | 10 | −5.648 | −4.459 | 0.170 | 1.00 | 0.00 |
| ATOM | 163 | HH2 | TRP | 10 | −7.662 | −5.807 | −0.377 | 1.00 | 0.00 |
| ATOM | 164 | N | GLY | 11 | −6.387 | 2.436 | 3.555 | 1.00 | 0.00 |
| ATOM | 165 | CA | GLY | 11 | −5.409 | 3.449 | 3.913 | 1.00 | 0.00 |
| ATOM | 166 | C | GLY | 11 | −4.051 | 3.128 | 3.289 | 1.00 | 0.00 |
| ATOM | 167 | O | GLY | 11 | −3.940 | 2.254 | 2.430 | 1.00 | 0.00 |
| ATOM | 168 | H | GLY | 11 | −7.002 | 2.630 | 2.777 | 1.00 | 0.00 |
| ATOM | 169 | 1HA | GLY | 11 | −5.752 | 4.413 | 3.538 | 1.00 | 0.00 |
| ATOM | 170 | 2HA | GLY | 11 | −5.313 | 3.511 | 4.998 | 1.00 | 0.00 |
| ATOM | 171 | N | TRP | 12 | −3.010 | 3.841 | 3.729 | 1.00 | 0.00 |
| ATOM | 172 | CA | TRP | 12 | −1.655 | 3.639 | 3.242 | 1.00 | 0.00 |
| ATOM | 173 | C | TRP | 12 | −1.121 | 2.278 | 3.684 | 1.00 | 0.00 |
| ATOM | 174 | O | TRP | 12 | −0.992 | 2.020 | 4.879 | 1.00 | 0.00 |
| ATOM | 175 | CB | TRP | 12 | −0.748 | 4.777 | 3.715 | 1.00 | 0.00 |
| ATOM | 176 | CG | TRP | 12 | −0.957 | 6.069 | 2.993 | 1.00 | 0.00 |
| ATOM | 177* | CD1 | TRP | 12 | −1.925 | 6.973 | 3.258 | 1.00 | 0.00 |
| ATOM | 178 | CD2 | TRP | 12 | −0.216 | 6.601 | 1.854 | 1.00 | 0.00 |
| ATOM | 179 | NE1 | TRP | 12 | −1.837 | 8.026 | 2.373 | 1.00 | 0.00 |
| ATOM | 180 | CE2 | TRP | 12 | −0.804 | 7.843 | 1.477 | 1.00 | 0.00 |
| ATOM | 181 | CE3 | TRP | 12 | 0.892 | 6.160 | 1.100 | 1.00 | 0.00 |
| ATOM | 182 | CZ2 | TRP | 12 | −0.324 | 8.604 | 0.400 | 1.00 | 0.00 |
| ATOM | 183 | CZ3 | TRP | 12 | 1.385 | 6.917 | 0.020 | 1.00 | 0.00 |
| ATOM | 184 | CH2 | TRP | 12 | 0.775 | 8.132 | −0.335 | 1.00 | 0.00 |
| ATOM | 185 | H | TRP | 12 | −3.158 | 4.542 | 4.439 | 1.00 | 0.00 |
| ATOM | 186 | HA | TRP | 12 | −1.670 | 3.669 | 2.155 | 1.00 | 0.00 |
| ATOM | 187 | 1HB | TRP | 12 | −0.888 | 4.941 | 4.785 | 1.00 | 0.00 |
| ATOM | 188 | 2HB | TRP | 12 | 0.289 | 4.482 | 3.554 | 1.00 | 0.00 |
| ATOM | 189 | HD1 | TRP | 12 | −2.665 | 6.881 | 4.039 | 1.00 | 0.00 |
| ATOM | 190 | HE1 | TRP | 12 | −2.451 | 8.826 | 2.358 | 1.00 | 0.00 |
| ATOM | 191 | HE3 | TRP | 12 | 1.368 | 5.226 | 1.358 | 1.00 | 0.00 |
| ATOM | 192 | HZ2 | TRP | 12 | −0.795 | 9.541 | 0.140 | 1.00 | 0.00 |
| ATOM | 193 | HZ3 | TRP | 12 | 2.239 | 6.564 | −0.538 | 1.00 | 0.00 |
| ATOM | 194 | HH2 | TRP | 12 | 1.156 | 8.705 | −1.168 | 1.00 | 0.00 |
| ATOM | 195 | N | VAL | 13 | −0.802 | 1.427 | 2.703 | 1.00 | 0.00 |
| ATOM | 196 | CA | VAL | 13 | −0.150 | 0.142 | 2.905 | 1.00 | 0.00 |
| ATOM | 197 | C | VAL | 13 | 1.337 | 0.317 | 2.598 | 1.00 | 0.00 |
| ATOM | 198 | O | VAL | 13 | 1.697 | 1.137 | 1.754 | 1.00 | 0.00 |
| ATOM | 199 | CB | VAL | 13 | −0.806 | −0.951 | 2.040 | 1.00 | 0.00 |
| ATOM | 200 | CG1 | VAL | 13 | −2.266 | −1.165 | 2.459 | 1.00 | 0.00 |
| ATOM | 201 | CG2 | VAL | 13 | −0.745 | −0.656 | 0.534 | 1.00 | 0.00 |
| ATOM | 202 | H | VAL | 13 | −0.922 | 1.734 | 1.746 | 1.00 | 0.00 |
| ATOM | 203 | HA | VAL | 13 | −0.249 | −0.163 | 3.948 | 1.00 | 0.00 |
| ATOM | 204 | HB | VAL | 13 | −0.270 | −1.885 | 2.219 | 1.00 | 0.00 |
| ATOM | 205 | 1HG1 | VAL | 13 | −2.689 | −2.001 | 1.902 | 1.00 | 0.00 |
| ATOM | 206 | 2HG1 | VAL | 13 | −2.317 | −1.392 | 3.524 | 1.00 | 0.00 |
| ATOM | 207 | 3HG1 | VAL | 13 | −2.858 | −0.272 | 2.256 | 1.00 | 0.00 |
| ATOM | 208 | 1HG2 | VAL | 13 | 0.289 | −0.549 | 0.208 | 1.00 | 0.00 |
| ATOM | 209 | 2HG2 | VAL | 13 | −1.193 | −1.485 | −0.014 | 1.00 | 0.00 |
| ATOM | 210 | 3HG2 | VAL | 13 | −1.295 | 0.253 | 0.296 | 1.00 | 0.00 |
| ATOM | 211 | N | CYS | 14 | 2.195 | −0.434 | 3.299 | 1.00 | 0.00 |
| ATOM | 212 | CA | CYS | 14 | 3.642 | −0.286 | 3.229 | 1.00 | 0.00 |
| ATOM | 213 | C | CYS | 14 | 4.320 | −1.626 | 2.967 | 1.00 | 0.00 |
| ATOM | 214 | O | CYS | 14 | 3.877 | −2.665 | 3.453 | 1.00 | 0.00 |
| ATOM | 215 | CB | CYS | 14 | 4.169 | 0.345 | 4.520 | 1.00 | 0.00 |
| ATOM | 216 | SG | CYS | 14 | 3.655 | 2.057 | 4.828 | 1.00 | 0.00 |
| ATOM | 217 | H | CYS | 14 | 1.832 | −1.114 | 3.952 | 1.00 | 0.00 |
| ATOM | 218 | HA | CYS | 14 | 3.913 | 0.374 | 2.412 | 1.00 | 0.00 |
| ATOM | 219 | 1HB | CYS | 14 | 3.840 | −0.265 | 5.361 | 1.00 | 0.00 |
| ATOM | 220 | 2HB | CYS | 14 | 5.259 | 0.331 | 4.500 | 1.00 | 0.00 |
| ATOM | 223 | N | MET | 15 | 5.407 | −1.575 | 2.192 | 1.00 | 0.00 |
| ATOM | 224 | CA | MET | 15 | 6.247 | −2.711 | 1.851 | 1.00 | 0.00 |
| ATOM | 225 | C | MET | 15 | 7.141 | −3.060 | 3.042 | 1.00 | 0.00 |

TABLE 6-continued

Structural Coordinates of IGE063 (SEQ ID NO: 49)

| ATOM | 226 | O | MET | 15 | 7.865 | −2.148 | 3.500 | 1.00 | 0.00 |
|---|---|---|---|---|---|---|---|---|---|
| ATOM | 227 | CB | MET | 15 | 7.097 | −2.359 | 0.625 | 1.00 | 0.00 |
| ATOM | 228 | CG | MET | 15 | 6.240 | −2.149 | −0.628 | 1.00 | 0.00 |
| ATOM | 229 | SD | MET | 15 | 7.187 | −1.677 | −2.099 | 1.00 | 0.00 |
| ATOM | 230 | CE | MET | 15 | 5.837 | −1.568 | −3.299 | 1.00 | 0.00 |
| ATOM | 231 | OXT | MET | 15 | 7.085 | −4.232 | 3.472 | 1.00 | 0.00 |
| ATOM | 232 | H | MET | 15 | 5.686 | −0.673 | 1.829 | 1.00 | 0.00 |
| ATOM | 233 | HA | MET | 15 | 5.619 | −3.570 | 1.607 | 1.00 | 0.00 |
| ATOM | 234 | 1HB | MET | 15 | 7.663 | −1.449 | 0.826 | 1.00 | 0.00 |
| ATOM | 235 | 2HB | MET | 15 | 7.800 | −3.169 | 0.436 | 1.00 | 0.00 |
| ATOM | 236 | 1HG | MET | 15 | 5.706 | −3.074 | −0.845 | 1.00 | 0.00 |
| ATOM | 237 | 2HG | MET | 15 | 5.509 | −1.362 | −0.442 | 1.00 | 0.00 |
| ATOM | 240 | 1HE | MET | 15 | 5.115 | −0.820 | −2.971 | 1.00 | 0.00 |
| ATOM | 241 | 2HE | MET | 15 | 6.241 | −1.282 | −4.270 | 1.00 | 0.00 |
| ATOM | 242 | 3HE | MET | 15 | 5.344 | −2.537 | −3.385 | 1.00 | 0.00 |
| ATOM TER | | | | | | | | | |

Example 6

Peptide Activity in a Cell-Based Histamine-Release Assay

Peptides were assayed in a histamine release assay (Lowe et al., (1995) *J. Immunol. Methods*, 184:113–122) to determine: (1) if the peptides could trigger histamine release and (2) if the peptides could prevent histamine release in the presence of ragweed and ragweed specific IgE. Rat basophil cell line RBL-48, which expresses the human FcεRI alpha subunit was cultured overnight in Falcon 96 flat well microtiter dishes. The cells were washed three times with growth media and then incubated in Iscove's MEM medium containing 10% fetal bovine serum and 3 USP units per milliliter of heparin (histamine assay buffer).

Peptides NLPRCTEGPWGWVCMAAD (SEQ ID NO:28), NLPRCTEGPWGWVCM (SEQ ID NO:27), and PRCTEGPWGWVCM (SEQ ID NO:91) (0.5 mM) were added to RBL-48 cells and assayed for histamine release. The levels of histamine released were equivalent to that of the negative control implying that the peptides themselves were not capable of inducing histamine release in the human FcεRI rat basophil cell.

Next the peptides NLPRCTEGPWGWVCMAAD (SEQ ID NO:28), NLPRCTEGPWGWVCM (SEQ ID NO:27) and DGCAWDGVQMVDCTF (SEQ ID NO:92) were assayed for the ability to inhibit ragweed induced histamine release. Peptides were serially diluted 1:2 in a 96 well microtiter dish containing 95 uL of assay histamine assay buffer with concentrations ranging from 100–0.5 uM. The diluted peptides were transferred to the 96 flat well plate containing the RBL-48 cells and allowed to incubate at room temperature for 15 minutes before adding 5 uL of ragweed specific IgE plasma to each well. The plasma contained 1027 ng/mL total IgE and 420 ng/mL of ragweed specific IgE. This plate was incubated for 1 hour at 37° C. in a $CO_2$ controlled incubator. After the incubation the supernatants were collected and diluted 1/200 in PBS. Released histamine levels were determined using a commercial histamine ELISA kit (Immunotech, Marseille, France). Levels of released histamine were plotted against peptide concentration using KaleidaGraph 3.0. Curves were fitted by a 4-parameter fit and $IC_{50}$ values were determined for each peptide. The control peptide DGCAWDGVQMVDCTF (SEQ ID NO:92) had no activity in inhibiting histamine release whereas peptides NLPRCTEGPWGWVCMAAD (SEQ ID NO:28), NLPRCTEGPWGWVCM (SEQ ID NO:27) had $IC_{50}$ values of 10 and 13 uM respectively.

These data show that the selected peptides did not induce histamine release and were effective in inhibiting ragweed induced IgE-dependent histamine release in a relevant cell based bioassay.

Example 7

Further Libraries and Selection Against FcεRI-IgG

Twenty-two naive peptide libraries were assembled for display on M13 filamentous phage. Each peptide library was fused to the p8 major coat protein of M13 phage allowing for polyvalent display of the peptide (Sidhu et al., (2000) *Methods Enzymol.* 328:333–363). The length of the displayed peptides ranged from 8–27 residues. Seventeen of the libraries contained a putative disulfide constrained loop formed through introducing a pair of cysteine residues separated by a 2–10 residue interval. One of these libraries also contains a glycine and proline within the loop, introduced to favorably permit the formation of a beta turn. Four other libraries contained multiple cysteine pairs introduced at various intervals based on cysteine residue patterns observed among conotoxin peptides (Olivera et al., (1995) *Trends Biotech.* 13:422–426). An eight residue linear peptide library was also assembled. The diversity of each library based on the number of transformations was determined to be $10^9$.

Phage particles from these libraries were propagated in XL-1 Blue *E. coli* and purified by polyethylene glycol precipitation. Phage particles were panned against FcεRI-Fc which had been immobilized through absorption (2 ug/mL) to 96 microwell plates. FcεRI-Fc is a soluble form of the IgE high affinity receptor fused to the CH2 constant domain region of IgG. Unoccupied sites on the FcεRI coated plates were blocked with PBS containing 0.5% bovine serum albumin prior to the addition of $10^{11}$ phage particles per well. A repetitive process of panning, eluting, propagating and re-panning was performed for four rounds, whereupon completion of a round of panning, the levels of enrichment for binding to FcεRI over bovine serum albumin was determined. Individual clones from the enriching peptide libraries were analyzed for specific binding to FcεRI and the ability to inhibit IgE binding.

Result of FcεRI Selection.

Twenty-two peptide libraries were panned against immobilized FcεRI-Fc for four rounds. Following the completion of each round, the level of enrichment for binding FcεRI-IgG over bovine serum albumin was determined. Significant enrichment of binding was not observed until round 2, where libraries 301, 309, 515, 516, 513 and 514 all had a greater than 10 fold increase. At round 3, additional libraries had significant enrichment as seen in libraries 305, 308, 510, 512, 553 and 556. Two libraries, 309 and 515 had a lower enrichment in round 3 than what was observed at round 2.

Fold Enrichment of Libraries at Rounds 1, 2 and 3

| Library | (SEQ ID NO:) | Sequence | Rd.1 | Rd.2 | Rd.3 |
|---|---|---|---|---|---|
| 301. | 17 | $X_4CX_2GPX_4CX_4$ | 1 | 10 | 125 |
| 303. | 94 | $X_7CX_4CX_7$ | 3 | 1 | 5 |
| 304. | 95 | $X_7CX_5CX_6$ | 1 | 1 | 5 |
| 305. | 96 | $X_6CX_6CX_6$ | 1 | 1 | 150 |
| 306. | 97 | $X_6CX_7CX_5$ | 1 | 1 | 1 |
| 307. | 98 | $X_5CX_8CX_5$ | 1 | 1 | 7 |
| 308. | 99 | $X_5CX_9CX_4$ | 1 | 4 | 1600 |
| 309. | 100 | $X_4CX_{10}CX_4$ | 1 | 20 | 3 |
| 507. | 102 | $X_8$ | 1 | 2 | 4 |
| 515. | 103 | $X_2CX_2CX_2$ | 1 | 47 | 2 |
| 516. | 104 | $X_2CX_3CX_2$ | 1 | 12 | 100 |
| 508. | 105 | $X_2CX_4CX_2$ | 1 | 2 | 2 |
| 509. | 106 | $X_2CX_5CX_2$ | 1 | 3 | 1 |
| 510. | 107 | $X_2CX_6CX_2$ | 1 | 1 | 220 |
| 511. | 108 | $X_2CX_7CX_2$ | 1 | 7 | 20 |
| 512. | 109 | $X_2CX_8CX_2$ | 1 | 6 | 100 |
| 513. | 110 | $X_2CX_9CX_2$ | 1 | 12 | 3438 |
| 514. | 111 | $X_2CX_{10}CX_2$ | 1 | 22 | 16000 |
| 553. | 112 | $CX_6CX_6CCX_3CX_6C$ | 1 | 1 | 10 |
| 554. | 113 | $CCX_3CX_6C$ | 1 | 3 | 1 |
| 555. | 114 | $CCX_5CX_4CX_4CC$ | 1 | 1 | 1 |
| 556. | 115 | $CXCX_7CX_3CX_6$ | 1 | 1 | 15 |

Individual clones from enriching libraries were selected for propagation of phage to analyze for specific binding to FcεRI-IgG and the ability to block IgE binding. Clones positive for binding receptor and positive for inhibiting IgE binding were found in libraries 301 ($X_4CX_2GPX_4CX_4$) (SEQ ID NO:17), 516 ($X_2CX_3CX_2$) (SEQ ID NO:104), 510 ($X_2CX_6CX_2$) (SEQ ID NO:107), 512 ($X_2CX_8CX_2$) (SEQ ID NO:109), and 513 ($X_2CX_9CX_2$) (SEQ ID NO:110). None of these clones demonstrated binding to bovine serum albumin or to the Fc region of a human antibody. DNA sequences of clones from library 516 ($X_2CX_3CX_2$) (SEQ ID NO:104):

DNA from individual clones that bind FcεRI and were inhibited by IgE were sequenced to determine the peptide amino acid sequence. Seven unique sequences were identified with all of the clones originating from the $X_2CX_3CX_2$ (SEQ ID NO:104) library. Conserved among 6 of the 7 sequences was a Pro at position 4 and Tyr at position 8 ($X_2CPX_2CYX$) (SEQ ID NO:116). One clone differed from the six in having the sequence LNCSQPCQR (SEQ ID NO:117). The sequence of the remaining clones was the following:

| | |
|---|---|
| VECPAVCYV | (SEQ ID NO:118) |
| QVCPAICYS | (SEQ ID NO:119) |
| AICPALCYE | (SEQ ID NO:120) |
| AECPIMCYS | (SEQ ID NO:121) |
| SVCPSLCYV | (SEQ ID NO:122) |
| ALCPEVCYV | (SEQ ID NO:123) |
| LNCSQPCQR | (SEQ ID NO:124) |
| LVCPDLCYG | (SEQ ID NO:208) |
| AECPLGCYA | (SEQ ID NO:209) |

$IC_{50}$ of Peptides IGE035-38 (SEQ ID NOS:124–125, 128–129, respectively) in a CHO Cell based Inhibition assay.

Six peptides based on selected clones from library #516 were synthesized and assayed for the ability to inhibit the binding of $^{125}$I-IgE to a Chinese hamster ovary cell line expressing the alpha subunit of the IgE high affinity receptor, FcεRI. The peptides were synthesized as nine residue monomers and oxidized to allow the formation of a disulfide bridge resulting in a cyclic peptide.

The size of each peptide was confirmed by mass spectrometry. Peptides IGE035 (ALCPEVCYV-nh$_2$) (SEQ ID NO:124) and IGE036 (Ac-ALCPEVCYV-nh$_2$) (SEQ ID NO:125) were directly based on a phage selected clone as were IGE053 (LNCSQPCQR-nh$_2$) (SEQ ID NO:126) and IGE054 (Ac-LNCSQPCQR-nh$_2$) (SEQ ID NO:127), while another set of peptides, IGE037 (ALCPAVCYV-nh$_2$) (SEQ ID NO:128), and IGE038 (Ac-ALCPAVCYV-nh$_2$) (SEQ ID NO:129), were based on the consensus sequences of several clones. Peptides IGE035 (SEQ ID NO:124) and IGE036 (SEQ ID NO:125) were not active in inhibiting $^{125}$I-IgE binding to cell surface expressed FcεRI. Peptide IGE038 (SEQ ID NO:129) was very weak with an $IC_{50}$ value of greater than 500 uM. Peptide IGE037 (SEQ ID NO:128) initially showed only weak inhibition with an $IC_{50}$ value of about 300 uM, however, this inhibition was observed to increase with time becoming as low as 25 uM, 7–10 days later. This increase over time was not observed with the other peptides.

Disulfide Reshuffling Results in Monomer Peptide IGE037 (SEQ ID NO:128) Converting to a Homodimer.

The increase in activity of IGE037 (SEQ ID NO:128) was found to be in direct correlation with a reshuffling of disulfide bonds, resulting in the formation of an IGE037 (SEQ ID NO:128) homodimer. This change occurs slowly, over a 3–12 day period following the solubilization of the peptide in water or buffer at neutral pH. The formation of a covalent, disulfide linked, homodimer was confirmed by mass spectrometry data indicating that the dimer, rather than the monomer form of the molecule, was the active form. Additional support for the occurrence of a change came from NMR data detecting a change in the one-dimensional NMR spectrum. Also HPLC reverse phase data indicated a change in retention time that correlated with the activity and the conversion of a monomer to a dimer. Final confirmation of the formation of an active dimer followed the syntheses of both parallel (IGE088, SEQ ID NO:128, 128) and anti-parallel (IGE089, SEQ ID NOS:128, 157) disulfide-linked dimer peptides. Both peptide forms were assayed for activity in inhibiting $I^{125}$-IgE binding to cell surface expressed FcεRI. Significant inhibitory activity was found only with the anti-parallel (i.e. $C_3$–$C_7$', $C_7$–$C_3$' disulfide) form.

Histamine Release and Safety Assay.

Peptide IGE089 (SEQ ID NO:128, 157) was assayed in a RBL-48 cell based histamine release assay to determine if the peptide was capable of inducing histamine release upon binding to FcεRI and also if the peptide was capable of inhibiting ragweed induced histamine release (see Example 6). Peptide IGE089 (SEQ ID NO:128, 157 was assayed to determine if a high concentration of peptide could trigger the release of histamine upon binding to FcεRI 0.5 uM of peptide IGE089 (SEQ ID NOS:128, 157) was incubated with RBL-48 cells for 2 hours at 37 degrees centigrade. Following the incubation the media was assayed for histamine. The amount of histamine released in the IGE089 (SEQ ID NO:128, 157) peptide media was similar to levels found in media of the control peptide and also the media of the buffer control. This was significantly less than histamine levels from the positive control media containing ragweed and ragweed specific IgE. This demonstrated that peptide IGE089 (SEQ ID NO:128, 157) does not induce histamine release in RBL-48 cells.

The activity of peptide IGE089 (SEQ ID NO:128, 157) in inhibiting ragweed induced was also determined. Peptide IGE089 (SEQ ID NO:128, 157) was titrated on cells in the presence of 0.1 nM of ragweed specific human IgE. After 1–2 hours 10 ng of ragweed was added and incubated for an additional 30 minutes. The reaction was stopped on ice and the levels of histamine was determine. Peptide IGE089 (SEQ ID NO:128, 157) inhibited ragweed induced histamine release with an $IC_{50}$ of 8 uM whereas control peptides did not have any inhibitory activity.

Example 8

Peptide-g3-Phage Libraries.

To ensure efficient biosynthesis of the active form of IGE037 (SEQ ID NO:128) on phage, a "single chain dimer" form was generated by introducing a short GlyGlyLys linker between two copies of the nine residue "monomer" sequence. The linker sequence was chosen based on NMR three-dimensional structural analysis of the IGE037 dimer (aka IGE089, SEQ ID NO:128, 157). It was intended to be sufficiently long to connect the C-terminus of one monomer to the N-terminus of the next and sufficiently flexible so as not to distort the structure of the dimer core. The lysine was chosen to provide a positive charge to mimic that of the amino group of the N-terminus of the second monomer. Peptide IGE083 ALCPAVCYVGGKALCPDVCYV (SEQ ID NO:130) represents such a single chain dimer form of IGE089 (SEQ ID NO:128, 157), but includes a single mutation of Ala17Asp. A set of monovalently displayed IGE083 peptide-phage libraries were constructed with small sets of residues randomized in each, in order to select for higher affinity variants of the peptide. These libraries were constructed in a phagemid construct as described above, except that some libraries included human growth hormone (hGH), inserted as a fusion partner between the displayed peptide and the g3p fragment. hGH-phagemid constructs of this kind have previously been shown to yield monovalent display (Bass et al., *Proteins* 8, 309 (1990); Lowman et al., *Biochemistry* 30, 10832 (1991); Lowman et al., *J. Mol. Biol.* 234, 564 (1993); U.S. Pat. No. 5,821,047). Randomization was achieved using synthetic oligonucleotides incorporating NNS degenerate codons ("hard randomization"), or 70:10:10:10 (i.e., 70% wild-type nucleotide, with 10% each of the remaining nucleotides) mixtures of nucleotides within each codon to be randomized ("soft randomization" (Wrighton et al., supra).

The extracellular domain of the alpha subunit of the human FcεRI(aa 1–176) was expressed using a baculovirus secretion expression system (Pharminten). cDNA encoding this domain was obtained through PCR of a plasmid containing a full length clone. The DNA fragment was ligated into baculovirus transfer vector pAcGP67 and along with BaculoGold linearized baculovirus DNA was transfected into Sf9 cells *Spodoptera frugiperda* insect cells for baculovirus production (Pharmingen). Soluble FcεRI was affinity purified from the growth media of baculovirus infected Hi-5 insect cells (Expression Systems).

The sorting conditions for these libraries generally followed those previously described (Lowman, *Methods Mol. Biol.* 87, 249 (1998); Chen et al., *J. Mol. Biol.* 293, 865 (1999)) for binding selections using FcεRI coated onto immunosorbant plates. Variable coating and elution conditions were used to favor improved enrichment, as measured by the ratio of phage recovered from a target-coated versus a non-target coated plate. Briefly, Nunc Maxisorp plates were coated with 2 ug/mL FcεRI (Genentech, Inc. produced in baculovirus infected insect cells) in PBS. After coating, each plate was blocked with the appropriate blocking reagent. Phage libraries, grown in overnight *E. coli* XL-1 Blue (Stratagene) cultures, were purified by PEG precipitation, and diluted in ELISA buffer (0.5% BSA, 0.05% Tween-20 in PBS) to approximately $10^{10}$–$10^{11}$ phage/mL for binding. Phage binding was typically done at room temperature for 1 hour. The plate was then washed with 0.05% Tween-20 in PBS as indicated. In order to increase the stringency during sorting, bound phage were sometimes incubated with soluble FcεRI. Remaining bound phage were eluted by incubation with elution reagent. Enrichment was calculated by the ratio of bound phage eluted from a target coated well to that from a BSA coated well. For some libraries, sorting against hGHbp was done in an effort to screen out phage which had lost the hGH as a fusion protein to the displaying peptides. In some cases, representative clones were assayed by competitive phage ELISA. Peptides were also designed for synthesis based upon predominant, consensus, or affinity-improved (as measured by phage ELISA) peptide-phage selectants (see Example 12).

Sorting of the initial IGE083-phage libraries showed no enrichment, except for a library randomizing residues 1, 2, 5 and 6. From this library, two predominant clones were identified, IVCPRLCYVGGKALCPDVCYV (SEQ ID NO:131), and VQCPHFCYVGGKALCPDVCYV (SEQ ID NO:132)(FIG. 1), with improved binding affinity compared to IGE083-phage; these sequences correspond to peptides IGE120 (SEQ ID NO:159), and IGE122 (SEQ ID NO:161) (both in amide form), respectively (see, Example 12).

Phage Ala-Scan of Zeta Peptide IGE120 (SEQ ID NO:131, 159).

We used a phage-based alanine scanning approach (see Cunningham et al., EMBO J. 13: 2508–2515 (1994); Lowman, Methods Mol. Biol. 87: 249–264 (1998)) to map side chains important for binding to FcεRI. The peptide IGE120 (IVCPRLCYVGGKALCPDVCYV) (SEQ ID NO:131) was displayed as a fusion to g3p of bacteriophage M13, through the linker sequence GGGSGGGGSGSGDY (SEQ ID NO:133) where the underlined residues correspond to residues 250–257 of the mature g3p (van Wezenbeek and Schoenmakers, *Nucl. Acids Res.* 6: 2799 (1979)).

Site-directed mutagenesis was carried out using the method of Kunkel (*Methods Enzymol.* 204, 125 (1991)) and clones were confirmed using dideoxy DNA sequencing with Sequenase™. In some cases, multiple Ala substitutions were made in a single peptide-phage clone. Several deletion variants were also made. The Cys side chains were not substituted.

Phage ELISA assays were carried out as described (Lowman, 1998, supra), using Nunc Maxisorp™ plates coated with a 2 μg/mL solution of baculovirus-derived FcεRI. Peptide-phage were pre-incubated for 5–10 min with serial dilutions of receptor, then added to the receptor-coated plate. After incubation for 1 h at room temperature, the plates were washed and an anti-phage HRP-conjugated antibody (Pharmacia) was added. After further incubation for 20 min, plates were again washed and developed using the substrate OPD (Sigma). Optical density at 492 nm was read and plotted as a function of FcεRI concentration to determine an $IC_{50}$ of inhibition by each peptide-phage variant.

The results of alanine-scanning of IGE120 (SEQ ID NO:131, 159) are shown in Table 7. No detectable binding was observed for Ala substitutions of P4, Y8, P16, or Y20. This could result from loss of binding affinity or defects in structure and expression of these variants or both. Based upon the NMR structure of peptides of this variety (see Example 11), it appears that the Y8A and Y20A substitutions globally disrupt peptide structure. However, the P4A and P16A variants maintain the overall wild-type structure. Therefore, these side chains are implicated as contact points with the receptor. The D17A mutation caused a 25-fold reduction in binding affinity compared to IGE 120 (SEQ ID NO:131, 159), demonstrating that the Asp side chain is important for receptor binding. All the remaining side chain substitutions tested showed less than a 2-fold effect on receptor-binding affinity. In particular, substitutions or deletions at the amino-terminal two residues had little effect.

A second generation of peptide-phage libraries were constructed based upon IGE120 (SEQ ID NOS:131, 159) or IGE122 (SEQ ID NOS:132, 161). These libraries were sorted for FcεRI binding as described above. A predominant clone from the IGE120-phage library (NBO895-619D), having the sequence IVCPRLCYELDYELCPDVCYV (SEQ ID NO:153), was found to have about 2-fold improved affinity over IGE120 (SEQ ID NO:131, 159) (FIG. 2). The "linker region" (underlined) of the peptide was randomized in this library.

Because the IGE122 peptide (SEQ ID NOS:132, 161) and phage were known to have improved affinity over IGE120 (SEQ ID NOS:131, 159), a synthetic peptide was constructed in which the ELDYE (SEQ ID NO:154) linker sequence was incorporated into the IGE122 background. This peptide, known as IGE134 (SEQ ID NOS:155, 171), was shown to have improved affinity over IGE122 (SEQ ID NOS:132, 161), as was the corresponding phage construct (FIG. 3).

A third generation of peptide-phage libraries were constructed based upon IGE134 (SEQ ID NOS:155, 171). A variety of clones from these libraries were found to bind FcεRI with similar affinity to IGE 134-phage; however, none were found with greater than about 2-fold improvement in apparent binding affinity (FIG. 4).

Example 9

IGE134 (SEQ ID NOS:155, 171) Libraries with Insertions or Deletions in the Linker Region.

A set of monovalently displayed IGE134 peptide-phage libraries were constructed with variable lengths of the "linker region" residues ELDYE (SEQ ID NO:154) to test for improved affinity and for the peptide's ability to accommodate alternative sequences.

Insertions of 3 or 5 random residues were designed to follow the ELDYE (SEQ ID NO:154) sequence in 2 libraries, HL718 and HL719. Shorter linker regions were con-

TABLE 7

Alanine scanning of IGE120-Phage

| Peptide-Phage Sequence | SEQ ID NO: | Relative $IC_{50}$ |
|---|---|---|
| I V C P R L C Y V G G K A L C P D V C Y V | 131 | -1- |
| A A C P A L C Y V G G K A L C P D V C Y V | 134 | 0.67 |
| I V C A R L C Y V G G K A L C P D V C Y V | 135 | NDB |
| I V C P R L C Y V G G K A L C A D V C Y V | 136 | NDB |
| I V C P R A C Y V G G K A L C P D V C Y V | 137 | 1.8 |
| I V C P R A C Y V G G K A L C P D A C Y V | 138 | 2.2 |
| I V C P R L C Y A G G K A L C P D V C Y V | 139 | 0.72 |
| I V C P R L C Y V G G K A L C P D V C Y A | 140 | 0.88 |
| I V C P R L C Y A G G K A L C P D V C Y A | 141 | 0.70 |
| I V C P R L C A V G G K A L C P D V C Y V | 142 | NDB |
| I V C P R L C Y V G G K A L C P D V C A V | 143 | NDB |
| I V C P R L C Y V G G A A L C P D V C Y V | 144 | 0.56 |
| I V C P R L C Y V G G K A L C P A V C Y V | 145 | 25.0 |
| I V C P R L C Y V G G K A A C P A V C Y A | 146 | NDB |
| I V C P R A C Y V G G K A A C P D V C Y V | 147 | 2.9 |
| I V C P R L C Y V G G K A A C P D V C Y V | 148 | 2.5 |
| I V C P R L C Y V G G K A L C P D A C Y V | 149 | 0.72 |
| V C P R L C Y V G G K A L C P D V C Y V | 150 | 1.4 |
| C P R L C Y V G G K A L C P D V C Y V | 151 | 1.2 |
| I V C P R L C Y V G G K A L C P D V C | 152 | NDB |

(NDB = no detectable binding)

structed by substituting 3 or 4 random residues for the ELDYE (SEQ ID NO:154) sequence in libraries HL720 and HL721.

IGE134-hGH-g3 phage libraries were constructed as described above (Example II) and subjected to 3 rounds of receptor selection. Clones were sequenced from the round-3 eluted pools by SequenaseJ or capillary (Beckman CEQ2000) sequencing, and several were assayed by phage-ELISA (FIG. 5).

Example 10

Phage Ala-scan of Zeta Peptide IGE134 (SEQ ID NOS:155, 171).

A phage-based alanine scanning approach was used to map the FcεRI binding determinants of IGE134 (SEQ ID NOS:155, 171), as described above for IGE120 (SEQ ID NO:131, 159). The peptide IGE134 (VQCPHF-CYELDYELCPDVCYV) (SEQ ID NO:155) was displayed as a fusion to human growth hormone (hGH), fused to the C-terminal domain of g3p of bacteriophage M13 in a phagemid construct (see e.g., Lowman et al., 1993, supra). Additionally, combinations of Ala mutations, deletions, and other substitutions were tested.

The results of alanine-scanning of IGE134 (SEQ ID NOS:155, 171) are shown in FIG. 6. No detectable binding was observed for Ala substitutions of the two disulfide-bonded Cys pairs, P4, or P16. The Y8A caused a large loss (>50-fold) in binding affinity. This could result from loss of binding affinity or defects in structure and expression of these variants or both. As described above, it appears that the Y8A and Y20A substitutions globally disrupt peptide structure. However, the P4A and P16A variants maintain the canonical zeta structure. Therefore, these side chains are implicated as contact points with the receptor. The D 17A mutation caused no reduction in binding affinity compared to IGE134 (SEQ ID NOS:155, 171), demonstrating that the Asp side chain is no longer important for receptor binding [cf. IGE120 (SEQ ID NO:131, 159)]. However, a double substitution of E13A/D17A resulted in about 10-fold reduced binding affinity, suggesting that a carboxylate group is still needed for high-affinity binding to FcεRI. However, addition of two more acidic residues (L10E and Y12E) did not significantly alter affinity. Multiple mutations of the acidic residues in the linker region, combined with D17A, also caused large losses in binding affinity. Residue E13 of IGE134 (SEQ ID NOS:155, 171) [cf. A13 in IGE120 (SEQ ID NO:131, 159)] appears to compensate for the lost carboxylate in the D17A mutant.

Based on these data, results of random peptide libraries, and synthetic peptide binding assays, it is expected that peptides of the form CPXZCYX$_n$ZCPDXCY (with n=3, 4, or 5; Z=a large hydrophobic residue) will bind FcεRI with high affinity. It is further expected that peptides of the form CPXZCYX$_n$EZCPXXCY (with n=2, 3, or 4; Z=a large hydrophobic residue) will bind FcεRI with high affinity.

Example 11

NMR Analysis of Peptide IGE134 (SEQ ID NOS:155, 171).

An NMR sample of IGE134 (SEQ ID NOS:155, 171)(see Example 12) was prepared by dissolving 2–3 mg of peptide in 500 μL 92% (v/v) H$_2$O/8% D$_2$O, then adjusting the pH to 6.0 by addition of 0.1 N NaOH. The peaks in the ID NMR spectrum at 298K were rather broad, so 8% acetonitrile-d$_3$ was added to the sample and the temperature was raised to 308K. Under these conditions, the NMR peaks were significantly sharper and allowed for complete three-dimensional structure determination. No significant changes in chemical shift were observed, however, between the sample with and without acetonitrile, so the co-solvent appears to have only minimized the extent of non-specific aggregation without perturbing the structure. Two-dimensional double-quantum-filtered correlation spectroscopy (2QF-COSY), total correlation spectra (TOCSY), nuclear Overhauser effect spectra (NOESY), and rotating-frame Overhauser effect spectra (ROESY) were collected on a Bruker AMX-500 spectrometer equipped with a 5-mm triple axis pulsed-field gradient probe at 308K. The experiments were recorded as described by Cavanagh et al. in "Protein NMR Spectroscopy, Principles and Practice" (Academic Press, San Diego: ISBN 0-12-164490-1, 1995). After lyophilization and dissolution of the peptide in D$_2$O, a 2D NOESY and a COSY-35 spectrum, acquired with a 35° mixing pulse, were obtained. Complete $^1$H resonance assignments were derived from these data by standard methods (Wüthrich, in "*NMR of proteins and nucleic acids*", John Wiley & Sons, New York: ISBN 0471-82893-9, 1986.)

Evidence for a well-defined three-dimensional structure for IGE 134 (SEQ ID NOS:155, 171) was obtained from the following: (1) the $^1$H resonance positions are significantly different from those expected in an unstructured peptide. (2) Scalar coupling constants between amide and alpha protons (obtained from the 2QF-COSY spectrum) are distinct from the averaged values observed in unstructured peptides. The values are greater than 8.5 Hz for residues Cys3, Tyr8, Glu9, Cys15, and Tyr20 and less than 6 Hz for residues His5, Phe6, Cys7, Asp 17, Val18, and Cys 19. Scalar coupling constants were also measured between alpha and beta protons in the COSY-35 spectrum. These data indicate that the side chains of residues Phe6, Cys7, Tyr8, Glu9, Leu 10, Glu 13, Cys15, Val 18, Cys19 and Tyr20 have fixed chi-1 angles, i.e., these side chains do not sample the range of chi-1 rotamers that are populated in unstructured peptides. (3) Peaks in the NOESY and ROESY spectra indicate that there are many proton—proton contacts (<5 Å) between residues that are not adjacent in the primary sequence. These can only occur if the peptide folds up into a well-defined structure.

The NMR data were used to derive restraints that could be used to determine a three-dimensional model of the IGE134 (SEQ ID NOS:155, 171) structure. Dihedral angle restraints were derived from the amide-alpha and alpha-beta scalar coupling constants via an appropriate Karplus relationship (Karplus, *J. Phys. Chem.*, 30: 11–15 (1959)). Distance restraints were introduced between protons which exhibited a through-space interaction in the ROESY or NOESY spectra; the size of the upper bound, and corrections to the upper bound because of peak overlap or resonance degeneracy were as described by Starovasnik et al., *Biochemistry*, 35: 15558–69 (1996). These restraints were used to generate a family of structures using the program DGII (Havel, *Prog. Biophys. Mol. Biol.*, 56:43–78 (1991)) which were subsequently refined by restrained molecular dynamics with the program Discover (MSI, San Diego) using the AMBER all atom force field (Weiner et al., *J. Comput. Chem.*, 7: 230–252 (1986)). The resulting structures converged to a single global fold (average root-mean-squared deviation from the mean structure of 0.35±0.10 Å for N, C-alpha, and carbonyl carbons of residues 3–8 and 15–20). The best twenty models (least violation of the input data) agreed with the input data very well (no distance restraint violations greater than 0.1 Å and no dihedral angle violations greater than 2°), and had good covalent geometry as judged by the program PROCHECK™ (Laskowski et al., *J. Appl. Cryst.*, 26: 283–291 (1993)).

A representative member of the ensemble (the model that is closest to the mean coordinates) is shown in FIG. 8. IGE134 (SEQ ID NOS:155, 171) has little regular secondary structure, but presents two small 310 helical turns comprised of residues 4–8 and 16–20, connected by two disulfide bonds in the center of the molecule. The backbone conformation is nearly symmetric with residues 3–8 adopting essentially the same structure as residues 15–20. The helical backbone conformation appears to be stabilized by tight packing of the tyrosine rings (Tyr8 and Tyr20) "below" the disulfides with each tyrosine hydroxylproton donating a hydrogen bond across the "dimer interface" to the backbone carbonyl oxygen of a cysteine [Tyr8(HH)-Cys19(CO) and Tyr20(HH)-Cys7(CO)]. A peptide that has Tyr20 replaced by Asp (IGE150; SEQ ID NO:183) shows loss of stable structure for the C-terminal half of the peptide demonstrating the structural role of the tyrosine side chain. Val 1 and Gln2 are not well-defined by the NMR data and appear to be more flexible than the core of the molecule. The linker region involving residues 10–13 is also less well-defined by the NMR data than the structured core residues 3–8 and 15–20.

TABLE 8

Structural Coordinates of IGE134 (SEQ ID NOS: 155, 171)

| | | | | | | | | | |
|---|---|---|---|---|---|---|---|---|---|
| ATOM | 1 | N | VAL | 1 | −4.277 | −9.441 | 0.344 | 1.00 | 0.00 |
| ATOM | 2 | CA | VAL | 1 | −3.015 | −8.942 | 0.922 | 1.00 | 0.00 |
| ATOM | 3 | C | VAL | 1 | −3.267 | −8.347 | 2.309 | 1.00 | 0.00 |
| ATOM | 4 | O | VAL | 1 | −4.289 | −7.698 | 2.526 | 1.00 | 0.00 |
| ATOM | 5 | CB | VAL | 1 | −2.330 | −7.924 | −0.013 | 1.00 | 0.00 |
| ATOM | 6 | CG1 | VAL | 1 | −0.938 | −7.540 | 0.509 | 1.00 | 0.00 |
| ATOM | 7 | CG2 | VAL | 1 | −2.166 | −8.480 | −1.435 | 1.00 | 0.00 |
| ATOM | 8 | 1H | VAL | 1 | −4.695 | −10.106 | 0.980 | 1.00 | 0.00 |
| ATOM | 9 | 2H | VAL | 1 | −4.910 | −8.665 | 0.211 | 1.00 | 0.00 |
| ATOM | 10 | 3H | VAL | 1 | −4.098 | −9.892 | −0.541 | 1.00 | 0.00 |
| ATOM | 11 | HA | VAL | 1 | −2.358 | −9.807 | 1.028 | 1.00 | 0.00 |
| ATOM | 12 | HB | VAL | 1 | −2.942 | −7.022 | −0.069 | 1.00 | 0.00 |
| ATOM | 13 | 1HG1 | VAL | 1 | −0.326 | −8.433 | 0.637 | 1.00 | 0.00 |
| ATOM | 14 | 2HG1 | VAL | 1 | −0.447 | −6.878 | −0.204 | 1.00 | 0.00 |
| ATOM | 15 | 3HG1 | VAL | 1 | −1.016 | −7.017 | 1.461 | 1.00 | 0.00 |
| ATOM | 16 | 1HG2 | VAL | 1 | −1.615 | −9.421 | −1.407 | 1.00 | 0.00 |
| ATOM | 17 | 2HG2 | VAL | 1 | −3.139 | −8.644 | −1.899 | 1.00 | 0.00 |
| ATOM | 18 | 3HG2 | VAL | 1 | −1.617 | −7.766 | −2.049 | 1.00 | 0.00 |
| ATOM | 19 | N | GLN | 2 | −2.333 | −8.566 | 3.244 | 1.00 | 0.00 |
| ATOM | 20 | CA | GLN | 2 | −2.393 | −8.051 | 4.609 | 1.00 | 0.00 |
| ATOM | 21 | C | GLN | 2 | −1.946 | −6.584 | 4.643 | 1.00 | 0.00 |
| ATOM | 22 | O | GLN | 2 | −0.987 | −6.227 | 5.325 | 1.00 | 0.00 |
| ATOM | 23 | CB | GLN | 2 | −1.605 | −8.970 | 5.567 | 1.00 | 0.00 |
| ATOM | 24 | CG | GLN | 2 | −0.289 | −9.560 | 5.028 | 1.00 | 0.00 |
| ATOM | 25 | CD | GLN | 2 | 0.690 | −8.510 | 4.509 | 1.00 | 0.00 |
| ATOM | 26 | OE1 | GLN | 2 | 0.682 | −8.188 | 3.323 | 1.00 | 0.00 |
| ATOM | 27 | NE2 | GLN | 2 | 1.538 | −7.977 | 5.390 | 1.00 | 0.00 |
| ATOM | 28 | H | GLN | 2 | −1.502 | −9.071 | 2.972 | 1.00 | 0.00 |
| ATOM | 29 | HA | GLN | 2 | −3.430 | −8.068 | 4.950 | 1.00 | 0.00 |
| ATOM | 30 | 1HB | GLN | 2 | −1.410 | −8.444 | 6.503 | 1.00 | 0.00 |
| ATOM | 31 | 2HB | GLN | 2 | −2.247 | −9.820 | 5.804 | 1.00 | 0.00 |
| ATOM | 32 | 1HG | GLN | 2 | 0.189 | −10.122 | 5.832 | 1.00 | 0.00 |
| ATOM | 33 | 2HG | GLN | 2 | −0.506 | −10.267 | 4.227 | 1.00 | 0.00 |
| ATOM | 34 | 1HE2 | GLN | 2 | 2.194 | −7.274 | 5.084 | 1.00 | 0.00 |
| ATOM | 35 | 2HE2 | GLN | 2 | 1.509 | −8.261 | 6.358 | 1.00 | 0.00 |
| ATOM | 36 | N | CYS | 3 | −2.655 | −5.732 | 3.894 | 1.00 | 0.00 |
| ATOM | 37 | CA | CYS | 3 | −2.310 | −4.334 | 3.685 | 1.00 | 0.00 |
| ATOM | 38 | C | CYS | 3 | −3.593 | −3.525 | 3.457 | 1.00 | 0.00 |
| ATOM | 39 | O | CYS | 3 | −4.445 | −3.972 | 2.690 | 1.00 | 0.00 |
| ATOM | 40 | CB | CYS | 3 | −1.393 | −4.249 | 2.465 | 1.00 | 0.00 |
| ATOM | 41 | SG | CYS | 3 | −0.961 | −2.565 | 1.984 | 1.00 | 0.00 |
| ATOM | 42 | H | CYS | 3 | −3.455 | −6.087 | 3.386 | 1.00 | 0.00 |
| ATOM | 43 | HA | CYS | 3 | −1.767 | −3.967 | 4.554 | 1.00 | 0.00 |
| ATOM | 44 | 1HB | CYS | 3 | −0.477 | −4.804 | 2.666 | 1.00 | 0.00 |
| ATOM | 45 | 2HB | CYS | 3 | −1.902 | −4.714 | 1.624 | 1.00 | 0.00 |
| ATOM | 48 | N | PRO | 4 | −3.760 | −2.355 | 4.100 | 1.00 | 0.00 |
| ATOM | 49 | CA | PRO | 4 | −4.977 | −1.561 | 4.008 | 1.00 | 0.00 |
| ATOM | 50 | C | PRO | 4 | −5.106 | −0.843 | 2.658 | 1.00 | 0.00 |
| ATOM | 51 | O | PRO | 4 | −4.158 | −0.771 | 1.877 | 1.00 | 0.00 |
| ATOM | 52 | CB | PRO | 4 | −4.910 | −0.576 | 5.178 | 1.00 | 0.00 |
| ATOM | 53 | CG | PRO | 4 | −3.409 | −0.368 | 5.357 | 1.00 | 0.00 |
| ATOM | 54 | CD | PRO | 4 | −2.834 | −1.748 | 5.045 | 1.00 | 0.00 |
| ATOM | 55 | HA | PRO | 4 | −5.848 | −2.205 | 4.143 | 1.00 | 0.00 |
| ATOM | 56 | 1HB | PRO | 4 | −5.439 | 0.357 | 4.985 | 1.00 | 0.00 |
| ATOM | 57 | 2HB | PRO | 4 | −5.310 | −1.053 | 6.073 | 1.00 | 0.00 |
| ATOM | 58 | 1HG | PRO | 4 | −3.061 | 0.350 | 4.615 | 1.00 | 0.00 |
| ATOM | 59 | 2HG | PRO | 4 | −3.150 | −0.031 | 6.361 | 1.00 | 0.00 |
| ATOM | 60 | 1HD | PRO | 4 | −1.828 | −1.646 | 4.638 | 1.00 | 0.00 |
| ATOM | 61 | 2HD | PRO | 4 | −2.812 | −2.345 | 5.958 | 1.00 | 0.00 |
| ATOM | 62 | N | HIS | 5 | −6.313 | −0.325 | 2.399 | 1.00 | 0.00 |
| ATOM | 63 | CA | HIS | 5 | −6.737 | 0.222 | 1.117 | 1.00 | 0.00 |

TABLE 8-continued

Structural Coordinates of IGE134 (SEQ ID NOS: 155, 171)

| | | | | | | | | |
|---|---|---|---|---|---|---|---|---|
| ATOM | 64 | C | HIS | 5 | −5.930 | 1.447 | 0.685 | 1.00 | 0.00 |
| ATOM | 65 | O | HIS | 5 | −5.536 | 1.533 | −0.477 | 1.00 | 0.00 |
| ATOM | 66 | CB | HIS | 5 | −8.230 | 0.561 | 1.194 | 1.00 | 0.00 |
| ATOM | 67 | CG | HIS | 5 | −8.789 | 1.105 | −0.097 | 1.00 | 0.00 |
| ATOM | 68 | ND1 | HIS | 5 | −9.268 | 2.401 | −0.215 | 1.00 | 0.00 |
| ATOM | 69 | CD2 | HIS | 5 | −8.945 | 0.546 | −1.342 | 1.00 | 0.00 |
| ATOM | 70 | CE1 | HIS | 5 | −9.700 | 2.552 | −1.478 | 1.00 | 0.00 |
| ATOM | 71 | NE2 | HIS | 5 | −9.530 | 1.455 | −2.219 | 1.00 | 0.00 |
| ATOM | 72 | H | HIS | 5 | −7.019 | −0.399 | 3.117 | 1.00 | 0.00 |
| ATOM | 73 | HA | HIS | 5 | −6.613 | −0.557 | 0.364 | 1.00 | 0.00 |
| ATOM | 74 | 1HB | HIS | 5 | −8.785 | −0.343 | 1.447 | 1.00 | 0.00 |
| ATOM | 75 | 2HB | HIS | 5 | −8.391 | 1.294 | 1.985 | 1.00 | 0.00 |
| ATOM | 76 | HD1 | HIS | 5 | −9.297 | 3.099 | 0.514 | 1.00 | 0.00 |
| ATOM | 77 | HD2 | HIS | 5 | −8.666 | −0.464 | −1.602 | 1.00 | 0.00 |
| ATOM | 78 | HE1 | HIS | 5 | −10.136 | 3.466 | −1.855 | 1.00 | 0.00 |
| ATOM | 79 | N | PHE | 6 | −5.705 | 2.399 | 1.602 | 1.00 | 0.00 |
| ATOM | 80 | CA | PHE | 6 | −5.087 | 3.687 | 1.296 | 1.00 | 0.00 |
| ATOM | 81 | C | PHE | 6 | −3.713 | 3.550 | 0.632 | 1.00 | 0.00 |
| ATOM | 82 | O | PHE | 6 | −3.340 | 4.400 | −0.172 | 1.00 | 0.00 |
| ATOM | 83 | CB | PHE | 6 | −5.020 | 4.566 | 2.550 | 1.00 | 0.00 |
| ATOM | 84 | CG | PHE | 6 | −4.125 | 4.050 | 3.661 | 1.00 | 0.00 |
| ATOM | 85 | CD1 | PHE | 6 | −2.748 | 4.349 | 3.656 | 1.00 | 0.00 |
| ATOM | 86 | CD2 | PHE | 6 | −4.676 | 3.320 | 4.731 | 1.00 | 0.00 |
| ATOM | 87 | CE1 | PHE | 6 | −1.926 | 3.904 | 4.705 | 1.00 | 0.00 |
| ATOM | 88 | CE2 | PHE | 6 | −3.853 | 2.881 | 5.783 | 1.00 | 0.00 |
| ATOM | 89 | CZ | PHE | 6 | −2.476 | 3.164 | 5.764 | 1.00 | 0.00 |
| ATOM | 90 | H | PHE | 6 | −6.028 | 2.245 | 2.545 | 1.00 | 0.00 |
| ATOM | 91 | HA | PHE | 6 | −5.741 | 4.199 | 0.589 | 1.00 | 0.00 |
| ATOM | 92 | 1HB | PHE | 6 | −4.662 | 5.554 | 2.253 | 1.00 | 0.00 |
| ATOM | 93 | 2HB | PHE | 6 | −6.032 | 4.694 | 2.937 | 1.00 | 0.00 |
| ATOM | 94 | HD1 | PHE | 6 | −2.317 | 4.923 | 2.849 | 1.00 | 0.00 |
| ATOM | 95 | HD2 | PHE | 6 | −5.733 | 3.099 | 4.754 | 1.00 | 0.00 |
| ATOM | 96 | HE1 | PHE | 6 | −0.871 | 4.139 | 4.701 | 1.00 | 0.00 |
| ATOM | 97 | HE2 | PHE | 6 | −4.280 | 2.329 | 6.607 | 1.00 | 0.00 |
| ATOM | 98 | HZ | PHE | 6 | −1.843 | 2.818 | 6.569 | 1.00 | 0.00 |
| ATOM | 99 | N | CYS | 7 | −2.975 | 2.480 | 0.955 | 1.00 | 0.00 |
| ATOM | 100 | CA | CYS | 7 | −1.685 | 2.160 | 0.356 | 1.00 | 0.00 |
| ATOM | 101 | C | CYS | 7 | −1.763 | 2.083 | −1.171 | 1.00 | 0.00 |
| ATOM | 102 | O | CYS | 7 | −0.791 | 2.404 | −1.848 | 1.00 | 0.00 |
| ATOM | 103 | CB | CYS | 7 | −1.184 | 0.827 | 0.917 | 1.00 | 0.00 |
| ATOM | 104 | SG | CYS | 7 | −0.958 | 0.789 | 2.712 | 1.00 | 0.00 |
| ATOM | 105 | H | CYS | 7 | −3.343 | 1.830 | 1.635 | 1.00 | 0.00 |
| ATOM | 106 | HA | CYS | 7 | −0.973 | 2.941 | 0.625 | 1.00 | 0.00 |
| ATOM | 107 | 1HB | CYS | 7 | −1.897 | 0.047 | 0.648 | 1.00 | 0.00 |
| ATOM | 108 | 2HB | CYS | 7 | −0.227 | 0.582 | 0.454 | 1.00 | 0.00 |
| ATOM | 111 | N | TYR | 8 | −2.915 | 1.669 | −1.711 | 1.00 | 0.00 |
| ATOM | 112 | CA | TYR | 8 | −3.124 | 1.465 | −3.137 | 1.00 | 0.00 |
| ATOM | 113 | C | TYR | 8 | −3.831 | 2.661 | −3.783 | 1.00 | 0.00 |
| ATOM | 114 | O | TYR | 8 | −3.994 | 2.680 | −5.001 | 1.00 | 0.00 |
| ATOM | 115 | CB | TYR | 8 | −3.936 | 0.182 | −3.333 | 1.00 | 0.00 |
| ATOM | 116 | CG | TYR | 8 | −3.319 | −1.035 | −2.670 | 1.00 | 0.00 |
| ATOM | 117 | CD1 | TYR | 8 | −2.121 | −1.573 | −3.174 | 1.00 | 0.00 |
| ATOM | 118 | CD2 | TYR | 8 | −3.921 | −1.610 | −1.535 | 1.00 | 0.00 |
| ATOM | 119 | CE1 | TYR | 8 | −1.566 | −2.724 | −2.590 | 1.00 | 0.00 |
| ATOM | 120 | CE2 | TYR | 8 | −3.368 | −2.762 | −0.952 | 1.00 | 0.00 |
| ATOM | 121 | CZ | TYR | 8 | −2.202 | −3.331 | −1.494 | 1.00 | 0.00 |
| ATOM | 122 | OH | TYR | 8 | −1.689 | −4.473 | −0.958 | 1.00 | 0.00 |
| ATOM | 123 | H | TYR | 8 | −3.689 | 1.446 | −1.100 | 1.00 | 0.00 |
| ATOM | 124 | HA | TYR | 8 | −2.166 | 1.334 | −3.642 | 1.00 | 0.00 |
| ATOM | 125 | 1HB | TYR | 8 | −4.942 | 0.339 | −2.941 | 1.00 | 0.00 |
| ATOM | 126 | 2HB | TYR | 8 | −4.024 | −0.019 | −4.402 | 1.00 | 0.00 |
| ATOM | 127 | HD1 | TYR | 8 | −1.631 | −1.114 | −4.020 | 1.00 | 0.00 |
| ATOM | 128 | HD2 | TYR | 8 | −4.814 | −1.180 | −1.109 | 1.00 | 0.00 |
| ATOM | 129 | HE1 | TYR | 8 | −0.656 | −3.143 | −2.993 | 1.00 | 0.00 |
| ATOM | 130 | HE2 | TYR | 8 | −3.842 | −3.208 | −0.090 | 1.00 | 0.00 |
| ATOM | 131 | HH | TYR | 8 | −2.267 | −4.871 | −0.304 | 1.00 | 0.00 |
| ATOM | 132 | N | GLU | 9 | −4.226 | 3.664 | −2.988 | 1.00 | 0.00 |
| ATOM | 133 | CA | GLU | 9 | −4.710 | 4.944 | −3.484 | 1.00 | 0.00 |
| ATOM | 134 | C | GLU | 9 | −3.499 | 5.865 | −3.626 | 1.00 | 0.00 |
| ATOM | 135 | O | GLU | 9 | −3.281 | 6.460 | −4.679 | 1.00 | 0.00 |
| ATOM | 136 | CB | GLU | 9 | −5.757 | 5.525 | −2.522 | 1.00 | 0.00 |
| ATOM | 137 | CG | GLU | 9 | −6.908 | 4.548 | −2.243 | 1.00 | 0.00 |
| ATOM | 138 | CD | GLU | 9 | −7.572 | 4.057 | −3.526 | 1.00 | 0.00 |
| ATOM | 139 | OE1 | GLU | 9 | −8.400 | 4.822 | −4.065 | 1.00 | 0.00 |
| ATOM | 140 | OE2 | GLU | 9 | −7.240 | 2.926 | −3.943 | 1.00 | 0.00 |
| ATOM | 141 | H | GLU | 9 | −4.087 | 3.588 | −1.990 | 1.00 | 0.00 |
| ATOM | 142 | HA | GLU | 9 | −5.168 | 4.826 | −4.467 | 1.00 | 0.00 |

TABLE 8-continued

Structural Coordinates of IGE134 (SEQ ID NOS: 155, 171)

| ATOM | 143 | 1HB | GLU | 9 | −5.287 | 5.782 | −1.572 | 1.00 | 0.00 |
|------|-----|------|-----|----|--------|--------|--------|------|------|
| ATOM | 144 | 2HB | GLU | 9 | −6.164 | 6.437 | −2.961 | 1.00 | 0.00 |
| ATOM | 145 | 1HG | GLU | 9 | −6.538 | 3.689 | −1.684 | 1.00 | 0.00 |
| ATOM | 146 | 2HG | GLU | 9 | −7.654 | 5.052 | −1.628 | 1.00 | 0.00 |
| ATOM | 147 | N | LEU | 10 | −2.699 | 5.948 | −2.557 | 1.00 | 0.00 |
| ATOM | 148 | CA | LEU | 10 | −1.396 | 6.587 | −2.542 | 1.00 | 0.00 |
| ATOM | 149 | C | LEU | 10 | −0.367 | 5.519 | −2.919 | 1.00 | 0.00 |
| ATOM | 150 | O | LEU | 10 | 0.388 | 5.052 | −2.070 | 1.00 | 0.00 |
| ATOM | 151 | CB | LEU | 10 | −1.143 | 7.185 | −1.149 | 1.00 | 0.00 |
| ATOM | 152 | CG | LEU | 10 | −2.219 | 8.196 | −0.707 | 1.00 | 0.00 |
| ATOM | 153 | CD1 | LEU | 10 | −1.907 | 8.691 | 0.709 | 1.00 | 0.00 |
| ATOM | 154 | CD2 | LEU | 10 | −2.308 | 9.401 | −1.652 | 1.00 | 0.00 |
| ATOM | 155 | H | LEU | 10 | −2.966 | 5.446 | −1.722 | 1.00 | 0.00 |
| ATOM | 156 | HA | LEU | 10 | −1.343 | 7.385 | −3.284 | 1.00 | 0.00 |
| ATOM | 157 | 1HB | LEU | 10 | −1.125 | 6.375 | −0.418 | 1.00 | 0.00 |
| ATOM | 158 | 2HB | LEU | 10 | −0.169 | 7.673 | −1.148 | 1.00 | 0.00 |
| ATOM | 159 | HG | LEU | 10 | −3.192 | 7.704 | −0.676 | 1.00 | 0.00 |
| ATOM | 160 | 1HD1 | LEU | 10 | −2.701 | 9.356 | 1.050 | 1.00 | 0.00 |
| ATOM | 161 | 2HD1 | LEU | 10 | −1.842 | 7.844 | 1.393 | 1.00 | 0.00 |
| ATOM | 162 | 3HD1 | LEU | 10 | −0.962 | 9.235 | 0.716 | 1.00 | 0.00 |
| ATOM | 163 | 1HD2 | LEU | 10 | −2.662 | 9.091 | −2.634 | 1.00 | 0.00 |
| ATOM | 164 | 2HD2 | LEU | 10 | −3.013 | 10.129 | −1.250 | 1.00 | 0.00 |
| ATOM | 165 | 3HD2 | LEU | 10 | −1.330 | 9.872 | −1.750 | 1.00 | 0.00 |
| ATOM | 166 | N | ASP | 11 | −0.374 | 5.129 | −4.202 | 1.00 | 0.00 |
| ATOM | 167 | CA | ASP | 11 | 0.355 | 3.990 | −4.758 | 1.00 | 0.00 |
| ATOM | 168 | C | ASP | 11 | 1.850 | 3.971 | −4.431 | 1.00 | 0.00 |
| ATOM | 169 | O | ASP | 11 | 2.419 | 2.890 | −4.290 | 1.00 | 0.00 |
| ATOM | 170 | CB | ASP | 11 | 0.149 | 3.936 | −6.275 | 1.00 | 0.00 |
| ATOM | 171 | CG | ASP | 11 | −1.303 | 3.635 | −6.634 | 1.00 | 0.00 |
| ATOM | 172 | OD1 | ASP | 11 | −2.081 | 4.609 | −6.725 | 1.00 | 0.00 |
| ATOM | 173 | OD2 | ASP | 11 | −1.608 | 2.435 | −6.811 | 1.00 | 0.00 |
| ATOM | 174 | H | ASP | 11 | −1.026 | 5.592 | −4.821 | 1.00 | 0.00 |
| ATOM | 175 | HA | ASP | 11 | −0.079 | 3.083 | −4.336 | 1.00 | 0.00 |
| ATOM | 176 | 1HB | ASP | 11 | 0.450 | 4.884 | −6.723 | 1.00 | 0.00 |
| ATOM | 177 | 2HB | ASP | 11 | 0.775 | 3.146 | −6.692 | 1.00 | 0.00 |
| ATOM | 178 | N | TYR | 12 | 2.491 | 5.142 | −4.317 | 1.00 | 0.00 |
| ATOM | 179 | CA | TYR | 12 | 3.891 | 5.236 | −3.918 | 1.00 | 0.00 |
| ATOM | 180 | C | TYR | 12 | 4.103 | 4.555 | −2.561 | 1.00 | 0.00 |
| ATOM | 181 | O | TYR | 12 | 3.195 | 4.524 | −1.734 | 1.00 | 0.00 |
| ATOM | 182 | CB | TYR | 12 | 4.359 | 6.695 | −3.928 | 1.00 | 0.00 |
| ATOM | 183 | CG | TYR | 12 | 3.592 | 7.636 | −3.019 | 1.00 | 0.00 |
| ATOM | 184 | CD1 | TYR | 12 | 2.439 | 8.292 | −3.491 | 1.00 | 0.00 |
| ATOM | 185 | CD2 | TYR | 12 | 4.049 | 7.883 | −1.711 | 1.00 | 0.00 |
| ATOM | 186 | CE1 | TYR | 12 | 1.741 | 9.181 | −2.657 | 1.00 | 0.00 |
| ATOM | 187 | CE2 | TYR | 12 | 3.367 | 8.794 | −0.888 | 1.00 | 0.00 |
| ATOM | 188 | CZ | TYR | 12 | 2.202 | 9.429 | −1.353 | 1.00 | 0.00 |
| ATOM | 189 | OH | TYR | 12 | 1.517 | 10.287 | −0.543 | 1.00 | 0.00 |
| ATOM | 190 | H | TYR | 12 | 1.973 | 5.996 | −4.455 | 1.00 | 0.00 |
| ATOM | 191 | HA | TYR | 12 | 4.482 | 4.699 | −4.663 | 1.00 | 0.00 |
| ATOM | 192 | 1HB | TYR | 12 | 5.415 | 6.720 | −3.652 | 1.00 | 0.00 |
| ATOM | 193 | 2HB | TYR | 12 | 4.285 | 7.068 | −4.951 | 1.00 | 0.00 |
| ATOM | 194 | HD1 | TYR | 12 | 2.086 | 8.119 | −4.497 | 1.00 | 0.00 |
| ATOM | 195 | HD2 | TYR | 12 | 4.913 | 7.361 | −1.326 | 1.00 | 0.00 |
| ATOM | 196 | HE1 | TYR | 12 | 0.854 | 9.676 | −3.022 | 1.00 | 0.00 |
| ATOM | 197 | HE2 | TYR | 12 | 3.747 | 9.006 | 0.100 | 1.00 | 0.00 |
| ATOM | 198 | HH | TYR | 12 | 1.911 | 10.383 | 0.327 | 1.00 | 0.00 |
| ATOM | 199 | N | GLU | 13 | 5.298 | 3.990 | −2.346 | 1.00 | 0.00 |
| ATOM | 200 | CA | GLU | 13 | 5.572 | 3.101 | −1.225 | 1.00 | 0.00 |
| ATOM | 201 | C | GLU | 13 | 5.777 | 3.820 | 0.113 | 1.00 | 0.00 |
| ATOM | 202 | O | GLU | 13 | 6.858 | 3.752 | 0.695 | 1.00 | 0.00 |
| ATOM | 203 | CB | GLU | 13 | 6.747 | 2.169 | −1.563 | 1.00 | 0.00 |
| ATOM | 204 | CG | GLU | 13 | 6.499 | 1.376 | −2.853 | 1.00 | 0.00 |
| ATOM | 205 | CD | GLU | 13 | 7.492 | 0.225 | −2.992 | 1.00 | 0.00 |
| ATOM | 206 | OE1 | GLU | 13 | 8.671 | 0.525 | −3.283 | 1.00 | 0.00 |
| ATOM | 207 | OE2 | GLU | 13 | 7.057 | −0.932 | −2.805 | 1.00 | 0.00 |
| ATOM | 208 | H | GLU | 13 | 6.017 | 4.093 | −3.047 | 1.00 | 0.00 |
| ATOM | 209 | HA | GLU | 13 | 4.701 | 2.459 | −1.093 | 1.00 | 0.00 |
| ATOM | 210 | 1HB | GLU | 13 | 7.667 | 2.746 | −1.667 | 1.00 | 0.00 |
| ATOM | 211 | 2HB | GLU | 13 | 6.869 | 1.462 | −0.741 | 1.00 | 0.00 |
| ATOM | 212 | 1HG | GLU | 13 | 5.488 | 0.972 | −2.846 | 1.00 | 0.00 |
| ATOM | 213 | 2HG | GLU | 13 | 6.600 | 2.034 | −3.717 | 1.00 | 0.00 |
| ATOM | 214 | N | LEU | 14 | 4.726 | 4.482 | 0.614 | 1.00 | 0.00 |
| ATOM | 215 | CA | LEU | 14 | 4.678 | 4.992 | 1.979 | 1.00 | 0.00 |
| ATOM | 216 | C | LEU | 14 | 4.337 | 3.856 | 2.954 | 1.00 | 0.00 |
| ATOM | 217 | O | LEU | 14 | 4.704 | 3.923 | 4.126 | 1.00 | 0.00 |
| ATOM | 218 | CB | LEU | 14 | 3.739 | 6.205 | 2.121 | 1.00 | 0.00 |
| ATOM | 219 | CG | LEU | 14 | 2.430 | 6.230 | 1.308 | 1.00 | 0.00 |

TABLE 8-continued

Structural Coordinates of IGE134 (SEQ ID NOS: 155, 171)

| ATOM | 220 | CD1  | LEU | 14 | 1.558 | 4.983  | 1.459  | 1.00 | 0.00 |
|------|-----|------|-----|----|-------|--------|--------|------|------|
| ATOM | 221 | CD2  | LEU | 14 | 1.607 | 7.437  | 1.771  | 1.00 | 0.00 |
| ATOM | 222 | H    | LEU | 14 | 3.885 | 4.538  | 0.055  | 1.00 | 0.00 |
| ATOM | 223 | HA   | LEU | 14 | 5.671 | 5.349  | 2.258  | 1.00 | 0.00 |
| ATOM | 224 | 1HB  | LEU | 14 | 3.501 | 6.323  | 3.179  | 1.00 | 0.00 |
| ATOM | 225 | 2HB  | LEU | 14 | 4.308 | 7.084  | 1.816  | 1.00 | 0.00 |
| ATOM | 226 | HG   | LEU | 14 | 2.663 | 6.352  | 0.252  | 1.00 | 0.00 |
| ATOM | 227 | 1HD1 | LEU | 14 | 1.437 | 4.748  | 2.516  | 1.00 | 0.00 |
| ATOM | 228 | 2HD1 | LEU | 14 | 0.579 | 5.165  | 1.018  | 1.00 | 0.00 |
| ATOM | 229 | 3HD1 | LEU | 14 | 2.006 | 4.146  | 0.930  | 1.00 | 0.00 |
| ATOM | 230 | 1HD2 | LEU | 14 | 2.207 | 8.345  | 1.739  | 1.00 | 0.00 |
| ATOM | 231 | 2HD2 | LEU | 14 | 0.744 | 7.562  | 1.119  | 1.00 | 0.00 |
| ATOM | 232 | 3HD2 | LEU | 14 | 1.259 | 7.283  | 2.793  | 1.00 | 0.00 |
| ATOM | 233 | N    | CYS | 15 | 3.663 | 2.807  | 2.465  | 1.00 | 0.00 |
| ATOM | 234 | CA   | CYS | 15 | 3.402 | 1.567  | 3.180  | 1.00 | 0.00 |
| ATOM | 235 | C    | CYS | 15 | 4.558 | 0.599  | 2.904  | 1.00 | 0.00 |
| ATOM | 236 | O    | CYS | 15 | 5.262 | 0.771  | 1.908  | 1.00 | 0.00 |
| ATOM | 237 | CB   | CYS | 15 | 2.070 | 0.992  | 2.685  | 1.00 | 0.00 |
| ATOM | 238 | SG   | CYS | 15 | 0.632 | 2.029  | 3.044  | 1.00 | 0.00 |
| ATOM | 239 | H    | CYS | 15 | 3.392 | 2.820  | 1.493  | 1.00 | 0.00 |
| ATOM | 240 | HA   | CYS | 15 | 3.326 | 1.767  | 4.250  | 1.00 | 0.00 |
| ATOM | 241 | 1HB  | CYS | 15 | 2.123 | 0.831  | 1.608  | 1.00 | 0.00 |
| ATOM | 242 | 2HB  | CYS | 15 | 1.891 | 0.029  | 3.154  | 1.00 | 0.00 |
| ATOM | 245 | N    | PRO | 16 | 4.779 | −0.418 | 3.755  | 1.00 | 0.00 |
| ATOM | 246 | CA   | PRO | 16 | 5.850 | −1.384 | 3.560  | 1.00 | 0.00 |
| ATOM | 247 | C    | PRO | 16 | 5.685 | −2.154 | 2.248  | 1.00 | 0.00 |
| ATOM | 248 | O    | PRO | 16 | 4.568 | −2.390 | 1.787  | 1.00 | 0.00 |
| ATOM | 249 | CB   | PRO | 16 | 5.817 | −2.304 | 4.785  | 1.00 | 0.00 |
| ATOM | 250 | CG   | PRO | 16 | 4.383 | −2.169 | 5.294  | 1.00 | 0.00 |
| ATOM | 251 | CD   | PRO | 16 | 4.058 | −0.710 | 4.983  | 1.00 | 0.00 |
| ATOM | 252 | HA   | PRO | 16 | 6.805 | −0.856 | 3.545  | 1.00 | 0.00 |
| ATOM | 253 | 1HB  | PRO | 16 | 6.078 | −3.337 | 4.549  | 1.00 | 0.00 |
| ATOM | 254 | 2HB  | PRO | 16 | 6.497 | −1.915 | 5.543  | 1.00 | 0.00 |
| ATOM | 255 | 1HG  | PRO | 16 | 3.726 | −2.817 | 4.712  | 1.00 | 0.00 |
| ATOM | 256 | 2HG  | PRO | 16 | 4.295 | −2.398 | 6.357  | 1.00 | 0.00 |
| ATOM | 257 | 1HD  | PRO | 16 | 2.981 | −0.585 | 4.903  | 1.00 | 0.00 |
| ATOM | 258 | 2HD  | PRO | 16 | 4.443 | −0.071 | 5.779  | 1.00 | 0.00 |
| ATOM | 259 | N    | ASP | 17 | 6.825 | −2.528 | 1.654  | 1.00 | 0.00 |
| ATOM | 260 | CA   | ASP | 17 | 6.940 | −3.116 | 0.325  | 1.00 | 0.00 |
| ATOM | 261 | C    | ASP | 17 | 6.036 | −4.333 | 0.119  | 1.00 | 0.00 |
| ATOM | 262 | O    | ASP | 17 | 5.566 | −4.545 | −0.995 | 1.00 | 0.00 |
| ATOM | 263 | CB   | ASP | 17 | 8.403 | −3.482 | 0.049  | 1.00 | 0.00 |
| ATOM | 264 | CG   | ASP | 17 | 9.305 | −2.250 | 0.059  | 1.00 | 0.00 |
| ATOM | 265 | OD1  | ASP | 17 | 9.710 | −1.853 | 1.174  | 1.00 | 0.00 |
| ATOM | 266 | OD2  | ASP | 17 | 9.571 | −1.726 | −1.044 | 1.00 | 0.00 |
| ATOM | 267 | H    | ASP | 17 | 7.693 | −2.308 | 2.124  | 1.00 | 0.00 |
| ATOM | 268 | HA   | ASP | 17 | 6.649 | −2.356 | −0.400 | 1.00 | 0.00 |
| ATOM | 269 | 1HB  | ASP | 17 | 8.752 | −4.194 | 0.799  | 1.00 | 0.00 |
| ATOM | 270 | 2HB  | ASP | 17 | 8.473 | −3.954 | −0.931 | 1.00 | 0.00 |
| ATOM | 271 | N    | VAL | 18 | 5.791 | −5.117 | 1.178  | 1.00 | 0.00 |
| ATOM | 272 | CA   | VAL | 18 | 4.936 | −6.303 | 1.165  | 1.00 | 0.00 |
| ATOM | 273 | C    | VAL | 18 | 3.570 | −6.048 | 0.510  | 1.00 | 0.00 |
| ATOM | 274 | O    | VAL | 18 | 3.028 | −6.941 | −0.137 | 1.00 | 0.00 |
| ATOM | 275 | CB   | VAL | 18 | 4.808 | −6.854 | 2.597  | 1.00 | 0.00 |
| ATOM | 276 | CG1  | VAL | 18 | 4.010 | −5.923 | 3.522  | 1.00 | 0.00 |
| ATOM | 277 | CG2  | VAL | 18 | 4.176 | −8.252 | 2.603  | 1.00 | 0.00 |
| ATOM | 278 | H    | VAL | 18 | 6.219 | −4.871 | 2.058  | 1.00 | 0.00 |
| ATOM | 279 | HA   | VAL | 18 | 5.453 | −7.056 | 0.568  | 1.00 | 0.00 |
| ATOM | 280 | HB   | VAL | 18 | 5.814 | −6.952 | 3.008  | 1.00 | 0.00 |
| ATOM | 281 | 1HG1 | VAL | 18 | 2.960 | −5.895 | 3.228  | 1.00 | 0.00 |
| ATOM | 282 | 2HG1 | VAL | 18 | 4.077 | −6.289 | 4.546  | 1.00 | 0.00 |
| ATOM | 283 | 3HG1 | VAL | 18 | 4.419 | −4.915 | 3.486  | 1.00 | 0.00 |
| ATOM | 284 | 1HG2 | VAL | 18 | 4.166 | −8.645 | 3.620  | 1.00 | 0.00 |
| ATOM | 285 | 2HG2 | VAL | 18 | 3.153 | −8.213 | 2.231  | 1.00 | 0.00 |
| ATOM | 286 | 3HG2 | VAL | 18 | 4.760 | −8.924 | 1.973  | 1.00 | 0.00 |
| ATOM | 287 | N    | CYS | 19 | 3.025 | −4.833 | 0.665  | 1.00 | 0.00 |
| ATOM | 288 | CA   | CYS | 19 | 1.782 | −4.406 | 0.033  | 1.00 | 0.00 |
| ATOM | 289 | C    | CYS | 19 | 1.826 | −4.592 | −1.485 | 1.00 | 0.00 |
| ATOM | 290 | O    | CYS | 19 | 0.886 | −5.119 | −2.075 | 1.00 | 0.00 |
| ATOM | 291 | CB   | CYS | 19 | 1.545 | −2.924 | 0.337  | 1.00 | 0.00 |

TABLE 8-continued

Structural Coordinates of IGE134 (SEQ ID NOS: 155, 171)

| ATOM | 292 | SG | CYS | 19 | 1.085 | −2.526 | 2.038 | 1.00 | 0.00 |
|------|-----|-----|-----|-----|-------|--------|-------|------|------|
| ATOM | 293 | H | CYS | 19 | 3.523 | −4.145 | 1.215 | 1.00 | 0.00 |
| ATOM | 294 | HA | CYS | 19 | 0.953 | −4.986 | 0.440 | 1.00 | 0.00 |
| ATOM | 295 | 1HB | CYS | 19 | 2.453 | −2.371 | 0.107 | 1.00 | 0.00 |
| ATOM | 296 | 2HB | CYS | 19 | 0.752 | −2.549 | −0.311 | 1.00 | 0.00 |
| ATOM | 299 | N | TYR | 20 | 2.920 | −4.151 | −2.113 | 1.00 | 0.00 |
| ATOM | 300 | CA | TYR | 20 | 3.040 | −4.027 | −3.557 | 1.00 | 0.00 |
| ATOM | 301 | C | TYR | 20 | 3.787 | −5.233 | −4.125 | 1.00 | 0.00 |
| ATOM | 302 | O | TYR | 20 | 3.285 | −5.905 | −5.024 | 1.00 | 0.00 |
| ATOM | 303 | CB | TYR | 20 | 3.765 | −2.711 | −3.878 | 1.00 | 0.00 |
| ATOM | 304 | CG | TYR | 20 | 3.234 | −1.507 | −3.117 | 1.00 | 0.00 |
| ATOM | 305 | CD1 | TYR | 20 | 2.089 | −0.826 | −3.568 | 1.00 | 0.00 |
| ATOM | 306 | CD2 | TYR | 20 | 3.848 | −1.112 | −1.913 | 1.00 | 0.00 |
| ATOM | 307 | CE1 | TYR | 20 | 1.597 | 0.279 | −2.851 | 1.00 | 0.00 |
| ATOM | 308 | CE2 | TYR | 20 | 3.357 | −0.009 | −1.197 | 1.00 | 0.00 |
| ATOM | 309 | CZ | TYR | 20 | 2.246 | 0.704 | −1.676 | 1.00 | 0.00 |
| ATOM | 310 | OH | TYR | 20 | 1.805 | 1.799 | −0.993 | 1.00 | 0.00 |
| ATOM | 311 | H | TYR | 20 | 3.696 | −3.819 | −1.555 | 1.00 | 0.00 |
| ATOM | 312 | HA | TYR | 20 | 2.048 | −3.975 | −4.009 | 1.00 | 0.00 |
| ATOM | 313 | 1HB | TYR | 20 | 4.825 | −2.816 | −3.642 | 1.00 | 0.00 |
| ATOM | 314 | 2HB | TYR | 20 | 3.685 | −2.520 | −4.949 | 1.00 | 0.00 |
| ATOM | 315 | HD1 | TYR | 20 | 1.586 | −1.147 | −4.469 | 1.00 | 0.00 |
| ATOM | 316 | HD2 | TYR | 20 | 4.696 | −1.657 | −1.529 | 1.00 | 0.00 |
| ATOM | 317 | HE1 | TYR | 20 | 0.728 | 0.804 | −3.217 | 1.00 | 0.00 |
| ATOM | 318 | HE2 | TYR | 20 | 3.837 | 0.290 | −0.278 | 1.00 | 0.00 |
| ATOM | 319 | HH | TYR | 20 | 1.065 | 2.239 | −1.422 | 1.00 | 0.00 |
| ATOM | 320 | N | VAL | 21 | 4.978 | −5.504 | −3.581 | 1.00 | 0.00 |
| ATOM | 321 | CA | VAL | 21 | 5.810 | −6.656 | −3.885 | 1.00 | 0.00 |
| ATOM | 322 | C | VAL | 21 | 5.892 | −7.518 | −2.620 | 1.00 | 0.00 |
| ATOM | 323 | O | VAL | 21 | 6.917 | −7.596 | −1.947 | 1.00 | 0.00 |
| ATOM | 324 | CB | VAL | 21 | 7.158 | −6.186 | −4.474 | 1.00 | 0.00 |
| ATOM | 325 | CG1 | VAL | 21 | 7.943 | −5.207 | −3.587 | 1.00 | 0.00 |
| ATOM | 326 | CG2 | VAL | 21 | 8.046 | −7.369 | −4.879 | 1.00 | 0.00 |
| ATOM | 327 | H | VAL | 21 | 5.303 | −4.898 | −2.840 | 1.00 | 0.00 |
| ATOM | 328 | HA | VAL | 21 | 5.331 | −7.265 | −4.653 | 1.00 | 0.00 |
| ATOM | 329 | HB | VAL | 21 | 6.920 | −5.647 | −5.393 | 1.00 | 0.00 |
| ATOM | 330 | 1HG1 | VAL | 21 | 7.333 | −4.340 | −3.336 | 1.00 | 0.00 |
| ATOM | 331 | 2HG1 | VAL | 21 | 8.281 | −5.686 | −2.670 | 1.00 | 0.00 |
| ATOM | 332 | 3HG1 | VAL | 21 | 8.821 | −4.858 | −4.132 | 1.00 | 0.00 |
| ATOM | 333 | 1HG2 | VAL | 21 | 7.487 | −8.046 | −5.527 | 1.00 | 0.00 |
| ATOM | 334 | 2HG2 | VAL | 21 | 8.915 | −7.001 | −5.426 | 1.00 | 0.00 |
| ATOM | 335 | 3HG2 | VAL | 21 | 8.393 | −7.917 | −4.004 | 1.00 | 0.00 |
| ATOM | 336 | N | NH2 | 22 | 4.779 | −8.173 | −2.283 | 1.00 | 0.00 |
| ATOM | 337 | 1HN | NH2 | 22 | 3.947 | −8.073 | −2.847 | 1.00 | 0.00 |
| ATOM TER | 338 | 2HN | NH2 | 22 | 4.763 | −8.742 | −1.450 | 1.00 | 0.00 |

Example 12

Activity and Structural Analysis of Peptides

Peptides were synthesized to test phage-derived substitutions in the IGE083 (SEQ ID NOS:130, 156), IGE120 (SEQ ID NOS:131, 159), or IGE122 (SEQ ID NOS:132, 161) background, to test combinations of substitutions, or to test more specific features of the peptide-receptor binding interaction.

Peptide IGE132 (SEQ ID NO:170), IGE 142 (SEQ ID NO:175), IGE 143 (SEQ ID NO:176), IGE144 (SEQ ID NO:177), and IGE145 (SEQ ID NO:178), and IGE156 (SEQ ID NO:188) were produced biosynthetically, as fusions to the Z-domain of protein A (Smith, *Methods Mol. Biol.* 32, 289–296 (1994); Nilsson et al., *J. Biotechnol.* 48,241–250 (1996). Following secretion from *E. coli*, the fusion protein was purified and cleaved with TPCK-treated trypsin (Sigma), and the peptide was purified by reverse-phase HPLC.

A structural score was assigned to peptides analyzed by 2D NMR spectroscopy. For each of these peptides, backbone $^1$H resonances have been assigned, and the $^3J_{HN-H\alpha}$ coupling constants have been measured and compared to the reference peptide (i.e., IGE134 (SEQ ID NOS:155, 171)). Peptides are defined to be of similar structure to the reference peptide provided chemical shifts, coupling constants, and NOEs are consistent with that structure. Peptides are defined to be less stable when $^3J_{HN-H\alpha}$ coupling constants are less extreme than the reference (i.e., values change from $^3J_{HN-H\alpha}>8.5$ or $^3J_{HN-H\alpha}<6$ Hz to a range, $6<^3J_{HN-H\alpha}<8.5$ Hz) and/or when chemical shifts of backbone resonances are closer to random coil values in the peptide relative to the reference.

TABLE 9

IgE-inhibition activity and structural data on synthetic peptides (Peptides IGE088 and IGE089 represent parallel (SEQ ID NOS:128, 128) and antiparallel covalent (SEQ ID NOS:128, 157) dimers, respectively; +++, peptide structurally similar to reference; +, structurally similar to reference but significantly less stable; +/−, peptide has some elements of stable structure, but the conformation differs from the reference structure; −, peptide is predominantly unstructured; *peptide IGE037 (SEQ ID NO:128) was initially unstructured (monomeric form), but became structured after spontaneous dimer formation.)

| Name | SEQ ID NO: | Sequence | Inhibition activity: $IC_{50}$ (uM) ± s.d. (uM) | Structure Score |
|---|---|---|---|---|
| IGE035 | 124 | ALCPEVCYV-nh2 | >500 | |
| IGE036 | 125 | Ac-ALCPEVCYV-nh2 | >500 | |
| IGE037 | 128 | ALCPAVCYV-nh2 | 251 | +++* |
| IGE038 | 129 | Ac-ALCPAVCYV-nh2 | >300 | − |
| IGE083 | 156 | ALCPAVCYVGGKALCPDVCYV-nh2 | 1.1 ± 0.43 | +++ |
| IGE088 | 128* | ALCPAVCYV-nh2<br>   \|   \| | >450 | +/− |
| | 128* | ALCPAVCYV-nh2 | | |
| IGE089 | 128* | ALCPAVCYV-nh2<br>   \|   \| | 64 | +++ |
| | 157* | h2n-VYCVAPCLA | | |
| IGE119 | 158 | NGCPGWCYVGGKALCPDVCYV-nh2 | 1.4 | |
| IGE120 | 159 | IVCPRLCYVGGKALCPDVCYV-nh2 | 0.29 ± 0.13 | +++ |
| IGE121 | 160 | VVCPNMCYVGGKALCPDVCYV-nh2 | 0.34 | |
| IGE122 | 161 | VQCPHFCYVGGKALCPDVCYV-nh2 | 0.17 ± 0.12 | +++ |
| IGE123 | 162 | VKCPSLCYVGGKALCPDVCYV-nh2 | 0.18 ± 0.06 | |
| IGE124 | 163 | VPCPELCYVGGKALCPDVCYV-nh2 | 0.89 ± 0.18 | |
| IGE126 | 164 | VTCPRWCYVGGKALCPDVCYV-nh2 | 0.38 ± 0.21 | |
| IGE127 | 165 | IVCARLCYVGGKALCPDVCYV-nh2 | 13 ± 11 | +++ |
| IGE128 | 166 | KSCPLWCYVGGKALCPDVCYV-nh2 | 0.24 ± 0.02 | |
| IGE129 | 167 | VQCPHFCYV-nh2 | >90 | |
| IGE130 | 168 | ALCPDVCYVGGKVQCPHFCYV-nh2 | 0.25 | |
| IGE131 | 169 | VQCPHFCYVGGKVQCPHFCYV-nh2 | 2.3 | |
| IGE132 | 170 | VQCPHFCYVGGHALCPDVCYVGR | 0.08 | +++ |
| IGE134 | 171 | VQCPHFCYELDYELCPDVCYV-nh2 | 0.032 ± 0.013 | +++ |
| IGE135 | 172 | VQCPHFCYFGGAELCPDVCYV-nh2 | 0.047 ± 0.018 | +++ |
| IGE136 | 173 | VQCPHFCYFGGAELCPGVCYV-nh2 | 0.119 ± 0.02 | |
| IGE141 | 174 | IVCPRLCYELDYELCPDVCYV-nh2 | 0.131 | |
| IGE142 | 175 | VQCAHFCYVGGHALCPDVCYVGR | 1 | |
| IGE143 | 176 | VQCPHFCYVGGHALCADVCYVGR | >100 | +++ |
| IGE144 | 177 | VQCAHFCYVGGHALCADVCYVGR | >100 | |
| IGE145 | 178 | VQCPDFCYVGGHALCPDVCYVGR | 0.117 ± 0.04 | |
| IGE146 | 179 | VQCPHFCYVGEALCPDVCYV-nh2 | 0.89 | +++ |
| IGE147 | 180 | VQCPHFCYVGGKALCPDKCYV-nh2 | 0.158 ± 0.005 | |
| IGE148 | 181 | VQCPHFCYVGGKALCPDKCYT-nh2 | 0.094 | |
| IGE149 | 182 | VQCPHFCYVGGKALCPDPCYV-nh2 | 0.166 | |

TABLE 9-continued

IgE-inhibition activity and structural data on synthetic peptides (Peptides IGE088 and IGE089 represent parallel (SEQ ID NOS:128, 128) and antiparallel covalent (SEQ ID NOS:128, 157) dimers, respectively; +++, peptide structurally similar to reference; +, structurally similar to reference but significantly less stable; +/−, peptide has some elements of stable structure, but the conformation differs from the reference structure; −, peptide is predominantly unstructured; *peptide IGE037 (SEQ ID NO:128) was initially unstructured (monomeric form), but became structured after spontaneous dimer formation.)

| Name | SEQ ID NO: | Sequence | Inhibition activity: IC$_{50}$ (uM) ± s.d. (uM) | Structure Score |
|---|---|---|---|---|
| IGE150 | 183 | VQCPHFCYVGGKALCPDVCDV-nh2 | 1.23 | + |
| IGE151 | 184 | VQCPHFCYFGGAELCPDVCYV | 0.13 ± 0.055 | |
| IGE152 | 185 | VQCPHFCYFGAELCPDVCYV | 0.052 ± 0.005 | |
| IGE153 | 186 | VQCPHFCYELDYELCPDVCY-nh2 | 0.049 ± 0.025 | |
| IGE154 | 216 | QCPHFCPELDYELCPCVCY-nh2 | >1 | |
| IGE155 | 187 | CPHFCYELDYELCPDVCY-nh2 | 0.069 ± 0.009 | |
| IGE156 | 188 | VQCPHFCYELDYELCPDVCYVGR | 0.03 ± 0.009 | +++ |
| IGE157 | 189 | QCPHFCYELDYELCPDVCY-nh2 | 0.107 ± 0.026 | |
| IGE158 | 190 | VQCPHFCYFGGAELC(nmA)DVCYV-nh2 | 1.08 ± 0.76 | |
| IGE159 | 191 | VQC(nmA)HFCYFGGAELCPDVCYV-nh2 | 0.38 ± 0.29 | |
| IGE160 | 192 | VQC(nmA)HFCYFGGAELC(nmA)DVCYV-nh2 | >10 | |
| IGE161-1 | 193 | VQCPHFCYFGGAELC(pip)DVCYV-nh2 | 41.05 ± 0.07 | |
| IGE161-2 | 194 | VQCPHFCYFGGAELC(Pip)DVCYV-nh2 | 0.68 ± 0.43 | +++ |
| IGE162-1 | 195 | VQC(pip)HFCYFGGAELCPDVCYV-nh2 | 4.09 ± 0.98 | |
| IGE162-2 | 196 | VQC(Pip)HFCYFGGAELCPDVCYV-nh2 | 0.43 ± 0.15 | |
| IGE164 | 197 | VQCPHFCYFGGAEL(hC)PDVCYV-nh2 | 40.7 ± 25.1 | |
| IGE165 | 198 | VQCPHFCYFGGAELCPDV(hC)YV-nh2 | 1.17 ± 0.38 | |
| IGE166 | 199 | VQCPHF(hC)YFGGAELCPDVCYV-nh2 | 65 | |
| IGE167 | 200 | VQCPHFCYFGAELCPDVCYV-nh2 | 0.12 ± 0.06 | |
| IGE168 | 201 | AcVQCPHFCYFGAELCPDVCYV-nh2 | 0.26 ± 0.18 | |
| IGE169 | 202 | VQCPHFCYFGAELCPAVCYV-nh2 | 0.128 | |
| IGE170 | 203 | CPHFCYFGAELCPDVCY-nh2 | 0.20 ± 0.14 | |
| IGE171 | 204 | AcCPHFCYFGAELCPDVCY-nh2 | 0.29 ± 0.21 | |
| IGE173 | 205 | VQCPHFCYELDYELCPDKCYT-nh2 | 0.061 | |
| IGE174 | 206 | VQCPHFCYELDYELCPWKCYT-nh2 | 0.172 | |
| IGE175 | 207 | VQCPHFCYELDYELCPWVCYV-nh2 | 0.057 | |
| IGE179 | 217 | Ac-VQCPHFCYELDYELCPDVCYV-nh2 | 0.22 ± 0.02 | |
| IGE182 | 218 | VQCPHFCYELFSRLCPDVCYV-nh2 | 0.08 ± 0.03 | |
| IGE183 | 219 | VQCPHFCYDASRLCPDVCYV-nh2 | 0.03 ± 0.01 | |
| IGE184 | 220 | VQCPHFCYDYELCPDVCYV-nh2 | 0.11 ± 0.06 | |
| IGE185 | 221 | VQCPHFCYAEPLCPDVCYV-nh2 | 0.076 ± 0.0035 | |
| IGE186 | 222 | VQCPHFCYELavaELCPDVCYV-nh2 | 0.18 ± 0.0064 | |
| IGE187 | 223 | VQCPHFCYEavaELCPDVCYV-nh2 | 0.09 ± 0.02 | |

TABLE 9-continued

IgE-inhibition activity and structural data on synthetic peptides (Peptides IGE088 and IGE089 represent parallel (SEQ ID NOS:128, 128) and antiparallel covalent (SEQ ID NOS:128, 157) dimers, respectively; +++, peptide structurally similar to reference; +, structurally similar to reference but significantly less stable; +/−, peptide has some elements of stable structure, but the conformation differs from the reference structure; −, peptide is predominantly unstructured; *peptide IGE037 (SEQ ID NO:128) was initially unstructured (monomeric form), but became structured after spontaneous dimer formation.)

| Name | SEQ ID NO: | Sequence | Inhibition activity: $IC_{50}$ (uM) ± s.d. (uM) | Structure Score |
|---|---|---|---|---|
| IGE188 | 224 | VQCPHFCYELDYEADRLCPDVCYV-nh2 | 0.98 ± 0.014 | |
| IGE189 | 225 | VQCPHFCYELDYEAGDERLCPDVCYV-nh2 | 0.15 ± 0.054 | |
| IGE190 | 226 | VQCPDFCYELDYELCPDVCYV-nh2 | 0.058 ± 0.07 | |
| IGE191 | 227 | VQCPDFCYFGGAELCPDVCYV-nh2 | 0.21 ± 0.08 | |
| IGE196 | 228 | VQCPHFCYDASELCPDVCYV-nh2 | 0.09 ± 0.01 | |
| IGE197 | 229 | VQCPDFCYDASRLCPDVCYV-nh2 | 0.12 ± 0.0039 | |
| IGE198 | 230 | VQCPHFCYavaLCPDVCYV-nh2 | 7.8 ± 0.70 | |
| IGE199 | 231 | VQCPDFCYavaLCPDVCYV-nh2 | 6.67 ± 1.65 | |
| IGE200 | 232 | VQCPKFCYavaLCPDVCYV-nh2 | 11.7 ± 2.12 | |
| IGE201 | 233 | VQCPDFCYavaLCPDQCYV-nh2 | 14.6 ± 10.5 | |
| IGE202 | 234 | VQCPDFCYavaCPDVCYV-nh2 | 132 ± 75.7 | |
| IGE203 | 235 | VQCPKFCYEavaCPDVCYV-nh2 | 12.9 ± 5.87 | |

*peptide is a dimer. SEQ ID NO: describes each monomer of the dimer.
"ava" = amino-valeric acid Several peptides were also tested in a direct-binding assay using a surface plasmon resonance biosensor (Lofas & Johnsson, *J. Chem. Soc. Commun.* 21, 1526–1528 (1990)). FcεRIα, produced in baculovirus infected insect cells, was immobilized by the surface thiol method (BIAcore Methods Manual Supplement 5a, BIAcore, Inc., Piscataway, N.J.). Briefly, receptor was reacted with 2-(2-pyridinyldithio)ethaneamine hydrochloride (PDEA; Natake & Swaisgood, *J. Biochem.* 74, 77–86 (1973)), desalted into 10 mM sodium acetate (pH 4.8) and stored in aliquots at −80° C. Thawed PDEA-receptor was injected over carboxymethyl-dextran (B1 or CM5, BIAcore, Inc.) biosensor chips preactivated with N-ethyl-N'-(3-dimethylaminopropyl)-carbodiimide hydrochloride (EDC) and N-hydroxysuccinimide (NHS), cystamine, and DTT. Following coupling, reactive groups on the chip were quenched with PDEA and ethanolamine. Serial dilutions of peptide in running buffer (phosphate-buffered saline containing 0.05% Tween-20, 0.01% sodium azide) were injected over the immobilized receptor, and the net amount of peptide bound at steady-state was measured as the net change in response (RU) at a point just prior to termination of peptide injection, compared to a running-buffer baseline. Binding affinities (Table 10) are reported as the midpoint ($EC_{50}$) of a 4-parameter fit to the peptide saturation curve. In the case of IGE134 (SEQ ID NOS:), the value shown indicates the Kd calculated from the rate constants, $k_{on}$ and $k_{off}$. The results of binding assays (Table 8) correlate well with those of inhibition assays (Table 7).

TABLE 10

Binding affinity of peptides from biosensor assays
[$EC_{50}$ values are reported, except for IGE134
(SEQ ID NOS:155, 171), for which $K_d$ (apparent) is shown.]

| Name | SEQ ID NO: | Sequence | Binding affinity: $EC_{50}$ (uM) ± s.d. (uM) |
|---|---|---|---|
| IGE083 | 156 | ALCPAVCYVGGKALCPDVCYV-nh2 | 1.1 ± 0.43 |
| IGE088 | 128 | ALCPAVCYV-nh2 | >450 |
| | 128 | ALCPAVCYV-nh2 | |
| IGE089 | 128 | ALCPAVCYV-nh2 | 64 |
| | 157 | h2n-VYCVAPCLA | |

TABLE 10-continued

Binding affinity of peptides from biosensor assays
[$EC_{50}$ values are reported, except for IGE134
(SEQ ID NOS:155, 171), for which $K_d$ (apparent) is shown.]

| Name | SEQ ID NO: | Sequence | Binding affinity: $EC_{50}$ (uM) ± s.d. (uM) |
|---|---|---|---|
| IGE119 | 158 | NGCPGWCYVGGKALCPDVCYV-nh2 | 1.4 |
| IGE120 | 159 | IVCPRLCYVGGKALCPDVCYV-nh2 | 0.26 ± 0.1 |
| IGE121 | 160 | VVCPNMCYVGGKALCPDVCYV-nh2 | 0.34 |
| IGE122 | 161 | VQCPHFCYVGGKALCPDVCYV-nh2 | 0.15 ± 0.07 |
| IGE123 | 162 | VKCPSLCYVGGKALCPDVCYV-nh2 | 0.18 ± 0.06 |
| IGE124 | 163 | VPCPELCYVGGKALCPDVCYV-nh2 | 0.89 ± 0.18 |
| IGE126 | 164 | VTCPRWCYVGGKALCPDVCYV-nh2 | 0.38 ± 0.21 |
| IGE127 | 165 | IVCARLCYVGGKALCPDVCYV-nh2 | 13 ± 11 |
| IGE128 | 166 | KSCPLWCYVGGKALCPDVCYV-nh2 | 0.24 ± 0.02 |
| IGE129 | 167 | VQCPHFCYV-nh2 | >90 |
| IGE130 | 168 | ALCPDVCYVGGKVQCPHFCYV-nh2 | 0.25 |
| IGE131 | 169 | VQCPHFCYVGGKVQCPHFCYV-nh2 | 2.3 |
| IGE132 | 170 | VQCPHFCYVGGHALCPDVCYVGR | 0.68 |
| IGE134 | 171 | VQCPHFCYELDYELCPDVCYV-nh2 | 0.032* ± 0.013 |

The peptides with best potency identified from these experiments were IGE134 (amide variant, SEQ ID NO:171) and IGE135 (SEQ ID NO:172), with average $IC_{50}$s of 32 nM and 47 nM respectively in the inhibition assay (Table 9). A shorter peptide, IGE155 (SEQ ID NO:187), deleting the N-terminal two residues and the C-terminal residue of IGE134 (SEQ ID NOS:155, 171), also retained activity within about 2-fold of IGE134. The truncated peptide IGE170 (SEQ ID NO:203) and IGE171 (SEQ ID NO:204) retained activity within about 2-fold of IGE167 (SEQ ID NO:200).

The "linker region" of the peptide, corresponding to residues VGGKA (SEQ ID NO:210) in IGE083 (SEQ ID NOS:130, 156), VGGHA (SEQ ID. NO:211) in IGE132 (SEQ ID NO:170), ELDYE (SEQ ID NO:154) in IGE134 (SEQ ID NOS:155, 171), FGGAE (SEQ ID NO:212) in IGE135 (SEQ ID NO:172), and FGAE (SEQ ID NO:213) in IGE152 (SEQ ID NO:185) has been shown by phage and peptide assays to accommodate a variety of substitutions as well as deletions and insertions. However, comparing IGE120 (SEQ ID NOS:131,159) and IGE141 (SEQ ID NO:174) (differing by 2-fold in activity), or IGE122 (SEQ ID NOS:132, 161) and either IGE134 (SEQ ID NOS:155, 171), IGE135 (SEQ ID NO:172), or IGE152 (SEQ ID NO:185) (differing by about 3 to 5-fold in activity), it is clear that substitutions in this region can have effects on peptide binding to receptor.

An Asp residue at position 17 was initially identified in the phage clone corresponding to IGE083 (SEQ ID NOS: 130, 156). This sidechain is clearly important for receptor binding, based on peptide-phage data, as well as on peptide data for IGE131 (SEQ ID NO:169), which substitutes D17H. This peptide is >10-fold reduced in activity compared to IGE122 (SEQ ID NOS:132, 161). Interestingly, the role of D17 changes, however, with the introduction of acidic residues into the linker region. For example, IGE135 (SEQ ID NO:172) and IGE136 (SEQ ID NO:173) differ by the D17G substitution, yet differ by only about 2-fold in activity. Peptide-phage data support a similarly small effect for D17A in the IGE134 (SEQ ID NOS:155, 171) background. Therefore, it appears that carboxylate-containing sidechain(s) in the linker region can substitute for the carboxylate of D17.

Several peptides demonstrate the importance of the two Pro residues in the zeta peptides for receptor binding. Peptides IGE127 (SEQ ID NO:165) and IGE142 (SEQ ID NO:175), having the substitution P4A in two different sequence contexts, show 50-fold and >100-fold reduced activity compared to respective control peptides. These effects are likely due to changes in contacts with receptor because they do not perturb peptide structure (Table 9). On the other hand, substitution of N-methyl alanine (nmA), or L-pipecolic acid (Pip) for P4, as in peptides IGE159 (SEQ ID NO:191) and IGE162-2 (SEQ ID NO:196), leads to little change in activity. Therefore, position 4 need not be exclusively Pro. Similarly, the Pro at position 16 is a critical residue for receptor binding because substitution with Ala, as in peptide IGE143 (SEQ ID NO:176), causes a >100-fold loss in activity. Again, the peptide structure is not greatly perturbed. However, nmA or Pip can substitute for P 16 with about 3–4 fold losses in activity [IGE158 (SEQ ID NO:190) and IGE161-2 (SEQ ID NO:194)].

Data from peptide-phage experiments indicate that the two disulfide bonds ($C_3$–$C_{15}$ and C7–C19) and tyrosines Y8 and Y20 are also crucial for high affinity binding to receptor. No viable substitutions for the disulfides or for Y8 could be identified from phage-displayed libraries. Homocysteine (hC) substitution (which lengthen the distance between Cα's of the disulfide bonded residues) for individual Cys residues, as in IGE164 (SEQ ID NO:197), IGE165 (SEQ ID NO:198), and IGE166 (SEQ ID NO:199) each caused significant loss in activity. Asp was found occasionally to substitute for Y20; however, the peptide IGE150 (SEQ ID NO:183) demonstrates that this causes about 5-fold lose in activity, as well as loss in structural stability.

Example 13

The complex between IgE134 (SEQ ID NOS:155, 171) and the extracellular domain of FcεRI was purified using size exclusion chromatography. Crystals were grown in hanging drops using a 1:1 mixture of the complex (14 mg/ml) and reservoir consisting of 30% (w/v) polyethylene glycol monomethyl ether with average molecular weight 2000 Daltons (i.e. PEG MME 2000), 0.2 M ammonium sulfate, and 0.1 M sodium citrate pH 4.2. The space group is C2221 with cell parameters a=200 Å, b=150 Å, and c=104 Å and four complexes per asymmetric unit, each of which is approximately equivalent to the other three. There are numerous hydrophobic and H-bond interactions between each peptide and its receptor, listed in part A of Table 12. In addition to these interactions, each complex is close to a neighboring peptide and its receptor, with the contacts listed in parts B, C, and D of Table 12. There are other receptor/receptor contacts far from the peptide contact region that account for the other two complexes within the asymmetric unit. These contacts are not listed in Table 12.

TABLE 12

Table of Contacts in IgE134/receptor complex
NAG is N-acetylglucosamine (carbohydrate)

A. Within a single peptide-receptor complex

| peptide | receptor | peptide |
|---|---|---|
| Val1 N | | O= Val18 3.1 Å |
| Gln2 =O | OH Tyr160 3.2 Å | |
| Cys3 SG | NE1 Trp87 3.3 Å | |
| Pro4 | Tyr160, Trp87, Leu158 | Phe6 |
| Phe6 | Trp156, Trp113 | Pro4, 7-15SS |
| Tyr8 OH | | N Cys3 3.4 Å |
| | | O= Cys3 3.1 Å |
| Glu9 N | | O= Cys7 2.7 Å |
| Leu14 N | | OH Tyr20 3.3 Å |
| Leu14 =O | NE Arg111 2.9 Å | |
| Cys15 N | NE1 Trp110 3.2 Å | OH Tyr20 3.4 Å |
| Pro16 | Trp110, Trp87 | |
| Pro16 =O | | N Cys19 |
| Asp17 N | OG Ser85 3.1 Å | |
| Asp17 OD1 | OG Ser85 3.1 Å | |
| | NZ Lys18 4.7 Å | |
| Val18 =O | | N Val1 3.1 Å |
| Tyr20 N | | O= Asp17 3 Å |
| Tyr20 OH | | N Leu14 3.4 Å, N Cys15 3.4 Å |

B. Peptide to the other Receptor

| peptide | receptor' |
|---|---|
| Leu14 CD2 | Trp156 |
| Asp11 OD2 | Arg 111 NH1 4.7 Å |

| peptide' | receptor |
|---|---|
| Glu9 sidechain | NAG on Asn21 |
| Tyr 8 =O | NAG on Asn21 |

C. Peptide and Peptide'

| peptide | receptor' |
|---|---|
| Leu14 CD1 | Phe6 sidechain |

D. Receptor to Receptor' (receptor to receptor" and receptor' to receptor"" not included)

| receptor | receptor' |
|---|---|
| Trp156 | Tyr116 |
| | Trp156 |
| | Gln157 |
| Gln157 NE2 | OH Tyr131 3.8 Å |
| Trp113 | Gln157 |
| | Trp156 |
| Asp114 OD2 | Gln157 OE2 2.8 Å |
| | NZ Lys154 4 Å |
| Asp114 N | Gln157 OE1 3.2 Å |

The structure reveals two 2:2, peptide:receptor complexes in the asymmetric unit. Also, structured sugar moieties from the receptor were found to interact with the peptide to promote binding.

REMARK This file is complete asymmetric unit, 4 complexes.
REMARK receptor chain IDs are A, B, C, D.
REMARK peptide chains correspondingly are W, X, Y, Z.
REMARK Complex between peptide IgE134 and FcεRI
REMARK Space group C222(1) a = 199.7 b = 149.7 c = 104.1
REMARK Refinement resolution 30–3.0 Angstrom; R = 30.4 Rfree = 36.1
REMARK RMSD from ideal geometry: bonds = .008 A; angles = 1.4 deg
REMARK
REMARK  Refinement treated each of 4 complexes as unique. 
REMARK
REMARK Tight NCS restraints were applied to most of the 4 receptor molecules.
REMARK These tight restraints did not include the receptor residues contacting
REMARK peptides, the peptides, the sugars, and a few miscellaneous residues.
REMARK
REMARK The RMSD for the tightly restained sections (to chnA) are
REMARK 0.05, 0.06, and 0.06 Angstrom (chnB, chnC, chnD)

-continued

REMARK The unrestrained parts of the receptors have RMSDs of
REMARK 1.1, 0.8, and 2.1 Angstrom (chnA vs chnB, chnC, chnD)
REMARK The unrestrained peptide ligands have rmsds of
REMARK 1.1, 1.6, and 1.6 A (chnW vs chnX, chnY, chnZ)
REMARK
REMARK The same pattern of restraints were applied to B-factors, but
REMARK the restraint was the same across all relations (target sigma = 3
A**2)
REMARK The resulting RMSDs on B-factors across restraint groups are all ~2.5
REMARK Angstrom**2
REMARK
REMARK The normal RMSDs of B-factors throughout the model are 2.5 (bonded)
and
REMARK 4.3 (angled)
REMARK
REMARK 156 atoms with occupancy = 0.0, 669 atoms occupancy < 1.0
REMARK

| ATOM | 1 | N | LYS | A | 4 | 76.139 | 8.669 | 59.630 | 0.00 | 108.24 | chnA |
|------|---|---|-----|---|---|--------|-------|--------|------|--------|------|
| ATOM | 2 | CA | LYS | A | 4 | 77.025 | 8.676 | 58.472 | 0.00 | 108.30 | chnA |
| ATOM | 3 | CB | LYS | A | 4 | 76.208 | 8.772 | 57.180 | 0.00 | 107.89 | chnA |
| ATOM | 4 | CG | LYS | A | 4 | 77.049 | 8.805 | 55.912 | 0.00 | 107.28 | chnA |
| ATOM | 5 | CD | LYS | A | 4 | 76.187 | 9.017 | 54.681 | 0.00 | 106.64 | chnA |
| ATOM | 6 | CE | LYS | A | 4 | 77.034 | 9.079 | 53.422 | 0.00 | 106.00 | chnA |
| ATOM | 7 | NZ | LYS | A | 4 | 76.203 | 9.301 | 52.206 | 0.00 | 105.26 | chnA |
| ATOM | 8 | C | LYS | A | 4 | 78.019 | 9.834 | 58.546 | 0.00 | 108.67 | chnA |
| ATOM | 9 | O | LYS | A | 4 | 77.663 | 10.987 | 58.301 | 0.00 | 108.87 | chnA |
| ATOM | 10 | N | PRO | A | 5 | 79.277 | 9.540 | 58.914 | 1.00 | 108.62 | chnA |
| ATOM | 11 | CD | PRO | A | 5 | 79.748 | 8.251 | 59.457 | 1.00 | 109.47 | chnA |
| ATOM | 12 | CA | PRO | A | 5 | 80.326 | 10.565 | 59.021 | 1.00 | 108.19 | chnA |
| ATOM | 13 | CB | PRO | A | 5 | 81.307 | 9.934 | 60.011 | 1.00 | 107.37 | chnA |
| ATOM | 14 | CG | PRO | A | 5 | 81.244 | 8.489 | 59.642 | 1.00 | 108.63 | chnA |
| ATOM | 15 | C | PRO | A | 5 | 81.010 | 10.869 | 57.683 | 1.00 | 108.06 | chnA |
| ATOM | 16 | O | PRO | A | 5 | 80.665 | 10.278 | 56.650 | 1.00 | 109.27 | chnA |
| ATOM | 17 | N | LYS | A | 6 | 81.965 | 11.802 | 57.706 | 1.00 | 106.65 | chnA |
| ATOM | 18 | CA | LYS | A | 6 | 82.702 | 12.155 | 56.499 | 1.00 | 103.70 | chnA |
| ATOM | 19 | CB | LYS | A | 6 | 81.832 | 12.991 | 55.561 | 1.00 | 106.87 | chnA |
| ATOM | 20 | CG | LYS | A | 6 | 82.313 | 12.935 | 54.123 | 1.00 | 110.84 | chnA |
| ATOM | 21 | CD | LYS | A | 6 | 81.201 | 13.222 | 53.119 | 1.00 | 113.00 | chnA |
| ATOM | 22 | CE | LYS | A | 6 | 81.683 | 12.943 | 51.692 | 1.00 | 113.99 | chnA |
| ATOM | 23 | NZ | LYS | A | 6 | 80.655 | 13.245 | 50.657 | 1.00 | 115.00 | chnA |
| ATOM | 24 | C | LYS | A | 6 | 84.027 | 12.857 | 56.771 | 1.00 | 99.11 | chnA |
| ATOM | 25 | O | LYS | A | 6 | 84.073 | 13.897 | 57.422 | 1.00 | 98.43 | chnA |
| ATOM | 26 | N | VAL | A | 7 | 85.104 | 12.275 | 56.253 | 1.00 | 93.69 | chnA |
| ATOM | 27 | CA | VAL | A | 7 | 86.445 | 12.823 | 56.429 | 1.00 | 90.18 | chnA |
| ATOM | 28 | CB | VAL | A | 7 | 87.525 | 11.737 | 56.220 | 1.00 | 89.16 | chnA |
| ATOM | 29 | CG1 | VAL | A | 7 | 88.908 | 12.291 | 56.527 | 1.00 | 89.28 | chnA |
| ATOM | 30 | CG2 | VAL | A | 7 | 87.236 | 10.530 | 57.092 | 1.00 | 89.95 | chnA |
| ATOM | 31 | C | VAL | A | 7 | 86.714 | 13.981 | 55.469 | 1.00 | 88.67 | chnA |
| ATOM | 32 | O | VAL | A | 7 | 86.322 | 13.935 | 54.304 | 1.00 | 88.01 | chnA |
| ATOM | 33 | N | SER | A | 8 | 87.362 | 15.024 | 55.983 | 1.00 | 86.61 | chnA |
| ATOM | 34 | CA | SER | A | 8 | 87.716 | 16.206 | 55.199 | 1.00 | 83.61 | chnA |
| ATOM | 35 | CB | SER | A | 8 | 86.871 | 17.411 | 55.623 | 1.00 | 84.54 | chnA |
| ATOM | 36 | OG | SER | A | 8 | 87.137 | 17.801 | 56.959 | 1.00 | 85.63 | chnA |
| ATOM | 37 | C | SER | A | 8 | 89.207 | 16.506 | 55.373 | 1.00 | 80.20 | chnA |
| ATOM | 38 | O | SER | A | 8 | 89.799 | 16.185 | 56.412 | 1.00 | 79.08 | chnA |
| ATOM | 39 | N | LEU | A | 9 | 89.815 | 17.114 | 54.359 | 1.00 | 75.47 | chnA |
| ATOM | 40 | CA | LEU | A | 9 | 91.238 | 17.418 | 54.422 | 1.00 | 73.57 | chnA |
| ATOM | 41 | CB | LEU | A | 9 | 91.937 | 16.924 | 53.156 | 1.00 | 75.51 | chnA |
| ATOM | 42 | CG | LEU | A | 9 | 91.663 | 15.491 | 52.710 | 1.00 | 76.32 | chnA |
| ATOM | 43 | CD1 | LEU | A | 9 | 92.444 | 15.186 | 51.453 | 1.00 | 77.94 | chnA |
| ATOM | 44 | CD2 | LEU | A | 9 | 92.040 | 14.534 | 53.808 | 1.00 | 78.05 | chnA |
| ATOM | 45 | C | LEU | A | 9 | 91.502 | 18.903 | 54.587 | 1.00 | 71.14 | chnA |
| ATOM | 46 | O | LEU | A | 9 | 90.699 | 19.727 | 54.162 | 1.00 | 70.14 | chnA |
| ATOM | 47 | N | ASN | A | 10 | 92.635 | 19.237 | 55.198 | 1.00 | 68.72 | chnA |
| ATOM | 48 | CA | ASN | A | 10 | 93.025 | 20.625 | 55.389 | 1.00 | 66.03 | chnA |
| ATOM | 49 | CB | ASN | A | 10 | 92.413 | 21.203 | 56.666 | 1.00 | 69.57 | chnA |
| ATOM | 50 | CG | ASN | A | 10 | 92.737 | 22.681 | 56.845 | 1.00 | 72.40 | chnA |
| ATOM | 51 | OD1 | ASN | A | 10 | 92.261 | 23.528 | 56.084 | 1.00 | 73.08 | chnA |
| ATOM | 52 | ND2 | ASN | A | 10 | 93.571 | 22.993 | 57.839 | 1.00 | 73.41 | chnA |
| ATOM | 53 | C | ASN | A | 10 | 94.547 | 20.755 | 55.423 | 1.00 | 62.73 | chnA |
| ATOM | 54 | O | ASN | A | 10 | 95.189 | 20.383 | 56.405 | 1.00 | 61.17 | chnA |
| ATOM | 55 | N | PRO | A | 11 | 95.153 | 21.225 | 54.320 | 1.00 | 59.02 | chnA |
| ATOM | 56 | CD | PRO | A | 11 | 96.610 | 21.433 | 54.310 | 1.00 | 58.85 | chnA |
| ATOM | 57 | CA | PRO | A | 11 | 94.563 | 21.649 | 53.045 | 1.00 | 58.07 | chnA |
| ATOM | 58 | CB | PRO | A | 11 | 95.789 | 22.034 | 52.228 | 1.00 | 59.13 | chnA |
| ATOM | 59 | CG | PRO | A | 11 | 96.766 | 22.482 | 53.266 | 1.00 | 58.97 | chnA |
| ATOM | 60 | C | PRO | A | 11 | 93.804 | 20.504 | 52.368 | 1.00 | 59.34 | chnA |
| ATOM | 61 | O | PRO | A | 11 | 94.130 | 19.333 | 52.564 | 1.00 | 63.88 | chnA |

-continued

| | | | | | | | | | | |
|---|---|---|---|---|---|---|---|---|---|---|
| ATOM | 62 | N | PRO | A | 12 | 92.812 | 20.832 | 51.528 | 1.00 | 59.33 | chnA |
| ATOM | 63 | CD | PRO | A | 12 | 92.473 | 22.229 | 51.230 | 1.00 | 60.67 | chnA |
| ATOM | 64 | CA | PRO | A | 12 | 91.938 | 19.916 | 50.769 | 1.00 | 60.00 | chnA |
| ATOM | 65 | CB | PRO | A | 12 | 90.969 | 20.866 | 50.064 | 1.00 | 61.82 | chnA |
| ATOM | 66 | CG | PRO | A | 12 | 91.014 | 22.115 | 50.890 | 1.00 | 64.19 | chnA |
| ATOM | 67 | C | PRO | A | 12 | 92.631 | 19.044 | 49.728 | 1.00 | 57.56 | chnA |
| ATOM | 68 | O | PRO | A | 12 | 91.991 | 18.231 | 49.063 | 1.00 | 57.09 | chnA |
| ATOM | 69 | N | TRP | A | 13 | 93.935 | 19.218 | 49.587 | 1.00 | 54.35 | chnA |
| ATOM | 70 | CA | TRP | A | 13 | 94.702 | 18.474 | 48.608 | 1.00 | 53.30 | chnA |
| ATOM | 71 | CB | TRP | A | 13 | 96.049 | 19.163 | 48.392 | 1.00 | 55.69 | chnA |
| ATOM | 72 | CG | TRP | A | 13 | 95.955 | 20.658 | 48.197 | 1.00 | 55.86 | chnA |
| ATOM | 73 | CD2 | TRP | A | 13 | 95.129 | 21.360 | 47.259 | 1.00 | 55.73 | chnA |
| ATOM | 74 | CE2 | TRP | A | 13 | 95.382 | 22.737 | 47.430 | 1.00 | 55.54 | chnA |
| ATOM | 75 | CE3 | TRP | A | 13 | 94.195 | 20.962 | 46.298 | 1.00 | 55.16 | chnA |
| ATOM | 76 | CD1 | TRP | A | 13 | 96.654 | 21.611 | 48.872 | 1.00 | 56.59 | chnA |
| ATOM | 77 | NE1 | TRP | A | 13 | 96.319 | 22.861 | 48.419 | 1.00 | 55.84 | chnA |
| ATOM | 78 | CZ2 | TRP | A | 13 | 94.745 | 23.715 | 46.667 | 1.00 | 54.28 | chnA |
| ATOM | 79 | CZ3 | TRP | A | 13 | 93.564 | 21.933 | 45.543 | 1.00 | 54.66 | chnA |
| ATOM | 80 | CH2 | TRP | A | 13 | 93.838 | 23.294 | 45.736 | 1.00 | 55.45 | chnA |
| ATOM | 81 | C | TRP | A | 13 | 94.923 | 17.000 | 48.939 | 1.00 | 51.53 | chnA |
| ATOM | 82 | O | TRP | A | 13 | 95.677 | 16.682 | 49.855 | 1.00 | 53.34 | chnA |
| ATOM | 83 | N | ASN | A | 14 | 94.277 | 16.119 | 48.166 | 1.00 | 48.69 | chnA |
| ATOM | 84 | CA | ASN | A | 14 | 94.395 | 14.663 | 48.314 | 1.00 | 45.85 | chnA |
| ATOM | 85 | CB | ASN | A | 14 | 93.404 | 13.924 | 47.412 | 1.00 | 51.18 | chnA |
| ATOM | 86 | CG | ASN | A | 14 | 91.957 | 14.287 | 47.705 | 1.00 | 60.72 | chnA |
| ATOM | 87 | OD1 | ASN | A | 14 | 91.520 | 15.429 | 47.463 | 1.00 | 63.93 | chnA |
| ATOM | 88 | ND2 | ASN | A | 14 | 91.196 | 13.316 | 48.227 | 1.00 | 63.65 | chnA |
| ATOM | 89 | C | ASN | A | 14 | 95.775 | 14.240 | 47.882 | 1.00 | 43.88 | chnA |
| ATOM | 90 | O | ASN | A | 14 | 96.225 | 13.170 | 48.236 | 1.00 | 44.85 | chnA |
| ATOM | 91 | N | ARG | A | 15 | 96.420 | 15.049 | 47.051 | 1.00 | 41.68 | chnA |
| ATOM | 92 | CA | ARG | A | 15 | 97.761 | 14.742 | 46.570 | 1.00 | 40.61 | chnA |
| ATOM | 93 | CB | ARG | A | 15 | 97.804 | 14.796 | 45.044 | 1.00 | 42.27 | chnA |
| ATOM | 94 | CG | ARG | A | 15 | 96.561 | 14.276 | 44.356 | 1.00 | 44.56 | chnA |
| ATOM | 95 | CD | ARG | A | 15 | 96.621 | 14.528 | 42.860 | 1.00 | 47.74 | chnA |
| ATOM | 96 | NE | ARG | A | 15 | 97.254 | 13.429 | 42.141 | 1.00 | 53.30 | chnA |
| ATOM | 97 | CZ | ARG | A | 15 | 98.032 | 13.582 | 41.073 | 1.00 | 55.84 | chnA |
| ATOM | 98 | NH1 | ARG | A | 15 | 98.293 | 14.797 | 40.602 | 1.00 | 56.40 | chnA |
| ATOM | 99 | NH2 | ARG | A | 15 | 98.503 | 12.515 | 40.432 | 1.00 | 58.59 | chnA |
| ATOM | 100 | C | ARG | A | 15 | 98.724 | 15.777 | 47.154 | 1.00 | 38.30 | chnA |
| ATOM | 101 | O | ARG | A | 15 | 98.493 | 16.976 | 47.030 | 1.00 | 36.27 | chnA |
| ATOM | 102 | N | ILE | A | 16 | 99.779 | 15.307 | 47.817 | 1.00 | 35.56 | chnA |
| ATOM | 103 | CA | ILE | A | 16 | 100.755 | 16.190 | 48.425 | 1.00 | 33.18 | chnA |
| ATOM | 104 | CB | ILE | A | 16 | 100.510 | 16.343 | 49.936 | 1.00 | 30.87 | chnA |
| ATOM | 105 | CG2 | ILE | A | 16 | 99.068 | 16.718 | 50.200 | 1.00 | 30.59 | chnA |
| ATOM | 106 | CG1 | ILE | A | 16 | 100.858 | 15.063 | 50.677 | 1.00 | 31.08 | chnA |
| ATOM | 107 | CD1 | ILE | A | 16 | 100.736 | 15.198 | 52.156 | 1.00 | 29.32 | chnA |
| ATOM | 108 | C | ILE | A | 16 | 102.176 | 15.707 | 48.194 | 1.00 | 33.79 | chnA |
| ATOM | 109 | O | ILE | A | 16 | 102.384 | 14.593 | 47.724 | 1.00 | 36.14 | chnA |
| ATOM | 110 | N | PHE | A | 17 | 103.144 | 16.562 | 48.516 | 1.00 | 37.52 | chnA |
| ATOM | 111 | CA | PHE | A | 17 | 104.563 | 16.257 | 48.364 | 1.00 | 42.38 | chnA |
| ATOM | 112 | CB | PHE | A | 17 | 105.365 | 17.530 | 48.112 | 1.00 | 44.89 | chnA |
| ATOM | 113 | CG | PHE | A | 17 | 105.387 | 17.965 | 46.685 | 1.00 | 48.02 | chnA |
| ATOM | 114 | CD1 | PHE | A | 17 | 105.102 | 19.279 | 46.348 | 1.00 | 50.19 | chnA |
| ATOM | 115 | CD2 | PHE | A | 17 | 105.706 | 17.071 | 45.678 | 1.00 | 48.18 | chnA |
| ATOM | 116 | CE1 | PHE | A | 17 | 105.141 | 19.701 | 45.032 | 1.00 | 51.23 | chnA |
| ATOM | 117 | CE2 | PHE | A | 17 | 105.748 | 17.482 | 44.356 | 1.00 | 50.09 | chnA |
| ATOM | 118 | CZ | PHE | A | 17 | 105.462 | 18.801 | 44.032 | 1.00 | 51.54 | chnA |
| ATOM | 119 | C | PHE | A | 17 | 105.159 | 15.553 | 49.572 | 1.00 | 43.07 | chnA |
| ATOM | 120 | O | PHE | A | 17 | 104.623 | 15.603 | 50.670 | 1.00 | 44.28 | chnA |
| ATOM | 121 | N | LYS | A | 18 | 106.296 | 14.912 | 49.358 | 1.00 | 43.59 | chnA |
| ATOM | 122 | CA | LYS | A | 18 | 106.982 | 14.214 | 50.423 | 1.00 | 45.57 | chnA |
| ATOM | 123 | CB | LYS | A | 18 | 108.123 | 13.377 | 49.838 | 1.00 | 49.41 | chnA |
| ATOM | 124 | CG | LYS | A | 18 | 108.933 | 12.542 | 50.824 | 1.00 | 51.61 | chnA |
| ATOM | 125 | CD | LYS | A | 18 | 110.075 | 11.853 | 50.074 | 1.00 | 59.23 | chnA |
| ATOM | 126 | CE | LYS | A | 18 | 110.948 | 10.983 | 50.979 | 1.00 | 64.14 | chnA |
| ATOM | 127 | NZ | LYS | A | 18 | 111.765 | 11.749 | 51.972 | 1.00 | 68.59 | chnA |
| ATOM | 128 | C | LYS | A | 18 | 107.526 | 15.254 | 51.389 | 1.00 | 46.02 | chnA |
| ATOM | 129 | O | LYS | A | 18 | 108.339 | 16.106 | 51.026 | 1.00 | 49.17 | chnA |
| ATOM | 130 | N | GLY | A | 19 | 107.016 | 15.228 | 52.607 | 1.00 | 46.46 | chnA |
| ATOM | 131 | CA | GLY | A | 19 | 107.500 | 16.160 | 53.600 | 1.00 | 46.67 | chnA |
| ATOM | 132 | C | GLY | A | 19 | 106.503 | 17.212 | 53.989 | 1.00 | 46.86 | chnA |
| ATOM | 133 | O | GLY | A | 19 | 106.757 | 17.994 | 54.897 | 1.00 | 48.48 | chnA |
| ATOM | 134 | N | GLU | A | 20 | 105.365 | 17.233 | 53.313 | 1.00 | 47.13 | chnA |
| ATOM | 135 | CA | GLU | A | 20 | 104.348 | 18.224 | 53.618 | 1.00 | 50.95 | chnA |
| ATOM | 136 | CB | GLU | A | 20 | 103.552 | 18.593 | 52.367 | 1.00 | 53.18 | chnA |
| ATOM | 137 | CG | GLU | A | 20 | 104.427 | 19.136 | 51.242 | 1.00 | 53.78 | chnA |
| ATOM | 138 | CD | GLU | A | 20 | 103.676 | 19.996 | 50.252 | 1.00 | 54.50 | chnA |
| ATOM | 139 | OE1 | GLU | A | 20 | 102.568 | 19.615 | 49.807 | 1.00 | 53.45 | chnA |
| ATOM | 140 | OE2 | GLU | A | 20 | 104.209 | 21.069 | 49.921 | 1.00 | 53.85 | chnA |

-continued

| | | | | | | | | | | |
|---|---|---|---|---|---|---|---|---|---|---|
| ATOM | 141 | C | GLU | A | 20 | 103.443 | 17.775 | 54.745 | 1.00 | 52.52 chnA |
| ATOM | 142 | O | GLU | A | 20 | 103.631 | 16.704 | 55.305 | 1.00 | 51.58 chnA |
| ATOM | 143 | N | ASN | A | 21 | 102.492 | 18.623 | 55.107 | 1.00 | 55.43 chnA |
| ATOM | 144 | CA | ASN | A | 21 | 101.581 | 18.316 | 56.194 | 1.00 | 60.17 chnA |
| ATOM | 145 | CB | ASN | A | 21 | 101.764 | 19.320 | 57.330 | 1.00 | 62.00 chnA |
| ATOM | 146 | CG | ASN | A | 21 | 103.185 | 19.393 | 57.820 | 1.00 | 65.32 chnA |
| ATOM | 147 | OD1 | ASN | A | 21 | 103.933 | 18.423 | 57.738 | 1.00 | 63.15 chnA |
| ATOM | 148 | ND2 | ASN | A | 21 | 103.557 | 20.558 | 58.332 | 1.00 | 70.78 chnA |
| ATOM | 149 | C | ASN | A | 21 | 100.136 | 18.339 | 55.751 | 1.00 | 61.71 chnA |
| ATOM | 150 | O | ASN | A | 21 | 99.758 | 19.101 | 54.866 | 1.00 | 65.39 chnA |
| ATOM | 151 | N | VAL | A | 22 | 99.328 | 17.510 | 56.394 | 1.00 | 62.47 chnA |
| ATOM | 152 | CA | VAL | A | 22 | 97.910 | 17.443 | 56.100 | 1.00 | 62.97 chnA |
| ATOM | 153 | CB | VAL | A | 22 | 97.626 | 16.565 | 54.867 | 1.00 | 61.60 chnA |
| ATOM | 154 | CG1 | VAL | A | 22 | 98.068 | 15.147 | 55.108 | 1.00 | 61.70 chnA |
| ATOM | 155 | CG2 | VAL | A | 22 | 96.150 | 16.638 | 54.500 | 1.00 | 64.20 chnA |
| ATOM | 156 | C | VAL | A | 22 | 97.166 | 16.925 | 57.326 | 1.00 | 63.94 chnA |
| ATOM | 157 | O | VAL | A | 22 | 97.686 | 16.093 | 58.071 | 1.00 | 63.84 chnA |
| ATOM | 158 | N | THR | A | 23 | 95.965 | 17.454 | 57.546 | 1.00 | 64.41 chnA |
| ATOM | 159 | CA | THR | A | 23 | 95.136 | 17.076 | 58.685 | 1.00 | 67.25 chnA |
| ATOM | 160 | CB | THR | A | 23 | 94.936 | 18.278 | 59.618 | 1.00 | 66.32 chnA |
| ATOM | 161 | OG1 | THR | A | 23 | 96.216 | 18.809 | 59.977 | 1.00 | 67.43 chnA |
| ATOM | 162 | CG2 | THR | A | 23 | 94.174 | 17.873 | 60.874 | 1.00 | 66.26 chnA |
| ATOM | 163 | C | THR | A | 23 | 93.766 | 16.556 | 58.252 | 1.00 | 69.43 chnA |
| ATOM | 164 | O | THR | A | 23 | 92.960 | 17.298 | 57.691 | 1.00 | 70.48 chnA |
| ATOM | 165 | N | LEU | A | 24 | 93.501 | 15.282 | 58.524 | 1.00 | 72.16 chnA |
| ATOM | 166 | CA | LEU | A | 24 | 92.224 | 14.673 | 58.165 | 1.00 | 74.82 chnA |
| ATOM | 167 | CB | LEU | A | 24 | 92.401 | 13.182 | 57.888 | 1.00 | 73.85 chnA |
| ATOM | 168 | CG | LEU | A | 24 | 93.745 | 12.676 | 57.367 | 1.00 | 71.98 chnA |
| ATOM | 169 | CD1 | LEU | A | 24 | 93.561 | 11.268 | 56.923 | 1.00 | 73.74 chnA |
| ATOM | 170 | CD2 | LEU | A | 24 | 94.253 | 13.492 | 56.217 | 1.00 | 72.40 chnA |
| ATOM | 171 | C | LEU | A | 24 | 91.240 | 14.871 | 59.310 | 1.00 | 79.11 chnA |
| ATOM | 172 | O | LEU | A | 24 | 91.507 | 14.479 | 60.448 | 1.00 | 80.25 chnA |
| ATOM | 173 | N | THR | A | 25 | 90.101 | 15.476 | 59.004 | 1.00 | 83.34 chnA |
| ATOM | 174 | CA | THR | A | 25 | 89.095 | 15.742 | 60.020 | 1.00 | 88.85 chnA |
| ATOM | 175 | CB | THR | A | 25 | 88.711 | 17.250 | 60.048 | 1.00 | 89.87 chnA |
| ATOM | 176 | OG1 | THR | A | 25 | 89.893 | 18.048 | 60.193 | 1.00 | 91.23 chnA |
| ATOM | 177 | CG2 | THR | A | 25 | 87.774 | 17.549 | 61.213 | 1.00 | 91.54 chnA |
| ATOM | 178 | C | THR | A | 25 | 87.834 | 14.911 | 59.819 | 1.00 | 90.33 chnA |
| ATOM | 179 | O | THR | A | 25 | 87.265 | 14.891 | 58.734 | 1.00 | 91.13 chnA |
| ATOM | 180 | N | CYS | A | 26 | 87.420 | 14.213 | 60.872 | 1.00 | 93.91 chnA |
| ATOM | 181 | CA | CYS | A | 26 | 86.214 | 13.393 | 60.843 | 1.00 | 95.82 chnA |
| ATOM | 182 | C | CYS | A | 26 | 85.048 | 14.327 | 61.166 | 1.00 | 97.17 chnA |
| ATOM | 183 | O | CYS | A | 26 | 85.085 | 15.051 | 62.164 | 1.00 | 97.94 chnA |
| ATOM | 184 | CB | CYS | A | 26 | 86.319 | 12.264 | 61.881 | 1.00 | 95.26 chnA |
| ATOM | 185 | SG | CYS | A | 26 | 85.018 | 10.985 | 61.826 | 1.00 | 94.28 chnA |
| ATOM | 186 | N | ASN | A | 27 | 84.065 | 14.358 | 60.269 | 1.00 | 99.60 chnA |
| ATOM | 187 | CA | ASN | A | 27 | 82.864 | 15.192 | 60.395 | 1.00 | 101.37 chnA |
| ATOM | 188 | CB | ASN | A | 27 | 81.724 | 14.558 | 59.584 | 0.00 | 102.37 chnA |
| ATOM | 189 | CG | ASN | A | 27 | 80.441 | 15.373 | 59.619 | 0.00 | 103.49 chnA |
| ATOM | 190 | OD1 | ASN | A | 27 | 80.460 | 16.588 | 59.819 | 0.00 | 103.84 chnA |
| ATOM | 191 | ND2 | ASN | A | 27 | 79.315 | 14.700 | 59.410 | 0.00 | 104.01 chnA |
| ATOM | 192 | C | ASN | A | 27 | 82.424 | 15.395 | 61.844 | 1.00 | 101.05 chnA |
| ATOM | 193 | O | ASN | A | 27 | 81.890 | 14.479 | 62.472 | 1.00 | 103.11 chnA |
| ATOM | 194 | N | GLY | A | 28 | 82.683 | 16.589 | 62.374 | 0.50 | 99.38 chnA |
| ATOM | 195 | CA | GLY | A | 28 | 82.311 | 16.899 | 63.742 | 0.50 | 95.85 chnA |
| ATOM | 196 | C | GLY | A | 28 | 80.985 | 17.629 | 63.848 | 0.50 | 94.71 chnA |
| ATOM | 197 | O | GLY | A | 28 | 80.906 | 18.820 | 63.542 | 0.50 | 94.29 chnA |
| ATOM | 198 | N | ASN | A | 29 | 79.940 | 16.909 | 64.255 | 0.50 | 93.72 chnA |
| ATOM | 199 | CA | ASN | A | 29 | 78.604 | 17.486 | 64.421 | 0.50 | 92.00 chnA |
| ATOM | 200 | CB | ASN | A | 29 | 77.834 | 17.535 | 63.079 | 0.50 | 91.32 chnA |
| ATOM | 201 | CG | ASN | A | 29 | 77.564 | 16.154 | 62.482 | 0.50 | 90.40 chnA |
| ATOM | 202 | OD1 | ASN | A | 29 | 78.488 | 15.404 | 62.160 | 0.50 | 89.60 chnA |
| ATOM | 203 | ND2 | ASN | A | 29 | 76.286 | 15.835 | 62.298 | 0.50 | 89.57 chnA |
| ATOM | 204 | C | ASN | A | 29 | 77.808 | 16.755 | 65.510 | 0.50 | 91.55 chnA |
| ATOM | 205 | O | ASN | A | 29 | 78.388 | 16.003 | 66.300 | 0.50 | 89.11 chnA |
| ATOM | 206 | N | ASN | A | 30 | 76.499 | 17.016 | 65.571 | 0.50 | 93.21 chnA |
| ATOM | 207 | CA | ASN | A | 30 | 75.593 | 16.409 | 66.557 | 0.50 | 93.64 chnA |
| ATOM | 208 | CB | ASN | A | 30 | 75.783 | 14.880 | 66.614 | 0.50 | 93.92 chnA |
| ATOM | 209 | CG | ASN | A | 30 | 74.817 | 14.200 | 67.573 | 0.50 | 93.92 chnA |
| ATOM | 210 | OD1 | ASN | A | 30 | 75.137 | 13.976 | 68.744 | 0.50 | 93.90 chnA |
| ATOM | 211 | ND2 | ASN | A | 30 | 73.629 | 13.867 | 67.078 | 0.50 | 94.53 chnA |
| ATOM | 212 | C | ASN | A | 30 | 75.747 | 17.026 | 67.953 | 0.50 | 93.71 chnA |
| ATOM | 213 | O | ASN | A | 30 | 76.538 | 16.561 | 68.779 | 0.50 | 92.95 chnA |
| ATOM | 214 | N | VAL | A | 34 | 80.691 | 14.308 | 72.379 | 0.50 | 101.12 chnA |
| ATOM | 215 | CA | VAL | A | 34 | 82.044 | 13.762 | 72.446 | 0.50 | 101.26 chnA |
| ATOM | 216 | CB | VAL | A | 34 | 82.945 | 14.593 | 73.412 | 0.50 | 101.17 chnA |
| ATOM | 217 | CG1 | VAL | A | 34 | 84.364 | 14.019 | 73.455 | 0.50 | 100.13 chnA |
| ATOM | 218 | CG2 | VAL | A | 34 | 82.979 | 16.055 | 72.980 | 0.50 | 100.50 chnA |
| ATOM | 219 | C | VAL | A | 34 | 82.009 | 12.304 | 72.910 | 0.50 | 101.68 chnA |

-continued

| ATOM | 220 | O | VAL | A | 34 | 81.210 | 11.938 | 73.777 | 0.50 | 101.38 | chnA |
| ATOM | 221 | N | SER | A | 35 | 82.867 | 11.477 | 72.316 | 0.50 | 102.57 | chnA |
| ATOM | 222 | CA | SER | A | 35 | 82.946 | 10.063 | 72.674 | 0.50 | 103.04 | chnA |
| ATOM | 223 | CB | SER | A | 35 | 81.780 | 9.284 | 72.052 | 0.50 | 102.77 | chnA |
| ATOM | 224 | OG | SER | A | 35 | 81.727 | 9.459 | 70.646 | 0.50 | 102.67 | chnA |
| ATOM | 225 | C | SER | A | 35 | 84.288 | 9.444 | 72.270 | 0.50 | 103.14 | chnA |
| ATOM | 226 | O | SER | A | 35 | 85.143 | 9.189 | 73.123 | 0.50 | 102.79 | chnA |
| ATOM | 227 | N | SER | A | 36 | 84.463 | 9.212 | 70.971 | 0.50 | 102.95 | chnA |
| ATOM | 228 | CA | SER | A | 36 | 85.689 | 8.627 | 70.430 | 0.50 | 102.67 | chnA |
| ATOM | 229 | CB | SER | A | 36 | 85.826 | 7.157 | 70.848 | 0.50 | 101.96 | chnA |
| ATOM | 230 | OG | SER | A | 36 | 84.781 | 6.365 | 70.304 | 0.50 | 102.20 | chnA |
| ATOM | 231 | C | SER | A | 36 | 85.672 | 8.716 | 68.912 | 0.50 | 103.19 | chnA |
| ATOM | 232 | O | SER | A | 36 | 84.623 | 8.953 | 68.305 | 0.50 | 104.04 | chnA |
| ATOM | 233 | N | THR | A | 37 | 86.839 | 8.515 | 68.305 | 1.00 | 103.83 | chnA |
| ATOM | 234 | CA | THR | A | 37 | 86.972 | 8.563 | 66.852 | 1.00 | 102.72 | chnA |
| ATOM | 235 | CB | THR | A | 37 | 87.399 | 9.968 | 66.363 | 1.00 | 103.36 | chnA |
| ATOM | 236 | OG1 | THR | A | 37 | 86.591 | 10.969 | 67.000 | 1.00 | 105.07 | chnA |
| ATOM | 237 | CG2 | THR | A | 37 | 87.221 | 10.073 | 64.852 | 1.00 | 103.30 | chnA |
| ATOM | 238 | C | THR | A | 37 | 88.006 | 7.534 | 66.411 | 1.00 | 101.42 | chnA |
| ATOM | 239 | O | THR | A | 37 | 89.176 | 7.608 | 66.791 | 1.00 | 100.82 | chnA |
| ATOM | 240 | N | LYS | A | 38 | 87.556 | 6.563 | 65.627 | 1.00 | 99.59 | chnA |
| ATOM | 241 | CA | LYS | A | 38 | 88.426 | 5.503 | 65.129 | 1.00 | 99.13 | chnA |
| ATOM | 242 | CB | LYS | A | 38 | 87.666 | 4.179 | 65.105 | 1.00 | 103.68 | chnA |
| ATOM | 243 | CG | LYS | A | 38 | 87.143 | 3.734 | 66.461 | 1.00 | 108.28 | chnA |
| ATOM | 244 | CD | LYS | A | 38 | 86.400 | 2.409 | 66.352 | 1.00 | 111.44 | chnA |
| ATOM | 245 | CE | LYS | A | 38 | 85.927 | 1.922 | 67.722 | 1.00 | 113.71 | chnA |
| ATOM | 246 | NZ | LYS | A | 38 | 85.219 | 0.602 | 67.641 | 1.00 | 116.08 | chnA |
| ATOM | 247 | C | LYS | A | 38 | 88.973 | 5.808 | 63.733 | 1.00 | 96.09 | chnA |
| ATOM | 248 | O | LYS | A | 38 | 88.215 | 6.097 | 62.808 | 1.00 | 93.64 | chnA |
| ATOM | 249 | N | TRP | A | 39 | 90.293 | 5.722 | 63.593 | 1.00 | 92.16 | chnA |
| ATOM | 250 | CA | TRP | A | 39 | 90.964 | 5.986 | 62.325 | 1.00 | 89.80 | chnA |
| ATOM | 251 | CB | TRP | A | 39 | 92.093 | 7.004 | 62.520 | 1.00 | 91.51 | chnA |
| ATOM | 252 | CG | TRP | A | 39 | 91.618 | 8.407 | 62.725 | 1.00 | 91.65 | chnA |
| ATOM | 253 | CD2 | TRP | A | 39 | 90.996 | 9.246 | 61.754 | 1.00 | 91.83 | chnA |
| ATOM | 254 | CE2 | TRP | A | 39 | 90.727 | 10.480 | 62.379 | 1.00 | 90.99 | chnA |
| ATOM | 255 | CE3 | TRP | A | 39 | 90.650 | 9.081 | 60.407 | 1.00 | 92.88 | chnA |
| ATOM | 256 | CD1 | TRP | A | 39 | 91.693 | 9.135 | 63.868 | 1.00 | 91.48 | chnA |
| ATOM | 257 | NE1 | TRP | A | 39 | 91.160 | 10.382 | 63.673 | 1.00 | 90.54 | chnA |
| ATOM | 258 | CZ2 | TRP | A | 39 | 90.110 | 11.541 | 61.713 | 1.00 | 91.16 | chnA |
| ATOM | 259 | CZ3 | TRP | A | 39 | 90.038 | 10.133 | 59.742 | 1.00 | 92.31 | chnA |
| ATOM | 260 | CH2 | TRP | A | 39 | 89.780 | 11.353 | 60.397 | 1.00 | 92.17 | chnA |
| ATOM | 261 | C | TRP | A | 39 | 91.532 | 4.721 | 61.694 | 1.00 | 87.48 | chnA |
| ATOM | 262 | O | TRP | A | 39 | 92.303 | 3.995 | 62.326 | 1.00 | 84.69 | chnA |
| ATOM | 263 | N | PHE | A | 40 | 91.175 | 4.485 | 60.434 | 1.00 | 85.54 | chnA |
| ATOM | 264 | CA | PHE | A | 40 | 91.653 | 3.313 | 59.710 | 1.00 | 84.27 | chnA |
| ATOM | 265 | CB | PHE | A | 40 | 90.472 | 2.476 | 59.216 | 1.00 | 89.39 | chnA |
| ATOM | 266 | CG | PHE | A | 40 | 89.594 | 1.946 | 60.317 | 1.00 | 93.05 | chnA |
| ATOM | 267 | CD1 | PHE | A | 40 | 88.370 | 2.552 | 60.602 | 1.00 | 94.34 | chnA |
| ATOM | 268 | CD2 | PHE | A | 40 | 89.991 | 0.844 | 61.075 | 1.00 | 93.08 | chnA |
| ATOM | 269 | CE1 | PHE | A | 40 | 87.548 | 2.070 | 61.626 | 1.00 | 94.38 | chnA |
| ATOM | 270 | CE2 | PHE | A | 40 | 89.176 | 0.355 | 62.101 | 1.00 | 93.86 | chnA |
| ATOM | 271 | CZ | PHE | A | 40 | 87.951 | 0.972 | 62.376 | 1.00 | 94.20 | chnA |
| ATOM | 272 | C | PHE | A | 40 | 92.534 | 3.690 | 58.523 | 1.00 | 81.31 | chnA |
| ATOM | 273 | O | PHE | A | 40 | 92.061 | 4.312 | 57.574 | 1.00 | 81.46 | chnA |
| ATOM | 274 | N | HIS | A | 41 | 93.811 | 3.317 | 58.588 | 1.00 | 76.17 | chnA |
| ATOM | 275 | CA | HIS | A | 41 | 94.776 | 3.595 | 57.520 | 1.00 | 72.15 | chnA |
| ATOM | 276 | CB | HIS | A | 41 | 96.074 | 4.179 | 58.103 | 1.00 | 71.64 | chnA |
| ATOM | 277 | CG | HIS | A | 41 | 97.125 | 4.493 | 57.078 | 1.00 | 68.74 | chnA |
| ATOM | 278 | CD2 | HIS | A | 41 | 98.442 | 4.780 | 57.212 | 1.00 | 67.76 | chnA |
| ATOM | 279 | ND1 | HIS | A | 41 | 96.862 | 4.541 | 55.727 | 1.00 | 66.70 | chnA |
| ATOM | 280 | CE1 | HIS | A | 41 | 97.970 | 4.840 | 55.074 | 1.00 | 65.07 | chnA |
| ATOM | 281 | NE2 | HIS | A | 41 | 98.944 | 4.990 | 55.951 | 1.00 | 64.49 | chnA |
| ATOM | 282 | C | HIS | A | 41 | 95.081 | 2.293 | 56.796 | 1.00 | 70.76 | chnA |
| ATOM | 283 | O | HIS | A | 41 | 95.787 | 1.432 | 57.331 | 1.00 | 72.54 | chnA |
| ATOM | 284 | N | ASN | A | 42 | 94.564 | 2.163 | 55.577 | 1.00 | 68.52 | chnA |
| ATOM | 285 | CA | ASN | A | 42 | 94.764 | 0.962 | 54.766 | 1.00 | 70.96 | chnA |
| ATOM | 286 | CB | ASN | A | 42 | 96.259 | 0.685 | 54.552 | 1.00 | 66.68 | chnA |
| ATOM | 287 | CG | ASN | A | 42 | 96.882 | 1.576 | 53.497 | 1.00 | 63.40 | chnA |
| ATOM | 288 | OD1 | ASN | A | 42 | 96.182 | 2.178 | 52.687 | 1.00 | 63.91 | chnA |
| ATOM | 289 | ND2 | ASN | A | 42 | 98.212 | 1.630 | 53.501 | 1.00 | 59.75 | chnA |
| ATOM | 290 | C | ASN | A | 42 | 94.102 | −0.255 | 55.419 | 1.00 | 74.13 | chnA |
| ATOM | 291 | O | ASN | A | 42 | 94.578 | −1.390 | 55.287 | 1.00 | 75.42 | chnA |
| ATOM | 292 | N | GLY | A | 43 | 92.997 | −0.010 | 56.117 | 1.00 | 77.40 | chnA |
| ATOM | 293 | CA | GLY | A | 43 | 92.292 | −1.090 | 56.785 | 1.00 | 80.48 | chnA |
| ATOM | 294 | C | GLY | A | 43 | 92.706 | −1.264 | 58.236 | 1.00 | 83.01 | chnA |
| ATOM | 295 | O | GLY | A | 43 | 91.881 | −1.634 | 59.075 | 1.00 | 83.85 | chnA |
| ATOM | 296 | N | SER | A | 44 | 93.978 | −0.998 | 58.532 | 1.00 | 84.98 | chnA |
| ATOM | 297 | CA | SER | A | 44 | 94.498 | −1.115 | 59.893 | 1.00 | 87.75 | chnA |
| ATOM | 298 | CB | SER | A | 44 | 96.027 | −1.180 | 59.872 | 1.00 | 87.55 | chnA |

-continued

| | | | | | | | | | | |
|---|---|---|---|---|---|---|---|---|---|---|
| ATOM | 299 | OG | SER | A | 44 | 96.477 | -2.296 | 59.128 | 1.00 | 89.46 chnA |
| ATOM | 300 | C | SER | A | 44 | 94.048 | 0.034 | 60.805 | 1.00 | 88.51 chnA |
| ATOM | 301 | O | SER | A | 44 | 93.977 | 1.186 | 60.382 | 1.00 | 89.72 chnA |
| ATOM | 302 | N | LEU | A | 45 | 93.746 | -0.284 | 62.058 | 1.00 | 89.74 chnA |
| ATOM | 303 | CA | LEU | A | 45 | 93.324 | 0.728 | 63.013 | 1.00 | 91.62 chnA |
| ATOM | 304 | CB | LEU | A | 45 | 92.630 | 0.067 | 64.204 | 1.00 | 93.46 chnA |
| ATOM | 305 | CG | LEU | A | 45 | 92.106 | 0.997 | 65.302 | 1.00 | 95.76 chnA |
| ATOM | 306 | CD1 | LEU | A | 45 | 91.016 | 1.909 | 64.749 | 1.00 | 96.15 chnA |
| ATOM | 307 | CD2 | LEU | A | 45 | 91.570 | 0.167 | 66.461 | 1.00 | 97.38 chnA |
| ATOM | 308 | C | LEU | A | 45 | 94.529 | 1.551 | 63.490 | 1.00 | 93.01 chnA |
| ATOM | 309 | O | LEU | A | 45 | 95.538 | 0.997 | 63.940 | 1.00 | 92.44 chnA |
| ATOM | 310 | N | SER | A | 46 | 94.427 | 2.873 | 63.353 | 1.00 | 94.25 chnA |
| ATOM | 311 | CA | SER | A | 46 | 95.494 | 3.781 | 63.776 | 1.00 | 94.68 chnA |
| ATOM | 312 | CB | SER | A | 46 | 95.451 | 5.087 | 62.971 | 1.00 | 94.86 chnA |
| ATOM | 313 | OG | SER | A | 46 | 96.528 | 5.944 | 63.323 | 1.00 | 92.92 chnA |
| ATOM | 314 | C | SER | A | 46 | 95.353 | 4.088 | 65.263 | 1.00 | 95.99 chnA |
| ATOM | 315 | O | SER | A | 46 | 94.240 | 4.089 | 65.806 | 1.00 | 93.60 chnA |
| ATOM | 316 | N | GLU | A | 47 | 96.484 | 4.377 | 65.903 | 1.00 | 98.67 chnA |
| ATOM | 317 | CA | GLU | A | 47 | 96.509 | 4.682 | 67.331 | 1.00 | 104.50 chnA |
| ATOM | 318 | CB | GLU | A | 47 | 97.933 | 4.541 | 67.869 | 1.00 | 108.44 chnA |
| ATOM | 319 | CG | GLU | A | 47 | 98.508 | 3.135 | 67.711 | 1.00 | 114.59 chnA |
| ATOM | 320 | CD | GLU | A | 47 | 99.905 | 3.008 | 68.294 | 1.00 | 117.99 chnA |
| ATOM | 321 | OE1 | GLU | A | 47 | 100.885 | 3.278 | 67.558 | 1.00 | 120.00 chnA |
| ATOM | 322 | OE2 | GLU | A | 47 | 100.019 | 2.649 | 69.490 | 1.00 | 120.00 chnA |
| ATOM | 323 | C | GLU | A | 47 | 95.937 | 6.054 | 67.693 | 1.00 | 104.34 chnA |
| ATOM | 324 | O | GLU | A | 47 | 96.042 | 6.497 | 68.842 | 1.00 | 104.17 chnA |
| ATOM | 325 | N | GLU | A | 48 | 95.318 | 6.713 | 66.716 | 1.00 | 104.60 chnA |
| ATOM | 326 | CA | GLU | A | 48 | 94.721 | 8.026 | 66.939 | 1.00 | 106.81 chnA |
| ATOM | 327 | CB | GLU | A | 48 | 94.815 | 8.876 | 65.665 | 1.00 | 106.36 chnA |
| ATOM | 328 | CG | GLU | A | 48 | 94.371 | 10.338 | 65.828 | 1.00 | 106.57 chnA |
| ATOM | 329 | CD | GLU | A | 48 | 95.305 | 11.157 | 66.706 | 1.00 | 105.86 chnA |
| ATOM | 330 | OE1 | GLU | A | 48 | 96.131 | 11.909 | 66.140 | 1.00 | 103.66 chnA |
| ATOM | 331 | OE2 | GLU | A | 48 | 95.204 | 11.056 | 67.953 | 1.00 | 105.95 chnA |
| ATOM | 332 | C | GLU | A | 48 | 93.262 | 7.901 | 67.403 | 1.00 | 108.26 chnA |
| ATOM | 333 | O | GLU | A | 48 | 92.522 | 7.029 | 66.937 | 1.00 | 108.35 chnA |
| ATOM | 334 | N | THR | A | 49 | 92.856 | 8.783 | 68.315 | 1.00 | 110.13 chnA |
| ATOM | 335 | CA | THR | A | 49 | 91.497 | 8.771 | 68.858 | 1.00 | 110.76 chnA |
| ATOM | 336 | CB | THR | A | 49 | 91.502 | 8.374 | 70.362 | 1.00 | 112.09 chnA |
| ATOM | 337 | OG1 | THR | A | 49 | 92.419 | 9.211 | 71.086 | 1.00 | 112.93 chnA |
| ATOM | 338 | CG2 | THR | A | 49 | 91.908 | 6.907 | 70.526 | 1.00 | 112.16 chnA |
| ATOM | 339 | C | THR | A | 49 | 90.718 | 10.088 | 68.675 | 1.00 | 110.54 chnA |
| ATOM | 340 | O | THR | A | 49 | 89.489 | 10.114 | 68.819 | 1.00 | 110.15 chnA |
| ATOM | 341 | N | ASN | A | 50 | 91.430 | 11.171 | 68.364 | 1.00 | 110.23 chnA |
| ATOM | 342 | CA | ASN | A | 50 | 90.805 | 12.483 | 68.157 | 1.00 | 108.53 chnA |
| ATOM | 343 | CB | ASN | A | 50 | 91.863 | 13.595 | 68.150 | 1.00 | 108.73 chnA |
| ATOM | 344 | CG | ASN | A | 50 | 92.557 | 13.758 | 69.488 | 1.00 | 108.51 chnA |
| ATOM | 345 | OD1 | ASN | A | 50 | 91.921 | 14.074 | 70.494 | 1.00 | 109.08 chnA |
| ATOM | 346 | ND2 | ASN | A | 50 | 93.874 | 13.563 | 69.502 | 1.00 | 108.23 chnA |
| ATOM | 347 | C | ASN | A | 50 | 90.034 | 12.532 | 66.838 | 1.00 | 107.91 chnA |
| ATOM | 348 | O | ASN | A | 50 | 90.182 | 11.658 | 65.980 | 1.00 | 106.71 chnA |
| ATOM | 349 | N | SER | A | 51 | 89.221 | 13.571 | 66.671 | 1.00 | 107.65 chnA |
| ATOM | 350 | CA | SER | A | 51 | 88.439 | 13.733 | 65.445 | 1.00 | 106.72 chnA |
| ATOM | 351 | CB | SER | A | 51 | 87.248 | 14.685 | 65.670 | 1.00 | 108.22 chnA |
| ATOM | 352 | OG | SER | A | 51 | 87.671 | 15.990 | 66.037 | 1.00 | 108.84 chnA |
| ATOM | 353 | C | SER | A | 51 | 89.317 | 14.246 | 64.305 | 1.00 | 103.73 chnA |
| ATOM | 354 | O | SER | A | 51 | 88.864 | 14.364 | 63.165 | 1.00 | 103.69 chnA |
| ATOM | 355 | N | SER | A | 52 | 90.578 | 14.531 | 64.618 | 1.00 | 99.10 chnA |
| ATOM | 356 | CA | SER | A | 52 | 91.512 | 15.031 | 63.622 | 1.00 | 94.03 chnA |
| ATOM | 357 | CB | SER | A | 52 | 91.683 | 16.543 | 63.775 | 1.00 | 93.93 chnA |
| ATOM | 358 | OG | SER | A | 52 | 90.467 | 17.216 | 63.492 | 1.00 | 93.79 chnA |
| ATOM | 359 | C | SER | A | 52 | 92.868 | 14.336 | 63.673 | 1.00 | 90.99 chnA |
| ATOM | 360 | O | SER | A | 52 | 93.595 | 14.431 | 64.663 | 1.00 | 90.44 chnA |
| ATOM | 361 | N | LEU | A | 53 | 93.188 | 13.623 | 62.598 | 1.00 | 86.50 chnA |
| ATOM | 362 | CA | LEU | A | 53 | 94.453 | 12.912 | 62.477 | 1.00 | 83.80 chnA |
| ATOM | 363 | CB | LEU | A | 53 | 94.252 | 11.618 | 61.679 | 1.00 | 82.79 chnA |
| ATOM | 364 | CG | LEU | A | 53 | 95.477 | 10.791 | 61.265 | 1.00 | 81.11 chnA |
| ATOM | 365 | CD1 | LEU | A | 53 | 96.357 | 10.453 | 62.465 | 1.00 | 82.43 chnA |
| ATOM | 366 | CD2 | LEU | A | 53 | 95.003 | 9.533 | 60.583 | 1.00 | 81.44 chnA |
| ATOM | 367 | C | LEU | A | 53 | 95.476 | 13.810 | 61.787 | 1.00 | 81.76 chnA |
| ATOM | 368 | O | LEU | A | 53 | 95.287 | 14.204 | 60.641 | 1.00 | 80.30 chnA |
| ATOM | 369 | N | ASN | A | 54 | 96.561 | 14.121 | 62.491 | 1.00 | 81.17 chnA |
| ATOM | 370 | CA | ASN | A | 54 | 97.613 | 14.986 | 61.958 | 1.00 | 79.51 chnA |
| ATOM | 371 | CB | ASN | A | 54 | 98.165 | 15.905 | 63.055 | 1.00 | 85.46 chnA |
| ATOM | 372 | CG | ASN | A | 54 | 97.174 | 16.968 | 63.485 | 1.00 | 89.03 chnA |
| ATOM | 373 | OD1 | ASN | A | 54 | 96.767 | 17.812 | 62.684 | 1.00 | 92.92 chnA |
| ATOM | 374 | ND2 | ASN | A | 54 | 96.784 | 16.937 | 64.759 | 1.00 | 91.09 chnA |
| ATOM | 375 | C | ASN | A | 54 | 98.777 | 14.248 | 61.311 | 1.00 | 75.63 chnA |
| ATOM | 376 | O | ASN | A | 54 | 99.492 | 13.488 | 61.971 | 1.00 | 75.45 chnA |
| ATOM | 377 | N | ILE | A | 55 | 98.977 | 14.496 | 60.021 | 1.00 | 69.48 chnA |

-continued

| | | | | | | | | | | |
|---|---|---|---|---|---|---|---|---|---|---|
| ATOM | 378 | CA | ILE | A | 55 | 100.076 | 13.887 | 59.293 | 1.00 | 63.69 | chnA |
| ATOM | 379 | CB | ILE | A | 55 | 99.620 | 13.391 | 57.918 | 1.00 | 60.78 | chnA |
| ATOM | 380 | CG2 | ILE | A | 55 | 100.785 | 12.765 | 57.167 | 1.00 | 60.42 | chnA |
| ATOM | 381 | CG1 | ILE | A | 55 | 98.503 | 12.363 | 58.084 | 1.00 | 58.89 | chnA |
| ATOM | 382 | CD1 | ILE | A | 55 | 97.986 | 11.806 | 56.784 | 1.00 | 58.67 | chnA |
| ATOM | 383 | C | ILE | A | 55 | 101.163 | 14.956 | 59.141 | 1.00 | 62.88 | chnA |
| ATOM | 384 | O | ILE | A | 55 | 100.894 | 16.060 | 58.662 | 1.00 | 57.38 | chnA |
| ATOM | 385 | N | VAL | A | 56 | 102.373 | 14.632 | 59.597 | 1.00 | 62.92 | chnA |
| ATOM | 386 | CA | VAL | A | 56 | 103.512 | 15.549 | 59.544 | 1.00 | 64.22 | chnA |
| ATOM | 387 | CB | VAL | A | 56 | 103.944 | 15.949 | 60.977 | 1.00 | 66.17 | chnA |
| ATOM | 388 | CG1 | VAL | A | 56 | 105.199 | 16.799 | 60.947 | 1.00 | 69.24 | chnA |
| ATOM | 389 | CG2 | VAL | A | 56 | 102.815 | 16.699 | 61.676 | 1.00 | 66.32 | chnA |
| ATOM | 390 | C | VAL | A | 56 | 104.694 | 14.928 | 58.799 | 1.00 | 63.40 | chnA |
| ATOM | 391 | O | VAL | A | 56 | 104.919 | 13.722 | 58.882 | 1.00 | 68.62 | chnA |
| ATOM | 392 | N | ASN | A | 57 | 105.443 | 15.753 | 58.074 | 1.00 | 61.45 | chnA |
| ATOM | 393 | CA | ASN | A | 57 | 106.594 | 15.291 | 57.305 | 1.00 | 63.71 | chnA |
| ATOM | 394 | CB | ASN | A | 57 | 107.772 | 14.955 | 58.226 | 1.00 | 71.57 | chnA |
| ATOM | 395 | CG | ASN | A | 57 | 108.452 | 16.201 | 58.794 | 1.00 | 78.91 | chnA |
| ATOM | 396 | OD1 | ASN | A | 57 | 108.691 | 17.177 | 58.073 | 1.00 | 82.40 | chnA |
| ATOM | 397 | ND2 | ASN | A | 57 | 108.786 | 16.164 | 60.088 | 1.00 | 82.02 | chnA |
| ATOM | 398 | C | ASN | A | 57 | 106.233 | 14.090 | 56.453 | 1.00 | 62.06 | chnA |
| ATOM | 399 | O | ASN | A | 57 | 106.984 | 13.127 | 56.381 | 1.00 | 62.44 | chnA |
| ATOM | 400 | N | ALA | A | 58 | 105.079 | 14.179 | 55.801 | 1.00 | 61.10 | chnA |
| ATOM | 401 | CA | ALA | A | 58 | 104.541 | 13.128 | 54.950 | 1.00 | 60.68 | chnA |
| ATOM | 402 | CB | ALA | A | 58 | 103.566 | 13.716 | 53.966 | 1.00 | 61.99 | chnA |
| ATOM | 403 | C | ALA | A | 58 | 105.559 | 12.276 | 54.219 | 1.00 | 61.46 | chnA |
| ATOM | 404 | O | ALA | A | 58 | 106.448 | 12.785 | 53.544 | 1.00 | 61.86 | chnA |
| ATOM | 405 | N | LYS | A | 59 | 105.422 | 10.966 | 54.389 | 1.00 | 63.81 | chnA |
| ATOM | 406 | CA | LYS | A | 59 | 106.296 | 9.986 | 53.754 | 1.00 | 65.46 | chnA |
| ATOM | 407 | CB | LYS | A | 59 | 106.846 | 9.023 | 54.807 | 1.00 | 71.52 | chnA |
| ATOM | 408 | CG | LYS | A | 59 | 107.449 | 9.708 | 56.021 | 1.00 | 80.53 | chnA |
| ATOM | 409 | CD | LYS | A | 59 | 107.659 | 8.742 | 57.177 | 1.00 | 86.26 | chnA |
| ATOM | 410 | CE | LYS | A | 59 | 107.992 | 9.492 | 58.466 | 1.00 | 89.80 | chnA |
| ATOM | 411 | NZ | LYS | A | 59 | 108.145 | 8.576 | 59.635 | 1.00 | 93.57 | chnA |
| ATOM | 412 | C | LYS | A | 59 | 105.429 | 9.216 | 52.770 | 1.00 | 62.94 | chnA |
| ATOM | 413 | O | LYS | A | 59 | 104.205 | 9.265 | 52.862 | 1.00 | 61.63 | chnA |
| ATOM | 414 | N | PHE | A | 60 | 106.048 | 8.505 | 51.836 | 1.00 | 59.99 | chnA |
| ATOM | 415 | CA | PHE | A | 60 | 105.278 | 7.736 | 50.876 | 1.00 | 59.72 | chnA |
| ATOM | 416 | CB | PHE | A | 60 | 106.205 | 6.971 | 49.957 | 1.00 | 61.41 | chnA |
| ATOM | 417 | CG | PHE | A | 60 | 106.999 | 7.841 | 49.058 | 1.00 | 64.69 | chnA |
| ATOM | 418 | CD1 | PHE | A | 60 | 108.317 | 8.141 | 49.360 | 1.00 | 67.32 | chnA |
| ATOM | 419 | CD2 | PHE | A | 60 | 106.434 | 8.367 | 47.906 | 1.00 | 65.63 | chnA |
| ATOM | 420 | CE1 | PHE | A | 60 | 109.070 | 8.954 | 48.518 | 1.00 | 69.23 | chnA |
| ATOM | 421 | CE2 | PHE | A | 60 | 107.175 | 9.178 | 47.062 | 1.00 | 67.79 | chnA |
| ATOM | 422 | CZ | PHE | A | 60 | 108.498 | 9.474 | 47.369 | 1.00 | 68.05 | chnA |
| ATOM | 423 | C | PHE | A | 60 | 104.376 | 6.764 | 51.607 | 1.00 | 60.33 | chnA |
| ATOM | 424 | O | PHE | A | 60 | 103.242 | 6.539 | 51.208 | 1.00 | 61.81 | chnA |
| ATOM | 425 | N | GLU | A | 61 | 104.885 | 6.220 | 52.704 | 1.00 | 64.15 | chnA |
| ATOM | 426 | CA | GLU | A | 61 | 104.159 | 5.269 | 53.526 | 1.00 | 68.24 | chnA |
| ATOM | 427 | CB | GLU | A | 61 | 105.004 | 4.902 | 54.754 | 1.00 | 75.07 | chnA |
| ATOM | 428 | CG | GLU | A | 61 | 106.236 | 4.013 | 54.476 | 1.00 | 84.45 | chnA |
| ATOM | 429 | CD | GLU | A | 61 | 107.263 | 4.629 | 53.517 | 1.00 | 88.40 | chnA |
| ATOM | 430 | OE1 | GLU | A | 61 | 107.830 | 5.698 | 53.831 | 1.00 | 90.82 | chnA |
| ATOM | 431 | OE2 | GLU | A | 61 | 107.522 | 4.027 | 52.451 | 1.00 | 92.75 | chnA |
| ATOM | 432 | C | GLU | A | 61 | 102.798 | 5.815 | 53.967 | 1.00 | 65.52 | chnA |
| ATOM | 433 | O | GLU | A | 61 | 101.840 | 5.055 | 54.131 | 1.00 | 66.33 | chnA |
| ATOM | 434 | N | ASP | A | 62 | 102.705 | 7.137 | 54.111 | 1.00 | 61.53 | chnA |
| ATOM | 435 | CA | ASP | A | 62 | 101.465 | 7.785 | 54.545 | 1.00 | 56.58 | chnA |
| ATOM | 436 | CB | ASP | A | 62 | 101.740 | 9.202 | 55.042 | 1.00 | 58.89 | chnA |
| ATOM | 437 | CG | ASP | A | 62 | 102.547 | 9.217 | 56.313 | 1.00 | 62.16 | chnA |
| ATOM | 438 | OD1 | ASP | A | 62 | 102.246 | 8.404 | 57.211 | 1.00 | 63.73 | chnA |
| ATOM | 439 | OD2 | ASP | A | 62 | 103.487 | 10.030 | 56.415 | 1.00 | 64.48 | chnA |
| ATOM | 440 | C | ASP | A | 62 | 100.349 | 7.799 | 53.517 | 1.00 | 52.52 | chnA |
| ATOM | 441 | O | ASP | A | 62 | 99.215 | 8.147 | 53.841 | 1.00 | 47.94 | chnA |
| ATOM | 442 | N | SER | A | 63 | 100.673 | 7.419 | 52.285 | 1.00 | 48.34 | chnA |
| ATOM | 443 | CA | SER | A | 63 | 99.689 | 7.369 | 51.213 | 1.00 | 50.94 | chnA |
| ATOM | 444 | CB | SER | A | 63 | 100.367 | 7.078 | 49.884 | 1.00 | 49.70 | chnA |
| ATOM | 445 | OG | SER | A | 63 | 101.414 | 7.988 | 49.631 | 1.00 | 56.01 | chnA |
| ATOM | 446 | C | SER | A | 63 | 98.721 | 6.242 | 51.506 | 1.00 | 54.10 | chnA |
| ATOM | 447 | O | SER | A | 63 | 99.021 | 5.361 | 52.311 | 1.00 | 61.25 | chnA |
| ATOM | 448 | N | GLY | A | 64 | 97.553 | 6.274 | 50.874 | 1.00 | 57.97 | chnA |
| ATOM | 449 | CA | GLY | A | 64 | 96.587 | 5.210 | 51.088 | 1.00 | 60.30 | chnA |
| ATOM | 450 | C | GLY | A | 64 | 95.171 | 5.617 | 51.426 | 1.00 | 62.57 | chnA |
| ATOM | 451 | O | GLY | A | 64 | 94.804 | 6.780 | 51.323 | 1.00 | 61.40 | chnA |
| ATOM | 452 | N | GLU | A | 65 | 94.384 | 4.631 | 51.838 | 1.00 | 66.27 | chnA |
| ATOM | 453 | CA | GLU | A | 65 | 92.990 | 4.825 | 52.201 | 1.00 | 70.83 | chnA |
| ATOM | 454 | CB | GLU | A | 65 | 92.226 | 3.534 | 51.901 | 1.00 | 75.03 | chnA |
| ATOM | 455 | CG | GLU | A | 65 | 90.752 | 3.548 | 52.260 | 1.00 | 82.37 | chnA |
| ATOM | 456 | CD | GLU | A | 65 | 90.144 | 2.155 | 52.245 | 1.00 | 86.23 | chnA |

-continued

| ATOM | 457 | OE1 | GLU | A | 65 | 90.434 | 1.364 | 53.181 | 1.00 | 90.20 | chnA |
| ATOM | 458 | OE2 | GLU | A | 65 | 89.384 | 1.853 | 51.294 | 1.00 | 87.36 | chnA |
| ATOM | 459 | C | GLU | A | 65 | 92.817 | 5.217 | 53.675 | 1.00 | 69.17 | chnA |
| ATOM | 460 | O | GLU | A | 65 | 93.485 | 4.671 | 54.551 | 1.00 | 71.68 | chnA |
| ATOM | 461 | N | TYR | A | 66 | 91.931 | 6.175 | 53.937 | 1.00 | 65.97 | chnA |
| ATOM | 462 | CA | TYR | A | 66 | 91.654 | 6.625 | 55.296 | 1.00 | 64.16 | chnA |
| ATOM | 463 | CB | TYR | A | 66 | 92.255 | 7.999 | 55.546 | 1.00 | 55.98 | chnA |
| ATOM | 464 | CG | TYR | A | 66 | 93.744 | 7.993 | 55.775 | 1.00 | 49.50 | chnA |
| ATOM | 465 | CD1 | TYR | A | 66 | 94.628 | 8.061 | 54.708 | 1.00 | 48.16 | chnA |
| ATOM | 466 | CE1 | TYR | A | 66 | 95.997 | 8.100 | 54.910 | 1.00 | 46.59 | chnA |
| ATOM | 467 | CD2 | TYR | A | 66 | 94.270 | 7.958 | 57.059 | 1.00 | 46.85 | chnA |
| ATOM | 468 | CE2 | TYR | A | 66 | 95.636 | 8.000 | 57.275 | 1.00 | 46.11 | chnA |
| ATOM | 469 | CZ | TYR | A | 66 | 96.493 | 8.071 | 56.194 | 1.00 | 47.41 | chnA |
| ATOM | 470 | OH | TYR | A | 66 | 97.854 | 8.126 | 56.393 | 1.00 | 50.38 | chnA |
| ATOM | 471 | C | TYR | A | 66 | 90.161 | 6.674 | 55.595 | 1.00 | 68.88 | chnA |
| ATOM | 472 | O | TYR | A | 66 | 89.366 | 7.146 | 54.776 | 1.00 | 69.75 | chnA |
| ATOM | 473 | N | LYS | A | 67 | 89.793 | 6.187 | 56.782 | 1.00 | 76.23 | chnA |
| ATOM | 474 | CA | LYS | A | 67 | 88.397 | 6.161 | 57.242 | 1.00 | 83.43 | chnA |
| ATOM | 475 | CB | LYS | A | 67 | 87.800 | 4.763 | 57.099 | 1.00 | 86.00 | chnA |
| ATOM | 476 | CG | LYS | A | 67 | 87.693 | 4.207 | 55.701 | 1.00 | 91.12 | chnA |
| ATOM | 477 | CD | LYS | A | 67 | 87.266 | 2.746 | 55.792 | 1.00 | 95.07 | chnA |
| ATOM | 478 | CE | LYS | A | 67 | 87.202 | 2.078 | 54.433 | 1.00 | 98.75 | chnA |
| ATOM | 479 | NZ | LYS | A | 67 | 86.921 | 0.616 | 54.544 | 1.00 | 100.23 | chnA |
| ATOM | 480 | C | LYS | A | 67 | 88.306 | 6.522 | 58.717 | 1.00 | 85.38 | chnA |
| ATOM | 481 | O | LYS | A | 67 | 89.228 | 6.242 | 59.480 | 1.00 | 86.30 | chnA |
| ATOM | 482 | N | CYS | A | 68 | 87.174 | 7.094 | 59.119 | 1.00 | 87.87 | chnA |
| ATOM | 483 | CA | CYS | A | 68 | 86.955 | 7.450 | 60.514 | 1.00 | 92.84 | chnA |
| ATOM | 484 | C | CYS | A | 68 | 85.617 | 6.898 | 60.982 | 1.00 | 96.11 | chnA |
| ATOM | 485 | O | CYS | A | 68 | 84.638 | 6.886 | 60.232 | 1.00 | 96.73 | chnA |
| ATOM | 486 | CB | CYS | A | 68 | 86.994 | 8.962 | 60.713 | 1.00 | 93.05 | chnA |
| ATOM | 487 | SG | CYS | A | 68 | 85.492 | 9.854 | 60.205 | 1.00 | 94.74 | chnA |
| ATOM | 488 | N | GLN | A | 69 | 85.577 | 6.444 | 62.230 | 1.00 | 101.05 | chnA |
| ATOM | 489 | CA | GLN | A | 69 | 84.357 | 5.877 | 62.795 | 1.00 | 106.51 | chnA |
| ATOM | 490 | CB | GLN | A | 69 | 84.543 | 4.365 | 63.002 | 1.00 | 108.81 | chnA |
| ATOM | 491 | CG | GLN | A | 69 | 83.263 | 3.580 | 63.303 | 1.00 | 112.84 | chnA |
| ATOM | 492 | CD | GLN | A | 69 | 83.516 | 2.081 | 63.489 | 1.00 | 115.01 | chnA |
| ATOM | 493 | OE1 | GLN | A | 69 | 84.251 | 1.454 | 62.712 | 1.00 | 116.15 | chnA |
| ATOM | 494 | NE2 | GLN | A | 69 | 82.905 | 1.502 | 64.524 | 1.00 | 117.34 | chnA |
| ATOM | 495 | C | GLN | A | 69 | 83.969 | 6.550 | 64.118 | 1.00 | 108.55 | chnA |
| ATOM | 496 | O | GLN | A | 69 | 84.799 | 6.666 | 65.035 | 1.00 | 109.47 | chnA |
| ATOM | 497 | N | HIS | A | 70 | 82.730 | 7.046 | 64.184 | 1.00 | 109.79 | chnA |
| ATOM | 498 | CA | HIS | A | 70 | 82.206 | 7.686 | 65.396 | 1.00 | 110.68 | chnA |
| ATOM | 499 | CB | HIS | A | 70 | 81.466 | 8.983 | 65.044 | 0.00 | 108.98 | chnA |
| ATOM | 500 | CG | HIS | A | 70 | 81.262 | 9.898 | 66.211 | 0.00 | 107.93 | chnA |
| ATOM | 501 | CD2 | HIS | A | 70 | 80.136 | 10.412 | 66.762 | 0.00 | 107.30 | chnA |
| ATOM | 502 | ND1 | HIS | A | 70 | 82.309 | 10.383 | 66.969 | 0.00 | 107.45 | chnA |
| ATOM | 503 | CE1 | HIS | A | 70 | 81.837 | 11.150 | 67.931 | 0.00 | 107.13 | chnA |
| ATOM | 504 | NE2 | HIS | A | 70 | 80.519 | 11.185 | 67.829 | 0.00 | 107.17 | chnA |
| ATOM | 505 | C | HIS | A | 70 | 81.256 | 6.697 | 66.111 | 1.00 | 112.22 | chnA |
| ATOM | 506 | O | HIS | A | 70 | 81.450 | 5.474 | 66.045 | 1.00 | 113.72 | chnA |
| ATOM | 507 | N | GLN | A | 71 | 80.267 | 7.217 | 66.836 | 0.00 | 110.92 | chnA |
| ATOM | 508 | CA | GLN | A | 71 | 79.297 | 6.363 | 67.522 | 0.00 | 110.43 | chnA |
| ATOM | 509 | CB | GLN | A | 71 | 78.923 | 6.932 | 68.894 | 0.00 | 110.47 | chnA |
| ATOM | 510 | CG | GLN | A | 71 | 79.935 | 6.648 | 69.991 | 0.00 | 110.68 | chnA |
| ATOM | 511 | CD | GLN | A | 71 | 79.374 | 6.904 | 71.379 | 0.00 | 110.49 | chnA |
| ATOM | 512 | OE1 | GLN | A | 71 | 78.717 | 7.917 | 71.621 | 0.00 | 110.88 | chnA |
| ATOM | 513 | NE2 | GLN | A | 71 | 79.631 | 5.981 | 72.299 | 0.00 | 110.48 | chnA |
| ATOM | 514 | C | GLN | A | 71 | 78.045 | 6.215 | 66.663 | 0.00 | 109.98 | chnA |
| ATOM | 515 | O | GLN | A | 71 | 76.962 | 5.904 | 67.164 | 0.00 | 109.60 | chnA |
| ATOM | 516 | N | GLN | A | 72 | 78.210 | 6.438 | 65.362 | 0.00 | 109.74 | chnA |
| ATOM | 517 | CA | GLN | A | 72 | 77.115 | 6.347 | 64.404 | 0.00 | 109.79 | chnA |
| ATOM | 518 | CB | GLN | A | 72 | 77.216 | 7.495 | 63.393 | 0.00 | 109.75 | chnA |
| ATOM | 519 | CG | GLN | A | 72 | 77.217 | 8.882 | 64.032 | 0.00 | 109.87 | chnA |
| ATOM | 520 | CD | GLN | A | 72 | 77.441 | 10.001 | 63.031 | 0.00 | 109.96 | chnA |
| ATOM | 521 | OE1 | GLN | A | 72 | 78.062 | 9.803 | 61.986 | 0.00 | 110.35 | chnA |
| ATOM | 522 | NE2 | GLN | A | 72 | 76.940 | 11.189 | 63.352 | 0.00 | 109.93 | chnA |
| ATOM | 523 | C | GLN | A | 72 | 77.106 | 4.998 | 63.680 | 0.00 | 110.10 | chnA |
| ATOM | 524 | O | GLN | A | 72 | 76.579 | 4.885 | 62.572 | 0.00 | 110.04 | chnA |
| ATOM | 525 | N | VAL | A | 73 | 77.683 | 3.983 | 64.324 | 0.00 | 111.08 | chnA |
| ATOM | 526 | CA | VAL | A | 73 | 77.763 | 2.620 | 63.784 | 0.00 | 112.24 | chnA |
| ATOM | 527 | CB | VAL | A | 73 | 76.352 | 2.009 | 63.559 | 0.00 | 112.19 | chnA |
| ATOM | 528 | CG1 | VAL | A | 73 | 76.467 | 0.581 | 63.045 | 0.00 | 112.00 | chnA |
| ATOM | 529 | CG2 | VAL | A | 73 | 75.550 | 2.042 | 64.854 | 0.00 | 111.79 | chnA |
| ATOM | 530 | C | VAL | A | 73 | 78.587 | 2.530 | 62.494 | 0.00 | 113.61 | chnA |
| ATOM | 531 | O | VAL | A | 73 | 79.741 | 2.098 | 62.522 | 0.00 | 113.39 | chnA |
| ATOM | 532 | N | ASN | A | 74 | 77.978 | 2.914 | 61.373 | 1.00 | 115.74 | chnA |
| ATOM | 533 | CA | ASN | A | 74 | 78.630 | 2.903 | 60.059 | 1.00 | 117.99 | chnA |
| ATOM | 534 | CB | ASN | A | 74 | 77.678 | 3.456 | 58.978 | 1.00 | 120.00 | chnA |
| ATOM | 535 | CG | ASN | A | 74 | 76.596 | 2.460 | 58.558 | 1.00 | 120.00 | chnA |

-continued

| | | | | | | | | | | | |
|---|---|---|---|---|---|---|---|---|---|---|---|
| ATOM | 536 | OD1 | ASN | A | 74 | 76.883 | 1.293 | 58.264 | 1.00 | 120.00 | chnA |
| ATOM | 537 | ND2 | ASN | A | 74 | 75.347 | 2.934 | 58.491 | 1.00 | 120.00 | chnA |
| ATOM | 538 | C | ASN | A | 74 | 79.925 | 3.731 | 60.038 | 1.00 | 117.27 | chnA |
| ATOM | 539 | O | ASN | A | 74 | 80.097 | 4.669 | 60.830 | 1.00 | 116.31 | chnA |
| ATOM | 540 | N | GLU | A | 75 | 80.831 | 3.363 | 59.129 | 1.00 | 115.47 | chnA |
| ATOM | 541 | CA | GLU | A | 75 | 82.109 | 4.056 | 58.954 | 1.00 | 112.45 | chnA |
| ATOM | 542 | CB | GLU | A | 75 | 83.198 | 3.078 | 58.505 | 1.00 | 111.54 | chnA |
| ATOM | 543 | CG | GLU | A | 75 | 83.407 | 1.891 | 59.435 | 1.00 | 112.28 | chnA |
| ATOM | 544 | CD | GLU | A | 75 | 84.455 | 0.908 | 58.920 | 1.00 | 112.69 | chnA |
| ATOM | 545 | OE1 | GLU | A | 75 | 84.285 | 0.375 | 57.794 | 1.00 | 113.15 | chnA |
| ATOM | 546 | OE2 | GLU | A | 75 | 85.448 | 0.667 | 59.649 | 1.00 | 112.05 | chnA |
| ATOM | 547 | C | GLU | A | 75 | 81.940 | 5.134 | 57.885 | 1.00 | 112.02 | chnA |
| ATOM | 548 | O | GLU | A | 75 | 80.931 | 5.167 | 57.169 | 1.00 | 112.18 | chnA |
| ATOM | 549 | N | SER | A | 76 | 82.930 | 6.015 | 57.781 | 1.00 | 109.52 | chnA |
| ATOM | 550 | CA | SER | A | 76 | 82.900 | 7.090 | 56.796 | 1.00 | 105.87 | chnA |
| ATOM | 551 | CB | SER | A | 76 | 83.835 | 8.211 | 57.234 | 1.00 | 104.25 | chnA |
| ATOM | 552 | OG | SER | A | 76 | 85.169 | 7.728 | 57.307 | 1.00 | 101.23 | chnA |
| ATOM | 553 | C | SER | A | 76 | 83.356 | 6.575 | 55.432 | 1.00 | 105.62 | chnA |
| ATOM | 554 | O | SER | A | 76 | 83.947 | 5.491 | 55.328 | 1.00 | 104.72 | chnA |
| ATOM | 555 | N | GLU | A | 77 | 83.077 | 7.352 | 54.388 | 1.00 | 104.16 | chnA |
| ATOM | 556 | CA | GLU | A | 77 | 83.495 | 6.977 | 53.044 | 1.00 | 102.74 | chnA |
| ATOM | 557 | CB | GLU | A | 77 | 82.836 | 7.880 | 51.991 | 1.00 | 105.14 | chnA |
| ATOM | 558 | CG | GLU | A | 77 | 81.329 | 7.663 | 51.822 | 1.00 | 109.38 | chnA |
| ATOM | 559 | CD | GLU | A | 77 | 80.971 | 6.227 | 51.453 | 1.00 | 111.57 | chnA |
| ATOM | 560 | OE1 | GLU | A | 77 | 81.121 | 5.846 | 50.269 | 1.00 | 112.83 | chnA |
| ATOM | 561 | OE2 | GLU | A | 77 | 80.532 | 5.476 | 52.354 | 1.00 | 114.46 | chnA |
| ATOM | 562 | C | GLU | A | 77 | 85.020 | 7.099 | 52.979 | 1.00 | 99.36 | chnA |
| ATOM | 563 | O | GLU | A | 77 | 85.614 | 7.953 | 53.646 | 1.00 | 100.11 | chnA |
| ATOM | 564 | N | PRO | A | 78 | 85.676 | 6.199 | 52.230 | 1.00 | 95.31 | chnA |
| ATOM | 565 | CD | PRO | A | 78 | 85.083 | 5.023 | 51.572 | 1.00 | 95.00 | chnA |
| ATOM | 566 | CA | PRO | A | 78 | 87.135 | 6.201 | 52.081 | 1.00 | 90.46 | chnA |
| ATOM | 567 | CB | PRO | A | 78 | 87.392 | 4.967 | 51.216 | 1.00 | 92.56 | chnA |
| ATOM | 568 | CG | PRO | A | 78 | 86.244 | 4.068 | 51.548 | 1.00 | 95.30 | chnA |
| ATOM | 569 | C | PRO | A | 78 | 87.651 | 7.461 | 51.390 | 1.00 | 86.81 | chnA |
| ATOM | 570 | O | PRO | A | 78 | 87.051 | 7.955 | 50.432 | 1.00 | 85.50 | chnA |
| ATOM | 571 | N | VAL | A | 79 | 88.745 | 7.996 | 51.922 | 1.00 | 81.39 | chnA |
| ATOM | 572 | CA | VAL | A | 79 | 89.389 | 9.179 | 51.371 | 1.00 | 76.24 | chnA |
| ATOM | 573 | CB | VAL | A | 79 | 89.386 | 10.342 | 52.374 | 1.00 | 74.56 | chnA |
| ATOM | 574 | CG1 | VAL | A | 79 | 90.155 | 11.515 | 51.812 | 1.00 | 75.58 | chnA |
| ATOM | 575 | CG2 | VAL | A | 79 | 87.958 | 10.758 | 52.674 | 1.00 | 74.99 | chnA |
| ATOM | 576 | C | VAL | A | 79 | 90.814 | 8.751 | 51.063 | 1.00 | 73.95 | chnA |
| ATOM | 577 | O | VAL | A | 79 | 91.533 | 8.295 | 51.951 | 1.00 | 71.04 | chnA |
| ATOM | 578 | N | TYR | A | 80 | 91.197 | 8.864 | 49.793 | 1.00 | 73.23 | chnA |
| ATOM | 579 | CA | TYR | A | 80 | 92.527 | 8.461 | 49.346 | 1.00 | 73.59 | chnA |
| ATOM | 580 | CB | TYR | A | 80 | 92.439 | 7.743 | 47.993 | 1.00 | 80.47 | chnA |
| ATOM | 581 | CG | TYR | A | 80 | 91.522 | 6.523 | 48.020 | 1.00 | 88.50 | chnA |
| ATOM | 582 | CD1 | TYR | A | 80 | 90.175 | 6.621 | 47.643 | 1.00 | 89.86 | chnA |
| ATOM | 583 | CE1 | TYR | A | 80 | 89.316 | 5.514 | 47.716 | 1.00 | 92.63 | chnA |
| ATOM | 584 | CD2 | TYR | A | 80 | 91.990 | 5.280 | 48.468 | 1.00 | 91.66 | chnA |
| ATOM | 585 | CE2 | TYR | A | 80 | 91.141 | 4.165 | 48.548 | 1.00 | 93.84 | chnA |
| ATOM | 586 | CZ | TYR | A | 80 | 89.806 | 4.285 | 48.173 | 1.00 | 94.25 | chnA |
| ATOM | 587 | OH | TYR | A | 80 | 88.965 | 3.183 | 48.268 | 1.00 | 96.44 | chnA |
| ATOM | 588 | C | TYR | A | 80 | 93.528 | 9.604 | 49.295 | 1.00 | 69.73 | chnA |
| ATOM | 589 | O | TYR | A | 80 | 93.265 | 10.651 | 48.713 | 1.00 | 71.71 | chnA |
| ATOM | 590 | N | LEU | A | 81 | 94.663 | 9.394 | 49.951 | 1.00 | 64.18 | chnA |
| ATOM | 591 | CA | LEU | A | 81 | 95.735 | 10.370 | 50.019 | 1.00 | 59.06 | chnA |
| ATOM | 592 | CB | LEU | A | 81 | 96.087 | 10.636 | 51.480 | 1.00 | 58.66 | chnA |
| ATOM | 593 | CG | LEU | A | 81 | 97.338 | 11.458 | 51.778 | 1.00 | 59.24 | chnA |
| ATOM | 594 | CD1 | LEU | A | 81 | 97.128 | 12.893 | 51.363 | 1.00 | 62.12 | chnA |
| ATOM | 595 | CD2 | LEU | A | 81 | 97.643 | 11.390 | 53.250 | 1.00 | 60.16 | chnA |
| ATOM | 596 | C | LEU | A | 81 | 96.942 | 9.796 | 49.302 | 1.00 | 57.18 | chnA |
| ATOM | 597 | O | LEU | A | 81 | 97.266 | 8.630 | 49.478 | 1.00 | 60.66 | chnA |
| ATOM | 598 | N | GLU | A | 82 | 97.621 | 10.611 | 48.507 | 1.00 | 54.01 | chnA |
| ATOM | 599 | CA | GLU | A | 82 | 98.790 | 10.130 | 47.785 | 1.00 | 53.18 | chnA |
| ATOM | 600 | CB | GLU | A | 82 | 98.424 | 9.845 | 46.325 | 1.00 | 58.18 | chnA |
| ATOM | 601 | CG | GLU | A | 82 | 99.478 | 9.052 | 45.542 | 1.00 | 62.99 | chnA |
| ATOM | 602 | CD | GLU | A | 82 | 99.033 | 8.712 | 44.122 | 1.00 | 66.80 | chnA |
| ATOM | 603 | OE1 | GLU | A | 82 | 97.996 | 9.254 | 43.664 | 1.00 | 67.56 | chnA |
| ATOM | 604 | OE2 | GLU | A | 82 | 99.725 | 7.902 | 43.462 | 1.00 | 65.25 | chnA |
| ATOM | 605 | C | GLU | A | 82 | 99.972 | 11.098 | 47.882 | 1.00 | 49.80 | chnA |
| ATOM | 606 | O | GLU | A | 82 | 99.842 | 12.285 | 47.591 | 1.00 | 47.98 | chnA |
| ATOM | 607 | N | VAL | A | 83 | 101.120 | 10.572 | 48.302 | 1.00 | 44.78 | chnA |
| ATOM | 608 | CA | VAL | A | 83 | 102.340 | 11.355 | 48.467 | 1.00 | 38.28 | chnA |
| ATOM | 609 | CB | VAL | A | 83 | 103.096 | 10.916 | 49.734 | 1.00 | 37.92 | chnA |
| ATOM | 610 | CG1 | VAL | A | 83 | 104.404 | 11.652 | 49.863 | 1.00 | 35.51 | chnA |
| ATOM | 611 | CG2 | VAL | A | 83 | 102.240 | 11.158 | 50.953 | 1.00 | 35.51 | chnA |
| ATOM | 612 | C | VAL | A | 83 | 103.262 | 11.230 | 47.263 | 1.00 | 37.90 | chnA |
| ATOM | 613 | O | VAL | A | 83 | 103.661 | 10.128 | 46.880 | 1.00 | 41.05 | chnA |
| ATOM | 614 | N | PHE | A | 84 | 103.613 | 12.371 | 46.684 | 1.00 | 35.69 | chnA |

-continued

| ATOM | 615 | CA | PHE | A | 84 | 104.487 | 12.409 | 45.517 | 1.00 | 33.98 | chnA |
|------|-----|-----|-----|---|----|---------|--------|--------|------|-------|------|
| ATOM | 616 | CB | PHE | A | 84 | 103.833 | 13.228 | 44.401 | 1.00 | 34.58 | chnA |
| ATOM | 617 | CG | PHE | A | 84 | 102.544 | 12.653 | 43.884 | 1.00 | 37.52 | chnA |
| ATOM | 618 | CD1 | PHE | A | 84 | 101.349 | 12.841 | 44.571 | 1.00 | 37.07 | chnA |
| ATOM | 619 | CD2 | PHE | A | 84 | 102.522 | 11.947 | 42.690 | 1.00 | 36.85 | chnA |
| ATOM | 620 | CE1 | PHE | A | 84 | 100.157 | 12.337 | 44.073 | 1.00 | 35.72 | chnA |
| ATOM | 621 | CE2 | PHE | A | 84 | 101.330 | 11.439 | 42.189 | 1.00 | 37.72 | chnA |
| ATOM | 622 | CZ | PHE | A | 84 | 100.146 | 11.637 | 42.885 | 1.00 | 37.51 | chnA |
| ATOM | 623 | C | PHE | A | 84 | 105.832 | 13.044 | 45.835 | 1.00 | 33.62 | chnA |
| ATOM | 624 | O | PHE | A | 84 | 106.033 | 13.584 | 46.915 | 1.00 | 30.84 | chnA |
| ATOM | 625 | N | SER | A | 85 | 106.754 | 12.967 | 44.882 | 1.00 | 34.04 | chnA |
| ATOM | 626 | CA | SER | A | 85 | 108.067 | 13.580 | 45.019 | 1.00 | 37.72 | chnA |
| ATOM | 627 | CB | SER | A | 85 | 109.048 | 12.668 | 45.709 | 1.00 | 38.39 | chnA |
| ATOM | 628 | OG | SER | A | 85 | 110.278 | 13.346 | 45.843 | 1.00 | 39.48 | chnA |
| ATOM | 629 | C | SER | A | 85 | 108.579 | 13.915 | 43.634 | 1.00 | 42.89 | chnA |
| ATOM | 630 | O | SER | A | 85 | 109.399 | 13.197 | 43.074 | 1.00 | 45.32 | chnA |
| ATOM | 631 | N | ASP | A | 86 | 108.114 | 15.049 | 43.118 | 1.00 | 47.87 | chnA |
| ATOM | 632 | CA | ASP | A | 86 | 108.444 | 15.523 | 41.783 | 1.00 | 46.75 | chnA |
| ATOM | 633 | CB | ASP | A | 86 | 107.260 | 15.185 | 40.877 | 1.00 | 51.37 | chnA |
| ATOM | 634 | CG | ASP | A | 86 | 107.673 | 14.777 | 39.485 | 1.00 | 53.65 | chnA |
| ATOM | 635 | OD1 | ASP | A | 86 | 108.588 | 15.405 | 38.892 | 1.00 | 54.06 | chnA |
| ATOM | 636 | OD2 | ASP | A | 86 | 107.040 | 13.830 | 38.973 | 1.00 | 54.84 | chnA |
| ATOM | 637 | C | ASP | A | 86 | 108.638 | 17.047 | 41.846 | 1.00 | 44.51 | chnA |
| ATOM | 638 | O | ASP | A | 86 | 108.544 | 17.634 | 42.917 | 1.00 | 43.93 | chnA |
| ATOM | 639 | N | TRP | A | 87 | 108.899 | 17.686 | 40.706 | 1.00 | 40.82 | chnA |
| ATOM | 640 | CA | TRP | A | 87 | 109.084 | 19.135 | 40.670 | 1.00 | 37.11 | chnA |
| ATOM | 641 | CB | TRP | A | 87 | 109.812 | 19.566 | 39.404 | 1.00 | 36.15 | chnA |
| ATOM | 642 | CG | TRP | A | 87 | 111.268 | 19.290 | 39.440 | 1.00 | 37.55 | chnA |
| ATOM | 643 | CD2 | TRP | A | 87 | 112.273 | 20.044 | 40.123 | 1.00 | 36.84 | chnA |
| ATOM | 644 | CE2 | TRP | A | 87 | 113.505 | 19.422 | 39.867 | 1.00 | 37.24 | chnA |
| ATOM | 645 | CE3 | TRP | A | 87 | 112.253 | 21.188 | 40.919 | 1.00 | 38.13 | chnA |
| ATOM | 646 | CD1 | TRP | A | 87 | 111.912 | 18.275 | 38.821 | 1.00 | 39.01 | chnA |
| ATOM | 647 | NE1 | TRP | A | 87 | 113.257 | 18.342 | 39.068 | 1.00 | 39.14 | chnA |
| ATOM | 648 | CZ2 | TRP | A | 87 | 114.706 | 19.902 | 40.377 | 1.00 | 36.80 | chnA |
| ATOM | 649 | CZ3 | TRP | A | 87 | 113.450 | 21.666 | 41.423 | 1.00 | 37.14 | chnA |
| ATOM | 650 | CH2 | TRP | A | 87 | 114.658 | 21.024 | 41.150 | 1.00 | 36.04 | chnA |
| ATOM | 651 | C | TRP | A | 87 | 107.772 | 19.887 | 40.777 | 1.00 | 37.55 | chnA |
| ATOM | 652 | O | TRP | A | 87 | 107.680 | 20.881 | 41.494 | 1.00 | 36.06 | chnA |
| ATOM | 653 | N | LEU | A | 88 | 106.766 | 19.433 | 40.039 | 1.00 | 36.37 | chnA |
| ATOM | 654 | CA | LEU | A | 88 | 105.461 | 20.072 | 40.062 | 1.00 | 33.96 | chnA |
| ATOM | 655 | CB | LEU | A | 88 | 105.211 | 20.823 | 38.764 | 1.00 | 35.15 | chnA |
| ATOM | 656 | CG | LEU | A | 88 | 106.271 | 21.843 | 38.365 | 1.00 | 39.06 | chnA |
| ATOM | 657 | CD1 | LEU | A | 88 | 105.966 | 22.339 | 36.986 | 1.00 | 39.41 | chnA |
| ATOM | 658 | CD2 | LEU | A | 88 | 106.320 | 22.987 | 39.342 | 1.00 | 41.75 | chnA |
| ATOM | 659 | C | LEU | A | 88 | 104.400 | 19.018 | 40.247 | 1.00 | 32.58 | chnA |
| ATOM | 660 | O | LEU | A | 88 | 104.461 | 17.958 | 39.639 | 1.00 | 37.26 | chnA |
| ATOM | 661 | N | LEU | A | 89 | 103.407 | 19.332 | 41.067 | 1.00 | 32.25 | chnA |
| ATOM | 662 | CA | LEU | A | 89 | 102.320 | 18.418 | 41.361 | 1.00 | 34.03 | chnA |
| ATOM | 663 | CB | LEU | A | 89 | 102.460 | 17.925 | 42.792 | 1.00 | 33.87 | chnA |
| ATOM | 664 | CG | LEU | A | 89 | 101.318 | 17.117 | 43.393 | 1.00 | 34.12 | chnA |
| ATOM | 665 | CD1 | LEU | A | 89 | 101.145 | 15.858 | 42.595 | 1.00 | 32.53 | chnA |
| ATOM | 666 | CD2 | LEU | A | 89 | 101.613 | 16.800 | 44.853 | 1.00 | 33.78 | chnA |
| ATOM | 667 | C | LEU | A | 89 | 100.980 | 19.105 | 41.197 | 1.00 | 32.84 | chnA |
| ATOM | 668 | O | LEU | A | 89 | 100.706 | 20.079 | 41.863 | 1.00 | 32.98 | chnA |
| ATOM | 669 | N | LEU | A | 90 | 100.153 | 18.603 | 40.295 | 1.00 | 33.09 | chnA |
| ATOM | 670 | CA | LEU | A | 90 | 98.847 | 19.186 | 40.074 | 1.00 | 34.52 | chnA |
| ATOM | 671 | CB | LEU | A | 90 | 98.263 | 18.729 | 38.739 | 1.00 | 36.59 | chnA |
| ATOM | 672 | CG | LEU | A | 90 | 96.882 | 19.315 | 38.446 | 1.00 | 38.22 | chnA |
| ATOM | 673 | CD1 | LEU | A | 90 | 97.029 | 20.781 | 38.117 | 1.00 | 40.48 | chnA |
| ATOM | 674 | CD2 | LEU | A | 90 | 96.224 | 18.605 | 37.311 | 1.00 | 41.25 | chnA |
| ATOM | 675 | C | LEU | A | 90 | 97.932 | 18.749 | 41.190 | 1.00 | 34.82 | chnA |
| ATOM | 676 | O | LEU | A | 90 | 97.638 | 17.571 | 41.330 | 1.00 | 41.13 | chnA |
| ATOM | 677 | N | GLN | A | 91 | 97.474 | 19.701 | 41.982 | 1.00 | 33.95 | chnA |
| ATOM | 678 | CA | GLN | A | 91 | 96.581 | 19.394 | 43.082 | 1.00 | 34.57 | chnA |
| ATOM | 679 | CB | GLN | A | 91 | 97.025 | 20.153 | 44.322 | 1.00 | 34.36 | chnA |
| ATOM | 680 | CG | GLN | A | 91 | 98.436 | 19.828 | 44.714 | 1.00 | 36.87 | chnA |
| ATOM | 681 | CD | GLN | A | 91 | 98.845 | 20.487 | 45.995 | 1.00 | 38.89 | chnA |
| ATOM | 682 | OE1 | GLN | A | 91 | 99.192 | 21.658 | 46.009 | 1.00 | 42.22 | chnA |
| ATOM | 683 | NE2 | GLN | A | 91 | 98.820 | 19.736 | 47.087 | 1.00 | 40.03 | chnA |
| ATOM | 684 | C | GLN | A | 91 | 95.151 | 19.757 | 42.718 | 1.00 | 36.53 | chnA |
| ATOM | 685 | O | GLN | A | 91 | 94.927 | 20.722 | 41.997 | 1.00 | 41.10 | chnA |
| ATOM | 686 | N | ALA | A | 92 | 94.187 | 18.967 | 43.182 | 1.00 | 36.91 | chnA |
| ATOM | 687 | CA | ALA | A | 92 | 92.775 | 19.231 | 42.902 | 1.00 | 37.73 | chnA |
| ATOM | 688 | CB | ALA | A | 92 | 92.233 | 18.232 | 41.908 | 1.00 | 37.05 | chnA |
| ATOM | 689 | C | ALA | A | 92 | 91.942 | 19.199 | 44.172 | 1.00 | 39.38 | chnA |
| ATOM | 690 | O | ALA | A | 92 | 92.175 | 18.382 | 45.058 | 1.00 | 41.98 | chnA |
| ATOM | 691 | N | SER | A | 93 | 90.974 | 20.099 | 44.261 | 1.00 | 39.78 | chnA |
| ATOM | 692 | CA | SER | A | 93 | 90.096 | 20.176 | 45.420 | 1.00 | 43.39 | chnA |
| ATOM | 693 | CB | SER | A | 93 | 89.114 | 21.339 | 45.269 | 1.00 | 44.68 | chnA |

-continued

| ATOM | 694 | OG | SER | A | 93 | 88.330 | 21.223 | 44.089 | 1.00 | 49.45 | chnA |
| ATOM | 695 | C | SER | A | 93 | 89.323 | 18.884 | 45.559 | 1.00 | 46.60 | chnA |
| ATOM | 696 | O | SER | A | 93 | 88.978 | 18.481 | 46.665 | 1.00 | 49.86 | chnA |
| ATOM | 697 | N | ALA | A | 94 | 89.070 | 18.241 | 44.419 | 1.00 | 50.35 | chnA |
| ATOM | 698 | CA | ALA | A | 94 | 88.341 | 16.981 | 44.351 | 1.00 | 52.28 | chnA |
| ATOM | 699 | CB | ALA | A | 94 | 86.864 | 17.224 | 44.569 | 1.00 | 52.23 | chnA |
| ATOM | 700 | C | ALA | A | 94 | 88.575 | 16.352 | 42.993 | 1.00 | 53.89 | chnA |
| ATOM | 701 | O | ALA | A | 94 | 88.640 | 17.055 | 41.996 | 1.00 | 56.58 | chnA |
| ATOM | 702 | N | GLU | A | 95 | 88.746 | 15.035 | 42.966 | 1.00 | 55.43 | chnA |
| ATOM | 703 | CA | GLU | A | 95 | 88.970 | 14.320 | 41.717 | 1.00 | 60.24 | chnA |
| ATOM | 704 | CB | GLU | A | 95 | 89.915 | 13.139 | 41.918 | 1.00 | 60.30 | chnA |
| ATOM | 705 | CG | GLU | A | 95 | 91.366 | 13.522 | 42.156 | 1.00 | 61.79 | chnA |
| ATOM | 706 | CD | GLU | A | 95 | 91.676 | 13.872 | 43.595 | 1.00 | 63.67 | chnA |
| ATOM | 707 | OE1 | GLU | A | 95 | 92.852 | 14.155 | 43.889 | 1.00 | 66.01 | chnA |
| ATOM | 708 | OE2 | GLU | A | 95 | 90.763 | 13.850 | 44.445 | 1.00 | 66.22 | chnA |
| ATOM | 709 | C | GLU | A | 95 | 87.657 | 13.849 | 41.097 | 1.00 | 64.14 | chnA |
| ATOM | 710 | O | GLU | A | 95 | 87.598 | 13.525 | 39.907 | 1.00 | 66.99 | chnA |
| ATOM | 711 | N | VAL | A | 96 | 86.613 | 13.774 | 41.918 | 1.00 | 67.62 | chnA |
| ATOM | 712 | CA | VAL | A | 96 | 85.289 | 13.382 | 41.446 | 1.00 | 69.40 | chnA |
| ATOM | 713 | CB | VAL | A | 96 | 84.842 | 12.025 | 42.046 | 1.00 | 70.19 | chnA |
| ATOM | 714 | CG1 | VAL | A | 96 | 83.432 | 11.682 | 41.587 | 1.00 | 71.48 | chnA |
| ATOM | 715 | CG2 | VAL | A | 96 | 85.804 | 10.920 | 41.616 | 1.00 | 70.72 | chnA |
| ATOM | 716 | C | VAL | A | 96 | 84.367 | 14.515 | 41.890 | 1.00 | 71.12 | chnA |
| ATOM | 717 | O | VAL | A | 96 | 84.018 | 14.625 | 43.068 | 1.00 | 70.54 | chnA |
| ATOM | 718 | N | VAL | A | 97 | 84.048 | 15.399 | 40.948 | 1.00 | 73.91 | chnA |
| ATOM | 719 | CA | VAL | A | 97 | 83.209 | 16.561 | 41.220 | 1.00 | 74.89 | chnA |
| ATOM | 720 | CB | VAL | A | 97 | 83.784 | 17.832 | 40.569 | 1.00 | 73.89 | chnA |
| ATOM | 721 | CG1 | VAL | A | 97 | 83.090 | 19.052 | 41.103 | 1.00 | 72.91 | chnA |
| ATOM | 722 | CG2 | VAL | A | 97 | 85.267 | 17.927 | 40.811 | 1.00 | 74.62 | chnA |
| ATOM | 723 | C | VAL | A | 97 | 81.791 | 16.385 | 40.717 | 1.00 | 77.04 | chnA |
| ATOM | 724 | O | VAL | A | 97 | 81.559 | 15.846 | 39.636 | 1.00 | 77.27 | chnA |
| ATOM | 725 | N | MET | A | 98 | 80.848 | 16.895 | 41.494 | 1.00 | 79.26 | chnA |
| ATOM | 726 | CA | MET | A | 98 | 79.441 | 16.809 | 41.156 | 1.00 | 83.46 | chnA |
| ATOM | 727 | CB | MET | A | 98 | 78.636 | 16.561 | 42.430 | 1.00 | 86.65 | chnA |
| ATOM | 728 | CG | MET | A | 98 | 77.187 | 16.178 | 42.220 | 1.00 | 89.65 | chnA |
| ATOM | 729 | SD | MET | A | 98 | 76.550 | 15.438 | 43.739 | 1.00 | 93.61 | chnA |
| ATOM | 730 | CE | MET | A | 98 | 76.627 | 16.853 | 44.877 | 1.00 | 91.85 | chnA |
| ATOM | 731 | C | MET | A | 98 | 79.007 | 18.101 | 40.482 | 1.00 | 83.36 | chnA |
| ATOM | 732 | O | MET | A | 98 | 79.132 | 19.175 | 41.056 | 1.00 | 83.19 | chnA |
| ATOM | 733 | N | GLU | A | 99 | 78.513 | 17.981 | 39.253 | 1.00 | 84.71 | chnA |
| ATOM | 734 | CA | GLU | A | 99 | 78.059 | 19.118 | 38.454 | 1.00 | 84.29 | chnA |
| ATOM | 735 | CB | GLU | A | 99 | 77.132 | 18.631 | 37.333 | 1.00 | 89.30 | chnA |
| ATOM | 736 | CG | GLU | A | 99 | 76.522 | 19.738 | 36.458 | 1.00 | 95.35 | chnA |
| ATOM | 737 | CD | GLU | A | 99 | 75.492 | 19.200 | 35.467 | 1.00 | 98.40 | chnA |
| ATOM | 738 | OE1 | GLU | A | 99 | 74.461 | 18.640 | 35.913 | 1.00 | 100.57 | chnA |
| ATOM | 739 | OE2 | GLU | A | 99 | 75.718 | 19.330 | 34.243 | 1.00 | 99.61 | chnA |
| ATOM | 740 | C | GLU | A | 99 | 77.362 | 20.204 | 39.262 | 1.00 | 80.67 | chnA |
| ATOM | 741 | O | GLU | A | 99 | 76.376 | 19.952 | 39.952 | 1.00 | 82.13 | chnA |
| ATOM | 742 | N | GLY | A | 100 | 77.899 | 21.412 | 39.179 | 1.00 | 75.90 | chnA |
| ATOM | 743 | CA | GLY | A | 100 | 77.313 | 22.524 | 39.891 | 1.00 | 72.45 | chnA |
| ATOM | 744 | C | GLY | A | 100 | 78.207 | 23.085 | 40.970 | 1.00 | 71.01 | chnA |
| ATOM | 745 | O | GLY | A | 100 | 78.108 | 24.264 | 41.304 | 1.00 | 68.69 | chnA |
| ATOM | 746 | N | GLN | A | 101 | 79.064 | 22.243 | 41.536 | 1.00 | 70.17 | chnA |
| ATOM | 747 | CA | GLN | A | 101 | 79.977 | 22.676 | 42.589 | 1.00 | 69.14 | chnA |
| ATOM | 748 | CB | GLN | A | 101 | 80.141 | 21.577 | 43.655 | 1.00 | 72.68 | chnA |
| ATOM | 749 | CG | GLN | A | 101 | 80.822 | 20.308 | 43.185 | 1.00 | 77.50 | chnA |
| ATOM | 750 | CD | GLN | A | 101 | 80.815 | 19.208 | 44.233 | 1.00 | 79.45 | chnA |
| ATOM | 751 | OE1 | GLN | A | 101 | 79.916 | 19.137 | 45.071 | 1.00 | 81.92 | chnA |
| ATOM | 752 | NE2 | GLN | A | 101 | 81.816 | 18.333 | 44.180 | 1.00 | 81.94 | chnA |
| ATOM | 753 | C | GLN | A | 101 | 81.333 | 23.120 | 42.031 | 1.00 | 65.85 | chnA |
| ATOM | 754 | O | GLN | A | 101 | 81.654 | 22.848 | 40.883 | 1.00 | 64.49 | chnA |
| ATOM | 755 | N | PRO | A | 102 | 82.118 | 23.869 | 42.824 | 1.00 | 63.35 | chnA |
| ATOM | 756 | CD | PRO | A | 102 | 81.766 | 24.471 | 44.124 | 1.00 | 65.58 | chnA |
| ATOM | 757 | CA | PRO | A | 102 | 83.431 | 24.345 | 42.388 | 1.00 | 61.10 | chnA |
| ATOM | 758 | CB | PRO | A | 102 | 83.761 | 25.409 | 43.434 | 1.00 | 62.64 | chnA |
| ATOM | 759 | CG | PRO | A | 102 | 83.108 | 24.885 | 44.657 | 1.00 | 64.73 | chnA |
| ATOM | 760 | C | PRO | A | 102 | 84.524 | 23.286 | 42.317 | 1.00 | 59.50 | chnA |
| ATOM | 761 | O | PRO | A | 102 | 84.492 | 22.283 | 43.029 | 1.00 | 60.85 | chnA |
| ATOM | 762 | N | LEU | A | 103 | 85.503 | 23.549 | 41.458 | 1.00 | 55.51 | chnA |
| ATOM | 763 | CA | LEU | A | 103 | 86.656 | 22.682 | 41.252 | 1.00 | 50.80 | chnA |
| ATOM | 764 | CB | LEU | A | 103 | 86.548 | 21.949 | 39.910 | 1.00 | 53.98 | chnA |
| ATOM | 765 | CG | LEU | A | 103 | 87.752 | 21.114 | 39.465 | 1.00 | 53.88 | chnA |
| ATOM | 766 | CD1 | LEU | A | 103 | 88.121 | 20.098 | 40.520 | 1.00 | 52.34 | chnA |
| ATOM | 767 | CD2 | LEU | A | 103 | 87.448 | 20.438 | 38.154 | 1.00 | 53.92 | chnA |
| ATOM | 768 | C | LEU | A | 103 | 87.887 | 23.576 | 41.259 | 1.00 | 48.14 | chnA |
| ATOM | 769 | O | LEU | A | 103 | 87.960 | 24.548 | 40.520 | 1.00 | 44.57 | chnA |
| ATOM | 770 | N | PHE | A | 104 | 88.848 | 23.252 | 42.113 | 1.00 | 47.39 | chnA |
| ATOM | 771 | CA | PHE | A | 104 | 90.062 | 24.048 | 42.230 | 1.00 | 45.63 | chnA |
| ATOM | 772 | CB | PHE | A | 104 | 90.194 | 24.604 | 43.642 | 1.00 | 51.78 | chnA |

-continued

| | | | | | | | | | | |
|---|---|---|---|---|---|---|---|---|---|---|
| ATOM | 773 | CG | PHE | A | 104 | 89.046 | 25.471 | 44.059 | 1.00 | 57.37 | chnA |
| ATOM | 774 | CD1 | PHE | A | 104 | 88.079 | 24.996 | 44.934 | 1.00 | 60.32 | chnA |
| ATOM | 775 | CD2 | PHE | A | 104 | 88.923 | 26.759 | 43.566 | 1.00 | 59.72 | chnA |
| ATOM | 776 | CE1 | PHE | A | 104 | 87.011 | 25.789 | 45.306 | 1.00 | 59.56 | chnA |
| ATOM | 777 | CE2 | PHE | A | 104 | 87.860 | 27.555 | 43.933 | 1.00 | 61.56 | chnA |
| ATOM | 778 | CZ | PHE | A | 104 | 86.903 | 27.068 | 44.805 | 1.00 | 61.44 | chnA |
| ATOM | 779 | C | PHE | A | 104 | 91.295 | 23.242 | 41.914 | 1.00 | 43.58 | chnA |
| ATOM | 780 | O | PHE | A | 104 | 91.504 | 22.180 | 42.482 | 1.00 | 45.83 | chnA |
| ATOM | 781 | N | LEU | A | 105 | 92.108 | 23.740 | 40.996 | 1.00 | 38.82 | chnA |
| ATOM | 782 | CA | LEU | A | 105 | 93.328 | 23.049 | 40.623 | 1.00 | 36.63 | chnA |
| ATOM | 783 | CB | LEU | A | 105 | 93.329 | 22.701 | 39.139 | 1.00 | 36.56 | chnA |
| ATOM | 784 | CG | LEU | A | 105 | 92.189 | 21.859 | 38.601 | 1.00 | 34.63 | chnA |
| ATOM | 785 | CD1 | LEU | A | 105 | 92.492 | 21.489 | 37.184 | 1.00 | 37.42 | chnA |
| ATOM | 786 | CD2 | LEU | A | 105 | 92.056 | 20.636 | 39.433 | 1.00 | 39.41 | chnA |
| ATOM | 787 | C | LEU | A | 105 | 94.477 | 23.968 | 40.947 | 1.00 | 35.87 | chnA |
| ATOM | 788 | O | LEU | A | 105 | 94.360 | 25.179 | 40.810 | 1.00 | 35.96 | chnA |
| ATOM | 789 | N | ARG | A | 106 | 95.603 | 23.382 | 41.325 | 1.00 | 33.48 | chnA |
| ATOM | 790 | CA | ARG | A | 106 | 96.776 | 24.140 | 41.709 | 1.00 | 32.99 | chnA |
| ATOM | 791 | CB | ARG | A | 106 | 96.781 | 24.239 | 43.229 | 1.00 | 33.75 | chnA |
| ATOM | 792 | CG | ARG | A | 106 | 97.984 | 24.871 | 43.854 | 1.00 | 39.17 | chnA |
| ATOM | 793 | CD | ARG | A | 106 | 97.919 | 24.730 | 45.372 | 1.00 | 40.14 | chnA |
| ATOM | 794 | NE | ARG | A | 106 | 99.085 | 25.326 | 46.020 | 1.00 | 40.81 | chnA |
| ATOM | 795 | CZ | ARG | A | 106 | 99.596 | 24.925 | 47.177 | 1.00 | 41.22 | chnA |
| ATOM | 796 | NH1 | ARG | A | 106 | 99.056 | 23.916 | 47.837 | 1.00 | 40.96 | chnA |
| ATOM | 797 | NH2 | ARG | A | 106 | 100.651 | 25.545 | 47.677 | 1.00 | 42.25 | chnA |
| ATOM | 798 | C | ARG | A | 106 | 98.037 | 23.451 | 41.197 | 1.00 | 33.08 | chnA |
| ATOM | 799 | O | ARG | A | 106 | 98.196 | 22.253 | 41.372 | 1.00 | 34.23 | chnA |
| ATOM | 800 | N | CYS | A | 107 | 98.895 | 24.198 | 40.503 | 1.00 | 34.51 | chnA |
| ATOM | 801 | CA | CYS | A | 107 | 100.143 | 23.661 | 39.963 | 1.00 | 31.91 | chnA |
| ATOM | 802 | C | CYS | A | 107 | 101.223 | 23.890 | 40.997 | 1.00 | 32.33 | chnA |
| ATOM | 803 | O | CYS | A | 107 | 102.040 | 24.788 | 40.878 | 1.00 | 32.38 | chnA |
| ATOM | 804 | CB | CYS | A | 107 | 100.504 | 24.360 | 38.659 | 1.00 | 33.37 | chnA |
| ATOM | 805 | SG | CYS | A | 107 | 101.851 | 23.553 | 37.762 | 1.00 | 36.28 | chnA |
| ATOM | 806 | N | HIS | A | 108 | 101.216 | 23.039 | 42.007 | 1.00 | 32.57 | chnA |
| ATOM | 807 | CA | HIS | A | 108 | 102.129 | 23.105 | 43.135 | 1.00 | 33.35 | chnA |
| ATOM | 808 | CB | HIS | A | 108 | 101.611 | 22.168 | 44.229 | 1.00 | 35.82 | chnA |
| ATOM | 809 | CG | HIS | A | 108 | 102.282 | 22.348 | 45.546 | 1.00 | 37.49 | chnA |
| ATOM | 810 | CD2 | HIS | A | 108 | 102.636 | 21.454 | 46.491 | 1.00 | 39.47 | chnA |
| ATOM | 811 | ND1 | HIS | A | 108 | 102.687 | 23.580 | 46.011 | 1.00 | 39.55 | chnA |
| ATOM | 812 | CE1 | HIS | A | 108 | 103.265 | 23.432 | 47.186 | 1.00 | 40.52 | chnA |
| ATOM | 813 | NE2 | HIS | A | 108 | 103.248 | 22.151 | 47.502 | 1.00 | 40.04 | chnA |
| ATOM | 814 | C | HIS | A | 108 | 103.588 | 22.800 | 42.838 | 1.00 | 31.17 | chnA |
| ATOM | 815 | O | HIS | A | 108 | 103.901 | 21.793 | 42.238 | 1.00 | 35.19 | chnA |
| ATOM | 816 | N | GLY | A | 109 | 104.482 | 23.659 | 43.306 | 1.00 | 34.11 | chnA |
| ATOM | 817 | CA | GLY | A | 109 | 105.899 | 23.443 | 43.092 | 1.00 | 31.57 | chnA |
| ATOM | 818 | C | GLY | A | 109 | 106.591 | 22.810 | 44.285 | 1.00 | 32.87 | chnA |
| ATOM | 819 | O | GLY | A | 109 | 106.181 | 22.999 | 45.428 | 1.00 | 36.73 | chnA |
| ATOM | 820 | N | TRP | A | 110 | 107.646 | 22.052 | 44.009 | 1.00 | 32.29 | chnA |
| ATOM | 821 | CA | TRP | A | 110 | 108.438 | 21.379 | 45.037 | 1.00 | 31.95 | chnA |
| ATOM | 822 | CB | TRP | A | 110 | 109.678 | 20.787 | 44.380 | 1.00 | 33.89 | chnA |
| ATOM | 823 | CG | TRP | A | 110 | 110.555 | 19.983 | 45.257 | 1.00 | 35.40 | chnA |
| ATOM | 824 | CD2 | TRP | A | 110 | 110.212 | 18.779 | 45.953 | 1.00 | 38.05 | chnA |
| ATOM | 825 | CE2 | TRP | A | 110 | 111.380 | 18.317 | 46.584 | 1.00 | 38.38 | chnA |
| ATOM | 826 | CE3 | TRP | A | 110 | 109.031 | 18.042 | 46.097 | 1.00 | 38.81 | chnA |
| ATOM | 827 | CD1 | TRP | A | 110 | 111.872 | 20.199 | 45.493 | 1.00 | 37.10 | chnA |
| ATOM | 828 | NE1 | TRP | A | 110 | 112.380 | 19.201 | 46.286 | 1.00 | 41.87 | chnA |
| ATOM | 829 | CZ2 | TRP | A | 110 | 111.407 | 17.157 | 47.348 | 1.00 | 40.52 | chnA |
| ATOM | 830 | CZ3 | TRP | A | 110 | 109.058 | 16.880 | 46.858 | 1.00 | 39.36 | chnA |
| ATOM | 831 | CH2 | TRP | A | 110 | 110.239 | 16.451 | 47.474 | 1.00 | 38.71 | chnA |
| ATOM | 832 | C | TRP | A | 110 | 108.853 | 22.370 | 46.124 | 1.00 | 32.71 | chnA |
| ATOM | 833 | O | TRP | A | 110 | 109.085 | 23.536 | 45.839 | 1.00 | 33.12 | chnA |
| ATOM | 834 | N | ARG | A | 111 | 108.888 | 21.921 | 47.375 | 1.00 | 35.31 | chnA |
| ATOM | 835 | CA | ARG | A | 111 | 109.275 | 22.773 | 48.501 | 1.00 | 35.72 | chnA |
| ATOM | 836 | CB | ARG | A | 111 | 110.800 | 22.773 | 48.647 | 1.00 | 35.56 | chnA |
| ATOM | 837 | CG | ARG | A | 111 | 111.383 | 21.414 | 48.933 | 1.00 | 40.70 | chnA |
| ATOM | 838 | CD | ARG | A | 111 | 112.875 | 21.459 | 49.199 | 1.00 | 42.38 | chnA |
| ATOM | 839 | NE | ARG | A | 111 | 113.147 | 20.947 | 50.537 | 1.00 | 47.98 | chnA |
| ATOM | 840 | CZ | ARG | A | 111 | 113.452 | 19.686 | 50.822 | 1.00 | 50.92 | chnA |
| ATOM | 841 | NH1 | ARG | A | 111 | 113.546 | 18.788 | 49.854 | 1.00 | 52.87 | chnA |
| ATOM | 842 | NH2 | ARG | A | 111 | 113.594 | 19.305 | 52.085 | 1.00 | 52.54 | chnA |
| ATOM | 843 | C | ARG | A | 111 | 108.772 | 24.227 | 48.422 | 1.00 | 37.53 | chnA |
| ATOM | 844 | O | ARG | A | 111 | 109.449 | 25.141 | 48.900 | 1.00 | 41.23 | chnA |
| ATOM | 845 | N | ASN | A | 112 | 107.607 | 24.451 | 47.807 | 1.00 | 40.03 | chnA |
| ATOM | 846 | CA | ASN | A | 112 | 107.034 | 25.803 | 47.664 | 1.00 | 43.44 | chnA |
| ATOM | 847 | CB | ASN | A | 112 | 106.828 | 26.476 | 49.017 | 1.00 | 49.42 | chnA |
| ATOM | 848 | CG | ASN | A | 112 | 105.579 | 26.011 | 49.700 | 1.00 | 55.79 | chnA |
| ATOM | 849 | OD1 | ASN | A | 112 | 104.497 | 26.055 | 49.102 | 1.00 | 57.56 | chnA |
| ATOM | 850 | ND2 | ASN | A | 112 | 105.704 | 25.553 | 50.961 | 1.00 | 57.22 | chnA |
| ATOM | 851 | C | ASN | A | 112 | 107.871 | 26.729 | 46.812 | 1.00 | 43.14 | chnA |

-continued

| | | | | | | | | | | |
|---|---|---|---|---|---|---|---|---|---|---|
| ATOM | 852 | O | ASN | A | 112 | 107.598 | 27.932 | 46.744 | 1.00 | 44.87 | chnA |
| ATOM | 853 | N | TRP | A | 113 | 108.927 | 26.183 | 46.221 | 1.00 | 41.85 | chnA |
| ATOM | 854 | CA | TRP | A | 113 | 109.802 | 26.945 | 45.359 | 1.00 | 39.25 | chnA |
| ATOM | 855 | CB | TRP | A | 113 | 110.858 | 26.020 | 44.777 | 1.00 | 39.67 | chnA |
| ATOM | 856 | CG | TRP | A | 113 | 111.934 | 25.675 | 45.765 | 1.00 | 41.06 | chnA |
| ATOM | 857 | CD2 | TRP | A | 113 | 112.850 | 24.586 | 45.685 | 1.00 | 41.58 | chnA |
| ATOM | 858 | CE2 | TRP | A | 113 | 113.733 | 24.701 | 46.777 | 1.00 | 42.51 | chnA |
| ATOM | 859 | CE3 | TRP | A | 113 | 113.011 | 23.522 | 44.796 | 1.00 | 42.75 | chnA |
| ATOM | 860 | CD1 | TRP | A | 113 | 112.280 | 26.380 | 46.880 | 1.00 | 42.55 | chnA |
| ATOM | 861 | NE1 | TRP | A | 113 | 113.363 | 25.807 | 47.492 | 1.00 | 42.44 | chnA |
| ATOM | 862 | CZ2 | TRP | A | 113 | 114.766 | 23.792 | 47.003 | 1.00 | 42.60 | chnA |
| ATOM | 863 | CZ3 | TRP | A | 113 | 114.040 | 22.613 | 45.022 | 1.00 | 41.09 | chnA |
| ATOM | 864 | CH2 | TRP | A | 113 | 114.904 | 22.756 | 46.118 | 1.00 | 42.08 | chnA |
| ATOM | 865 | C | TRP | A | 113 | 108.964 | 27.594 | 44.265 | 1.00 | 39.25 | chnA |
| ATOM | 866 | O | TRP | A | 113 | 107.939 | 27.049 | 43.852 | 1.00 | 41.04 | chnA |
| ATOM | 867 | N | ASP | A | 114 | 109.379 | 28.780 | 43.831 | 1.00 | 40.46 | chnA |
| ATOM | 868 | CA | ASP | A | 114 | 108.646 | 29.537 | 42.821 | 1.00 | 41.62 | chnA |
| ATOM | 869 | CB | ASP | A | 114 | 109.299 | 30.903 | 42.624 | 1.00 | 45.52 | chnA |
| ATOM | 870 | CG | ASP | A | 114 | 109.212 | 31.782 | 43.857 | 1.00 | 47.74 | chnA |
| ATOM | 871 | OD1 | ASP | A | 114 | 108.228 | 31.651 | 44.617 | 1.00 | 48.61 | chnA |
| ATOM | 872 | OD2 | ASP | A | 114 | 110.129 | 32.614 | 44.052 | 1.00 | 49.30 | chnA |
| ATOM | 873 | C | ASP | A | 114 | 108.474 | 28.872 | 41.467 | 1.00 | 40.10 | chnA |
| ATOM | 874 | O | ASP | A | 114 | 109.399 | 28.252 | 40.954 | 1.00 | 39.29 | chnA |
| ATOM | 875 | N | VAL | A | 115 | 107.275 | 28.997 | 40.900 | 1.00 | 39.24 | chnA |
| ATOM | 876 | CA | VAL | A | 115 | 106.986 | 28.441 | 39.581 | 1.00 | 41.33 | chnA |
| ATOM | 877 | CB | VAL | A | 115 | 105.860 | 27.379 | 39.624 | 1.00 | 41.94 | chnA |
| ATOM | 878 | CG1 | VAL | A | 115 | 105.667 | 26.772 | 38.260 | 1.00 | 39.49 | chnA |
| ATOM | 879 | CG2 | VAL | A | 115 | 106.180 | 26.305 | 40.625 | 1.00 | 42.41 | chnA |
| ATOM | 880 | C | VAL | A | 115 | 106.532 | 29.572 | 38.661 | 1.00 | 43.92 | chnA |
| ATOM | 881 | O | VAL | A | 115 | 105.643 | 30.356 | 39.010 | 1.00 | 43.66 | chnA |
| ATOM | 882 | N | TYR | A | 116 | 107.168 | 29.683 | 37.503 | 1.00 | 46.34 | chnA |
| ATOM | 883 | CA | TYR | A | 116 | 106.793 | 30.716 | 36.543 | 1.00 | 48.51 | chnA |
| ATOM | 884 | CB | TYR | A | 116 | 107.957 | 31.682 | 36.280 | 1.00 | 52.09 | chnA |
| ATOM | 885 | CG | TYR | A | 116 | 108.432 | 32.465 | 37.494 | 1.00 | 56.98 | chnA |
| ATOM | 886 | CD1 | TYR | A | 116 | 109.752 | 32.365 | 37.931 | 1.00 | 58.03 | chnA |
| ATOM | 887 | CE1 | TYR | A | 116 | 110.193 | 33.052 | 39.053 | 1.00 | 60.98 | chnA |
| ATOM | 888 | CD2 | TYR | A | 116 | 107.562 | 33.285 | 38.216 | 1.00 | 58.53 | chnA |
| ATOM | 889 | CE2 | TYR | A | 116 | 107.997 | 33.975 | 39.345 | 1.00 | 60.66 | chnA |
| ATOM | 890 | CZ | TYR | A | 116 | 109.312 | 33.850 | 39.756 | 1.00 | 62.00 | chnA |
| ATOM | 891 | OH | TYR | A | 116 | 109.747 | 34.500 | 40.885 | 1.00 | 63.39 | chnA |
| ATOM | 892 | C | TYR | A | 116 | 106.352 | 30.052 | 35.245 | 1.00 | 46.82 | chnA |
| ATOM | 893 | O | TYR | A | 116 | 106.507 | 28.840 | 35.085 | 1.00 | 46.84 | chnA |
| ATOM | 894 | N | LYS | A | 117 | 105.788 | 30.844 | 34.333 | 1.00 | 46.18 | chnA |
| ATOM | 895 | CA | LYS | A | 117 | 105.318 | 30.350 | 33.040 | 1.00 | 45.63 | chnA |
| ATOM | 896 | CB | LYS | A | 117 | 106.504 | 29.955 | 32.154 | 1.00 | 51.14 | chnA |
| ATOM | 897 | CG | LYS | A | 117 | 107.646 | 30.962 | 32.066 | 1.00 | 57.14 | chnA |
| ATOM | 898 | CD | LYS | A | 117 | 107.315 | 32.163 | 31.191 | 1.00 | 62.31 | chnA |
| ATOM | 899 | CE | LYS | A | 117 | 108.556 | 33.024 | 30.938 | 1.00 | 65.16 | chnA |
| ATOM | 900 | NZ | LYS | A | 117 | 109.626 | 32.293 | 30.174 | 1.00 | 68.46 | chnA |
| ATOM | 901 | C | LYS | A | 117 | 104.417 | 29.133 | 33.253 | 1.00 | 43.44 | chnA |
| ATOM | 902 | O | LYS | A | 117 | 104.616 | 28.078 | 32.643 | 1.00 | 42.45 | chnA |
| ATOM | 903 | N | VAL | A | 118 | 103.448 | 29.274 | 34.151 | 1.00 | 42.86 | chnA |
| ATOM | 904 | CA | VAL | A | 118 | 102.523 | 28.193 | 34.466 | 1.00 | 45.18 | chnA |
| ATOM | 905 | CB | VAL | A | 118 | 101.813 | 28.434 | 35.804 | 1.00 | 42.87 | chnA |
| ATOM | 906 | CG1 | VAL | A | 118 | 101.018 | 27.213 | 36.205 | 1.00 | 43.59 | chnA |
| ATOM | 907 | CG2 | VAL | A | 118 | 102.818 | 28.771 | 36.868 | 1.00 | 48.18 | chnA |
| ATOM | 908 | C | VAL | A | 118 | 101.450 | 28.034 | 33.406 | 1.00 | 45.38 | chnA |
| ATOM | 909 | O | VAL | A | 118 | 100.793 | 29.001 | 33.035 | 1.00 | 48.05 | chnA |
| ATOM | 910 | N | ILE | A | 119 | 101.264 | 26.802 | 32.942 | 1.00 | 43.86 | chnA |
| ATOM | 911 | CA | ILE | A | 119 | 100.252 | 26.493 | 31.937 | 1.00 | 43.12 | chnA |
| ATOM | 912 | CB | ILE | A | 119 | 100.883 | 26.157 | 30.575 | 1.00 | 43.44 | chnA |
| ATOM | 913 | CG2 | ILE | A | 119 | 99.796 | 25.960 | 29.548 | 1.00 | 41.75 | chnA |
| ATOM | 914 | CG1 | ILE | A | 119 | 101.827 | 27.275 | 30.132 | 1.00 | 43.10 | chnA |
| ATOM | 915 | CD1 | ILE | A | 119 | 102.584 | 26.979 | 28.858 | 1.00 | 45.68 | chnA |
| ATOM | 916 | C | ILE | A | 119 | 99.457 | 25.271 | 32.379 | 1.00 | 43.32 | chnA |
| ATOM | 917 | O | ILE | A | 119 | 100.046 | 24.252 | 32.730 | 1.00 | 43.15 | chnA |
| ATOM | 918 | N | TYR | A | 120 | 98.131 | 25.387 | 32.395 | 1.00 | 41.22 | chnA |
| ATOM | 919 | CA | TYR | A | 120 | 97.262 | 24.272 | 32.766 | 1.00 | 42.59 | chnA |
| ATOM | 920 | CB | TYR | A | 120 | 96.095 | 24.740 | 33.634 | 1.00 | 41.53 | chnA |
| ATOM | 921 | CG | TYR | A | 120 | 96.497 | 25.149 | 35.022 | 1.00 | 43.15 | chnA |
| ATOM | 922 | CD1 | TYR | A | 120 | 96.901 | 26.445 | 35.290 | 1.00 | 45.64 | chnA |
| ATOM | 923 | CE1 | TYR | A | 120 | 97.276 | 26.829 | 36.579 | 1.00 | 46.14 | chnA |
| ATOM | 924 | CD2 | TYR | A | 120 | 96.478 | 24.233 | 36.075 | 1.00 | 43.71 | chnA |
| ATOM | 925 | CE2 | TYR | A | 120 | 96.854 | 24.604 | 37.367 | 1.00 | 42.34 | chnA |
| ATOM | 926 | CZ | TYR | A | 120 | 97.250 | 25.905 | 37.611 | 1.00 | 42.72 | chnA |
| ATOM | 927 | OH | TYR | A | 120 | 97.610 | 26.306 | 38.873 | 1.00 | 38.64 | chnA |
| ATOM | 928 | C | TYR | A | 120 | 96.713 | 23.666 | 31.495 | 1.00 | 44.71 | chnA |
| ATOM | 929 | O | TYR | A | 120 | 96.189 | 24.387 | 30.646 | 1.00 | 47.50 | chnA |
| ATOM | 930 | N | TYR | A | 121 | 96.827 | 22.348 | 31.369 | 1.00 | 46.30 | chnA |

-continued

| | | | | | | | | | | |
|---|---|---|---|---|---|---|---|---|---|---|
| ATOM | 931 | CA | TYR | A | 121 | 96.346 | 21.638 | 30.188 | 1.00 | 47.36 | chnA |
| ATOM | 932 | CB | TYR | A | 121 | 97.469 | 20.799 | 29.566 | 1.00 | 49.06 | chnA |
| ATOM | 933 | CG | TYR | A | 121 | 98.735 | 21.529 | 29.193 | 1.00 | 49.03 | chnA |
| ATOM | 934 | CD1 | TYR | A | 121 | 99.623 | 21.953 | 30.162 | 1.00 | 49.08 | chnA |
| ATOM | 935 | CE1 | TYR | A | 121 | 100.809 | 22.571 | 29.832 | 1.00 | 52.65 | chnA |
| ATOM | 936 | CD2 | TYR | A | 121 | 99.068 | 21.745 | 27.870 | 1.00 | 52.32 | chnA |
| ATOM | 937 | CE2 | TYR | A | 121 | 100.259 | 22.363 | 27.531 | 1.00 | 56.42 | chnA |
| ATOM | 938 | CZ | TYR | A | 121 | 101.126 | 22.773 | 28.521 | 1.00 | 55.21 | chnA |
| ATOM | 939 | OH | TYR | A | 121 | 102.314 | 23.382 | 28.205 | 1.00 | 60.48 | chnA |
| ATOM | 940 | C | TYR | A | 121 | 95.191 | 20.698 | 30.529 | 1.00 | 47.56 | chnA |
| ATOM | 941 | O | TYR | A | 121 | 95.043 | 20.281 | 31.673 | 1.00 | 45.69 | chnA |
| ATOM | 942 | N | LYS | A | 122 | 94.382 | 20.370 | 29.522 | 1.00 | 51.45 | chnA |
| ATOM | 943 | CA | LYS | A | 122 | 93.257 | 19.445 | 29.662 | 1.00 | 53.82 | chnA |
| ATOM | 944 | CB | LYS | A | 122 | 91.937 | 20.175 | 29.870 | 1.00 | 53.69 | chnA |
| ATOM | 945 | CG | LYS | A | 122 | 90.791 | 19.213 | 30.152 | 1.00 | 57.28 | chnA |
| ATOM | 946 | CD | LYS | A | 122 | 89.422 | 19.873 | 30.132 | 1.00 | 63.10 | chnA |
| ATOM | 947 | CE | LYS | A | 122 | 88.938 | 20.131 | 28.709 | 1.00 | 69.38 | chnA |
| ATOM | 948 | NZ | LYS | A | 122 | 87.553 | 20.702 | 28.652 | 1.00 | 72.34 | chnA |
| ATOM | 949 | C | LYS | A | 122 | 93.152 | 18.647 | 28.376 | 1.00 | 57.48 | chnA |
| ATOM | 950 | O | LYS | A | 122 | 92.846 | 19.211 | 27.329 | 1.00 | 62.64 | chnA |
| ATOM | 951 | N | ASP | A | 123 | 93.395 | 17.341 | 28.453 | 1.00 | 58.74 | chnA |
| ATOM | 952 | CA | ASP | A | 123 | 93.327 | 16.470 | 27.281 | 1.00 | 60.36 | chnA |
| ATOM | 953 | CB | ASP | A | 123 | 91.913 | 16.466 | 26.684 | 1.00 | 62.11 | chnA |
| ATOM | 954 | CG | ASP | A | 123 | 90.871 | 15.935 | 27.638 | 1.00 | 63.59 | chnA |
| ATOM | 955 | OD1 | ASP | A | 123 | 91.186 | 15.028 | 28.430 | 1.00 | 64.41 | chnA |
| ATOM | 956 | OD2 | ASP | A | 123 | 89.724 | 16.416 | 27.580 | 1.00 | 65.66 | chnA |
| ATOM | 957 | C | ASP | A | 123 | 94.321 | 16.904 | 26.209 | 1.00 | 61.44 | chnA |
| ATOM | 958 | O | ASP | A | 123 | 94.042 | 16.792 | 25.013 | 1.00 | 64.24 | chnA |
| ATOM | 959 | N | GLY | A | 124 | 95.466 | 17.422 | 26.641 | 1.00 | 60.77 | chnA |
| ATOM | 960 | CA | GLY | A | 124 | 96.479 | 17.864 | 25.703 | 1.00 | 62.67 | chnA |
| ATOM | 961 | C | GLY | A | 124 | 96.391 | 19.323 | 25.307 | 1.00 | 63.57 | chnA |
| ATOM | 962 | O | GLY | A | 124 | 97.322 | 19.855 | 24.720 | 1.00 | 66.13 | chnA |
| ATOM | 963 | N | GLU | A | 125 | 95.283 | 19.979 | 25.620 | 1.00 | 63.60 | chnA |
| ATOM | 964 | CA | GLU | A | 125 | 95.124 | 21.384 | 25.267 | 1.00 | 66.83 | chnA |
| ATOM | 965 | CB | GLU | A | 125 | 93.704 | 21.664 | 24.754 | 1.00 | 74.20 | chnA |
| ATOM | 966 | CG | GLU | A | 125 | 93.391 | 21.044 | 23.398 | 1.00 | 86.55 | chnA |
| ATOM | 967 | CD | GLU | A | 125 | 92.004 | 21.410 | 22.870 | 1.00 | 91.12 | chnA |
| ATOM | 968 | OE1 | GLU | A | 125 | 91.116 | 20.519 | 22.879 | 1.00 | 94.82 | chnA |
| ATOM | 969 | OE2 | GLU | A | 125 | 91.811 | 22.574 | 22.432 | 1.00 | 92.92 | chnA |
| ATOM | 970 | C | GLU | A | 125 | 95.440 | 22.338 | 26.408 | 1.00 | 63.76 | chnA |
| ATOM | 971 | O | GLU | A | 125 | 94.957 | 22.169 | 27.523 | 1.00 | 65.52 | chnA |
| ATOM | 972 | N | ALA | A | 126 | 96.253 | 23.345 | 26.117 | 1.00 | 58.87 | chnA |
| ATOM | 973 | CA | ALA | A | 126 | 96.605 | 24.358 | 27.096 | 1.00 | 56.00 | chnA |
| ATOM | 974 | CB | ALA | A | 126 | 97.861 | 25.073 | 26.665 | 1.00 | 52.66 | chnA |
| ATOM | 975 | C | ALA | A | 126 | 95.437 | 25.335 | 27.145 | 1.00 | 57.30 | chnA |
| ATOM | 976 | O | ALA | A | 126 | 95.074 | 25.913 | 26.120 | 1.00 | 59.29 | chnA |
| ATOM | 977 | N | LEU | A | 127 | 94.815 | 25.491 | 28.311 | 1.00 | 56.92 | chnA |
| ATOM | 978 | CA | LEU | A | 127 | 93.691 | 26.412 | 28.412 | 1.00 | 59.95 | chnA |
| ATOM | 979 | CB | LEU | A | 127 | 92.432 | 25.724 | 28.944 | 1.00 | 62.31 | chnA |
| ATOM | 980 | CG | LEU | A | 127 | 92.474 | 24.835 | 30.179 | 1.00 | 61.26 | chnA |
| ATOM | 981 | CD1 | LEU | A | 127 | 91.070 | 24.650 | 30.753 | 1.00 | 61.90 | chnA |
| ATOM | 982 | CD2 | LEU | A | 127 | 93.059 | 23.509 | 29.780 | 1.00 | 62.57 | chnA |
| ATOM | 983 | C | LEU | A | 127 | 93.934 | 27.714 | 29.156 | 1.00 | 61.56 | chnA |
| ATOM | 984 | O | LEU | A | 127 | 93.152 | 28.659 | 29.004 | 1.00 | 65.33 | chnA |
| ATOM | 985 | N | LYS | A | 128 | 95.000 | 27.774 | 29.954 | 1.00 | 61.52 | chnA |
| ATOM | 986 | CA | LYS | A | 128 | 95.331 | 28.996 | 30.693 | 1.00 | 60.58 | chnA |
| ATOM | 987 | CB | LYS | A | 128 | 94.529 | 29.105 | 31.989 | 1.00 | 61.95 | chnA |
| ATOM | 988 | CG | LYS | A | 128 | 93.196 | 29.795 | 31.794 | 1.00 | 68.05 | chnA |
| ATOM | 989 | CD | LYS | A | 128 | 92.340 | 29.771 | 33.040 | 1.00 | 72.22 | chnA |
| ATOM | 990 | CE | LYS | A | 128 | 90.978 | 30.423 | 32.790 | 1.00 | 74.47 | chnA |
| ATOM | 991 | NZ | LYS | A | 128 | 90.167 | 29.693 | 31.762 | 1.00 | 72.56 | chnA |
| ATOM | 992 | C | LYS | A | 128 | 96.802 | 29.180 | 30.975 | 1.00 | 59.63 | chnA |
| ATOM | 993 | O | LYS | A | 128 | 97.516 | 28.228 | 31.279 | 1.00 | 60.29 | chnA |
| ATOM | 994 | N | TYR | A | 129 | 97.236 | 30.431 | 30.882 | 1.00 | 61.40 | chnA |
| ATOM | 995 | CA | TYR | A | 129 | 98.622 | 30.802 | 31.112 | 1.00 | 62.11 | chnA |
| ATOM | 996 | CB | TYR | A | 129 | 99.246 | 31.290 | 29.810 | 1.00 | 60.82 | chnA |
| ATOM | 997 | CG | TYR | A | 129 | 100.638 | 31.851 | 29.953 | 1.00 | 61.82 | chnA |
| ATOM | 998 | CD1 | TYR | A | 129 | 101.752 | 31.026 | 29.835 | 1.00 | 62.74 | chnA |
| ATOM | 999 | CE1 | TYR | A | 129 | 103.040 | 31.541 | 29.926 | 1.00 | 63.56 | chnA |
| ATOM | 1000 | CD2 | TYR | A | 129 | 100.845 | 33.215 | 30.175 | 1.00 | 62.49 | chnA |
| ATOM | 1001 | CE2 | TYR | A | 129 | 102.129 | 33.742 | 30.271 | 1.00 | 63.04 | chnA |
| ATOM | 1002 | CZ | TYR | A | 129 | 103.223 | 32.898 | 30.142 | 1.00 | 63.80 | chnA |
| ATOM | 1003 | OH | TYR | A | 129 | 104.501 | 33.404 | 30.206 | 1.00 | 65.21 | chnA |
| ATOM | 1004 | C | TYR | A | 129 | 98.719 | 31.897 | 32.158 | 1.00 | 62.96 | chnA |
| ATOM | 1005 | O | TYR | A | 129 | 97.815 | 32.718 | 32.293 | 1.00 | 66.43 | chnA |
| ATOM | 1006 | N | TRP | A | 130 | 99.836 | 31.907 | 32.878 | 1.00 | 62.36 | chnA |
| ATOM | 1007 | CA | TRP | A | 130 | 100.101 | 32.895 | 33.914 | 1.00 | 61.96 | chnA |
| ATOM | 1008 | CB | TRP | A | 130 | 99.490 | 32.469 | 35.237 | 1.00 | 62.29 | chnA |
| ATOM | 1009 | CG | TRP | A | 130 | 98.106 | 32.882 | 35.354 | 1.00 | 66.57 | chnA |

-continued

| | | | | | | | | | | |
|---|---|---|---|---|---|---|---|---|---|---|
| ATOM | 1010 | CD2 | TRP | A | 130 | 96.965 | 32.035 | 35.380 | 1.00 | 67.93 | chnA |
| ATOM | 1011 | CE2 | TRP | A | 130 | 95.832 | 32.866 | 35.481 | 1.00 | 69.61 | chnA |
| ATOM | 1012 | CE3 | TRP | A | 130 | 96.786 | 30.652 | 35.328 | 1.00 | 68.41 | chnA |
| ATOM | 1013 | CD1 | TRP | A | 130 | 97.644 | 34.158 | 35.436 | 1.00 | 69.24 | chnA |
| ATOM | 1014 | NE1 | TRP | A | 130 | 96.276 | 34.162 | 35.514 | 1.00 | 71.13 | chnA |
| ATOM | 1015 | CZ2 | TRP | A | 130 | 94.534 | 32.360 | 35.531 | 1.00 | 70.78 | chnA |
| ATOM | 1016 | CZ3 | TRP | A | 130 | 95.499 | 30.148 | 35.377 | 1.00 | 69.74 | chnA |
| ATOM | 1017 | CH2 | TRP | A | 130 | 94.388 | 31.002 | 35.478 | 1.00 | 71.03 | chnA |
| ATOM | 1018 | C | TRP | A | 130 | 101.581 | 33.048 | 34.108 | 1.00 | 62.06 | chnA |
| ATOM | 1019 | O | TRP | A | 130 | 102.307 | 32.057 | 34.115 | 1.00 | 63.19 | chnA |
| ATOM | 1020 | N | TYR | A | 131 | 102.039 | 34.288 | 34.241 | 1.00 | 64.41 | chnA |
| ATOM | 1021 | CA | TYR | A | 131 | 103.459 | 34.509 | 34.456 | 1.00 | 68.31 | chnA |
| ATOM | 1022 | CB | TYR | A | 131 | 103.856 | 35.967 | 34.211 | 1.00 | 68.99 | chnA |
| ATOM | 1023 | CG | TYR | A | 131 | 105.343 | 36.182 | 34.341 | 1.00 | 69.03 | chnA |
| ATOM | 1024 | CD1 | TYR | A | 131 | 106.245 | 35.397 | 33.619 | 1.00 | 69.30 | chnA |
| ATOM | 1025 | CE1 | TYR | A | 131 | 107.619 | 35.530 | 33.796 | 1.00 | 71.03 | chnA |
| ATOM | 1026 | CD2 | TYR | A | 131 | 105.854 | 37.114 | 35.237 | 1.00 | 70.05 | chnA |
| ATOM | 1027 | CE2 | TYR | A | 131 | 107.225 | 37.255 | 35.423 | 1.00 | 72.19 | chnA |
| ATOM | 1028 | CZ | TYR | A | 131 | 108.101 | 36.459 | 34.704 | 1.00 | 71.41 | chnA |
| ATOM | 1029 | OH | TYR | A | 131 | 109.454 | 36.576 | 34.919 | 1.00 | 71.66 | chnA |
| ATOM | 1030 | C | TYR | A | 131 | 103.765 | 34.087 | 35.892 | 1.00 | 68.89 | chnA |
| ATOM | 1031 | O | TYR | A | 131 | 104.566 | 33.182 | 36.129 | 1.00 | 69.71 | chnA |
| ATOM | 1032 | N | GLU | A | 132 | 103.109 | 34.739 | 36.843 | 1.00 | 68.98 | chnA |
| ATOM | 1033 | CA | GLU | A | 132 | 103.279 | 34.407 | 38.248 | 1.00 | 66.29 | chnA |
| ATOM | 1034 | CB | GLU | A | 132 | 102.836 | 35.583 | 39.125 | 1.00 | 69.37 | chnA |
| ATOM | 1035 | CG | GLU | A | 132 | 103.693 | 36.838 | 38.988 | 1.00 | 70.66 | chnA |
| ATOM | 1036 | CD | GLU | A | 132 | 105.088 | 36.664 | 39.559 | 1.00 | 73.21 | chnA |
| ATOM | 1037 | OE1 | GLU | A | 132 | 106.058 | 37.084 | 38.898 | 1.00 | 75.85 | chnA |
| ATOM | 1038 | OE2 | GLU | A | 132 | 105.221 | 36.115 | 40.676 | 1.00 | 76.51 | chnA |
| ATOM | 1039 | C | GLU | A | 132 | 102.386 | 33.191 | 38.485 | 1.00 | 64.07 | chnA |
| ATOM | 1040 | O | GLU | A | 132 | 101.279 | 33.124 | 37.944 | 1.00 | 61.28 | chnA |
| ATOM | 1041 | N | ASN | A | 133 | 102.879 | 32.215 | 39.246 | 1.00 | 61.95 | chnA |
| ATOM | 1042 | CA | ASN | A | 133 | 102.095 | 31.015 | 39.518 | 1.00 | 63.05 | chnA |
| ATOM | 1043 | CB | ASN | A | 133 | 102.792 | 30.103 | 40.529 | 1.00 | 66.31 | chnA |
| ATOM | 1044 | CG | ASN | A | 133 | 102.148 | 28.721 | 40.618 | 1.00 | 66.70 | chnA |
| ATOM | 1045 | OD1 | ASN | A | 133 | 101.053 | 28.490 | 40.111 | 1.00 | 63.25 | chnA |
| ATOM | 1046 | ND2 | ASN | A | 133 | 102.837 | 27.799 | 41.270 | 1.00 | 69.74 | chnA |
| ATOM | 1047 | C | ASN | A | 133 | 100.738 | 31.426 | 40.044 | 1.00 | 60.85 | chnA |
| ATOM | 1048 | O | ASN | A | 133 | 100.629 | 32.250 | 40.948 | 1.00 | 58.78 | chnA |
| ATOM | 1049 | N | HIS | A | 134 | 99.701 | 30.863 | 39.448 | 1.00 | 61.82 | chnA |
| ATOM | 1050 | CA | HIS | A | 134 | 98.349 | 31.190 | 39.841 | 1.00 | 64.45 | chnA |
| ATOM | 1051 | CB | HIS | A | 134 | 97.808 | 32.316 | 38.954 | 1.00 | 71.21 | chnA |
| ATOM | 1052 | CG | HIS | A | 134 | 96.550 | 32.941 | 39.465 | 1.00 | 77.91 | chnA |
| ATOM | 1053 | CD2 | HIS | A | 134 | 95.514 | 33.521 | 38.814 | 1.00 | 78.77 | chnA |
| ATOM | 1054 | ND1 | HIS | A | 134 | 96.239 | 33.004 | 40.809 | 1.00 | 81.59 | chnA |
| ATOM | 1055 | CE1 | HIS | A | 134 | 95.067 | 33.591 | 40.962 | 1.00 | 82.73 | chnA |
| ATOM | 1056 | NE2 | HIS | A | 134 | 94.605 | 33.915 | 39.765 | 1.00 | 82.41 | chnA |
| ATOM | 1057 | C | HIS | A | 134 | 97.441 | 29.968 | 39.794 | 1.00 | 62.42 | chnA |
| ATOM | 1058 | O | HIS | A | 134 | 97.624 | 29.043 | 39.002 | 1.00 | 59.12 | chnA |
| ATOM | 1059 | N | ASN | A | 135 | 96.477 | 29.962 | 40.694 | 1.00 | 62.15 | chnA |
| ATOM | 1060 | CA | ASN | A | 135 | 95.533 | 28.878 | 40.799 | 1.00 | 62.22 | chnA |
| ATOM | 1061 | CB | ASN | A | 135 | 94.880 | 28.929 | 42.168 | 1.00 | 67.86 | chnA |
| ATOM | 1062 | CG | ASN | A | 135 | 95.341 | 27.821 | 43.063 | 1.00 | 71.85 | chnA |
| ATOM | 1063 | OD1 | ASN | A | 135 | 96.409 | 27.887 | 43.666 | 1.00 | 72.80 | chnA |
| ATOM | 1064 | ND2 | ASN | A | 135 | 94.532 | 26.779 | 43.157 | 1.00 | 78.05 | chnA |
| ATOM | 1065 | C | ASN | A | 135 | 94.464 | 28.994 | 39.742 | 1.00 | 60.07 | chnA |
| ATOM | 1066 | O | ASN | A | 135 | 94.069 | 30.094 | 39.372 | 1.00 | 63.15 | chnA |
| ATOM | 1067 | N | ILE | A | 136 | 94.009 | 27.858 | 39.237 | 1.00 | 56.90 | chnA |
| ATOM | 1068 | CA | ILE | A | 136 | 92.952 | 27.856 | 38.240 | 1.00 | 57.22 | chnA |
| ATOM | 1069 | CB | ILE | A | 136 | 93.269 | 26.904 | 37.082 | 1.00 | 57.05 | chnA |
| ATOM | 1070 | CG2 | ILE | A | 136 | 93.400 | 25.509 | 37.574 | 1.00 | 59.94 | chnA |
| ATOM | 1071 | CG1 | ILE | A | 136 | 92.171 | 26.956 | 36.033 | 1.00 | 58.31 | chnA |
| ATOM | 1072 | CD1 | ILE | A | 136 | 92.453 | 26.086 | 34.850 | 1.00 | 61.55 | chnA |
| ATOM | 1073 | C | ILE | A | 136 | 91.689 | 27.434 | 38.971 | 1.00 | 56.37 | chnA |
| ATOM | 1074 | O | ILE | A | 136 | 91.712 | 26.482 | 39.750 | 1.00 | 58.34 | chnA |
| ATOM | 1075 | N | SER | A | 137 | 90.595 | 28.152 | 38.737 | 1.00 | 57.16 | chnA |
| ATOM | 1076 | CA | SER | A | 137 | 89.349 | 27.863 | 39.425 | 1.00 | 58.27 | chnA |
| ATOM | 1077 | CB | SER | A | 137 | 89.118 | 28.945 | 40.474 | 1.00 | 59.29 | chnA |
| ATOM | 1078 | OG | SER | A | 137 | 87.884 | 28.775 | 41.133 | 1.00 | 65.58 | chnA |
| ATOM | 1079 | C | SER | A | 137 | 88.128 | 27.737 | 38.529 | 1.00 | 58.08 | chnA |
| ATOM | 1080 | O | SER | A | 137 | 87.778 | 28.662 | 37.813 | 1.00 | 62.66 | chnA |
| ATOM | 1081 | N | ILE | A | 138 | 87.484 | 26.578 | 38.575 | 1.00 | 59.05 | chnA |
| ATOM | 1082 | CA | ILE | A | 138 | 86.280 | 26.320 | 37.790 | 1.00 | 61.52 | chnA |
| ATOM | 1083 | CB | ILE | A | 138 | 86.268 | 24.883 | 37.250 | 1.00 | 60.58 | chnA |
| ATOM | 1084 | CG2 | ILE | A | 138 | 84.962 | 24.593 | 36.548 | 1.00 | 60.79 | chnA |
| ATOM | 1085 | CG1 | ILE | A | 138 | 87.445 | 24.681 | 36.306 | 1.00 | 60.79 | chnA |
| ATOM | 1086 | CD1 | ILE | A | 138 | 87.530 | 23.298 | 35.740 | 1.00 | 62.91 | chnA |
| ATOM | 1087 | C | ILE | A | 138 | 85.072 | 26.526 | 38.696 | 1.00 | 63.87 | chnA |
| ATOM | 1088 | O | ILE | A | 138 | 84.701 | 25.642 | 39.462 | 1.00 | 64.15 | chnA |

-continued

| | | | | | | | | | | |
|---|---|---|---|---|---|---|---|---|---|---|
| ATOM | 1089 | N | THR | A | 139 | 84.469 | 27.705 | 38.607 | 1.00 | 66.95 chnA |
| ATOM | 1090 | CA | THR | A | 139 | 83.322 | 28.058 | 39.434 | 1.00 | 71.40 chnA |
| ATOM | 1091 | CB | THR | A | 139 | 82.850 | 29.489 | 39.129 | 1.00 | 72.25 chnA |
| ATOM | 1092 | OG1 | THR | A | 139 | 82.514 | 29.607 | 37.739 | 1.00 | 77.22 chnA |
| ATOM | 1093 | CG2 | THR | A | 139 | 83.960 | 30.483 | 39.445 | 1.00 | 73.91 chnA |
| ATOM | 1094 | C | THR | A | 139 | 82.141 | 27.082 | 39.381 | 1.00 | 72.96 chnA |
| ATOM | 1095 | O | THR | A | 139 | 81.741 | 26.547 | 40.419 | 1.00 | 75.89 chnA |
| ATOM | 1096 | N | ASN | A | 140 | 81.599 | 26.842 | 38.184 | 1.00 | 72.33 chnA |
| ATOM | 1097 | CA | ASN | A | 140 | 80.465 | 25.925 | 37.990 | 1.00 | 70.19 chnA |
| ATOM | 1098 | CB | ASN | A | 140 | 79.327 | 26.638 | 37.235 | 1.00 | 69.22 chnA |
| ATOM | 1099 | CG | ASN | A | 140 | 78.020 | 25.829 | 37.196 | 1.00 | 67.48 chnA |
| ATOM | 1100 | OD1 | ASN | A | 140 | 77.971 | 24.660 | 37.608 | 1.00 | 69.47 chnA |
| ATOM | 1101 | ND2 | ASN | A | 140 | 76.960 | 26.465 | 36.692 | 1.00 | 62.36 chnA |
| ATOM | 1102 | C | ASN | A | 140 | 80.940 | 24.707 | 37.201 | 1.00 | 69.86 chnA |
| ATOM | 1103 | O | ASN | A | 140 | 81.053 | 24.760 | 35.978 | 1.00 | 69.41 chnA |
| ATOM | 1104 | N | ALA | A | 141 | 81.216 | 23.616 | 37.909 | 1.00 | 69.83 chnA |
| ATOM | 1105 | CA | ALA | A | 141 | 81.696 | 22.395 | 37.281 | 1.00 | 71.24 chnA |
| ATOM | 1106 | CB | ALA | A | 141 | 82.087 | 21.378 | 38.334 | 1.00 | 71.85 chnA |
| ATOM | 1107 | C | ALA | A | 141 | 80.689 | 21.797 | 36.316 | 1.00 | 73.08 chnA |
| ATOM | 1108 | O | ALA | A | 141 | 79.536 | 21.560 | 36.670 | 1.00 | 74.64 chnA |
| ATOM | 1109 | N | THR | A | 142 | 81.150 | 21.546 | 35.095 | 1.00 | 75.36 chnA |
| ATOM | 1110 | CA | THR | A | 142 | 80.325 | 20.975 | 34.034 | 1.00 | 74.65 chnA |
| ATOM | 1111 | CB | THR | A | 142 | 80.307 | 21.912 | 32.804 | 1.00 | 73.80 chnA |
| ATOM | 1112 | OG1 | THR | A | 142 | 79.810 | 23.198 | 33.194 | 1.00 | 75.33 chnA |
| ATOM | 1113 | CG2 | THR | A | 142 | 79.416 | 21.351 | 31.700 | 1.00 | 75.41 chnA |
| ATOM | 1114 | C | THR | A | 142 | 80.909 | 19.633 | 33.612 | 1.00 | 73.87 chnA |
| ATOM | 1115 | O | THR | A | 142 | 82.110 | 19.413 | 33.741 | 1.00 | 76.00 chnA |
| ATOM | 1116 | N | VAL | A | 143 | 80.061 | 18.744 | 33.102 | 1.00 | 73.70 chnA |
| ATOM | 1117 | CA | VAL | A | 143 | 80.505 | 17.431 | 32.641 | 1.00 | 74.46 chnA |
| ATOM | 1118 | CB | VAL | A | 143 | 79.312 | 16.585 | 32.138 | 1.00 | 75.10 chnA |
| ATOM | 1119 | CG1 | VAL | A | 143 | 78.651 | 17.260 | 30.938 | 1.00 | 79.05 chnA |
| ATOM | 1120 | CG2 | VAL | A | 143 | 79.766 | 15.171 | 31.800 | 1.00 | 75.60 chnA |
| ATOM | 1121 | C | VAL | A | 143 | 81.555 | 17.577 | 31.531 | 1.00 | 73.93 chnA |
| ATOM | 1122 | O | VAL | A | 143 | 82.350 | 16.673 | 31.293 | 1.00 | 71.96 chnA |
| ATOM | 1123 | N | GLU | A | 144 | 81.546 | 18.726 | 30.861 | 1.00 | 76.00 chnA |
| ATOM | 1124 | CA | GLU | A | 144 | 82.503 | 19.013 | 29.802 | 1.00 | 78.22 chnA |
| ATOM | 1125 | CB | GLU | A | 144 | 82.118 | 20.305 | 29.074 | 1.00 | 86.79 chnA |
| ATOM | 1126 | CG | GLU | A | 144 | 80.774 | 20.267 | 28.345 | 1.00 | 96.19 chnA |
| ATOM | 1127 | CD | GLU | A | 144 | 80.379 | 21.634 | 27.762 | 1.00 | 101.14 chnA |
| ATOM | 1128 | OE1 | GLU | A | 144 | 81.026 | 22.080 | 26.777 | 1.00 | 102.82 chnA |
| ATOM | 1129 | OE2 | GLU | A | 144 | 79.424 | 22.260 | 28.295 | 1.00 | 103.48 chnA |
| ATOM | 1130 | C | GLU | A | 144 | 83.886 | 19.183 | 30.429 | 1.00 | 74.76 chnA |
| ATOM | 1131 | O | GLU | A | 144 | 84.906 | 18.876 | 29.808 | 1.00 | 72.93 chnA |
| ATOM | 1132 | N | ASP | A | 145 | 83.907 | 19.666 | 31.670 | 1.00 | 70.18 chnA |
| ATOM | 1133 | CA | ASP | A | 145 | 85.150 | 19.886 | 32.396 | 1.00 | 65.56 chnA |
| ATOM | 1134 | CB | ASP | A | 145 | 84.900 | 20.750 | 33.628 | 1.00 | 64.75 chnA |
| ATOM | 1135 | CG | ASP | A | 145 | 84.509 | 22.164 | 33.268 | 1.00 | 66.06 chnA |
| ATOM | 1136 | OD1 | ASP | A | 145 | 85.141 | 22.740 | 32.350 | 1.00 | 64.01 chnA |
| ATOM | 1137 | OD2 | ASP | A | 145 | 83.575 | 22.703 | 33.899 | 1.00 | 65.74 chnA |
| ATOM | 1138 | C | ASP | A | 145 | 85.872 | 18.600 | 32.783 | 1.00 | 63.51 chnA |
| ATOM | 1139 | O | ASP | A | 145 | 86.906 | 18.644 | 33.446 | 1.00 | 62.27 chnA |
| ATOM | 1140 | N | SER | A | 146 | 85.332 | 17.461 | 32.356 | 1.00 | 60.91 chnA |
| ATOM | 1141 | CA | SER | A | 146 | 85.945 | 16.166 | 32.639 | 1.00 | 60.56 chnA |
| ATOM | 1142 | CB | SER | A | 146 | 84.926 | 15.039 | 32.503 | 1.00 | 59.59 chnA |
| ATOM | 1143 | OG | SER | A | 146 | 83.872 | 15.186 | 33.436 | 1.00 | 62.22 chnA |
| ATOM | 1144 | C | SER | A | 146 | 87.095 | 15.912 | 31.682 | 1.00 | 61.33 chnA |
| ATOM | 1145 | O | SER | A | 146 | 87.038 | 16.310 | 30.515 | 1.00 | 64.47 chnA |
| ATOM | 1146 | N | GLY | A | 147 | 88.137 | 15.252 | 32.178 | 1.00 | 61.35 chnA |
| ATOM | 1147 | CA | GLY | A | 147 | 89.291 | 14.960 | 31.348 | 1.00 | 62.39 chnA |
| ATOM | 1148 | C | GLY | A | 147 | 90.571 | 14.871 | 32.147 | 1.00 | 60.96 chnA |
| ATOM | 1149 | O | GLY | A | 147 | 90.540 | 15.001 | 33.366 | 1.00 | 61.61 chnA |
| ATOM | 1150 | N | THR | A | 148 | 91.691 | 14.630 | 31.469 | 1.00 | 59.47 chnA |
| ATOM | 1151 | CA | THR | A | 148 | 92.981 | 14.528 | 32.141 | 1.00 | 58.29 chnA |
| ATOM | 1152 | CB | THR | A | 148 | 93.893 | 13.467 | 31.497 | 1.00 | 58.32 chnA |
| ATOM | 1153 | OG1 | THR | A | 148 | 94.565 | 14.032 | 30.370 | 1.00 | 67.71 chnA |
| ATOM | 1154 | CG2 | THR | A | 148 | 93.077 | 12.284 | 31.021 | 1.00 | 61.82 chnA |
| ATOM | 1155 | C | THR | A | 148 | 93.663 | 15.889 | 32.121 | 1.00 | 55.31 chnA |
| ATOM | 1156 | O | THR | A | 148 | 93.865 | 16.482 | 31.066 | 1.00 | 56.22 chnA |
| ATOM | 1157 | N | TYR | A | 149 | 93.961 | 16.398 | 33.310 | 1.00 | 53.08 chnA |
| ATOM | 1158 | CA | TYR | A | 149 | 94.606 | 17.692 | 33.468 | 1.00 | 50.06 chnA |
| ATOM | 1159 | CB | TYR | A | 149 | 93.883 | 18.520 | 34.531 | 1.00 | 50.59 chnA |
| ATOM | 1160 | CG | TYR | A | 149 | 92.518 | 19.050 | 34.170 | 1.00 | 51.08 chnA |
| ATOM | 1161 | CD1 | TYR | A | 149 | 91.386 | 18.253 | 34.268 | 1.00 | 50.25 chnA |
| ATOM | 1162 | CE1 | TYR | A | 149 | 90.111 | 18.770 | 34.016 | 1.00 | 51.28 chnA |
| ATOM | 1163 | CD2 | TYR | A | 149 | 92.349 | 20.376 | 33.805 | 1.00 | 53.58 chnA |
| ATOM | 1164 | CE2 | TYR | A | 149 | 91.081 | 20.904 | 33.554 | 1.00 | 54.85 chnA |
| ATOM | 1165 | CZ | TYR | A | 149 | 89.968 | 20.096 | 33.663 | 1.00 | 52.48 chnA |
| ATOM | 1166 | OH | TYR | A | 149 | 88.721 | 20.627 | 33.427 | 1.00 | 51.41 chnA |
| ATOM | 1167 | C | TYR | A | 149 | 96.048 | 17.521 | 33.913 | 1.00 | 48.11 chnA |

-continued

| | | | | | | | | | |
|---|---|---|---|---|---|---|---|---|---|
| ATOM | 1168 | O | TYR | A | 149 | 96.401 | 16.526 | 34.539 | 1.00 | 48.37 | chnA |
| ATOM | 1169 | N | TYR | A | 150 | 96.870 | 18.511 | 33.594 | 1.00 | 45.09 | chnA |
| ATOM | 1170 | CA | TYR | A | 150 | 98.270 | 18.536 | 33.987 | 1.00 | 41.57 | chnA |
| ATOM | 1171 | CB | TYR | A | 150 | 99.100 | 17.466 | 33.250 | 1.00 | 42.09 | chnA |
| ATOM | 1172 | CG | TYR | A | 150 | 99.389 | 17.713 | 31.791 | 1.00 | 46.35 | chnA |
| ATOM | 1173 | CD1 | TYR | A | 150 | 100.570 | 18.322 | 31.396 | 1.00 | 47.90 | chnA |
| ATOM | 1174 | CE1 | TYR | A | 150 | 100.854 | 18.534 | 30.059 | 1.00 | 51.62 | chnA |
| ATOM | 1175 | CD2 | TYR | A | 150 | 98.496 | 17.317 | 30.803 | 1.00 | 48.47 | chnA |
| ATOM | 1176 | CE2 | TYR | A | 150 | 98.774 | 17.522 | 29.460 | 1.00 | 50.99 | chnA |
| ATOM | 1177 | CZ | TYR | A | 150 | 99.954 | 18.133 | 29.095 | 1.00 | 51.29 | chnA |
| ATOM | 1178 | OH | TYR | A | 150 | 100.232 | 18.355 | 27.767 | 1.00 | 55.15 | chnA |
| ATOM | 1179 | C | TYR | A | 150 | 98.786 | 19.958 | 33.766 | 1.00 | 40.13 | chnA |
| ATOM | 1180 | O | TYR | A | 150 | 98.097 | 20.775 | 33.169 | 1.00 | 41.35 | chnA |
| ATOM | 1181 | N | CYS | A | 151 | 99.953 | 20.280 | 34.309 | 1.00 | 37.72 | chnA |
| ATOM | 1182 | CA | CYS | A | 151 | 100.510 | 21.617 | 34.158 | 1.00 | 37.30 | chnA |
| ATOM | 1183 | C | CYS | A | 151 | 102.002 | 21.594 | 33.936 | 1.00 | 36.18 | chnA |
| ATOM | 1184 | O | CYS | A | 151 | 102.666 | 20.618 | 34.267 | 1.00 | 38.33 | chnA |
| ATOM | 1185 | CB | CYS | A | 151 | 100.211 | 22.476 | 35.396 | 1.00 | 36.52 | chnA |
| ATOM | 1186 | SG | CYS | A | 151 | 100.987 | 21.915 | 36.946 | 1.00 | 36.98 | chnA |
| ATOM | 1187 | N | THR | A | 152 | 102.523 | 22.676 | 33.364 | 1.00 | 32.29 | chnA |
| ATOM | 1188 | CA | THR | A | 152 | 103.951 | 22.818 | 33.122 | 1.00 | 35.13 | chnA |
| ATOM | 1189 | CB | THR | A | 152 | 104.274 | 22.844 | 31.624 | 1.00 | 35.38 | chnA |
| ATOM | 1190 | OG1 | THR | A | 152 | 103.567 | 23.921 | 30.995 | 1.00 | 40.64 | chnA |
| ATOM | 1191 | CG2 | THR | A | 152 | 103.860 | 21.555 | 30.983 | 1.00 | 36.64 | chnA |
| ATOM | 1192 | C | THR | A | 152 | 104.392 | 24.135 | 33.763 | 1.00 | 37.03 | chnA |
| ATOM | 1193 | O | THR | A | 152 | 103.612 | 25.090 | 33.827 | 1.00 | 39.93 | chnA |
| ATOM | 1194 | N | GLY | A | 153 | 105.634 | 24.186 | 34.239 | 1.00 | 37.46 | chnA |
| ATOM | 1195 | CA | GLY | A | 153 | 106.132 | 25.393 | 34.875 | 1.00 | 36.76 | chnA |
| ATOM | 1196 | C | GLY | A | 153 | 107.634 | 25.567 | 34.770 | 1.00 | 39.24 | chnA |
| ATOM | 1197 | O | GLY | A | 153 | 108.315 | 24.727 | 34.194 | 1.00 | 38.39 | chnA |
| ATOM | 1198 | N | LYS | A | 154 | 108.162 | 26.636 | 35.359 | 1.00 | 41.10 | chnA |
| ATOM | 1199 | CA | LYS | A | 154 | 109.592 | 26.907 | 35.281 | 1.00 | 43.34 | chnA |
| ATOM | 1200 | CB | LYS | A | 154 | 109.814 | 28.143 | 34.385 | 1.00 | 49.36 | chnA |
| ATOM | 1201 | CG | LYS | A | 154 | 111.029 | 28.092 | 33.438 | 1.00 | 56.83 | chnA |
| ATOM | 1202 | CD | LYS | A | 154 | 111.458 | 29.511 | 32.939 | 1.00 | 64.56 | chnA |
| ATOM | 1203 | CE | LYS | A | 154 | 111.659 | 30.518 | 34.127 | 1.00 | 69.79 | chnA |
| ATOM | 1204 | NZ | LYS | A | 154 | 112.486 | 31.763 | 33.871 | 1.00 | 67.41 | chnA |
| ATOM | 1205 | C | LYS | A | 154 | 110.251 | 27.113 | 36.665 | 1.00 | 43.66 | chnA |
| ATOM | 1206 | O | LYS | A | 154 | 110.613 | 28.236 | 37.039 | 1.00 | 45.40 | chnA |
| ATOM | 1207 | N | VAL | A | 155 | 110.382 | 26.036 | 37.434 | 1.00 | 42.43 | chnA |
| ATOM | 1208 | CA | VAL | A | 155 | 111.026 | 26.101 | 38.745 | 1.00 | 43.23 | chnA |
| ATOM | 1209 | CB | VAL | A | 155 | 110.829 | 24.822 | 39.528 | 1.00 | 41.85 | chnA |
| ATOM | 1210 | CG1 | VAL | A | 155 | 111.600 | 24.883 | 40.827 | 1.00 | 40.16 | chnA |
| ATOM | 1211 | CG2 | VAL | A | 155 | 109.366 | 24.621 | 39.791 | 1.00 | 44.28 | chnA |
| ATOM | 1212 | C | VAL | A | 155 | 112.523 | 26.328 | 38.559 | 1.00 | 45.18 | chnA |
| ATOM | 1213 | O | VAL | A | 155 | 113.190 | 25.587 | 37.839 | 1.00 | 42.58 | chnA |
| ATOM | 1214 | N | TRP | A | 156 | 113.056 | 27.306 | 39.285 | 1.00 | 49.03 | chnA |
| ATOM | 1215 | CA | TRP | A | 156 | 114.458 | 27.686 | 39.165 | 1.00 | 50.11 | chnA |
| ATOM | 1216 | CB | TRP | A | 156 | 115.398 | 26.500 | 39.413 | 1.00 | 45.40 | chnA |
| ATOM | 1217 | CG | TRP | A | 156 | 115.414 | 26.164 | 40.873 | 1.00 | 43.86 | chnA |
| ATOM | 1218 | CD2 | TRP | A | 156 | 115.806 | 27.033 | 41.937 | 1.00 | 41.97 | chnA |
| ATOM | 1219 | CE2 | TRP | A | 156 | 115.515 | 26.373 | 43.143 | 1.00 | 40.66 | chnA |
| ATOM | 1220 | CE3 | TRP | A | 156 | 116.370 | 28.316 | 41.987 | 1.00 | 42.08 | chnA |
| ATOM | 1221 | CD1 | TRP | A | 156 | 114.934 | 25.037 | 41.462 | 1.00 | 43.10 | chnA |
| ATOM | 1222 | NE1 | TRP | A | 156 | 114.981 | 25.154 | 42.825 | 1.00 | 40.50 | chnA |
| ATOM | 1223 | CZ2 | TRP | A | 156 | 115.764 | 26.950 | 44.386 | 1.00 | 41.89 | chnA |
| ATOM | 1224 | CZ3 | TRP | A | 156 | 116.616 | 28.887 | 43.215 | 1.00 | 39.16 | chnA |
| ATOM | 1225 | CH2 | TRP | A | 156 | 116.315 | 28.207 | 44.400 | 1.00 | 40.87 | chnA |
| ATOM | 1226 | C | TRP | A | 156 | 114.576 | 28.261 | 37.766 | 1.00 | 54.10 | chnA |
| ATOM | 1227 | O | TRP | A | 156 | 113.901 | 29.253 | 37.451 | 1.00 | 58.02 | chnA |
| ATOM | 1228 | N | GLN | A | 157 | 115.349 | 27.631 | 36.896 | 1.00 | 55.33 | chnA |
| ATOM | 1229 | CA | GLN | A | 157 | 115.457 | 28.173 | 35.554 | 1.00 | 59.48 | chnA |
| ATOM | 1230 | CB | GLN | A | 157 | 116.876 | 28.684 | 35.331 | 1.00 | 64.78 | chnA |
| ATOM | 1231 | CG | GLN | A | 157 | 117.183 | 29.953 | 36.110 | 1.00 | 68.48 | chnA |
| ATOM | 1232 | CD | GLN | A | 157 | 116.430 | 31.152 | 35.564 | 1.00 | 70.09 | chnA |
| ATOM | 1233 | OE1 | GLN | A | 157 | 117.042 | 32.078 | 35.021 | 1.00 | 73.30 | chnA |
| ATOM | 1234 | NE2 | GLN | A | 157 | 115.094 | 31.130 | 35.671 | 1.00 | 67.50 | chnA |
| ATOM | 1235 | C | GLN | A | 157 | 115.055 | 27.194 | 34.465 | 1.00 | 60.25 | chnA |
| ATOM | 1236 | O | GLN | A | 157 | 114.976 | 27.570 | 33.295 | 1.00 | 59.41 | chnA |
| ATOM | 1237 | N | LEU | A | 158 | 114.740 | 25.963 | 34.871 | 1.00 | 60.62 | chnA |
| ATOM | 1238 | CA | LEU | A | 158 | 114.378 | 24.887 | 33.954 | 1.00 | 60.11 | chnA |
| ATOM | 1239 | CB | LEU | A | 158 | 115.126 | 23.621 | 34.358 | 1.00 | 62.86 | chnA |
| ATOM | 1240 | CG | LEU | A | 158 | 116.600 | 23.861 | 34.710 | 1.00 | 65.07 | chnA |
| ATOM | 1241 | CD1 | LEU | A | 158 | 117.247 | 22.591 | 35.262 | 1.00 | 65.86 | chnA |
| ATOM | 1242 | CD2 | LEU | A | 158 | 117.347 | 24.375 | 33.479 | 1.00 | 66.00 | chnA |
| ATOM | 1243 | C | LEU | A | 158 | 112.882 | 24.599 | 33.851 | 1.00 | 58.70 | chnA |
| ATOM | 1244 | O | LEU | A | 158 | 112.085 | 25.044 | 34.682 | 1.00 | 54.25 | chnA |
| ATOM | 1245 | N | ASP | A | 159 | 112.506 | 23.882 | 32.795 | 1.00 | 57.98 | chnA |
| ATOM | 1246 | CA | ASP | A | 159 | 111.112 | 23.531 | 32.571 | 1.00 | 57.47 | chnA |

-continued

| | | | | | | | | | | |
|---|---|---|---|---|---|---|---|---|---|---|
| ATOM | 1247 | CB | ASP | A | 159 | 110.748 | 23.620 | 31.090 | 1.00 | 60.50 | chnA |
| ATOM | 1248 | CG | ASP | A | 159 | 110.568 | 25.049 | 30.618 | 1.00 | 64.28 | chnA |
| ATOM | 1249 | OD1 | ASP | A | 159 | 109.437 | 25.576 | 30.723 | 1.00 | 67.38 | chnA |
| ATOM | 1250 | OD2 | ASP | A | 159 | 111.559 | 25.645 | 30.141 | 1.00 | 66.18 | chnA |
| ATOM | 1251 | C | ASP | A | 159 | 110.808 | 22.144 | 33.096 | 1.00 | 55.97 | chnA |
| ATOM | 1252 | O | ASP | A | 159 | 111.626 | 21.225 | 32.989 | 1.00 | 57.47 | chnA |
| ATOM | 1253 | N | TYR | A | 160 | 109.626 | 22.009 | 33.682 | 1.00 | 51.87 | chnA |
| ATOM | 1254 | CA | TYR | A | 160 | 109.187 | 20.745 | 34.243 | 1.00 | 49.30 | chnA |
| ATOM | 1255 | CB | TYR | A | 160 | 109.413 | 20.731 | 35.762 | 1.00 | 47.62 | chnA |
| ATOM | 1256 | CG | TYR | A | 160 | 110.861 | 20.878 | 36.187 | 1.00 | 44.35 | chnA |
| ATOM | 1257 | CD1 | TYR | A | 160 | 111.295 | 22.011 | 36.855 | 1.00 | 44.78 | chnA |
| ATOM | 1258 | CE1 | TYR | A | 160 | 112.616 | 22.153 | 37.234 | 1.00 | 45.36 | chnA |
| ATOM | 1259 | CD2 | TYR | A | 160 | 111.797 | 19.886 | 35.911 | 1.00 | 42.81 | chnA |
| ATOM | 1260 | CE2 | TYR | A | 160 | 113.118 | 20.022 | 36.285 | 1.00 | 43.37 | chnA |
| ATOM | 1261 | CZ | TYR | A | 160 | 113.519 | 21.157 | 36.944 | 1.00 | 45.08 | chnA |
| ATOM | 1262 | OH | TYR | A | 160 | 114.827 | 21.317 | 37.314 | 1.00 | 45.40 | chnA |
| ATOM | 1263 | C | TYR | A | 160 | 107.713 | 20.528 | 33.932 | 1.00 | 48.71 | chnA |
| ATOM | 1264 | O | TYR | A | 160 | 106.980 | 21.477 | 33.673 | 1.00 | 48.18 | chnA |
| ATOM | 1265 | N | GLU | A | 161 | 107.292 | 19.270 | 33.939 | 1.00 | 50.49 | chnA |
| ATOM | 1266 | CA | GLU | A | 161 | 105.908 | 18.918 | 33.665 | 1.00 | 51.84 | chnA |
| ATOM | 1267 | CB | GLU | A | 161 | 105.818 | 18.155 | 32.347 | 1.00 | 56.97 | chnA |
| ATOM | 1268 | CG | GLU | A | 161 | 104.401 | 17.973 | 31.837 | 1.00 | 62.33 | chnA |
| ATOM | 1269 | CD | GLU | A | 161 | 104.323 | 17.126 | 30.582 | 1.00 | 64.83 | chnA |
| ATOM | 1270 | OE1 | GLU | A | 161 | 103.411 | 16.270 | 30.499 | 1.00 | 66.04 | chnA |
| ATOM | 1271 | OE2 | GLU | A | 161 | 105.171 | 17.319 | 29.684 | 1.00 | 67.39 | chnA |
| ATOM | 1272 | C | GLU | A | 161 | 105.386 | 18.056 | 34.808 | 1.00 | 51.60 | chnA |
| ATOM | 1273 | O | GLU | A | 161 | 106.133 | 17.287 | 35.411 | 1.00 | 53.19 | chnA |
| ATOM | 1274 | N | SER | A | 162 | 104.102 | 18.178 | 35.110 | 1.00 | 50.54 | chnA |
| ATOM | 1275 | CA | SER | A | 162 | 103.528 | 17.406 | 36.202 | 1.00 | 53.27 | chnA |
| ATOM | 1276 | CB | SER | A | 162 | 102.509 | 18.240 | 36.966 | 1.00 | 54.58 | chnA |
| ATOM | 1277 | OG | SER | A | 162 | 101.352 | 18.447 | 36.178 | 1.00 | 54.68 | chnA |
| ATOM | 1278 | C | SER | A | 162 | 102.835 | 16.158 | 35.726 | 1.00 | 54.41 | chnA |
| ATOM | 1279 | O | SER | A | 162 | 102.445 | 16.056 | 34.574 | 1.00 | 58.06 | chnA |
| ATOM | 1280 | N | GLU | A | 163 | 102.646 | 15.219 | 36.636 | 1.00 | 57.88 | chnA |
| ATOM | 1281 | CA | GLU | A | 163 | 101.951 | 13.993 | 36.303 | 1.00 | 59.89 | chnA |
| ATOM | 1282 | CB | GLU | A | 163 | 101.978 | 13.040 | 37.496 | 1.00 | 69.59 | chnA |
| ATOM | 1283 | CG | GLU | A | 163 | 103.346 | 12.491 | 37.826 | 1.00 | 75.26 | chnA |
| ATOM | 1284 | CD | GLU | A | 163 | 103.847 | 11.553 | 36.759 | 1.00 | 78.09 | chnA |
| ATOM | 1285 | OE1 | GLU | A | 163 | 103.260 | 10.459 | 36.620 | 1.00 | 79.61 | chnA |
| ATOM | 1286 | OE2 | GLU | A | 163 | 104.817 | 11.910 | 36.057 | 1.00 | 81.24 | chnA |
| ATOM | 1287 | C | GLU | A | 163 | 100.506 | 14.362 | 36.001 | 1.00 | 56.53 | chnA |
| ATOM | 1288 | O | GLU | A | 163 | 99.946 | 15.271 | 36.609 | 1.00 | 56.35 | chnA |
| ATOM | 1289 | N | PRO | A | 164 | 99.902 | 13.696 | 35.019 | 1.00 | 51.95 | chnA |
| ATOM | 1290 | CD | PRO | A | 164 | 100.514 | 12.722 | 34.105 | 1.00 | 51.31 | chnA |
| ATOM | 1291 | CA | PRO | A | 164 | 98.514 | 13.958 | 34.646 | 1.00 | 51.13 | chnA |
| ATOM | 1292 | CB | PRO | A | 164 | 98.355 | 13.133 | 33.370 | 1.00 | 51.15 | chnA |
| ATOM | 1293 | CG | PRO | A | 164 | 99.312 | 12.009 | 33.573 | 1.00 | 51.32 | chnA |
| ATOM | 1294 | C | PRO | A | 164 | 97.558 | 13.494 | 35.743 | 1.00 | 51.68 | chnA |
| ATOM | 1295 | O | PRO | A | 164 | 97.895 | 12.613 | 36.530 | 1.00 | 51.89 | chnA |
| ATOM | 1296 | N | LEU | A | 165 | 96.375 | 14.098 | 35.799 | 1.00 | 50.46 | chnA |
| ATOM | 1297 | CA | LEU | A | 165 | 95.381 | 13.738 | 36.797 | 1.00 | 49.45 | chnA |
| ATOM | 1298 | CB | LEU | A | 165 | 95.387 | 14.758 | 37.925 | 1.00 | 48.98 | chnA |
| ATOM | 1299 | CG | LEU | A | 165 | 94.387 | 14.539 | 39.059 | 1.00 | 48.44 | chnA |
| ATOM | 1300 | CD1 | LEU | A | 165 | 94.619 | 13.202 | 39.704 | 1.00 | 51.64 | chnA |
| ATOM | 1301 | CD2 | LEU | A | 165 | 94.516 | 15.641 | 40.081 | 1.00 | 48.59 | chnA |
| ATOM | 1302 | C | LEU | A | 165 | 93.986 | 13.640 | 36.206 | 1.00 | 51.03 | chnA |
| ATOM | 1303 | O | LEU | A | 165 | 93.487 | 14.592 | 35.623 | 1.00 | 50.40 | chnA |
| ATOM | 1304 | N | ASN | A | 166 | 93.362 | 12.481 | 36.364 | 1.00 | 56.05 | chnA |
| ATOM | 1305 | CA | ASN | A | 166 | 92.021 | 12.260 | 35.852 | 1.00 | 60.72 | chnA |
| ATOM | 1306 | CB | ASN | A | 166 | 91.706 | 10.762 | 35.756 | 1.00 | 68.68 | chnA |
| ATOM | 1307 | CG | ASN | A | 166 | 92.285 | 10.119 | 34.516 | 1.00 | 73.37 | chnA |
| ATOM | 1308 | OD1 | ASN | A | 166 | 92.586 | 10.799 | 33.546 | 1.00 | 73.32 | chnA |
| ATOM | 1309 | ND2 | ASN | A | 166 | 92.439 | 8.801 | 34.531 | 1.00 | 77.93 | chnA |
| ATOM | 1310 | C | ASN | A | 166 | 90.984 | 12.931 | 36.730 | 1.00 | 61.13 | chnA |
| ATOM | 1311 | O | ASN | A | 166 | 90.873 | 12.638 | 37.920 | 1.00 | 59.78 | chnA |
| ATOM | 1312 | N | ILE | A | 167 | 90.231 | 13.843 | 36.133 | 1.00 | 61.86 | chnA |
| ATOM | 1313 | CA | ILE | A | 167 | 89.181 | 14.548 | 36.843 | 1.00 | 61.49 | chnA |
| ATOM | 1314 | CB | ILE | A | 167 | 89.460 | 16.060 | 36.913 | 1.00 | 60.38 | chnA |
| ATOM | 1315 | CG2 | ILE | A | 167 | 88.196 | 16.826 | 37.271 | 1.00 | 59.02 | chnA |
| ATOM | 1316 | CG1 | ILE | A | 167 | 90.557 | 16.326 | 37.939 | 1.00 | 58.37 | chnA |
| ATOM | 1317 | CD1 | ILE | A | 167 | 90.815 | 17.766 | 38.188 | 1.00 | 62.01 | chnA |
| ATOM | 1318 | C | ILE | A | 167 | 87.873 | 14.280 | 36.129 | 1.00 | 64.59 | chnA |
| ATOM | 1319 | O | ILE | A | 167 | 87.759 | 14.486 | 34.922 | 1.00 | 66.85 | chnA |
| ATOM | 1320 | N | THR | A | 168 | 86.895 | 13.787 | 36.879 | 1.00 | 66.36 | chnA |
| ATOM | 1321 | CA | THR | A | 168 | 85.593 | 13.472 | 36.316 | 1.00 | 67.00 | chnA |
| ATOM | 1322 | CB | THR | A | 168 | 85.277 | 11.977 | 36.473 | 1.00 | 66.96 | chnA |
| ATOM | 1323 | OG1 | THR | A | 168 | 86.355 | 11.208 | 35.932 | 1.00 | 69.64 | chnA |
| ATOM | 1324 | CG2 | THR | A | 168 | 84.001 | 11.619 | 35.728 | 1.00 | 69.88 | chnA |
| ATOM | 1325 | C | THR | A | 168 | 84.492 | 14.282 | 36.977 | 1.00 | 68.02 | chnA |

-continued

| | | | | | | | | | | |
|---|---|---|---|---|---|---|---|---|---|---|
| ATOM | 1326 | O | THR | A | 168 | 84.471 | 14.428 | 38.196 | 1.00 | 64.33 chnA |
| ATOM | 1327 | N | VAL | A | 169 | 83.586 | 14.810 | 36.156 | 1.00 | 72.00 chnA |
| ATOM | 1328 | CA | VAL | A | 169 | 82.455 | 15.601 | 36.628 | 1.00 | 75.43 chnA |
| ATOM | 1329 | CB | VAL | A | 169 | 82.451 | 17.000 | 36.009 | 1.00 | 73.20 chnA |
| ATOM | 1330 | CG1 | VAL | A | 169 | 81.325 | 17.826 | 36.592 | 1.00 | 71.18 chnA |
| ATOM | 1331 | CG2 | VAL | A | 169 | 83.779 | 17.674 | 36.239 | 1.00 | 74.42 chnA |
| ATOM | 1332 | C | VAL | A | 169 | 81.149 | 14.917 | 36.247 | 1.00 | 80.92 chnA |
| ATOM | 1333 | O | VAL | A | 169 | 80.745 | 14.943 | 35.085 | 1.00 | 84.05 chnA |
| ATOM | 1334 | N | ILE | A | 170 | 80.497 | 14.306 | 37.233 | 1.00 | 87.09 chnA |
| ATOM | 1335 | CA | ILE | A | 170 | 79.227 | 13.603 | 37.027 | 1.00 | 92.34 chnA |
| ATOM | 1336 | CB | ILE | A | 170 | 79.083 | 12.398 | 37.992 | 1.00 | 94.70 chnA |
| ATOM | 1337 | CG2 | ILE | A | 170 | 80.043 | 11.282 | 37.599 | 1.00 | 97.40 chnA |
| ATOM | 1338 | CG1 | ILE | A | 170 | 79.317 | 12.847 | 39.436 | 1.00 | 95.69 chnA |
| ATOM | 1339 | CD1 | ILE | A | 170 | 79.168 | 11.751 | 40.463 | 1.00 | 97.52 chnA |
| ATOM | 1340 | C | ILE | A | 170 | 78.049 | 14.537 | 37.268 | 1.00 | 93.23 chnA |
| ATOM | 1341 | O | ILE | A | 170 | 78.226 | 15.751 | 37.378 | 1.00 | 91.80 chnA |
| ATOM | 1342 | N | LYS | A | 171 | 76.846 | 13.972 | 37.320 | 1.00 | 96.94 chnA |
| ATOM | 1343 | CA | LYS | A | 171 | 75.661 | 14.773 | 37.587 | 1.00 | 103.06 chnA |
| ATOM | 1344 | CB | LYS | A | 171 | 74.463 | 14.270 | 36.791 | 1.00 | 105.24 chnA |
| ATOM | 1345 | CG | LYS | A | 171 | 73.173 | 15.012 | 37.134 | 1.00 | 109.23 chnA |
| ATOM | 1346 | CD | LYS | A | 171 | 72.109 | 14.760 | 36.084 | 1.00 | 113.16 chnA |
| ATOM | 1347 | CE | LYS | A | 171 | 72.609 | 15.212 | 34.706 | 1.00 | 114.85 chnA |
| ATOM | 1348 | NZ | LYS | A | 171 | 71.631 | 14.947 | 33.613 | 1.00 | 115.40 chnA |
| ATOM | 1349 | C | LYS | A | 171 | 75.331 | 14.766 | 39.088 | 1.00 | 105.82 chnA |
| ATOM | 1350 | O | LYS | A | 171 | 75.843 | 13.940 | 39.862 | 1.00 | 109.56 chnA |
| ATOM | 1351 | N | LYS | B | 4 | 128.063 | 66.075 | 54.614 | 1.00 | 108.61 chnB |
| ATOM | 1352 | CA | LYS | B | 4 | 128.072 | 64.742 | 54.017 | 1.00 | 107.97 chnB |
| ATOM | 1353 | CB | LYS | B | 4 | 129.462 | 64.089 | 54.178 | 1.00 | 106.18 chnB |
| ATOM | 1354 | CG | LYS | B | 4 | 130.004 | 64.008 | 55.613 | 1.00 | 105.52 chnB |
| ATOM | 1355 | CD | LYS | B | 4 | 131.503 | 63.678 | 55.626 | 1.00 | 104.61 chnB |
| ATOM | 1356 | CE | LYS | B | 4 | 132.107 | 63.793 | 57.031 | 1.00 | 103.60 chnB |
| ATOM | 1357 | NZ | LYS | B | 4 | 133.605 | 63.726 | 57.035 | 1.00 | 101.36 chnB |
| ATOM | 1358 | C | LYS | B | 4 | 126.950 | 63.744 | 54.405 | 1.00 | 109.14 chnB |
| ATOM | 1359 | O | LYS | B | 4 | 126.848 | 62.674 | 53.785 | 1.00 | 109.96 chnB |
| ATOM | 1360 | N | PRO | B | 5 | 126.086 | 64.073 | 55.405 | 1.00 | 109.48 chnB |
| ATOM | 1361 | CD | PRO | B | 5 | 125.976 | 65.267 | 56.268 | 1.00 | 108.81 chnB |
| ATOM | 1362 | CA | PRO | B | 5 | 125.032 | 63.100 | 55.742 | 1.00 | 108.69 chnB |
| ATOM | 1363 | CB | PRO | B | 5 | 124.411 | 63.694 | 57.007 | 1.00 | 108.61 chnB |
| ATOM | 1364 | CG | PRO | B | 5 | 124.562 | 65.163 | 56.797 | 1.00 | 108.59 chnB |
| ATOM | 1365 | C | PRO | B | 5 | 124.011 | 62.966 | 54.610 | 1.00 | 108.71 chnB |
| ATOM | 1366 | O | PRO | B | 5 | 124.140 | 63.627 | 53.571 | 1.00 | 109.12 chnB |
| ATOM | 1367 | N | LYS | B | 6 | 122.980 | 62.149 | 54.815 | 1.00 | 108.12 chnB |
| ATOM | 1368 | CA | LYS | B | 6 | 121.989 | 61.955 | 53.757 | 1.00 | 106.61 chnB |
| ATOM | 1369 | CB | LYS | B | 6 | 122.613 | 61.150 | 52.620 | 1.00 | 107.82 chnB |
| ATOM | 1370 | CG | LYS | B | 6 | 121.901 | 61.326 | 51.308 | 1.00 | 110.59 chnB |
| ATOM | 1371 | CD | LYS | B | 6 | 122.832 | 61.050 | 50.142 | 1.00 | 113.36 chnB |
| ATOM | 1372 | CE | LYS | B | 6 | 122.157 | 61.414 | 48.813 | 1.00 | 114.49 chnB |
| ATOM | 1373 | NZ | LYS | B | 6 | 123.020 | 61.107 | 47.622 | 1.00 | 115.22 chnB |
| ATOM | 1374 | C | LYS | B | 6 | 120.695 | 61.292 | 54.200 | 1.00 | 103.12 chnB |
| ATOM | 1375 | O | LYS | B | 6 | 120.711 | 60.211 | 54.784 | 1.00 | 102.77 chnB |
| ATOM | 1376 | N | VAL | B | 7 | 119.574 | 61.928 | 53.874 | 1.00 | 98.43 chnB |
| ATOM | 1377 | CA | VAL | B | 7 | 118.260 | 61.413 | 54.251 | 1.00 | 94.74 chnB |
| ATOM | 1378 | CB | VAL | B | 7 | 117.192 | 62.538 | 54.281 | 1.00 | 95.22 chnB |
| ATOM | 1379 | CG1 | VAL | B | 7 | 115.863 | 61.996 | 54.797 | 1.00 | 93.88 chnB |
| ATOM | 1380 | CG2 | VAL | B | 7 | 117.664 | 63.698 | 55.144 | 1.00 | 95.97 chnB |
| ATOM | 1381 | C | VAL | B | 7 | 117.790 | 60.307 | 53.314 | 1.00 | 91.83 chnB |
| ATOM | 1382 | O | VAL | B | 7 | 117.981 | 60.387 | 52.105 | 1.00 | 90.09 chnB |
| ATOM | 1383 | N | SER | B | 8 | 117.194 | 59.270 | 53.896 | 1.00 | 89.27 chnB |
| ATOM | 1384 | CA | SER | B | 8 | 116.675 | 58.134 | 53.137 | 1.00 | 87.21 chnB |
| ATOM | 1385 | CB | SER | B | 8 | 117.535 | 56.884 | 53.348 | 1.00 | 89.06 chnB |
| ATOM | 1386 | OG | SER | B | 8 | 117.475 | 56.425 | 54.687 | 1.00 | 93.42 chnB |
| ATOM | 1387 | C | SER | B | 8 | 115.238 | 57.851 | 53.551 | 1.00 | 83.38 chnB |
| ATOM | 1388 | O | SER | B | 8 | 114.838 | 58.133 | 54.686 | 1.00 | 80.85 chnB |
| ATOM | 1389 | N | LEU | B | 9 | 114.473 | 57.273 | 52.632 | 1.00 | 79.00 chnB |
| ATOM | 1390 | CA | LEU | B | 9 | 113.071 | 56.980 | 52.884 | 1.00 | 75.77 chnB |
| ATOM | 1391 | CB | LEU | B | 9 | 112.212 | 57.566 | 51.760 | 1.00 | 78.67 chnB |
| ATOM | 1392 | CG | LEU | B | 9 | 112.437 | 59.020 | 51.336 | 1.00 | 79.99 chnB |
| ATOM | 1393 | CD1 | LEU | B | 9 | 111.469 | 59.388 | 50.212 | 1.00 | 79.58 chnB |
| ATOM | 1394 | CD2 | LEU | B | 9 | 112.251 | 59.945 | 52.523 | 1.00 | 82.18 chnB |
| ATOM | 1395 | C | LEU | B | 9 | 112.766 | 55.490 | 53.027 | 1.00 | 72.19 chnB |
| ATOM | 1396 | O | LEU | B | 9 | 113.419 | 54.644 | 52.421 | 1.00 | 68.44 chnB |
| ATOM | 1397 | N | ASN | B | 10 | 111.742 | 55.183 | 53.815 | 1.00 | 69.52 chnB |
| ATOM | 1398 | CA | ASN | B | 10 | 111.334 | 53.808 | 54.031 | 1.00 | 66.75 chnB |
| ATOM | 1399 | CB | ASN | B | 10 | 112.113 | 53.181 | 55.182 | 1.00 | 73.87 chnB |
| ATOM | 1400 | CG | ASN | B | 10 | 111.758 | 51.717 | 55.380 | 1.00 | 77.74 chnB |
| ATOM | 1401 | OD1 | ASN | B | 10 | 112.038 | 50.888 | 54.516 | 1.00 | 80.50 chnB |
| ATOM | 1402 | ND2 | ASN | B | 10 | 111.106 | 51.399 | 56.498 | 1.00 | 78.00 chnB |
| ATOM | 1403 | C | ASN | B | 10 | 109.846 | 53.723 | 54.326 | 1.00 | 63.03 chnB |
| ATOM | 1404 | O | ASN | B | 10 | 109.399 | 54.055 | 55.415 | 1.00 | 61.65 chnB |

-continued

| | | | | | | | | | | |
|---|---|---|---|---|---|---|---|---|---|---|
| ATOM | 1405 | N | PRO | B | 11 | 109.049 | 53.322 | 53.339 | 1.00 | 60.70 | chnB |
| ATOM | 1406 | CD | PRO | B | 11 | 107.615 | 53.097 | 53.588 | 1.00 | 59.81 | chnB |
| ATOM | 1407 | CA | PRO | B | 11 | 109.416 | 52.945 | 51.967 | 1.00 | 60.62 | chnB |
| ATOM | 1408 | CB | PRO | B | 11 | 108.067 | 52.581 | 51.352 | 1.00 | 59.89 | chnB |
| ATOM | 1409 | CG | PRO | B | 11 | 107.270 | 52.087 | 52.544 | 1.00 | 58.63 | chnB |
| ATOM | 1410 | C | PRO | B | 11 | 110.095 | 54.086 | 51.190 | 1.00 | 62.14 | chnB |
| ATOM | 1411 | O | PRO | B | 11 | 109.821 | 55.270 | 51.434 | 1.00 | 64.14 | chnB |
| ATOM | 1412 | N | PRO | B | 12 | 110.949 | 53.736 | 50.207 | 1.00 | 63.38 | chnB |
| ATOM | 1413 | CD | PRO | B | 12 | 111.190 | 52.335 | 49.819 | 1.00 | 62.49 | chnB |
| ATOM | 1414 | CA | PRO | B | 12 | 111.720 | 54.646 | 49.337 | 1.00 | 63.74 | chnB |
| ATOM | 1415 | CB | PRO | B | 12 | 112.522 | 53.677 | 48.460 | 1.00 | 65.72 | chnB |
| ATOM | 1416 | CG | PRO | B | 12 | 112.582 | 52.406 | 49.286 | 1.00 | 66.72 | chnB |
| ATOM | 1417 | C | PRO | B | 12 | 110.897 | 55.585 | 48.450 | 1.00 | 63.80 | chnB |
| ATOM | 1418 | O | PRO | B | 12 | 111.453 | 56.406 | 47.703 | 1.00 | 64.71 | chnB |
| ATOM | 1419 | N | TRP | B | 13 | 109.577 | 55.463 | 48.539 | 1.00 | 62.01 | chnB |
| ATOM | 1420 | CA | TRP | B | 13 | 108.672 | 56.266 | 47.725 | 1.00 | 61.05 | chnB |
| ATOM | 1421 | CB | TRP | B | 13 | 107.287 | 55.608 | 47.672 | 1.00 | 60.59 | chnB |
| ATOM | 1422 | CG | TRP | B | 13 | 107.313 | 54.111 | 47.413 | 1.00 | 60.68 | chnB |
| ATOM | 1423 | CD2 | TRP | B | 13 | 107.970 | 53.423 | 46.342 | 1.00 | 59.75 | chnB |
| ATOM | 1424 | CE2 | TRP | B | 13 | 107.715 | 52.045 | 46.511 | 1.00 | 58.83 | chnB |
| ATOM | 1425 | CE3 | TRP | B | 13 | 108.748 | 53.836 | 45.257 | 1.00 | 59.99 | chnB |
| ATOM | 1426 | CD1 | TRP | B | 13 | 106.709 | 53.145 | 48.164 | 1.00 | 62.04 | chnB |
| ATOM | 1427 | NE1 | TRP | B | 13 | 106.944 | 51.901 | 47.631 | 1.00 | 59.75 | chnB |
| ATOM | 1428 | CZ2 | TRP | B | 13 | 108.210 | 51.082 | 45.639 | 1.00 | 58.65 | chnB |
| ATOM | 1429 | CZ3 | TRP | B | 13 | 109.241 | 52.875 | 44.389 | 1.00 | 60.05 | chnB |
| ATOM | 1430 | CH2 | TRP | B | 13 | 108.969 | 51.514 | 44.585 | 1.00 | 59.55 | chnB |
| ATOM | 1431 | C | TRP | B | 13 | 108.544 | 57.738 | 48.132 | 1.00 | 59.96 | chnB |
| ATOM | 1432 | O | TRP | B | 13 | 108.022 | 58.060 | 49.200 | 1.00 | 60.06 | chnB |
| ATOM | 1433 | N | ASN | B | 14 | 109.022 | 58.613 | 47.246 | 1.00 | 58.00 | chnB |
| ATOM | 1434 | CA | ASN | B | 14 | 108.974 | 60.066 | 47.417 | 1.00 | 55.11 | chnB |
| ATOM | 1435 | CB | ASN | B | 14 | 109.679 | 60.780 | 46.249 | 1.00 | 58.92 | chnB |
| ATOM | 1436 | CG | ASN | B | 14 | 111.101 | 60.293 | 46.024 | 1.00 | 64.60 | chnB |
| ATOM | 1437 | OD1 | ASN | B | 14 | 111.335 | 59.134 | 45.636 | 1.00 | 67.62 | chnB |
| ATOM | 1438 | ND2 | ASN | B | 14 | 112.065 | 61.181 | 46.252 | 1.00 | 66.87 | chnB |
| ATOM | 1439 | C | ASN | B | 14 | 107.523 | 60.482 | 47.345 | 1.00 | 52.37 | chnB |
| ATOM | 1440 | O | ASN | B | 14 | 107.099 | 61.411 | 48.016 | 1.00 | 53.03 | chnB |
| ATOM | 1441 | N | ARG | B | 15 | 106.782 | 59.810 | 46.471 | 1.00 | 49.47 | chnB |
| ATOM | 1442 | CA | ARG | B | 15 | 105.376 | 60.107 | 46.239 | 1.00 | 46.34 | chnB |
| ATOM | 1443 | CB | ARG | B | 15 | 105.109 | 60.051 | 44.741 | 1.00 | 44.43 | chnB |
| ATOM | 1444 | CG | ARG | B | 15 | 106.255 | 60.593 | 43.913 | 1.00 | 45.72 | chnB |
| ATOM | 1445 | CD | ARG | B | 15 | 105.999 | 60.411 | 42.443 | 1.00 | 47.75 | chnB |
| ATOM | 1446 | NE | ARG | B | 15 | 105.296 | 61.543 | 41.862 | 1.00 | 52.02 | chnB |
| ATOM | 1447 | CZ | ARG | B | 15 | 104.348 | 61.436 | 40.940 | 1.00 | 52.63 | chnB |
| ATOM | 1448 | NH1 | ARG | B | 15 | 103.983 | 60.242 | 40.505 | 1.00 | 52.22 | chnB |
| ATOM | 1449 | NH2 | ARG | B | 15 | 103.793 | 62.525 | 40.425 | 1.00 | 55.29 | chnB |
| ATOM | 1450 | C | ARG | B | 15 | 104.497 | 59.100 | 46.964 | 1.00 | 44.94 | chnB |
| ATOM | 1451 | O | ARG | B | 15 | 104.662 | 57.904 | 46.788 | 1.00 | 48.90 | chnB |
| ATOM | 1452 | N | ILE | B | 16 | 103.586 | 59.574 | 47.806 | 1.00 | 41.84 | chnB |
| ATOM | 1453 | CA | ILE | B | 16 | 102.716 | 58.675 | 48.546 | 1.00 | 38.00 | chnB |
| ATOM | 1454 | CB | ILE | B | 16 | 103.201 | 58.458 | 49.988 | 1.00 | 36.78 | chnB |
| ATOM | 1455 | CG2 | ILE | B | 16 | 104.670 | 58.048 | 49.998 | 1.00 | 37.91 | chnB |
| ATOM | 1456 | CG1 | ILE | B | 16 | 102.990 | 59.721 | 50.821 | 1.00 | 37.59 | chnB |
| ATOM | 1457 | CD1 | ILE | B | 16 | 103.386 | 59.556 | 52.258 | 1.00 | 40.31 | chnB |
| ATOM | 1458 | C | ILE | B | 16 | 101.315 | 59.217 | 48.605 | 1.00 | 38.02 | chnB |
| ATOM | 1459 | O | ILE | B | 16 | 101.085 | 60.381 | 48.325 | 1.00 | 38.87 | chnB |
| ATOM | 1460 | N | PHE | B | 17 | 100.382 | 58.361 | 48.990 | 1.00 | 42.26 | chnB |
| ATOM | 1461 | CA | PHE | B | 17 | 98.973 | 58.726 | 49.098 | 1.00 | 46.20 | chnB |
| ATOM | 1462 | CB | PHE | B | 17 | 98.086 | 57.494 | 48.932 | 1.00 | 49.02 | chnB |
| ATOM | 1463 | CG | PHE | B | 17 | 97.854 | 57.097 | 47.516 | 1.00 | 51.38 | chnB |
| ATOM | 1464 | CD1 | PHE | B | 17 | 98.013 | 55.777 | 47.120 | 1.00 | 53.40 | chnB |
| ATOM | 1465 | CD2 | PHE | B | 17 | 97.424 | 58.026 | 46.585 | 1.00 | 54.41 | chnB |
| ATOM | 1466 | CE1 | PHE | B | 17 | 97.744 | 55.389 | 45.815 | 1.00 | 55.91 | chnB |
| ATOM | 1467 | CE2 | PHE | B | 17 | 97.152 | 57.649 | 45.276 | 1.00 | 55.76 | chnB |
| ATOM | 1468 | CZ | PHE | B | 17 | 97.309 | 56.328 | 44.890 | 1.00 | 56.57 | chnB |
| ATOM | 1469 | C | PHE | B | 17 | 98.605 | 59.400 | 50.413 | 1.00 | 47.89 | chnB |
| ATOM | 1470 | O | PHE | B | 17 | 99.323 | 59.310 | 51.414 | 1.00 | 45.17 | chnB |
| ATOM | 1471 | N | LYS | B | 18 | 97.450 | 60.049 | 50.403 | 1.00 | 48.18 | chnB |
| ATOM | 1472 | CA | LYS | B | 18 | 96.954 | 60.729 | 51.579 | 1.00 | 49.58 | chnB |
| ATOM | 1473 | CB | LYS | B | 18 | 95.766 | 61.616 | 51.202 | 1.00 | 52.49 | chnB |
| ATOM | 1474 | CG | LYS | B | 18 | 95.158 | 62.436 | 52.330 | 1.00 | 57.88 | chnB |
| ATOM | 1475 | CD | LYS | B | 18 | 93.943 | 63.207 | 51.807 | 1.00 | 64.18 | chnB |
| ATOM | 1476 | CE | LYS | B | 18 | 93.260 | 64.078 | 52.869 | 1.00 | 66.22 | chnB |
| ATOM | 1477 | NZ | LYS | B | 18 | 92.581 | 63.287 | 53.933 | 1.00 | 69.58 | chnB |
| ATOM | 1478 | C | LYS | B | 18 | 96.526 | 59.670 | 52.577 | 1.00 | 50.07 | chnB |
| ATOM | 1479 | O | LYS | B | 18 | 95.608 | 58.886 | 52.320 | 1.00 | 55.10 | chnB |
| ATOM | 1480 | N | GLY | B | 19 | 97.230 | 59.610 | 53.697 | 1.00 | 49.06 | chnB |
| ATOM | 1481 | CA | GLY | B | 19 | 96.872 | 58.650 | 54.714 | 1.00 | 49.98 | chnB |
| ATOM | 1482 | C | GLY | B | 19 | 97.911 | 57.584 | 54.899 | 1.00 | 49.79 | chnB |
| ATOM | 1483 | O | GLY | B | 19 | 97.794 | 56.768 | 55.807 | 1.00 | 52.93 | chnB |

-continued

| | | | | | | | | | | |
|---|---|---|---|---|---|---|---|---|---|---|
| ATOM | 1484 | N | GLU | B | 20 | 98.941 | 57.594 | 54.066 | 1.00 | 48.83 chnB |
| ATOM | 1485 | CA | GLU | B | 20 | 99.978 | 56.584 | 54.187 | 1.00 | 53.50 chnB |
| ATOM | 1486 | CB | GLU | B | 20 | 100.562 | 56.242 | 52.818 | 1.00 | 56.60 chnB |
| ATOM | 1487 | CG | GLU | B | 20 | 99.500 | 55.743 | 51.842 | 1.00 | 58.92 chnB |
| ATOM | 1488 | CD | GLU | B | 20 | 100.054 | 54.904 | 50.712 | 1.00 | 59.05 chnB |
| ATOM | 1489 | OE1 | GLU | B | 20 | 101.094 | 55.274 | 50.120 | 1.00 | 59.40 chnB |
| ATOM | 1490 | OE2 | GLU | B | 20 | 99.429 | 53.866 | 50.415 | 1.00 | 60.14 chnB |
| ATOM | 1491 | C | GLU | B | 20 | 101.061 | 56.956 | 55.187 | 1.00 | 53.91 chnB |
| ATOM | 1492 | O | GLU | B | 20 | 101.001 | 58.011 | 55.808 | 1.00 | 52.77 chnB |
| ATOM | 1493 | N | ASN | B | 21 | 102.017 | 56.054 | 55.378 | 1.00 | 59.05 chnB |
| ATOM | 1494 | CA | ASN | B | 21 | 103.105 | 56.270 | 56.321 | 1.00 | 63.10 chnB |
| ATOM | 1495 | CB | ASN | B | 21 | 103.067 | 55.213 | 57.429 | 1.00 | 65.81 chnB |
| ATOM | 1496 | CG | ASN | B | 21 | 101.729 | 55.164 | 58.157 | 1.00 | 70.40 chnB |
| ATOM | 1497 | OD1 | ASN | B | 21 | 101.011 | 56.162 | 58.229 | 1.00 | 71.63 chnB |
| ATOM | 1498 | ND2 | ASN | B | 21 | 101.405 | 53.981 | 58.682 | 1.00 | 72.94 chnB |
| ATOM | 1499 | C | ASN | B | 21 | 104.462 | 56.218 | 55.642 | 1.00 | 64.07 chnB |
| ATOM | 1500 | O | ASN | B | 21 | 104.661 | 55.458 | 54.696 | 1.00 | 68.39 chnB |
| ATOM | 1501 | N | VAL | B | 22 | 105.392 | 57.029 | 56.141 | 1.00 | 65.34 chnB |
| ATOM | 1502 | CA | VAL | B | 22 | 106.753 | 57.082 | 55.617 | 1.00 | 66.12 chnB |
| ATOM | 1503 | CB | VAL | B | 22 | 106.872 | 58.013 | 54.381 | 1.00 | 66.16 chnB |
| ATOM | 1504 | CG1 | VAL | B | 22 | 106.552 | 59.446 | 54.751 | 1.00 | 67.57 chnB |
| ATOM | 1505 | CG2 | VAL | B | 22 | 108.257 | 57.898 | 53.763 | 1.00 | 66.89 chnB |
| ATOM | 1506 | C | VAL | B | 22 | 107.695 | 57.539 | 56.722 | 1.00 | 67.91 chnB |
| ATOM | 1507 | O | VAL | B | 22 | 107.324 | 58.357 | 57.570 | 1.00 | 68.17 chnB |
| ATOM | 1508 | N | THR | B | 23 | 108.906 | 56.985 | 56.714 | 1.00 | 69.14 chnB |
| ATOM | 1509 | CA | THR | B | 23 | 109.917 | 57.302 | 57.720 | 1.00 | 72.64 chnB |
| ATOM | 1510 | CB | THR | B | 23 | 110.216 | 56.067 | 58.613 | 1.00 | 73.80 chnB |
| ATOM | 1511 | OG1 | THR | B | 23 | 108.991 | 55.566 | 59.162 | 1.00 | 75.19 chnB |
| ATOM | 1512 | CG2 | THR | B | 23 | 111.153 | 56.446 | 59.754 | 1.00 | 75.26 chnB |
| ATOM | 1513 | C | THR | B | 23 | 111.216 | 57.789 | 57.082 | 1.00 | 73.38 chnB |
| ATOM | 1514 | O | THR | B | 23 | 111.883 | 57.042 | 56.361 | 1.00 | 71.59 chnB |
| ATOM | 1515 | N | LEU | B | 24 | 111.562 | 59.045 | 57.352 | 1.00 | 75.55 chnB |
| ATOM | 1516 | CA | LEU | B | 24 | 112.783 | 59.641 | 56.818 | 1.00 | 78.18 chnB |
| ATOM | 1517 | CB | LEU | B | 24 | 112.612 | 61.146 | 56.613 | 1.00 | 76.23 chnB |
| ATOM | 1518 | CG | LEU | B | 24 | 111.208 | 61.694 | 56.373 | 1.00 | 73.76 chnB |
| ATOM | 1519 | CD1 | LEU | B | 24 | 111.342 | 63.138 | 56.005 | 1.00 | 77.43 chnB |
| ATOM | 1520 | CD2 | LEU | B | 24 | 110.495 | 60.949 | 55.273 | 1.00 | 74.64 chnB |
| ATOM | 1521 | C | LEU | B | 24 | 113.913 | 59.385 | 57.807 | 1.00 | 81.67 chnB |
| ATOM | 1522 | O | LEU | B | 24 | 113.813 | 59.728 | 58.993 | 1.00 | 81.97 chnB |
| ATOM | 1523 | N | THR | B | 25 | 114.985 | 58.777 | 57.313 | 1.00 | 85.49 chnB |
| ATOM | 1524 | CA | THR | B | 25 | 116.134 | 58.459 | 58.150 | 1.00 | 91.76 chnB |
| ATOM | 1525 | CB | THR | B | 25 | 116.480 | 56.948 | 58.082 | 1.00 | 92.40 chnB |
| ATOM | 1526 | OG1 | THR | B | 25 | 115.310 | 56.169 | 58.361 | 1.00 | 95.58 chnB |
| ATOM | 1527 | CG2 | THR | B | 25 | 117.569 | 56.597 | 59.092 | 1.00 | 92.06 chnB |
| ATOM | 1528 | C | THR | B | 25 | 117.372 | 59.261 | 57.752 | 1.00 | 94.26 chnB |
| ATOM | 1529 | O | THR | B | 25 | 117.755 | 59.299 | 56.579 | 1.00 | 94.94 chnB |
| ATOM | 1530 | N | CYS | B | 26 | 117.981 | 59.916 | 58.736 | 1.00 | 97.95 chnB |
| ATOM | 1531 | CA | CYS | B | 26 | 119.192 | 60.697 | 58.517 | 1.00 | 100.17 chnB |
| ATOM | 1532 | C | CYS | B | 26 | 120.364 | 59.725 | 58.672 | 1.00 | 101.71 chnB |
| ATOM | 1533 | O | CYS | B | 26 | 120.387 | 58.935 | 59.619 | 1.00 | 103.72 chnB |
| ATOM | 1534 | CB | CYS | B | 26 | 119.279 | 61.804 | 59.566 | 1.00 | 100.09 chnB |
| ATOM | 1535 | SG | CYS | B | 26 | 120.600 | 63.021 | 59.292 | 1.00 | 99.97 chnB |
| ATOM | 1536 | N | ASN | B | 27 | 121.310 | 59.747 | 57.734 | 1.00 | 103.70 chnB |
| ATOM | 1537 | CA | ASN | B | 27 | 122.479 | 58.853 | 57.788 | 1.00 | 105.53 chnB |
| ATOM | 1538 | CB | ASN | B | 27 | 123.529 | 59.270 | 56.749 | 1.00 | 107.22 chnB |
| ATOM | 1539 | CG | ASN | B | 27 | 124.854 | 58.512 | 56.904 | 1.00 | 108.67 chnB |
| ATOM | 1540 | OD1 | ASN | B | 27 | 124.876 | 57.313 | 57.212 | 1.00 | 108.36 chnB |
| ATOM | 1541 | ND2 | ASN | B | 27 | 125.965 | 59.217 | 56.690 | 1.00 | 109.44 chnB |
| ATOM | 1542 | C | ASN | B | 27 | 123.132 | 58.788 | 59.175 | 1.00 | 105.30 chnB |
| ATOM | 1543 | O | ASN | B | 27 | 123.687 | 59.786 | 59.664 | 1.00 | 106.93 chnB |
| ATOM | 1544 | N | GLY | B | 28 | 123.053 | 57.610 | 59.796 | 0.50 | 102.79 chnB |
| ATOM | 1545 | CA | GLY | B | 28 | 123.630 | 57.405 | 61.114 | 0.50 | 98.55 chnB |
| ATOM | 1546 | C | GLY | B | 28 | 125.140 | 57.246 | 61.073 | 0.50 | 96.67 chnB |
| ATOM | 1547 | O | GLY | B | 28 | 125.655 | 56.249 | 60.559 | 0.50 | 96.79 chnB |
| ATOM | 1548 | N | ASN | B | 29 | 125.852 | 58.238 | 61.603 | 0.50 | 94.48 chnB |
| ATOM | 1549 | CA | ASN | B | 29 | 127.314 | 58.206 | 61.630 | 0.50 | 92.52 chnB |
| ATOM | 1550 | CB | ASN | B | 29 | 127.909 | 59.393 | 60.846 | 0.50 | 92.61 chnB |
| ATOM | 1551 | CG | ASN | B | 29 | 127.440 | 60.752 | 61.365 | 0.50 | 92.36 chnB |
| ATOM | 1552 | OD1 | ASN | B | 29 | 126.556 | 61.390 | 60.779 | 0.50 | 92.16 chnB |
| ATOM | 1553 | ND2 | ASN | B | 29 | 128.053 | 61.212 | 62.453 | 0.50 | 92.66 chnB |
| ATOM | 1554 | C | ASN | B | 29 | 127.839 | 58.184 | 63.062 | 0.50 | 91.85 chnB |
| ATOM | 1555 | O | ASN | B | 29 | 127.181 | 57.662 | 63.964 | 0.50 | 89.99 chnB |
| ATOM | 1556 | N | VAL | B | 34 | 126.249 | 59.266 | 69.339 | 0.50 | 103.35 chnB |
| ATOM | 1557 | CA | VAL | B | 34 | 124.937 | 59.811 | 69.689 | 0.50 | 103.23 chnB |
| ATOM | 1558 | CB | VAL | B | 34 | 124.266 | 59.012 | 70.852 | 0.50 | 102.59 chnB |
| ATOM | 1559 | CG1 | VAL | B | 34 | 122.891 | 59.592 | 71.171 | 0.50 | 101.59 chnB |
| ATOM | 1560 | CG2 | VAL | B | 34 | 124.142 | 57.537 | 70.489 | 0.50 | 102.15 chnB |
| ATOM | 1561 | C | VAL | B | 34 | 125.062 | 61.270 | 70.122 | 0.50 | 103.57 chnB |
| ATOM | 1562 | O | VAL | B | 34 | 125.824 | 61.589 | 71.041 | 0.50 | 104.07 chnB |

-continued

| | | | | | | | | | | |
|---|---|---|---|---|---|---|---|---|---|---|
| ATOM | 1563 | N | SER | B | 35 | 124.333 | 62.156 | 69.449 | 0.50 | 103.52 chnB |
| ATOM | 1564 | CA | SER | B | 35 | 124.364 | 63.569 | 69.806 | 0.50 | 103.47 chnB |
| ATOM | 1565 | CB | SER | B | 35 | 125.439 | 64.318 | 69.007 | 0.50 | 103.13 chnB |
| ATOM | 1566 | OG | SER | B | 35 | 125.239 | 64.202 | 67.611 | 0.50 | 102.85 chnB |
| ATOM | 1567 | C | SER | B | 35 | 122.998 | 64.219 | 69.634 | 0.50 | 103.58 chnB |
| ATOM | 1568 | O | SER | B | 35 | 122.285 | 64.444 | 70.615 | 0.50 | 103.75 chnB |
| ATOM | 1569 | N | SER | B | 36 | 122.635 | 64.501 | 68.387 | 0.50 | 103.63 chnB |
| ATOM | 1570 | CA | SER | B | 36 | 121.354 | 65.125 | 68.064 | 0.50 | 103.17 chnB |
| ATOM | 1571 | CB | SER | B | 36 | 121.320 | 66.586 | 68.546 | 0.50 | 102.80 chnB |
| ATOM | 1572 | OG | SER | B | 36 | 122.292 | 67.387 | 67.885 | 0.50 | 101.54 chnB |
| ATOM | 1573 | C | SER | B | 36 | 121.116 | 65.078 | 66.559 | 0.50 | 102.79 chnB |
| ATOM | 1574 | O | SER | B | 36 | 122.040 | 64.817 | 65.782 | 0.50 | 101.66 chnB |
| ATOM | 1575 | N | THR | B | 37 | 119.870 | 65.319 | 66.160 | 1.00 | 103.58 chnB |
| ATOM | 1576 | CA | THR | B | 37 | 119.496 | 65.324 | 64.750 | 1.00 | 103.89 chnB |
| ATOM | 1577 | CB | THR | B | 37 | 118.963 | 63.947 | 64.301 | 1.00 | 104.87 chnB |
| ATOM | 1578 | OG1 | THR | B | 37 | 119.843 | 62.913 | 64.769 | 1.00 | 105.41 chnB |
| ATOM | 1579 | CG2 | THR | B | 37 | 118.888 | 63.882 | 62.774 | 1.00 | 105.15 chnB |
| ATOM | 1580 | C | THR | B | 37 | 118.430 | 66.393 | 64.506 | 1.00 | 102.98 chnB |
| ATOM | 1581 | O | THR | B | 37 | 117.324 | 66.321 | 65.052 | 1.00 | 101.00 chnB |
| ATOM | 1582 | N | LYS | B | 38 | 118.783 | 67.389 | 63.696 | 1.00 | 102.72 chnB |
| ATOM | 1583 | CA | LYS | B | 38 | 117.880 | 68.491 | 63.376 | 1.00 | 102.72 chnB |
| ATOM | 1584 | CB | LYS | B | 38 | 118.664 | 69.800 | 63.270 | 1.00 | 107.57 chnB |
| ATOM | 1585 | CG | LYS | B | 38 | 119.416 | 70.189 | 64.537 | 1.00 | 111.19 chnB |
| ATOM | 1586 | CD | LYS | B | 38 | 120.157 | 71.514 | 64.344 | 1.00 | 113.07 chnB |
| ATOM | 1587 | CE | LYS | B | 38 | 120.898 | 71.936 | 65.615 | 1.00 | 113.79 chnB |
| ATOM | 1588 | NZ | LYS | B | 38 | 121.577 | 73.257 | 65.448 | 1.00 | 114.40 chnB |
| ATOM | 1589 | C | LYS | B | 38 | 117.103 | 68.257 | 62.083 | 1.00 | 99.44 chnB |
| ATOM | 1590 | O | LYS | B | 38 | 117.689 | 68.006 | 61.029 | 1.00 | 96.39 chnB |
| ATOM | 1591 | N | TRP | B | 39 | 115.780 | 68.365 | 62.169 | 1.00 | 96.16 chnB |
| ATOM | 1592 | CA | TRP | B | 39 | 114.907 | 68.166 | 61.013 | 1.00 | 92.92 chnB |
| ATOM | 1593 | CB | TRP | B | 39 | 113.790 | 67.175 | 61.354 | 1.00 | 93.22 chnB |
| ATOM | 1594 | CG | TRP | B | 39 | 114.253 | 65.750 | 61.430 | 1.00 | 92.35 chnB |
| ATOM | 1595 | CD2 | TRP | B | 39 | 114.694 | 64.932 | 60.339 | 1.00 | 91.08 chnB |
| ATOM | 1596 | CE2 | TRP | B | 39 | 115.032 | 63.672 | 60.873 | 1.00 | 90.56 chnB |
| ATOM | 1597 | CE3 | TRP | B | 39 | 114.843 | 65.144 | 58.963 | 1.00 | 91.43 chnB |
| ATOM | 1598 | CD1 | TRP | B | 39 | 114.334 | 64.973 | 62.549 | 1.00 | 92.21 chnB |
| ATOM | 1599 | NE1 | TRP | B | 39 | 114.801 | 63.722 | 62.222 | 1.00 | 91.99 chnB |
| ATOM | 1600 | CZ2 | TRP | B | 39 | 115.499 | 62.623 | 60.076 | 1.00 | 90.15 chnB |
| ATOM | 1601 | CZ3 | TRP | B | 39 | 115.307 | 64.099 | 58.172 | 1.00 | 90.49 chnB |
| ATOM | 1602 | CH2 | TRP | B | 39 | 115.633 | 62.857 | 58.733 | 1.00 | 90.27 chnB |
| ATOM | 1603 | C | TRP | B | 39 | 114.290 | 69.460 | 60.501 | 1.00 | 91.13 chnB |
| ATOM | 1604 | O | TRP | B | 39 | 113.650 | 70.193 | 61.261 | 1.00 | 89.75 chnB |
| ATOM | 1605 | N | PHE | B | 40 | 114.459 | 69.718 | 59.205 | 1.00 | 87.54 chnB |
| ATOM | 1606 | CA | PHE | B | 40 | 113.913 | 70.926 | 58.590 | 1.00 | 85.82 chnB |
| ATOM | 1607 | CB | PHE | B | 40 | 115.032 | 71.761 | 57.958 | 0.00 | 86.92 chnB |
| ATOM | 1608 | CG | PHE | B | 40 | 116.080 | 72.217 | 58.935 | 0.00 | 87.94 chnB |
| ATOM | 1609 | CD1 | PHE | B | 40 | 117.313 | 71.576 | 58.999 | 0.00 | 88.29 chnB |
| ATOM | 1610 | CD2 | PHE | B | 40 | 115.837 | 73.289 | 59.790 | 0.00 | 88.31 chnB |
| ATOM | 1611 | CE1 | PHE | B | 40 | 118.292 | 71.997 | 59.896 | 0.00 | 89.09 chnB |
| ATOM | 1612 | CE2 | PHE | B | 40 | 116.810 | 73.718 | 60.691 | 0.00 | 88.51 chnB |
| ATOM | 1613 | CZ | PHE | B | 40 | 118.040 | 73.068 | 60.745 | 0.00 | 88.71 chnB |
| ATOM | 1614 | C | PHE | B | 40 | 112.833 | 70.628 | 57.547 | 1.00 | 82.69 chnB |
| ATOM | 1615 | O | PHE | B | 40 | 113.115 | 70.054 | 56.494 | 1.00 | 80.11 chnB |
| ATOM | 1616 | N | HIS | B | 41 | 111.598 | 71.019 | 57.855 | 1.00 | 79.39 chnB |
| ATOM | 1617 | CA | HIS | B | 41 | 110.462 | 70.815 | 56.956 | 1.00 | 76.29 chnB |
| ATOM | 1618 | CB | HIS | B | 41 | 109.271 | 70.220 | 57.723 | 1.00 | 74.76 chnB |
| ATOM | 1619 | CG | HIS | B | 41 | 108.064 | 69.968 | 56.872 | 1.00 | 72.46 chnB |
| ATOM | 1620 | CD2 | HIS | B | 41 | 106.783 | 69.675 | 57.204 | 1.00 | 70.68 chnB |
| ATOM | 1621 | ND1 | HIS | B | 41 | 108.098 | 70.025 | 55.492 | 1.00 | 68.86 chnB |
| ATOM | 1622 | CE1 | HIS | B | 41 | 106.892 | 69.782 | 55.015 | 1.00 | 67.88 chnB |
| ATOM | 1623 | NE2 | HIS | B | 41 | 106.074 | 69.566 | 56.032 | 1.00 | 68.33 chnB |
| ATOM | 1624 | C | HIS | B | 41 | 110.070 | 72.156 | 56.328 | 1.00 | 75.08 chnB |
| ATOM | 1625 | O | HIS | B | 41 | 109.474 | 73.013 | 56.994 | 1.00 | 73.36 chnB |
| ATOM | 1626 | N | ASN | B | 42 | 110.386 | 72.315 | 55.042 | 1.00 | 73.81 chnB |
| ATOM | 1627 | CA | ASN | B | 42 | 110.102 | 73.549 | 54.306 | 1.00 | 75.00 chnB |
| ATOM | 1628 | CB | ASN | B | 42 | 108.602 | 73.882 | 54.345 | 1.00 | 71.52 chnB |
| ATOM | 1629 | CG | ASN | B | 42 | 107.789 | 73.079 | 53.341 | 1.00 | 67.65 chnB |
| ATOM | 1630 | OD1 | ASN | B | 42 | 108.345 | 72.486 | 52.410 | 1.00 | 66.05 chnB |
| ATOM | 1631 | ND2 | ASN | B | 42 | 106.467 | 73.090 | 53.518 | 1.00 | 63.65 chnB |
| ATOM | 1632 | C | ASN | B | 42 | 110.907 | 74.717 | 54.877 | 1.00 | 78.39 chnB |
| ATOM | 1633 | O | ASN | B | 42 | 110.448 | 75.862 | 54.870 | 1.00 | 79.03 chnB |
| ATOM | 1634 | N | GLY | B | 43 | 112.109 | 74.416 | 55.367 | 1.00 | 82.32 chnB |
| ATOM | 1635 | CA | GLY | B | 43 | 112.964 | 75.433 | 55.955 | 1.00 | 83.95 chnB |
| ATOM | 1636 | C | GLY | B | 43 | 112.792 | 75.570 | 57.462 | 1.00 | 86.18 chnB |
| ATOM | 1637 | O | GLY | B | 43 | 113.754 | 75.874 | 58.174 | 1.00 | 84.74 chnB |
| ATOM | 1638 | N | SER | B | 44 | 111.570 | 75.351 | 57.946 | 1.00 | 89.29 chnB |
| ATOM | 1639 | CA | SER | B | 44 | 111.267 | 75.444 | 59.375 | 1.00 | 92.98 chnB |
| ATOM | 1640 | CB | SER | B | 44 | 109.743 | 75.548 | 59.599 | 1.00 | 93.82 chnB |
| ATOM | 1641 | OG | SER | B | 44 | 109.186 | 76.700 | 58.977 | 1.00 | 94.10 chnB |

-continued

| | | | | | | | | | | |
|---|---|---|---|---|---|---|---|---|---|---|
| ATOM | 1642 | C | SER | B | 44 | 111.823 | 74.245 | 60.154 | 1.00 | 93.39 chnB |
| ATOM | 1643 | O | SER | B | 44 | 111.794 | 73.113 | 59.669 | 1.00 | 93.74 chnB |
| ATOM | 1644 | N | LEU | B | 45 | 112.327 | 74.502 | 61.358 | 1.00 | 94.69 chnB |
| ATOM | 1645 | CA | LEU | B | 45 | 112.871 | 73.443 | 62.204 | 1.00 | 97.05 chnB |
| ATOM | 1646 | CB | LEU | B | 45 | 113.756 | 74.041 | 63.301 | 1.00 | 98.13 chnB |
| ATOM | 1647 | CG | LEU | B | 45 | 114.413 | 73.067 | 64.289 | 1.00 | 100.22 chnB |
| ATOM | 1648 | CD1 | LEU | B | 45 | 115.366 | 72.131 | 63.549 | 1.00 | 99.81 chnB |
| ATOM | 1649 | CD2 | LEU | B | 45 | 115.159 | 73.850 | 65.375 | 1.00 | 100.96 chnB |
| ATOM | 1650 | C | LEU | B | 45 | 111.737 | 72.632 | 62.839 | 1.00 | 98.06 chnB |
| ATOM | 1651 | O | LEU | B | 45 | 110.813 | 73.200 | 63.435 | 1.00 | 99.74 chnB |
| ATOM | 1652 | N | SER | B | 46 | 111.800 | 71.310 | 62.683 | 1.00 | 98.01 chnB |
| ATOM | 1653 | CA | SER | B | 46 | 110.789 | 70.418 | 63.242 | 1.00 | 98.83 chnB |
| ATOM | 1654 | CB | SER | B | 46 | 110.666 | 69.140 | 62.404 | 1.00 | 99.68 chnB |
| ATOM | 1655 | OG | SER | B | 46 | 109.631 | 68.299 | 62.900 | 1.00 | 100.29 chnB |
| ATOM | 1656 | C | SER | B | 46 | 111.149 | 70.057 | 64.672 | 1.00 | 99.55 chnB |
| ATOM | 1657 | O | SER | B | 46 | 112.325 | 69.989 | 65.024 | 1.00 | 96.69 chnB |
| ATOM | 1658 | N | GLU | B | 47 | 110.125 | 69.792 | 65.478 | 1.00 | 102.74 chnB |
| ATOM | 1659 | CA | GLU | B | 47 | 110.306 | 69.437 | 66.883 | 1.00 | 106.42 chnB |
| ATOM | 1660 | CB | GLU | B | 47 | 108.980 | 69.582 | 67.642 | 1.00 | 108.50 chnB |
| ATOM | 1661 | CG | GLU | B | 47 | 108.431 | 71.009 | 67.636 | 1.00 | 112.97 chnB |
| ATOM | 1662 | CD | GLU | B | 47 | 107.135 | 71.155 | 68.425 | 1.00 | 115.49 chnB |
| ATOM | 1663 | OE1 | GLU | B | 47 | 106.048 | 70.956 | 67.824 | 1.00 | 117.18 chnB |
| ATOM | 1664 | OE2 | GLU | B | 47 | 107.206 | 71.476 | 69.641 | 1.00 | 115.96 chnB |
| ATOM | 1665 | C | GLU | B | 47 | 110.890 | 68.041 | 67.094 | 1.00 | 106.19 chnB |
| ATOM | 1666 | O | GLU | B | 47 | 110.944 | 67.552 | 68.226 | 1.00 | 105.98 chnB |
| ATOM | 1667 | N | GLU | B | 48 | 111.333 | 67.410 | 66.009 | 1.00 | 106.52 chnB |
| ATOM | 1668 | CA | GLU | B | 48 | 111.916 | 66.073 | 66.085 | 1.00 | 108.13 chnB |
| ATOM | 1669 | CB | GLU | B | 48 | 111.603 | 65.266 | 64.818 | 1.00 | 109.06 chnB |
| ATOM | 1670 | CG | GLU | B | 48 | 112.013 | 63.778 | 64.883 | 1.00 | 110.75 chnB |
| ATOM | 1671 | CD | GLU | B | 48 | 111.188 | 62.959 | 65.882 | 1.00 | 112.13 chnB |
| ATOM | 1672 | OE1 | GLU | B | 48 | 110.235 | 62.268 | 65.446 | 1.00 | 111.01 chnB |
| ATOM | 1673 | OE2 | GLU | B | 48 | 111.502 | 63.003 | 67.097 | 1.00 | 113.29 chnB |
| ATOM | 1674 | C | GLU | B | 48 | 113.427 | 66.143 | 66.305 | 1.00 | 108.16 chnB |
| ATOM | 1675 | O | GLU | B | 48 | 114.113 | 66.985 | 65.715 | 1.00 | 106.89 chnB |
| ATOM | 1676 | N | THR | B | 49 | 113.935 | 65.239 | 67.143 | 1.00 | 109.68 chnB |
| ATOM | 1677 | CA | THR | B | 49 | 115.360 | 65.187 | 67.469 | 1.00 | 110.92 chnB |
| ATOM | 1678 | CB | THR | B | 49 | 115.600 | 65.511 | 68.969 | 1.00 | 110.97 chnB |
| ATOM | 1679 | OG1 | THR | B | 49 | 114.740 | 64.702 | 69.788 | 1.00 | 110.08 chnB |
| ATOM | 1680 | CG2 | THR | B | 49 | 115.327 | 66.986 | 69.245 | 1.00 | 110.64 chnB |
| ATOM | 1681 | C | THR | B | 49 | 116.063 | 63.866 | 67.115 | 1.00 | 111.98 chnB |
| ATOM | 1682 | O | THR | B | 49 | 117.299 | 63.819 | 67.060 | 1.00 | 112.22 chnB |
| ATOM | 1683 | N | ASN | B | 50 | 115.281 | 62.805 | 66.886 | 1.00 | 112.05 chnB |
| ATOM | 1684 | CA | ASN | B | 50 | 115.827 | 61.485 | 66.527 | 1.00 | 110.57 chnB |
| ATOM | 1685 | CB | ASN | B | 50 | 114.763 | 60.387 | 66.668 | 1.00 | 110.76 chnB |
| ATOM | 1686 | CG | ASN | B | 50 | 114.292 | 60.202 | 68.105 | 1.00 | 111.95 chnB |
| ATOM | 1687 | OD1 | ASN | B | 50 | 115.080 | 59.858 | 68.993 | 1.00 | 111.89 chnB |
| ATOM | 1688 | ND2 | ASN | B | 50 | 112.995 | 60.421 | 68.338 | 1.00 | 112.97 chnB |
| ATOM | 1689 | C | ASN | B | 50 | 116.372 | 61.463 | 65.096 | 1.00 | 109.65 chnB |
| ATOM | 1690 | O | ASN | B | 50 | 116.115 | 62.376 | 64.305 | 1.00 | 110.53 chnB |
| ATOM | 1691 | N | SER | B | 51 | 117.125 | 60.416 | 64.768 | 1.00 | 107.94 chnB |
| ATOM | 1692 | CA | SER | B | 51 | 117.698 | 60.274 | 63.428 | 1.00 | 105.66 chnB |
| ATOM | 1693 | CB | SER | B | 51 | 118.870 | 59.279 | 63.435 | 1.00 | 107.00 chnB |
| ATOM | 1694 | OG | SER | B | 51 | 118.458 | 57.978 | 63.820 | 1.00 | 107.14 chnB |
| ATOM | 1695 | C | SER | B | 51 | 116.635 | 59.829 | 62.426 | 1.00 | 102.98 chnB |
| ATOM | 1696 | O | SER | B | 51 | 116.892 | 59.761 | 61.226 | 1.00 | 102.34 chnB |
| ATOM | 1697 | N | SER | B | 52 | 115.437 | 59.540 | 62.931 | 1.00 | 99.77 chnB |
| ATOM | 1698 | CA | SER | B | 52 | 114.335 | 59.099 | 62.091 | 1.00 | 95.49 chnB |
| ATOM | 1699 | CB | SER | B | 52 | 114.123 | 57.593 | 62.242 | 1.00 | 95.54 chnB |
| ATOM | 1700 | OG | SER | B | 52 | 115.221 | 56.874 | 61.712 | 1.00 | 96.54 chnB |
| ATOM | 1701 | C | SER | B | 52 | 113.039 | 59.834 | 62.389 | 1.00 | 93.33 chnB |
| ATOM | 1702 | O | SER | B | 52 | 112.496 | 59.743 | 63.493 | 1.00 | 93.41 chnB |
| ATOM | 1703 | N | LEU | B | 53 | 112.559 | 60.569 | 61.389 | 1.00 | 89.57 chnB |
| ATOM | 1704 | CA | LEU | B | 53 | 111.319 | 61.326 | 61.495 | 1.00 | 87.27 chnB |
| ATOM | 1705 | CB | LEU | B | 53 | 111.436 | 62.634 | 60.707 | 1.00 | 86.51 chnB |
| ATOM | 1706 | CG | LEU | B | 53 | 110.191 | 63.509 | 60.545 | 1.00 | 86.51 chnB |
| ATOM | 1707 | CD1 | LEU | B | 53 | 109.544 | 63.822 | 61.896 | 1.00 | 87.13 chnB |
| ATOM | 1708 | CD2 | LEU | B | 53 | 110.590 | 64.778 | 59.825 | 1.00 | 85.90 chnB |
| ATOM | 1709 | C | LEU | B | 53 | 110.177 | 60.480 | 60.950 | 1.00 | 86.43 chnB |
| ATOM | 1710 | O | LEU | B | 53 | 110.183 | 60.117 | 59.775 | 1.00 | 85.04 chnB |
| ATOM | 1711 | N | ASN | B | 54 | 109.210 | 60.165 | 61.811 | 1.00 | 85.90 chnB |
| ATOM | 1712 | CA | ASN | B | 54 | 108.055 | 59.341 | 61.434 | 1.00 | 82.32 chnB |
| ATOM | 1713 | CB | ASN | B | 54 | 107.678 | 58.384 | 62.578 | 1.00 | 85.82 chnB |
| ATOM | 1714 | CG | ASN | B | 54 | 108.700 | 57.280 | 62.788 | 1.00 | 86.85 chnB |
| ATOM | 1715 | OD1 | ASN | B | 54 | 108.909 | 56.446 | 61.913 | 1.00 | 87.79 chnB |
| ATOM | 1716 | ND2 | ASN | B | 54 | 109.328 | 57.263 | 63.960 | 1.00 | 88.86 chnB |
| ATOM | 1717 | C | ASN | B | 54 | 106.814 | 60.132 | 61.021 | 1.00 | 78.26 chnB |
| ATOM | 1718 | O | ASN | B | 54 | 106.239 | 60.868 | 61.826 | 1.00 | 78.77 chnB |
| ATOM | 1719 | N | ILE | B | 55 | 106.393 | 59.952 | 59.772 | 1.00 | 70.86 chnB |
| ATOM | 1720 | CA | ILE | B | 55 | 105.209 | 60.623 | 59.251 | 1.00 | 65.20 chnB |

-continued

| | | | | | | | | | | |
|---|---|---|---|---|---|---|---|---|---|---|
| ATOM | 1721 | CB | ILE | B | 55 | 105.451 | 61.147 | 57.830 | 1.00 | 62.17 chnB |
| ATOM | 1722 | CG2 | ILE | B | 55 | 104.202 | 61.836 | 57.306 | 1.00 | 61.10 chnB |
| ATOM | 1723 | CG1 | ILE | B | 55 | 106.634 | 62.120 | 57.829 | 1.00 | 61.11 chnB |
| ATOM | 1724 | CD1 | ILE | B | 55 | 106.986 | 62.681 | 56.464 | 1.00 | 58.67 chnB |
| ATOM | 1725 | C | ILE | B | 55 | 104.067 | 59.612 | 59.240 | 1.00 | 64.55 chnB |
| ATOM | 1726 | O | ILE | B | 55 | 104.193 | 58.546 | 58.651 | 1.00 | 65.06 chnB |
| ATOM | 1727 | N | VAL | B | 56 | 102.965 | 59.943 | 59.906 | 1.00 | 63.96 chnB |
| ATOM | 1728 | CA | VAL | B | 56 | 101.813 | 59.048 | 59.994 | 1.00 | 64.14 chnB |
| ATOM | 1729 | CB | VAL | B | 56 | 101.598 | 58.587 | 61.450 | 1.00 | 64.18 chnB |
| ATOM | 1730 | CG1 | VAL | B | 56 | 100.323 | 57.771 | 61.584 | 1.00 | 64.74 chnB |
| ATOM | 1731 | CG2 | VAL | B | 56 | 102.797 | 57.779 | 61.917 | 1.00 | 65.36 chnB |
| ATOM | 1732 | C | VAL | B | 56 | 100.550 | 59.725 | 59.483 | 1.00 | 64.10 chnB |
| ATOM | 1733 | O | VAL | B | 56 | 100.359 | 60.923 | 59.690 | 1.00 | 66.96 chnB |
| ATOM | 1734 | N | ASN | B | 57 | 99.688 | 58.947 | 58.830 | 1.00 | 63.27 chnB |
| ATOM | 1735 | CA | ASN | B | 57 | 98.438 | 59.446 | 58.265 | 1.00 | 65.25 chnB |
| ATOM | 1736 | CB | ASN | B | 57 | 97.427 | 59.764 | 59.363 | 1.00 | 72.25 chnB |
| ATOM | 1737 | CG | ASN | B | 57 | 96.823 | 58.519 | 59.966 | 1.00 | 78.86 chnB |
| ATOM | 1738 | OD1 | ASN | B | 57 | 96.430 | 57.600 | 59.243 | 1.00 | 81.91 chnB |
| ATOM | 1739 | ND2 | ASN | B | 57 | 96.741 | 58.475 | 61.298 | 1.00 | 83.62 chnB |
| ATOM | 1740 | C | ASN | B | 57 | 98.695 | 60.672 | 57.410 | 1.00 | 64.68 chnB |
| ATOM | 1741 | O | ASN | B | 57 | 97.979 | 61.668 | 57.499 | 1.00 | 64.81 chnB |
| ATOM | 1742 | N | ALA | B | 58 | 99.711 | 60.564 | 56.557 | 1.00 | 63.23 chnB |
| ATOM | 1743 | CA | ALA | B | 58 | 100.136 | 61.640 | 55.665 | 1.00 | 62.72 chnB |
| ATOM | 1744 | CB | ALA | B | 58 | 100.930 | 61.079 | 54.509 | 1.00 | 63.34 chnB |
| ATOM | 1745 | C | ALA | B | 58 | 99.030 | 62.537 | 55.141 | 1.00 | 62.93 chnB |
| ATOM | 1746 | O | ALA | B | 58 | 98.018 | 62.071 | 54.627 | 1.00 | 62.54 chnB |
| ATOM | 1747 | N | LYS | B | 59 | 99.223 | 63.836 | 55.334 | 1.00 | 66.49 chnB |
| ATOM | 1748 | CA | LYS | B | 59 | 98.286 | 64.854 | 54.877 | 1.00 | 68.71 chnB |
| ATOM | 1749 | CB | LYS | B | 59 | 97.926 | 65.790 | 56.026 | 1.00 | 74.09 chnB |
| ATOM | 1750 | CG | LYS | B | 59 | 97.511 | 65.066 | 57.292 | 1.00 | 82.70 chnB |
| ATOM | 1751 | CD | LYS | B | 59 | 97.551 | 65.989 | 58.496 | 1.00 | 89.95 chnB |
| ATOM | 1752 | CE | LYS | B | 59 | 97.441 | 65.195 | 59.791 | 1.00 | 94.09 chnB |
| ATOM | 1753 | NZ | LYS | B | 59 | 97.532 | 66.080 | 60.988 | 1.00 | 100.15 chnB |
| ATOM | 1754 | C | LYS | B | 59 | 99.027 | 65.634 | 53.806 | 1.00 | 66.52 chnB |
| ATOM | 1755 | O | LYS | B | 59 | 100.252 | 65.535 | 53.702 | 1.00 | 65.89 chnB |
| ATOM | 1756 | N | PHE | B | 60 | 98.295 | 66.409 | 53.013 | 1.00 | 63.49 chnB |
| ATOM | 1757 | CA | PHE | B | 60 | 98.922 | 67.201 | 51.955 | 1.00 | 63.16 chnB |
| ATOM | 1758 | CB | PHE | B | 60 | 97.879 | 68.006 | 51.202 | 1.00 | 62.40 chnB |
| ATOM | 1759 | CG | PHE | B | 60 | 96.927 | 67.170 | 50.426 | 1.00 | 63.54 chnB |
| ATOM | 1760 | CD1 | PHE | B | 60 | 95.679 | 66.869 | 50.939 | 1.00 | 64.94 chnB |
| ATOM | 1761 | CD2 | PHE | B | 60 | 97.271 | 66.693 | 49.169 | 1.00 | 63.39 chnB |
| ATOM | 1762 | CE1 | PHE | B | 60 | 94.779 | 66.104 | 50.207 | 1.00 | 66.94 chnB |
| ATOM | 1763 | CE2 | PHE | B | 60 | 96.378 | 65.928 | 48.430 | 1.00 | 66.41 chnB |
| ATOM | 1764 | CZ | PHE | B | 60 | 95.129 | 65.632 | 48.950 | 1.00 | 65.42 chnB |
| ATOM | 1765 | C | PHE | B | 60 | 99.967 | 68.139 | 52.535 | 1.00 | 64.53 chnB |
| ATOM | 1766 | O | PHE | B | 60 | 101.016 | 68.365 | 51.939 | 1.00 | 64.07 chnB |
| ATOM | 1767 | N | GLU | B | 61 | 99.667 | 68.650 | 53.723 | 1.00 | 68.17 chnB |
| ATOM | 1768 | CA | GLU | B | 61 | 100.541 | 69.556 | 54.455 | 1.00 | 68.97 chnB |
| ATOM | 1769 | CB | GLU | B | 61 | 99.918 | 69.877 | 55.824 | 1.00 | 73.51 chnB |
| ATOM | 1770 | CG | GLU | B | 61 | 98.672 | 70.778 | 55.791 | 1.00 | 82.61 chnB |
| ATOM | 1771 | CD | GLU | B | 61 | 97.501 | 70.216 | 54.970 | 1.00 | 86.98 chnB |
| ATOM | 1772 | OE1 | GLU | B | 61 | 96.961 | 69.143 | 55.323 | 1.00 | 91.39 chnB |
| ATOM | 1773 | OE2 | GLU | B | 61 | 97.105 | 70.866 | 53.975 | 1.00 | 88.49 chnB |
| ATOM | 1774 | C | GLU | B | 61 | 101.941 | 68.956 | 54.649 | 1.00 | 66.23 chnB |
| ATOM | 1775 | O | GLU | B | 61 | 102.933 | 69.685 | 54.652 | 1.00 | 66.09 chnB |
| ATOM | 1776 | N | ASP | B | 62 | 102.017 | 67.629 | 54.771 | 1.00 | 62.57 chnB |
| ATOM | 1777 | CA | ASP | B | 62 | 103.285 | 66.936 | 54.983 | 1.00 | 58.98 chnB |
| ATOM | 1778 | CB | ASP | B | 62 | 103.041 | 65.514 | 55.468 | 1.00 | 63.36 chnB |
| ATOM | 1779 | CG | ASP | B | 62 | 102.388 | 65.472 | 56.826 | 1.00 | 65.88 chnB |
| ATOM | 1780 | OD1 | ASP | B | 62 | 102.786 | 66.271 | 57.703 | 1.00 | 70.02 chnB |
| ATOM | 1781 | OD2 | ASP | B | 62 | 101.478 | 64.641 | 57.019 | 1.00 | 66.10 chnB |
| ATOM | 1782 | C | ASP | B | 62 | 104.207 | 66.920 | 53.786 | 1.00 | 56.49 chnB |
| ATOM | 1783 | O | ASP | B | 62 | 105.364 | 66.520 | 53.897 | 1.00 | 50.34 chnB |
| ATOM | 1784 | N | SER | B | 63 | 103.691 | 67.343 | 52.638 | 1.00 | 55.29 chnB |
| ATOM | 1785 | CA | SER | B | 63 | 104.491 | 67.400 | 51.418 | 1.00 | 60.56 chnB |
| ATOM | 1786 | CB | SER | B | 63 | 103.609 | 67.748 | 50.223 | 1.00 | 59.12 chnB |
| ATOM | 1787 | OG | SER | B | 63 | 102.520 | 66.859 | 50.129 | 1.00 | 63.68 chnB |
| ATOM | 1788 | C | SER | B | 63 | 105.551 | 68.488 | 51.571 | 1.00 | 62.32 chnB |
| ATOM | 1789 | O | SER | B | 63 | 105.418 | 69.369 | 52.425 | 1.00 | 68.24 chnB |
| ATOM | 1790 | N | GLY | B | 64 | 106.602 | 68.430 | 50.760 | 1.00 | 63.20 chnB |
| ATOM | 1791 | CA | GLY | B | 64 | 107.623 | 69.453 | 50.847 | 1.00 | 64.08 chnB |
| ATOM | 1792 | C | GLY | B | 64 | 109.058 | 68.994 | 50.962 | 1.00 | 67.08 chnB |
| ATOM | 1793 | O | GLY | B | 64 | 109.373 | 67.818 | 50.811 | 1.00 | 65.80 chnB |
| ATOM | 1794 | N | GLU | B | 65 | 109.926 | 69.956 | 51.248 | 1.00 | 72.59 chnB |
| ATOM | 1795 | CA | GLU | B | 65 | 111.355 | 69.727 | 51.382 | 1.00 | 77.30 chnB |
| ATOM | 1796 | CB | GLU | B | 65 | 112.094 | 71.016 | 51.011 | 1.00 | 82.55 chnB |
| ATOM | 1797 | CG | GLU | B | 65 | 113.608 | 70.961 | 51.156 | 1.00 | 89.66 chnB |
| ATOM | 1798 | CD | GLU | B | 65 | 114.248 | 72.339 | 51.084 | 1.00 | 93.74 chnB |
| ATOM | 1799 | OE1 | GLU | B | 65 | 114.105 | 73.114 | 52.062 | 1.00 | 97.19 chnB |

-continued

| | | | | | | | | | | |
|---|---|---|---|---|---|---|---|---|---|---|
| ATOM | 1800 | OE2 | GLU | B | 65 | 114.889 | 72.648 | 50.051 | 1.00 | 96.06 chnB |
| ATOM | 1801 | C | GLU | B | 65 | 111.750 | 69.285 | 52.792 | 1.00 | 75.17 chnB |
| ATOM | 1802 | O | GLU | B | 65 | 111.264 | 69.841 | 53.782 | 1.00 | 76.63 chnB |
| ATOM | 1803 | N | TYR | B | 66 | 112.629 | 68.287 | 52.872 | 1.00 | 69.72 chnB |
| ATOM | 1804 | CA | TYR | B | 66 | 113.113 | 67.783 | 54.151 | 1.00 | 66.54 chnB |
| ATOM | 1805 | CB | TYR | B | 66 | 112.518 | 66.418 | 54.454 | 1.00 | 58.20 chnB |
| ATOM | 1806 | CG | TYR | B | 66 | 111.083 | 66.463 | 54.908 | 1.00 | 50.97 chnB |
| ATOM | 1807 | CD1 | TYR | B | 66 | 110.038 | 66.499 | 53.991 | 1.00 | 46.89 chnB |
| ATOM | 1808 | CE1 | TYR | B | 66 | 108.717 | 66.488 | 54.416 | 1.00 | 46.02 chnB |
| ATOM | 1809 | CD2 | TYR | B | 66 | 110.768 | 66.422 | 56.262 | 1.00 | 49.11 chnB |
| ATOM | 1810 | CE2 | TYR | B | 66 | 109.455 | 66.409 | 56.699 | 1.00 | 46.25 chnB |
| ATOM | 1811 | CZ | TYR | B | 66 | 108.435 | 66.438 | 55.776 | 1.00 | 45.99 chnB |
| ATOM | 1812 | OH | TYR | B | 66 | 107.131 | 66.399 | 56.222 | 1.00 | 47.30 chnB |
| ATOM | 1813 | C | TYR | B | 66 | 114.632 | 67.701 | 54.189 | 1.00 | 70.55 chnB |
| ATOM | 1814 | O | TYR | B | 66 | 115.270 | 67.317 | 53.206 | 1.00 | 68.13 chnB |
| ATOM | 1815 | N | LYS | B | 67 | 115.201 | 68.080 | 55.332 | 1.00 | 78.75 chnB |
| ATOM | 1816 | CA | LYS | B | 67 | 116.650 | 68.069 | 55.549 | 1.00 | 85.63 chnB |
| ATOM | 1817 | CB | LYS | B | 67 | 117.240 | 69.462 | 55.338 | 1.00 | 90.79 chnB |
| ATOM | 1818 | CG | LYS | B | 67 | 117.125 | 70.065 | 53.957 | 1.00 | 94.71 chnB |
| ATOM | 1819 | CD | LYS | B | 67 | 117.619 | 71.509 | 54.023 | 1.00 | 98.23 chnB |
| ATOM | 1820 | CE | LYS | B | 67 | 117.486 | 72.238 | 52.701 | 1.00 | 100.51 chnB |
| ATOM | 1821 | NZ | LYS | B | 67 | 117.879 | 73.669 | 52.859 | 1.00 | 102.67 chnB |
| ATOM | 1822 | C | LYS | B | 67 | 116.959 | 67.678 | 56.992 | 1.00 | 88.40 chnB |
| ATOM | 1823 | O | LYS | B | 67 | 116.176 | 67.973 | 57.907 | 1.00 | 88.04 chnB |
| ATOM | 1824 | N | CYS | B | 68 | 118.124 | 67.064 | 57.199 | 1.00 | 91.17 chnB |
| ATOM | 1825 | CA | CYS | B | 68 | 118.553 | 66.663 | 58.538 | 1.00 | 96.06 chnB |
| ATOM | 1826 | C | CYS | B | 68 | 119.966 | 67.176 | 58.797 | 1.00 | 99.17 chnB |
| ATOM | 1827 | O | CYS | B | 68 | 120.808 | 67.189 | 57.895 | 1.00 | 98.56 chnB |
| ATOM | 1828 | CB | CYS | B | 68 | 118.507 | 65.144 | 58.710 | 1.00 | 96.46 chnB |
| ATOM | 1829 | SG | CYS | B | 68 | 119.832 | 64.233 | 57.851 | 1.00 | 98.25 chnB |
| ATOM | 1830 | N | GLN | B | 69 | 120.220 | 67.584 | 60.038 | 1.00 | 104.93 chnB |
| ATOM | 1831 | CA | GLN | B | 69 | 121.523 | 68.118 | 60.423 | 1.00 | 109.51 chnB |
| ATOM | 1832 | CB | GLN | B | 69 | 121.402 | 69.630 | 60.678 | 1.00 | 112.52 chnB |
| ATOM | 1833 | CG | GLN | B | 69 | 122.732 | 70.377 | 60.811 | 1.00 | 117.20 chnB |
| ATOM | 1834 | CD | GLN | B | 69 | 122.557 | 71.884 | 61.054 | 1.00 | 118.80 chnB |
| ATOM | 1835 | OE1 | GLN | B | 69 | 121.697 | 72.534 | 60.442 | 1.00 | 120.00 chnB |
| ATOM | 1836 | NE2 | GLN | B | 69 | 123.386 | 72.445 | 61.944 | 1.00 | 119.71 chnB |
| ATOM | 1837 | C | GLN | B | 69 | 122.092 | 67.423 | 61.662 | 1.00 | 109.61 chnB |
| ATOM | 1838 | O | GLN | B | 69 | 121.390 | 67.247 | 62.664 | 1.00 | 109.85 chnB |
| ATOM | 1839 | N | HIS | B | 70 | 123.365 | 67.028 | 61.575 | 1.00 | 110.65 chnB |
| ATOM | 1840 | CA | HIS | B | 70 | 124.074 | 66.370 | 62.679 | 1.00 | 110.17 chnB |
| ATOM | 1841 | CB | HIS | B | 70 | 124.696 | 65.055 | 62.194 | 0.00 | 108.83 chnB |
| ATOM | 1842 | CG | HIS | B | 70 | 124.978 | 64.075 | 63.293 | 0.00 | 107.62 chnB |
| ATOM | 1843 | CD2 | HIS | B | 70 | 126.146 | 63.644 | 63.826 | 0.00 | 107.59 chnB |
| ATOM | 1844 | ND1 | HIS | B | 70 | 123.979 | 63.415 | 63.973 | 0.00 | 107.36 chnB |
| ATOM | 1845 | CE1 | HIS | B | 70 | 124.519 | 62.618 | 64.879 | 0.00 | 107.11 chnB |
| ATOM | 1846 | NE2 | HIS | B | 70 | 125.831 | 62.738 | 64.810 | 0.00 | 107.15 chnB |
| ATOM | 1847 | C | HIS | B | 70 | 125.162 | 67.318 | 63.224 | 1.00 | 110.43 chnB |
| ATOM | 1848 | O | HIS | B | 70 | 124.975 | 68.542 | 63.244 | 1.00 | 109.30 chnB |
| ATOM | 1849 | N | GLN | B | 71 | 126.271 | 66.761 | 63.705 | 0.00 | 109.81 chnB |
| ATOM | 1850 | CA | GLN | B | 71 | 127.372 | 67.573 | 64.223 | 0.00 | 109.76 chnB |
| ATOM | 1851 | CB | GLN | B | 71 | 127.965 | 66.954 | 65.491 | 0.00 | 110.05 chnB |
| ATOM | 1852 | CG | GLN | B | 71 | 127.083 | 67.068 | 66.723 | 0.00 | 110.26 chnB |
| ATOM | 1853 | CD | GLN | B | 71 | 127.825 | 66.720 | 68.000 | 0.00 | 110.46 chnB |
| ATOM | 1854 | OE1 | GLN | B | 71 | 128.432 | 65.654 | 68.111 | 0.00 | 110.46 chnB |
| ATOM | 1855 | NE2 | GLN | B | 71 | 127.784 | 67.624 | 68.972 | 0.00 | 110.80 chnB |
| ATOM | 1856 | C | GLN | B | 71 | 128.462 | 67.726 | 63.165 | 0.00 | 109.70 chnB |
| ATOM | 1857 | O | GLN | B | 71 | 129.593 | 68.110 | 63.470 | 0.00 | 109.41 chnB |
| ATOM | 1858 | N | GLN | B | 72 | 128.107 | 67.423 | 61.919 | 0.00 | 109.70 chnB |
| ATOM | 1859 | CA | GLN | B | 72 | 129.033 | 67.514 | 60.796 | 0.00 | 110.07 chnB |
| ATOM | 1860 | CB | GLN | B | 72 | 128.741 | 66.395 | 59.792 | 0.00 | 109.77 chnB |
| ATOM | 1861 | CG | GLN | B | 72 | 128.829 | 64.995 | 60.391 | 0.00 | 109.89 chnB |
| ATOM | 1862 | CD | GLN | B | 72 | 128.433 | 63.907 | 59.413 | 0.00 | 110.01 chnB |
| ATOM | 1863 | OE1 | GLN | B | 72 | 127.307 | 63.881 | 58.917 | 0.00 | 109.91 chnB |
| ATOM | 1864 | NE2 | GLN | B | 72 | 129.357 | 62.993 | 59.138 | 0.00 | 109.95 chnB |
| ATOM | 1865 | C | GLN | B | 72 | 128.957 | 68.881 | 60.113 | 0.00 | 110.52 chnB |
| ATOM | 1866 | O | GLN | B | 72 | 129.350 | 69.028 | 58.954 | 0.00 | 110.61 chnB |
| ATOM | 1867 | N | VAL | B | 73 | 128.460 | 69.873 | 60.853 | 0.00 | 111.65 chnB |
| ATOM | 1868 | CA | VAL | B | 73 | 128.313 | 71.253 | 60.378 | 0.00 | 113.09 chnB |
| ATOM | 1869 | CB | VAL | B | 73 | 129.681 | 71.875 | 59.986 | 0.00 | 112.41 chnB |
| ATOM | 1870 | CG1 | VAL | B | 73 | 129.497 | 73.316 | 59.527 | 0.00 | 111.96 chnB |
| ATOM | 1871 | CG2 | VAL | B | 73 | 130.643 | 71.817 | 61.165 | 0.00 | 111.95 chnB |
| ATOM | 1872 | C | VAL | B | 73 | 127.319 | 71.406 | 59.224 | 0.00 | 114.46 chnB |
| ATOM | 1873 | O | VAL | B | 73 | 126.237 | 71.966 | 59.404 | 0.00 | 114.67 chnB |
| ATOM | 1874 | N | ASN | B | 74 | 127.699 | 70.926 | 58.042 | 1.00 | 117.69 chnB |
| ATOM | 1875 | CA | ASN | B | 74 | 126.846 | 71.001 | 56.850 | 1.00 | 119.32 chnB |
| ATOM | 1876 | CB | ASN | B | 74 | 127.593 | 70.469 | 55.603 | 1.00 | 120.00 chnB |
| ATOM | 1877 | CG | ASN | B | 74 | 128.640 | 71.456 | 55.052 | 1.00 | 120.00 chnB |
| ATOM | 1878 | OD1 | ASN | B | 74 | 128.367 | 72.656 | 54.873 | 1.00 | 120.00 chnB |

-continued

| ATOM | 1879 | ND2 | ASN | B | 74 | 129.833 | 70.937 | 54.748 | 1.00 | 120.00 | chnB |
|------|------|-----|-----|---|----|---------|--------|--------|------|--------|------|
| ATOM | 1880 | C | ASN | B | 74 | 125.531 | 70.223 | 57.018 | 1.00 | 117.37 | chnB |
| ATOM | 1881 | O | ASN | B | 74 | 125.438 | 69.285 | 57.820 | 1.00 | 116.68 | chnB |
| ATOM | 1882 | N | GLU | B | 75 | 124.513 | 70.652 | 56.277 | 0.00 | 113.93 | chnB |
| ATOM | 1883 | CA | GLU | B | 75 | 123.206 | 70.005 | 56.299 | 0.00 | 111.31 | chnB |
| ATOM | 1884 | CB | GLU | B | 75 | 122.090 | 71.032 | 56.069 | 0.00 | 110.79 | chnB |
| ATOM | 1885 | CG | GLU | B | 75 | 122.071 | 72.193 | 57.053 | 0.00 | 109.94 | chnB |
| ATOM | 1886 | CD | GLU | B | 75 | 120.977 | 73.200 | 56.746 | 0.00 | 109.60 | chnB |
| ATOM | 1887 | OE1 | GLU | B | 75 | 120.981 | 73.770 | 55.635 | 0.00 | 109.65 | chnB |
| ATOM | 1888 | OE2 | GLU | B | 75 | 120.111 | 73.422 | 57.617 | 0.00 | 109.29 | chnB |
| ATOM | 1889 | C | GLU | B | 75 | 123.178 | 68.968 | 55.177 | 0.00 | 109.92 | chnB |
| ATOM | 1890 | O | GLU | B | 75 | 124.052 | 68.955 | 54.310 | 0.00 | 109.93 | chnB |
| ATOM | 1891 | N | SER | B | 76 | 122.175 | 68.100 | 55.202 | 1.00 | 108.75 | chnB |
| ATOM | 1892 | CA | SER | B | 76 | 122.009 | 67.057 | 54.188 | 1.00 | 104.83 | chnB |
| ATOM | 1893 | CB | SER | B | 76 | 121.133 | 65.917 | 54.737 | 1.00 | 104.73 | chnB |
| ATOM | 1894 | OG | SER | B | 76 | 119.832 | 66.378 | 55.086 | 1.00 | 102.23 | chnB |
| ATOM | 1895 | C | SER | B | 76 | 121.355 | 67.630 | 52.933 | 1.00 | 103.69 | chnB |
| ATOM | 1896 | O | SER | B | 76 | 120.829 | 68.747 | 52.947 | 1.00 | 103.36 | chnB |
| ATOM | 1897 | N | GLU | B | 77 | 121.400 | 66.873 | 51.843 | 1.00 | 101.30 | chnB |
| ATOM | 1898 | CA | GLU | B | 77 | 120.772 | 67.317 | 50.604 | 1.00 | 100.30 | chnB |
| ATOM | 1899 | CB | GLU | B | 77 | 121.220 | 66.460 | 49.424 | 1.00 | 103.56 | chnB |
| ATOM | 1900 | CG | GLU | B | 77 | 122.680 | 66.664 | 49.038 | 1.00 | 109.64 | chnB |
| ATOM | 1901 | CD | GLU | B | 77 | 123.002 | 68.112 | 48.672 | 1.00 | 111.98 | chnB |
| ATOM | 1902 | OE1 | GLU | B | 77 | 122.664 | 68.537 | 47.537 | 1.00 | 113.21 | chnB |
| ATOM | 1903 | OE2 | GLU | B | 77 | 123.591 | 68.823 | 49.524 | 1.00 | 114.14 | chnB |
| ATOM | 1904 | C | GLU | B | 77 | 119.265 | 67.225 | 50.762 | 1.00 | 98.03 | chnB |
| ATOM | 1905 | O | GLU | B | 77 | 118.755 | 66.334 | 51.441 | 1.00 | 96.97 | chnB |
| ATOM | 1906 | N | PRO | B | 78 | 118.531 | 68.172 | 50.167 | 1.00 | 96.43 | chnB |
| ATOM | 1907 | CD | PRO | B | 78 | 119.045 | 69.347 | 49.444 | 1.00 | 96.90 | chnB |
| ATOM | 1908 | CA | PRO | B | 78 | 117.067 | 68.208 | 50.241 | 1.00 | 93.26 | chnB |
| ATOM | 1909 | CB | PRO | B | 78 | 116.714 | 69.470 | 49.449 | 1.00 | 94.75 | chnB |
| ATOM | 1910 | CG | PRO | B | 78 | 117.921 | 70.340 | 49.628 | 1.00 | 97.01 | chnB |
| ATOM | 1911 | C | PRO | B | 78 | 116.407 | 66.982 | 49.620 | 1.00 | 90.49 | chnB |
| ATOM | 1912 | O | PRO | B | 78 | 116.829 | 66.503 | 48.560 | 1.00 | 88.56 | chnB |
| ATOM | 1913 | N | VAL | B | 79 | 115.403 | 66.456 | 50.315 | 1.00 | 85.76 | chnB |
| ATOM | 1914 | CA | VAL | B | 79 | 114.638 | 65.309 | 49.838 | 1.00 | 80.85 | chnB |
| ATOM | 1915 | CB | VAL | B | 79 | 114.749 | 64.115 | 50.789 | 1.00 | 79.46 | chnB |
| ATOM | 1916 | CG1 | VAL | B | 79 | 113.860 | 62.983 | 50.317 | 1.00 | 78.33 | chnB |
| ATOM | 1917 | CG2 | VAL | B | 79 | 116.188 | 63.655 | 50.858 | 1.00 | 81.32 | chnB |
| ATOM | 1918 | C | VAL | B | 79 | 113.196 | 65.784 | 49.767 | 1.00 | 80.43 | chnB |
| ATOM | 1919 | O | VAL | B | 79 | 112.631 | 66.235 | 50.770 | 1.00 | 80.46 | chnB |
| ATOM | 1920 | N | TYR | B | 80 | 112.618 | 65.726 | 48.572 | 1.00 | 78.98 | chnB |
| ATOM | 1921 | CA | TYR | B | 80 | 111.247 | 66.186 | 48.370 | 1.00 | 79.19 | chnB |
| ATOM | 1922 | CB | TYR | B | 80 | 111.135 | 66.957 | 47.048 | 1.00 | 84.24 | chnB |
| ATOM | 1923 | CG | TYR | B | 80 | 112.074 | 68.154 | 46.968 | 1.00 | 90.85 | chnB |
| ATOM | 1924 | CD1 | TYR | B | 80 | 113.335 | 68.040 | 46.367 | 1.00 | 92.29 | chnB |
| ATOM | 1925 | CE1 | TYR | B | 80 | 114.229 | 69.121 | 46.342 | 1.00 | 93.69 | chnB |
| ATOM | 1926 | CD2 | TYR | B | 80 | 111.723 | 69.390 | 47.539 | 1.00 | 92.51 | chnB |
| ATOM | 1927 | CE2 | TYR | B | 80 | 112.610 | 70.480 | 47.520 | 1.00 | 93.44 | chnB |
| ATOM | 1928 | CZ | TYR | B | 80 | 113.862 | 70.337 | 46.923 | 1.00 | 94.04 | chnB |
| ATOM | 1929 | OH | TYR | B | 80 | 114.756 | 71.393 | 46.921 | 1.00 | 94.71 | chnB |
| ATOM | 1930 | C | TYR | B | 80 | 110.203 | 65.077 | 48.444 | 1.00 | 76.17 | chnB |
| ATOM | 1931 | O | TYR | B | 80 | 110.310 | 64.061 | 47.759 | 1.00 | 80.45 | chnB |
| ATOM | 1932 | N | LEU | B | 81 | 109.206 | 65.280 | 49.299 | 1.00 | 69.31 | chnB |
| ATOM | 1933 | CA | LEU | B | 81 | 108.121 | 64.331 | 49.505 | 1.00 | 61.33 | chnB |
| ATOM | 1934 | CB | LEU | B | 81 | 107.986 | 64.043 | 50.995 | 1.00 | 60.34 | chnB |
| ATOM | 1935 | CG | LEU | B | 81 | 106.785 | 63.230 | 51.462 | 1.00 | 61.99 | chnB |
| ATOM | 1936 | CD1 | LEU | B | 81 | 106.920 | 61.797 | 50.991 | 1.00 | 65.57 | chnB |
| ATOM | 1937 | CD2 | LEU | B | 81 | 106.716 | 63.264 | 52.967 | 1.00 | 62.90 | chnB |
| ATOM | 1938 | C | LEU | B | 81 | 106.836 | 64.953 | 48.998 | 1.00 | 59.14 | chnB |
| ATOM | 1939 | O | LEU | B | 81 | 106.579 | 66.119 | 49.249 | 1.00 | 63.09 | chnB |
| ATOM | 1940 | N | GLU | B | 82 | 106.014 | 64.182 | 48.305 | 1.00 | 57.21 | chnB |
| ATOM | 1941 | CA | GLU | B | 82 | 104.767 | 64.725 | 47.788 | 1.00 | 56.22 | chnB |
| ATOM | 1942 | CB | GLU | B | 82 | 104.915 | 65.039 | 46.300 | 1.00 | 59.55 | chnB |
| ATOM | 1943 | CG | GLU | B | 82 | 103.807 | 65.906 | 45.723 | 1.00 | 66.12 | chnB |
| ATOM | 1944 | CD | GLU | B | 82 | 104.028 | 66.257 | 44.256 | 1.00 | 69.72 | chnB |
| ATOM | 1945 | OE1 | GLU | B | 82 | 104.960 | 65.705 | 43.622 | 1.00 | 69.95 | chnB |
| ATOM | 1946 | OE2 | GLU | B | 82 | 103.256 | 67.087 | 43.731 | 1.00 | 73.16 | chnB |
| ATOM | 1947 | C | GLU | B | 82 | 103.587 | 63.784 | 48.046 | 1.00 | 53.37 | chnB |
| ATOM | 1948 | O | GLU | B | 82 | 103.636 | 62.600 | 47.715 | 1.00 | 53.80 | chnB |
| ATOM | 1949 | N | VAL | B | 83 | 102.537 | 64.324 | 48.661 | 1.00 | 48.09 | chnB |
| ATOM | 1950 | CA | VAL | B | 83 | 101.341 | 63.563 | 48.996 | 1.00 | 43.26 | chnB |
| ATOM | 1951 | CB | VAL | B | 83 | 100.804 | 63.979 | 50.366 | 1.00 | 42.06 | chnB |
| ATOM | 1952 | CG1 | VAL | B | 83 | 99.512 | 63.274 | 50.662 | 1.00 | 39.94 | chnB |
| ATOM | 1953 | CG2 | VAL | B | 83 | 101.827 | 63.673 | 51.435 | 1.00 | 40.57 | chnB |
| ATOM | 1954 | C | VAL | B | 83 | 100.245 | 63.745 | 47.961 | 1.00 | 43.15 | chnB |
| ATOM | 1955 | O | VAL | B | 83 | 99.825 | 64.867 | 47.691 | 1.00 | 48.28 | chnB |
| ATOM | 1956 | N | PHE | B | 84 | 99.770 | 62.630 | 47.411 | 1.00 | 40.00 | chnB |
| ATOM | 1957 | CA | PHE | B | 84 | 98.725 | 62.630 | 46.394 | 1.00 | 36.09 | chnB |

-continued

| | | | | | | | | | | |
|---|---|---|---|---|---|---|---|---|---|---|
| ATOM | 1958 | CB | PHE | B | 84 | 99.185 | 61.823 | 45.185 | 1.00 | 35.29 | chnB |
| ATOM | 1959 | CG | PHE | B | 84 | 100.364 | 62.397 | 44.475 | 1.00 | 35.04 | chnB |
| ATOM | 1960 | CD1 | PHE | B | 84 | 101.639 | 62.196 | 44.957 | 1.00 | 35.24 | chnB |
| ATOM | 1961 | CD2 | PHE | B | 84 | 100.200 | 63.114 | 43.294 | 1.00 | 37.38 | chnB |
| ATOM | 1962 | CE1 | PHE | B | 84 | 102.738 | 62.695 | 44.275 | 1.00 | 39.75 | chnB |
| ATOM | 1963 | CE2 | PHE | B | 84 | 101.298 | 63.618 | 42.605 | 1.00 | 39.52 | chnB |
| ATOM | 1964 | CZ | PHE | B | 84 | 102.568 | 63.407 | 43.098 | 1.00 | 39.81 | chnB |
| ATOM | 1965 | C | PHE | B | 84 | 97.425 | 62.010 | 46.893 | 1.00 | 37.77 | chnB |
| ATOM | 1966 | O | PHE | B | 84 | 97.382 | 61.409 | 47.966 | 1.00 | 32.71 | chnB |
| ATOM | 1967 | N | SER | B | 85 | 96.374 | 62.130 | 46.083 | 1.00 | 39.84 | chnB |
| ATOM | 1968 | CA | SER | B | 85 | 95.071 | 61.553 | 46.401 | 1.00 | 43.58 | chnB |
| ATOM | 1969 | CB | SER | B | 85 | 94.267 | 62.486 | 47.304 | 1.00 | 46.31 | chnB |
| ATOM | 1970 | OG | SER | B | 85 | 93.058 | 61.869 | 47.731 | 1.00 | 50.94 | chnB |
| ATOM | 1971 | C | SER | B | 85 | 94.281 | 61.247 | 45.125 | 1.00 | 46.69 | chnB |
| ATOM | 1972 | O | SER | B | 85 | 93.372 | 61.991 | 44.762 | 1.00 | 48.78 | chnB |
| ATOM | 1973 | N | ASP | B | 86 | 94.609 | 60.127 | 44.477 | 1.00 | 48.10 | chnB |
| ATOM | 1974 | CA | ASP | B | 86 | 93.973 | 59.680 | 43.227 | 1.00 | 47.83 | chnB |
| ATOM | 1975 | CB | ASP | B | 86 | 94.908 | 60.014 | 42.051 | 1.00 | 51.68 | chnB |
| ATOM | 1976 | CG | ASP | B | 86 | 94.160 | 60.268 | 40.735 | 1.00 | 55.69 | chnB |
| ATOM | 1977 | OD1 | ASP | B | 86 | 93.710 | 59.293 | 40.074 | 1.00 | 56.43 | chnB |
| ATOM | 1978 | OD2 | ASP | B | 86 | 94.059 | 61.455 | 40.340 | 1.00 | 57.35 | chnB |
| ATOM | 1979 | C | ASP | B | 86 | 93.771 | 58.150 | 43.315 | 1.00 | 46.91 | chnB |
| ATOM | 1980 | O | ASP | B | 86 | 94.031 | 57.545 | 44.354 | 1.00 | 47.19 | chnB |
| ATOM | 1981 | N | TRP | B | 87 | 93.303 | 57.525 | 42.237 | 1.00 | 44.27 | chnB |
| ATOM | 1982 | CA | TRP | B | 87 | 93.111 | 56.076 | 42.219 | 1.00 | 37.80 | chnB |
| ATOM | 1983 | CB | TRP | B | 87 | 92.172 | 55.675 | 41.093 | 1.00 | 37.94 | chnB |
| ATOM | 1984 | CG | TRP | B | 87 | 90.746 | 55.888 | 41.403 | 1.00 | 37.21 | chnB |
| ATOM | 1985 | CD2 | TRP | B | 87 | 89.942 | 55.114 | 42.294 | 1.00 | 37.70 | chnB |
| ATOM | 1986 | CE2 | TRP | B | 87 | 88.653 | 55.668 | 42.275 | 1.00 | 39.91 | chnB |
| ATOM | 1987 | CE3 | TRP | B | 87 | 90.189 | 54.007 | 43.112 | 1.00 | 36.91 | chnB |
| ATOM | 1988 | CD1 | TRP | B | 87 | 89.939 | 56.851 | 40.896 | 1.00 | 38.15 | chnB |
| ATOM | 1989 | NE1 | TRP | B | 87 | 88.679 | 56.728 | 41.409 | 1.00 | 40.98 | chnB |
| ATOM | 1990 | CZ2 | TRP | B | 87 | 87.608 | 55.153 | 43.044 | 1.00 | 37.84 | chnB |
| ATOM | 1991 | CZ3 | TRP | B | 87 | 89.153 | 53.498 | 43.872 | 1.00 | 35.60 | chnB |
| ATOM | 1992 | CH2 | TRP | B | 87 | 87.880 | 54.069 | 43.833 | 1.00 | 36.78 | chnB |
| ATOM | 1993 | C | TRP | B | 87 | 94.425 | 55.344 | 42.034 | 1.00 | 38.60 | chnB |
| ATOM | 1994 | O | TRP | B | 87 | 94.648 | 54.296 | 42.635 | 1.00 | 38.14 | chnB |
| ATOM | 1995 | N | LEU | B | 88 | 95.279 | 55.885 | 41.169 | 1.00 | 38.01 | chnB |
| ATOM | 1996 | CA | LEU | B | 88 | 96.577 | 55.278 | 40.893 | 1.00 | 38.16 | chnB |
| ATOM | 1997 | CB | LEU | B | 88 | 96.574 | 54.670 | 39.493 | 1.00 | 38.08 | chnB |
| ATOM | 1998 | CG | LEU | B | 88 | 95.570 | 53.542 | 39.249 | 1.00 | 40.72 | chnB |
| ATOM | 1999 | CD1 | LEU | B | 88 | 95.588 | 53.147 | 37.789 | 1.00 | 41.54 | chnB |
| ATOM | 2000 | CD2 | LEU | B | 88 | 95.880 | 52.350 | 40.150 | 1.00 | 42.60 | chnB |
| ATOM | 2001 | C | LEU | B | 88 | 97.721 | 56.274 | 41.013 | 1.00 | 37.78 | chnB |
| ATOM | 2002 | O | LEU | B | 88 | 97.604 | 57.411 | 40.576 | 1.00 | 44.74 | chnB |
| ATOM | 2003 | N | LEU | B | 89 | 98.840 | 55.838 | 41.575 | 1.00 | 35.82 | chnB |
| ATOM | 2004 | CA | LEU | B | 89 | 99.992 | 56.706 | 41.744 | 1.00 | 36.89 | chnB |
| ATOM | 2005 | CB | LEU | B | 89 | 100.090 | 57.148 | 43.202 | 1.00 | 37.74 | chnB |
| ATOM | 2006 | CG | LEU | B | 89 | 101.325 | 57.921 | 43.646 | 1.00 | 37.12 | chnB |
| ATOM | 2007 | CD1 | LEU | B | 89 | 101.422 | 59.205 | 42.843 | 1.00 | 37.91 | chnB |
| ATOM | 2008 | CD2 | LEU | B | 89 | 101.251 | 58.198 | 45.138 | 1.00 | 34.83 | chnB |
| ATOM | 2009 | C | LEU | B | 89 | 101.270 | 55.993 | 41.337 | 1.00 | 37.19 | chnB |
| ATOM | 2010 | O | LEU | B | 89 | 101.602 | 54.951 | 41.884 | 1.00 | 37.57 | chnB |
| ATOM | 2011 | N | LEU | B | 90 | 101.980 | 56.554 | 40.365 | 1.00 | 38.56 | chnB |
| ATOM | 2012 | CA | LEU | B | 90 | 103.232 | 55.965 | 39.911 | 1.00 | 37.46 | chnB |
| ATOM | 2013 | CB | LEU | B | 90 | 103.594 | 56.432 | 38.509 | 1.00 | 37.61 | chnB |
| ATOM | 2014 | CG | LEU | B | 90 | 104.898 | 55.799 | 38.014 | 1.00 | 40.40 | chnB |
| ATOM | 2015 | CD1 | LEU | B | 90 | 104.687 | 54.328 | 37.748 | 1.00 | 42.03 | chnB |
| ATOM | 2016 | CD2 | LEU | B | 90 | 105.367 | 56.486 | 36.758 | 1.00 | 44.63 | chnB |
| ATOM | 2017 | C | LEU | B | 90 | 104.348 | 56.353 | 40.858 | 1.00 | 37.99 | chnB |
| ATOM | 2018 | O | LEU | B | 90 | 104.734 | 57.517 | 40.940 | 1.00 | 41.60 | chnB |
| ATOM | 2019 | N | GLN | B | 91 | 104.871 | 55.366 | 41.566 | 1.00 | 35.00 | chnB |
| ATOM | 2020 | CA | GLN | B | 91 | 105.934 | 55.605 | 42.508 | 1.00 | 37.56 | chnB |
| ATOM | 2021 | CB | GLN | B | 91 | 105.661 | 54.821 | 43.790 | 1.00 | 37.91 | chnB |
| ATOM | 2022 | CG | GLN | B | 91 | 104.319 | 55.153 | 44.429 | 1.00 | 40.17 | chnB |
| ATOM | 2023 | CD | GLN | B | 91 | 104.093 | 54.441 | 45.748 | 1.00 | 40.67 | chnB |
| ATOM | 2024 | OE1 | GLN | B | 91 | 103.713 | 53.277 | 45.781 | 1.00 | 43.50 | chnB |
| ATOM | 2025 | NE2 | GLN | B | 91 | 104.300 | 55.148 | 46.841 | 1.00 | 41.48 | chnB |
| ATOM | 2026 | C | GLN | B | 91 | 107.262 | 55.207 | 41.893 | 1.00 | 38.46 | chnB |
| ATOM | 2027 | O | GLN | B | 91 | 107.332 | 54.272 | 41.104 | 1.00 | 39.96 | chnB |
| ATOM | 2028 | N | ALA | B | 92 | 108.309 | 55.956 | 42.220 | 1.00 | 40.41 | chnB |
| ATOM | 2029 | CA | ALA | B | 92 | 109.643 | 55.671 | 41.710 | 1.00 | 42.66 | chnB |
| ATOM | 2030 | CB | ALA | B | 92 | 110.039 | 56.701 | 40.692 | 1.00 | 42.86 | chnB |
| ATOM | 2031 | C | ALA | B | 92 | 110.663 | 55.642 | 42.840 | 1.00 | 45.04 | chnB |
| ATOM | 2032 | O | ALA | B | 92 | 110.581 | 56.435 | 43.785 | 1.00 | 45.19 | chnB |
| ATOM | 2033 | N | SER | B | 93 | 111.614 | 54.715 | 42.747 | 1.00 | 46.94 | chnB |
| ATOM | 2034 | CA | SER | B | 93 | 112.669 | 54.584 | 43.750 | 1.00 | 50.78 | chnB |
| ATOM | 2035 | CB | SER | B | 93 | 113.586 | 53.414 | 43.383 | 1.00 | 49.69 | chnB |
| ATOM | 2036 | OG | SER | B | 93 | 114.101 | 53.560 | 42.066 | 1.00 | 52.95 | chnB |

-continued

| | | | | | | | | | | |
|---|---|---|---|---|---|---|---|---|---|---|
| ATOM | 2037 | C | SER | B | 93 | 113.481 | 55.884 | 43.830 | 1.00 | 53.55 | chnB |
| ATOM | 2038 | O | SER | B | 93 | 113.973 | 56.273 | 44.895 | 1.00 | 52.66 | chnB |
| ATOM | 2039 | N | ALA | B | 94 | 113.573 | 56.554 | 42.683 | 1.00 | 55.64 | chnB |
| ATOM | 2040 | CA | ALA | B | 94 | 114.295 | 57.803 | 42.525 | 1.00 | 55.22 | chnB |
| ATOM | 2041 | CB | ALA | B | 94 | 115.785 | 57.546 | 42.523 | 1.00 | 57.57 | chnB |
| ATOM | 2042 | C | ALA | B | 94 | 113.874 | 58.413 | 41.198 | 1.00 | 55.81 | chnB |
| ATOM | 2043 | O | ALA | B | 94 | 113.643 | 57.704 | 40.222 | 1.00 | 53.47 | chnB |
| ATOM | 2044 | N | GLU | B | 95 | 113.757 | 59.736 | 41.176 | 1.00 | 60.58 | chnB |
| ATOM | 2045 | CA | GLU | B | 95 | 113.367 | 60.468 | 39.973 | 1.00 | 63.80 | chnB |
| ATOM | 2046 | CB | GLU | B | 95 | 112.565 | 61.717 | 40.355 | 1.00 | 63.29 | chnB |
| ATOM | 2047 | CG | GLU | B | 95 | 111.152 | 61.437 | 40.890 | 1.00 | 62.84 | chnB |
| ATOM | 2048 | CD | GLU | B | 95 | 111.110 | 60.900 | 42.322 | 1.00 | 62.82 | chnB |
| ATOM | 2049 | OE1 | GLU | B | 95 | 110.042 | 60.396 | 42.727 | 1.00 | 63.31 | chnB |
| ATOM | 2050 | OE2 | GLU | B | 95 | 112.120 | 60.998 | 43.053 | 1.00 | 62.71 | chnB |
| ATOM | 2051 | C | GLU | B | 95 | 114.612 | 60.851 | 39.163 | 1.00 | 65.37 | chnB |
| ATOM | 2052 | O | GLU | B | 95 | 114.607 | 60.816 | 37.925 | 1.00 | 66.57 | chnB |
| ATOM | 2053 | N | VAL | B | 96 | 115.670 | 61.239 | 39.867 | 1.00 | 66.70 | chnB |
| ATOM | 2054 | CA | VAL | B | 96 | 116.919 | 61.600 | 39.215 | 1.00 | 69.72 | chnB |
| ATOM | 2055 | CB | VAL | B | 96 | 117.542 | 62.871 | 39.811 | 1.00 | 71.96 | chnB |
| ATOM | 2056 | CG1 | VAL | B | 96 | 118.774 | 63.268 | 39.011 | 1.00 | 72.23 | chnB |
| ATOM | 2057 | CG2 | VAL | B | 96 | 116.524 | 64.003 | 39.835 | 1.00 | 74.55 | chnB |
| ATOM | 2058 | C | VAL | B | 96 | 117.853 | 60.438 | 39.466 | 1.00 | 70.82 | chnB |
| ATOM | 2059 | O | VAL | B | 96 | 118.490 | 60.348 | 40.516 | 1.00 | 69.00 | chnB |
| ATOM | 2060 | N | VAL | B | 97 | 117.898 | 59.521 | 38.509 | 1.00 | 73.78 | chnB |
| ATOM | 2061 | CA | VAL | B | 97 | 118.742 | 58.348 | 38.645 | 1.00 | 76.42 | chnB |
| ATOM | 2062 | CB | VAL | B | 97 | 118.063 | 57.073 | 38.094 | 1.00 | 77.56 | chnB |
| ATOM | 2063 | CG1 | VAL | B | 97 | 118.747 | 55.843 | 38.652 | 1.00 | 77.14 | chnB |
| ATOM | 2064 | CG2 | VAL | B | 97 | 116.585 | 57.056 | 38.439 | 1.00 | 79.73 | chnB |
| ATOM | 2065 | C | VAL | B | 97 | 120.064 | 58.528 | 37.936 | 1.00 | 76.99 | chnB |
| ATOM | 2066 | O | VAL | B | 97 | 120.145 | 59.163 | 36.886 | 1.00 | 75.87 | chnB |
| ATOM | 2067 | N | MET | B | 98 | 121.100 | 57.967 | 38.544 | 1.00 | 78.98 | chnB |
| ATOM | 2068 | CA | MET | B | 98 | 122.448 | 58.002 | 38.008 | 1.00 | 81.90 | chnB |
| ATOM | 2069 | CB | MET | B | 98 | 123.438 | 58.006 | 39.168 | 1.00 | 83.54 | chnB |
| ATOM | 2070 | CG | MET | B | 98 | 124.862 | 58.294 | 38.790 | 1.00 | 87.36 | chnB |
| ATOM | 2071 | SD | MET | B | 98 | 125.848 | 58.457 | 40.281 | 1.00 | 90.18 | chnB |
| ATOM | 2072 | CE | MET | B | 98 | 125.533 | 60.209 | 40.677 | 1.00 | 88.93 | chnB |
| ATOM | 2073 | C | MET | B | 98 | 122.624 | 56.752 | 37.127 | 1.00 | 81.93 | chnB |
| ATOM | 2074 | O | MET | B | 98 | 122.049 | 55.705 | 37.402 | 1.00 | 81.83 | chnB |
| ATOM | 2075 | N | GLU | B | 99 | 123.386 | 56.881 | 36.048 | 1.00 | 84.22 | chnB |
| ATOM | 2076 | CA | GLU | B | 99 | 123.624 | 55.781 | 35.107 | 1.00 | 85.49 | chnB |
| ATOM | 2077 | CB | GLU | B | 99 | 124.478 | 56.304 | 33.943 | 1.00 | 88.87 | chnB |
| ATOM | 2078 | CG | GLU | B | 99 | 124.752 | 55.333 | 32.804 | 1.00 | 92.42 | chnB |
| ATOM | 2079 | CD | GLU | B | 99 | 125.490 | 56.000 | 31.642 | 1.00 | 94.60 | chnB |
| ATOM | 2080 | OE1 | GLU | B | 99 | 126.589 | 56.564 | 31.867 | 1.00 | 95.97 | chnB |
| ATOM | 2081 | OE2 | GLU | B | 99 | 124.964 | 55.968 | 30.505 | 1.00 | 95.36 | chnB |
| ATOM | 2082 | C | GLU | B | 99 | 124.310 | 54.585 | 35.770 | 1.00 | 83.90 | chnB |
| ATOM | 2083 | O | GLU | B | 99 | 125.314 | 54.748 | 36.470 | 1.00 | 84.47 | chnB |
| ATOM | 2084 | N | GLY | B | 100 | 123.736 | 53.396 | 35.593 | 1.00 | 81.55 | chnB |
| ATOM | 2085 | CA | GLY | B | 100 | 124.331 | 52.196 | 36.161 | 1.00 | 80.60 | chnB |
| ATOM | 2086 | C | GLY | B | 100 | 123.633 | 51.584 | 37.360 | 1.00 | 79.55 | chnB |
| ATOM | 2087 | O | GLY | B | 100 | 123.778 | 50.386 | 37.612 | 1.00 | 80.91 | chnB |
| ATOM | 2088 | N | GLN | B | 101 | 122.910 | 52.402 | 38.121 | 1.00 | 78.34 | chnB |
| ATOM | 2089 | CA | GLN | B | 101 | 122.186 | 51.924 | 39.297 | 1.00 | 75.80 | chnB |
| ATOM | 2090 | CB | GLN | B | 101 | 122.220 | 52.983 | 40.405 | 1.00 | 76.93 | chnB |
| ATOM | 2091 | CG | GLN | B | 101 | 121.536 | 54.286 | 40.055 | 1.00 | 81.34 | chnB |
| ATOM | 2092 | CD | GLN | B | 101 | 121.705 | 55.350 | 41.123 | 1.00 | 83.09 | chnB |
| ATOM | 2093 | OE1 | GLN | B | 101 | 122.736 | 55.421 | 41.792 | 1.00 | 81.97 | chnB |
| ATOM | 2094 | NE2 | GLN | B | 101 | 120.688 | 56.194 | 41.280 | 1.00 | 86.64 | chnB |
| ATOM | 2095 | C | GLN | B | 101 | 120.740 | 51.533 | 38.950 | 1.00 | 72.79 | chnB |
| ATOM | 2096 | O | GLN | B | 101 | 120.241 | 51.867 | 37.876 | 1.00 | 73.10 | chnB |
| ATOM | 2097 | N | PRO | B | 102 | 120.064 | 50.786 | 39.842 | 1.00 | 69.29 | chnB |
| ATOM | 2098 | CD | PRO | B | 102 | 120.589 | 50.164 | 41.071 | 1.00 | 68.95 | chnB |
| ATOM | 2099 | CA | PRO | B | 102 | 118.683 | 50.357 | 39.604 | 1.00 | 66.67 | chnB |
| ATOM | 2100 | CB | PRO | B | 102 | 118.501 | 49.249 | 40.640 | 1.00 | 67.77 | chnB |
| ATOM | 2101 | CG | PRO | B | 102 | 119.331 | 49.734 | 41.777 | 1.00 | 68.12 | chnB |
| ATOM | 2102 | C | PRO | B | 102 | 117.606 | 51.441 | 39.742 | 1.00 | 63.17 | chnB |
| ATOM | 2103 | O | PRO | B | 102 | 117.754 | 52.414 | 40.492 | 1.00 | 60.54 | chnB |
| ATOM | 2104 | N | LEU | B | 103 | 116.518 | 51.239 | 39.009 | 1.00 | 57.53 | chnB |
| ATOM | 2105 | CA | LEU | B | 103 | 115.380 | 52.140 | 39.020 | 1.00 | 54.77 | chnB |
| ATOM | 2106 | CB | LEU | B | 103 | 115.303 | 52.899 | 37.693 | 1.00 | 54.79 | chnB |
| ATOM | 2107 | CG | LEU | B | 103 | 114.071 | 53.781 | 37.494 | 1.00 | 54.79 | chnB |
| ATOM | 2108 | CD1 | LEU | B | 103 | 113.952 | 54.750 | 38.642 | 1.00 | 50.81 | chnB |
| ATOM | 2109 | CD2 | LEU | B | 103 | 114.147 | 54.510 | 36.174 | 1.00 | 54.39 | chnB |
| ATOM | 2110 | C | LEU | B | 103 | 114.139 | 51.271 | 39.214 | 1.00 | 53.53 | chnB |
| ATOM | 2111 | O | LEU | B | 103 | 113.936 | 50.303 | 38.483 | 1.00 | 52.52 | chnB |
| ATOM | 2112 | N | PHE | B | 104 | 113.322 | 51.603 | 40.209 | 1.00 | 50.48 | chnB |
| ATOM | 2113 | CA | PHE | B | 104 | 112.117 | 50.832 | 40.487 | 1.00 | 49.32 | chnB |
| ATOM | 2114 | CB | PHE | B | 104 | 112.195 | 50.230 | 41.888 | 1.00 | 53.29 | chnB |
| ATOM | 2115 | CG | PHE | B | 104 | 113.360 | 49.313 | 42.089 | 1.00 | 56.59 | chnB |

-continued

| | | | | | | | | | | |
|---|---|---|---|---|---|---|---|---|---|---|
| ATOM | 2116 | CD1 | PHE | B | 104 | 114.464 | 49.725 | 42.820 | 1.00 | 57.21 | chnB |
| ATOM | 2117 | CD2 | PHE | B | 104 | 113.353 | 48.033 | 41.549 | 1.00 | 60.19 | chnB |
| ATOM | 2118 | CE1 | PHE | B | 104 | 115.542 | 48.880 | 43.013 | 1.00 | 59.74 | chnB |
| ATOM | 2119 | CE2 | PHE | B | 104 | 114.428 | 47.179 | 41.736 | 1.00 | 63.58 | chnB |
| ATOM | 2120 | CZ | PHE | B | 104 | 115.527 | 47.605 | 42.470 | 1.00 | 62.73 | chnB |
| ATOM | 2121 | C | PHE | B | 104 | 110.859 | 51.676 | 40.375 | 1.00 | 47.07 | chnB |
| ATOM | 2122 | O | PHE | B | 104 | 110.777 | 52.753 | 40.964 | 1.00 | 47.37 | chnB |
| ATOM | 2123 | N | LEU | B | 105 | 109.890 | 51.200 | 39.603 | 1.00 | 40.82 | chnB |
| ATOM | 2124 | CA | LEU | B | 105 | 108.638 | 51.916 | 39.446 | 1.00 | 37.36 | chnB |
| ATOM | 2125 | CB | LEU | B | 105 | 108.395 | 52.299 | 37.997 | 1.00 | 38.89 | chnB |
| ATOM | 2126 | CG | LEU | B | 105 | 109.484 | 53.128 | 37.341 | 1.00 | 39.23 | chnB |
| ATOM | 2127 | CD1 | LEU | B | 105 | 109.038 | 53.535 | 35.953 | 1.00 | 43.24 | chnB |
| ATOM | 2128 | CD2 | LEU | B | 105 | 109.747 | 54.335 | 38.196 | 1.00 | 40.18 | chnB |
| ATOM | 2129 | C | LEU | B | 105 | 107.540 | 51.003 | 39.933 | 1.00 | 37.44 | chnB |
| ATOM | 2130 | O | LEU | B | 105 | 107.613 | 49.798 | 39.766 | 1.00 | 38.53 | chnB |
| ATOM | 2131 | N | ARG | B | 106 | 106.493 | 51.598 | 40.483 | 1.00 | 37.26 | chnB |
| ATOM | 2132 | CA | ARG | B | 106 | 105.380 | 50.855 | 41.049 | 1.00 | 36.04 | chnB |
| ATOM | 2133 | CB | ARG | B | 106 | 105.621 | 50.749 | 42.557 | 1.00 | 34.99 | chnB |
| ATOM | 2134 | CG | ARG | B | 106 | 104.522 | 50.123 | 43.349 | 1.00 | 39.56 | chnB |
| ATOM | 2135 | CD | ARG | B | 106 | 104.836 | 50.185 | 44.820 | 1.00 | 40.21 | chnB |
| ATOM | 2136 | NE | ARG | B | 106 | 103.750 | 49.612 | 45.608 | 1.00 | 46.54 | chnB |
| ATOM | 2137 | CZ | ARG | B | 106 | 103.439 | 49.985 | 46.847 | 1.00 | 48.19 | chnB |
| ATOM | 2138 | NH1 | ARG | B | 106 | 104.129 | 50.942 | 47.456 | 1.00 | 50.01 | chnB |
| ATOM | 2139 | NH2 | ARG | B | 106 | 102.440 | 49.392 | 47.487 | 1.00 | 50.07 | chnB |
| ATOM | 2140 | C | ARG | B | 106 | 104.070 | 51.580 | 40.770 | 1.00 | 36.47 | chnB |
| ATOM | 2141 | O | ARG | B | 106 | 103.951 | 52.759 | 41.056 | 1.00 | 38.31 | chnB |
| ATOM | 2142 | N | CYS | B | 107 | 103.099 | 50.885 | 40.190 | 1.00 | 37.22 | chnB |
| ATOM | 2143 | CA | CYS | B | 107 | 101.803 | 51.485 | 39.886 | 1.00 | 36.14 | chnB |
| ATOM | 2144 | C | CYS | B | 107 | 100.877 | 51.244 | 41.075 | 1.00 | 37.99 | chnB |
| ATOM | 2145 | O | CYS | B | 107 | 99.987 | 50.398 | 41.040 | 1.00 | 39.54 | chnB |
| ATOM | 2146 | CB | CYS | B | 107 | 101.228 | 50.873 | 38.621 | 1.00 | 36.14 | chnB |
| ATOM | 2147 | SG | CYS | B | 107 | 99.791 | 51.766 | 37.994 | 1.00 | 42.49 | chnB |
| ATOM | 2148 | N | HIS | B | 108 | 101.092 | 52.040 | 42.116 | 1.00 | 37.01 | chnB |
| ATOM | 2149 | CA | HIS | B | 108 | 100.368 | 51.963 | 43.379 | 1.00 | 37.43 | chnB |
| ATOM | 2150 | CB | HIS | B | 108 | 101.116 | 52.800 | 44.400 | 1.00 | 37.88 | chnB |
| ATOM | 2151 | CG | HIS | B | 108 | 100.633 | 52.613 | 45.797 | 1.00 | 39.43 | chnB |
| ATOM | 2152 | CD2 | HIS | B | 108 | 100.462 | 53.501 | 46.803 | 1.00 | 41.73 | chnB |
| ATOM | 2153 | ND1 | HIS | B | 108 | 100.220 | 51.397 | 46.279 | 1.00 | 41.53 | chnB |
| ATOM | 2154 | CE1 | HIS | B | 108 | 99.805 | 51.541 | 47.527 | 1.00 | 42.04 | chnB |
| ATOM | 2155 | NE2 | HIS | B | 108 | 99.941 | 52.806 | 47.866 | 1.00 | 43.34 | chnB |
| ATOM | 2156 | C | HIS | B | 108 | 98.886 | 52.347 | 43.374 | 1.00 | 38.64 | chnB |
| ATOM | 2157 | O | HIS | B | 108 | 98.516 | 53.425 | 42.919 | 1.00 | 41.37 | chnB |
| ATOM | 2158 | N | GLY | B | 109 | 98.047 | 51.472 | 43.929 | 1.00 | 41.05 | chnB |
| ATOM | 2159 | CA | GLY | B | 109 | 96.611 | 51.721 | 43.988 | 1.00 | 38.41 | chnB |
| ATOM | 2160 | C | GLY | B | 109 | 96.132 | 52.341 | 45.295 | 1.00 | 40.54 | chnB |
| ATOM | 2161 | O | GLY | B | 109 | 96.763 | 52.174 | 46.345 | 1.00 | 40.93 | chnB |
| ATOM | 2162 | N | TRP | B | 110 | 95.008 | 53.053 | 45.233 | 1.00 | 40.35 | chnB |
| ATOM | 2163 | CA | TRP | B | 110 | 94.413 | 53.717 | 46.392 | 1.00 | 37.86 | chnB |
| ATOM | 2164 | CB | TRP | B | 110 | 93.161 | 54.479 | 45.954 | 1.00 | 40.75 | chnB |
| ATOM | 2165 | CG | TRP | B | 110 | 92.426 | 55.250 | 47.028 | 1.00 | 42.93 | chnB |
| ATOM | 2166 | CD2 | TRP | B | 110 | 92.882 | 56.423 | 47.728 | 1.00 | 44.35 | chnB |
| ATOM | 2167 | CE2 | TRP | B | 110 | 91.846 | 56.821 | 48.595 | 1.00 | 43.79 | chnB |
| ATOM | 2168 | CE3 | TRP | B | 110 | 94.064 | 57.175 | 47.703 | 1.00 | 46.48 | chnB |
| ATOM | 2169 | CD1 | TRP | B | 110 | 91.168 | 55.000 | 47.490 | 1.00 | 43.74 | chnB |
| ATOM | 2170 | NE1 | TRP | B | 110 | 90.812 | 55.940 | 48.430 | 1.00 | 44.37 | chnB |
| ATOM | 2171 | CZ2 | TRP | B | 110 | 91.957 | 57.934 | 49.432 | 1.00 | 44.87 | chnB |
| ATOM | 2172 | CZ3 | TRP | B | 110 | 94.173 | 58.289 | 48.539 | 1.00 | 45.88 | chnB |
| ATOM | 2173 | CH2 | TRP | B | 110 | 93.125 | 58.653 | 49.389 | 1.00 | 43.97 | chnB |
| ATOM | 2174 | C | TRP | B | 110 | 94.047 | 52.705 | 47.454 | 1.00 | 36.26 | chnB |
| ATOM | 2175 | O | TRP | B | 110 | 93.366 | 51.736 | 47.180 | 1.00 | 32.33 | chnB |
| ATOM | 2176 | N | ARG | B | 111 | 94.516 | 52.941 | 48.672 | 1.00 | 38.21 | chnB |
| ATOM | 2177 | CA | ARG | B | 111 | 94.249 | 52.067 | 49.815 | 1.00 | 41.38 | chnB |
| ATOM | 2178 | CB | ARG | B | 111 | 92.769 | 52.139 | 50.204 | 1.00 | 43.63 | chnB |
| ATOM | 2179 | CG | ARG | B | 111 | 92.271 | 53.565 | 50.356 | 1.00 | 51.18 | chnB |
| ATOM | 2180 | CD | ARG | B | 111 | 90.882 | 53.665 | 50.978 | 1.00 | 54.12 | chnB |
| ATOM | 2181 | NE | ARG | B | 111 | 90.982 | 53.980 | 52.400 | 1.00 | 57.06 | chnB |
| ATOM | 2182 | CZ | ARG | B | 111 | 90.490 | 55.071 | 52.970 | 1.00 | 57.77 | chnB |
| ATOM | 2183 | NH1 | ARG | B | 111 | 89.840 | 55.970 | 52.248 | 1.00 | 59.31 | chnB |
| ATOM | 2184 | NH2 | ARG | B | 111 | 90.701 | 55.282 | 54.257 | 1.00 | 58.18 | chnB |
| ATOM | 2185 | C | ARG | B | 111 | 94.677 | 50.615 | 49.577 | 1.00 | 40.59 | chnB |
| ATOM | 2186 | O | ARG | B | 111 | 94.062 | 49.679 | 50.093 | 1.00 | 41.33 | chnB |
| ATOM | 2187 | N | ASN | B | 112 | 95.754 | 50.441 | 48.815 | 1.00 | 40.57 | chnB |
| ATOM | 2188 | CA | ASN | B | 112 | 96.291 | 49.122 | 48.493 | 1.00 | 41.75 | chnB |
| ATOM | 2189 | CB | ASN | B | 112 | 96.801 | 48.407 | 49.730 | 1.00 | 46.69 | chnB |
| ATOM | 2190 | CG | ASN | B | 112 | 98.244 | 48.693 | 49.989 | 1.00 | 53.84 | chnB |
| ATOM | 2191 | OD1 | ASN | B | 112 | 99.094 | 48.442 | 49.128 | 1.00 | 54.99 | chnB |
| ATOM | 2192 | ND2 | ASN | B | 112 | 98.545 | 49.243 | 51.173 | 1.00 | 57.35 | chnB |
| ATOM | 2193 | C | ASN | B | 112 | 95.314 | 48.225 | 47.788 | 1.00 | 42.56 | chnB |
| ATOM | 2194 | O | ASN | B | 112 | 95.557 | 47.023 | 47.660 | 1.00 | 45.97 | chnB |

-continued

| | | | | | | | | | | |
|---|---|---|---|---|---|---|---|---|---|---|
| ATOM | 2195 | N | TRP | B | 113 | 94.194 | 48.801 | 47.362 | 1.00 | 42.78 | chnB |
| ATOM | 2196 | CA | TRP | B | 113 | 93.185 | 48.050 | 46.649 | 1.00 | 43.95 | chnB |
| ATOM | 2197 | CB | TRP | B | 113 | 92.017 | 48.957 | 46.278 | 1.00 | 44.04 | chnB |
| ATOM | 2198 | CG | TRP | B | 113 | 91.120 | 49.298 | 47.442 | 1.00 | 45.86 | chnB |
| ATOM | 2199 | CD2 | TRP | B | 113 | 90.192 | 50.384 | 47.518 | 1.00 | 45.93 | chnB |
| ATOM | 2200 | CE2 | TRP | B | 113 | 89.545 | 50.293 | 48.765 | 1.00 | 46.10 | chnB |
| ATOM | 2201 | CE3 | TRP | B | 113 | 89.847 | 51.426 | 46.653 | 1.00 | 46.59 | chnB |
| ATOM | 2202 | CD1 | TRP | B | 113 | 91.003 | 48.617 | 48.620 | 1.00 | 45.73 | chnB |
| ATOM | 2203 | NE1 | TRP | B | 113 | 90.058 | 49.206 | 49.418 | 1.00 | 44.45 | chnB |
| ATOM | 2204 | CZ2 | TRP | B | 113 | 88.569 | 51.204 | 49.165 | 1.00 | 47.17 | chnB |
| ATOM | 2205 | CZ3 | TRP | B | 113 | 88.878 | 52.329 | 47.052 | 1.00 | 47.00 | chnB |
| ATOM | 2206 | CH2 | TRP | B | 113 | 88.251 | 52.212 | 48.295 | 1.00 | 46.81 | chnB |
| ATOM | 2207 | C | TRP | B | 113 | 93.838 | 47.462 | 45.408 | 1.00 | 44.68 | chnB |
| ATOM | 2208 | O | TRP | B | 113 | 94.692 | 48.087 | 44.780 | 1.00 | 45.48 | chnB |
| ATOM | 2209 | N | ASP | B | 114 | 93.481 | 46.227 | 45.098 | 1.00 | 46.33 | chnB |
| ATOM | 2210 | CA | ASP | B | 114 | 94.044 | 45.536 | 43.953 | 1.00 | 47.62 | chnB |
| ATOM | 2211 | CB | ASP | B | 114 | 93.457 | 44.125 | 43.869 | 1.00 | 51.47 | chnB |
| ATOM | 2212 | CG | ASP | B | 114 | 93.721 | 43.298 | 45.125 | 1.00 | 55.30 | chnB |
| ATOM | 2213 | OD1 | ASP | B | 114 | 94.786 | 43.478 | 45.765 | 1.00 | 57.16 | chnB |
| ATOM | 2214 | OD2 | ASP | B | 114 | 92.854 | 42.463 | 45.469 | 1.00 | 54.71 | chnB |
| ATOM | 2215 | C | ASP | B | 114 | 93.853 | 46.263 | 42.625 | 1.00 | 46.70 | chnB |
| ATOM | 2216 | O | ASP | B | 114 | 92.795 | 46.827 | 42.364 | 1.00 | 43.07 | chnB |
| ATOM | 2217 | N | VAL | B | 115 | 94.909 | 46.272 | 41.815 | 1.00 | 45.22 | chnB |
| ATOM | 2218 | CA | VAL | B | 115 | 94.899 | 46.880 | 40.489 | 1.00 | 46.51 | chnB |
| ATOM | 2219 | CB | VAL | B | 115 | 96.012 | 47.925 | 40.356 | 1.00 | 45.17 | chnB |
| ATOM | 2220 | CG1 | VAL | B | 115 | 95.974 | 48.572 | 38.992 | 1.00 | 41.81 | chnB |
| ATOM | 2221 | CG2 | VAL | B | 115 | 95.879 | 48.960 | 41.431 | 1.00 | 46.80 | chnB |
| ATOM | 2222 | C | VAL | B | 115 | 95.174 | 45.771 | 39.464 | 1.00 | 49.11 | chnB |
| ATOM | 2223 | O | VAL | B | 115 | 96.101 | 44.974 | 39.634 | 1.00 | 48.46 | chnB |
| ATOM | 2224 | N | TYR | B | 116 | 94.357 | 45.701 | 38.420 | 1.00 | 50.43 | chnB |
| ATOM | 2225 | CA | TYR | B | 116 | 94.534 | 44.692 | 37.377 | 1.00 | 52.31 | chnB |
| ATOM | 2226 | CB | TYR | B | 116 | 93.295 | 43.796 | 37.279 | 1.00 | 56.51 | chnB |
| ATOM | 2227 | CG | TYR | B | 116 | 92.997 | 42.997 | 38.530 | 1.00 | 60.10 | chnB |
| ATOM | 2228 | CD1 | TYR | B | 116 | 91.758 | 43.091 | 39.154 | 1.00 | 63.12 | chnB |
| ATOM | 2229 | CE1 | TYR | B | 116 | 91.477 | 42.359 | 40.305 | 1.00 | 65.63 | chnB |
| ATOM | 2230 | CD2 | TYR | B | 116 | 93.954 | 42.147 | 39.090 | 1.00 | 60.22 | chnB |
| ATOM | 2231 | CE2 | TYR | B | 116 | 93.684 | 41.411 | 40.239 | 1.00 | 61.34 | chnB |
| ATOM | 2232 | CZ | TYR | B | 116 | 92.444 | 41.523 | 40.839 | 1.00 | 64.59 | chnB |
| ATOM | 2233 | OH | TYR | B | 116 | 92.158 | 40.808 | 41.974 | 1.00 | 67.26 | chnB |
| ATOM | 2234 | C | TYR | B | 116 | 94.792 | 45.380 | 36.038 | 1.00 | 52.24 | chnB |
| ATOM | 2235 | O | TYR | B | 116 | 94.667 | 46.605 | 35.936 | 1.00 | 56.27 | chnB |
| ATOM | 2236 | N | LYS | B | 117 | 95.164 | 44.602 | 35.020 | 1.00 | 49.47 | chnB |
| ATOM | 2237 | CA | LYS | B | 117 | 95.429 | 45.139 | 33.677 | 1.00 | 48.64 | chnB |
| ATOM | 2238 | CB | LYS | B | 117 | 94.124 | 45.584 | 32.997 | 1.00 | 54.91 | chnB |
| ATOM | 2239 | CG | LYS | B | 117 | 92.949 | 44.608 | 33.082 | 1.00 | 61.91 | chnB |
| ATOM | 2240 | CD | LYS | B | 117 | 93.072 | 43.447 | 32.113 | 1.00 | 66.06 | chnB |
| ATOM | 2241 | CE | LYS | B | 117 | 91.771 | 42.643 | 32.034 | 1.00 | 68.01 | chnB |
| ATOM | 2242 | NZ | LYS | B | 117 | 90.627 | 43.424 | 31.463 | 1.00 | 69.17 | chnB |
| ATOM | 2243 | C | LYS | B | 117 | 96.375 | 46.338 | 33.770 | 1.00 | 45.09 | chnB |
| ATOM | 2244 | O | LYS | B | 117 | 96.108 | 47.412 | 33.223 | 1.00 | 44.07 | chnB |
| ATOM | 2245 | N | VAL | B | 118 | 97.457 | 46.156 | 34.510 | 1.00 | 42.37 | chnB |
| ATOM | 2246 | CA | VAL | B | 118 | 98.432 | 47.210 | 34.702 | 1.00 | 45.24 | chnB |
| ATOM | 2247 | CB | VAL | B | 118 | 99.338 | 46.919 | 35.907 | 1.00 | 45.96 | chnB |
| ATOM | 2248 | CG1 | VAL | B | 118 | 100.197 | 48.125 | 36.231 | 1.00 | 48.65 | chnB |
| ATOM | 2249 | CG2 | VAL | B | 118 | 98.504 | 46.549 | 37.103 | 1.00 | 52.43 | chnB |
| ATOM | 2250 | C | VAL | B | 118 | 99.314 | 47.367 | 33.486 | 1.00 | 45.69 | chnB |
| ATOM | 2251 | O | VAL | B | 118 | 99.822 | 46.387 | 32.950 | 1.00 | 43.99 | chnB |
| ATOM | 2252 | N | ILE | B | 119 | 99.501 | 48.614 | 33.068 | 1.00 | 47.45 | chnB |
| ATOM | 2253 | CA | ILE | B | 119 | 100.340 | 48.938 | 31.923 | 1.00 | 44.77 | chnB |
| ATOM | 2254 | CB | ILE | B | 119 | 99.506 | 49.346 | 30.687 | 1.00 | 43.56 | chnB |
| ATOM | 2255 | CG2 | ILE | B | 119 | 100.421 | 49.496 | 29.497 | 1.00 | 43.07 | chnB |
| ATOM | 2256 | CG1 | ILE | B | 119 | 98.433 | 48.306 | 30.385 | 1.00 | 44.42 | chnB |
| ATOM | 2257 | CD1 | ILE | B | 119 | 97.484 | 48.708 | 29.284 | 1.00 | 46.69 | chnB |
| ATOM | 2258 | C | ILE | B | 119 | 101.219 | 50.130 | 32.274 | 1.00 | 43.84 | chnB |
| ATOM | 2259 | O | ILE | B | 119 | 100.720 | 51.155 | 32.742 | 1.00 | 42.71 | chnB |
| ATOM | 2260 | N | TYR | B | 120 | 102.524 | 49.985 | 32.077 | 1.00 | 42.54 | chnB |
| ATOM | 2261 | CA | TYR | B | 120 | 103.459 | 51.076 | 32.332 | 1.00 | 43.97 | chnB |
| ATOM | 2262 | CB | TYR | B | 120 | 104.737 | 50.557 | 32.971 | 1.00 | 44.86 | chnB |
| ATOM | 2263 | CG | TYR | B | 120 | 104.559 | 50.103 | 34.381 | 1.00 | 43.48 | chnB |
| ATOM | 2264 | CD1 | TYR | B | 120 | 104.201 | 48.801 | 34.668 | 1.00 | 46.32 | chnB |
| ATOM | 2265 | CE1 | TYR | B | 120 | 104.041 | 48.374 | 35.966 | 1.00 | 46.76 | chnB |
| ATOM | 2266 | CD2 | TYR | B | 120 | 104.753 | 50.973 | 35.428 | 1.00 | 44.13 | chnB |
| ATOM | 2267 | CE2 | TYR | B | 120 | 104.594 | 50.557 | 36.733 | 1.00 | 45.78 | chnB |
| ATOM | 2268 | CZ | TYR | B | 120 | 104.239 | 49.257 | 36.995 | 1.00 | 45.98 | chnB |
| ATOM | 2269 | OH | TYR | B | 120 | 104.093 | 48.841 | 38.297 | 1.00 | 48.62 | chnB |
| ATOM | 2270 | C | TYR | B | 120 | 103.810 | 51.723 | 31.005 | 1.00 | 46.55 | chnB |
| ATOM | 2271 | O | TYR | B | 120 | 104.170 | 51.028 | 30.050 | 1.00 | 47.78 | chnB |
| ATOM | 2272 | N | TYR | B | 121 | 103.712 | 53.045 | 30.944 | 1.00 | 49.06 | chnB |
| ATOM | 2273 | CA | TYR | B | 121 | 104.026 | 53.783 | 29.723 | 1.00 | 52.58 | chnB |

-continued

| ATOM | 2274 | CB | TYR | B | 121 | 102.848 | 54.662 | 29.293 | 1.00 | 50.95 | chnB |
| ATOM | 2275 | CG | TYR | B | 121 | 101.523 | 53.959 | 29.106 | 1.00 | 52.67 | chnB |
| ATOM | 2276 | CD1 | TYR | B | 121 | 100.795 | 53.496 | 30.195 | 1.00 | 52.71 | chnB |
| ATOM | 2277 | CE1 | TYR | B | 121 | 99.537 | 52.944 | 30.033 | 1.00 | 55.64 | chnB |
| ATOM | 2278 | CD2 | TYR | B | 121 | 100.957 | 53.838 | 27.847 | 1.00 | 54.72 | chnB |
| ATOM | 2279 | CE2 | TYR | B | 121 | 99.695 | 53.285 | 27.678 | 1.00 | 57.18 | chnB |
| ATOM | 2280 | CZ | TYR | B | 121 | 98.992 | 52.845 | 28.774 | 1.00 | 56.44 | chnB |
| ATOM | 2281 | OH | TYR | B | 121 | 97.736 | 52.325 | 28.608 | 1.00 | 59.81 | chnB |
| ATOM | 2282 | C | TYR | B | 121 | 105.252 | 54.680 | 29.894 | 1.00 | 54.19 | chnB |
| ATOM | 2283 | O | TYR | B | 121 | 105.612 | 55.046 | 31.012 | 1.00 | 54.32 | chnB |
| ATOM | 2284 | N | LYS | B | 122 | 105.888 | 55.016 | 28.771 | 1.00 | 57.18 | chnB |
| ATOM | 2285 | CA | LYS | B | 122 | 107.051 | 55.905 | 28.736 | 1.00 | 58.86 | chnB |
| ATOM | 2286 | CB | LYS | B | 122 | 108.367 | 55.130 | 28.741 | 1.00 | 61.68 | chnB |
| ATOM | 2287 | CG | LYS | B | 122 | 109.589 | 56.041 | 28.858 | 1.00 | 65.83 | chnB |
| ATOM | 2288 | CD | LYS | B | 122 | 110.917 | 55.326 | 28.587 | 1.00 | 68.44 | chnB |
| ATOM | 2289 | CE | LYS | B | 122 | 111.162 | 55.124 | 27.097 | 1.00 | 71.81 | chnB |
| ATOM | 2290 | NZ | LYS | B | 122 | 112.485 | 54.490 | 26.823 | 1.00 | 73.62 | chnB |
| ATOM | 2291 | C | LYS | B | 122 | 106.959 | 56.724 | 27.453 | 1.00 | 60.89 | chnB |
| ATOM | 2292 | O | LYS | B | 122 | 107.003 | 56.169 | 26.350 | 1.00 | 61.04 | chnB |
| ATOM | 2293 | N | ASP | B | 123 | 106.798 | 58.038 | 27.606 | 1.00 | 62.23 | chnB |
| ATOM | 2294 | CA | ASP | B | 123 | 106.687 | 58.961 | 26.477 | 1.00 | 63.65 | chnB |
| ATOM | 2295 | CB | ASP | B | 123 | 107.990 | 59.002 | 25.661 | 1.00 | 67.85 | chnB |
| ATOM | 2296 | CG | ASP | B | 123 | 109.192 | 59.427 | 26.484 | 1.00 | 69.87 | chnB |
| ATOM | 2297 | OD1 | ASP | B | 123 | 109.055 | 60.337 | 27.325 | 1.00 | 70.48 | chnB |
| ATOM | 2298 | OD2 | ASP | B | 123 | 110.283 | 58.852 | 26.277 | 1.00 | 71.58 | chnB |
| ATOM | 2299 | C | ASP | B | 123 | 105.533 | 58.562 | 25.567 | 1.00 | 62.90 | chnB |
| ATOM | 2300 | O | ASP | B | 123 | 105.637 | 58.641 | 24.345 | 1.00 | 65.46 | chnB |
| ATOM | 2301 | N | GLY | B | 124 | 104.445 | 58.104 | 26.166 | 1.00 | 61.12 | chnB |
| ATOM | 2302 | CA | GLY | B | 124 | 103.295 | 57.710 | 25.383 | 1.00 | 61.71 | chnB |
| ATOM | 2303 | C | GLY | B | 124 | 103.305 | 56.272 | 24.915 | 1.00 | 61.96 | chnB |
| ATOM | 2304 | O | GLY | B | 124 | 102.300 | 55.794 | 24.389 | 1.00 | 63.96 | chnB |
| ATOM | 2305 | N | GLU | B | 125 | 104.420 | 55.572 | 25.095 | 1.00 | 62.99 | chnB |
| ATOM | 2306 | CA | GLU | B | 125 | 104.494 | 54.173 | 24.667 | 1.00 | 67.31 | chnB |
| ATOM | 2307 | CB | GLU | B | 125 | 105.800 | 53.894 | 23.905 | 1.00 | 76.81 | chnB |
| ATOM | 2308 | CG | GLU | B | 125 | 105.878 | 54.541 | 22.525 | 1.00 | 86.95 | chnB |
| ATOM | 2309 | CD | GLU | B | 125 | 107.144 | 54.172 | 21.771 | 1.00 | 91.48 | chnB |
| ATOM | 2310 | OE1 | GLU | B | 125 | 108.051 | 55.034 | 21.684 | 1.00 | 93.14 | chnB |
| ATOM | 2311 | OE2 | GLU | B | 125 | 107.226 | 53.026 | 21.263 | 1.00 | 95.74 | chnB |
| ATOM | 2312 | C | GLU | B | 125 | 104.345 | 53.164 | 25.801 | 1.00 | 63.11 | chnB |
| ATOM | 2313 | O | GLU | B | 125 | 105.043 | 53.242 | 26.802 | 1.00 | 65.51 | chnB |
| ATOM | 2314 | N | ALA | B | 126 | 103.443 | 52.206 | 25.626 | 1.00 | 55.86 | chnB |
| ATOM | 2315 | CA | ALA | B | 126 | 103.222 | 51.168 | 26.616 | 1.00 | 52.13 | chnB |
| ATOM | 2316 | CB | ALA | B | 126 | 101.881 | 50.511 | 26.366 | 1.00 | 50.11 | chnB |
| ATOM | 2317 | C | ALA | B | 126 | 104.340 | 50.148 | 26.464 | 1.00 | 54.10 | chnB |
| ATOM | 2318 | O | ALA | B | 126 | 104.470 | 49.529 | 25.407 | 1.00 | 57.36 | chnB |
| ATOM | 2319 | N | LEU | B | 127 | 105.159 | 49.970 | 27.495 | 1.00 | 55.78 | chnB |
| ATOM | 2320 | CA | LEU | B | 127 | 106.242 | 49.001 | 27.385 | 1.00 | 59.14 | chnB |
| ATOM | 2321 | CB | LEU | B | 127 | 107.600 | 49.630 | 27.691 | 1.00 | 59.99 | chnB |
| ATOM | 2322 | CG | LEU | B | 127 | 107.756 | 50.492 | 28.929 | 1.00 | 60.21 | chnB |
| ATOM | 2323 | CD1 | LEU | B | 127 | 109.232 | 50.619 | 29.263 | 1.00 | 64.60 | chnB |
| ATOM | 2324 | CD2 | LEU | B | 127 | 107.154 | 51.848 | 28.678 | 1.00 | 60.23 | chnB |
| ATOM | 2325 | C | LEU | B | 127 | 106.075 | 47.677 | 28.124 | 1.00 | 61.67 | chnB |
| ATOM | 2326 | O | LEU | B | 127 | 106.788 | 46.714 | 27.827 | 1.00 | 65.49 | chnB |
| ATOM | 2327 | N | LYS | B | 128 | 105.146 | 47.619 | 29.075 | 1.00 | 62.15 | chnB |
| ATOM | 2328 | CA | LYS | B | 128 | 104.897 | 46.381 | 29.812 | 1.00 | 62.62 | chnB |
| ATOM | 2329 | CB | LYS | B | 128 | 105.908 | 46.195 | 30.939 | 1.00 | 63.21 | chnB |
| ATOM | 2330 | CG | LYS | B | 128 | 107.154 | 45.451 | 30.494 | 1.00 | 67.83 | chnB |
| ATOM | 2331 | CD | LYS | B | 128 | 108.203 | 45.386 | 31.588 | 1.00 | 72.61 | chnB |
| ATOM | 2332 | CE | LYS | B | 128 | 109.486 | 44.725 | 31.085 | 1.00 | 74.96 | chnB |
| ATOM | 2333 | NZ | LYS | B | 128 | 110.164 | 45.518 | 30.010 | 1.00 | 75.53 | chnB |
| ATOM | 2334 | C | LYS | B | 128 | 103.483 | 46.251 | 30.350 | 1.00 | 62.19 | chnB |
| ATOM | 2335 | O | LYS | B | 128 | 102.879 | 47.230 | 30.792 | 1.00 | 62.46 | chnB |
| ATOM | 2336 | N | TYR | B | 129 | 102.970 | 45.025 | 30.309 | 1.00 | 62.67 | chnB |
| ATOM | 2337 | CA | TYR | B | 129 | 101.626 | 44.716 | 30.784 | 1.00 | 63.68 | chnB |
| ATOM | 2338 | CB | TYR | B | 129 | 100.696 | 44.486 | 29.589 | 1.00 | 63.74 | chnB |
| ATOM | 2339 | CG | TYR | B | 129 | 99.312 | 43.948 | 29.910 | 1.00 | 65.61 | chnB |
| ATOM | 2340 | CD1 | TYR | B | 129 | 98.201 | 44.793 | 29.927 | 1.00 | 65.99 | chnB |
| ATOM | 2341 | CE1 | TYR | B | 129 | 96.916 | 44.290 | 30.145 | 1.00 | 66.21 | chnB |
| ATOM | 2342 | CD2 | TYR | B | 129 | 99.104 | 42.581 | 30.128 | 1.00 | 66.49 | chnB |
| ATOM | 2343 | CE2 | TYR | B | 129 | 97.828 | 42.069 | 30.350 | 1.00 | 67.59 | chnB |
| ATOM | 2344 | CZ | TYR | B | 129 | 96.738 | 42.927 | 30.354 | 1.00 | 67.17 | chnB |
| ATOM | 2345 | OH | TYR | B | 129 | 95.473 | 42.415 | 30.550 | 1.00 | 67.94 | chnB |
| ATOM | 2346 | C | TYR | B | 129 | 101.643 | 43.493 | 31.696 | 1.00 | 64.48 | chnB |
| ATOM | 2347 | O | TYR | B | 129 | 102.414 | 42.551 | 31.495 | 1.00 | 66.53 | chnB |
| ATOM | 2348 | N | TRP | B | 130 | 100.785 | 43.525 | 32.706 | 1.00 | 63.21 | chnB |
| ATOM | 2349 | CA | TRP | B | 130 | 100.675 | 42.439 | 33.657 | 1.00 | 63.76 | chnB |
| ATOM | 2350 | CB | TRP | B | 130 | 101.588 | 42.695 | 34.845 | 1.00 | 65.82 | chnB |
| ATOM | 2351 | CG | TRP | B | 130 | 102.993 | 42.265 | 34.634 | 1.00 | 69.01 | chnB |
| ATOM | 2352 | CD2 | TRP | B | 130 | 104.154 | 43.099 | 34.619 | 1.00 | 68.89 | chnB |

-continued

| ATOM | 2353 | CE2 | TRP | B | 130 | 105.274 | 42.253 | 34.481 | 1.00 | 70.59 | chnB |
|---|---|---|---|---|---|---|---|---|---|---|---|
| ATOM | 2354 | CE3 | TRP | B | 130 | 104.358 | 44.477 | 34.715 | 1.00 | 68.61 | chnB |
| ATOM | 2355 | CD1 | TRP | B | 130 | 103.439 | 40.987 | 34.494 | 1.00 | 72.60 | chnB |
| ATOM | 2356 | NE1 | TRP | B | 130 | 104.811 | 40.968 | 34.406 | 1.00 | 72.69 | chnB |
| ATOM | 2357 | CZ2 | TRP | B | 130 | 106.577 | 42.739 | 34.440 | 1.00 | 72.00 | chnB |
| ATOM | 2358 | CZ3 | TRP | B | 130 | 105.656 | 44.961 | 34.675 | 1.00 | 69.96 | chnB |
| ATOM | 2359 | CH2 | TRP | B | 130 | 106.749 | 44.093 | 34.538 | 1.00 | 71.57 | chnB |
| ATOM | 2360 | C | TRP | B | 130 | 99.245 | 42.369 | 34.136 | 1.00 | 64.71 | chnB |
| ATOM | 2361 | O | TRP | B | 130 | 98.609 | 43.402 | 34.318 | 1.00 | 65.98 | chnB |
| ATOM | 2362 | N | TYR | B | 131 | 98.723 | 41.157 | 34.302 | 1.00 | 66.06 | chnB |
| ATOM | 2363 | CA | TYR | B | 131 | 97.356 | 40.998 | 34.783 | 1.00 | 66.96 | chnB |
| ATOM | 2364 | CB | TYR | B | 131 | 96.863 | 39.563 | 34.619 | 1.00 | 66.78 | chnB |
| ATOM | 2365 | CG | TYR | B | 131 | 95.394 | 39.433 | 34.926 | 1.00 | 66.99 | chnB |
| ATOM | 2366 | CD1 | TYR | B | 131 | 94.494 | 40.387 | 34.467 | 1.00 | 67.56 | chnB |
| ATOM | 2367 | CE1 | TYR | B | 131 | 93.151 | 40.305 | 34.752 | 1.00 | 70.95 | chnB |
| ATOM | 2368 | CD2 | TYR | B | 131 | 94.906 | 38.379 | 35.686 | 1.00 | 66.52 | chnB |
| ATOM | 2369 | CE2 | TYR | B | 131 | 93.552 | 38.285 | 35.981 | 1.00 | 69.53 | chnB |
| ATOM | 2370 | CZ | TYR | B | 131 | 92.677 | 39.260 | 35.509 | 1.00 | 71.02 | chnB |
| ATOM | 2371 | OH | TYR | B | 131 | 91.328 | 39.216 | 35.797 | 1.00 | 70.98 | chnB |
| ATOM | 2372 | C | TYR | B | 131 | 97.341 | 41.375 | 36.256 | 1.00 | 66.34 | chnB |
| ATOM | 2373 | O | TYR | B | 131 | 96.607 | 42.270 | 36.674 | 1.00 | 65.50 | chnB |
| ATOM | 2374 | N | GLU | B | 132 | 98.135 | 40.650 | 37.036 | 1.00 | 66.06 | chnB |
| ATOM | 2375 | CA | GLU | B | 132 | 98.276 | 40.906 | 38.458 | 1.00 | 66.72 | chnB |
| ATOM | 2376 | CB | GLU | B | 132 | 98.901 | 39.696 | 39.162 | 1.00 | 68.66 | chnB |
| ATOM | 2377 | CG | GLU | B | 132 | 98.023 | 38.462 | 39.245 | 1.00 | 71.64 | chnB |
| ATOM | 2378 | CD | GLU | B | 132 | 96.945 | 38.581 | 40.302 | 1.00 | 74.63 | chnB |
| ATOM | 2379 | OE1 | GLU | B | 132 | 95.745 | 38.585 | 39.948 | 1.00 | 78.64 | chnB |
| ATOM | 2380 | OE2 | GLU | B | 132 | 97.297 | 38.658 | 41.496 | 1.00 | 78.17 | chnB |
| ATOM | 2381 | C | GLU | B | 132 | 99.239 | 42.082 | 38.532 | 1.00 | 66.33 | chnB |
| ATOM | 2382 | O | GLU | B | 132 | 100.281 | 42.069 | 37.874 | 1.00 | 67.03 | chnB |
| ATOM | 2383 | N | ASN | B | 133 | 98.871 | 43.111 | 39.292 | 1.00 | 65.85 | chnB |
| ATOM | 2384 | CA | ASN | B | 133 | 99.714 | 44.288 | 39.451 | 1.00 | 63.70 | chnB |
| ATOM | 2385 | CB | ASN | B | 133 | 99.162 | 45.188 | 40.551 | 1.00 | 66.67 | chnB |
| ATOM | 2386 | CG | ASN | B | 133 | 99.846 | 46.537 | 40.605 | 1.00 | 66.70 | chnB |
| ATOM | 2387 | OD1 | ASN | B | 133 | 101.049 | 46.659 | 40.373 | 1.00 | 65.11 | chnB |
| ATOM | 2388 | ND2 | ASN | B | 133 | 99.075 | 47.564 | 40.923 | 1.00 | 68.76 | chnB |
| ATOM | 2389 | C | ASN | B | 133 | 101.112 | 43.808 | 39.807 | 1.00 | 61.96 | chnB |
| ATOM | 2390 | O | ASN | B | 133 | 101.321 | 43.116 | 40.796 | 1.00 | 60.46 | chnB |
| ATOM | 2391 | N | HIS | B | 134 | 102.060 | 44.147 | 38.955 | 1.00 | 61.56 | chnB |
| ATOM | 2392 | CA | HIS | B | 134 | 103.430 | 43.733 | 39.145 | 1.00 | 61.93 | chnB |
| ATOM | 2393 | CB | HIS | B | 134 | 103.773 | 42.693 | 38.081 | 1.00 | 68.82 | chnB |
| ATOM | 2394 | CG | HIS | B | 134 | 105.016 | 41.916 | 38.365 | 1.00 | 76.12 | chnB |
| ATOM | 2395 | CD2 | HIS | B | 134 | 105.207 | 40.597 | 38.594 | 1.00 | 78.96 | chnB |
| ATOM | 2396 | ND1 | HIS | B | 134 | 106.261 | 42.504 | 38.447 | 1.00 | 80.46 | chnB |
| ATOM | 2397 | CE1 | HIS | B | 134 | 107.165 | 41.580 | 38.718 | 1.00 | 81.86 | chnB |
| ATOM | 2398 | NE2 | HIS | B | 134 | 106.553 | 40.413 | 38.813 | 1.00 | 82.74 | chnB |
| ATOM | 2399 | C | HIS | B | 134 | 104.327 | 44.947 | 39.006 | 1.00 | 59.65 | chnB |
| ATOM | 2400 | O | HIS | B | 134 | 104.086 | 45.810 | 38.177 | 1.00 | 60.51 | chnB |
| ATOM | 2401 | N | ASN | B | 135 | 105.349 | 45.019 | 39.844 | 1.00 | 59.44 | chnB |
| ATOM | 2402 | CA | ASN | B | 135 | 106.305 | 46.117 | 39.833 | 1.00 | 60.75 | chnB |
| ATOM | 2403 | CB | ASN | B | 135 | 107.187 | 46.013 | 41.071 | 1.00 | 63.26 | chnB |
| ATOM | 2404 | CG | ASN | B | 135 | 106.909 | 47.093 | 42.076 | 1.00 | 65.32 | chnB |
| ATOM | 2405 | OD1 | ASN | B | 135 | 105.985 | 47.000 | 42.881 | 1.00 | 65.47 | chnB |
| ATOM | 2406 | ND2 | ASN | B | 135 | 107.724 | 48.129 | 42.047 | 1.00 | 71.01 | chnB |
| ATOM | 2407 | C | ASN | B | 135 | 107.197 | 46.038 | 38.600 | 1.00 | 60.93 | chnB |
| ATOM | 2408 | O | ASN | B | 135 | 107.485 | 44.950 | 38.110 | 1.00 | 65.49 | chnB |
| ATOM | 2409 | N | ILE | B | 136 | 107.615 | 47.187 | 38.081 | 1.00 | 59.57 | chnB |
| ATOM | 2410 | CA | ILE | B | 136 | 108.509 | 47.217 | 36.925 | 1.00 | 60.64 | chnB |
| ATOM | 2411 | CB | ILE | B | 136 | 108.042 | 48.209 | 35.853 | 1.00 | 62.06 | chnB |
| ATOM | 2412 | CG2 | ILE | B | 136 | 108.009 | 49.587 | 36.396 | 1.00 | 64.30 | chnB |
| ATOM | 2413 | CG1 | ILE | B | 136 | 108.991 | 48.182 | 34.663 | 1.00 | 62.97 | chnB |
| ATOM | 2414 | CD1 | ILE | B | 136 | 108.546 | 49.075 | 33.537 | 1.00 | 65.85 | chnB |
| ATOM | 2415 | C | ILE | B | 136 | 109.891 | 47.590 | 37.442 | 1.00 | 59.34 | chnB |
| ATOM | 2416 | O | ILE | B | 136 | 110.045 | 48.539 | 38.209 | 1.00 | 56.80 | chnB |
| ATOM | 2417 | N | SER | B | 137 | 110.898 | 46.840 | 37.020 | 1.00 | 62.04 | chnB |
| ATOM | 2418 | CA | SER | B | 137 | 112.244 | 47.075 | 37.512 | 1.00 | 64.56 | chnB |
| ATOM | 2419 | CB | SER | B | 137 | 112.610 | 45.961 | 38.496 | 1.00 | 64.46 | chnB |
| ATOM | 2420 | OG | SER | B | 137 | 113.949 | 46.073 | 38.926 | 1.00 | 68.25 | chnB |
| ATOM | 2421 | C | SER | B | 137 | 113.313 | 47.186 | 36.442 | 1.00 | 65.96 | chnB |
| ATOM | 2422 | O | SER | B | 137 | 113.530 | 46.251 | 35.676 | 1.00 | 69.72 | chnB |
| ATOM | 2423 | N | ILE | B | 138 | 113.989 | 48.333 | 36.420 | 1.00 | 65.90 | chnB |
| ATOM | 2424 | CA | ILE | B | 138 | 115.067 | 48.601 | 35.473 | 1.00 | 66.27 | chnB |
| ATOM | 2425 | CB | ILE | B | 138 | 115.024 | 50.060 | 34.968 | 1.00 | 64.63 | chnB |
| ATOM | 2426 | CG2 | ILE | B | 138 | 116.210 | 50.335 | 34.055 | 1.00 | 66.04 | chnB |
| ATOM | 2427 | CG1 | ILE | B | 138 | 113.708 | 50.308 | 34.229 | 1.00 | 65.32 | chnB |
| ATOM | 2428 | CD1 | ILE | B | 138 | 113.549 | 51.704 | 33.692 | 1.00 | 66.88 | chnB |
| ATOM | 2429 | C | ILE | B | 138 | 116.393 | 48.342 | 36.186 | 1.00 | 68.17 | chnB |
| ATOM | 2430 | O | ILE | B | 138 | 116.883 | 49.190 | 36.935 | 1.00 | 65.23 | chnB |
| ATOM | 2431 | N | THR | B | 139 | 116.955 | 47.158 | 35.949 | 1.00 | 72.83 | chnB |

-continued

| | | | | | | | | | | |
|---|---|---|---|---|---|---|---|---|---|---|
| ATOM | 2432 | CA | THR | B | 139 | 118.204 | 46.730 | 36.576 | 1.00 | 74.69 chnB |
| ATOM | 2433 | CB | THR | B | 139 | 118.576 | 45.298 | 36.136 | 1.00 | 76.60 chnB |
| ATOM | 2434 | OG1 | THR | B | 139 | 118.708 | 45.247 | 34.711 | 1.00 | 81.28 chnB |
| ATOM | 2435 | CG2 | THR | B | 139 | 117.483 | 44.322 | 36.545 | 1.00 | 76.92 chnB |
| ATOM | 2436 | C | THR | B | 139 | 119.387 | 47.671 | 36.352 | 1.00 | 74.73 chnB |
| ATOM | 2437 | O | THR | B | 139 | 119.992 | 48.147 | 37.313 | 1.00 | 72.73 chnB |
| ATOM | 2438 | N | ASN | B | 140 | 119.702 | 47.950 | 35.090 | 1.00 | 75.97 chnB |
| ATOM | 2439 | CA | ASN | B | 140 | 120.815 | 48.834 | 34.751 | 1.00 | 74.71 chnB |
| ATOM | 2440 | CB | ASN | B | 140 | 121.795 | 48.110 | 33.820 | 1.00 | 75.54 chnB |
| ATOM | 2441 | CG | ASN | B | 140 | 123.073 | 48.893 | 33.590 | 1.00 | 76.92 chnB |
| ATOM | 2442 | OD1 | ASN | B | 140 | 123.205 | 50.040 | 34.043 | 1.00 | 78.35 chnB |
| ATOM | 2443 | ND2 | ASN | B | 140 | 124.027 | 48.272 | 32.897 | 1.00 | 76.03 chnB |
| ATOM | 2444 | C | ASN | B | 140 | 120.267 | 50.088 | 34.080 | 1.00 | 74.22 chnB |
| ATOM | 2445 | O | ASN | B | 140 | 119.959 | 50.081 | 32.887 | 1.00 | 73.28 chnB |
| ATOM | 2446 | N | ALA | B | 141 | 120.155 | 51.167 | 34.850 | 1.00 | 73.72 chnB |
| ATOM | 2447 | CA | ALA | B | 141 | 119.622 | 52.427 | 34.334 | 1.00 | 74.56 chnB |
| ATOM | 2448 | CB | ALA | B | 141 | 119.404 | 53.415 | 35.468 | 1.00 | 73.74 chnB |
| ATOM | 2449 | C | ALA | B | 141 | 120.476 | 53.053 | 33.234 | 1.00 | 75.23 chnB |
| ATOM | 2450 | O | ALA | B | 141 | 121.676 | 53.294 | 33.411 | 1.00 | 75.06 chnB |
| ATOM | 2451 | N | THR | B | 142 | 119.831 | 53.321 | 32.104 | 1.00 | 75.37 chnB |
| ATOM | 2452 | CA | THR | B | 142 | 120.483 | 53.911 | 30.945 | 1.00 | 75.47 chnB |
| ATOM | 2453 | CB | THR | B | 142 | 120.272 | 53.025 | 29.698 | 1.00 | 75.77 chnB |
| ATOM | 2454 | OG1 | THR | B | 142 | 120.770 | 51.708 | 29.961 | 1.00 | 78.39 chnB |
| ATOM | 2455 | CG2 | THR | B | 142 | 120.996 | 53.598 | 28.489 | 1.00 | 77.81 chnB |
| ATOM | 2456 | C | THR | B | 142 | 119.880 | 55.276 | 30.671 | 1.00 | 75.10 chnB |
| ATOM | 2457 | O | THR | B | 142 | 118.732 | 55.533 | 31.032 | 1.00 | 73.81 chnB |
| ATOM | 2458 | N | VAL | B | 143 | 120.655 | 56.149 | 30.032 | 1.00 | 76.36 chnB |
| ATOM | 2459 | CA | VAL | B | 143 | 120.188 | 57.492 | 29.693 | 1.00 | 78.85 chnB |
| ATOM | 2460 | CB | VAL | B | 143 | 121.310 | 58.326 | 29.016 | 1.00 | 80.21 chnB |
| ATOM | 2461 | CG1 | VAL | B | 143 | 121.735 | 57.691 | 27.694 | 1.00 | 82.71 chnB |
| ATOM | 2462 | CG2 | VAL | B | 143 | 120.852 | 59.764 | 28.810 | 1.00 | 83.17 chnB |
| ATOM | 2463 | C | VAL | B | 143 | 118.968 | 57.402 | 28.773 | 1.00 | 78.31 chnB |
| ATOM | 2464 | O | VAL | B | 143 | 118.149 | 58.320 | 28.708 | 1.00 | 77.47 chnB |
| ATOM | 2465 | N | GLU | B | 144 | 118.851 | 56.272 | 28.082 | 1.00 | 80.26 chnB |
| ATOM | 2466 | CA | GLU | B | 144 | 117.731 | 56.033 | 27.181 | 1.00 | 82.67 chnB |
| ATOM | 2467 | CB | GLU | B | 144 | 117.965 | 54.752 | 26.371 | 1.00 | 88.72 chnB |
| ATOM | 2468 | CG | GLU | B | 144 | 119.153 | 54.804 | 25.415 | 1.00 | 96.08 chnB |
| ATOM | 2469 | CD | GLU | B | 144 | 119.431 | 53.451 | 24.771 | 1.00 | 99.97 chnB |
| ATOM | 2470 | OE1 | GLU | B | 144 | 118.638 | 53.017 | 23.901 | 1.00 | 101.93 chnB |
| ATOM | 2471 | OE2 | GLU | B | 144 | 120.443 | 52.814 | 25.139 | 1.00 | 102.74 chnB |
| ATOM | 2472 | C | GLU | B | 144 | 116.454 | 55.894 | 28.005 | 1.00 | 78.88 chnB |
| ATOM | 2473 | O | GLU | B | 144 | 115.371 | 56.291 | 27.566 | 1.00 | 77.33 chnB |
| ATOM | 2474 | N | ASP | B | 145 | 116.607 | 55.358 | 29.215 | 1.00 | 74.11 chnB |
| ATOM | 2475 | CA | ASP | B | 145 | 115.490 | 55.144 | 30.127 | 1.00 | 69.48 chnB |
| ATOM | 2476 | CB | ASP | B | 145 | 115.908 | 54.226 | 31.281 | 1.00 | 70.56 chnB |
| ATOM | 2477 | CG | ASP | B | 145 | 116.215 | 52.796 | 30.820 | 1.00 | 71.86 chnB |
| ATOM | 2478 | OD1 | ASP | B | 145 | 115.466 | 52.265 | 29.964 | 1.00 | 71.98 chnB |
| ATOM | 2479 | OD2 | ASP | B | 145 | 117.198 | 52.199 | 31.325 | 1.00 | 70.38 chnB |
| ATOM | 2480 | C | ASP | B | 145 | 114.875 | 56.426 | 30.670 | 1.00 | 65.82 chnB |
| ATOM | 2481 | O | ASP | B | 145 | 113.960 | 56.373 | 31.487 | 1.00 | 63.05 chnB |
| ATOM | 2482 | N | SER | B | 146 | 115.373 | 57.570 | 30.212 | 1.00 | 63.03 chnB |
| ATOM | 2483 | CA | SER | B | 146 | 114.836 | 58.850 | 30.647 | 1.00 | 63.51 chnB |
| ATOM | 2484 | CB | SER | B | 146 | 115.845 | 59.969 | 30.404 | 1.00 | 63.70 chnB |
| ATOM | 2485 | OG | SER | B | 146 | 117.042 | 59.739 | 31.119 | 1.00 | 63.81 chnB |
| ATOM | 2486 | C | SER | B | 146 | 113.557 | 59.141 | 29.883 | 1.00 | 65.35 chnB |
| ATOM | 2487 | O | SER | B | 146 | 113.407 | 58.741 | 28.728 | 1.00 | 66.57 chnB |
| ATOM | 2488 | N | GLY | B | 147 | 112.627 | 59.817 | 30.544 | 1.00 | 66.70 chnB |
| ATOM | 2489 | CA | GLY | B | 147 | 111.368 | 60.157 | 29.909 | 1.00 | 69.36 chnB |
| ATOM | 2490 | C | GLY | B | 147 | 110.242 | 60.301 | 30.912 | 1.00 | 68.61 chnB |
| ATOM | 2491 | O | GLY | B | 147 | 110.468 | 60.197 | 32.120 | 1.00 | 68.63 chnB |
| ATOM | 2492 | N | THR | B | 148 | 109.038 | 60.584 | 30.417 | 1.00 | 68.20 chnB |
| ATOM | 2493 | CA | THR | B | 148 | 107.869 | 60.725 | 31.282 | 1.00 | 66.97 chnB |
| ATOM | 2494 | CB | THR | B | 148 | 106.893 | 61.820 | 30.771 | 1.00 | 68.46 chnB |
| ATOM | 2495 | OG1 | THR | B | 148 | 106.069 | 61.295 | 29.721 | 1.00 | 74.68 chnB |
| ATOM | 2496 | CG2 | THR | B | 148 | 107.668 | 63.013 | 30.228 | 1.00 | 67.87 chnB |
| ATOM | 2497 | C | THR | B | 148 | 107.150 | 59.375 | 31.360 | 1.00 | 63.60 chnB |
| ATOM | 2498 | O | THR | B | 148 | 106.730 | 58.822 | 30.344 | 1.00 | 63.66 chnB |
| ATOM | 2499 | N | TYR | B | 149 | 107.061 | 58.829 | 32.567 | 1.00 | 58.55 chnB |
| ATOM | 2500 | CA | TYR | B | 149 | 106.409 | 57.547 | 32.786 | 1.00 | 54.80 chnB |
| ATOM | 2501 | CB | TYR | B | 149 | 107.262 | 56.661 | 33.688 | 1.00 | 54.95 chnB |
| ATOM | 2502 | CG | TYR | B | 149 | 108.532 | 56.110 | 33.083 | 1.00 | 57.03 chnB |
| ATOM | 2503 | CD1 | TYR | B | 149 | 109.692 | 56.877 | 33.028 | 1.00 | 57.50 chnB |
| ATOM | 2504 | CE1 | TYR | B | 149 | 110.884 | 56.342 | 32.551 | 1.00 | 58.83 chnB |
| ATOM | 2505 | CD2 | TYR | B | 149 | 108.596 | 54.791 | 32.639 | 1.00 | 58.87 chnB |
| ATOM | 2506 | CE2 | TYR | B | 149 | 109.784 | 54.247 | 32.164 | 1.00 | 59.06 chnB |
| ATOM | 2507 | CZ | TYR | B | 149 | 110.926 | 55.027 | 32.124 | 1.00 | 58.67 chnB |
| ATOM | 2508 | OH | TYR | B | 149 | 112.110 | 54.490 | 31.668 | 1.00 | 58.29 chnB |
| ATOM | 2509 | C | TYR | B | 149 | 105.062 | 57.730 | 33.463 | 1.00 | 52.66 chnB |
| ATOM | 2510 | O | TYR | B | 149 | 104.858 | 58.700 | 34.190 | 1.00 | 49.70 chnB |

-continued

| ATOM | 2511 | N | TYR | B | 150 | 104.157 | 56.784 | 33.229 | 1.00 | 48.57 | chnB |
| ATOM | 2512 | CA | TYR | B | 150 | 102.831 | 56.779 | 33.838 | 1.00 | 46.48 | chnB |
| ATOM | 2513 | CB | TYR | B | 150 | 101.928 | 57.891 | 33.279 | 1.00 | 49.22 | chnB |
| ATOM | 2514 | CG | TYR | B | 150 | 101.387 | 57.696 | 31.876 | 1.00 | 53.24 | chnB |
| ATOM | 2515 | CD1 | TYR | B | 150 | 100.122 | 57.144 | 31.665 | 1.00 | 54.63 | chnB |
| ATOM | 2516 | CE1 | TYR | B | 150 | 99.598 | 57.005 | 30.376 | 1.00 | 57.22 | chnB |
| ATOM | 2517 | CD2 | TYR | B | 150 | 102.118 | 58.105 | 30.760 | 1.00 | 56.71 | chnB |
| ATOM | 2518 | CE2 | TYR | B | 150 | 101.600 | 57.971 | 29.468 | 1.00 | 59.30 | chnB |
| ATOM | 2519 | CZ | TYR | B | 150 | 100.341 | 57.420 | 29.287 | 1.00 | 58.72 | chnB |
| ATOM | 2520 | OH | TYR | B | 150 | 99.837 | 57.275 | 28.019 | 1.00 | 59.97 | chnB |
| ATOM | 2521 | C | TYR | B | 150 | 102.228 | 55.398 | 33.635 | 1.00 | 45.17 | chnB |
| ATOM | 2522 | O | TYR | B | 150 | 102.718 | 54.634 | 32.812 | 1.00 | 46.12 | chnB |
| ATOM | 2523 | N | CYS | B | 151 | 101.205 | 55.051 | 34.408 | 1.00 | 43.38 | chnB |
| ATOM | 2524 | CA | CYS | B | 151 | 100.584 | 53.733 | 34.286 | 1.00 | 41.29 | chnB |
| ATOM | 2525 | C | CYS | B | 151 | 99.076 | 53.783 | 34.326 | 1.00 | 38.28 | chnB |
| ATOM | 2526 | O | CYS | B | 151 | 98.496 | 54.734 | 34.835 | 1.00 | 38.53 | chnB |
| ATOM | 2527 | CB | CYS | B | 151 | 101.065 | 52.816 | 35.404 | 1.00 | 42.95 | chnB |
| ATOM | 2528 | SG | CYS | B | 151 | 100.594 | 53.382 | 37.062 | 1.00 | 46.51 | chnB |
| ATOM | 2529 | N | THR | B | 152 | 98.442 | 52.755 | 33.775 | 1.00 | 36.88 | chnB |
| ATOM | 2530 | CA | THR | B | 152 | 96.985 | 52.669 | 33.772 | 1.00 | 41.18 | chnB |
| ATOM | 2531 | CB | THR | B | 152 | 96.407 | 52.663 | 32.365 | 1.00 | 40.26 | chnB |
| ATOM | 2532 | OG1 | THR | B | 152 | 96.965 | 51.565 | 31.628 | 1.00 | 45.95 | chnB |
| ATOM | 2533 | CG2 | THR | B | 152 | 96.713 | 53.963 | 31.667 | 1.00 | 40.50 | chnB |
| ATOM | 2534 | C | THR | B | 152 | 96.624 | 51.352 | 34.428 | 1.00 | 42.87 | chnB |
| ATOM | 2535 | O | THR | B | 152 | 97.372 | 50.379 | 34.321 | 1.00 | 46.30 | chnB |
| ATOM | 2536 | N | GLY | B | 153 | 95.477 | 51.317 | 35.095 | 1.00 | 41.44 | chnB |
| ATOM | 2537 | CA | GLY | B | 153 | 95.073 | 50.106 | 35.774 | 1.00 | 40.27 | chnB |
| ATOM | 2538 | C | GLY | B | 153 | 93.577 | 49.971 | 35.882 | 1.00 | 41.56 | chnB |
| ATOM | 2539 | O | GLY | B | 153 | 92.816 | 50.816 | 35.413 | 1.00 | 42.05 | chnB |
| ATOM | 2540 | N | LYS | B | 154 | 93.161 | 48.938 | 36.591 | 1.00 | 43.82 | chnB |
| ATOM | 2541 | CA | LYS | B | 154 | 91.756 | 48.640 | 36.747 | 1.00 | 46.65 | chnB |
| ATOM | 2542 | CB | LYS | B | 154 | 91.476 | 47.393 | 35.895 | 1.00 | 51.77 | chnB |
| ATOM | 2543 | CG | LYS | B | 154 | 90.106 | 47.295 | 35.249 | 1.00 | 60.90 | chnB |
| ATOM | 2544 | CD | LYS | B | 154 | 89.865 | 45.870 | 34.714 | 1.00 | 64.81 | chnB |
| ATOM | 2545 | CE | LYS | B | 154 | 88.370 | 45.577 | 34.497 | 1.00 | 68.33 | chnB |
| ATOM | 2546 | NZ | LYS | B | 154 | 88.097 | 44.123 | 34.222 | 1.00 | 68.85 | chnB |
| ATOM | 2547 | C | LYS | B | 154 | 91.428 | 48.388 | 38.230 | 1.00 | 45.42 | chnB |
| ATOM | 2548 | O | LYS | B | 154 | 91.474 | 47.253 | 38.691 | 1.00 | 43.24 | chnB |
| ATOM | 2549 | N | VAL | B | 155 | 91.167 | 49.452 | 38.992 | 1.00 | 46.51 | chnB |
| ATOM | 2550 | CA | VAL | B | 155 | 90.824 | 49.318 | 40.421 | 1.00 | 46.14 | chnB |
| ATOM | 2551 | CB | VAL | B | 155 | 91.180 | 50.560 | 41.236 | 1.00 | 43.51 | chnB |
| ATOM | 2552 | CG1 | VAL | B | 155 | 90.838 | 50.328 | 42.684 | 1.00 | 42.23 | chnB |
| ATOM | 2553 | CG2 | VAL | B | 155 | 92.661 | 50.885 | 41.095 | 1.00 | 43.74 | chnB |
| ATOM | 2554 | C | VAL | B | 155 | 89.329 | 49.078 | 40.500 | 1.00 | 47.39 | chnB |
| ATOM | 2555 | O | VAL | B | 155 | 88.543 | 49.868 | 39.984 | 1.00 | 49.53 | chnB |
| ATOM | 2556 | N | TRP | B | 156 | 88.942 | 48.023 | 41.208 | 1.00 | 50.74 | chnB |
| ATOM | 2557 | CA | TRP | B | 156 | 87.540 | 47.606 | 41.284 | 1.00 | 52.83 | chnB |
| ATOM | 2558 | CB | TRP | B | 156 | 86.617 | 48.722 | 41.788 | 1.00 | 45.80 | chnB |
| ATOM | 2559 | CG | TRP | B | 156 | 86.867 | 49.012 | 43.245 | 1.00 | 44.95 | chnB |
| ATOM | 2560 | CD2 | TRP | B | 156 | 86.727 | 48.096 | 44.334 | 1.00 | 42.76 | chnB |
| ATOM | 2561 | CE2 | TRP | B | 156 | 87.211 | 48.742 | 45.488 | 1.00 | 42.61 | chnB |
| ATOM | 2562 | CE3 | TRP | B | 156 | 86.248 | 46.786 | 44.444 | 1.00 | 42.19 | chnB |
| ATOM | 2563 | CD1 | TRP | B | 156 | 87.393 | 50.153 | 43.776 | 1.00 | 44.86 | chnB |
| ATOM | 2564 | NE1 | TRP | B | 156 | 87.609 | 49.996 | 45.120 | 1.00 | 42.47 | chnB |
| ATOM | 2565 | CZ2 | TRP | B | 156 | 87.234 | 48.122 | 46.738 | 1.00 | 42.85 | chnB |
| ATOM | 2566 | CZ3 | TRP | B | 156 | 86.270 | 46.166 | 45.693 | 1.00 | 41.61 | chnB |
| ATOM | 2567 | CH2 | TRP | B | 156 | 86.762 | 46.836 | 46.822 | 1.00 | 40.48 | chnB |
| ATOM | 2568 | C | TRP | B | 156 | 87.195 | 47.154 | 39.862 | 1.00 | 55.99 | chnB |
| ATOM | 2569 | O | TRP | B | 156 | 87.899 | 46.304 | 39.291 | 1.00 | 62.03 | chnB |
| ATOM | 2570 | N | GLN | B | 157 | 86.175 | 47.733 | 39.250 | 1.00 | 56.62 | chnB |
| ATOM | 2571 | CA | GLN | B | 157 | 85.840 | 47.306 | 37.894 | 1.00 | 59.63 | chnB |
| ATOM | 2572 | CB | GLN | B | 157 | 84.375 | 46.856 | 37.829 | 1.00 | 65.09 | chnB |
| ATOM | 2573 | CG | GLN | B | 157 | 84.153 | 45.431 | 38.306 | 1.00 | 67.79 | chnB |
| ATOM | 2574 | CD | GLN | B | 157 | 84.812 | 44.425 | 37.389 | 1.00 | 69.18 | chnB |
| ATOM | 2575 | OE1 | GLN | B | 157 | 84.128 | 43.670 | 36.684 | 1.00 | 69.89 | chnB |
| ATOM | 2576 | NE2 | GLN | B | 157 | 86.148 | 44.427 | 37.364 | 1.00 | 67.72 | chnB |
| ATOM | 2577 | C | GLN | B | 157 | 86.100 | 48.396 | 36.873 | 1.00 | 58.95 | chnB |
| ATOM | 2578 | O | GLN | B | 157 | 85.837 | 48.229 | 35.678 | 1.00 | 59.08 | chnB |
| ATOM | 2579 | N | LEU | B | 158 | 86.678 | 49.491 | 37.341 | 1.00 | 57.12 | chnB |
| ATOM | 2580 | CA | LEU | B | 158 | 86.920 | 50.617 | 36.477 | 1.00 | 60.14 | chnB |
| ATOM | 2581 | CB | LEU | B | 158 | 86.347 | 51.864 | 37.143 | 1.00 | 61.85 | chnB |
| ATOM | 2582 | CG | LEU | B | 158 | 84.944 | 51.616 | 37.710 | 1.00 | 62.75 | chnB |
| ATOM | 2583 | CD1 | LEU | B | 158 | 84.407 | 52.879 | 38.345 | 1.00 | 64.18 | chnB |
| ATOM | 2584 | CD2 | LEU | B | 158 | 83.998 | 51.120 | 36.615 | 1.00 | 65.67 | chnB |
| ATOM | 2585 | C | LEU | B | 158 | 88.372 | 50.824 | 36.080 | 1.00 | 60.30 | chnB |
| ATOM | 2586 | O | LEU | B | 158 | 89.283 | 50.239 | 36.669 | 1.00 | 57.92 | chnB |
| ATOM | 2587 | N | ASP | B | 159 | 88.558 | 51.609 | 35.020 | 1.00 | 61.03 | chnB |
| ATOM | 2588 | CA | ASP | B | 159 | 89.876 | 51.948 | 34.504 | 1.00 | 60.26 | chnB |
| ATOM | 2589 | CB | ASP | B | 159 | 89.879 | 51.989 | 32.972 | 1.00 | 63.91 | chnB |

-continued

| | | | | | | | | | | |
|---|---|---|---|---|---|---|---|---|---|---|
| ATOM | 2590 | CG | ASP | B | 159 | 90.317 | 50.678 | 32.348 | 1.00 | 67.60 | chnB |
| ATOM | 2591 | OD1 | ASP | B | 159 | 91.510 | 50.568 | 32.007 | 1.00 | 70.03 | chnB |
| ATOM | 2592 | OD2 | ASP | B | 159 | 89.473 | 49.768 | 32.186 | 1.00 | 70.11 | chnB |
| ATOM | 2593 | C | ASP | B | 159 | 90.225 | 53.322 | 35.033 | 1.00 | 57.95 | chnB |
| ATOM | 2594 | O | ASP | B | 159 | 89.341 | 54.163 | 35.222 | 1.00 | 57.66 | chnB |
| ATOM | 2595 | N | TYR | B | 160 | 91.514 | 53.532 | 35.279 | 1.00 | 54.62 | chnB |
| ATOM | 2596 | CA | TYR | B | 160 | 92.036 | 54.797 | 35.795 | 1.00 | 52.15 | chnB |
| ATOM | 2597 | CB | TYR | B | 160 | 92.064 | 54.787 | 37.329 | 1.00 | 48.41 | chnB |
| ATOM | 2598 | CG | TYR | B | 160 | 90.701 | 54.661 | 37.975 | 1.00 | 47.05 | chnB |
| ATOM | 2599 | CD1 | TYR | B | 160 | 90.347 | 53.518 | 38.692 | 1.00 | 45.74 | chnB |
| ATOM | 2600 | CE1 | TYR | B | 160 | 89.093 | 53.388 | 39.265 | 1.00 | 43.99 | chnB |
| ATOM | 2601 | CD2 | TYR | B | 160 | 89.760 | 55.669 | 37.853 | 1.00 | 47.74 | chnB |
| ATOM | 2602 | CE2 | TYR | B | 160 | 88.504 | 55.544 | 38.426 | 1.00 | 47.84 | chnB |
| ATOM | 2603 | CZ | TYR | B | 160 | 88.180 | 54.407 | 39.125 | 1.00 | 46.27 | chnB |
| ATOM | 2604 | OH | TYR | B | 160 | 86.933 | 54.303 | 39.676 | 1.00 | 45.95 | chnB |
| ATOM | 2605 | C | TYR | B | 160 | 93.450 | 55.005 | 35.259 | 1.00 | 52.27 | chnB |
| ATOM | 2606 | O | TYR | B | 160 | 94.119 | 54.046 | 34.860 | 1.00 | 51.89 | chnB |
| ATOM | 2607 | N | GLU | B | 161 | 93.887 | 56.263 | 35.226 | 1.00 | 52.21 | chnB |
| ATOM | 2608 | CA | GLU | B | 161 | 95.219 | 56.604 | 34.738 | 1.00 | 53.32 | chnB |
| ATOM | 2609 | CB | GLU | B | 161 | 95.120 | 57.420 | 33.452 | 1.00 | 56.41 | chnB |
| ATOM | 2610 | CG | GLU | B | 161 | 96.452 | 57.595 | 32.734 | 1.00 | 59.64 | chnB |
| ATOM | 2611 | CD | GLU | B | 161 | 96.348 | 58.442 | 31.472 | 1.00 | 61.51 | chnB |
| ATOM | 2612 | OE1 | GLU | B | 161 | 97.258 | 59.278 | 31.250 | 1.00 | 64.03 | chnB |
| ATOM | 2613 | OE2 | GLU | B | 161 | 95.367 | 58.272 | 30.709 | 1.00 | 60.36 | chnB |
| ATOM | 2614 | C | GLU | B | 161 | 95.944 | 57.410 | 35.797 | 1.00 | 53.04 | chnB |
| ATOM | 2615 | O | GLU | B | 161 | 95.328 | 58.197 | 36.503 | 1.00 | 54.44 | chnB |
| ATOM | 2616 | N | SER | B | 162 | 97.254 | 57.227 | 35.899 | 1.00 | 53.54 | chnB |
| ATOM | 2617 | CA | SER | B | 162 | 98.038 | 57.940 | 36.899 | 1.00 | 54.66 | chnB |
| ATOM | 2618 | CB | SER | B | 162 | 99.129 | 57.037 | 37.476 | 1.00 | 55.46 | chnB |
| ATOM | 2619 | OG | SER | B | 162 | 100.146 | 56.789 | 36.526 | 1.00 | 55.25 | chnB |
| ATOM | 2620 | C | SER | B | 162 | 98.682 | 59.189 | 36.345 | 1.00 | 55.77 | chnB |
| ATOM | 2621 | O | SER | B | 162 | 98.844 | 59.331 | 35.137 | 1.00 | 56.15 | chnB |
| ATOM | 2622 | N | GLU | B | 163 | 99.056 | 60.091 | 37.245 | 1.00 | 58.79 | chnB |
| ATOM | 2623 | CA | GLU | B | 163 | 99.721 | 61.322 | 36.863 | 1.00 | 60.00 | chnB |
| ATOM | 2624 | CB | GLU | B | 163 | 99.908 | 62.225 | 38.081 | 1.00 | 67.38 | chnB |
| ATOM | 2625 | CG | GLU | B | 163 | 98.618 | 62.816 | 38.643 | 1.00 | 75.81 | chnB |
| ATOM | 2626 | CD | GLU | B | 163 | 97.981 | 63.809 | 37.696 | 1.00 | 78.25 | chnB |
| ATOM | 2627 | OE1 | GLU | B | 163 | 98.573 | 64.887 | 37.491 | 1.00 | 80.25 | chnB |
| ATOM | 2628 | OE2 | GLU | B | 163 | 96.900 | 63.508 | 37.145 | 1.00 | 82.58 | chnB |
| ATOM | 2629 | C | GLU | B | 163 | 101.079 | 60.936 | 36.325 | 1.00 | 56.43 | chnB |
| ATOM | 2630 | O | GLU | B | 163 | 101.705 | 60.006 | 36.823 | 1.00 | 55.63 | chnB |
| ATOM | 2631 | N | PRO | B | 164 | 101.530 | 61.612 | 35.266 | 1.00 | 53.34 | chnB |
| ATOM | 2632 | CD | PRO | B | 164 | 100.793 | 62.635 | 34.506 | 1.00 | 53.63 | chnB |
| ATOM | 2633 | CA | PRO | B | 164 | 102.831 | 61.340 | 34.652 | 1.00 | 52.68 | chnB |
| ATOM | 2634 | CB | PRO | B | 164 | 102.786 | 62.191 | 33.384 | 1.00 | 54.00 | chnB |
| ATOM | 2635 | CG | PRO | B | 164 | 101.897 | 63.328 | 33.768 | 1.00 | 53.99 | chnB |
| ATOM | 2636 | C | PRO | B | 164 | 103.970 | 61.751 | 35.575 | 1.00 | 51.30 | chnB |
| ATOM | 2637 | O | PRO | B | 164 | 103.799 | 62.629 | 36.414 | 1.00 | 52.22 | chnB |
| ATOM | 2638 | N | LEU | B | 165 | 105.120 | 61.105 | 35.435 | 1.00 | 50.54 | chnB |
| ATOM | 2639 | CA | LEU | B | 165 | 106.261 | 61.417 | 36.278 | 1.00 | 54.76 | chnB |
| ATOM | 2640 | CB | LEU | B | 165 | 106.401 | 60.361 | 37.377 | 1.00 | 53.68 | chnB |
| ATOM | 2641 | CG | LEU | B | 165 | 107.563 | 60.503 | 38.364 | 1.00 | 53.77 | chnB |
| ATOM | 2642 | CD1 | LEU | B | 165 | 107.431 | 61.811 | 39.113 | 1.00 | 55.75 | chnB |
| ATOM | 2643 | CD2 | LEU | B | 165 | 107.591 | 59.337 | 39.333 | 1.00 | 52.33 | chnB |
| ATOM | 2644 | C | LEU | B | 165 | 107.550 | 61.513 | 35.473 | 1.00 | 57.77 | chnB |
| ATOM | 2645 | O | LEU | B | 165 | 107.930 | 60.572 | 34.777 | 1.00 | 56.31 | chnB |
| ATOM | 2646 | N | ASN | B | 166 | 108.220 | 62.656 | 35.577 | 1.00 | 63.14 | chnB |
| ATOM | 2647 | CA | ASN | B | 166 | 109.466 | 62.881 | 34.862 | 1.00 | 66.64 | chnB |
| ATOM | 2648 | CB | ASN | B | 166 | 109.785 | 64.382 | 34.793 | 1.00 | 74.05 | chnB |
| ATOM | 2649 | CG | ASN | B | 166 | 109.048 | 65.097 | 33.659 | 1.00 | 78.27 | chnB |
| ATOM | 2650 | OD1 | ASN | B | 166 | 108.625 | 64.472 | 32.689 | 1.00 | 79.86 | chnB |
| ATOM | 2651 | ND2 | ASN | B | 166 | 108.905 | 66.413 | 33.768 | 1.00 | 80.32 | chnB |
| ATOM | 2652 | C | ASN | B | 166 | 110.623 | 62.154 | 35.521 | 1.00 | 65.61 | chnB |
| ATOM | 2653 | O | ASN | B | 166 | 110.961 | 62.435 | 36.673 | 1.00 | 64.41 | chnB |
| ATOM | 2654 | N | ILE | B | 167 | 111.215 | 61.212 | 34.790 | 1.00 | 64.56 | chnB |
| ATOM | 2655 | CA | ILE | B | 167 | 112.358 | 60.452 | 35.289 | 1.00 | 65.46 | chnB |
| ATOM | 2656 | CB | ILE | B | 167 | 112.059 | 58.944 | 35.365 | 1.00 | 64.23 | chnB |
| ATOM | 2657 | CG2 | ILE | B | 167 | 113.346 | 58.145 | 35.495 | 1.00 | 63.11 | chnB |
| ATOM | 2658 | CG1 | ILE | B | 167 | 111.152 | 58.668 | 36.557 | 1.00 | 64.20 | chnB |
| ATOM | 2659 | CD1 | ILE | B | 167 | 110.907 | 57.219 | 36.794 | 1.00 | 67.21 | chnB |
| ATOM | 2660 | C | ILE | B | 167 | 113.560 | 60.707 | 34.396 | 1.00 | 66.85 | chnB |
| ATOM | 2661 | O | ILE | B | 167 | 113.494 | 60.525 | 33.176 | 1.00 | 67.95 | chnB |
| ATOM | 2662 | N | THR | B | 168 | 114.656 | 61.142 | 35.009 | 1.00 | 68.07 | chnB |
| ATOM | 2663 | CA | THR | B | 168 | 115.869 | 61.445 | 34.262 | 1.00 | 70.13 | chnB |
| ATOM | 2664 | CB | THR | B | 168 | 116.235 | 62.938 | 34.396 | 1.00 | 71.88 | chnB |
| ATOM | 2665 | OG1 | THR | B | 168 | 115.088 | 63.738 | 34.076 | 1.00 | 73.71 | chnB |
| ATOM | 2666 | CG2 | THR | B | 168 | 117.368 | 63.300 | 33.442 | 1.00 | 74.02 | chnB |
| ATOM | 2667 | C | THR | B | 168 | 117.048 | 60.589 | 34.711 | 1.00 | 69.68 | chnB |
| ATOM | 2668 | O | THR | B | 168 | 117.268 | 60.391 | 35.904 | 1.00 | 65.74 | chnB |

-continued

| | | | | | | | | | | |
|---|---|---|---|---|---|---|---|---|---|---|
| ATOM | 2669 | N | VAL | B | 169 | 117.793 | 60.078 | 33.735 | 1.00 | 73.73 chnB |
| ATOM | 2670 | CA | VAL | B | 169 | 118.958 | 59.238 | 33.989 | 1.00 | 78.78 chnB |
| ATOM | 2671 | CB | VAL | B | 169 | 118.823 | 57.854 | 33.310 | 1.00 | 75.32 chnB |
| ATOM | 2672 | CG1 | VAL | B | 169 | 119.997 | 56.980 | 33.673 | 1.00 | 73.76 chnB |
| ATOM | 2673 | CG2 | VAL | B | 169 | 117.530 | 57.189 | 33.706 | 1.00 | 75.69 chnB |
| ATOM | 2674 | C | VAL | B | 169 | 120.209 | 59.913 | 33.431 | 1.00 | 84.78 chnB |
| ATOM | 2675 | O | VAL | B | 169 | 120.433 | 59.910 | 32.220 | 1.00 | 88.73 chnB |
| ATOM | 2676 | N | ILE | B | 170 | 121.015 | 60.494 | 34.318 | 1.00 | 90.70 chnB |
| ATOM | 2677 | CA | ILE | B | 170 | 122.256 | 61.176 | 33.931 | 1.00 | 94.01 chnB |
| ATOM | 2678 | CB | ILE | B | 170 | 122.581 | 62.344 | 34.894 | 1.00 | 95.20 chnB |
| ATOM | 2679 | CG2 | ILE | B | 170 | 121.604 | 63.492 | 34.687 | 1.00 | 97.25 chnB |
| ATOM | 2680 | CG1 | ILE | B | 170 | 122.573 | 61.854 | 36.345 | 1.00 | 95.05 chnB |
| ATOM | 2681 | CD1 | ILE | B | 170 | 122.914 | 62.925 | 37.368 | 1.00 | 94.53 chnB |
| ATOM | 2682 | C | ILE | B | 170 | 123.436 | 60.212 | 33.954 | 1.00 | 94.83 chnB |
| ATOM | 2683 | O | ILE | B | 170 | 123.247 | 59.001 | 34.058 | 1.00 | 94.73 chnB |
| ATOM | 2684 | N | LYS | B | 171 | 124.650 | 60.743 | 33.834 | 1.00 | 96.72 chnB |
| ATOM | 2685 | CA | LYS | B | 171 | 125.835 | 59.894 | 33.885 | 1.00 | 100.52 chnB |
| ATOM | 2686 | CB | LYS | B | 171 | 126.910 | 60.381 | 32.918 | 1.00 | 102.50 chnB |
| ATOM | 2687 | CG | LYS | B | 171 | 128.221 | 59.590 | 33.032 | 1.00 | 106.30 chnB |
| ATOM | 2688 | CD | LYS | B | 171 | 129.137 | 59.866 | 31.856 | 1.00 | 109.42 chnB |
| ATOM | 2689 | CE | LYS | B | 171 | 128.449 | 59.484 | 30.546 | 1.00 | 112.34 chnB |
| ATOM | 2690 | NZ | LYS | B | 171 | 129.306 | 59.751 | 29.350 | 1.00 | 114.39 chnB |
| ATOM | 2691 | C | LYS | B | 171 | 126.412 | 59.802 | 35.305 | 1.00 | 101.54 chnB |
| ATOM | 2692 | O | LYS | B | 171 | 126.098 | 60.618 | 36.177 | 1.00 | 102.66 chnB |
| ATOM | 2693 | N | LYS | C | 4 | 159.848 | 45.077 | 59.934 | 1.00 | 108.86 chnC |
| ATOM | 2694 | CA | LYS | C | 4 | 158.465 | 45.004 | 60.416 | 1.00 | 108.70 chnC |
| ATOM | 2695 | CB | LYS | C | 4 | 157.807 | 46.391 | 60.362 | 1.00 | 109.62 chnC |
| ATOM | 2696 | CG | LYS | C | 4 | 156.304 | 46.410 | 60.664 | 1.00 | 109.66 chnC |
| ATOM | 2697 | CD | LYS | C | 4 | 155.692 | 47.743 | 60.228 | 1.00 | 110.96 chnC |
| ATOM | 2698 | CE | LYS | C | 4 | 154.168 | 47.717 | 60.231 | 1.00 | 110.42 chnC |
| ATOM | 2699 | NZ | LYS | C | 4 | 153.593 | 49.023 | 59.772 | 1.00 | 109.46 chnC |
| ATOM | 2700 | C | LYS | C | 4 | 157.632 | 43.998 | 59.614 | 1.00 | 107.58 chnC |
| ATOM | 2701 | O | LYS | C | 4 | 157.439 | 44.155 | 58.400 | 1.00 | 107.59 chnC |
| ATOM | 2702 | N | PRO | C | 5 | 157.136 | 42.942 | 60.286 | 1.00 | 105.73 chnC |
| ATOM | 2703 | CD | PRO | C | 5 | 157.387 | 42.646 | 61.706 | 1.00 | 106.00 chnC |
| ATOM | 2704 | CA | PRO | C | 5 | 156.318 | 41.888 | 59.673 | 1.00 | 105.06 chnC |
| ATOM | 2705 | CB | PRO | C | 5 | 156.449 | 40.746 | 60.671 | 1.00 | 105.21 chnC |
| ATOM | 2706 | CG | PRO | C | 5 | 156.463 | 41.472 | 61.963 | 1.00 | 106.31 chnC |
| ATOM | 2707 | C | PRO | C | 5 | 154.870 | 42.340 | 59.531 | 1.00 | 104.31 chnC |
| ATOM | 2708 | O | PRO | C | 5 | 154.414 | 43.218 | 60.264 | 1.00 | 105.09 chnC |
| ATOM | 2709 | N | LYS | C | 6 | 154.152 | 41.756 | 58.585 | 1.00 | 102.97 chnC |
| ATOM | 2710 | CA | LYS | C | 6 | 152.764 | 42.134 | 58.373 | 1.00 | 102.84 chnC |
| ATOM | 2711 | CB | LYS | C | 6 | 152.665 | 43.199 | 57.268 | 1.00 | 106.53 chnC |
| ATOM | 2712 | CG | LYS | C | 6 | 151.324 | 43.916 | 57.243 | 1.00 | 110.92 chnC |
| ATOM | 2713 | CD | LYS | C | 6 | 151.394 | 45.279 | 56.557 | 1.00 | 112.44 chnC |
| ATOM | 2714 | CE | LYS | C | 6 | 150.082 | 46.042 | 56.748 | 1.00 | 113.92 chnC |
| ATOM | 2715 | NZ | LYS | C | 6 | 150.105 | 47.387 | 56.121 | 1.00 | 113.63 chnC |
| ATOM | 2716 | C | LYS | C | 6 | 151.911 | 40.911 | 58.040 | 1.00 | 100.05 chnC |
| ATOM | 2717 | O | LYS | C | 6 | 152.221 | 40.153 | 57.117 | 1.00 | 100.93 chnC |
| ATOM | 2718 | N | VAL | C | 7 | 150.841 | 40.718 | 58.806 | 1.00 | 95.61 chnC |
| ATOM | 2719 | CA | VAL | C | 7 | 149.945 | 39.582 | 58.602 | 1.00 | 90.35 chnC |
| ATOM | 2720 | CB | VAL | C | 7 | 149.139 | 39.269 | 59.890 | 1.00 | 89.53 chnC |
| ATOM | 2721 | CG1 | VAL | C | 7 | 148.331 | 37.987 | 59.715 | 1.00 | 88.75 chnC |
| ATOM | 2722 | CG2 | VAL | C | 7 | 150.070 | 39.157 | 61.089 | 1.00 | 88.49 chnC |
| ATOM | 2723 | C | VAL | C | 7 | 148.973 | 39.810 | 57.439 | 1.00 | 88.74 chnC |
| ATOM | 2724 | O | VAL | C | 7 | 148.444 | 40.911 | 57.259 | 1.00 | 88.15 chnC |
| ATOM | 2725 | N | SER | C | 8 | 148.761 | 38.760 | 56.650 | 1.00 | 85.74 chnC |
| ATOM | 2726 | CA | SER | C | 8 | 147.857 | 38.803 | 55.504 | 1.00 | 84.30 chnC |
| ATOM | 2727 | CB | SER | C | 8 | 148.642 | 38.746 | 54.188 | 1.00 | 85.34 chnC |
| ATOM | 2728 | OG | SER | C | 8 | 149.306 | 37.495 | 54.024 | 1.00 | 86.91 chnC |
| ATOM | 2729 | C | SER | C | 8 | 146.890 | 37.622 | 55.583 | 1.00 | 82.70 chnC |
| ATOM | 2730 | O | SER | C | 8 | 147.227 | 36.558 | 56.119 | 1.00 | 81.52 chnC |
| ATOM | 2731 | N | LEU | C | 9 | 145.698 | 37.801 | 55.020 | 1.00 | 81.13 chnC |
| ATOM | 2732 | CA | LEU | C | 9 | 144.674 | 36.758 | 55.052 | 1.00 | 78.33 chnC |
| ATOM | 2733 | CB | LEU | C | 9 | 143.349 | 37.340 | 55.564 | 1.00 | 81.03 chnC |
| ATOM | 2734 | CG | LEU | C | 9 | 143.370 | 38.206 | 56.832 | 1.00 | 81.58 chnC |
| ATOM | 2735 | CD1 | LEU | C | 9 | 141.963 | 38.652 | 57.173 | 1.00 | 80.77 chnC |
| ATOM | 2736 | CD2 | LEU | C | 9 | 143.966 | 37.439 | 57.994 | 1.00 | 82.75 chnC |
| ATOM | 2737 | C | LEU | C | 9 | 144.445 | 36.092 | 53.703 | 1.00 | 74.12 chnC |
| ATOM | 2738 | O | LEU | C | 9 | 144.624 | 36.706 | 52.656 | 1.00 | 74.62 chnC |
| ATOM | 2739 | N | ASN | C | 10 | 144.043 | 34.829 | 53.738 | 1.00 | 68.90 chnC |
| ATOM | 2740 | CA | ASN | C | 10 | 143.766 | 34.093 | 52.522 | 1.00 | 65.93 chnC |
| ATOM | 2741 | CB | ASN | C | 10 | 145.040 | 33.456 | 51.960 | 1.00 | 70.58 chnC |
| ATOM | 2742 | CG | ASN | C | 10 | 144.797 | 32.748 | 50.633 | 1.00 | 72.60 chnC |
| ATOM | 2743 | OD1 | ASN | C | 10 | 144.536 | 33.396 | 49.608 | 1.00 | 72.48 chnC |
| ATOM | 2744 | ND2 | ASN | C | 10 | 144.849 | 31.412 | 50.651 | 1.00 | 72.37 chnC |
| ATOM | 2745 | C | ASN | C | 10 | 142.700 | 33.029 | 52.768 | 1.00 | 61.82 chnC |
| ATOM | 2746 | O | ASN | C | 10 | 142.974 | 31.986 | 53.379 | 1.00 | 55.63 chnC |
| ATOM | 2747 | N | PRO | C | 11 | 141.452 | 33.305 | 52.345 | 1.00 | 59.62 chnC |

-continued

| ATOM | 2748 | CD | PRO | C | 11 | 140.391 | 32.283 | 52.435 | 1.00 | 59.83 | chnC |
|---|---|---|---|---|---|---|---|---|---|---|---|
| ATOM | 2749 | CA | PRO | C | 11 | 140.959 | 34.512 | 51.658 | 1.00 | 58.77 | chnC |
| ATOM | 2750 | CB | PRO | C | 11 | 139.478 | 34.193 | 51.460 | 1.00 | 61.24 | chnC |
| ATOM | 2751 | CG | PRO | C | 11 | 139.467 | 32.683 | 51.333 | 1.00 | 61.00 | chnC |
| ATOM | 2752 | C | PRO | C | 11 | 141.143 | 35.805 | 52.480 | 1.00 | 57.72 | chnC |
| ATOM | 2753 | O | PRO | C | 11 | 141.094 | 35.771 | 53.706 | 1.00 | 61.42 | chnC |
| ATOM | 2754 | N | PRO | C | 12 | 141.293 | 36.965 | 51.808 | 1.00 | 56.99 | chnC |
| ATOM | 2755 | CD | PRO | C | 12 | 141.212 | 37.075 | 50.345 | 1.00 | 58.31 | chnC |
| ATOM | 2756 | CA | PRO | C | 12 | 141.489 | 38.300 | 52.404 | 1.00 | 58.15 | chnC |
| ATOM | 2757 | CB | PRO | C | 12 | 141.594 | 39.214 | 51.173 | 1.00 | 57.81 | chnC |
| ATOM | 2758 | CG | PRO | C | 12 | 142.023 | 38.309 | 50.086 | 1.00 | 60.69 | chnC |
| ATOM | 2759 | C | PRO | C | 12 | 140.358 | 38.791 | 53.316 | 1.00 | 59.49 | chnC |
| ATOM | 2760 | O | PRO | C | 12 | 140.456 | 39.871 | 53.913 | 1.00 | 59.31 | chnC |
| ATOM | 2761 | N | TRP | C | 13 | 139.290 | 38.006 | 53.410 | 1.00 | 58.84 | chnC |
| ATOM | 2762 | CA | TRP | C | 13 | 138.131 | 38.371 | 54.198 | 1.00 | 57.56 | chnC |
| ATOM | 2763 | CB | TRP | C | 13 | 136.956 | 37.481 | 53.810 | 1.00 | 60.41 | chnC |
| ATOM | 2764 | CG | TRP | C | 13 | 136.763 | 37.320 | 52.339 | 1.00 | 61.93 | chnC |
| ATOM | 2765 | CD2 | TRP | C | 13 | 136.645 | 38.361 | 51.364 | 1.00 | 62.36 | chnC |
| ATOM | 2766 | CE2 | TRP | C | 13 | 136.452 | 37.738 | 50.113 | 1.00 | 62.25 | chnC |
| ATOM | 2767 | CE3 | TRP | C | 13 | 136.675 | 39.758 | 51.426 | 1.00 | 62.45 | chnC |
| ATOM | 2768 | CD1 | TRP | C | 13 | 136.642 | 36.146 | 51.661 | 1.00 | 63.57 | chnC |
| ATOM | 2769 | NE1 | TRP | C | 13 | 136.455 | 36.386 | 50.323 | 1.00 | 64.17 | chnC |
| ATOM | 2770 | CZ2 | TRP | C | 13 | 136.294 | 38.461 | 48.934 | 1.00 | 62.46 | chnC |
| ATOM | 2771 | CZ3 | TRP | C | 13 | 136.515 | 40.478 | 50.250 | 1.00 | 62.06 | chnC |
| ATOM | 2772 | CH2 | TRP | C | 13 | 136.326 | 39.826 | 49.020 | 1.00 | 62.90 | chnC |
| ATOM | 2773 | C | TRP | C | 13 | 138.362 | 38.284 | 55.700 | 1.00 | 57.44 | chnC |
| ATOM | 2774 | O | TRP | C | 13 | 138.536 | 37.193 | 56.241 | 1.00 | 57.58 | chnC |
| ATOM | 2775 | N | ASN | C | 14 | 138.357 | 39.440 | 56.366 | 1.00 | 56.74 | chnC |
| ATOM | 2776 | CA | ASN | C | 14 | 138.530 | 39.507 | 57.819 | 1.00 | 54.89 | chnC |
| ATOM | 2777 | CB | ASN | C | 14 | 138.976 | 40.902 | 58.254 | 1.00 | 57.12 | chnC |
| ATOM | 2778 | CG | ASN | C | 14 | 138.048 | 41.998 | 57.752 | 1.00 | 62.38 | chnC |
| ATOM | 2779 | OD1 | ASN | C | 14 | 137.169 | 41.753 | 56.916 | 1.00 | 66.51 | chnC |
| ATOM | 2780 | ND2 | ASN | C | 14 | 138.252 | 43.223 | 58.243 | 1.00 | 64.14 | chnC |
| ATOM | 2781 | C | ASN | C | 14 | 137.226 | 39.127 | 58.528 | 1.00 | 53.30 | chnC |
| ATOM | 2782 | O | ASN | C | 14 | 137.224 | 38.857 | 59.733 | 1.00 | 54.60 | chnC |
| ATOM | 2783 | N | ARG | C | 15 | 136.122 | 39.142 | 57.776 | 1.00 | 48.42 | chnC |
| ATOM | 2784 | CA | ARG | C | 15 | 134.802 | 38.768 | 58.283 | 1.00 | 43.07 | chnC |
| ATOM | 2785 | CB | ARG | C | 15 | 133.758 | 39.820 | 57.904 | 1.00 | 42.60 | chnC |
| ATOM | 2786 | CG | ARG | C | 15 | 134.207 | 41.245 | 58.094 | 1.00 | 45.48 | chnC |
| ATOM | 2787 | CD | ARG | C | 15 | 133.128 | 42.243 | 57.722 | 1.00 | 45.86 | chnC |
| ATOM | 2788 | NE | ARG | C | 15 | 132.302 | 42.628 | 58.862 | 1.00 | 48.44 | chnC |
| ATOM | 2789 | CZ | ARG | C | 15 | 130.990 | 42.826 | 58.796 | 1.00 | 51.11 | chnC |
| ATOM | 2790 | NH1 | ARG | C | 15 | 130.355 | 42.668 | 57.644 | 1.00 | 54.67 | chnC |
| ATOM | 2791 | NH2 | ARG | C | 15 | 130.311 | 43.207 | 59.870 | 1.00 | 53.48 | chnC |
| ATOM | 2792 | C | ARG | C | 15 | 134.435 | 37.447 | 57.615 | 1.00 | 40.26 | chnC |
| ATOM | 2793 | O | ARG | C | 15 | 134.379 | 37.368 | 56.393 | 1.00 | 40.27 | chnC |
| ATOM | 2794 | N | ILE | C | 16 | 134.213 | 36.404 | 58.405 | 1.00 | 36.86 | chnC |
| ATOM | 2795 | CA | ILE | C | 16 | 133.852 | 35.111 | 57.829 | 1.00 | 38.83 | chnC |
| ATOM | 2796 | CB | ILE | C | 16 | 135.055 | 34.142 | 57.768 | 1.00 | 40.33 | chnC |
| ATOM | 2797 | CG2 | ILE | C | 16 | 136.247 | 34.820 | 57.112 | 1.00 | 38.92 | chnC |
| ATOM | 2798 | CG1 | ILE | C | 16 | 135.434 | 33.664 | 59.166 | 1.00 | 39.93 | chnC |
| ATOM | 2799 | CD1 | ILE | C | 16 | 136.556 | 32.675 | 59.154 | 1.00 | 40.62 | chnC |
| ATOM | 2800 | C | ILE | C | 16 | 132.726 | 34.432 | 58.595 | 1.00 | 38.66 | chnC |
| ATOM | 2801 | O | ILE | C | 16 | 132.372 | 34.861 | 59.696 | 1.00 | 38.67 | chnC |
| ATOM | 2802 | N | PHE | C | 17 | 132.170 | 33.379 | 58.003 | 1.00 | 38.61 | chnC |
| ATOM | 2803 | CA | PHE | C | 17 | 131.086 | 32.634 | 58.620 | 1.00 | 44.50 | chnC |
| ATOM | 2804 | CB | PHE | C | 17 | 130.201 | 31.984 | 57.554 | 1.00 | 48.33 | chnC |
| ATOM | 2805 | CG | PHE | C | 17 | 129.174 | 32.899 | 56.969 | 1.00 | 52.73 | chnC |
| ATOM | 2806 | CD1 | PHE | C | 17 | 129.013 | 32.986 | 55.592 | 1.00 | 54.75 | chnC |
| ATOM | 2807 | CD2 | PHE | C | 17 | 128.336 | 33.642 | 57.789 | 1.00 | 56.14 | chnC |
| ATOM | 2808 | CE1 | PHE | C | 17 | 128.031 | 33.795 | 55.035 | 1.00 | 56.28 | chnC |
| ATOM | 2809 | CE2 | PHE | C | 17 | 127.348 | 34.456 | 57.242 | 1.00 | 57.60 | chnC |
| ATOM | 2810 | CZ | PHE | C | 17 | 127.196 | 34.530 | 55.858 | 1.00 | 58.04 | chnC |
| ATOM | 2811 | C | PHE | C | 17 | 131.574 | 31.553 | 59.578 | 1.00 | 46.01 | chnC |
| ATOM | 2812 | O | PHE | C | 17 | 132.714 | 31.100 | 59.506 | 1.00 | 44.82 | chnC |
| ATOM | 2813 | N | LYS | C | 18 | 130.675 | 31.137 | 60.465 | 1.00 | 49.21 | chnC |
| ATOM | 2814 | CA | LYS | C | 18 | 130.957 | 30.102 | 61.435 | 1.00 | 49.79 | chnC |
| ATOM | 2815 | CB | LYS | C | 18 | 129.776 | 29.988 | 62.406 | 1.00 | 54.02 | chnC |
| ATOM | 2816 | CG | LYS | C | 18 | 129.916 | 28.949 | 63.519 | 1.00 | 60.77 | chnC |
| ATOM | 2817 | CD | LYS | C | 18 | 128.645 | 28.929 | 64.394 | 1.00 | 66.85 | chnC |
| ATOM | 2818 | CE | LYS | C | 18 | 128.724 | 27.938 | 65.562 | 1.00 | 68.58 | chnC |
| ATOM | 2819 | NZ | LYS | C | 18 | 128.749 | 26.509 | 65.124 | 1.00 | 74.41 | chnC |
| ATOM | 2820 | C | LYS | C | 18 | 131.127 | 28.812 | 60.650 | 1.00 | 50.32 | chnC |
| ATOM | 2821 | O | LYS | C | 18 | 130.224 | 28.382 | 59.937 | 1.00 | 54.35 | chnC |
| ATOM | 2822 | N | GLY | C | 19 | 132.318 | 28.241 | 60.707 | 1.00 | 50.96 | chnC |
| ATOM | 2823 | CA | GLY | C | 19 | 132.544 | 26.990 | 60.015 | 1.00 | 52.60 | chnC |
| ATOM | 2824 | C | GLY | C | 19 | 133.436 | 27.108 | 58.808 | 1.00 | 53.39 | chnC |
| ATOM | 2825 | O | GLY | C | 19 | 133.796 | 26.090 | 58.207 | 1.00 | 53.59 | chnC |
| ATOM | 2826 | N | GLU | C | 20 | 133.791 | 28.340 | 58.444 | 1.00 | 53.41 | chnC |

-continued

| | | | | | | | | | | |
|---|---|---|---|---|---|---|---|---|---|---|
| ATOM | 2827 | CA | GLU | C | 20 | 134.652 | 28.560 | 57.289 | 1.00 | 55.16 chnC |
| ATOM | 2828 | CB | GLU | C | 20 | 134.338 | 29.897 | 56.617 | 1.00 | 53.85 chnC |
| ATOM | 2829 | CG | GLU | C | 20 | 132.910 | 29.966 | 56.133 | 1.00 | 57.45 chnC |
| ATOM | 2830 | CD | GLU | C | 20 | 132.694 | 30.974 | 55.041 | 1.00 | 58.56 chnC |
| ATOM | 2831 | OE1 | GLU | C | 20 | 133.227 | 32.093 | 55.132 | 1.00 | 58.92 chnC |
| ATOM | 2832 | OE2 | GLU | C | 20 | 131.968 | 30.645 | 54.090 | 1.00 | 58.82 chnC |
| ATOM | 2833 | C | GLU | C | 20 | 136.125 | 28.455 | 57.646 | 1.00 | 57.85 chnC |
| ATOM | 2834 | O | GLU | C | 20 | 136.481 | 28.224 | 58.803 | 1.00 | 56.16 chnC |
| ATOM | 2835 | N | ASN | C | 21 | 136.978 | 28.600 | 56.638 | 1.00 | 63.65 chnC |
| ATOM | 2836 | CA | ASN | C | 21 | 138.422 | 28.498 | 56.823 | 1.00 | 67.84 chnC |
| ATOM | 2837 | CB | ASN | C | 21 | 138.966 | 27.303 | 56.036 | 1.00 | 70.58 chnC |
| ATOM | 2838 | CG | ASN | C | 21 | 138.288 | 26.014 | 56.412 | 1.00 | 76.14 chnC |
| ATOM | 2839 | OD1 | ASN | C | 21 | 137.902 | 25.833 | 57.564 | 1.00 | 75.30 chnC |
| ATOM | 2840 | ND2 | ASN | C | 21 | 138.118 | 25.115 | 55.451 | 1.00 | 82.70 chnC |
| ATOM | 2841 | C | ASN | C | 21 | 139.154 | 29.751 | 56.391 | 1.00 | 68.01 chnC |
| ATOM | 2842 | O | ASN | C | 21 | 138.747 | 30.427 | 55.448 | 1.00 | 70.09 chnC |
| ATOM | 2843 | N | VAL | C | 22 | 140.251 | 30.038 | 57.079 | 1.00 | 67.41 chnC |
| ATOM | 2844 | CA | VAL | C | 22 | 141.072 | 31.199 | 56.780 | 1.00 | 67.27 chnC |
| ATOM | 2845 | CB | VAL | C | 22 | 140.522 | 32.489 | 57.444 | 1.00 | 67.55 chnC |
| ATOM | 2846 | CG1 | VAL | C | 22 | 140.550 | 32.376 | 58.964 | 1.00 | 67.81 chnC |
| ATOM | 2847 | CG2 | VAL | C | 22 | 141.307 | 33.701 | 56.975 | 1.00 | 65.25 chnC |
| ATOM | 2848 | C | VAL | C | 22 | 142.494 | 30.925 | 57.249 | 1.00 | 69.13 chnC |
| ATOM | 2849 | O | VAL | C | 22 | 142.709 | 30.238 | 58.254 | 1.00 | 68.34 chnC |
| ATOM | 2850 | N | THR | C | 23 | 143.461 | 31.442 | 56.495 | 1.00 | 70.52 chnC |
| ATOM | 2851 | CA | THR | C | 23 | 144.871 | 31.250 | 56.813 | 1.00 | 70.05 chnC |
| ATOM | 2852 | CB | THR | C | 23 | 145.554 | 30.389 | 55.747 | 1.00 | 70.89 chnC |
| ATOM | 2853 | OG1 | THR | C | 23 | 144.825 | 29.163 | 55.580 | 1.00 | 70.90 chnC |
| ATOM | 2854 | CG2 | THR | C | 23 | 146.992 | 30.086 | 56.155 | 1.00 | 70.26 chnC |
| ATOM | 2855 | C | THR | C | 23 | 145.618 | 32.574 | 56.926 | 1.00 | 70.34 chnC |
| ATOM | 2856 | O | THR | C | 23 | 145.737 | 33.330 | 55.954 | 1.00 | 68.17 chnC |
| ATOM | 2857 | N | LEU | C | 24 | 146.127 | 32.844 | 58.122 | 1.00 | 71.35 chnC |
| ATOM | 2858 | CA | LEU | C | 24 | 146.860 | 34.076 | 58.370 | 1.00 | 75.51 chnC |
| ATOM | 2859 | CB | LEU | C | 24 | 146.685 | 34.535 | 59.822 | 1.00 | 74.84 chnC |
| ATOM | 2860 | CG | LEU | C | 24 | 145.401 | 34.174 | 60.575 | 1.00 | 74.72 chnC |
| ATOM | 2861 | CD1 | LEU | C | 24 | 145.383 | 34.962 | 61.854 | 1.00 | 74.70 chnC |
| ATOM | 2862 | CD2 | LEU | C | 24 | 144.150 | 34.480 | 59.768 | 1.00 | 78.09 chnC |
| ATOM | 2863 | C | LEU | C | 24 | 148.329 | 33.832 | 58.080 | 1.00 | 78.35 chnC |
| ATOM | 2864 | O | LEU | C | 24 | 148.930 | 32.903 | 58.620 | 1.00 | 76.42 chnC |
| ATOM | 2865 | N | THR | C | 25 | 148.895 | 34.664 | 57.210 | 1.00 | 83.46 chnC |
| ATOM | 2866 | CA | THR | C | 25 | 150.298 | 34.551 | 56.820 | 1.00 | 86.93 chnC |
| ATOM | 2867 | CB | THR | C | 25 | 150.446 | 34.443 | 55.291 | 1.00 | 88.00 chnC |
| ATOM | 2868 | OG1 | THR | C | 25 | 149.618 | 33.379 | 54.799 | 1.00 | 91.06 chnC |
| ATOM | 2869 | CG2 | THR | C | 25 | 151.891 | 34.161 | 54.923 | 1.00 | 89.13 chnC |
| ATOM | 2870 | C | THR | C | 25 | 151.124 | 35.740 | 57.297 | 1.00 | 88.25 chnC |
| ATOM | 2871 | O | THR | C | 25 | 150.801 | 36.895 | 57.028 | 1.00 | 87.76 chnC |
| ATOM | 2872 | N | CYS | C | 26 | 152.195 | 35.436 | 58.016 | 1.00 | 91.78 chnC |
| ATOM | 2873 | CA | CYS | C | 26 | 153.096 | 36.452 | 58.535 | 1.00 | 96.25 chnC |
| ATOM | 2874 | C | CYS | C | 26 | 154.082 | 36.821 | 57.429 | 1.00 | 98.31 chnC |
| ATOM | 2875 | O | CYS | C | 26 | 154.688 | 35.935 | 56.810 | 1.00 | 99.92 chnC |
| ATOM | 2876 | CB | CYS | C | 26 | 153.840 | 35.897 | 59.748 | 1.00 | 96.52 chnC |
| ATOM | 2877 | SG | CYS | C | 26 | 154.829 | 37.109 | 60.683 | 1.00 | 100.58 chnC |
| ATOM | 2878 | N | ASN | C | 27 | 154.237 | 38.125 | 57.193 | 1.00 | 99.60 chnC |
| ATOM | 2879 | CA | ASN | C | 27 | 155.122 | 38.659 | 56.152 | 1.00 | 101.14 chnC |
| ATOM | 2880 | CB | ASN | C | 27 | 155.334 | 40.168 | 56.352 | 1.00 | 102.98 chnC |
| ATOM | 2881 | CG | ASN | C | 27 | 155.934 | 40.859 | 55.119 | 1.00 | 104.78 chnC |
| ATOM | 2882 | OD1 | ASN | C | 27 | 155.720 | 40.430 | 53.977 | 1.00 | 104.94 chnC |
| ATOM | 2883 | ND2 | ASN | C | 27 | 156.675 | 41.949 | 55.351 | 1.00 | 104.52 chnC |
| ATOM | 2884 | C | ASN | C | 27 | 156.478 | 37.960 | 56.091 | 1.00 | 101.51 chnC |
| ATOM | 2885 | O | ASN | C | 27 | 157.161 | 37.815 | 57.114 | 1.00 | 103.12 chnC |
| ATOM | 2886 | N | GLY | C | 28 | 156.855 | 37.544 | 54.879 | 0.50 | 99.82 chnC |
| ATOM | 2887 | CA | GLY | C | 28 | 158.121 | 36.864 | 54.660 | 0.50 | 95.55 chnC |
| ATOM | 2888 | C | GLY | C | 28 | 158.922 | 37.466 | 53.520 | 0.50 | 93.15 chnC |
| ATOM | 2889 | O | GLY | C | 28 | 158.365 | 37.829 | 52.479 | 0.50 | 92.11 chnC |
| ATOM | 2890 | N | ASN | C | 29 | 160.232 | 37.588 | 53.737 | 0.50 | 90.50 chnC |
| ATOM | 2891 | CA | ASN | C | 29 | 161.180 | 38.148 | 52.764 | 0.50 | 86.53 chnC |
| ATOM | 2892 | CB | ASN | C | 29 | 160.816 | 39.610 | 52.428 | 0.50 | 86.67 chnC |
| ATOM | 2893 | CG | ASN | C | 29 | 160.521 | 40.456 | 53.672 | 0.50 | 86.32 chnC |
| ATOM | 2894 | OD1 | ASN | C | 29 | 159.503 | 40.270 | 54.344 | 0.50 | 85.28 chnC |
| ATOM | 2895 | ND2 | ASN | C | 29 | 161.407 | 41.402 | 53.966 | 0.50 | 87.11 chnC |
| ATOM | 2896 | C | ASN | C | 29 | 162.604 | 38.043 | 53.334 | 0.50 | 84.42 chnC |
| ATOM | 2897 | O | ASN | C | 29 | 163.048 | 36.941 | 53.665 | 0.50 | 84.20 chnC |
| ATOM | 2898 | N | ASN | C | 30 | 163.300 | 39.181 | 53.424 | 0.50 | 79.92 chnC |
| ATOM | 2899 | CA | ASN | C | 30 | 164.663 | 39.309 | 53.975 | 0.50 | 76.50 chnC |
| ATOM | 2900 | CB | ASN | C | 30 | 164.619 | 40.150 | 55.265 | 0.50 | 77.95 chnC |
| ATOM | 2901 | CG | ASN | C | 30 | 165.976 | 40.239 | 55.966 | 0.50 | 78.47 chnC |
| ATOM | 2902 | OD1 | ASN | C | 30 | 166.145 | 39.747 | 57.086 | 0.50 | 77.12 chnC |
| ATOM | 2903 | ND2 | ASN | C | 30 | 166.944 | 40.870 | 55.306 | 0.50 | 78.30 chnC |
| ATOM | 2904 | C | ASN | C | 30 | 165.463 | 38.030 | 54.235 | 0.50 | 73.93 chnC |
| ATOM | 2905 | O | ASN | C | 30 | 166.352 | 37.678 | 53.459 | 0.50 | 73.08 chnC |

-continued

| | | | | | | | | | | |
|---|---|---|---|---|---|---|---|---|---|---|
| ATOM | 2906 | N | GLY | C | 31 | 165.181 | 37.383 | 55.366 | 0.50 | 70.96 chnC |
| ATOM | 2907 | CA | GLY | C | 31 | 165.873 | 36.160 | 55.726 | 0.50 | 68.13 chnC |
| ATOM | 2908 | C | GLY | C | 31 | 164.928 | 35.102 | 56.261 | 0.50 | 66.93 chnC |
| ATOM | 2909 | O | GLY | C | 31 | 164.596 | 34.142 | 55.563 | 0.50 | 65.31 chnC |
| ATOM | 2910 | N | VAL | C | 34 | 164.329 | 32.009 | 57.649 | 0.50 | 102.12 chnC |
| ATOM | 2911 | CA | VAL | C | 34 | 163.728 | 30.953 | 58.455 | 0.50 | 103.18 chnC |
| ATOM | 2912 | CB | VAL | C | 34 | 163.904 | 29.559 | 57.788 | 0.50 | 103.73 chnC |
| ATOM | 2913 | CG1 | VAL | C | 34 | 163.261 | 28.460 | 58.655 | 0.50 | 102.57 chnC |
| ATOM | 2914 | CG2 | VAL | C | 34 | 163.299 | 29.563 | 56.384 | 0.50 | 102.62 chnC |
| ATOM | 2915 | C | VAL | C | 34 | 164.339 | 30.914 | 59.853 | 0.50 | 103.50 chnC |
| ATOM | 2916 | O | VAL | C | 34 | 165.557 | 30.790 | 60.006 | 0.50 | 104.04 chnC |
| ATOM | 2917 | N | SER | C | 35 | 163.478 | 30.998 | 60.864 | 0.50 | 103.72 chnC |
| ATOM | 2918 | CA | SER | C | 35 | 163.895 | 30.974 | 62.265 | 0.50 | 104.40 chnC |
| ATOM | 2919 | CB | SER | C | 35 | 164.386 | 32.360 | 62.702 | 0.50 | 104.54 chnC |
| ATOM | 2920 | OG | SER | C | 35 | 163.431 | 33.366 | 62.399 | 0.50 | 104.65 chnC |
| ATOM | 2921 | C | SER | C | 35 | 162.730 | 30.530 | 63.146 | 0.50 | 104.20 chnC |
| ATOM | 2922 | O | SER | C | 35 | 162.738 | 29.423 | 63.691 | 0.50 | 104.19 chnC |
| ATOM | 2923 | N | SER | C | 36 | 161.724 | 31.394 | 63.261 | 0.50 | 104.19 chnC |
| ATOM | 2924 | CA | SER | C | 36 | 160.534 | 31.120 | 64.058 | 0.50 | 104.37 chnC |
| ATOM | 2925 | CB | SER | C | 36 | 160.878 | 31.080 | 65.553 | 0.50 | 103.64 chnC |
| ATOM | 2926 | OG | SER | C | 36 | 161.325 | 32.344 | 66.018 | 0.50 | 102.82 chnC |
| ATOM | 2927 | C | SER | C | 36 | 159.485 | 32.198 | 63.801 | 0.50 | 105.13 chnC |
| ATOM | 2928 | O | SER | C | 36 | 159.792 | 33.269 | 63.268 | 0.50 | 104.88 chnC |
| ATOM | 2929 | N | THR | C | 37 | 158.243 | 31.903 | 64.171 | 1.00 | 105.66 chnC |
| ATOM | 2930 | CA | THR | C | 37 | 157.147 | 32.850 | 64.000 | 1.00 | 105.74 chnC |
| ATOM | 2931 | CB | THR | C | 37 | 156.362 | 32.576 | 62.703 | 0.00 | 105.29 chnC |
| ATOM | 2932 | OG1 | THR | C | 37 | 157.279 | 32.413 | 61.614 | 0.00 | 104.99 chnC |
| ATOM | 2933 | CG2 | THR | C | 37 | 155.429 | 33.736 | 62.391 | 0.00 | 104.90 chnC |
| ATOM | 2934 | C | THR | C | 37 | 156.209 | 32.739 | 65.204 | 1.00 | 105.80 chnC |
| ATOM | 2935 | O | THR | C | 37 | 155.658 | 31.669 | 65.480 | 1.00 | 106.27 chnC |
| ATOM | 2936 | N | LYS | C | 38 | 156.071 | 33.836 | 65.944 | 1.00 | 105.16 chnC |
| ATOM | 2937 | CA | LYS | C | 38 | 155.211 | 33.864 | 67.123 | 1.00 | 103.72 chnC |
| ATOM | 2938 | CB | LYS | C | 38 | 155.861 | 34.696 | 68.227 | 1.00 | 107.73 chnC |
| ATOM | 2939 | CG | LYS | C | 38 | 157.215 | 34.177 | 68.696 | 1.00 | 110.96 chnC |
| ATOM | 2940 | CD | LYS | C | 38 | 157.784 | 35.073 | 69.794 | 1.00 | 112.78 chnC |
| ATOM | 2941 | CE | LYS | C | 38 | 159.111 | 34.550 | 70.326 | 1.00 | 113.01 chnC |
| ATOM | 2942 | NZ | LYS | C | 38 | 159.640 | 35.414 | 71.428 | 1.00 | 112.98 chnC |
| ATOM | 2943 | C | LYS | C | 38 | 153.823 | 34.423 | 66.813 | 1.00 | 101.20 chnC |
| ATOM | 2944 | O | LYS | C | 38 | 153.692 | 35.529 | 66.285 | 1.00 | 100.78 chnC |
| ATOM | 2945 | N | TRP | C | 39 | 152.790 | 33.659 | 67.160 | 1.00 | 96.05 chnC |
| ATOM | 2946 | CA | TRP | C | 39 | 151.407 | 34.075 | 66.928 | 1.00 | 91.96 chnC |
| ATOM | 2947 | CB | TRP | C | 39 | 150.631 | 32.957 | 66.242 | 1.00 | 91.32 chnC |
| ATOM | 2948 | CG | TRP | C | 39 | 150.980 | 32.797 | 64.824 | 1.00 | 90.70 chnC |
| ATOM | 2949 | CD2 | TRP | C | 39 | 150.674 | 33.703 | 63.763 | 1.00 | 90.94 chnC |
| ATOM | 2950 | CE2 | TRP | C | 39 | 151.161 | 33.127 | 62.572 | 1.00 | 91.60 chnC |
| ATOM | 2951 | CE3 | TRP | C | 39 | 150.034 | 34.949 | 63.702 | 1.00 | 90.91 chnC |
| ATOM | 2952 | CD1 | TRP | C | 39 | 151.624 | 31.745 | 64.259 | 1.00 | 90.95 chnC |
| ATOM | 2953 | NE1 | TRP | C | 39 | 151.734 | 31.929 | 62.903 | 1.00 | 91.21 chnC |
| ATOM | 2954 | CZ2 | TRP | C | 39 | 151.024 | 33.748 | 61.328 | 1.00 | 92.40 chnC |
| ATOM | 2955 | CZ3 | TRP | C | 39 | 149.896 | 35.570 | 62.464 | 1.00 | 91.16 chnC |
| ATOM | 2956 | CH2 | TRP | C | 39 | 150.392 | 34.968 | 61.294 | 1.00 | 92.01 chnC |
| ATOM | 2957 | C | TRP | C | 39 | 150.682 | 34.479 | 68.207 | 1.00 | 90.59 chnC |
| ATOM | 2958 | O | TRP | C | 39 | 150.628 | 33.711 | 69.166 | 1.00 | 90.14 chnC |
| ATOM | 2959 | N | PHE | C | 40 | 150.104 | 35.675 | 68.206 | 1.00 | 88.27 chnC |
| ATOM | 2960 | CA | PHE | C | 40 | 149.371 | 36.165 | 69.366 | 1.00 | 85.76 chnC |
| ATOM | 2961 | CB | PHE | C | 40 | 149.955 | 37.499 | 69.839 | 0.00 | 87.30 chnC |
| ATOM | 2962 | CG | PHE | C | 40 | 151.394 | 37.415 | 70.258 | 0.00 | 88.20 chnC |
| ATOM | 2963 | CD1 | PHE | C | 40 | 152.404 | 37.868 | 69.415 | 0.00 | 88.58 chnC |
| ATOM | 2964 | CD2 | PHE | C | 40 | 151.742 | 36.873 | 71.491 | 0.00 | 88.33 chnC |
| ATOM | 2965 | CE1 | PHE | C | 40 | 153.741 | 37.786 | 69.795 | 0.00 | 88.85 chnC |
| ATOM | 2966 | CE2 | PHE | C | 40 | 153.077 | 36.787 | 71.881 | 0.00 | 88.60 chnC |
| ATOM | 2967 | CZ | PHE | C | 40 | 154.078 | 37.243 | 71.030 | 0.00 | 88.73 chnC |
| ATOM | 2968 | C | PHE | C | 40 | 147.873 | 36.326 | 69.082 | 1.00 | 84.60 chnC |
| ATOM | 2969 | O | PHE | C | 40 | 147.474 | 37.153 | 68.253 | 1.00 | 85.55 chnC |
| ATOM | 2970 | N | HIS | C | 41 | 147.055 | 35.514 | 69.753 | 1.00 | 80.81 chnC |
| ATOM | 2971 | CA | HIS | C | 41 | 145.596 | 35.575 | 69.611 | 1.00 | 75.75 chnC |
| ATOM | 2972 | CB | HIS | C | 41 | 145.009 | 34.176 | 69.419 | 1.00 | 75.68 chnC |
| ATOM | 2973 | CG | HIS | C | 41 | 143.520 | 34.165 | 69.242 | 1.00 | 73.89 chnC |
| ATOM | 2974 | CD2 | HIS | C | 41 | 142.636 | 33.138 | 69.214 | 1.00 | 72.38 chnC |
| ATOM | 2975 | ND1 | HIS | C | 41 | 142.783 | 35.314 | 69.049 | 1.00 | 72.47 chnC |
| ATOM | 2976 | CE1 | HIS | C | 41 | 141.507 | 34.997 | 68.907 | 1.00 | 70.44 chnC |
| ATOM | 2977 | NE2 | HIS | C | 41 | 141.392 | 33.685 | 69.003 | 1.00 | 72.43 chnC |
| ATOM | 2978 | C | HIS | C | 41 | 144.997 | 36.218 | 70.864 | 1.00 | 73.25 chnC |
| ATOM | 2979 | O | HIS | C | 41 | 144.959 | 35.603 | 71.930 | 1.00 | 67.59 chnC |
| ATOM | 2980 | N | ASN | C | 42 | 144.512 | 37.447 | 70.712 | 1.00 | 72.21 chnC |
| ATOM | 2981 | CA | ASN | C | 42 | 143.932 | 38.210 | 71.814 | 1.00 | 73.35 chnC |
| ATOM | 2982 | CB | ASN | C | 42 | 142.730 | 37.479 | 72.424 | 1.00 | 69.86 chnC |
| ATOM | 2983 | CG | ASN | C | 42 | 141.461 | 37.640 | 71.610 | 1.00 | 65.36 chnC |
| ATOM | 2984 | OD1 | ASN | C | 42 | 141.338 | 38.557 | 70.806 | 1.00 | 65.10 chnC |

-continued

| | | | | | | | | | | |
|---|---|---|---|---|---|---|---|---|---|---|
| ATOM | 2985 | ND2 | ASN | C | 42 | 140.506 | 36.746 | 71.849 | 1.00 | 60.36 chnC |
| ATOM | 2986 | C | ASN | C | 42 | 144.978 | 38.494 | 72.894 | 1.00 | 74.72 chnC |
| ATOM | 2987 | O | ASN | C | 42 | 144.656 | 38.592 | 74.075 | 1.00 | 77.38 chnC |
| ATOM | 2988 | N | GLY | C | 43 | 146.233 | 38.634 | 72.481 | 1.00 | 77.14 chnC |
| ATOM | 2989 | CA | GLY | C | 43 | 147.293 | 38.910 | 73.433 | 1.00 | 79.64 chnC |
| ATOM | 2990 | C | GLY | C | 43 | 147.999 | 37.660 | 73.911 | 1.00 | 81.19 chnC |
| ATOM | 2991 | O | GLY | C | 43 | 149.171 | 37.719 | 74.277 | 1.00 | 79.71 chnC |
| ATOM | 2992 | N | SER | C | 44 | 147.289 | 36.535 | 73.919 | 1.00 | 83.42 chnC |
| ATOM | 2993 | CA | SER | C | 44 | 147.855 | 35.253 | 74.350 | 1.00 | 87.71 chnC |
| ATOM | 2994 | CB | SER | C | 44 | 146.744 | 34.276 | 74.757 | 1.00 | 89.76 chnC |
| ATOM | 2995 | OG | SER | C | 44 | 145.981 | 34.745 | 75.856 | 1.00 | 92.82 chnC |
| ATOM | 2996 | C | SER | C | 44 | 148.687 | 34.602 | 73.249 | 1.00 | 87.77 chnC |
| ATOM | 2997 | O | SER | C | 44 | 148.305 | 34.625 | 72.081 | 1.00 | 89.53 chnC |
| ATOM | 2998 | N | LEU | C | 45 | 149.806 | 33.992 | 73.627 | 1.00 | 88.88 chnC |
| ATOM | 2999 | CA | LEU | C | 45 | 150.668 | 33.333 | 72.654 | 1.00 | 91.80 chnC |
| ATOM | 3000 | CB | LEU | C | 45 | 152.062 | 33.086 | 73.249 | 1.00 | 93.63 chnC |
| ATOM | 3001 | CG | LEU | C | 45 | 153.115 | 32.425 | 72.346 | 1.00 | 92.97 chnC |
| ATOM | 3002 | CD1 | LEU | C | 45 | 153.443 | 33.327 | 71.169 | 1.00 | 93.28 chnC |
| ATOM | 3003 | CD2 | LEU | C | 45 | 154.364 | 32.125 | 73.145 | 1.00 | 94.28 chnC |
| ATOM | 3004 | C | LEU | C | 45 | 150.056 | 32.010 | 72.190 | 1.00 | 92.23 chnC |
| ATOM | 3005 | O | LEU | C | 45 | 149.703 | 31.164 | 73.009 | 1.00 | 93.00 chnC |
| ATOM | 3006 | N | SER | C | 46 | 149.922 | 31.848 | 70.875 | 1.00 | 92.44 chnC |
| ATOM | 3007 | CA | SER | C | 46 | 149.367 | 30.627 | 70.306 | 1.00 | 94.35 chnC |
| ATOM | 3008 | CB | SER | C | 46 | 148.709 | 30.911 | 68.954 | 1.00 | 95.22 chnC |
| ATOM | 3009 | OG | SER | C | 46 | 148.112 | 29.736 | 68.418 | 1.00 | 97.39 chnC |
| ATOM | 3010 | C | SER | C | 46 | 150.463 | 29.584 | 70.142 | 1.00 | 95.01 chnC |
| ATOM | 3011 | O | SER | C | 46 | 151.625 | 29.923 | 69.927 | 1.00 | 95.19 chnC |
| ATOM | 3012 | N | GLU | C | 47 | 150.076 | 28.316 | 70.205 | 1.00 | 97.56 chnC |
| ATOM | 3013 | CA | GLU | C | 47 | 151.021 | 27.215 | 70.083 | 1.00 | 102.82 chnC |
| ATOM | 3014 | CB | GLU | C | 47 | 150.391 | 25.925 | 70.604 | 1.00 | 106.40 chnC |
| ATOM | 3015 | CG | GLU | C | 47 | 149.973 | 26.009 | 72.067 | 1.00 | 113.48 chnC |
| ATOM | 3016 | CD | GLU | C | 47 | 149.364 | 24.718 | 72.583 | 1.00 | 116.42 chnC |
| ATOM | 3017 | OE1 | GLU | C | 47 | 148.125 | 24.557 | 72.468 | 1.00 | 118.51 chnC |
| ATOM | 3018 | OE2 | GLU | C | 47 | 150.129 | 23.867 | 73.103 | 1.00 | 119.06 chnC |
| ATOM | 3019 | C | GLU | C | 47 | 151.558 | 27.002 | 68.675 | 1.00 | 103.72 chnC |
| ATOM | 3020 | O | GLU | C | 47 | 152.248 | 26.013 | 68.413 | 1.00 | 103.55 chnC |
| ATOM | 3021 | N | GLU | C | 48 | 151.253 | 27.933 | 67.774 | 1.00 | 105.97 chnC |
| ATOM | 3022 | CA | GLU | C | 48 | 151.718 | 27.842 | 66.394 | 1.00 | 108.23 chnC |
| ATOM | 3023 | CB | GLU | C | 48 | 150.711 | 28.492 | 65.446 | 1.00 | 109.67 chnC |
| ATOM | 3024 | CG | GLU | C | 48 | 151.017 | 28.276 | 63.963 | 1.00 | 111.67 chnC |
| ATOM | 3025 | CD | GLU | C | 48 | 150.855 | 26.820 | 63.518 | 1.00 | 112.57 chnC |
| ATOM | 3026 | OE1 | GLU | C | 48 | 149.798 | 26.495 | 62.921 | 1.00 | 112.83 chnC |
| ATOM | 3027 | OE2 | GLU | C | 48 | 151.785 | 26.009 | 63.756 | 1.00 | 112.21 chnC |
| ATOM | 3028 | C | GLU | C | 48 | 153.086 | 28.498 | 66.230 | 1.00 | 109.58 chnC |
| ATOM | 3029 | O | GLU | C | 48 | 153.368 | 29.539 | 66.834 | 1.00 | 108.60 chnC |
| ATOM | 3030 | N | THR | C | 49 | 153.923 | 27.883 | 65.395 | 1.00 | 111.51 chnC |
| ATOM | 3031 | CA | THR | C | 49 | 155.281 | 28.371 | 65.134 | 1.00 | 112.47 chnC |
| ATOM | 3032 | CB | THR | C | 49 | 156.342 | 27.369 | 65.663 | 1.00 | 112.55 chnC |
| ATOM | 3033 | OG1 | THR | C | 49 | 156.057 | 26.054 | 65.162 | 1.00 | 111.38 chnC |
| ATOM | 3034 | CG2 | THR | C | 49 | 156.347 | 27.350 | 67.195 | 1.00 | 111.60 chnC |
| ATOM | 3035 | C | THR | C | 49 | 155.587 | 28.700 | 63.660 | 1.00 | 113.59 chnC |
| ATOM | 3036 | O | THR | C | 49 | 156.559 | 29.413 | 63.370 | 1.00 | 113.06 chnC |
| ATOM | 3037 | N | ASN | C | 50 | 154.769 | 28.182 | 62.741 | 1.00 | 113.60 chnC |
| ATOM | 3038 | CA | ASN | C | 50 | 154.951 | 28.434 | 61.307 | 1.00 | 113.66 chnC |
| ATOM | 3039 | CB | ASN | C | 50 | 154.090 | 27.471 | 60.477 | 1.00 | 112.94 chnC |
| ATOM | 3040 | CG | ASN | C | 50 | 154.507 | 26.019 | 60.637 | 1.00 | 113.06 chnC |
| ATOM | 3041 | OD1 | ASN | C | 50 | 155.623 | 25.637 | 60.287 | 1.00 | 112.73 chnC |
| ATOM | 3042 | ND2 | ASN | C | 50 | 153.598 | 25.197 | 61.150 | 1.00 | 113.65 chnC |
| ATOM | 3043 | C | ASN | C | 50 | 154.601 | 29.882 | 60.926 | 1.00 | 113.86 chnC |
| ATOM | 3044 | O | ASN | C | 50 | 154.023 | 30.626 | 61.724 | 1.00 | 115.50 chnC |
| ATOM | 3045 | N | SER | C | 51 | 154.957 | 30.282 | 59.706 | 1.00 | 113.35 chnC |
| ATOM | 3046 | CA | SER | C | 51 | 154.663 | 31.637 | 59.228 | 1.00 | 110.97 chnC |
| ATOM | 3047 | CB | SER | C | 51 | 155.582 | 32.010 | 58.052 | 1.00 | 111.80 chnC |
| ATOM | 3048 | OG | SER | C | 51 | 155.405 | 31.135 | 56.945 | 1.00 | 111.66 chnC |
| ATOM | 3049 | C | SER | C | 51 | 153.196 | 31.752 | 58.806 | 1.00 | 108.77 chnC |
| ATOM | 3050 | O | SER | C | 51 | 152.725 | 32.839 | 58.458 | 1.00 | 108.12 chnC |
| ATOM | 3051 | N | SER | C | 52 | 152.485 | 30.623 | 58.846 | 1.00 | 104.50 chnC |
| ATOM | 3052 | CA | SER | C | 52 | 151.075 | 30.575 | 58.470 | 1.00 | 98.90 chnC |
| ATOM | 3053 | CB | SER | C | 52 | 150.911 | 29.977 | 57.066 | 1.00 | 98.88 chnC |
| ATOM | 3054 | OG | SER | C | 52 | 151.442 | 30.845 | 56.076 | 1.00 | 97.36 chnC |
| ATOM | 3055 | C | SER | C | 52 | 150.199 | 29.812 | 59.460 | 1.00 | 95.97 chnC |
| ATOM | 3056 | O | SER | C | 52 | 150.323 | 28.590 | 59.614 | 1.00 | 93.65 chnC |
| ATOM | 3057 | N | LEU | C | 53 | 149.312 | 30.551 | 60.122 | 1.00 | 91.18 chnC |
| ATOM | 3058 | CA | LEU | C | 53 | 148.379 | 29.984 | 61.088 | 1.00 | 87.43 chnC |
| ATOM | 3059 | CB | LEU | C | 53 | 148.091 | 31.004 | 62.198 | 1.00 | 86.88 chnC |
| ATOM | 3060 | CG | LEU | C | 53 | 147.017 | 30.699 | 63.246 | 1.00 | 86.07 chnC |
| ATOM | 3061 | CD1 | LEU | C | 53 | 147.261 | 29.353 | 63.902 | 1.00 | 85.91 chnC |
| ATOM | 3062 | CD2 | LEU | C | 53 | 147.001 | 31.797 | 64.289 | 1.00 | 85.44 chnC |
| ATOM | 3063 | C | LEU | C | 53 | 147.085 | 29.589 | 60.366 | 1.00 | 85.61 chnC |

-continued

| | | | | | | | | | | |
|---|---|---|---|---|---|---|---|---|---|---|
| ATOM | 3064 | O | LEU | C | 53 | 146.412 | 30.430 | 59.757 | 1.00 | 84.32 chnC |
| ATOM | 3065 | N | ASN | C | 54 | 146.760 | 28.301 | 60.411 | 1.00 | 83.05 chnC |
| ATOM | 3066 | CA | ASN | C | 54 | 145.556 | 27.797 | 59.764 | 1.00 | 82.72 chnC |
| ATOM | 3067 | CB | ASN | C | 54 | 145.817 | 26.425 | 59.139 | 1.00 | 87.38 chnC |
| ATOM | 3068 | CG | ASN | C | 54 | 146.707 | 26.500 | 57.919 | 1.00 | 91.31 chnC |
| ATOM | 3069 | OD1 | ASN | C | 54 | 146.339 | 27.092 | 56.899 | 1.00 | 93.31 chnC |
| ATOM | 3070 | ND2 | ASN | C | 54 | 147.888 | 25.892 | 58.012 | 1.00 | 95.40 chnC |
| ATOM | 3071 | C | ASN | C | 54 | 144.357 | 27.693 | 60.699 | 1.00 | 80.32 chnC |
| ATOM | 3072 | O | ASN | C | 54 | 144.414 | 27.002 | 61.721 | 1.00 | 83.07 chnC |
| ATOM | 3073 | N | ILE | C | 55 | 143.275 | 28.381 | 60.341 | 1.00 | 73.22 chnC |
| ATOM | 3074 | CA | ILE | C | 55 | 142.047 | 28.343 | 61.120 | 1.00 | 65.36 chnC |
| ATOM | 3075 | CB | ILE | C | 55 | 141.470 | 29.751 | 61.325 | 1.00 | 62.66 chnC |
| ATOM | 3076 | CG2 | ILE | C | 55 | 140.172 | 29.678 | 62.092 | 1.00 | 62.42 chnC |
| ATOM | 3077 | CG1 | ILE | C | 55 | 142.470 | 30.609 | 62.096 | 1.00 | 59.48 chnC |
| ATOM | 3078 | CD1 | ILE | C | 55 | 142.005 | 32.024 | 62.328 | 1.00 | 59.61 chnC |
| ATOM | 3079 | C | ILE | C | 55 | 141.064 | 27.469 | 60.347 | 1.00 | 64.19 chnC |
| ATOM | 3080 | O | ILE | C | 55 | 140.819 | 27.702 | 59.164 | 1.00 | 60.40 chnC |
| ATOM | 3081 | N | VAL | C | 56 | 140.552 | 26.433 | 61.007 | 1.00 | 63.92 chnC |
| ATOM | 3082 | CA | VAL | C | 56 | 139.606 | 25.501 | 60.392 | 1.00 | 67.91 chnC |
| ATOM | 3083 | CB | VAL | C | 56 | 140.223 | 24.094 | 60.277 | 1.00 | 66.65 chnC |
| ATOM | 3084 | CG1 | VAL | C | 56 | 139.211 | 23.110 | 59.698 | 1.00 | 67.39 chnC |
| ATOM | 3085 | CG2 | VAL | C | 56 | 141.474 | 24.145 | 59.414 | 1.00 | 68.21 chnC |
| ATOM | 3086 | C | VAL | C | 56 | 138.311 | 25.409 | 61.196 | 1.00 | 70.40 chnC |
| ATOM | 3087 | O | VAL | C | 56 | 138.342 | 25.445 | 62.432 | 1.00 | 74.58 chnC |
| ATOM | 3088 | N | ASN | C | 57 | 137.188 | 25.260 | 60.488 | 1.00 | 71.82 chnC |
| ATOM | 3089 | CA | ASN | C | 57 | 135.857 | 25.175 | 61.100 | 1.00 | 72.32 chnC |
| ATOM | 3090 | CB | ASN | C | 57 | 135.653 | 23.827 | 61.803 | 1.00 | 76.53 chnC |
| ATOM | 3091 | CG | ASN | C | 57 | 135.437 | 22.689 | 60.833 | 1.00 | 80.10 chnC |
| ATOM | 3092 | OD1 | ASN | C | 57 | 134.670 | 22.807 | 59.875 | 1.00 | 82.73 chnC |
| ATOM | 3093 | ND2 | ASN | C | 57 | 136.105 | 21.569 | 61.083 | 1.00 | 83.72 chnC |
| ATOM | 3094 | C | ASN | C | 57 | 135.652 | 26.327 | 62.083 | 1.00 | 71.50 chnC |
| ATOM | 3095 | O | ASN | C | 57 | 135.190 | 26.129 | 63.210 | 1.00 | 70.98 chnC |
| ATOM | 3096 | N | ALA | C | 58 | 135.986 | 27.529 | 61.619 | 1.00 | 69.35 chnC |
| ATOM | 3097 | CA | ALA | C | 58 | 135.900 | 28.760 | 62.397 | 1.00 | 69.15 chnC |
| ATOM | 3098 | CB | ALA | C | 58 | 135.875 | 29.952 | 61.478 | 1.00 | 67.65 chnC |
| ATOM | 3099 | C | ALA | C | 58 | 134.752 | 28.849 | 63.386 | 1.00 | 71.07 chnC |
| ATOM | 3100 | O | ALA | C | 58 | 133.583 | 28.697 | 63.027 | 1.00 | 73.59 chnC |
| ATOM | 3101 | N | LYS | C | 59 | 135.109 | 29.089 | 64.641 | 1.00 | 71.92 chnC |
| ATOM | 3102 | CA | LYS | C | 59 | 134.146 | 29.222 | 65.722 | 1.00 | 71.60 chnC |
| ATOM | 3103 | CB | LYS | C | 59 | 134.570 | 28.347 | 66.906 | 1.00 | 76.51 chnC |
| ATOM | 3104 | CG | LYS | C | 59 | 134.902 | 26.909 | 66.518 | 1.00 | 81.96 chnC |
| ATOM | 3105 | CD | LYS | C | 59 | 135.627 | 26.171 | 67.633 | 1.00 | 86.65 chnC |
| ATOM | 3106 | CE | LYS | C | 59 | 136.196 | 24.842 | 67.134 | 1.00 | 89.82 chnC |
| ATOM | 3107 | NZ | LYS | C | 59 | 137.006 | 24.133 | 68.173 | 1.00 | 92.33 chnC |
| ATOM | 3108 | C | LYS | C | 59 | 134.161 | 30.684 | 66.128 | 1.00 | 67.84 chnC |
| ATOM | 3109 | O | LYS | C | 59 | 135.076 | 31.413 | 65.772 | 1.00 | 63.60 chnC |
| ATOM | 3110 | N | PHE | C | 60 | 133.145 | 31.117 | 66.862 | 1.00 | 65.89 chnC |
| ATOM | 3111 | CA | PHE | C | 60 | 133.086 | 32.504 | 67.311 | 1.00 | 65.52 chnC |
| ATOM | 3112 | CB | PHE | C | 60 | 131.842 | 32.734 | 68.164 | 1.00 | 67.17 chnC |
| ATOM | 3113 | CG | PHE | C | 60 | 130.564 | 32.613 | 67.407 | 1.00 | 68.05 chnC |
| ATOM | 3114 | CD1 | PHE | C | 60 | 129.821 | 31.438 | 67.449 | 1.00 | 68.38 chnC |
| ATOM | 3115 | CD2 | PHE | C | 60 | 130.097 | 33.675 | 66.652 | 1.00 | 68.29 chnC |
| ATOM | 3116 | CE1 | PHE | C | 60 | 128.628 | 31.329 | 66.751 | 1.00 | 68.68 chnC |
| ATOM | 3117 | CE2 | PHE | C | 60 | 128.905 | 33.575 | 65.951 | 1.00 | 69.48 chnC |
| ATOM | 3118 | CZ | PHE | C | 60 | 128.170 | 32.398 | 66.000 | 1.00 | 68.58 chnC |
| ATOM | 3119 | C | PHE | C | 60 | 134.328 | 32.814 | 68.131 | 1.00 | 65.98 chnC |
| ATOM | 3120 | O | PHE | C | 60 | 134.880 | 33.908 | 68.057 | 1.00 | 64.14 chnC |
| ATOM | 3121 | N | GLU | C | 61 | 134.780 | 31.810 | 68.878 | 1.00 | 68.83 chnC |
| ATOM | 3122 | CA | GLU | C | 61 | 135.957 | 31.910 | 69.732 | 1.00 | 70.38 chnC |
| ATOM | 3123 | CB | GLU | C | 61 | 136.226 | 30.557 | 70.412 | 1.00 | 76.25 chnC |
| ATOM | 3124 | CG | GLU | C | 61 | 135.226 | 30.169 | 71.531 | 1.00 | 87.30 chnC |
| ATOM | 3125 | CD | GLU | C | 61 | 133.751 | 30.061 | 71.072 | 1.00 | 91.85 chnC |
| ATOM | 3126 | OE1 | GLU | C | 61 | 133.436 | 29.229 | 70.174 | 1.00 | 92.80 chnC |
| ATOM | 3127 | OE2 | GLU | C | 61 | 132.904 | 30.803 | 71.637 | 1.00 | 94.20 chnC |
| ATOM | 3128 | C | GLU | C | 61 | 137.189 | 32.349 | 68.951 | 1.00 | 66.44 chnC |
| ATOM | 3129 | O | GLU | C | 61 | 138.053 | 33.035 | 69.490 | 1.00 | 67.40 chnC |
| ATOM | 3130 | N | ASP | C | 62 | 137.246 | 31.981 | 67.672 | 1.00 | 60.55 chnC |
| ATOM | 3131 | CA | ASP | C | 62 | 138.375 | 32.325 | 66.822 | 1.00 | 54.34 chnC |
| ATOM | 3132 | CB | ASP | C | 62 | 138.385 | 31.457 | 65.574 | 1.00 | 56.99 chnC |
| ATOM | 3133 | CG | ASP | C | 62 | 138.633 | 30.008 | 65.892 | 1.00 | 61.08 chnC |
| ATOM | 3134 | OD1 | ASP | C | 62 | 139.473 | 29.723 | 66.774 | 1.00 | 62.89 chnC |
| ATOM | 3135 | OD2 | ASP | C | 62 | 137.980 | 29.150 | 65.271 | 1.00 | 64.17 chnC |
| ATOM | 3136 | C | ASP | C | 62 | 138.443 | 33.783 | 66.444 | 1.00 | 51.03 chnC |
| ATOM | 3137 | O | ASP | C | 62 | 139.446 | 34.241 | 65.916 | 1.00 | 48.83 chnC |
| ATOM | 3138 | N | SER | C | 63 | 137.382 | 34.520 | 66.730 | 1.00 | 49.42 chnC |
| ATOM | 3139 | CA | SER | C | 63 | 137.361 | 35.938 | 66.415 | 1.00 | 55.65 chnC |
| ATOM | 3140 | CB | SER | C | 63 | 135.967 | 36.510 | 66.675 | 1.00 | 56.51 chnC |
| ATOM | 3187 | CG | GLN | C | 69 | 157.843 | 39.017 | 67.546 | 1.00 | 114.53 chnC |
| ATOM | 3188 | CD | GLN | C | 69 | 157.944 | 39.108 | 69.063 | 1.00 | 116.32 chnC |

-continued

| ATOM | 3189 | OE1 | GLN | C | 69 | 156.941 | 39.319 | 69.755 | 1.00 | 118.25 | chnC |
| ATOM | 3190 | NE2 | GLN | C | 69 | 159.157 | 38.945 | 69.588 | 1.00 | 117.20 | chnC |
| ATOM | 3191 | C | GLN | C | 69 | 157.611 | 37.214 | 65.033 | 1.00 | 109.33 | chnC |
| ATOM | 3192 | O | GLN | C | 69 | 157.595 | 35.986 | 65.174 | 1.00 | 109.78 | chnC |
| ATOM | 3193 | N | HIS | C | 70 | 158.592 | 37.860 | 64.414 | 1.00 | 109.84 | chnC |
| ATOM | 3194 | CA | HIS | C | 70 | 159.734 | 37.157 | 63.851 | 1.00 | 109.73 | chnC |
| ATOM | 3195 | CB | HIS | C | 70 | 159.953 | 37.628 | 62.405 | 0.00 | 108.43 | chnC |
| ATOM | 3196 | CG | HIS | C | 70 | 160.808 | 36.712 | 61.582 | 0.00 | 107.78 | chnC |
| ATOM | 3197 | CD2 | HIS | C | 70 | 161.973 | 36.930 | 60.929 | 0.00 | 107.33 | chnC |
| ATOM | 3198 | ND1 | HIS | C | 70 | 160.466 | 35.401 | 61.328 | 0.00 | 107.18 | chnC |
| ATOM | 3199 | CE1 | HIS | C | 70 | 161.383 | 34.852 | 60.553 | 0.00 | 107.09 | chnC |
| ATOM | 3200 | NE2 | HIS | C | 70 | 162.309 | 35.758 | 60.296 | 0.00 | 107.13 | chnC |
| ATOM | 3201 | C | HIS | C | 70 | 160.936 | 37.511 | 64.734 | 1.00 | 111.12 | chnC |
| ATOM | 3202 | O | HIS | C | 70 | 160.812 | 37.584 | 65.964 | 1.00 | 110.27 | chnC |
| ATOM | 3203 | N | GLN | C | 71 | 162.093 | 37.714 | 64.105 | 0.00 | 110.04 | chnC |
| ATOM | 3204 | CA | GLN | C | 71 | 163.316 | 38.087 | 64.811 | 0.00 | 110.13 | chnC |
| ATOM | 3205 | CB | GLN | C | 71 | 164.504 | 37.245 | 64.334 | 0.00 | 110.39 | chnC |
| ATOM | 3206 | CG | GLN | C | 71 | 164.454 | 35.784 | 64.746 | 0.00 | 110.56 | chnC |
| ATOM | 3207 | CD | GLN | C | 71 | 165.753 | 35.055 | 64.455 | 0.00 | 110.71 | chnC |
| ATOM | 3208 | OE1 | GLN | C | 71 | 166.232 | 35.040 | 63.321 | 0.00 | 110.62 | chnC |
| ATOM | 3209 | NE2 | GLN | C | 71 | 166.333 | 34.448 | 65.485 | 0.00 | 110.77 | chnC |
| ATOM | 3210 | C | GLN | C | 71 | 163.615 | 39.567 | 64.578 | 0.00 | 109.84 | chnC |
| ATOM | 3211 | O | GLN | C | 71 | 164.677 | 40.065 | 64.958 | 0.00 | 109.61 | chnC |
| ATOM | 3212 | N | GLN | C | 72 | 162.669 | 40.262 | 63.951 | 0.00 | 109.52 | chnC |
| ATOM | 3213 | CA | GLN | C | 72 | 162.806 | 41.685 | 63.653 | 0.00 | 109.55 | chnC |
| ATOM | 3214 | CB | GLN | C | 72 | 161.938 | 42.052 | 62.445 | 0.00 | 109.30 | chnC |
| ATOM | 3215 | CG | GLN | C | 72 | 162.244 | 41.244 | 61.187 | 0.00 | 109.34 | chnC |
| ATOM | 3216 | CD | GLN | C | 72 | 161.330 | 41.589 | 60.026 | 0.00 | 109.51 | chnC |
| ATOM | 3217 | OE1 | GLN | C | 72 | 160.128 | 41.789 | 60.203 | 0.00 | 109.09 | chnC |
| ATOM | 3218 | NE2 | GLN | C | 72 | 161.897 | 41.655 | 58.227 | 0.00 | 109.66 | chnC |
| ATOM | 3219 | C | GLN | C | 72 | 162.430 | 42.555 | 64.856 | 0.00 | 109.95 | chnC |
| ATOM | 3220 | O | GLN | C | 72 | 162.094 | 43.730 | 64.700 | 0.00 | 109.66 | chnC |
| ATOM | 3221 | N | VAL | C | 73 | 162.504 | 41.965 | 66.050 | 0.00 | 110.81 | chnC |
| ATOM | 3222 | CA | VAL | C | 73 | 162.188 | 42.635 | 67.315 | 0.00 | 111.61 | chnC |
| ATOM | 3223 | CB | VAL | C | 73 | 163.100 | 43.869 | 67.558 | 0.00 | 111.55 | chnC |
| ATOM | 3224 | CG1 | VAL | C | 73 | 162.782 | 44.507 | 68.903 | 0.00 | 111.43 | chnC |
| ATOM | 3225 | CG2 | VAL | C | 73 | 164.566 | 43.458 | 67.503 | 0.00 | 111.47 | chnC |
| ATOM | 3226 | C | VAL | C | 73 | 160.717 | 43.043 | 67.431 | 0.00 | 112.53 | chnC |
| ATOM | 3227 | O | VAL | C | 73 | 159.956 | 42.428 | 68.179 | 0.00 | 112.79 | chnC |
| ATOM | 3228 | N | ASN | C | 74 | 160.334 | 44.091 | 66.705 | 0.00 | 113.57 | chnC |
| ATOM | 3229 | CA | ASN | C | 74 | 158.962 | 44.595 | 66.708 | 0.00 | 114.04 | chnC |
| ATOM | 3230 | CB | ASN | C | 74 | 158.853 | 45.851 | 65.833 | 0.00 | 115.92 | chnC |
| ATOM | 3231 | CG | ASN | C | 74 | 159.455 | 47.082 | 66.487 | 0.00 | 117.01 | chnC |
| ATOM | 3232 | OD1 | ASN | C | 74 | 159.181 | 47.379 | 67.649 | 0.00 | 117.50 | chnC |
| ATOM | 3233 | ND2 | ASN | C | 74 | 160.260 | 47.818 | 65.731 | 0.00 | 117.57 | chnC |
| ATOM | 3234 | C | ASN | C | 74 | 157.947 | 43.559 | 66.223 | 0.00 | 113.07 | chnC |
| ATOM | 3235 | O | ASN | C | 74 | 158.274 | 42.664 | 65.440 | 0.00 | 112.93 | chnC |
| ATOM | 3236 | N | GLU | C | 75 | 156.717 | 43.685 | 66.715 | 1.00 | 110.88 | chnC |
| ATOM | 3237 | CA | GLU | C | 75 | 155.617 | 42.797 | 66.337 | 1.00 | 109.12 | chnC |
| ATOM | 3238 | CB | GLU | C | 75 | 154.627 | 42.646 | 67.490 | 0.00 | 109.17 | chnC |
| ATOM | 3239 | CG | GLU | C | 75 | 155.233 | 42.148 | 68.784 | 0.00 | 108.82 | chnC |
| ATOM | 3240 | CD | GLU | C | 75 | 154.213 | 42.062 | 69.900 | 0.00 | 108.67 | chnC |
| ATOM | 3241 | OE1 | GLU | C | 75 | 153.615 | 43.104 | 70.245 | 0.00 | 109.10 | chnC |
| ATOM | 3242 | OE2 | GLU | C | 75 | 154.008 | 40.952 | 70.432 | 0.00 | 108.79 | chnC |
| ATOM | 3243 | C | GLU | C | 75 | 154.887 | 43.405 | 65.140 | 1.00 | 108.37 | chnC |
| ATOM | 3244 | O | GLU | C | 75 | 155.090 | 44.579 | 64.806 | 1.00 | 108.60 | chnC |
| ATOM | 3245 | N | SER | C | 76 | 154.028 | 42.611 | 64.508 | 1.00 | 106.36 | chnC |
| ATOM | 3246 | CA | SER | C | 76 | 153.271 | 43.071 | 63.351 | 1.00 | 104.25 | chnC |
| ATOM | 3247 | CB | SER | C | 76 | 152.788 | 41.874 | 62.531 | 1.00 | 104.47 | chnC |
| ATOM | 3248 | OG | SER | C | 76 | 151.914 | 41.059 | 63.289 | 1.00 | 101.53 | chnC |
| ATOM | 3249 | C | SER | C | 76 | 152.073 | 43.895 | 63.785 | 1.00 | 103.76 | chnC |
| ATOM | 3250 | O | SER | C | 76 | 151.725 | 43.925 | 64.964 | 1.00 | 101.31 | chnC |
| ATOM | 3251 | N | GLU | C | 77 | 151.461 | 44.590 | 62.834 | 1.00 | 104.89 | chnC |
| ATOM | 3252 | CA | GLU | C | 77 | 150.272 | 45.372 | 63.143 | 1.00 | 106.55 | chnC |
| ATOM | 3253 | CB | GLU | C | 77 | 149.936 | 46.348 | 62.005 | 1.00 | 108.78 | chnC |
| ATOM | 3254 | CG | GLU | C | 77 | 150.914 | 47.520 | 61.867 | 1.00 | 112.12 | chnC |
| ATOM | 3255 | CD | GLU | C | 77 | 151.028 | 48.357 | 63.138 | 1.00 | 113.41 | chnC |
| ATOM | 3256 | OE1 | GLU | C | 77 | 150.110 | 49.162 | 63.407 | 1.00 | 113.73 | chnC |
| ATOM | 3257 | OE2 | GLU | C | 77 | 152.037 | 48.212 | 63.866 | 1.00 | 115.20 | chnC |
| ATOM | 3258 | C | GLU | C | 77 | 149.113 | 44.394 | 63.376 | 1.00 | 103.95 | chnC |
| ATOM | 3259 | O | GLU | C | 77 | 149.045 | 43.330 | 62.749 | 1.00 | 105.66 | chnC |
| ATOM | 3260 | N | PRO | C | 78 | 148.218 | 44.720 | 64.321 | 1.00 | 100.11 | chnC |
| ATOM | 3261 | CD | PRO | C | 78 | 148.291 | 45.878 | 65.230 | 1.00 | 99.29 | chnC |
| ATOM | 3262 | CA | PRO | C | 78 | 147.064 | 43.877 | 64.646 | 1.00 | 94.82 | chnC |
| ATOM | 3263 | CB | PRO | C | 78 | 146.395 | 44.644 | 65.787 | 1.00 | 97.04 | chnC |
| ATOM | 3264 | CG | PRO | C | 78 | 147.536 | 45.380 | 66.424 | 1.00 | 98.91 | chnC |
| ATOM | 3265 | C | PRO | C | 78 | 146.103 | 43.710 | 63.473 | 1.00 | 90.55 | chnC |
| ATOM | 3266 | O | PRO | C | 78 | 145.801 | 44.665 | 62.744 | 1.00 | 88.40 | chnC |
| ATOM | 3267 | N | VAL | C | 79 | 145.651 | 42.478 | 63.285 | 1.00 | 85.10 | chnC |

-continued

| ATOM | 3268 | CA  | VAL | C | 79 | 144.702 | 42.162 | 62.236 | 1.00 | 82.38 | chnC |
| ATOM | 3269 | CB  | VAL | C | 79 | 145.295 | 41.162 | 61.226 | 1.00 | 81.56 | chnC |
| ATOM | 3270 | CG1 | VAL | C | 79 | 144.258 | 40.782 | 60.186 | 1.00 | 84.80 | chnC |
| ATOM | 3271 | CG2 | VAL | C | 79 | 146.485 | 41.778 | 60.537 | 1.00 | 81.27 | chnC |
| ATOM | 3272 | C   | VAL | C | 79 | 143.499 | 41.557 | 62.953 | 1.00 | 80.56 | chnC |
| ATOM | 3273 | O   | VAL | C | 79 | 143.633 | 40.563 | 63.670 | 1.00 | 80.51 | chnC |
| ATOM | 3274 | N   | TYR | C | 80 | 142.341 | 42.193 | 62.799 | 1.00 | 78.90 | chnC |
| ATOM | 3275 | CA  | TYR | C | 80 | 141.121 | 41.730 | 63.445 | 1.00 | 77.97 | chnC |
| ATOM | 3276 | CB  | TYR | C | 80 | 140.316 | 42.926 | 63.957 | 1.00 | 84.08 | chnC |
| ATOM | 3277 | CG  | TYR | C | 80 | 141.109 | 43.798 | 64.911 | 1.00 | 89.25 | chnC |
| ATOM | 3278 | CD1 | TYR | C | 80 | 141.790 | 44.930 | 64.452 | 1.00 | 90.62 | chnC |
| ATOM | 3279 | CE1 | TYR | C | 80 | 142.553 | 45.716 | 65.318 | 1.00 | 93.30 | chnC |
| ATOM | 3280 | CD2 | TYR | C | 80 | 141.210 | 43.474 | 66.267 | 1.00 | 90.43 | chnC |
| ATOM | 3281 | CE2 | TYR | C | 80 | 141.972 | 44.255 | 67.142 | 1.00 | 92.35 | chnC |
| ATOM | 3282 | CZ  | TYR | C | 80 | 142.639 | 45.372 | 66.661 | 1.00 | 93.27 | chnC |
| ATOM | 3283 | OH  | TYR | C | 80 | 143.389 | 46.143 | 67.520 | 1.00 | 94.86 | chnC |
| ATOM | 3284 | C   | TYR | C | 80 | 140.260 | 40.836 | 62.565 | 1.00 | 73.93 | chnC |
| ATOM | 3285 | O   | TYR | C | 80 | 139.939 | 41.182 | 61.430 | 1.00 | 75.02 | chnC |
| ATOM | 3286 | N   | LEU | C | 81 | 139.921 | 39.668 | 63.098 | 1.00 | 69.06 | chnC |
| ATOM | 3287 | CA  | LEU | C | 81 | 139.093 | 38.684 | 62.412 | 1.00 | 63.89 | chnC |
| ATOM | 3288 | CB  | LEU | C | 81 | 139.804 | 37.342 | 62.406 | 1.00 | 62.09 | chnC |
| ATOM | 3289 | CG  | LEU | C | 81 | 139.012 | 36.130 | 61.932 | 1.00 | 62.19 | chnC |
| ATOM | 3290 | CD1 | LEU | C | 81 | 138.736 | 36.250 | 60.448 | 1.00 | 62.73 | chnC |
| ATOM | 3291 | CD2 | LEU | C | 81 | 139.804 | 34.864 | 62.226 | 1.00 | 61.68 | chnC |
| ATOM | 3292 | C   | LEU | C | 81 | 137.781 | 38.555 | 63.173 | 1.00 | 62.94 | chnC |
| ATOM | 3293 | O   | LEU | C | 81 | 137.783 | 38.527 | 64.401 | 1.00 | 65.56 | chnC |
| ATOM | 3294 | N   | GLU | C | 82 | 136.664 | 38.482 | 62.455 | 1.00 | 60.47 | chnC |
| ATOM | 3295 | CA  | GLU | C | 82 | 135.359 | 38.364 | 63.105 | 1.00 | 58.58 | chnC |
| ATOM | 3296 | CB  | GLU | C | 82 | 134.650 | 39.717 | 63.104 | 1.00 | 62.88 | chnC |
| ATOM | 3297 | CG  | GLU | C | 82 | 133.468 | 39.796 | 64.065 | 1.00 | 70.31 | chnC |
| ATOM | 3298 | CD  | GLU | C | 82 | 132.828 | 41.187 | 64.131 | 1.00 | 74.16 | chnC |
| ATOM | 3299 | OE1 | GLU | C | 82 | 133.191 | 42.067 | 63.310 | 1.00 | 75.56 | chnC |
| ATOM | 3300 | OE2 | GLU | C | 82 | 131.951 | 41.394 | 65.005 | 1.00 | 76.42 | chnC |
| ATOM | 3301 | C   | GLU | C | 82 | 134.476 | 37.273 | 62.479 | 1.00 | 54.30 | chnC |
| ATOM | 3302 | O   | GLU | C | 82 | 134.250 | 37.252 | 61.261 | 1.00 | 52.49 | chnC |
| ATOM | 3303 | N   | VAL | C | 83 | 134.004 | 36.356 | 63.323 | 1.00 | 47.17 | chnC |
| ATOM | 3304 | CA  | VAL | C | 83 | 133.173 | 35.241 | 62.884 | 1.00 | 41.25 | chnC |
| ATOM | 3305 | CB  | VAL | C | 83 | 133.546 | 33.958 | 63.632 | 1.00 | 38.95 | chnC |
| ATOM | 3306 | CG1 | VAL | C | 83 | 132.649 | 32.832 | 63.216 | 1.00 | 37.26 | chnC |
| ATOM | 3307 | CG2 | VAL | C | 83 | 134.975 | 33.600 | 63.348 | 1.00 | 36.88 | chnC |
| ATOM | 3308 | C   | VAL | C | 83 | 131.689 | 35.521 | 63.069 | 1.00 | 42.01 | chnC |
| ATOM | 3309 | O   | VAL | C | 83 | 131.233 | 35.810 | 64.172 | 1.00 | 46.53 | chnC |
| ATOM | 3310 | N   | PHE | C | 84 | 130.938 | 35.421 | 61.978 | 1.00 | 41.56 | chnC |
| ATOM | 3311 | CA  | PHE | C | 84 | 129.505 | 35.676 | 62.001 | 1.00 | 39.26 | chnC |
| ATOM | 3312 | CB  | PHE | C | 84 | 129.129 | 36.694 | 60.925 | 1.00 | 39.48 | chnC |
| ATOM | 3313 | CG  | PHE | C | 84 | 129.731 | 38.048 | 61.118 | 1.00 | 40.60 | chnC |
| ATOM | 3314 | CD1 | PHE | C | 84 | 131.031 | 38.308 | 60.720 | 1.00 | 42.24 | chnC |
| ATOM | 3315 | CD2 | PHE | C | 84 | 128.983 | 39.081 | 61.659 | 1.00 | 41.50 | chnC |
| ATOM | 3316 | CE1 | PHE | C | 84 | 131.579 | 39.578 | 60.859 | 1.00 | 43.56 | chnC |
| ATOM | 3317 | CE2 | PHE | C | 84 | 129.525 | 40.355 | 61.801 | 1.00 | 43.75 | chnC |
| ATOM | 3318 | CZ  | PHE | C | 84 | 130.824 | 40.599 | 61.397 | 1.00 | 44.37 | chnC |
| ATOM | 3319 | C   | PHE | C | 84 | 128.710 | 34.414 | 61.722 | 1.00 | 40.11 | chnC |
| ATOM | 3320 | O   | PHE | C | 84 | 129.259 | 33.379 | 61.329 | 1.00 | 36.22 | chnC |
| ATOM | 3321 | N   | SER | C | 85 | 127.401 | 34.515 | 61.933 | 1.00 | 41.42 | chnC |
| ATOM | 3322 | CA  | SER | C | 85 | 126.501 | 33.411 | 61.652 | 1.00 | 44.62 | chnC |
| ATOM | 3323 | CB  | SER | C | 85 | 126.355 | 32.473 | 62.838 | 1.00 | 46.86 | chnC |
| ATOM | 3324 | OG  | SER | C | 85 | 125.581 | 31.343 | 62.464 | 1.00 | 48.60 | chnC |
| ATOM | 3325 | C   | SER | C | 85 | 125.158 | 33.989 | 61.261 | 1.00 | 45.56 | chnC |
| ATOM | 3326 | O   | SER | C | 85 | 124.245 | 34.094 | 62.081 | 1.00 | 47.97 | chnC |
| ATOM | 3327 | N   | ASP | C | 86 | 125.065 | 34.357 | 59.986 | 1.00 | 46.51 | chnC |
| ATOM | 3328 | CA  | ASP | C | 86 | 123.870 | 34.943 | 59.407 | 1.00 | 47.21 | chnC |
| ATOM | 3329 | CB  | ASP | C | 86 | 124.080 | 36.454 | 59.297 | 1.00 | 53.10 | chnC |
| ATOM | 3330 | CG  | ASP | C | 86 | 122.823 | 37.246 | 59.613 | 1.00 | 60.27 | chnC |
| ATOM | 3331 | OD1 | ASP | C | 86 | 121.750 | 36.921 | 59.046 | 1.00 | 64.75 | chnC |
| ATOM | 3332 | OD2 | ASP | C | 86 | 122.910 | 38.199 | 60.424 | 1.00 | 62.55 | chnC |
| ATOM | 3333 | C   | ASP | C | 86 | 123.627 | 34.323 | 58.015 | 1.00 | 44.45 | chnC |
| ATOM | 3334 | O   | ASP | C | 86 | 124.297 | 33.355 | 57.630 | 1.00 | 42.82 | chnC |
| ATOM | 3335 | N   | TRP | C | 87 | 122.627 | 34.830 | 57.295 | 1.00 | 41.47 | chnC |
| ATOM | 3336 | CA  | TRP | C | 87 | 122.342 | 34.333 | 55.952 | 1.00 | 39.89 | chnC |
| ATOM | 3337 | CB  | TRP | C | 87 | 120.880 | 34.539 | 55.559 | 1.00 | 37.69 | chnC |
| ATOM | 3338 | CG  | TRP | C | 87 | 119.966 | 33.496 | 56.116 | 1.00 | 35.49 | chnC |
| ATOM | 3339 | CD2 | TRP | C | 87 | 119.742 | 32.192 | 55.595 | 1.00 | 35.14 | chnC |
| ATOM | 3340 | CE2 | TRP | C | 87 | 118.823 | 31.556 | 56.443 | 1.00 | 35.97 | chnC |
| ATOM | 3341 | CE3 | TRP | C | 87 | 120.230 | 31.497 | 54.491 | 1.00 | 37.95 | chnC |
| ATOM | 3342 | CD1 | TRP | C | 87 | 119.198 | 33.598 | 57.227 | 1.00 | 36.93 | chnC |
| ATOM | 3343 | NE1 | TRP | C | 87 | 118.506 | 32.438 | 57.436 | 1.00 | 37.44 | chnC |
| ATOM | 3344 | CZ2 | TRP | C | 87 | 118.382 | 30.255 | 56.227 | 1.00 | 37.62 | chnC |
| ATOM | 3345 | CZ3 | TRP | C | 87 | 119.794 | 30.205 | 54.274 | 1.00 | 39.20 | chnC |
| ATOM | 3346 | CH2 | TRP | C | 87 | 118.877 | 29.595 | 55.138 | 1.00 | 38.64 | chnC |

-continued

| | | | | | | | | | | |
|---|---|---|---|---|---|---|---|---|---|---|
| ATOM | 3347 | C | TRP | C | 87 | 123.246 | 35.040 | 54.975 | 1.00 | 39.06 chnC |
| ATOM | 3348 | O | TRP | C | 87 | 123.771 | 34.423 | 54.065 | 1.00 | 39.95 chnC |
| ATOM | 3349 | N | LEU | C | 88 | 123.426 | 36.339 | 55.159 | 1.00 | 39.33 chnC |
| ATOM | 3350 | CA | LEU | C | 88 | 124.307 | 37.093 | 54.280 | 1.00 | 39.82 chnC |
| ATOM | 3351 | CB | LEU | C | 88 | 123.533 | 38.117 | 53.455 | 1.00 | 38.95 chnC |
| ATOM | 3352 | CG | LEU | C | 88 | 122.480 | 37.628 | 52.475 | 1.00 | 38.10 chnC |
| ATOM | 3353 | CD1 | LEU | C | 88 | 121.976 | 38.811 | 51.689 | 1.00 | 36.73 chnC |
| ATOM | 3354 | CD2 | LEU | C | 88 | 123.070 | 36.593 | 51.557 | 1.00 | 38.86 chnC |
| ATOM | 3355 | C | LEU | C | 88 | 125.370 | 37.806 | 55.097 | 1.00 | 40.51 chnC |
| ATOM | 3356 | O | LEU | C | 88 | 125.126 | 38.235 | 56.222 | 1.00 | 43.08 chnC |
| ATOM | 3357 | N | LEU | C | 89 | 126.553 | 37.934 | 54.518 | 1.00 | 38.42 chnC |
| ATOM | 3358 | CA | LEU | C | 89 | 127.652 | 38.593 | 55.186 | 1.00 | 35.97 chnC |
| ATOM | 3359 | CB | LEU | C | 89 | 128.589 | 37.560 | 55.814 | 1.00 | 36.89 chnC |
| ATOM | 3360 | CG | LEU | C | 89 | 129.880 | 38.061 | 56.453 | 1.00 | 35.05 chnC |
| ATOM | 3361 | CD1 | LEU | C | 89 | 129.577 | 39.092 | 57.523 | 1.00 | 34.36 chnC |
| ATOM | 3362 | CD2 | LEU | C | 89 | 130.627 | 36.887 | 57.027 | 1.00 | 34.29 chnC |
| ATOM | 3363 | C | LEU | C | 89 | 128.410 | 39.419 | 54.182 | 1.00 | 34.86 chnC |
| ATOM | 3364 | O | LEU | C | 89 | 128.944 | 38.892 | 53.217 | 1.00 | 29.95 chnC |
| ATOM | 3365 | N | LEU | C | 90 | 128.440 | 40.723 | 54.409 | 1.00 | 37.39 chnC |
| ATOM | 3366 | CA | LEU | C | 90 | 129.157 | 41.610 | 53.520 | 1.00 | 40.94 chnC |
| ATOM | 3367 | CB | LEU | C | 90 | 128.662 | 43.050 | 53.654 | 1.00 | 41.58 chnC |
| ATOM | 3368 | CG | LEU | C | 90 | 129.399 | 44.024 | 52.727 | 1.00 | 43.08 chnC |
| ATOM | 3369 | CD1 | LEU | C | 90 | 129.039 | 43.751 | 51.287 | 1.00 | 41.98 chnC |
| ATOM | 3370 | CD2 | LEU | C | 90 | 129.061 | 45.443 | 53.083 | 1.00 | 44.50 chnC |
| ATOM | 3371 | C | LEU | C | 90 | 130.634 | 41.544 | 53.864 | 1.00 | 40.76 chnC |
| ATOM | 3372 | O | LEU | C | 90 | 131.047 | 41.966 | 54.942 | 1.00 | 44.18 chnC |
| ATOM | 3373 | N | GLN | C | 91 | 131.421 | 41.001 | 52.945 | 1.00 | 40.73 chnC |
| ATOM | 3374 | CA | GLN | C | 91 | 132.851 | 40.879 | 53.137 | 1.00 | 39.25 chnC |
| ATOM | 3375 | CB | GLN | C | 91 | 133.314 | 39.516 | 52.653 | 1.00 | 36.10 chnC |
| ATOM | 3376 | CG | GLN | C | 91 | 132.605 | 38.382 | 53.347 | 1.00 | 37.95 chnC |
| ATOM | 3377 | CD | GLN | C | 91 | 133.126 | 37.023 | 52.949 | 1.00 | 40.38 chnC |
| ATOM | 3378 | OE1 | GLN | C | 91 | 132.812 | 36.510 | 51.876 | 1.00 | 41.91 chnC |
| ATOM | 3379 | NE2 | GLN | C | 91 | 133.914 | 36.420 | 53.822 | 1.00 | 42.01 chnC |
| ATOM | 3380 | C | GLN | C | 91 | 133.564 | 41.985 | 52.383 | 1.00 | 41.39 chnC |
| ATOM | 3381 | O | GLN | C | 91 | 133.117 | 42.407 | 51.321 | 1.00 | 43.66 chnC |
| ATOM | 3382 | N | ALA | C | 92 | 134.643 | 42.493 | 52.969 | 1.00 | 46.10 chnC |
| ATOM | 3383 | CA | ALA | C | 92 | 135.430 | 43.560 | 52.350 | 1.00 | 48.80 chnC |
| ATOM | 3384 | CB | ALA | C | 92 | 135.239 | 44.860 | 53.090 | 1.00 | 47.86 chnC |
| ATOM | 3385 | C | ALA | C | 92 | 136.902 | 43.185 | 52.336 | 1.00 | 51.67 chnC |
| ATOM | 3386 | O | ALA | C | 92 | 137.391 | 42.508 | 53.254 | 1.00 | 52.43 chnC |
| ATOM | 3387 | N | SER | C | 93 | 137.588 | 43.591 | 51.268 | 1.00 | 53.03 chnC |
| ATOM | 3388 | CA | SER | C | 93 | 139.018 | 43.328 | 51.091 | 1.00 | 55.77 chnC |
| ATOM | 3389 | CB | SER | C | 93 | 139.467 | 43.853 | 49.733 | 1.00 | 55.89 chnC |
| ATOM | 3390 | OG | SER | C | 93 | 139.150 | 45.234 | 49.610 | 1.00 | 50.82 chnC |
| ATOM | 3391 | C | SER | C | 93 | 139.795 | 44.045 | 52.190 | 1.00 | 57.95 chnC |
| ATOM | 3392 | O | SER | C | 93 | 140.863 | 43.595 | 52.612 | 1.00 | 57.68 chnC |
| ATOM | 3393 | N | ALA | C | 94 | 139.233 | 45.167 | 52.636 | 1.00 | 58.89 chnC |
| ATOM | 3394 | CA | ALA | C | 94 | 139.804 | 45.990 | 53.693 | 1.00 | 60.27 chnC |
| ATOM | 3395 | CB | ALA | C | 94 | 141.053 | 46.697 | 53.192 | 1.00 | 60.14 chnC |
| ATOM | 3396 | C | ALA | C | 94 | 138.744 | 47.005 | 54.125 | 1.00 | 60.10 chnC |
| ATOM | 3397 | O | ALA | C | 94 | 138.012 | 47.532 | 53.295 | 1.00 | 60.58 chnC |
| ATOM | 3398 | N | GLU | C | 95 | 138.636 | 47.247 | 55.426 | 1.00 | 63.46 chnC |
| ATOM | 3399 | CA | GLU | C | 95 | 137.652 | 48.193 | 55.949 | 1.00 | 66.95 chnC |
| ATOM | 3400 | CB | GLU | C | 95 | 137.247 | 47.801 | 57.369 | 1.00 | 67.88 chnC |
| ATOM | 3401 | CG | GLU | C | 95 | 136.880 | 46.322 | 57.539 | 1.00 | 70.42 chnC |
| ATOM | 3402 | CD | GLU | C | 95 | 136.567 | 45.957 | 58.993 | 1.00 | 75.07 chnC |
| ATOM | 3403 | OE1 | GLU | C | 95 | 136.208 | 44.782 | 59.239 | 1.00 | 77.94 chnC |
| ATOM | 3404 | OE2 | GLU | C | 95 | 136.674 | 46.832 | 59.895 | 1.00 | 77.06 chnC |
| ATOM | 3405 | C | GLU | C | 95 | 138.211 | 49.616 | 55.934 | 1.00 | 70.16 chnC |
| ATOM | 3406 | O | GLU | C | 95 | 137.448 | 50.586 | 55.902 | 1.00 | 70.01 chnC |
| ATOM | 3407 | N | VAL | C | 96 | 139.544 | 49.724 | 56.010 | 1.00 | 73.43 chnC |
| ATOM | 3408 | CA | VAL | C | 96 | 140.260 | 51.011 | 55.974 | 1.00 | 74.36 chnC |
| ATOM | 3409 | CB | VAL | C | 96 | 141.098 | 51.255 | 57.258 | 1.00 | 74.45 chnC |
| ATOM | 3410 | CG1 | VAL | C | 96 | 141.728 | 52.643 | 57.217 | 1.00 | 75.24 chnC |
| ATOM | 3411 | CG2 | VAL | C | 96 | 140.215 | 51.128 | 58.501 | 1.00 | 74.61 chnC |
| ATOM | 3412 | C | VAL | C | 96 | 141.171 | 50.984 | 54.738 | 1.00 | 75.86 chnC |
| ATOM | 3413 | O | VAL | C | 96 | 142.202 | 50.299 | 54.713 | 1.00 | 73.61 chnC |
| ATOM | 3414 | N | VAL | C | 97 | 140.762 | 51.730 | 53.713 | 1.00 | 78.05 chnC |
| ATOM | 3415 | CA | VAL | C | 97 | 141.465 | 51.774 | 52.435 | 1.00 | 82.15 chnC |
| ATOM | 3416 | CB | VAL | C | 97 | 140.482 | 51.484 | 51.269 | 1.00 | 82.59 chnC |
| ATOM | 3417 | CG1 | VAL | C | 97 | 141.246 | 51.177 | 49.989 | 1.00 | 81.93 chnC |
| ATOM | 3418 | CG2 | VAL | C | 97 | 139.559 | 50.328 | 51.623 | 1.00 | 83.43 chnC |
| ATOM | 3419 | C | VAL | C | 97 | 142.203 | 53.072 | 52.111 | 1.00 | 84.79 chnC |
| ATOM | 3420 | O | VAL | C | 97 | 141.677 | 54.175 | 52.304 | 1.00 | 83.59 chnC |
| ATOM | 3421 | N | MET | C | 98 | 143.401 | 52.912 | 51.549 | 1.00 | 88.84 chnC |
| ATOM | 3422 | CA | MET | C | 98 | 144.257 | 54.031 | 51.148 | 1.00 | 92.46 chnC |
| ATOM | 3423 | CB | MET | C | 98 | 145.719 | 53.557 | 51.043 | 1.00 | 95.11 chnC |
| ATOM | 3424 | CG | MET | C | 98 | 146.782 | 54.661 | 50.936 | 1.00 | 98.11 chnC |
| ATOM | 3425 | SD | MET | C | 98 | 146.711 | 55.692 | 49.422 | 1.00 | 104.84 chnC |

-continued

| | | | | | | | | | | |
|---|---|---|---|---|---|---|---|---|---|---|
| ATOM | 3426 | CE | MET | C | 98 | 147.463 | 54.569 | 48.168 | 1.00 | 99.21 | chnC |
| ATOM | 3427 | C | MET | C | 98 | 143.775 | 54.585 | 49.798 | 1.00 | 92.92 | chnC |
| ATOM | 3428 | O | MET | C | 98 | 143.514 | 53.823 | 48.856 | 1.00 | 92.60 | chnC |
| ATOM | 3429 | N | GLU | C | 99 | 143.672 | 55.914 | 49.724 | 1.00 | 92.37 | chnC |
| ATOM | 3430 | CA | GLU | C | 99 | 143.222 | 56.636 | 48.526 | 1.00 | 93.02 | chnC |
| ATOM | 3431 | CB | GLU | C | 99 | 143.312 | 58.141 | 48.790 | 1.00 | 95.51 | chnC |
| ATOM | 3432 | CG | GLU | C | 99 | 142.695 | 59.046 | 47.736 | 1.00 | 98.55 | chnC |
| ATOM | 3433 | CD | GLU | C | 99 | 142.729 | 60.504 | 48.171 | 1.00 | 99.76 | chnC |
| ATOM | 3434 | OE1 | GLU | C | 99 | 143.692 | 61.210 | 47.797 | 1.00 | 100.29 | chnC |
| ATOM | 3435 | OE2 | GLU | C | 99 | 141.810 | 60.932 | 48.912 | 1.00 | 100.28 | chnC |
| ATOM | 3436 | C | GLU | C | 99 | 144.016 | 56.280 | 47.263 | 1.00 | 91.50 | chnC |
| ATOM | 3437 | O | GLU | C | 99 | 145.136 | 56.761 | 47.061 | 1.00 | 93.25 | chnC |
| ATOM | 3438 | N | GLY | C | 100 | 143.427 | 55.445 | 46.412 | 1.00 | 87.93 | chnC |
| ATOM | 3439 | CA | GLY | C | 100 | 144.111 | 55.050 | 45.196 | 1.00 | 85.04 | chnC |
| ATOM | 3440 | C | GLY | C | 100 | 144.179 | 53.552 | 44.978 | 1.00 | 84.17 | chnC |
| ATOM | 3441 | O | GLY | C | 100 | 144.329 | 53.108 | 43.833 | 1.00 | 85.61 | chnC |
| ATOM | 3442 | N | GLN | C | 101 | 144.099 | 52.774 | 46.060 | 1.00 | 82.06 | chnC |
| ATOM | 3443 | CA | GLN | C | 101 | 144.142 | 51.312 | 45.953 | 1.00 | 81.82 | chnC |
| ATOM | 3444 | CB | GLN | C | 101 | 144.860 | 50.704 | 47.168 | 1.00 | 85.07 | chnC |
| ATOM | 3445 | CG | GLN | C | 101 | 144.184 | 50.969 | 48.512 | 1.00 | 90.71 | chnC |
| ATOM | 3446 | CD | GLN | C | 101 | 144.976 | 50.433 | 49.709 | 1.00 | 92.70 | chnC |
| ATOM | 3447 | OE1 | GLN | C | 101 | 146.217 | 50.418 | 49.703 | 1.00 | 92.61 | chnC |
| ATOM | 3448 | NE2 | GLN | C | 101 | 144.256 | 50.010 | 50.752 | 1.00 | 94.17 | chnC |
| ATOM | 3449 | C | GLN | C | 101 | 142.738 | 50.701 | 45.775 | 1.00 | 78.79 | chnC |
| ATOM | 3450 | O | GLN | C | 101 | 141.722 | 51.369 | 45.990 | 1.00 | 76.82 | chnC |
| ATOM | 3451 | N | PRO | C | 102 | 142.667 | 49.432 | 45.337 | 1.00 | 75.71 | chnC |
| ATOM | 3452 | CD | PRO | C | 102 | 143.773 | 48.572 | 44.877 | 1.00 | 74.72 | chnC |
| ATOM | 3453 | CA | PRO | C | 102 | 141.375 | 48.764 | 45.136 | 1.00 | 72.82 | chnC |
| ATOM | 3454 | CB | PRO | C | 102 | 141.759 | 47.535 | 44.308 | 1.00 | 72.51 | chnC |
| ATOM | 3455 | CG | PRO | C | 102 | 143.123 | 47.207 | 44.827 | 1.00 | 72.91 | chnC |
| ATOM | 3456 | C | PRO | C | 102 | 140.619 | 48.367 | 46.415 | 1.00 | 70.13 | chnC |
| ATOM | 3457 | O | PRO | C | 102 | 141.218 | 48.143 | 47.473 | 1.00 | 67.88 | chnC |
| ATOM | 3458 | N | LEU | C | 103 | 139.294 | 48.298 | 46.287 | 1.00 | 66.57 | chnC |
| ATOM | 3459 | CA | LEU | C | 103 | 138.388 | 47.915 | 47.367 | 1.00 | 62.86 | chnC |
| ATOM | 3460 | CB | LEU | C | 103 | 137.576 | 49.124 | 47.846 | 1.00 | 62.12 | chnC |
| ATOM | 3461 | CG | LEU | C | 103 | 136.506 | 48.834 | 48.903 | 1.00 | 61.19 | chnC |
| ATOM | 3462 | CD1 | LEU | C | 103 | 137.112 | 48.087 | 50.084 | 1.00 | 59.69 | chnC |
| ATOM | 3463 | CD2 | LEU | C | 103 | 135.876 | 50.135 | 49.356 | 1.00 | 60.83 | chnC |
| ATOM | 3464 | C | LEU | C | 103 | 137.449 | 46.853 | 46.804 | 1.00 | 60.30 | chnC |
| ATOM | 3465 | O | LEU | C | 103 | 136.837 | 47.053 | 45.759 | 1.00 | 57.00 | chnC |
| ATOM | 3466 | N | PHE | C | 104 | 137.354 | 45.716 | 47.481 | 1.00 | 58.61 | chnC |
| ATOM | 3467 | CA | PHE | C | 104 | 136.490 | 44.650 | 47.010 | 1.00 | 58.66 | chnC |
| ATOM | 3468 | CB | PHE | C | 104 | 137.314 | 43.415 | 46.652 | 1.00 | 64.21 | chnC |
| ATOM | 3469 | CG | PHE | C | 104 | 138.334 | 43.653 | 45.579 | 1.00 | 70.43 | chnC |
| ATOM | 3470 | CD1 | PHE | C | 104 | 139.689 | 43.739 | 45.898 | 1.00 | 72.64 | chnC |
| ATOM | 3471 | CD2 | PHE | C | 104 | 137.948 | 43.779 | 44.246 | 1.00 | 70.99 | chnC |
| ATOM | 3472 | CE1 | PHE | C | 104 | 140.650 | 43.949 | 44.900 | 1.00 | 73.37 | chnC |
| ATOM | 3473 | CE2 | PHE | C | 104 | 138.901 | 43.988 | 43.241 | 1.00 | 72.96 | chnC |
| ATOM | 3474 | CZ | PHE | C | 104 | 140.254 | 44.073 | 43.569 | 1.00 | 73.39 | chnC |
| ATOM | 3475 | C | PHE | C | 104 | 135.441 | 44.275 | 48.044 | 1.00 | 57.04 | chnC |
| ATOM | 3476 | O | PHE | C | 104 | 135.768 | 44.009 | 49.205 | 1.00 | 56.75 | chnC |
| ATOM | 3477 | N | LEU | C | 105 | 134.179 | 44.274 | 47.622 | 1.00 | 50.51 | chnC |
| ATOM | 3478 | CA | LEU | C | 105 | 133.079 | 43.907 | 48.501 | 1.00 | 47.43 | chnC |
| ATOM | 3479 | CB | LEU | C | 105 | 132.080 | 45.047 | 48.637 | 1.00 | 47.39 | chnC |
| ATOM | 3480 | CG | LEU | C | 105 | 132.641 | 46.367 | 49.139 | 1.00 | 47.58 | chnC |
| ATOM | 3481 | CD1 | LEU | C | 105 | 131.504 | 47.327 | 49.415 | 1.00 | 47.67 | chnC |
| ATOM | 3482 | CD2 | LEU | C | 105 | 133.431 | 46.115 | 50.403 | 1.00 | 47.27 | chnC |
| ATOM | 3483 | C | LEU | C | 105 | 132.397 | 42.688 | 47.916 | 1.00 | 46.62 | chnC |
| ATOM | 3484 | O | LEU | C | 105 | 132.273 | 42.569 | 46.703 | 1.00 | 49.31 | chnC |
| ATOM | 3485 | N | ARG | C | 106 | 131.905 | 41.815 | 48.785 | 1.00 | 43.35 | chnC |
| ATOM | 3486 | CA | ARG | C | 106 | 131.271 | 40.573 | 48.371 | 1.00 | 43.20 | chnC |
| ATOM | 3487 | CB | ARG | C | 106 | 132.321 | 39.467 | 48.467 | 1.00 | 41.58 | chnC |
| ATOM | 3488 | CG | ARG | C | 106 | 131.837 | 38.068 | 48.266 | 1.00 | 45.06 | chnC |
| ATOM | 3489 | CD | ARG | C | 106 | 132.965 | 37.088 | 48.546 | 1.00 | 43.81 | chnC |
| ATOM | 3490 | NE | ARG | C | 106 | 132.556 | 35.711 | 48.300 | 1.00 | 47.25 | chnC |
| ATOM | 3491 | CZ | ARG | C | 106 | 133.040 | 34.659 | 48.947 | 1.00 | 45.92 | chnC |
| ATOM | 3492 | NH1 | ARG | C | 106 | 133.958 | 34.834 | 49.883 | 1.00 | 44.56 | chnC |
| ATOM | 3493 | NH2 | ARG | C | 106 | 132.601 | 33.436 | 48.661 | 1.00 | 47.02 | chnC |
| ATOM | 3494 | C | ARG | C | 106 | 130.091 | 40.265 | 49.282 | 1.00 | 43.19 | chnC |
| ATOM | 3495 | O | ARG | C | 106 | 130.236 | 40.230 | 50.499 | 1.00 | 47.36 | chnC |
| ATOM | 3496 | N | CYS | C | 107 | 128.912 | 40.075 | 48.700 | 1.00 | 43.84 | chnC |
| ATOM | 3497 | CA | CYS | C | 107 | 127.711 | 39.759 | 49.477 | 1.00 | 43.10 | chnC |
| ATOM | 3498 | C | CYS | C | 107 | 127.648 | 38.234 | 49.618 | 1.00 | 44.27 | chnC |
| ATOM | 3499 | O | CYS | C | 107 | 126.917 | 37.564 | 48.904 | 1.00 | 47.13 | chnC |
| ATOM | 3500 | CB | CYS | C | 107 | 126.484 | 40.291 | 48.749 | 1.00 | 39.73 | chnC |
| ATOM | 3501 | SG | CYS | C | 107 | 124.942 | 40.208 | 49.694 | 1.00 | 41.86 | chnC |
| ATOM | 3502 | N | HIS | C | 108 | 128.447 | 37.710 | 50.543 | 1.00 | 43.77 | chnC |
| ATOM | 3503 | CA | HIS | C | 108 | 128.584 | 36.277 | 50.816 | 1.00 | 41.29 | chnC |
| ATOM | 3504 | CB | HIS | C | 108 | 129.807 | 36.076 | 51.708 | 1.00 | 42.25 | chnC |

-continued

| | | | | | | | | | | |
|---|---|---|---|---|---|---|---|---|---|---|
| ATOM | 3505 | CG | HIS | C | 108 | 130.220 | 34.651 | 51.863 | 1.00 | 43.75 | chnC |
| ATOM | 3506 | CD2 | HIS | C | 108 | 130.786 | 33.996 | 52.901 | 1.00 | 42.18 | chnC |
| ATOM | 3507 | ND1 | HIS | C | 108 | 130.070 | 33.723 | 50.856 | 1.00 | 44.66 | chnC |
| ATOM | 3508 | CE1 | HIS | C | 108 | 130.528 | 32.557 | 51.270 | 1.00 | 45.73 | chnC |
| ATOM | 3509 | NE2 | HIS | C | 108 | 130.968 | 32.695 | 52.509 | 1.00 | 44.63 | chnC |
| ATOM | 3510 | C | HIS | C | 108 | 127.382 | 35.558 | 51.441 | 1.00 | 41.32 | chnC |
| ATOM | 3511 | O | HIS | C | 108 | 126.867 | 35.967 | 52.487 | 1.00 | 40.26 | chnC |
| ATOM | 3512 | N | GLY | C | 109 | 127.001 | 34.436 | 50.832 | 1.00 | 40.59 | chnC |
| ATOM | 3513 | CA | GLY | C | 109 | 125.876 | 33.649 | 51.319 | 1.00 | 40.20 | chnC |
| ATOM | 3514 | C | GLY | C | 109 | 126.274 | 32.513 | 52.245 | 1.00 | 38.67 | chnC |
| ATOM | 3515 | O | GLY | C | 109 | 127.354 | 31.954 | 52.122 | 1.00 | 36.15 | chnC |
| ATOM | 3516 | N | TRP | C | 110 | 125.369 | 32.126 | 53.132 | 1.00 | 37.77 | chnC |
| ATOM | 3517 | CA | TRP | C | 110 | 125.641 | 31.065 | 54.090 | 1.00 | 39.58 | chnC |
| ATOM | 3518 | CB | TRP | C | 110 | 124.409 | 30.817 | 54.957 | 1.00 | 40.22 | chnC |
| ATOM | 3519 | CG | TRP | C | 110 | 124.595 | 29.716 | 55.938 | 1.00 | 40.25 | chnC |
| ATOM | 3520 | CD2 | TRP | C | 110 | 125.304 | 29.784 | 57.173 | 1.00 | 41.68 | chnC |
| ATOM | 3521 | CE2 | TRP | C | 110 | 125.263 | 28.501 | 57.749 | 1.00 | 40.22 | chnC |
| ATOM | 3522 | CE3 | TRP | C | 110 | 125.976 | 30.807 | 57.848 | 1.00 | 44.48 | chnC |
| ATOM | 3523 | CD1 | TRP | C | 110 | 124.155 | 28.437 | 55.820 | 1.00 | 39.88 | chnC |
| ATOM | 3524 | NE1 | TRP | C | 110 | 124.553 | 27.695 | 56.904 | 1.00 | 39.26 | chnC |
| ATOM | 3525 | CZ2 | TRP | C | 110 | 125.865 | 28.211 | 58.966 | 1.00 | 41.84 | chnC |
| ATOM | 3526 | CZ3 | TRP | C | 110 | 126.577 | 30.516 | 59.062 | 1.00 | 46.26 | chnC |
| ATOM | 3527 | CH2 | TRP | C | 110 | 126.517 | 29.224 | 59.606 | 1.00 | 44.02 | chnC |
| ATOM | 3528 | C | TRP | C | 110 | 126.053 | 29.780 | 53.410 | 1.00 | 38.11 | chnC |
| ATOM | 3529 | O | TRP | C | 110 | 125.275 | 29.221 | 52.645 | 1.00 | 35.91 | chnC |
| ATOM | 3530 | N | ARG | C | 111 | 127.256 | 29.299 | 53.725 | 1.00 | 39.11 | chnC |
| ATOM | 3531 | CA | ARG | C | 111 | 127.786 | 28.070 | 53.132 | 1.00 | 43.00 | chnC |
| ATOM | 3532 | CB | ARG | C | 111 | 126.850 | 26.895 | 53.396 | 1.00 | 46.68 | chnC |
| ATOM | 3533 | CG | ARG | C | 111 | 126.833 | 26.360 | 54.776 | 1.00 | 52.15 | chnC |
| ATOM | 3534 | CD | ARG | C | 111 | 125.855 | 25.224 | 54.819 | 1.00 | 54.35 | chnC |
| ATOM | 3535 | NE | ARG | C | 111 | 126.037 | 24.428 | 56.018 | 1.00 | 60.10 | chnC |
| ATOM | 3536 | CZ | ARG | C | 111 | 126.551 | 23.205 | 56.025 | 1.00 | 62.87 | chnC |
| ATOM | 3537 | NH1 | ARG | C | 111 | 126.932 | 22.628 | 54.890 | 1.00 | 64.10 | chnC |
| ATOM | 3538 | NH2 | ARG | C | 111 | 126.705 | 22.567 | 57.180 | 1.00 | 64.83 | chnC |
| ATOM | 3539 | C | ARG | C | 111 | 127.944 | 28.189 | 51.616 | 1.00 | 43.78 | chnC |
| ATOM | 3540 | O | ARG | C | 111 | 127.792 | 27.192 | 50.892 | 1.00 | 44.64 | chnC |
| ATOM | 3541 | N | ASN | C | 112 | 128.209 | 29.404 | 51.137 | 1.00 | 43.55 | chnC |
| ATOM | 3542 | CA | ASN | C | 112 | 128.374 | 29.661 | 49.706 | 1.00 | 46.73 | chnC |
| ATOM | 3543 | CB | ASN | C | 112 | 129.510 | 28.817 | 49.107 | 1.00 | 48.90 | chnC |
| ATOM | 3544 | CG | ASN | C | 112 | 130.817 | 29.567 | 49.050 | 1.00 | 51.86 | chnC |
| ATOM | 3545 | OD1 | ASN | C | 112 | 130.913 | 30.626 | 48.417 | 1.00 | 52.19 | chnC |
| ATOM | 3546 | ND2 | ASN | C | 112 | 131.835 | 29.034 | 49.724 | 1.00 | 53.91 | chnC |
| ATOM | 3547 | C | ASN | C | 112 | 127.099 | 29.448 | 48.890 | 1.00 | 46.82 | chnC |
| ATOM | 3548 | O | ASN | C | 112 | 127.135 | 29.454 | 47.652 | 1.00 | 48.61 | chnC |
| ATOM | 3549 | N | TRP | C | 113 | 125.978 | 29.250 | 49.576 | 1.00 | 44.67 | chnC |
| ATOM | 3550 | CA | TRP | C | 113 | 124.711 | 29.063 | 48.894 | 1.00 | 43.68 | chnC |
| ATOM | 3551 | CB | TRP | C | 113 | 123.576 | 28.932 | 49.912 | 1.00 | 44.83 | chnC |
| ATOM | 3552 | CG | TRP | C | 113 | 123.503 | 27.586 | 50.602 | 1.00 | 44.43 | chnC |
| ATOM | 3553 | CD2 | TRP | C | 113 | 122.731 | 27.264 | 51.764 | 1.00 | 45.17 | chnC |
| ATOM | 3554 | CE2 | TRP | C | 113 | 122.905 | 25.886 | 52.013 | 1.00 | 43.41 | chnC |
| ATOM | 3555 | CE3 | TRP | C | 113 | 121.903 | 28.006 | 52.613 | 1.00 | 44.51 | chnC |
| ATOM | 3556 | CD1 | TRP | C | 113 | 124.104 | 26.424 | 50.211 | 1.00 | 43.43 | chmC |
| ATOM | 3557 | NE1 | TRP | C | 113 | 123.746 | 25.399 | 51.051 | 1.00 | 43.26 | chnC |
| ATOM | 3558 | CZ2 | TRP | C | 113 | 122.280 | 25.235 | 53.073 | 1.00 | 43.63 | chnC |
| ATOM | 3559 | CZ3 | TRP | C | 113 | 121.280 | 27.354 | 53.670 | 1.00 | 44.38 | chnC |
| ATOM | 3560 | CH2 | TRP | C | 113 | 121.473 | 25.983 | 53.888 | 1.00 | 44.14 | chnC |
| ATOM | 3561 | C | TRP | C | 113 | 124.465 | 30.238 | 47.944 | 1.00 | 44.45 | chnC |
| ATOM | 3562 | O | TRP | C | 113 | 124.941 | 31.350 | 48.173 | 1.00 | 42.97 | chnC |
| ATOM | 3563 | N | ASP | C | 114 | 123.769 | 29.965 | 46.848 | 1.00 | 45.74 | chnC |
| ATOM | 3564 | CA | ASP | C | 114 | 123.486 | 30.980 | 45.849 | 1.00 | 44.68 | chnC |
| ATOM | 3565 | CB | ASP | C | 114 | 122.929 | 30.355 | 44.569 | 1.00 | 52.92 | chnC |
| ATOM | 3566 | CG | ASP | C | 114 | 123.931 | 29.474 | 43.859 | 1.00 | 56.44 | chnC |
| ATOM | 3567 | OD1 | ASP | C | 114 | 125.115 | 29.870 | 43.755 | 1.00 | 57.91 | chnC |
| ATOM | 3568 | OD2 | ASP | C | 114 | 123.519 | 28.386 | 43.400 | 1.00 | 56.51 | chnC |
| ATOM | 3569 | C | ASP | C | 114 | 122.531 | 32.043 | 46.322 | 1.00 | 42.65 | chnC |
| ATOM | 3570 | O | ASP | C | 114 | 121.453 | 31.768 | 46.842 | 1.00 | 40.84 | chnC |
| ATOM | 3571 | N | VAL | C | 115 | 122.932 | 33.270 | 46.074 | 1.00 | 41.41 | chnC |
| ATOM | 3572 | CA | VAL | C | 115 | 122.159 | 34.433 | 46.435 | 1.00 | 42.44 | chnC |
| ATOM | 3573 | CB | VAL | C | 115 | 123.042 | 35.437 | 47.195 | 1.00 | 40.93 | chnC |
| ATOM | 3574 | CG1 | VAL | C | 115 | 122.245 | 36.640 | 47.577 | 1.00 | 39.22 | chnC |
| ATOM | 3575 | CG2 | VAL | C | 115 | 123.665 | 34.789 | 48.415 | 1.00 | 41.02 | chnC |
| ATOM | 3576 | C | VAL | C | 115 | 121.708 | 35.081 | 45.130 | 1.00 | 42.29 | chnC |
| ATOM | 3577 | O | VAL | C | 115 | 122.497 | 35.230 | 44.199 | 1.00 | 45.70 | chnC |
| ATOM | 3578 | N | TYR | C | 116 | 120.435 | 35.422 | 45.034 | 1.00 | 41.35 | chnC |
| ATOM | 3579 | CA | TYR | C | 116 | 119.948 | 36.067 | 43.834 | 1.00 | 44.89 | chnC |
| ATOM | 3580 | CB | TYR | C | 116 | 118.833 | 35.249 | 43.180 | 1.00 | 49.66 | chnC |
| ATOM | 3581 | CG | TYR | C | 116 | 119.256 | 33.880 | 42.686 | 1.00 | 56.05 | chnC |
| ATOM | 3582 | CD1 | TYR | C | 116 | 118.623 | 32.734 | 43.144 | 1.00 | 60.90 | chnC |
| ATOM | 3583 | CE1 | TYR | C | 116 | 119.002 | 31.470 | 42.695 | 1.00 | 65.58 | chnC |

-continued

| | | | | | | | | | | |
|---|---|---|---|---|---|---|---|---|---|---|
| ATOM | 3584 | CD2 | TYR | C | 116 | 120.286 | 33.730 | 41.762 | 1.00 | 60.30 | chnC |
| ATOM | 3585 | CE2 | TYR | C | 116 | 120.675 | 32.467 | 41.305 | 1.00 | 64.30 | chnC |
| ATOM | 3586 | CZ | TYR | C | 116 | 120.027 | 31.341 | 41.778 | 1.00 | 65.79 | chnC |
| ATOM | 3587 | OH | TYR | C | 116 | 120.403 | 30.085 | 41.355 | 1.00 | 68.20 | chnC |
| ATOM | 3588 | C | TYR | C | 116 | 119.457 | 37.448 | 44.213 | 1.00 | 44.05 | chnC |
| ATOM | 3589 | O | TYR | C | 116 | 119.419 | 37.783 | 45.397 | 1.00 | 41.11 | chnC |
| ATOM | 3590 | N | LYS | C | 117 | 119.116 | 38.254 | 43.209 | 1.00 | 44.15 | chnC |
| ATOM | 3591 | CA | LYS | C | 117 | 118.622 | 39.617 | 43.423 | 1.00 | 46.29 | chnC |
| ATOM | 3592 | CB | LYS | C | 117 | 117.190 | 39.586 | 43.972 | 1.00 | 49.44 | chnC |
| ATOM | 3593 | CG | LYS | C | 117 | 116.228 | 38.637 | 43.267 | 1.00 | 55.15 | chnC |
| ATOM | 3594 | CD | LYS | C | 117 | 115.730 | 39.174 | 41.944 | 1.00 | 61.84 | chnC |
| ATOM | 3595 | CE | LYS | C | 117 | 114.592 | 38.319 | 41.395 | 1.00 | 63.38 | chnC |
| ATOM | 3596 | NZ | LYS | C | 117 | 113.371 | 38.354 | 42.251 | 1.00 | 66.29 | chnC |
| ATOM | 3597 | C | LYS | C | 117 | 119.519 | 40.372 | 44.410 | 1.00 | 45.47 | chnC |
| ATOM | 3598 | O | LYS | C | 117 | 119.036 | 40.965 | 45.376 | 1.00 | 47.01 | chnC |
| ATOM | 3599 | N | VAL | C | 118 | 120.824 | 40.322 | 44.180 | 1.00 | 43.48 | chnC |
| ATOM | 3600 | CA | VAL | C | 118 | 121.784 | 40.981 | 45.055 | 1.00 | 42.47 | chnC |
| ATOM | 3601 | CB | VAL | C | 118 | 123.201 | 40.442 | 44.822 | 1.00 | 42.12 | chnC |
| ATOM | 3602 | CG1 | VAL | C | 118 | 124.139 | 40.961 | 45.886 | 1.00 | 42.28 | chnC |
| ATOM | 3603 | CG2 | VAL | C | 118 | 123.188 | 38.931 | 44.824 | 1.00 | 45.00 | chnC |
| ATOM | 3604 | C | VAL | C | 118 | 121.805 | 42.482 | 44.849 | 1.00 | 41.75 | chnC |
| ATOM | 3605 | O | VAL | C | 118 | 121.826 | 42.955 | 43.717 | 1.00 | 43.37 | chnC |
| ATOM | 3606 | N | ILE | C | 119 | 121.766 | 43.230 | 45.945 | 1.00 | 41.02 | chnC |
| ATOM | 3607 | CA | ILE | C | 119 | 121.812 | 44.684 | 45.867 | 1.00 | 41.19 | chnC |
| ATOM | 3608 | CB | ILE | C | 119 | 120.467 | 45.328 | 46.176 | 1.00 | 39.63 | chnC |
| ATOM | 3609 | CG2 | ILE | C | 119 | 120.554 | 46.810 | 45.919 | 1.00 | 38.32 | chnC |
| ATOM | 3610 | CG1 | ILE | C | 119 | 119.367 | 44.747 | 45.298 | 1.00 | 42.54 | chnC |
| ATOM | 3611 | CD1 | ILE | C | 119 | 117.991 | 45.279 | 45.621 | 1.00 | 40.94 | chnC |
| ATOM | 3612 | C | ILE | C | 119 | 122.782 | 45.208 | 46.902 | 1.00 | 43.11 | chnC |
| ATOM | 3613 | O | ILE | C | 119 | 122.660 | 44.859 | 48.073 | 1.00 | 43.41 | chnC |
| ATOM | 3614 | N | TYR | C | 120 | 123.752 | 46.016 | 46.470 | 1.00 | 41.90 | chnC |
| ATOM | 3615 | CA | TYR | C | 120 | 124.729 | 46.605 | 47.379 | 1.00 | 42.74 | chnC |
| ATOM | 3616 | CB | TYR | C | 120 | 126.116 | 46.622 | 46.755 | 1.00 | 41.88 | chnC |
| ATOM | 3617 | CG | TYR | C | 120 | 126.736 | 45.268 | 46.622 | 1.00 | 42.10 | chnC |
| ATOM | 3618 | CD1 | TYR | C | 120 | 126.509 | 44.491 | 45.489 | 1.00 | 43.76 | chnC |
| ATOM | 3619 | CE1 | TYR | C | 120 | 127.101 | 43.241 | 45.338 | 1.00 | 43.79 | chnC |
| ATOM | 3620 | CD2 | TYR | C | 120 | 127.570 | 44.764 | 47.614 | 1.00 | 42.99 | chnC |
| ATOM | 3621 | CE2 | TYR | C | 120 | 128.170 | 43.515 | 47.476 | 1.00 | 44.29 | chnC |
| ATOM | 3622 | CZ | TYR | C | 120 | 127.931 | 42.757 | 46.332 | 1.00 | 44.66 | chnC |
| ATOM | 3623 | OH | TYR | C | 120 | 128.529 | 41.525 | 46.172 | 1.00 | 46.60 | chnC |
| ATOM | 3624 | C | TYR | C | 120 | 124.314 | 48.026 | 47.695 | 1.00 | 43.93 | chnC |
| ATOM | 3625 | O | TYR | C | 120 | 124.063 | 48.812 | 46.787 | 1.00 | 43.99 | chnC |
| ATOM | 3626 | N | TYR | C | 121 | 124.249 | 48.354 | 48.980 | 1.00 | 47.33 | chnC |
| ATOM | 3627 | CA | TYR | C | 121 | 123.867 | 49.696 | 49.417 | 1.00 | 51.75 | chnC |
| ATOM | 3628 | CB | TYR | C | 121 | 122.700 | 49.644 | 50.401 | 1.00 | 51.89 | chnC |
| ATOM | 3629 | CG | TYR | C | 121 | 121.463 | 48.907 | 49.945 | 1.00 | 56.63 | chnC |
| ATOM | 3630 | CD1 | TYR | C | 121 | 121.457 | 47.516 | 49.838 | 1.00 | 61.11 | chnC |
| ATOM | 3631 | CE1 | TYR | C | 121 | 120.290 | 46.823 | 49.489 | 1.00 | 63.72 | chnC |
| ATOM | 3632 | CD2 | TYR | C | 121 | 120.271 | 49.596 | 49.687 | 1.00 | 55.82 | chnC |
| ATOM | 3633 | CE2 | TYR | C | 121 | 119.096 | 48.917 | 49.333 | 1.00 | 58.89 | chnC |
| ATOM | 3634 | CZ | TYR | C | 121 | 119.110 | 47.530 | 49.237 | 1.00 | 62.37 | chnC |
| ATOM | 3635 | OH | TYR | C | 121 | 117.957 | 46.846 | 48.895 | 1.00 | 62.17 | chnC |
| ATOM | 3636 | C | TYR | C | 121 | 125.004 | 50.441 | 50.111 | 1.00 | 54.27 | chnC |
| ATOM | 3637 | O | TYR | C | 121 | 125.911 | 49.833 | 50.689 | 1.00 | 56.28 | chnC |
| ATOM | 3638 | N | LYS | C | 122 | 124.915 | 51.768 | 50.081 | 1.00 | 57.63 | chnC |
| ATOM | 3639 | CA | LYS | C | 122 | 125.898 | 52.645 | 50.722 | 1.00 | 62.55 | chnC |
| ATOM | 3640 | CB | LYS | C | 122 | 126.950 | 53.160 | 49.726 | 1.00 | 65.32 | chnC |
| ATOM | 3641 | CG | LYS | C | 122 | 128.111 | 53.917 | 50.396 | 1.00 | 66.42 | chnC |
| ATOM | 3642 | CD | LYS | C | 122 | 128.997 | 54.680 | 49.405 | 1.00 | 67.29 | chnC |
| ATOM | 3643 | CE | LYS | C | 122 | 128.318 | 55.956 | 48.906 | 1.00 | 69.87 | chnC |
| ATOM | 3644 | NZ | LYS | C | 122 | 129.184 | 56.767 | 47.999 | 1.00 | 71.84 | chnC |
| ATOM | 3645 | C | LYS | C | 122 | 125.150 | 53.835 | 51.305 | 1.00 | 63.91 | chnC |
| ATOM | 3646 | O | LYS | C | 122 | 124.561 | 54.627 | 50.571 | 1.00 | 64.25 | chnC |
| ATOM | 3647 | N | ASP | C | 123 | 125.178 | 53.953 | 52.627 | 1.00 | 65.68 | chnC |
| ATOM | 3648 | CA | ASP | C | 123 | 124.503 | 55.042 | 53.328 | 1.00 | 68.24 | chnC |
| ATOM | 3649 | CB | ASP | C | 123 | 125.115 | 56.399 | 52.956 | 1.00 | 71.74 | chnC |
| ATOM | 3650 | CG | ASP | C | 123 | 126.596 | 56.493 | 53.286 | 1.00 | 75.81 | chnC |
| ATOM | 3651 | OD1 | ASP | C | 123 | 127.019 | 55.980 | 54.353 | 1.00 | 77.04 | chnC |
| ATOM | 3652 | OD2 | ASP | C | 123 | 127.334 | 57.098 | 52.472 | 1.00 | 76.98 | chnC |
| ATOM | 3653 | C | ASP | C | 123 | 123.013 | 55.051 | 53.015 | 1.00 | 67.89 | chnC |
| ATOM | 3654 | O | ASP | C | 123 | 122.405 | 56.114 | 52.890 | 1.00 | 69.27 | chnC |
| ATOM | 3655 | N | GLY | C | 124 | 122.434 | 53.864 | 52.865 | 1.00 | 67.78 | chnC |
| ATOM | 3656 | CA | GLY | C | 124 | 121.017 | 53.773 | 52.571 | 1.00 | 67.60 | chnC |
| ATOM | 3657 | C | GLY | C | 124 | 120.664 | 53.799 | 51.096 | 1.00 | 68.66 | chnC |
| ATOM | 3658 | O | GLY | C | 124 | 119.504 | 53.600 | 50.741 | 1.00 | 68.58 | chnC |
| ATOM | 3659 | N | GLU | C | 125 | 121.642 | 54.055 | 50.233 | 1.00 | 70.00 | chnC |
| ATOM | 3660 | CA | GLU | C | 125 | 121.383 | 54.085 | 48.792 | 1.00 | 72.67 | chnC |
| ATOM | 3661 | CB | GLU | C | 125 | 122.025 | 55.308 | 48.139 | 1.00 | 79.22 | chnC |
| ATOM | 3662 | CG | GLU | C | 125 | 121.327 | 56.613 | 48.454 | 1.00 | 90.03 | chnC |

-continued

| | | | | | | | | | | |
|---|---|---|---|---|---|---|---|---|---|---|
| ATOM | 3663 | CD | GLU | C | 125 | 121.969 | 57.788 | 47.754 | 1.00 | 93.68 | chnC |
| ATOM | 3664 | OE1 | GLU | C | 125 | 122.793 | 58.478 | 48.390 | 1.00 | 97.87 | chnC |
| ATOM | 3665 | OE2 | GLU | C | 125 | 121.655 | 58.011 | 46.566 | 1.00 | 94.28 | chnC |
| ATOM | 3666 | C | GLU | C | 125 | 121.860 | 52.836 | 48.070 | 1.00 | 70.02 | chnC |
| ATOM | 3667 | O | GLU | C | 125 | 122.987 | 52.374 | 48.269 | 1.00 | 70.70 | chnC |
| ATOM | 3668 | N | ALA | C | 126 | 120.990 | 52.304 | 47.222 | 1.00 | 64.87 | chnC |
| ATOM | 3669 | CA | ALA | C | 126 | 121.307 | 51.121 | 46.443 | 1.00 | 62.43 | chnC |
| ATOM | 3670 | CB | ALA | C | 126 | 120.018 | 50.429 | 46.016 | 1.00 | 62.27 | chnC |
| ATOM | 3671 | C | ALA | C | 126 | 122.089 | 51.581 | 45.223 | 1.00 | 61.20 | chnC |
| ATOM | 3672 | O | ALA | C | 126 | 121.566 | 52.358 | 44.428 | 1.00 | 61.61 | chnC |
| ATOM | 3673 | N | LEU | C | 127 | 123.332 | 51.123 | 45.077 | 1.00 | 59.56 | chnC |
| ATOM | 3674 | CA | LEU | C | 127 | 124.131 | 51.537 | 43.930 | 1.00 | 62.48 | chnC |
| ATOM | 3675 | CB | LEU | C | 127 | 125.471 | 52.138 | 44.359 | 1.00 | 62.87 | chnC |
| ATOM | 3676 | CG | LEU | C | 127 | 126.352 | 51.426 | 45.378 | 1.00 | 64.44 | chnC |
| ATOM | 3677 | CD1 | LEU | C | 127 | 127.772 | 51.956 | 45.290 | 1.00 | 67.40 | chnC |
| ATOM | 3678 | CD2 | LEU | C | 127 | 125.796 | 51.657 | 46.762 | 1.00 | 67.45 | chnC |
| ATOM | 3679 | C | LEU | C | 127 | 124.327 | 50.511 | 42.815 | 1.00 | 64.39 | chnC |
| ATOM | 3680 | O | LEU | C | 127 | 124.712 | 50.882 | 41.697 | 1.00 | 65.30 | chnC |
| ATOM | 3681 | N | LYS | C | 128 | 124.051 | 49.238 | 43.101 | 1.00 | 65.04 | chnC |
| ATOM | 3682 | CA | LYS | C | 128 | 124.182 | 48.171 | 42.102 | 1.00 | 64.91 | chnC |
| ATOM | 3683 | CB | LYS | C | 128 | 125.648 | 47.735 | 41.949 | 1.00 | 68.35 | chnC |
| ATOM | 3684 | CG | LYS | C | 128 | 126.434 | 48.594 | 40.941 | 1.00 | 73.54 | chnC |
| ATOM | 3685 | CD | LYS | C | 128 | 127.924 | 48.274 | 40.916 | 1.00 | 78.59 | chnC |
| ATOM | 3686 | CE | LYS | C | 128 | 128.673 | 49.156 | 39.920 | 1.00 | 79.57 | chnC |
| ATOM | 3687 | NZ | LYS | C | 128 | 128.608 | 50.605 | 40.285 | 1.00 | 82.06 | chnC |
| ATOM | 3688 | C | LYS | C | 128 | 123.276 | 46.979 | 42.411 | 1.00 | 63.71 | chnC |
| ATOM | 3689 | O | LYS | C | 128 | 123.184 | 46.549 | 43.554 | 1.00 | 63.81 | chnC |
| ATOM | 3690 | N | TYR | C | 129 | 122.548 | 46.509 | 41.395 | 1.00 | 62.89 | chnC |
| ATOM | 3691 | CA | TYR | C | 129 | 121.621 | 45.371 | 41.503 | 1.00 | 60.94 | chnC |
| ATOM | 3692 | CB | TYR | C | 129 | 120.173 | 45.875 | 41.421 | 1.00 | 62.72 | chnC |
| ATOM | 3693 | CG | TYR | C | 129 | 119.128 | 44.808 | 41.148 | 1.00 | 63.98 | chnC |
| ATOM | 3694 | CD1 | TYR | C | 129 | 118.400 | 44.232 | 42.184 | 1.00 | 64.02 | chnC |
| ATOM | 3695 | CE1 | TYR | C | 129 | 117.421 | 43.263 | 41.934 | 1.00 | 64.59 | chnC |
| ATOM | 3696 | CD2 | TYR | C | 129 | 118.854 | 44.387 | 39.850 | 1.00 | 65.19 | chnC |
| ATOM | 3697 | CE2 | TYR | C | 129 | 117.883 | 43.418 | 39.593 | 1.00 | 66.03 | chnC |
| ATOM | 3698 | CZ | TYR | C | 129 | 117.171 | 42.865 | 40.636 | 1.00 | 65.00 | chnC |
| ATOM | 3699 | OH | TYR | C | 129 | 116.195 | 41.935 | 40.373 | 1.00 | 65.03 | chnC |
| ATOM | 3700 | C | TYR | C | 129 | 121.873 | 44.338 | 40.399 | 1.00 | 60.46 | chnC |
| ATOM | 3701 | O | TYR | C | 129 | 122.057 | 44.696 | 39.244 | 1.00 | 62.46 | chnC |
| ATOM | 3702 | N | TRP | C | 130 | 121.847 | 43.058 | 40.757 | 1.00 | 61.61 | chnC |
| ATOM | 3703 | CA | TRP | C | 130 | 122.060 | 41.969 | 39.800 | 1.00 | 63.56 | chnC |
| ATOM | 3704 | CB | TRP | C | 130 | 123.528 | 41.558 | 39.753 | 1.00 | 65.70 | chnC |
| ATOM | 3705 | CG | TRP | C | 130 | 124.449 | 42.563 | 39.169 | 1.00 | 68.27 | chnC |
| ATOM | 3706 | CD2 | TRP | C | 130 | 125.463 | 43.288 | 39.864 | 1.00 | 67.31 | chnC |
| ATOM | 3707 | CE2 | TRP | C | 130 | 126.142 | 44.073 | 38.913 | 1.00 | 69.15 | chnC |
| ATOM | 3708 | CE3 | TRP | C | 130 | 125.870 | 43.344 | 41.200 | 1.00 | 66.64 | chnC |
| ATOM | 3709 | CD1 | TRP | C | 130 | 124.539 | 42.934 | 37.856 | 1.00 | 70.14 | chnC |
| ATOM | 3710 | NE1 | TRP | C | 130 | 125.557 | 43.841 | 37.694 | 1.00 | 70.12 | chnC |
| ATOM | 3711 | CZ2 | TRP | C | 130 | 127.206 | 44.907 | 39.258 | 1.00 | 70.68 | chnC |
| ATOM | 3712 | CZ3 | TRP | C | 130 | 126.924 | 44.168 | 41.541 | 1.00 | 68.08 | chnC |
| ATOM | 3713 | CH2 | TRP | C | 130 | 127.583 | 44.936 | 40.575 | 1.00 | 70.14 | chnC |
| ATOM | 3714 | C | TRP | C | 130 | 121.254 | 40.733 | 40.177 | 1.00 | 63.23 | chnC |
| ATOM | 3715 | O | TRP | C | 130 | 121.231 | 40.339 | 41.337 | 1.00 | 63.75 | chnC |
| ATOM | 3716 | N | TYR | C | 131 | 120.632 | 40.098 | 39.190 | 1.00 | 64.87 | chnC |
| ATOM | 3717 | CA | TYR | C | 131 | 119.844 | 38.895 | 39.438 | 1.00 | 66.55 | chnC |
| ATOM | 3718 | CB | TYR | C | 131 | 119.115 | 38.457 | 38.161 | 1.00 | 68.64 | chnC |
| ATOM | 3719 | CG | TYR | C | 131 | 118.474 | 37.081 | 38.244 | 1.00 | 70.35 | chnC |
| ATOM | 3720 | CD1 | TYR | C | 131 | 117.343 | 36.865 | 39.026 | 1.00 | 70.80 | chnC |
| ATOM | 3721 | CE1 | TYR | C | 131 | 116.771 | 35.600 | 39.129 | 1.00 | 71.52 | chnC |
| ATOM | 3722 | CD2 | TYR | C | 131 | 119.018 | 35.992 | 37.560 | 1.00 | 70.26 | chnC |
| ATOM | 3723 | CE2 | TYR | C | 131 | 118.454 | 34.727 | 37.658 | 1.00 | 69.58 | chnC |
| ATOM | 3724 | CZ | TYR | C | 131 | 117.331 | 34.537 | 38.447 | 1.00 | 70.55 | chnC |
| ATOM | 3725 | OH | TYR | C | 131 | 116.771 | 33.283 | 38.569 | 1.00 | 70.93 | chnC |
| ATOM | 3726 | C | TYR | C | 131 | 120.744 | 37.769 | 39.942 | 1.00 | 66.00 | chnC |
| ATOM | 3727 | O | TYR | C | 131 | 120.318 | 36.950 | 40.746 | 1.00 | 66.20 | chnC |
| ATOM | 3728 | N | GLU | C | 132 | 121.978 | 37.737 | 39.442 | 1.00 | 67.65 | chnC |
| ATOM | 3729 | CA | GLU | C | 132 | 122.985 | 36.733 | 39.808 | 1.00 | 68.00 | chnC |
| ATOM | 3730 | CB | GLU | C | 132 | 123.833 | 36.380 | 38.578 | 1.00 | 71.50 | chnC |
| ATOM | 3731 | CG | GLU | C | 132 | 123.073 | 35.764 | 37.421 | 1.00 | 74.75 | chnC |
| ATOM | 3732 | CD | GLU | C | 132 | 122.589 | 34.364 | 37.737 | 1.00 | 77.82 | chnC |
| ATOM | 3733 | OE1 | GLU | C | 132 | 121.532 | 34.230 | 38.392 | 1.00 | 78.20 | chnC |
| ATOM | 3734 | OE2 | GLU | C | 132 | 123.274 | 33.398 | 37.336 | 1.00 | 80.41 | chnC |
| ATOM | 3735 | C | GLU | C | 132 | 123.910 | 37.337 | 40.853 | 1.00 | 66.36 | chnC |
| ATOM | 3736 | O | GLU | C | 132 | 124.221 | 38.520 | 40.770 | 1.00 | 67.67 | chnC |
| ATOM | 3737 | N | ASN | C | 133 | 124.372 | 36.548 | 41.819 | 1.00 | 63.17 | chnC |
| ATOM | 3738 | CA | ASN | C | 133 | 125.275 | 37.110 | 42.818 | 1.00 | 65.05 | chnC |
| ATOM | 3739 | CB | ASN | C | 133 | 125.731 | 36.070 | 43.844 | 1.00 | 69.03 | chnC |
| ATOM | 3740 | CG | ASN | C | 133 | 126.504 | 36.692 | 45.016 | 1.00 | 71.01 | chnC |
| ATOM | 3741 | OD1 | ASN | C | 133 | 126.598 | 37.918 | 45.154 | 1.00 | 69.16 | chnC |

-continued

| | | | | | | | | | |
|---|---|---|---|---|---|---|---|---|---|
| ATOM | 3742 | ND2 | ASN | C | 133 | 127.059 | 35.836 | 45.866 | 1.00 | 72.52 | chnC |
| ATOM | 3743 | C | ASN | C | 133 | 126.457 | 37.630 | 42.034 | 1.00 | 63.69 | chnC |
| ATOM | 3744 | O | ASN | C | 133 | 126.957 | 36.955 | 41.141 | 1.00 | 62.60 | chnC |
| ATOM | 3745 | N | HIS | C | 134 | 126.872 | 38.847 | 42.349 | 1.00 | 65.80 | chnC |
| ATOM | 3746 | CA | HIS | C | 134 | 127.964 | 39.486 | 41.636 | 1.00 | 70.06 | chnC |
| ATOM | 3747 | CB | HIS | C | 134 | 127.344 | 40.459 | 40.618 | 1.00 | 75.99 | chnC |
| ATOM | 3748 | CG | HIS | C | 134 | 128.196 | 40.746 | 39.418 | 1.00 | 81.01 | chnC |
| ATOM | 3749 | CD2 | HIS | C | 134 | 128.049 | 40.393 | 38.117 | 1.00 | 81.78 | chnC |
| ATOM | 3750 | ND1 | HIS | C | 134 | 129.331 | 41.526 | 39.476 | 1.00 | 82.60 | chnC |
| ATOM | 3751 | CE1 | HIS | C | 134 | 129.847 | 41.642 | 38.263 | 1.00 | 84.09 | chnC |
| ATOM | 3752 | NE2 | HIS | C | 134 | 129.087 | 40.964 | 37.422 | 1.00 | 84.03 | chnC |
| ATOM | 3753 | C | HIS | C | 134 | 128.819 | 40.253 | 42.640 | 1.00 | 68.19 | chnC |
| ATOM | 3754 | O | HIS | C | 134 | 128.284 | 40.915 | 43.527 | 1.00 | 68.09 | chnC |
| ATOM | 3755 | N | ASN | C | 135 | 130.139 | 40.104 | 42.546 | 1.00 | 67.95 | chnC |
| ATOM | 3756 | CA | ASN | C | 135 | 131.056 | 40.828 | 43.426 | 1.00 | 68.15 | chnC |
| ATOM | 3757 | CB | ASN | C | 135 | 132.461 | 40.233 | 43.331 | 1.00 | 70.92 | chnC |
| ATOM | 3758 | CG | ASN | C | 135 | 132.915 | 39.598 | 44.618 | 1.00 | 72.97 | chnC |
| ATOM | 3759 | OD1 | ASN | C | 135 | 132.644 | 38.426 | 44.870 | 1.00 | 74.00 | chnC |
| ATOM | 3760 | ND2 | ASN | C | 135 | 133.641 | 40.359 | 45.432 | 1.00 | 77.38 | chnC |
| ATOM | 3761 | C | ASN | C | 135 | 131.100 | 42.288 | 42.954 | 1.00 | 67.72 | chnC |
| ATOM | 3762 | O | ASN | C | 135 | 130.956 | 42.569 | 41.757 | 1.00 | 69.07 | chnC |
| ATOM | 3763 | N | ILE | C | 136 | 131.249 | 43.217 | 43.888 | 1.00 | 64.04 | chnC |
| ATOM | 3764 | CA | ILE | C | 136 | 131.331 | 44.626 | 43.526 | 1.00 | 64.14 | chnC |
| ATOM | 3765 | CB | ILE | C | 136 | 130.387 | 45.490 | 44.374 | 1.00 | 63.48 | chnC |
| ATOM | 3766 | CG2 | ILE | C | 136 | 130.752 | 45.403 | 45.818 | 1.00 | 66.10 | chnC |
| ATOM | 3767 | CG1 | ILE | C | 136 | 130.455 | 46.944 | 43.945 | 1.00 | 62.52 | chnC |
| ATOM | 3768 | CD1 | ILE | C | 136 | 129.517 | 47.823 | 44.727 | 1.00 | 63.81 | chnC |
| ATOM | 3769 | C | ILE | C | 136 | 132.782 | 45.023 | 43.730 | 1.00 | 65.11 | chnC |
| ATOM | 3770 | O | ILE | C | 136 | 133.396 | 44.663 | 44.732 | 1.00 | 64.23 | chnC |
| ATOM | 3771 | N | SER | C | 137 | 133.344 | 45.718 | 42.747 | 1.00 | 68.96 | chnC |
| ATOM | 3772 | CA | SER | C | 137 | 134.746 | 46.119 | 42.803 | 1.00 | 70.15 | chnC |
| ATOM | 3773 | CB | SER | C | 137 | 135.566 | 45.254 | 41.847 | 1.00 | 69.45 | chnC |
| ATOM | 3774 | OG | SER | C | 137 | 136.899 | 45.718 | 41.788 | 1.00 | 70.20 | chnC |
| ATOM | 3775 | C | SER | C | 137 | 135.025 | 47.593 | 42.516 | 1.00 | 70.94 | chnC |
| ATOM | 3776 | O | SER | C | 137 | 134.734 | 48.090 | 41.428 | 1.00 | 70.55 | chnC |
| ATOM | 3777 | N | ILE | C | 138 | 135.608 | 48.274 | 43.501 | 1.00 | 72.39 | chnC |
| ATOM | 3778 | CA | ILE | C | 138 | 135.960 | 49.687 | 43.380 | 1.00 | 73.91 | chnC |
| ATOM | 3779 | CB | ILE | C | 138 | 135.686 | 50.468 | 44.690 | 1.00 | 73.89 | chnC |
| ATOM | 3780 | CG2 | ILE | C | 138 | 136.150 | 51.913 | 44.556 | 1.00 | 71.28 | chnC |
| ATOM | 3781 | CG1 | ILE | C | 138 | 134.189 | 50.450 | 45.002 | 1.00 | 75.95 | chnC |
| ATOM | 3782 | CD1 | ILE | C | 138 | 133.808 | 51.186 | 46.274 | 1.00 | 78.61 | chnC |
| ATOM | 3783 | C | ILE | C | 138 | 137.443 | 49.763 | 43.028 | 1.00 | 76.64 | chnC |
| ATOM | 3784 | O | ILE | C | 138 | 138.311 | 49.643 | 43.899 | 1.00 | 76.24 | chnC |
| ATOM | 3785 | N | THR | C | 139 | 137.711 | 49.944 | 41.734 | 1.00 | 81.03 | chnC |
| ATOM | 3786 | CA | THR | C | 139 | 139.072 | 50.030 | 41.186 | 1.00 | 81.56 | chnC |
| ATOM | 3787 | CB | THR | C | 139 | 139.038 | 50.277 | 39.636 | 1.00 | 82.30 | chnC |
| ATOM | 3788 | OG1 | THR | C | 139 | 138.261 | 51.451 | 39.337 | 1.00 | 80.76 | chnC |
| ATOM | 3789 | CG2 | THR | C | 139 | 138.421 | 49.071 | 38.910 | 1.00 | 81.78 | chnC |
| ATOM | 3790 | C | THR | C | 139 | 139.956 | 51.081 | 41.873 | 1.00 | 80.16 | chnC |
| ATOM | 3791 | O | THR | C | 139 | 140.983 | 50.741 | 42.467 | 1.00 | 76.52 | chnC |
| ATOM | 3792 | N | ASN | C | 140 | 139.535 | 52.343 | 41.811 | 1.00 | 79.38 | chnC |
| ATOM | 3793 | CA | ASN | C | 140 | 140.278 | 53.440 | 42.420 | 1.00 | 78.59 | chnC |
| ATOM | 3794 | CB | ASN | C | 140 | 140.521 | 54.547 | 41.378 | 1.00 | 80.25 | chnC |
| ATOM | 3795 | CG | ASN | C | 140 | 141.489 | 55.634 | 41.867 | 1.00 | 81.36 | chnC |
| ATOM | 3796 | OD1 | ASN | C | 140 | 141.953 | 55.613 | 43.018 | 1.00 | 82.69 | chnC |
| ATOM | 3797 | ND2 | ASN | C | 140 | 141.798 | 56.583 | 40.982 | 1.00 | 78.74 | chnC |
| ATOM | 3798 | C | ASN | C | 140 | 139.495 | 53.988 | 43.619 | 1.00 | 79.09 | chnC |
| ATOM | 3799 | O | ASN | C | 140 | 138.544 | 54.766 | 43.453 | 1.00 | 76.96 | chnC |
| ATOM | 3800 | N | ALA | C | 141 | 139.905 | 53.588 | 44.823 | 1.00 | 78.10 | chnC |
| ATOM | 3801 | CA | ALA | C | 141 | 139.237 | 54.033 | 46.049 | 1.00 | 79.45 | chnC |
| ATOM | 3802 | CB | ALA | C | 141 | 139.765 | 53.277 | 47.254 | 1.00 | 79.48 | chnC |
| ATOM | 3803 | C | ALA | C | 141 | 139.344 | 55.536 | 46.283 | 1.00 | 80.14 | chnC |
| ATOM | 3804 | O | ALA | C | 141 | 140.439 | 56.107 | 46.299 | 1.00 | 82.35 | chnC |
| ATOM | 3805 | N | THR | C | 142 | 138.189 | 56.161 | 46.479 | 1.00 | 79.27 | chnC |
| ATOM | 3806 | CA | THR | C | 142 | 138.098 | 57.594 | 46.708 | 1.00 | 78.30 | chnC |
| ATOM | 3807 | CB | THR | C | 142 | 137.171 | 58.232 | 45.670 | 1.00 | 77.72 | chnC |
| ATOM | 3808 | OG1 | THR | C | 142 | 137.653 | 57.926 | 44.354 | 1.00 | 79.16 | chnC |
| ATOM | 3809 | CG2 | THR | C | 142 | 137.098 | 59.745 | 45.864 | 1.00 | 78.51 | chnC |
| ATOM | 3810 | C | THR | C | 142 | 137.515 | 57.845 | 48.084 | 1.00 | 78.28 | chnC |
| ATOM | 3811 | O | THR | C | 142 | 136.786 | 57.012 | 48.610 | 1.00 | 78.13 | chnC |
| ATOM | 3812 | N | VAL | C | 143 | 137.840 | 58.994 | 48.668 | 1.00 | 80.95 | chnC |
| ATOM | 3813 | CA | VAL | C | 143 | 137.331 | 59.360 | 49.990 | 1.00 | 83.17 | chnC |
| ATOM | 3814 | CB | VAL | C | 143 | 137.932 | 60.712 | 50.477 | 1.00 | 84.36 | chnC |
| ATOM | 3815 | CG1 | VAL | C | 143 | 137.530 | 61.841 | 49.533 | 1.00 | 85.25 | chnC |
| ATOM | 3816 | CG2 | VAL | C | 143 | 137.494 | 61.018 | 51.918 | 1.00 | 83.85 | chnC |
| ATOM | 3817 | C | VAL | C | 143 | 135.802 | 59.443 | 49.952 | 1.00 | 83.43 | chnC |
| ATOM | 3818 | O | VAL | C | 143 | 135.138 | 59.366 | 50.990 | 1.00 | 83.18 | chnC |
| ATOM | 3819 | N | GLU | C | 144 | 135.254 | 59.601 | 48.748 | 1.00 | 84.00 | chnC |
| ATOM | 3820 | CA | GLU | C | 144 | 133.807 | 59.661 | 48.561 | 1.00 | 85.93 | chnC |

-continued

| | | | | | | | | | | |
|---|---|---|---|---|---|---|---|---|---|---|
| ATOM | 3821 | CB | GLU | C | 144 | 133.475 | 60.117 | 47.143 | 1.00 | 92.56 chnC |
| ATOM | 3822 | CG | GLU | C | 144 | 133.917 | 61.536 | 46.824 | 1.00 | 101.31 chnC |
| ATOM | 3823 | CD | GLU | C | 144 | 133.699 | 61.888 | 45.363 | 1.00 | 105.62 chnC |
| ATOM | 3824 | OE1 | GLU | C | 144 | 132.522 | 62.035 | 44.947 | 1.00 | 107.48 chnC |
| ATOM | 3825 | OE2 | GLU | C | 144 | 134.708 | 62.002 | 44.630 | 1.00 | 109.18 chnC |
| ATOM | 3826 | C | GLU | C | 144 | 133.199 | 58.275 | 48.799 | 1.00 | 82.48 chnC |
| ATOM | 3827 | O | GLU | C | 144 | 132.058 | 58.150 | 49.258 | 1.00 | 82.15 chnC |
| ATOM | 3828 | N | ASP | C | 145 | 133.981 | 57.242 | 48.490 | 1.00 | 76.50 chnC |
| ATOM | 3829 | CA | ASP | C | 145 | 133.562 | 55.857 | 48.668 | 1.00 | 71.12 chnC |
| ATOM | 3830 | CB | ASP | C | 145 | 134.526 | 54.922 | 47.936 | 1.00 | 71.92 chnC |
| ATOM | 3831 | CG | ASP | C | 145 | 134.444 | 55.065 | 46.426 | 1.00 | 73.73 chnC |
| ATOM | 3832 | OD1 | ASP | C | 145 | 133.316 | 55.245 | 45.917 | 1.00 | 72.34 chnC |
| ATOM | 3833 | OD2 | ASP | C | 145 | 135.498 | 54.985 | 45.749 | 1.00 | 74.82 chnC |
| ATOM | 3834 | C | ASP | C | 145 | 133.436 | 55.435 | 50.137 | 1.00 | 69.66 chnC |
| ATOM | 3835 | O | ASP | C | 145 | 133.143 | 54.277 | 50.428 | 1.00 | 67.50 chnC |
| ATOM | 3836 | N | SER | C | 146 | 133.675 | 56.365 | 51.058 | 1.00 | 70.07 chnC |
| ATOM | 3837 | CA | SER | C | 146 | 133.562 | 56.075 | 52.491 | 1.00 | 69.88 chnC |
| ATOM | 3838 | CB | SER | C | 146 | 134.323 | 57.117 | 53.332 | 1.00 | 69.43 chnC |
| ATOM | 3839 | OG | SER | C | 146 | 135.717 | 57.109 | 53.046 | 1.00 | 68.28 chnC |
| ATOM | 3840 | C | SER | C | 146 | 132.087 | 56.073 | 52.887 | 1.00 | 70.54 chnC |
| ATOM | 3841 | O | SER | C | 146 | 131.287 | 56.853 | 52.355 | 1.00 | 72.86 chnC |
| ATOM | 3842 | N | GLY | C | 147 | 131.727 | 55.187 | 53.807 | 1.00 | 70.30 chnC |
| ATOM | 3843 | CA | GLY | C | 147 | 130.346 | 55.114 | 54.250 | 1.00 | 68.88 chnC |
| ATOM | 3844 | C | GLY | C | 147 | 129.980 | 53.729 | 54.740 | 1.00 | 68.52 chnC |
| ATOM | 3845 | O | GLY | C | 147 | 130.813 | 52.810 | 54.718 | 1.00 | 68.61 chnC |
| ATOM | 3846 | N | THR | C | 148 | 128.742 | 53.575 | 55.199 | 1.00 | 66.59 chnC |
| ATOM | 3847 | CA | THR | C | 148 | 128.284 | 52.285 | 55.691 | 1.00 | 66.63 chnC |
| ATOM | 3848 | CB | THR | C | 148 | 127.254 | 52.441 | 56.840 | 1.00 | 69.25 chnC |
| ATOM | 3849 | OG1 | THR | C | 148 | 125.956 | 52.721 | 56.302 | 1.00 | 72.65 chnC |
| ATOM | 3850 | CG2 | THR | C | 148 | 127.655 | 53.592 | 57.766 | 1.00 | 70.40 chnC |
| ATOM | 3851 | C | THR | C | 148 | 127.680 | 51.484 | 54.540 | 1.00 | 63.11 chnC |
| ATOM | 3852 | O | THR | C | 148 | 126.741 | 51.932 | 53.878 | 1.00 | 63.19 chnC |
| ATOM | 3853 | N | TYR | C | 149 | 128.262 | 50.323 | 54.267 | 1.00 | 58.51 chnC |
| ATOM | 3854 | CA | TYR | C | 149 | 127.781 | 49.468 | 53.195 | 1.00 | 54.96 chnC |
| ATOM | 3855 | CB | TYR | C | 149 | 128.948 | 48.976 | 52.331 | 1.00 | 55.18 chnC |
| ATOM | 3856 | CG | TYR | C | 149 | 129.622 | 50.008 | 51.453 | 1.00 | 56.07 chnC |
| ATOM | 3857 | CD1 | TYR | C | 149 | 130.584 | 50.875 | 51.968 | 1.00 | 57.34 chnC |
| ATOM | 3858 | CE1 | TYR | C | 149 | 131.277 | 51.747 | 51.136 | 1.00 | 58.99 chnC |
| ATOM | 3859 | CD2 | TYR | C | 149 | 129.368 | 50.050 | 50.083 | 1.00 | 55.85 chnC |
| ATOM | 3860 | CE2 | TYR | C | 149 | 130.054 | 50.915 | 49.248 | 1.00 | 57.36 chnC |
| ATOM | 3861 | CZ | TYR | C | 149 | 131.007 | 51.757 | 49.777 | 1.00 | 58.07 chnC |
| ATOM | 3862 | OH | TYR | C | 149 | 131.694 | 52.601 | 48.939 | 1.00 | 57.48 chnC |
| ATOM | 3863 | C | TYR | C | 149 | 127.059 | 48.252 | 53.761 | 1.00 | 54.19 chnC |
| ATOM | 3864 | O | TYR | C | 149 | 127.317 | 47.839 | 54.893 | 1.00 | 52.61 chnC |
| ATOM | 3865 | N | TYR | C | 150 | 126.145 | 47.706 | 52.959 | 1.00 | 50.95 chnC |
| ATOM | 3866 | CA | TYR | C | 150 | 125.387 | 46.498 | 53.286 | 1.00 | 47.18 chnC |
| ATOM | 3867 | CB | TYR | C | 150 | 124.397 | 46.718 | 54.442 | 1.00 | 47.53 chnC |
| ATOM | 3868 | CG | TYR | C | 150 | 123.152 | 47.498 | 54.108 | 1.00 | 51.35 chnC |
| ATOM | 3869 | CD1 | TYR | C | 150 | 121.967 | 46.844 | 53.773 | 1.00 | 53.19 chnC |
| ATOM | 3870 | CE1 | TYR | C | 150 | 120.808 | 47.559 | 53.477 | 1.00 | 55.59 chnC |
| ATOM | 3871 | CD2 | TYR | C | 150 | 123.151 | 48.887 | 54.143 | 1.00 | 54.29 chnC |
| ATOM | 3872 | CE2 | TYR | C | 150 | 121.998 | 49.615 | 53.850 | 1.00 | 57.38 chnC |
| ATOM | 3873 | CZ | TYR | C | 150 | 120.828 | 48.945 | 53.516 | 1.00 | 57.05 chnC |
| ATOM | 3874 | OH | TYR | C | 150 | 119.692 | 49.668 | 53.208 | 1.00 | 57.39 chnC |
| ATOM | 3875 | C | TYR | C | 150 | 124.688 | 46.010 | 52.020 | 1.00 | 44.32 chnC |
| ATOM | 3876 | O | TYR | C | 150 | 124.525 | 46.768 | 51.073 | 1.00 | 43.65 chnC |
| ATOM | 3877 | N | CYS | C | 151 | 124.308 | 44.737 | 51.992 | 1.00 | 41.21 chnC |
| ATOM | 3878 | CA | CYS | C | 151 | 123.649 | 44.162 | 50.823 | 1.00 | 39.30 chnC |
| ATOM | 3879 | C | CYS | C | 151 | 122.435 | 43.356 | 51.210 | 1.00 | 41.29 chnC |
| ATOM | 3880 | O | CYS | C | 151 | 122.304 | 42.922 | 52.355 | 1.00 | 43.37 chnC |
| ATOM | 3881 | CB | CYS | C | 151 | 124.604 | 43.237 | 50.068 | 1.00 | 40.68 chnC |
| ATOM | 3882 | SG | CYS | C | 151 | 125.078 | 41.743 | 51.008 | 1.00 | 41.09 chnC |
| ATOM | 3883 | N | THR | C | 152 | 121.548 | 43.162 | 50.242 | 1.00 | 41.17 chnC |
| ATOM | 3884 | CA | THR | C | 152 | 120.343 | 42.364 | 50.434 | 1.00 | 38.58 chnC |
| ATOM | 3885 | CB | THR | C | 152 | 119.081 | 43.192 | 50.288 | 1.00 | 38.56 chnC |
| ATOM | 3886 | OG1 | THR | C | 152 | 119.050 | 43.781 | 48.987 | 1.00 | 42.87 chnC |
| ATOM | 3887 | CG2 | THR | C | 152 | 119.047 | 44.282 | 51.316 | 1.00 | 37.90 chnC |
| ATOM | 3888 | C | THR | C | 152 | 120.342 | 41.315 | 49.336 | 1.00 | 40.06 chnC |
| ATOM | 3889 | O | THR | C | 152 | 120.808 | 41.574 | 48.220 | 1.00 | 43.48 chnC |
| ATOM | 3890 | N | GLY | C | 153 | 119.814 | 40.138 | 49.644 | 1.00 | 41.74 chnC |
| ATOM | 3891 | CA | GLY | C | 153 | 119.781 | 39.082 | 48.656 | 1.00 | 40.06 chnC |
| ATOM | 3892 | C | GLY | C | 153 | 118.643 | 38.128 | 48.894 | 1.00 | 39.64 chnC |
| ATOM | 3893 | O | GLY | C | 153 | 117.804 | 38.336 | 49.763 | 1.00 | 37.49 chnC |
| ATOM | 3894 | N | LYS | C | 154 | 118.643 | 37.055 | 48.125 | 1.00 | 40.86 chnC |
| ATOM | 3895 | CA | LYS | C | 154 | 117.612 | 36.050 | 48.218 | 1.00 | 43.22 chnC |
| ATOM | 3896 | CB | LYS | C | 154 | 116.682 | 36.170 | 46.978 | 1.00 | 47.94 chnC |
| ATOM | 3897 | CG | LYS | C | 154 | 116.030 | 34.844 | 46.442 | 1.00 | 57.22 chnC |
| ATOM | 3898 | CD | LYS | C | 154 | 115.247 | 35.010 | 45.083 | 1.00 | 57.73 chnC |
| ATOM | 3899 | CE | LYS | C | 154 | 114.871 | 33.657 | 44.421 | 1.00 | 54.99 chnC |

-continued

| ATOM | 3900 | NZ | LYS | C | 154 | 114.211 | 33.788 | 43.079 | 1.00 | 49.05 | chnC |
| --- | --- | --- | --- | --- | --- | --- | --- | --- | --- | --- | --- |
| ATOM | 3901 | C | LYS | C | 154 | 118.279 | 34.685 | 48.296 | 1.00 | 41.26 | chnC |
| ATOM | 3902 | O | LYS | C | 154 | 118.753 | 34.193 | 47.288 | 1.00 | 43.46 | chnC |
| ATOM | 3903 | N | VAL | C | 155 | 118.465 | 34.140 | 49.494 | 1.00 | 38.93 | chnC |
| ATOM | 3904 | CA | VAL | C | 155 | 119.030 | 32.796 | 49.571 | 1.00 | 39.88 | chnC |
| ATOM | 3905 | CB | VAL | C | 155 | 119.903 | 32.547 | 50.775 | 1.00 | 38.38 | chnC |
| ATOM | 3906 | CG1 | VAL | C | 155 | 120.446 | 31.124 | 50.709 | 1.00 | 36.54 | chnC |
| ATOM | 3907 | CG2 | VAL | C | 155 | 121.038 | 33.538 | 50.803 | 1.00 | 38.44 | chnC |
| ATOM | 3908 | C | VAL | C | 155 | 117.793 | 31.930 | 49.646 | 1.00 | 42.09 | chnC |
| ATOM | 3909 | O | VAL | C | 155 | 116.963 | 32.082 | 50.549 | 1.00 | 42.13 | chnC |
| ATOM | 3910 | N | TRP | C | 156 | 117.678 | 31.032 | 48.672 | 1.00 | 44.71 | chnC |
| ATOM | 3911 | CA | TRP | C | 156 | 116.504 | 30.184 | 48.513 | 1.00 | 45.85 | chnC |
| ATOM | 3912 | CB | TRP | C | 156 | 116.219 | 29.390 | 49.773 | 1.00 | 39.79 | chnC |
| ATOM | 3913 | CG | TRP | C | 156 | 117.360 | 28.439 | 50.025 | 1.00 | 41.07 | chnC |
| ATOM | 3914 | CD2 | TRP | C | 156 | 117.805 | 27.381 | 49.164 | 1.00 | 39.86 | chnC |
| ATOM | 3915 | CE2 | TRP | C | 156 | 118.966 | 26.832 | 49.740 | 1.00 | 38.71 | chnC |
| ATOM | 3916 | CE3 | TRP | C | 156 | 117.337 | 26.851 | 47.959 | 1.00 | 40.81 | chnC |
| ATOM | 3917 | CD1 | TRP | C | 156 | 118.243 | 28.471 | 51.064 | 1.00 | 42.60 | chnC |
| ATOM | 3918 | NE1 | TRP | C | 156 | 119.214 | 27.511 | 50.899 | 1.00 | 38.81 | chnC |
| ATOM | 3919 | CZ2 | TRP | C | 156 | 119.664 | 25.793 | 49.153 | 1.00 | 38.47 | chnC |
| ATOM | 3920 | CZ3 | TRP | C | 156 | 118.032 | 25.813 | 47.375 | 1.00 | 39.08 | chnC |
| ATOM | 3921 | CH2 | TRP | C | 156 | 119.182 | 25.295 | 47.971 | 1.00 | 38.86 | chnC |
| ATOM | 3922 | C | TRP | C | 156 | 115.369 | 31.128 | 48.073 | 1.00 | 50.23 | chnC |
| ATOM | 3923 | O | TRP | C | 156 | 115.625 | 32.090 | 47.327 | 1.00 | 53.74 | chnC |
| ATOM | 3924 | N | GLN | C | 157 | 114.128 | 30.888 | 48.454 | 1.00 | 50.96 | chnC |
| ATOM | 3925 | CA | GLN | C | 157 | 113.126 | 31.828 | 47.969 | 1.00 | 55.56 | chnC |
| ATOM | 3926 | CB | GLN | C | 157 | 111.783 | 31.130 | 47.678 | 1.00 | 60.62 | chnC |
| ATOM | 3927 | CG | GLN | C | 157 | 111.834 | 29.945 | 46.696 | 1.00 | 62.73 | chnC |
| ATOM | 3928 | CD | GLN | C | 157 | 112.576 | 30.225 | 45.393 | 1.00 | 60.70 | chnC |
| ATOM | 3929 | OE1 | GLN | C | 157 | 111.972 | 30.587 | 44.392 | 1.00 | 60.22 | chnC |
| ATOM | 3930 | NE2 | GLN | C | 157 | 113.880 | 30.001 | 45.394 | 1.00 | 61.05 | chnC |
| ATOM | 3931 | C | GLN | C | 157 | 112.926 | 32.981 | 48.948 | 1.00 | 55.46 | chnC |
| ATOM | 3932 | O | GLN | C | 157 | 112.101 | 33.868 | 48.714 | 1.00 | 57.72 | chnC |
| ATOM | 3933 | N | LEU | C | 158 | 113.735 | 33.012 | 50.001 | 1.00 | 53.39 | chnC |
| ATOM | 3934 | CA | LEU | C | 158 | 113.585 | 34.027 | 51.032 | 1.00 | 53.16 | chnC |
| ATOM | 3935 | CB | LEU | C | 158 | 113.659 | 33.366 | 52.399 | 1.00 | 55.00 | chnC |
| ATOM | 3936 | CG | LEU | C | 158 | 112.646 | 32.249 | 52.589 | 1.00 | 55.74 | chnC |
| ATOM | 3937 | CD1 | LEU | C | 158 | 113.016 | 31.424 | 53.793 | 1.00 | 56.37 | chnC |
| ATOM | 3938 | CD2 | LEU | C | 158 | 111.257 | 32.842 | 52.713 | 1.00 | 58.48 | chnC |
| ATOM | 3939 | C | LEU | C | 158 | 114.550 | 35.188 | 50.980 | 1.00 | 51.91 | chnC |
| ATOM | 3940 | O | LEU | C | 158 | 115.720 | 35.021 | 50.640 | 1.00 | 49.37 | chnC |
| ATOM | 3941 | N | ASP | C | 159 | 114.045 | 36.357 | 51.371 | 1.00 | 53.42 | chnC |
| ATOM | 3942 | CA | ASP | C | 159 | 114.812 | 37.598 | 51.393 | 1.00 | 55.73 | chnC |
| ATOM | 3943 | CB | ASP | C | 159 | 113.894 | 38.808 | 51.214 | 1.00 | 60.13 | chnC |
| ATOM | 3944 | CG | ASP | C | 159 | 113.271 | 38.871 | 49.849 | 1.00 | 65.05 | chnC |
| ATOM | 3945 | OD1 | ASP | C | 159 | 114.026 | 39.008 | 48.857 | 1.00 | 68.16 | chnC |
| ATOM | 3946 | OD2 | ASP | C | 159 | 112.026 | 38.788 | 49.776 | 1.00 | 66.57 | chnC |
| ATOM | 3947 | C | ASP | C | 159 | 115.554 | 37.761 | 52.699 | 1.00 | 53.82 | chnC |
| ATOM | 3948 | O | ASP | C | 159 | 115.040 | 37.416 | 53.761 | 1.00 | 53.07 | chnC |
| ATOM | 3949 | N | TYR | C | 160 | 116.741 | 38.350 | 52.617 | 1.00 | 51.84 | chnC |
| ATOM | 3950 | CA | TYR | C | 160 | 117.570 | 38.573 | 53.788 | 1.00 | 51.56 | chnC |
| ATOM | 3951 | CB | TYR | C | 160 | 118.477 | 37.358 | 54.038 | 1.00 | 52.04 | chnC |
| ATOM | 3952 | CG | TYR | C | 160 | 117.744 | 36.054 | 54.297 | 1.00 | 49.38 | chnC |
| ATOM | 3953 | CD1 | TYR | C | 160 | 117.825 | 34.997 | 53.395 | 1.00 | 48.27 | chnC |
| ATOM | 3954 | CE1 | TYR | C | 160 | 117.144 | 33.813 | 53.615 | 1.00 | 48.08 | chnC |
| ATOM | 3955 | CD2 | TYR | C | 160 | 116.958 | 35.888 | 55.433 | 1.00 | 50.41 | chnC |
| ATOM | 3956 | CE2 | TYR | C | 160 | 116.270 | 34.708 | 55.665 | 1.00 | 50.32 | chnC |
| ATOM | 3957 | CZ | TYR | C | 160 | 116.367 | 33.675 | 54.753 | 1.00 | 49.89 | chnC |
| ATOM | 3958 | OH | TYR | C | 160 | 115.682 | 32.505 | 54.974 | 1.00 | 50.23 | chnC |
| ATOM | 3959 | C | TYR | C | 160 | 118.422 | 39.819 | 53.605 | 1.00 | 52.61 | chnC |
| ATOM | 3960 | O | TYR | C | 160 | 118.686 | 40.242 | 52.479 | 1.00 | 52.42 | chnC |
| ATOM | 3961 | N | GLU | C | 161 | 118.831 | 40.410 | 54.723 | 1.00 | 54.19 | chnC |
| ATOM | 3962 | CA | GLU | C | 161 | 119.669 | 41.602 | 54.707 | 1.00 | 55.59 | chnC |
| ATOM | 3963 | CB | GLU | C | 161 | 118.915 | 42.794 | 55.279 | 1.00 | 56.92 | chnC |
| ATOM | 3964 | CG | GLU | C | 161 | 119.628 | 44.114 | 55.078 | 1.00 | 60.82 | chnC |
| ATOM | 3965 | CD | GLU | C | 161 | 118.872 | 45.296 | 55.670 | 1.00 | 64.18 | chnC |
| ATOM | 3966 | OE1 | GLU | C | 161 | 119.529 | 46.154 | 56.307 | 1.00 | 67.27 | chnC |
| ATOM | 3967 | OE2 | GLU | C | 161 | 117.632 | 45.373 | 55.492 | 1.00 | 63.82 | chnC |
| ATOM | 3968 | C | GLU | C | 161 | 120.916 | 41.328 | 55.531 | 1.00 | 55.09 | chnC |
| ATOM | 3969 | O | GLU | C | 161 | 120.868 | 40.563 | 56.495 | 1.00 | 57.02 | chnC |
| ATOM | 3970 | N | SER | C | 162 | 122.032 | 41.931 | 55.139 | 1.00 | 54.19 | chnC |
| ATOM | 3971 | CA | SER | C | 162 | 123.286 | 41.724 | 55.846 | 1.00 | 54.50 | chnC |
| ATOM | 3972 | CB | SER | C | 162 | 124.449 | 41.614 | 54.856 | 1.00 | 56.48 | chnC |
| ATOM | 3973 | OG | SER | C | 162 | 124.742 | 42.863 | 54.246 | 1.00 | 57.53 | chnC |
| ATOM | 3974 | C | SER | C | 162 | 123.579 | 42.836 | 56.832 | 1.00 | 54.16 | chnC |
| ATOM | 3975 | O | SER | C | 162 | 123.040 | 43.932 | 56.724 | 1.00 | 54.17 | chnC |
| ATOM | 3976 | N | GLU | C | 163 | 124.439 | 42.540 | 57.795 | 1.00 | 56.27 | chnC |
| ATOM | 3977 | CA | GLU | C | 163 | 124.829 | 43.524 | 58.778 | 1.00 | 58.60 | chnC |
| ATOM | 3978 | CB | GLU | C | 163 | 125.712 | 42.876 | 59.843 | 1.00 | 66.88 | chnC |

-continued

| | | | | | | | | | | |
|---|---|---|---|---|---|---|---|---|---|---|
| ATOM | 3979 | CG | GLU | C | 163 | 124.990 | 41.896 | 60.743 | 1.00 | 75.86 chnC |
| ATOM | 3980 | CD | GLU | C | 163 | 123.973 | 42.578 | 61.642 | 1.00 | 79.24 chnC |
| ATOM | 3981 | OE1 | GLU | C | 163 | 124.400 | 43.320 | 62.557 | 1.00 | 82.02 chnC |
| ATOM | 3982 | OE2 | GLU | C | 163 | 122.752 | 42.375 | 61.430 | 1.00 | 82.50 chnC |
| ATOM | 3983 | C | GLU | C | 163 | 125.620 | 44.602 | 58.046 | 1.00 | 55.28 chnC |
| ATOM | 3984 | O | GLU | C | 163 | 126.369 | 44.303 | 57.116 | 1.00 | 52.96 chnC |
| ATOM | 3985 | N | PRO | C | 164 | 125.415 | 45.877 | 58.416 | 1.00 | 52.87 chnC |
| ATOM | 3986 | CD | PRO | C | 164 | 124.433 | 46.362 | 59.399 | 1.00 | 53.91 chnC |
| ATOM | 3987 | CA | PRO | C | 164 | 126.118 | 46.999 | 57.797 | 1.00 | 53.33 chnC |
| ATOM | 3988 | CB | PRO | C | 164 | 125.418 | 48.209 | 58.406 | 1.00 | 52.14 chnC |
| ATOM | 3989 | CG | PRO | C | 164 | 124.978 | 47.709 | 59.737 | 1.00 | 54.50 chnC |
| ATOM | 3990 | C | PRO | C | 164 | 127.595 | 46.962 | 58.171 | 1.00 | 55.97 chnC |
| ATOM | 3991 | O | PRO | C | 164 | 127.959 | 46.417 | 59.213 | 1.00 | 57.81 chnC |
| ATOM | 3992 | N | LEU | C | 165 | 128.441 | 47.535 | 57.317 | 1.00 | 57.76 chnC |
| ATOM | 3993 | CA | LEU | C | 165 | 129.884 | 47.556 | 57.554 | 1.00 | 59.44 chnC |
| ATOM | 3994 | CB | LEU | C | 165 | 130.571 | 46.507 | 56.683 | 1.00 | 58.79 chnC |
| ATOM | 3995 | CG | LEU | C | 165 | 132.090 | 46.365 | 56.795 | 1.00 | 59.55 chnC |
| ATOM | 3996 | CD1 | LEU | C | 165 | 132.495 | 46.074 | 58.235 | 1.00 | 59.33 chnC |
| ATOM | 3997 | CD2 | LEU | C | 165 | 132.561 | 45.259 | 55.863 | 1.00 | 57.79 chnC |
| ATOM | 3998 | C | LEU | C | 165 | 130.488 | 48.918 | 57.259 | 1.00 | 60.94 chnC |
| ATOM | 3999 | O | LEU | C | 165 | 130.375 | 49.419 | 56.143 | 1.00 | 59.88 chnC |
| ATOM | 4000 | N | ASN | C | 166 | 131.137 | 49.508 | 58.261 | 1.00 | 64.76 chnC |
| ATOM | 4001 | CA | ASN | C | 166 | 131.766 | 50.817 | 58.095 | 1.00 | 67.38 chnC |
| ATOM | 4002 | CB | ASN | C | 166 | 132.148 | 51.445 | 59.438 | 1.00 | 72.60 chnC |
| ATOM | 4003 | CG | ASN | C | 166 | 130.961 | 51.965 | 60.240 | 1.00 | 76.49 chnC |
| ATOM | 4004 | OD1 | ASN | C | 166 | 129.944 | 52.432 | 59.705 | 1.00 | 77.82 chnC |
| ATOM | 4005 | ND2 | ASN | C | 166 | 131.207 | 51.921 | 61.552 | 1.00 | 78.38 chnC |
| ATOM | 4006 | C | ASN | C | 166 | 133.051 | 50.682 | 57.290 | 1.00 | 66.79 chnC |
| ATOM | 4007 | O | ASN | C | 166 | 133.984 | 49.990 | 57.704 | 1.00 | 65.74 chnC |
| ATOM | 4008 | N | ILE | C | 167 | 133.093 | 51.361 | 56.150 | 1.00 | 65.69 chnC |
| ATOM | 4009 | CA | ILE | C | 167 | 134.266 | 51.364 | 55.288 | 1.00 | 66.86 chnC |
| ATOM | 4010 | CB | ILE | C | 167 | 133.959 | 50.763 | 53.913 | 1.00 | 65.09 chnC |
| ATOM | 4011 | CG2 | ILE | C | 167 | 135.018 | 51.173 | 52.890 | 1.00 | 63.38 chnC |
| ATOM | 4012 | CG1 | ILE | C | 167 | 133.884 | 49.247 | 54.039 | 1.00 | 64.34 chnC |
| ATOM | 4013 | CD1 | ILE | C | 167 | 133.729 | 48.554 | 52.729 | 1.00 | 65.37 chnC |
| ATOM | 4014 | C | ILE | C | 167 | 134.750 | 52.798 | 55.128 | 1.00 | 70.11 chnC |
| ATOM | 4015 | O | ILE | C | 167 | 134.004 | 53.668 | 54.659 | 1.00 | 69.35 chnC |
| ATOM | 4016 | N | THR | C | 168 | 136.001 | 53.035 | 55.514 | 1.00 | 73.31 chnC |
| ATOM | 4017 | CA | THR | C | 168 | 136.582 | 54.368 | 55.436 | 1.00 | 75.18 chnC |
| ATOM | 4018 | CB | THR | C | 168 | 137.029 | 54.851 | 56.844 | 1.00 | 75.02 chnC |
| ATOM | 4019 | OG1 | THR | C | 168 | 135.942 | 54.700 | 57.771 | 1.00 | 75.23 chnC |
| ATOM | 4020 | CG2 | THR | C | 168 | 137.440 | 56.318 | 56.806 | 1.00 | 74.70 chnC |
| ATOM | 4021 | C | THR | C | 168 | 137.756 | 54.423 | 54.465 | 1.00 | 75.53 chnC |
| ATOM | 4022 | O | THR | C | 168 | 138.589 | 53.516 | 54.439 | 1.00 | 74.18 chnC |
| ATOM | 4023 | N | VAL | C | 169 | 137.788 | 55.476 | 53.649 | 1.00 | 78.28 chnC |
| ATOM | 4024 | CA | VAL | C | 169 | 138.856 | 55.686 | 52.675 | 1.00 | 82.35 chnC |
| ATOM | 4025 | CB | VAL | C | 169 | 138.322 | 55.772 | 51.245 | 1.00 | 78.72 chnC |
| ATOM | 4026 | CG1 | VAL | C | 169 | 139.481 | 55.831 | 50.267 | 1.00 | 76.86 chnC |
| ATOM | 4027 | CG2 | VAL | C | 169 | 137.449 | 54.587 | 50.942 | 1.00 | 78.39 chnC |
| ATOM | 4028 | C | VAL | C | 169 | 139.590 | 56.988 | 52.974 | 1.00 | 87.78 chnC |
| ATOM | 4029 | O | VAL | C | 169 | 139.074 | 58.072 | 52.697 | 1.00 | 89.93 chnC |
| ATOM | 4030 | N | ILE | C | 170 | 140.790 | 56.867 | 53.541 | 1.00 | 94.43 chnC |
| ATOM | 4031 | CA | ILE | C | 170 | 141.632 | 58.019 | 53.888 | 1.00 | 99.17 chnC |
| ATOM | 4032 | CB | ILE | C | 170 | 142.506 | 57.719 | 55.140 | 1.00 | 99.95 chnC |
| ATOM | 4033 | CG2 | ILE | C | 170 | 141.638 | 57.666 | 56.396 | 1.00 | 100.14 chnC |
| ATOM | 4034 | CG1 | ILE | C | 170 | 143.300 | 56.415 | 54.934 | 1.00 | 101.01 chnC |
| ATOM | 4035 | CD1 | ILE | C | 170 | 144.229 | 56.043 | 56.095 | 1.00 | 101.68 chnC |
| ATOM | 4036 | C | ILE | C | 170 | 142.572 | 58.364 | 52.727 | 1.00 | 101.47 chnC |
| ATOM | 4037 | O | ILE | C | 170 | 142.422 | 57.845 | 51.616 | 1.00 | 100.15 chnC |
| ATOM | 4038 | N | LYS | C | 171 | 143.535 | 59.246 | 52.986 | 1.00 | 105.31 chnC |
| ATOM | 4039 | CA | LYS | C | 171 | 144.511 | 59.622 | 51.963 | 1.00 | 107.93 chnC |
| ATOM | 4040 | CB | LYS | C | 171 | 144.891 | 61.102 | 52.085 | 1.00 | 108.53 chnC |
| ATOM | 4041 | CG | LYS | C | 171 | 145.984 | 61.539 | 51.107 | 1.00 | 109.64 chnC |
| ATOM | 4042 | CD | LYS | C | 171 | 146.033 | 63.053 | 50.980 | 1.00 | 111.89 chnC |
| ATOM | 4043 | CE | LYS | C | 171 | 144.691 | 63.599 | 50.480 | 1.00 | 113.15 chnC |
| ATOM | 4044 | NZ | LYS | C | 171 | 144.678 | 65.089 | 50.357 | 1.00 | 115.77 chnC |
| ATOM | 4045 | C | LYS | C | 171 | 145.767 | 58.746 | 52.047 | 1.00 | 108.03 chnC |
| ATOM | 4046 | O | LYS | C | 171 | 146.015 | 58.073 | 53.056 | 1.00 | 107.89 chnC |
| ATOM | 4047 | N | LYS | D | 4 | 48.364 | 27.669 | 68.300 | 1.00 | 108.81 chnD |
| ATOM | 4048 | CA | LYS | D | 4 | 47.525 | 28.442 | 67.384 | 1.00 | 109.60 chnD |
| ATOM | 4049 | CB | LYS | D | 4 | 46.184 | 28.799 | 68.065 | 1.00 | 108.77 chnD |
| ATOM | 4050 | CG | LYS | D | 4 | 45.140 | 29.526 | 67.204 | 1.00 | 107.74 chnD |
| ATOM | 4051 | CD | LYS | D | 4 | 43.822 | 29.699 | 67.987 | 1.00 | 107.30 chnD |
| ATOM | 4052 | CE | LYS | D | 4 | 42.765 | 30.515 | 67.225 | 1.00 | 106.28 chnD |
| ATOM | 4053 | NZ | LYS | D | 4 | 41.448 | 30.562 | 67.941 | 1.00 | 103.45 chnD |
| ATOM | 4054 | C | LYS | D | 4 | 48.288 | 29.685 | 66.873 | 1.00 | 109.07 chnD |
| ATOM | 4055 | O | LYS | D | 4 | 48.459 | 29.857 | 65.658 | 1.00 | 109.95 chnD |
| ATOM | 4056 | N | PRO | D | 5 | 48.769 | 30.558 | 67.785 | 1.00 | 107.96 chnD |
| ATOM | 4057 | CD | PRO | D | 5 | 48.576 | 30.634 | 69.247 | 1.00 | 107.08 chnD |

-continued

| | | | | | | | | | | |
|---|---|---|---|---|---|---|---|---|---|---|
| ATOM | 4058 | CA | PRO | D | 5 | 49.500 | 31.731 | 67.291 | 1.00 | 107.05 chnD |
| ATOM | 4059 | CB | PRO | D | 5 | 49.470 | 32.678 | 68.490 | 1.00 | 106.10 chnD |
| ATOM | 4060 | CG | PRO | D | 5 | 49.511 | 31.745 | 69.650 | 1.00 | 107.13 chnD |
| ATOM | 4061 | C | PRO | D | 5 | 50.929 | 31.348 | 66.888 | 1.00 | 106.32 chnD |
| ATOM | 4062 | O | PRO | D | 5 | 51.459 | 30.344 | 67.374 | 1.00 | 106.81 chnD |
| ATOM | 4063 | N | LYS | D | 6 | 51.534 | 32.107 | 65.973 | 1.00 | 105.25 chnD |
| ATOM | 4064 | CA | LYS | D | 6 | 52.902 | 31.810 | 65.536 | 1.00 | 103.88 chnD |
| ATOM | 4065 | CB | LYS | D | 6 | 52.905 | 30.742 | 64.430 | 1.00 | 106.40 chnD |
| ATOM | 4066 | CG | LYS | D | 6 | 54.263 | 30.065 | 64.250 | 1.00 | 110.66 chnD |
| ATOM | 4067 | CD | LYS | D | 6 | 54.150 | 28.681 | 63.604 | 1.00 | 113.51 chnD |
| ATOM | 4068 | CE | LYS | D | 6 | 55.502 | 27.935 | 63.635 | 1.00 | 115.05 chnD |
| ATOM | 4069 | NZ | LYS | D | 6 | 55.449 | 26.559 | 63.042 | 1.00 | 115.16 chnD |
| ATOM | 4070 | C | LYS | D | 6 | 53.670 | 33.053 | 65.088 | 1.00 | 100.35 chnD |
| ATOM | 4071 | O | LYS | D | 6 | 53.220 | 33.793 | 64.212 | 1.00 | 98.47 chnD |
| ATOM | 4072 | N | VAL | D | 7 | 54.837 | 33.267 | 65.694 | 1.00 | 95.79 chnD |
| ATOM | 4073 | CA | VAL | D | 7 | 55.680 | 34.422 | 65.382 | 1.00 | 90.44 chnD |
| ATOM | 4074 | CB | VAL | D | 7 | 56.644 | 34.761 | 66.552 | 1.00 | 89.26 chnD |
| ATOM | 4075 | CG1 | VAL | D | 7 | 57.421 | 36.038 | 66.251 | 1.00 | 87.85 chnD |
| ATOM | 4076 | CG2 | VAL | D | 7 | 55.871 | 34.904 | 67.856 | 1.00 | 88.69 chnD |
| ATOM | 4077 | C | VAL | D | 7 | 56.500 | 34.219 | 64.109 | 1.00 | 89.82 chnD |
| ATOM | 4078 | O | VAL | D | 7 | 57.047 | 33.138 | 63.868 | 1.00 | 89.36 chnD |
| ATOM | 4079 | N | SER | D | 8 | 56.571 | 35.271 | 63.299 | 1.00 | 87.32 chnD |
| ATOM | 4080 | CA | SER | D | 8 | 57.321 | 35.248 | 62.047 | 1.00 | 86.20 chnD |
| ATOM | 4081 | CB | SER | D | 8 | 56.371 | 35.259 | 60.839 | 1.00 | 88.14 chnD |
| ATOM | 4082 | OG | SER | D | 8 | 55.640 | 36.473 | 60.743 | 1.00 | 89.64 chnD |
| ATOM | 4083 | C | SER | D | 8 | 58.254 | 36.455 | 61.999 | 1.00 | 83.76 chnD |
| ATOM | 4084 | O | SER | D | 8 | 57.967 | 37.496 | 62.597 | 1.00 | 82.11 chnD |
| ATOM | 4085 | N | LEU | D | 9 | 59.368 | 36.312 | 61.283 | 1.00 | 80.53 chnD |
| ATOM | 4086 | CA | LEU | D | 9 | 60.356 | 37.382 | 61.178 | 1.00 | 76.07 chnD |
| ATOM | 4087 | CB | LEU | D | 9 | 61.751 | 36.841 | 61.494 | 1.00 | 77.86 chnD |
| ATOM | 4088 | CG | LEU | D | 9 | 61.904 | 35.981 | 62.745 | 1.00 | 78.44 chnD |
| ATOM | 4089 | CD1 | LEU | D | 9 | 63.348 | 35.578 | 62.909 | 1.00 | 81.06 chnD |
| ATOM | 4090 | CD2 | LEU | D | 9 | 61.429 | 36.742 | 63.953 | 1.00 | 81.70 chnD |
| ATOM | 4091 | C | LEU | D | 9 | 60.379 | 38.025 | 59.806 | 1.00 | 72.67 chnD |
| ATOM | 4092 | O | LEU | D | 9 | 60.080 | 37.383 | 58.800 | 1.00 | 71.31 chnD |
| ATOM | 4093 | N | ASN | D | 10 | 60.756 | 39.297 | 59.777 | 1.00 | 69.07 chnD |
| ATOM | 4094 | CA | ASN | D | 10 | 60.851 | 40.045 | 58.534 | 1.00 | 67.49 chnD |
| ATOM | 4095 | CB | ASN | D | 10 | 59.500 | 40.659 | 58.165 | 1.00 | 73.37 chnD |
| ATOM | 4096 | CG | ASN | D | 10 | 59.533 | 41.354 | 56.817 | 1.00 | 77.55 chnD |
| ATOM | 4097 | OD1 | ASN | D | 10 | 59.669 | 40.704 | 55.779 | 1.00 | 78.62 chnD |
| ATOM | 4098 | ND2 | ASN | D | 10 | 59.446 | 42.683 | 56.828 | 1.00 | 79.67 chnD |
| ATOM | 4099 | C | ASN | D | 10 | 61.918 | 41.135 | 58.636 | 1.00 | 63.91 chnD |
| ATOM | 4100 | O | ASN | D | 10 | 61.695 | 42.184 | 59.254 | 1.00 | 59.64 chnD |
| ATOM | 4101 | N | PRO | D | 11 | 63.105 | 40.894 | 58.045 | 1.00 | 61.56 chnD |
| ATOM | 4102 | CD | PRO | D | 11 | 64.168 | 41.918 | 58.033 | 1.00 | 61.50 chnD |
| ATOM | 4103 | CA | PRO | D | 11 | 63.531 | 39.701 | 57.302 | 1.00 | 59.46 chnD |
| ATOM | 4104 | CB | PRO | D | 11 | 64.958 | 40.059 | 56.891 | 1.00 | 61.46 chnD |
| ATOM | 4105 | CG | PRO | D | 11 | 64.939 | 41.557 | 56.799 | 1.00 | 61.24 chnD |
| ATOM | 4106 | C | PRO | D | 11 | 63.510 | 38.431 | 58.161 | 1.00 | 58.33 chnD |
| ATOM | 4107 | O | PRO | D | 11 | 63.741 | 38.486 | 59.368 | 1.00 | 58.53 chnD |
| ATOM | 4108 | N | PRO | D | 12 | 63.316 | 37.261 | 57.527 | 1.00 | 58.62 chnD |
| ATOM | 4109 | CD | PRO | D | 12 | 63.229 | 37.148 | 56.064 | 1.00 | 58.79 chnD |
| ATOM | 4110 | CA | PRO | D | 12 | 63.247 | 35.924 | 58.144 | 1.00 | 59.02 chnD |
| ATOM | 4111 | CB | PRO | D | 12 | 62.989 | 35.005 | 56.940 | 1.00 | 59.32 chnD |
| ATOM | 4112 | CG | PRO | D | 12 | 62.407 | 35.912 | 55.909 | 1.00 | 61.91 chnD |
| ATOM | 4113 | C | PRO | D | 12 | 64.498 | 35.461 | 58.891 | 1.00 | 58.27 chnD |
| ATOM | 4114 | O | PRO | D | 12 | 64.518 | 34.371 | 59.474 | 1.00 | 56.97 chnD |
| ATOM | 4115 | N | TRP | D | 13 | 65.541 | 36.279 | 58.851 | 1.00 | 55.38 chnD |
| ATOM | 4116 | CA | TRP | D | 13 | 66.804 | 35.943 | 59.477 | 1.00 | 52.59 chnD |
| ATOM | 4117 | CB | TRP | D | 13 | 67.896 | 36.847 | 58.933 | 1.00 | 55.50 chnD |
| ATOM | 4118 | CG | TRP | D | 13 | 67.881 | 37.000 | 57.455 | 1.00 | 55.29 chnD |
| ATOM | 4119 | CD2 | TRP | D | 13 | 67.894 | 35.954 | 56.475 | 1.00 | 56.46 chnD |
| ATOM | 4120 | CE2 | TRP | D | 13 | 67.921 | 36.572 | 55.212 | 1.00 | 59.07 chnD |
| ATOM | 4121 | CE3 | TRP | D | 13 | 67.888 | 34.556 | 56.542 | 1.00 | 55.82 chnD |
| ATOM | 4122 | CD1 | TRP | D | 13 | 67.893 | 38.169 | 56.768 | 1.00 | 55.56 chnD |
| ATOM | 4123 | NE1 | TRP | D | 13 | 67.920 | 37.926 | 55.419 | 1.00 | 58.19 chnD |
| ATOM | 4124 | CZ2 | TRP | D | 13 | 67.944 | 35.841 | 54.023 | 1.00 | 60.86 chnD |
| ATOM | 4125 | CZ3 | TRP | D | 13 | 67.912 | 33.832 | 55.364 | 1.00 | 54.75 chnD |
| ATOM | 4126 | CH2 | TRP | D | 13 | 67.939 | 34.475 | 54.121 | 1.00 | 58.65 chnD |
| ATOM | 4127 | C | TRP | D | 13 | 66.773 | 36.057 | 60.980 | 1.00 | 50.98 chnD |
| ATOM | 4128 | O | TRP | D | 13 | 66.660 | 37.153 | 61.524 | 1.00 | 47.56 chnD |
| ATOM | 4129 | N | ASN | D | 14 | 66.871 | 34.919 | 61.650 | 1.00 | 48.93 chnD |
| ATOM | 4130 | CA | ASN | D | 14 | 66.878 | 34.893 | 63.101 | 1.00 | 47.17 chnD |
| ATOM | 4131 | CB | ASN | D | 14 | 66.510 | 33.505 | 63.617 | 1.00 | 52.14 chnD |
| ATOM | 4132 | CG | ASN | D | 14 | 67.289 | 32.396 | 62.936 | 1.00 | 56.86 chnD |
| ATOM | 4133 | OD1 | ASN | D | 14 | 68.018 | 32.625 | 61.969 | 1.00 | 61.11 chnD |
| ATOM | 4134 | ND2 | ASN | D | 14 | 67.122 | 31.179 | 63.428 | 1.00 | 59.74 chnD |
| ATOM | 4135 | C | ASN | D | 14 | 68.245 | 35.311 | 63.621 | 1.00 | 46.26 chnD |
| ATOM | 4136 | O | ASN | D | 14 | 68.391 | 35.636 | 64.798 | 1.00 | 47.60 chnD |

-continued

| | | | | | | | | | | |
|---|---|---|---|---|---|---|---|---|---|---|
| ATOM | 4137 | N | ARG | D | 15 | 69.255 | 35.253 | 62.748 | 1.00 | 44.31 | chnD |
| ATOM | 4138 | CA | ARG | D | 15 | 70.619 | 35.668 | 63.098 | 1.00 | 40.95 | chnD |
| ATOM | 4139 | CB | ARG | D | 15 | 71.658 | 34.640 | 62.631 | 1.00 | 41.89 | chnD |
| ATOM | 4140 | CG | ARG | D | 15 | 71.263 | 33.201 | 62.852 | 1.00 | 46.65 | chnD |
| ATOM | 4141 | CD | ARG | D | 15 | 72.307 | 32.238 | 62.318 | 1.00 | 49.17 | chnD |
| ATOM | 4142 | NE | ARG | D | 15 | 73.290 | 31.867 | 63.331 | 1.00 | 54.90 | chnD |
| ATOM | 4143 | CZ | ARG | D | 15 | 74.588 | 31.708 | 63.092 | 1.00 | 55.72 | chnD |
| ATOM | 4144 | NH1 | ARG | D | 15 | 75.066 | 31.892 | 61.870 | 1.00 | 57.16 | chnD |
| ATOM | 4145 | NH2 | ARG | D | 15 | 75.411 | 31.355 | 64.072 | 1.00 | 58.54 | chnD |
| ATOM | 4146 | C | ARG | D | 15 | 70.856 | 36.994 | 62.373 | 1.00 | 38.00 | chnD |
| ATOM | 4147 | O | ARG | D | 15 | 70.700 | 37.074 | 61.158 | 1.00 | 40.11 | chnD |
| ATOM | 4148 | N | ILE | D | 16 | 71.187 | 38.041 | 63.118 | 1.00 | 34.18 | chnD |
| ATOM | 4149 | CA | ILE | D | 16 | 71.428 | 39.340 | 62.510 | 1.00 | 33.42 | chnD |
| ATOM | 4150 | CB | ILE | D | 16 | 70.199 | 40.266 | 62.630 | 1.00 | 32.29 | chnD |
| ATOM | 4151 | CG2 | ILE | D | 16 | 68.944 | 39.557 | 62.117 | 1.00 | 33.42 | chnD |
| ATOM | 4152 | CG1 | ILE | D | 16 | 70.019 | 40.720 | 64.082 | 1.00 | 32.52 | chnD |
| ATOM | 4153 | CD1 | ILE | D | 16 | 68.859 | 41.660 | 64.288 | 1.00 | 34.43 | chnD |
| ATOM | 4154 | C | ILE | D | 16 | 72.624 | 40.045 | 63.136 | 1.00 | 35.14 | chnD |
| ATOM | 4155 | O | ILE | D | 16 | 73.111 | 39.655 | 64.189 | 1.00 | 36.06 | chnD |
| ATOM | 4156 | N | PHE | D | 17 | 73.083 | 41.096 | 62.473 | 1.00 | 39.38 | chnD |
| ATOM | 4157 | CA | PHE | D | 17 | 74.221 | 41.868 | 62.941 | 1.00 | 44.07 | chnD |
| ATOM | 4158 | CB | PHE | D | 17 | 74.934 | 42.542 | 61.764 | 1.00 | 46.97 | chnD |
| ATOM | 4159 | CG | PHE | D | 17 | 75.898 | 41.654 | 61.039 | 1.00 | 49.31 | chnD |
| ATOM | 4160 | CD1 | PHE | D | 17 | 75.872 | 41.566 | 59.655 | 1.00 | 51.89 | chnD |
| ATOM | 4161 | CD2 | PHE | D | 17 | 76.863 | 40.943 | 61.732 | 1.00 | 50.94 | chnD |
| ATOM | 4162 | CE1 | PHE | D | 17 | 76.797 | 40.786 | 58.970 | 1.00 | 53.78 | chnD |
| ATOM | 4163 | CE2 | PHE | D | 17 | 77.794 | 40.159 | 61.060 | 1.00 | 51.87 | chnD |
| ATOM | 4164 | CZ | PHE | D | 17 | 77.762 | 40.082 | 59.675 | 1.00 | 54.11 | chnD |
| ATOM | 4165 | C | PHE | D | 17 | 73.830 | 42.936 | 63.947 | 1.00 | 44.64 | chnD |
| ATOM | 4166 | O | PHE | D | 17 | 72.671 | 43.347 | 64.035 | 1.00 | 44.49 | chnD |
| ATOM | 4167 | N | LYS | D | 18 | 74.828 | 43.402 | 64.684 | 1.00 | 45.81 | chnD |
| ATOM | 4168 | CA | LYS | D | 18 | 74.635 | 44.438 | 65.677 | 1.00 | 47.35 | chnD |
| ATOM | 4169 | CB | LYS | D | 18 | 75.905 | 44.571 | 66.522 | 1.00 | 52.60 | chnD |
| ATOM | 4170 | CG | LYS | D | 18 | 75.861 | 45.605 | 67.630 | 1.00 | 58.05 | chnD |
| ATOM | 4171 | CD | LYS | D | 18 | 77.224 | 45.686 | 68.308 | 1.00 | 65.04 | chnD |
| ATOM | 4172 | CE | LYS | D | 18 | 77.244 | 46.698 | 69.453 | 1.00 | 69.27 | chnD |
| ATOM | 4173 | NZ | LYS | D | 18 | 77.112 | 48.117 | 69.005 | 1.00 | 71.54 | chnD |
| ATOM | 4174 | C | LYS | D | 18 | 74.349 | 45.733 | 64.931 | 1.00 | 46.12 | chnD |
| ATOM | 4175 | O | LYS | D | 18 | 75.167 | 46.204 | 64.153 | 1.00 | 49.77 | chnD |
| ATOM | 4176 | N | GLY | D | 19 | 73.154 | 46.267 | 65.117 | 1.00 | 46.45 | chnD |
| ATOM | 4177 | CA | GLY | D | 19 | 72.804 | 47.510 | 64.462 | 1.00 | 48.21 | chnD |
| ATOM | 4178 | C | GLY | D | 19 | 71.756 | 47.347 | 63.385 | 1.00 | 50.04 | chnD |
| ATOM | 4179 | O | GLY | D | 19 | 71.287 | 48.343 | 62.826 | 1.00 | 52.62 | chnD |
| ATOM | 4180 | N | GLU | D | 20 | 71.383 | 46.102 | 63.095 | 1.00 | 48.97 | chnD |
| ATOM | 4181 | CA | GLU | D | 20 | 70.379 | 45.835 | 62.077 | 1.00 | 52.13 | chnD |
| ATOM | 4182 | CB | GLU | D | 20 | 70.657 | 44.496 | 61.404 | 1.00 | 52.28 | chnD |
| ATOM | 4183 | CG | GLU | D | 20 | 72.019 | 44.457 | 60.740 | 1.00 | 53.76 | chnD |
| ATOM | 4184 | CD | GLU | D | 20 | 72.106 | 43.455 | 59.610 | 1.00 | 53.76 | chnD |
| ATOM | 4185 | OE1 | GLU | D | 20 | 71.629 | 42.310 | 59.776 | 1.00 | 53.45 | chnD |
| ATOM | 4186 | OE2 | GLU | D | 20 | 72.656 | 43.822 | 58.550 | 1.00 | 54.13 | chnD |
| ATOM | 4187 | C | GLU | D | 20 | 68.945 | 45.911 | 62.601 | 1.00 | 53.08 | chnD |
| ATOM | 4188 | O | GLU | D | 20 | 68.715 | 46.158 | 63.786 | 1.00 | 52.13 | chnD |
| ATOM | 4189 | N | ASN | D | 21 | 67.981 | 45.738 | 61.706 | 1.00 | 55.96 | chnD |
| ATOM | 4190 | CA | ASN | D | 21 | 66.581 | 45.818 | 62.081 | 1.00 | 61.64 | chnD |
| ATOM | 4191 | CB | ASN | D | 21 | 65.927 | 47.007 | 61.372 | 1.00 | 66.31 | chnD |
| ATOM | 4192 | CG | ASN | D | 21 | 66.610 | 48.321 | 61.698 | 1.00 | 70.98 | chnD |
| ATOM | 4193 | OD1 | ASN | D | 21 | 67.157 | 48.480 | 62.787 | 1.00 | 70.74 | chnD |
| ATOM | 4194 | ND2 | ASN | D | 21 | 66.627 | 49.260 | 60.762 | 1.00 | 75.52 | chnD |
| ATOM | 4195 | C | ASN | D | 21 | 65.822 | 44.547 | 61.763 | 1.00 | 63.34 | chnD |
| ATOM | 4196 | O | ASN | D | 21 | 66.119 | 43.871 | 60.774 | 1.00 | 67.70 | chnD |
| ATOM | 4197 | N | VAL | D | 22 | 64.854 | 44.216 | 62.615 | 1.00 | 63.90 | chnD |
| ATOM | 4198 | CA | VAL | D | 22 | 64.018 | 43.034 | 62.423 | 1.00 | 62.58 | chnD |
| ATOM | 4199 | CB | VAL | D | 22 | 64.665 | 41.755 | 63.005 | 1.00 | 61.01 | chnD |
| ATOM | 4200 | CG1 | VAL | D | 22 | 64.840 | 41.872 | 64.489 | 1.00 | 61.28 | chnD |
| ATOM | 4201 | CG2 | VAL | D | 22 | 63.840 | 40.537 | 62.657 | 1.00 | 59.40 | chnD |
| ATOM | 4202 | C | VAL | D | 22 | 62.659 | 43.283 | 63.056 | 1.00 | 63.48 | chnD |
| ATOM | 4203 | O | VAL | D | 22 | 62.554 | 44.012 | 64.047 | 1.00 | 62.01 | chnD |
| ATOM | 4204 | N | THR | D | 23 | 61.618 | 42.727 | 62.437 | 1.00 | 64.58 | chnD |
| ATOM | 4205 | CA | THR | D | 23 | 60.251 | 42.890 | 62.918 | 1.00 | 66.80 | chnD |
| ATOM | 4206 | CB | THR | D | 23 | 59.398 | 43.713 | 61.922 | 1.00 | 65.91 | chnD |
| ATOM | 4207 | OG1 | THR | D | 23 | 60.034 | 44.969 | 61.665 | 1.00 | 64.82 | chnD |
| ATOM | 4208 | CG2 | THR | D | 23 | 58.014 | 43.972 | 62.485 | 1.00 | 64.74 | chnD |
| ATOM | 4209 | C | THR | D | 23 | 59.582 | 41.538 | 63.138 | 1.00 | 69.08 | chnD |
| ATOM | 4210 | O | THR | D | 23 | 59.389 | 40.771 | 62.192 | 1.00 | 67.93 | chnD |
| ATOM | 4211 | N | LEU | D | 24 | 59.241 | 41.250 | 64.391 | 1.00 | 72.20 | chnD |
| ATOM | 4212 | CA | LEU | D | 24 | 58.584 | 39.997 | 64.733 | 1.00 | 75.68 | chnD |
| ATOM | 4213 | CB | LEU | D | 24 | 58.962 | 39.558 | 66.138 | 1.00 | 75.16 | chnD |
| ATOM | 4214 | CG | LEU | D | 24 | 60.315 | 39.988 | 66.696 | 1.00 | 74.66 | chnD |
| ATOM | 4215 | CD1 | LEU | D | 24 | 60.523 | 39.229 | 67.980 | 1.00 | 78.39 | chnD |

-continued

| | | | | | | | | | | |
|---|---|---|---|---|---|---|---|---|---|---|
| ATOM | 4216 | CD2 | LEU | D | 24 | 61.451 | 39.712 | 65.736 | 1.00 | 76.75 chnD |
| ATOM | 4217 | C | LEU | D | 24 | 57.075 | 40.202 | 64.649 | 1.00 | 78.98 chnD |
| ATOM | 4218 | O | LEU | D | 24 | 56.523 | 41.103 | 65.279 | 1.00 | 77.53 chnD |
| ATOM | 4219 | N | THR | D | 25 | 56.412 | 39.368 | 63.858 | 1.00 | 83.43 chnD |
| ATOM | 4220 | CA | THR | D | 25 | 54.976 | 39.476 | 63.677 | 1.00 | 85.46 chnD |
| ATOM | 4221 | CB | THR | D | 25 | 54.620 | 39.593 | 62.193 | 1.00 | 86.71 chnD |
| ATOM | 4222 | OG1 | THR | D | 25 | 55.331 | 40.700 | 61.620 | 1.00 | 89.26 chnD |
| ATOM | 4223 | CG2 | THR | D | 25 | 53.126 | 39.801 | 62.022 | 1.00 | 87.63 chnD |
| ATOM | 4224 | C | THR | D | 25 | 54.252 | 38.285 | 64.269 | 1.00 | 87.37 chnD |
| ATOM | 4225 | O | THR | D | 25 | 54.583 | 37.129 | 63.988 | 1.00 | 86.80 chnD |
| ATOM | 4226 | N | CYS | D | 26 | 53.257 | 38.581 | 65.095 | 1.00 | 91.51 chnD |
| ATOM | 4227 | CA | CYS | D | 26 | 52.475 | 37.544 | 65.741 | 1.00 | 96.61 chnD |
| ATOM | 4228 | C | CYS | D | 26 | 51.344 | 37.069 | 64.845 | 1.00 | 97.87 chnD |
| ATOM | 4229 | O | CYS | D | 26 | 50.688 | 37.878 | 64.178 | 1.00 | 97.52 chnD |
| ATOM | 4230 | CB | CYS | D | 26 | 51.915 | 38.051 | 67.069 | 1.00 | 97.63 chnD |
| ATOM | 4231 | SG | CYS | D | 26 | 51.078 | 36.783 | 68.077 | 1.00 | 100.81 chnD |
| ATOM | 4232 | N | ASN | D | 27 | 51.139 | 35.749 | 64.885 | 1.00 | 100.12 chnD |
| ATOM | 4233 | CA | ASN | D | 27 | 50.127 | 34.995 | 64.140 | 1.00 | 101.06 chnD |
| ATOM | 4234 | CB | ASN | D | 27 | 49.228 | 34.231 | 65.115 | 1.00 | 102.98 chnD |
| ATOM | 4235 | CG | ASN | D | 27 | 48.452 | 33.115 | 64.442 | 1.00 | 104.85 chnD |
| ATOM | 4236 | OD1 | ASN | D | 27 | 49.036 | 32.156 | 63.930 | 1.00 | 104.78 chnD |
| ATOM | 4237 | ND2 | ASN | D | 27 | 47.128 | 33.226 | 64.452 | 1.00 | 106.02 chnD |
| ATOM | 4238 | C | ASN | D | 27 | 49.276 | 35.786 | 63.154 | 1.00 | 100.41 chnD |
| ATOM | 4239 | O | ASN | D | 27 | 48.262 | 36.384 | 63.532 | 1.00 | 102.71 chnD |
| ATOM | 4240 | N | GLY | D | 28 | 49.683 | 35.751 | 61.886 | 0.50 | 97.59 chnD |
| ATOM | 4241 | CA | GLY | D | 28 | 48.975 | 36.462 | 60.836 | 0.50 | 92.94 chnD |
| ATOM | 4242 | C | GLY | D | 28 | 47.546 | 36.010 | 60.587 | 0.50 | 90.73 chnD |
| ATOM | 4243 | O | GLY | D | 28 | 47.305 | 35.025 | 59.881 | 0.50 | 89.27 chnD |
| ATOM | 4244 | N | ASN | D | 29 | 46.600 | 36.719 | 61.198 | 0.50 | 87.76 chnD |
| ATOM | 4245 | CA | ASN | D | 29 | 45.181 | 36.431 | 61.030 | 0.50 | 83.81 chnD |
| ATOM | 4246 | CB | ASN | D | 29 | 44.580 | 35.823 | 62.297 | 0.50 | 84.26 chnD |
| ATOM | 4247 | CG | ASN | D | 29 | 44.715 | 34.308 | 62.333 | 0.50 | 84.54 chnD |
| ATOM | 4248 | OD1 | ASN | D | 29 | 44.865 | 33.662 | 61.293 | 0.50 | 85.09 chnD |
| ATOM | 4249 | ND2 | ASN | D | 29 | 44.650 | 33.733 | 63.528 | 0.50 | 85.48 chnD |
| ATOM | 4250 | C | ASN | D | 29 | 44.462 | 37.709 | 60.614 | 0.50 | 81.92 chnD |
| ATOM | 4251 | O | ASN | D | 29 | 44.300 | 38.648 | 61.398 | 0.50 | 80.15 chnD |
| ATOM | 4252 | N | ASN | D | 30 | 44.078 | 37.732 | 59.342 | 0.50 | 78.14 chnD |
| ATOM | 4253 | CA | ASN | D | 30 | 43.409 | 38.866 | 58.721 | 0.50 | 74.73 chnD |
| ATOM | 4254 | CB | ASN | D | 30 | 43.661 | 38.845 | 57.206 | 0.50 | 74.75 chnD |
| ATOM | 4255 | CG | ASN | D | 30 | 45.120 | 38.563 | 56.845 | 0.50 | 74.89 chnD |
| ATOM | 4256 | OD1 | ASN | D | 30 | 46.012 | 38.576 | 57.705 | 0.50 | 73.35 chnD |
| ATOM | 4257 | ND2 | ASN | D | 30 | 45.364 | 38.300 | 55.561 | 0.50 | 74.39 chnD |
| ATOM | 4258 | C | ASN | D | 30 | 41.903 | 38.913 | 58.974 | 0.50 | 72.13 chnD |
| ATOM | 4259 | O | ASN | D | 30 | 41.174 | 39.572 | 58.228 | 0.50 | 72.39 chnD |
| ATOM | 4260 | N | ALA | D | 31 | 41.432 | 38.213 | 60.005 | 0.50 | 67.62 chnD |
| ATOM | 4261 | CA | ALA | D | 31 | 40.001 | 38.202 | 60.327 | 0.50 | 63.75 chnD |
| ATOM | 4262 | CB | ALA | D | 31 | 39.622 | 36.907 | 61.054 | 0.50 | 62.18 chnD |
| ATOM | 4263 | C | ALA | D | 31 | 39.588 | 39.434 | 61.151 | 0.50 | 61.83 chnD |
| ATOM | 4264 | O | ALA | D | 31 | 40.009 | 39.591 | 62.303 | 0.50 | 60.68 chnD |
| ATOM | 4265 | N | PHE | D | 32 | 38.770 | 40.294 | 60.531 | 0.50 | 59.13 chnD |
| ATOM | 4266 | CA | PHE | D | 32 | 38.256 | 41.539 | 61.126 | 0.50 | 56.79 chnD |
| ATOM | 4267 | CB | PHE | D | 32 | 37.122 | 42.117 | 60.250 | 0.50 | 53.16 chnD |
| ATOM | 4268 | CG | PHE | D | 32 | 35.845 | 41.295 | 60.268 | 0.50 | 50.50 chnD |
| ATOM | 4269 | CD1 | PHE | D | 32 | 34.786 | 41.646 | 61.111 | 0.50 | 48.39 chnD |
| ATOM | 4270 | CD2 | PHE | D | 32 | 35.714 | 40.156 | 59.467 | 0.50 | 49.53 chnD |
| ATOM | 4271 | CE1 | PHE | D | 32 | 33.620 | 40.876 | 61.160 | 0.50 | 46.53 chnD |
| ATOM | 4272 | CE2 | PHE | D | 32 | 34.549 | 39.376 | 59.507 | 0.50 | 48.22 chnD |
| ATOM | 4273 | CZ | PHE | D | 32 | 33.501 | 39.737 | 60.358 | 0.50 | 47.07 chnD |
| ATOM | 4274 | C | PHE | D | 32 | 37.755 | 41.363 | 62.568 | 0.50 | 57.62 chnD |
| ATOM | 4275 | O | PHE | D | 32 | 37.525 | 42.340 | 63.287 | 0.50 | 58.06 chnD |
| ATOM | 4276 | N | VAL | D | 34 | 41.205 | 41.538 | 66.297 | 0.50 | 99.19 chnD |
| ATOM | 4277 | CA | VAL | D | 34 | 41.856 | 42.620 | 67.029 | 0.50 | 100.20 chnD |
| ATOM | 4278 | CB | VAL | D | 34 | 41.621 | 43.983 | 66.332 | 0.50 | 99.90 chnD |
| ATOM | 4279 | CG1 | VAL | D | 34 | 42.328 | 45.106 | 67.094 | 0.50 | 99.49 chnD |
| ATOM | 4280 | CG2 | VAL | D | 34 | 42.112 | 43.922 | 64.891 | 0.50 | 99.58 chnD |
| ATOM | 4281 | C | VAL | D | 34 | 41.388 | 42.697 | 68.486 | 0.50 | 101.14 chnD |
| ATOM | 4282 | O | VAL | D | 34 | 40.196 | 42.857 | 68.765 | 0.50 | 101.79 chnD |
| ATOM | 4283 | N | SER | D | 35 | 42.351 | 42.618 | 69.402 | 0.50 | 101.94 chnD |
| ATOM | 4284 | CA | SER | D | 35 | 42.102 | 42.659 | 70.844 | 0.50 | 102.88 chnD |
| ATOM | 4285 | CB | SER | D | 35 | 41.706 | 41.264 | 71.352 | 0.50 | 103.17 chnD |
| ATOM | 4286 | OG | SER | D | 35 | 42.631 | 40.270 | 70.928 | 0.50 | 102.84 chnD |
| ATOM | 4287 | C | SER | D | 35 | 43.361 | 43.141 | 71.572 | 0.50 | 102.60 chnD |
| ATOM | 4288 | O | SER | D | 35 | 43.389 | 44.245 | 72.118 | 0.50 | 103.36 chnD |
| ATOM | 4289 | N | SER | D | 36 | 44.398 | 42.307 | 71.559 | 0.50 | 102.19 chnD |
| ATOM | 4290 | CA | SER | D | 36 | 45.670 | 42.623 | 72.197 | 0.50 | 101.62 chnD |
| ATOM | 4291 | CB | SER | D | 36 | 45.525 | 42.648 | 73.724 | 0.50 | 101.66 chnD |
| ATOM | 4292 | OG | SER | D | 36 | 45.190 | 41.366 | 74.230 | 0.50 | 100.67 chnD |
| ATOM | 4293 | C | SER | D | 36 | 46.698 | 41.575 | 71.804 | 0.50 | 102.43 chnD |
| ATOM | 4294 | O | SER | D | 36 | 46.349 | 40.495 | 71.320 | 0.50 | 101.32 chnD |

-continued

| | | | | | | | | | | |
|---|---|---|---|---|---|---|---|---|---|---|
| ATOM | 4295 | N | THR | D | 37 | 47.968 | 41.904 | 72.014 | 1.00 | 103.74 chnD |
| ATOM | 4296 | CA | THR | D | 37 | 49.059 | 40.992 | 71.700 | 1.00 | 104.35 chnD |
| ATOM | 4297 | CB | THR | D | 37 | 49.672 | 41.299 | 70.311 | 1.00 | 105.41 chnD |
| ATOM | 4298 | OG1 | THR | D | 37 | 48.622 | 41.474 | 69.351 | 1.00 | 106.18 chnD |
| ATOM | 4299 | CG2 | THR | D | 37 | 50.576 | 40.145 | 69.857 | 1.00 | 104.71 chnD |
| ATOM | 4300 | C | THR | D | 37 | 50.134 | 41.129 | 72.773 | 1.00 | 104.11 chnD |
| ATOM | 4301 | O | THR | D | 37 | 50.672 | 42.219 | 72.992 | 1.00 | 104.39 chnD |
| ATOM | 4302 | N | LYS | D | 38 | 50.416 | 40.027 | 73.462 | 1.00 | 103.21 chnD |
| ATOM | 4303 | CA | LYS | D | 38 | 51.425 | 40.025 | 74.512 | 1.00 | 101.82 chnD |
| ATOM | 4304 | CB | LYS | D | 38 | 50.958 | 39.164 | 75.690 | 1.00 | 105.15 chnD |
| ATOM | 4305 | CG | LYS | D | 38 | 49.680 | 39.650 | 76.357 | 1.00 | 108.75 chnD |
| ATOM | 4306 | CD | LYS | D | 38 | 49.302 | 38.753 | 77.525 | 1.00 | 111.73 chnD |
| ATOM | 4307 | CE | LYS | D | 38 | 48.034 | 39.237 | 78.206 | 1.00 | 114.91 chnD |
| ATOM | 4308 | NZ | LYS | D | 38 | 47.682 | 38.363 | 79.364 | 1.00 | 116.02 chnD |
| ATOM | 4309 | C | LYS | D | 38 | 52.773 | 39.520 | 74.000 | 1.00 | 98.94 chnD |
| ATOM | 4310 | O | LYS | D | 38 | 52.854 | 38.458 | 73.388 | 1.00 | 96.86 chnD |
| ATOM | 4311 | N | TRP | D | 39 | 53.826 | 40.292 | 74.254 | 1.00 | 94.88 chnD |
| ATOM | 4312 | CA | TRP | D | 39 | 55.176 | 39.926 | 73.836 | 1.00 | 91.77 chnD |
| ATOM | 4313 | CB | TRP | D | 39 | 55.812 | 41.068 | 73.056 | 1.00 | 91.33 chnD |
| ATOM | 4314 | CG | TRP | D | 39 | 55.265 | 41.219 | 71.688 | 1.00 | 89.84 chnD |
| ATOM | 4315 | CD2 | TRP | D | 39 | 55.459 | 40.324 | 70.588 | 1.00 | 89.65 chnD |
| ATOM | 4316 | CE2 | TRP | D | 39 | 54.792 | 40.878 | 69.479 | 1.00 | 89.21 chnD |
| ATOM | 4317 | CE3 | TRP | D | 39 | 56.136 | 39.108 | 70.431 | 1.00 | 90.26 chnD |
| ATOM | 4318 | CD1 | TRP | D | 39 | 54.505 | 42.247 | 71.219 | 1.00 | 88.27 chnD |
| ATOM | 4319 | NE1 | TRP | D | 39 | 54.216 | 42.052 | 69.892 | 1.00 | 87.85 chnD |
| ATOM | 4320 | CZ2 | TRP | D | 39 | 54.781 | 40.258 | 68.226 | 1.00 | 90.02 chnD |
| ATOM | 4321 | CZ3 | TRP | D | 39 | 56.124 | 38.492 | 69.185 | 1.00 | 90.45 chnD |
| ATOM | 4322 | CH2 | TRP | D | 39 | 55.451 | 39.070 | 68.101 | 1.00 | 90.13 chnD |
| ATOM | 4323 | C | TRP | D | 39 | 56.071 | 39.561 | 75.015 | 1.00 | 90.08 chnD |
| ATOM | 4324 | O | TRP | D | 39 | 56.201 | 40.330 | 75.964 | 1.00 | 89.27 chnD |
| ATOM | 4325 | N | PHE | D | 40 | 56.700 | 38.393 | 74.933 | 1.00 | 88.05 chnD |
| ATOM | 4326 | CA | PHE | D | 40 | 57.589 | 37.919 | 75.985 | 1.00 | 85.39 chnD |
| ATOM | 4327 | CB | PHE | D | 40 | 57.093 | 36.576 | 76.522 | 1.00 | 87.35 chnD |
| ATOM | 4328 | CG | PHE | D | 40 | 55.722 | 36.636 | 77.125 | 1.00 | 86.94 chnD |
| ATOM | 4329 | CD1 | PHE | D | 40 | 54.632 | 36.107 | 76.449 | 1.00 | 86.97 chnD |
| ATOM | 4330 | CD2 | PHE | D | 40 | 55.521 | 37.228 | 78.369 | 1.00 | 87.25 chnD |
| ATOM | 4331 | CE1 | PHE | D | 40 | 53.357 | 36.171 | 76.998 | 1.00 | 88.33 chnD |
| ATOM | 4332 | CE2 | PHE | D | 40 | 54.250 | 37.299 | 78.928 | 1.00 | 86.84 chnD |
| ATOM | 4333 | CZ | PHE | D | 40 | 53.164 | 36.767 | 78.241 | 1.00 | 88.17 chnD |
| ATOM | 4334 | C | PHE | D | 40 | 59.044 | 37.789 | 75.523 | 1.00 | 82.97 chnD |
| ATOM | 4335 | O | PHE | D | 40 | 59.369 | 36.952 | 74.685 | 1.00 | 83.70 chnD |
| ATOM | 4336 | N | HIS | D | 41 | 59.912 | 38.633 | 76.069 | 1.00 | 79.48 chnD |
| ATOM | 4337 | CA | HIS | D | 41 | 61.330 | 38.611 | 75.735 | 1.00 | 76.82 chnD |
| ATOM | 4338 | CB | HIS | D | 41 | 61.835 | 40.030 | 75.459 | 1.00 | 75.45 chnD |
| ATOM | 4339 | CG | HIS | D | 41 | 63.286 | 40.099 | 75.084 | 1.00 | 75.07 chnD |
| ATOM | 4340 | CD2 | HIS | D | 41 | 64.126 | 41.154 | 74.970 | 1.00 | 73.30 chnD |
| ATOM | 4341 | ND1 | HIS | D | 41 | 64.034 | 38.980 | 74.775 | 1.00 | 73.86 chnD |
| ATOM | 4342 | CE1 | HIS | D | 41 | 65.269 | 39.345 | 74.487 | 1.00 | 71.79 chnD |
| ATOM | 4343 | NE2 | HIS | D | 41 | 65.352 | 40.660 | 74.598 | 1.00 | 73.03 chnD |
| ATOM | 4344 | C | HIS | D | 41 | 62.102 | 37.996 | 76.897 | 1.00 | 75.51 chnD |
| ATOM | 4345 | O | HIS | D | 41 | 62.264 | 38.622 | 77.943 | 1.00 | 74.86 chnD |
| ATOM | 4346 | N | ASN | D | 42 | 62.587 | 36.774 | 76.690 | 1.00 | 76.07 chnD |
| ATOM | 4347 | CA | ASN | D | 42 | 63.338 | 36.029 | 77.701 | 1.00 | 77.12 chnD |
| ATOM | 4348 | CB | ASN | D | 42 | 64.588 | 36.799 | 78.149 | 1.00 | 73.70 chnD |
| ATOM | 4349 | CG | ASN | D | 42 | 65.740 | 36.690 | 77.164 | 1.00 | 68.98 chnD |
| ATOM | 4350 | OD1 | ASN | D | 42 | 65.806 | 35.768 | 76.346 | 1.00 | 68.26 chnD |
| ATOM | 4351 | ND2 | ASN | D | 42 | 66.673 | 37.629 | 77.279 | 1.00 | 64.46 chnD |
| ATOM | 4352 | C | ASN | D | 42 | 62.459 | 35.721 | 78.906 | 1.00 | 78.57 chnD |
| ATOM | 4353 | O | ASN | D | 42 | 62.945 | 35.647 | 80.037 | 1.00 | 81.20 chnD |
| ATOM | 4354 | N | GLY | D | 43 | 61.165 | 35.546 | 78.653 | 1.00 | 79.35 chnD |
| ATOM | 4355 | CA | GLY | D | 43 | 60.229 | 35.253 | 79.722 | 1.00 | 81.01 chnD |
| ATOM | 4356 | C | GLY | D | 43 | 59.542 | 36.487 | 80.278 | 1.00 | 81.71 chnD |
| ATOM | 4357 | O | GLY | D | 43 | 58.411 | 36.394 | 80.747 | 1.00 | 80.80 chnD |
| ATOM | 4358 | N | SER | D | 44 | 60.226 | 37.632 | 80.240 | 1.00 | 84.87 chnD |
| ATOM | 4359 | CA | SER | D | 44 | 59.678 | 38.898 | 80.744 | 1.00 | 87.96 chnD |
| ATOM | 4360 | CB | SER | D | 44 | 60.790 | 39.922 | 81.013 | 1.00 | 87.99 chnD |
| ATOM | 4361 | OG | SER | D | 44 | 61.695 | 39.483 | 82.007 | 1.00 | 91.31 chnD |
| ATOM | 4362 | C | SER | D | 44 | 58.705 | 39.507 | 79.749 | 1.00 | 88.77 chnD |
| ATOM | 4363 | O | SER | D | 44 | 58.922 | 39.444 | 78.544 | 1.00 | 91.64 chnD |
| ATOM | 4364 | N | LEU | D | 45 | 57.653 | 40.131 | 80.260 | 1.00 | 91.23 chnD |
| ATOM | 4365 | CA | LEU | D | 45 | 56.651 | 40.760 | 79.410 | 1.00 | 92.61 chnD |
| ATOM | 4366 | CB | LEU | D | 45 | 55.344 | 40.959 | 80.179 | 1.00 | 94.46 chnD |
| ATOM | 4367 | CG | LEU | D | 45 | 54.169 | 41.581 | 79.418 | 1.00 | 94.83 chnD |
| ATOM | 4368 | CD1 | LEU | D | 45 | 53.730 | 40.671 | 78.276 | 1.00 | 95.34 chnD |
| ATOM | 4369 | CD2 | LEU | D | 45 | 53.020 | 41.818 | 80.383 | 1.00 | 96.75 chnD |
| ATOM | 4370 | C | LEU | D | 45 | 57.137 | 42.101 | 78.874 | 1.00 | 92.21 chnD |
| ATOM | 4371 | O | LEU | D | 45 | 57.542 | 42.983 | 79.635 | 1.00 | 89.29 chnD |
| ATOM | 4372 | N | SER | D | 46 | 57.088 | 42.243 | 77.554 | 1.00 | 93.57 chnD |
| ATOM | 4373 | CA | SER | D | 46 | 57.514 | 43.470 | 76.896 | 1.00 | 95.28 chnD |

-continued

| | | | | | | | | | | |
|---|---|---|---|---|---|---|---|---|---|---|
| ATOM | 4374 | CB | SER | D | 46 | 57.978 | 43.190 | 75.466 | 1.00 | 96.19 chnD |
| ATOM | 4375 | OG | SER | D | 46 | 58.458 | 44.377 | 74.842 | 1.00 | 97.95 chnD |
| ATOM | 4376 | C | SER | D | 46 | 56.385 | 44.478 | 76.865 | 1.00 | 95.78 chnD |
| ATOM | 4377 | O | SER | D | 46 | 55.217 | 44.113 | 76.753 | 1.00 | 93.80 chnD |
| ATOM | 4378 | N | GLU | D | 47 | 56.756 | 45.752 | 76.899 | 1.00 | 98.21 chnD |
| ATOM | 4379 | CA | GLU | D | 47 | 55.787 | 46.838 | 76.895 | 1.00 | 102.50 chnD |
| ATOM | 4380 | CB | GLU | D | 47 | 56.460 | 48.143 | 77.330 | 1.00 | 105.78 chnD |
| ATOM | 4381 | CG | GLU | D | 47 | 57.049 | 48.085 | 78.747 | 1.00 | 112.14 chnD |
| ATOM | 4382 | CD | GLU | D | 47 | 57.672 | 49.406 | 79.190 | 1.00 | 114.92 chnD |
| ATOM | 4383 | OE1 | GLU | D | 47 | 58.881 | 49.624 | 78.925 | 1.00 | 117.21 chnD |
| ATOM | 4384 | OE2 | GLU | D | 47 | 56.950 | 50.222 | 79.808 | 1.00 | 116.55 chnD |
| ATOM | 4385 | C | GLU | D | 47 | 55.071 | 47.029 | 75.562 | 1.00 | 102.89 chnD |
| ATOM | 4386 | O | GLU | D | 47 | 54.353 | 48.017 | 75.372 | 1.00 | 103.52 chnD |
| ATOM | 4387 | N | GLU | D | 48 | 55.255 | 46.080 | 74.647 | 1.00 | 104.81 chnD |
| ATOM | 4388 | CA | GLU | D | 48 | 54.621 | 46.150 | 73.332 | 1.00 | 106.97 chnD |
| ATOM | 4389 | CB | GLU | D | 48 | 55.510 | 45.512 | 72.263 | 1.00 | 108.03 chnD |
| ATOM | 4390 | CG | GLU | D | 48 | 55.001 | 45.698 | 70.838 | 1.00 | 110.40 chnD |
| ATOM | 4391 | CD | GLU | D | 48 | 55.055 | 47.152 | 70.374 | 1.00 | 111.73 chnD |
| ATOM | 4392 | OE1 | GLU | D | 48 | 56.028 | 47.511 | 69.665 | 1.00 | 113.07 chnD |
| ATOM | 4393 | OE2 | GLU | D | 48 | 54.126 | 47.928 | 70.707 | 1.00 | 111.16 chnD |
| ATOM | 4394 | C | GLU | D | 48 | 53.259 | 45.463 | 73.343 | 1.00 | 107.08 chnD |
| ATOM | 4395 | O | GLU | D | 48 | 53.091 | 44.410 | 73.966 | 1.00 | 106.50 chnD |
| ATOM | 4396 | N | THR | D | 49 | 52.302 | 46.060 | 72.630 | 1.00 | 108.85 chnD |
| ATOM | 4397 | CA | THR | D | 49 | 50.932 | 45.538 | 72.546 | 1.00 | 109.22 chnD |
| ATOM | 4398 | CB | THR | D | 49 | 49.924 | 46.501 | 73.220 | 1.00 | 108.42 chnD |
| ATOM | 4399 | OG1 | THR | D | 49 | 50.094 | 47.827 | 72.698 | 1.00 | 105.71 chnD |
| ATOM | 4400 | CG2 | THR | D | 49 | 50.138 | 46.515 | 74.737 | 1.00 | 107.43 chnD |
| ATOM | 4401 | C | THR | D | 49 | 50.443 | 45.193 | 71.129 | 1.00 | 109.24 chnD |
| ATOM | 4402 | O | THR | D | 49 | 49.467 | 44.450 | 70.975 | 1.00 | 108.76 chnD |
| ATOM | 4403 | N | ASN | D | 50 | 51.124 | 45.722 | 70.110 | 1.00 | 108.64 chnD |
| ATOM | 4404 | CA | ASN | D | 50 | 50.779 | 45.456 | 68.707 | 1.00 | 108.10 chnD |
| ATOM | 4405 | CB | ASN | D | 50 | 51.520 | 46.420 | 67.788 | 1.00 | 109.05 chnD |
| ATOM | 4406 | CG | ASN | D | 50 | 51.100 | 47.854 | 67.999 | 1.00 | 110.27 chnD |
| ATOM | 4407 | OD1 | ASN | D | 50 | 49.932 | 48.203 | 67.810 | 1.00 | 111.40 chnD |
| ATOM | 4408 | ND2 | ASN | D | 50 | 52.047 | 48.698 | 68.401 | 1.00 | 111.35 chnD |
| ATOM | 4409 | C | ASN | D | 50 | 51.115 | 44.030 | 68.280 | 1.00 | 107.37 chnD |
| ATOM | 4410 | O | ASN | D | 50 | 51.845 | 43.320 | 68.974 | 1.00 | 108.20 chnD |
| ATOM | 4411 | N | SER | D | 51 | 50.595 | 43.616 | 67.128 | 1.00 | 106.33 chnD |
| ATOM | 4412 | CA | SER | D | 51 | 50.867 | 42.269 | 66.634 | 1.00 | 105.34 chnD |
| ATOM | 4413 | CB | SER | D | 51 | 49.812 | 41.836 | 65.616 | 1.00 | 105.31 chnD |
| ATOM | 4414 | OG | SER | D | 51 | 49.840 | 42.679 | 64.480 | 1.00 | 106.34 chnD |
| ATOM | 4415 | C | SER | D | 51 | 52.264 | 42.186 | 66.015 | 1.00 | 104.06 chnD |
| ATOM | 4416 | O | SER | D | 51 | 52.704 | 41.103 | 65.604 | 1.00 | 104.53 chnD |
| ATOM | 4417 | N | SER | D | 52 | 52.952 | 43.331 | 65.960 | 1.00 | 99.19 chnD |
| ATOM | 4418 | CA | SER | D | 52 | 54.300 | 43.408 | 65.404 | 1.00 | 94.26 chnD |
| ATOM | 4419 | CB | SER | D | 52 | 54.267 | 44.011 | 64.005 | 1.00 | 93.71 chnD |
| ATOM | 4420 | OG | SER | D | 52 | 53.664 | 43.119 | 63.090 | 1.00 | 95.12 chnD |
| ATOM | 4421 | C | SER | D | 52 | 55.272 | 44.201 | 66.274 | 1.00 | 92.18 chnD |
| ATOM | 4422 | O | SER | D | 52 | 55.119 | 45.415 | 66.458 | 1.00 | 91.22 chnD |
| ATOM | 4423 | N | LEU | D | 53 | 56.276 | 43.499 | 66.798 | 1.00 | 88.65 chnD |
| ATOM | 4424 | CA | LEU | D | 53 | 57.308 | 44.091 | 67.645 | 1.00 | 83.92 chnD |
| ATOM | 4425 | CB | LEU | D | 53 | 57.758 | 43.073 | 68.703 | 1.00 | 84.06 chnD |
| ATOM | 4426 | CG | LEU | D | 53 | 58.963 | 43.390 | 69.594 | 1.00 | 83.84 chnD |
| ATOM | 4427 | CD1 | LEU | D | 53 | 58.799 | 44.732 | 70.283 | 1.00 | 84.06 chnD |
| ATOM | 4428 | CD2 | LEU | D | 53 | 59.129 | 42.278 | 70.612 | 1.00 | 83.80 chnD |
| ATOM | 4429 | C | LEU | D | 53 | 58.486 | 44.513 | 66.775 | 1.00 | 81.03 chnD |
| ATOM | 4430 | O | LEU | D | 53 | 59.104 | 43.677 | 66.120 | 1.00 | 81.59 chnD |
| ATOM | 4431 | N | ASN | D | 54 | 58.778 | 45.811 | 66.760 | 1.00 | 77.98 chnD |
| ATOM | 4432 | CA | ASN | D | 54 | 59.883 | 46.351 | 65.962 | 1.00 | 76.55 chnD |
| ATOM | 4433 | CB | ASN | D | 54 | 59.502 | 47.702 | 65.353 | 1.00 | 81.05 chnD |
| ATOM | 4434 | CG | ASN | D | 54 | 58.437 | 47.581 | 64.299 | 1.00 | 85.18 chnD |
| ATOM | 4435 | OD1 | ASN | D | 54 | 58.642 | 46.954 | 63.260 | 1.00 | 88.19 chnD |
| ATOM | 4436 | ND2 | ASN | D | 54 | 57.281 | 48.178 | 64.560 | 1.00 | 89.02 chnD |
| ATOM | 4437 | C | ASN | D | 54 | 61.203 | 46.517 | 66.719 | 1.00 | 74.48 chnD |
| ATOM | 4438 | O | ASN | D | 54 | 61.298 | 47.298 | 67.671 | 1.00 | 74.13 chnD |
| ATOM | 4439 | N | ILE | D | 55 | 62.229 | 45.801 | 66.265 | 1.00 | 69.84 chnD |
| ATOM | 4440 | CA | ILE | D | 55 | 63.556 | 45.879 | 66.871 | 1.00 | 63.67 chnD |
| ATOM | 4441 | CB | ILE | D | 55 | 64.205 | 44.496 | 66.969 | 1.00 | 60.97 chnD |
| ATOM | 4442 | CG2 | ILE | D | 55 | 65.607 | 44.622 | 67.534 | 1.00 | 59.55 chnD |
| ATOM | 4443 | CG1 | ILE | D | 55 | 63.329 | 43.575 | 67.824 | 1.00 | 59.99 chnD |
| ATOM | 4444 | CD1 | ILE | D | 55 | 63.872 | 42.183 | 68.000 | 1.00 | 57.54 chnD |
| ATOM | 4445 | C | ILE | D | 55 | 64.412 | 46.768 | 65.985 | 1.00 | 62.28 chnD |
| ATOM | 4446 | O | ILE | D | 55 | 64.560 | 46.494 | 64.794 | 1.00 | 60.50 chnD |
| ATOM | 4447 | N | VAL | D | 56 | 64.948 | 47.840 | 66.561 | 1.00 | 61.82 chnD |
| ATOM | 4448 | CA | VAL | D | 56 | 65.776 | 48.790 | 65.823 | 1.00 | 64.68 chnD |
| ATOM | 4449 | CB | VAL | D | 56 | 65.089 | 50.166 | 65.766 | 1.00 | 64.77 chnD |
| ATOM | 4450 | CG1 | VAL | D | 56 | 65.988 | 51.190 | 65.090 | 1.00 | 65.65 chnD |
| ATOM | 4451 | CG2 | VAL | D | 56 | 63.773 | 50.052 | 65.019 | 1.00 | 67.07 chnD |
| ATOM | 4452 | C | VAL | D | 56 | 67.169 | 48.945 | 66.433 | 1.00 | 66.43 chnD |

-continued

| | | | | | | | | | | |
|---|---|---|---|---|---|---|---|---|---|---|
| ATOM | 4453 | O | VAL | D | 56 | 67.313 | 48.976 | 67.657 | 1.00 | 68.68 | chnD |
| ATOM | 4454 | N | ASN | D | 57 | 68.179 | 49.081 | 65.571 | 1.00 | 68.09 | chnD |
| ATOM | 4455 | CA | ASN | D | 57 | 69.577 | 49.220 | 65.991 | 1.00 | 70.24 | chnD |
| ATOM | 4456 | CB | ASN | D | 57 | 69.835 | 50.589 | 66.636 | 1.00 | 75.74 | chnD |
| ATOM | 4457 | CG | ASN | D | 57 | 69.827 | 51.728 | 65.620 | 1.00 | 80.98 | chnD |
| ATOM | 4458 | OD1 | ASN | D | 57 | 70.423 | 51.624 | 64.540 | 1.00 | 83.12 | chnD |
| ATOM | 4459 | ND2 | ASN | D | 57 | 69.153 | 52.824 | 65.962 | 1.00 | 84.44 | chnD |
| ATOM | 4460 | C | ASN | D | 57 | 69.957 | 48.089 | 66.939 | 1.00 | 68.89 | chnD |
| ATOM | 4461 | O | ASN | D | 57 | 70.590 | 48.307 | 67.971 | 1.00 | 68.20 | chnD |
| ATOM | 4462 | N | ALA | D | 58 | 69.584 | 46.874 | 66.539 | 1.00 | 67.35 | chnD |
| ATOM | 4463 | CA | ALA | D | 58 | 69.815 | 45.651 | 67.300 | 1.00 | 66.12 | chnD |
| ATOM | 4464 | CB | ALA | D | 58 | 69.744 | 44.443 | 66.390 | 1.00 | 63.87 | chnD |
| ATOM | 4465 | C | ALA | D | 58 | 71.090 | 45.609 | 68.122 | 1.00 | 67.10 | chnD |
| ATOM | 4466 | O | ALA | D | 58 | 72.187 | 45.822 | 67.613 | 1.00 | 67.64 | chnD |
| ATOM | 4467 | N | LYS | D | 59 | 70.914 | 45.360 | 69.415 | 1.00 | 70.44 | chnD |
| ATOM | 4468 | CA | LYS | D | 59 | 72.011 | 45.262 | 70.368 | 1.00 | 71.39 | chnD |
| ATOM | 4469 | CB | LYS | D | 59 | 71.722 | 46.132 | 71.591 | 1.00 | 76.45 | chnD |
| ATOM | 4470 | CG | LYS | D | 59 | 71.351 | 47.569 | 71.255 | 1.00 | 83.52 | chnD |
| ATOM | 4471 | CD | LYS | D | 59 | 70.733 | 48.280 | 72.454 | 1.00 | 87.37 | chnD |
| ATOM | 4472 | CE | LYS | D | 59 | 70.033 | 49.580 | 72.029 | 1.00 | 90.32 | chnD |
| ATOM | 4473 | NZ | LYS | D | 59 | 69.336 | 50.272 | 73.165 | 1.00 | 91.49 | chnD |
| ATOM | 4474 | C | LYS | D | 59 | 72.080 | 43.802 | 70.787 | 1.00 | 68.74 | chnD |
| ATOM | 4475 | O | LYS | D | 59 | 71.134 | 43.050 | 70.568 | 1.00 | 67.50 | chnD |
| ATOM | 4476 | N | PHE | D | 60 | 73.195 | 43.399 | 71.383 | 1.00 | 66.40 | chnD |
| ATOM | 4477 | CA | PHE | D | 60 | 73.353 | 42.019 | 71.822 | 1.00 | 67.51 | chnD |
| ATOM | 4478 | CB | PHE | D | 60 | 74.705 | 41.826 | 72.496 | 1.00 | 65.90 | chnD |
| ATOM | 4479 | CG | PHE | D | 60 | 75.861 | 41.955 | 71.564 | 1.00 | 65.03 | chnD |
| ATOM | 4480 | CD1 | PHE | D | 60 | 76.568 | 43.144 | 71.483 | 1.00 | 66.10 | chnD |
| ATOM | 4481 | CD2 | PHE | D | 60 | 76.253 | 40.881 | 70.777 | 1.00 | 65.20 | chnD |
| ATOM | 4482 | CE1 | PHE | D | 60 | 77.647 | 43.268 | 70.629 | 1.00 | 67.74 | chnD |
| ATOM | 4483 | CE2 | PHE | D | 60 | 77.331 | 40.993 | 69.918 | 1.00 | 67.04 | chnD |
| ATOM | 4484 | CZ | PHE | D | 60 | 78.033 | 42.191 | 69.846 | 1.00 | 68.69 | chnD |
| ATOM | 4485 | C | PHE | D | 60 | 72.245 | 41.655 | 72.788 | 1.00 | 68.27 | chnD |
| ATOM | 4486 | O | PHE | D | 60 | 71.753 | 40.529 | 72.789 | 1.00 | 67.41 | chnD |
| ATOM | 4487 | N | GLU | D | 61 | 71.847 | 42.643 | 73.585 | 1.00 | 70.96 | chnD |
| ATOM | 4488 | CA | GLU | D | 61 | 70.794 | 42.514 | 74.588 | 1.00 | 71.38 | chnD |
| ATOM | 4489 | CB | GLU | D | 61 | 70.587 | 43.866 | 75.300 | 1.00 | 76.43 | chnD |
| ATOM | 4490 | CG | GLU | D | 61 | 71.721 | 44.301 | 76.277 | 1.00 | 85.07 | chnD |
| ATOM | 4491 | CD | GLU | D | 61 | 73.116 | 44.476 | 75.631 | 1.00 | 87.99 | chnD |
| ATOM | 4492 | OE1 | GLU | D | 61 | 73.283 | 45.339 | 74.738 | 1.00 | 89.80 | chnD |
| ATOM | 4493 | OE2 | GLU | D | 61 | 74.057 | 43.763 | 76.043 | 1.00 | 88.08 | chnD |
| ATOM | 4494 | C | GLU | D | 61 | 69.476 | 42.031 | 73.972 | 1.00 | 67.46 | chnD |
| ATOM | 4495 | O | GLU | D | 61 | 68.726 | 41.298 | 74.604 | 1.00 | 68.01 | chnD |
| ATOM | 4496 | N | ASP | D | 62 | 69.228 | 42.408 | 72.721 | 1.00 | 63.41 | chnD |
| ATOM | 4497 | CA | ASP | D | 62 | 68.008 | 42.026 | 72.019 | 1.00 | 57.61 | chnD |
| ATOM | 4498 | CB | ASP | D | 62 | 67.821 | 42.892 | 70.780 | 1.00 | 60.73 | chnD |
| ATOM | 4499 | CG | ASP | D | 62 | 67.583 | 44.338 | 71.124 | 1.00 | 63.50 | chnD |
| ATOM | 4500 | OD1 | ASP | D | 62 | 66.846 | 44.598 | 72.096 | 1.00 | 66.83 | chnD |
| ATOM | 4501 | OD2 | ASP | D | 62 | 68.137 | 45.216 | 70.435 | 1.00 | 64.30 | chnD |
| ATOM | 4502 | C | ASP | D | 62 | 67.933 | 40.562 | 71.638 | 1.00 | 54.87 | chnD |
| ATOM | 4503 | O | ASP | D | 62 | 66.891 | 40.091 | 71.199 | 1.00 | 50.55 | chnD |
| ATOM | 4504 | N | SER | D | 63 | 69.037 | 39.845 | 71.803 | 1.00 | 52.68 | chnD |
| ATOM | 4505 | CA | SER | D | 63 | 69.080 | 38.422 | 71.481 | 1.00 | 56.01 | chnD |
| ATOM | 4506 | CB | SER | D | 63 | 70.511 | 37.889 | 71.600 | 1.00 | 55.78 | chnD |
| ATOM | 4507 | OG | SER | D | 63 | 71.413 | 38.640 | 70.806 | 1.00 | 60.07 | chnD |
| ATOM | 4508 | C | SER | D | 63 | 68.201 | 37.694 | 72.476 | 1.00 | 56.03 | chnD |
| ATOM | 4509 | O | SER | D | 63 | 67.865 | 38.248 | 73.514 | 1.00 | 59.79 | chnD |
| ATOM | 4510 | N | GLY | D | 64 | 67.799 | 36.472 | 72.156 | 1.00 | 56.57 | chnD |
| ATOM | 4511 | CA | GLY | D | 64 | 66.982 | 35.728 | 73.092 | 1.00 | 59.19 | chnD |
| ATOM | 4512 | C | GLY | D | 64 | 65.719 | 35.100 | 72.552 | 1.00 | 62.88 | chnD |
| ATOM | 4513 | O | GLY | D | 64 | 65.473 | 35.075 | 71.347 | 1.00 | 64.50 | chnD |
| ATOM | 4514 | N | GLU | D | 65 | 64.908 | 34.601 | 73.478 | 1.00 | 67.36 | chnD |
| ATOM | 4515 | CA | GLU | D | 65 | 63.643 | 33.939 | 73.173 | 1.00 | 69.01 | chnD |
| ATOM | 4516 | CB | GLU | D | 65 | 63.344 | 32.912 | 74.269 | 1.00 | 75.54 | chnD |
| ATOM | 4517 | CG | GLU | D | 65 | 62.008 | 32.195 | 74.152 | 1.00 | 82.24 | chnD |
| ATOM | 4518 | CD | GLU | D | 65 | 61.647 | 31.430 | 75.421 | 1.00 | 85.45 | chnD |
| ATOM | 4519 | OE1 | GLU | D | 65 | 61.254 | 32.076 | 76.421 | 1.00 | 87.81 | chnD |
| ATOM | 4520 | OE2 | GLU | D | 65 | 61.744 | 30.182 | 75.415 | 1.00 | 88.20 | chnD |
| ATOM | 4521 | C | GLU | D | 65 | 62.492 | 34.931 | 73.075 | 1.00 | 65.90 | chnD |
| ATOM | 4522 | O | GLU | D | 65 | 62.375 | 35.829 | 73.901 | 1.00 | 65.15 | chnD |
| ATOM | 4523 | N | TYR | D | 66 | 61.649 | 34.767 | 72.060 | 1.00 | 63.18 | chnD |
| ATOM | 4524 | CA | TYR | D | 66 | 60.494 | 35.639 | 71.874 | 1.00 | 61.99 | chnD |
| ATOM | 4525 | CB | TYR | D | 66 | 60.697 | 36.551 | 70.683 | 1.00 | 52.41 | chnD |
| ATOM | 4526 | CG | TYR | D | 66 | 61.620 | 37.701 | 70.944 | 1.00 | 46.40 | chnD |
| ATOM | 4527 | CD1 | TYR | D | 66 | 62.988 | 37.574 | 70.779 | 1.00 | 45.65 | chnD |
| ATOM | 4528 | CE1 | TYR | D | 66 | 63.830 | 38.667 | 70.945 | 1.00 | 43.73 | chnD |
| ATOM | 4529 | CD2 | TYR | D | 66 | 61.118 | 38.946 | 71.289 | 1.00 | 45.14 | chnD |
| ATOM | 4530 | CE2 | TYR | D | 66 | 61.951 | 40.043 | 71.453 | 1.00 | 43.33 | chnD |
| ATOM | 4531 | CZ | TYR | D | 66 | 63.299 | 39.896 | 71.279 | 1.00 | 42.20 | chnD |

-continued

| | | | | | | | | | | |
|---|---|---|---|---|---|---|---|---|---|---|
| ATOM | 4532 | OH | TYR | D | 66 | 64.110 | 40.986 | 71.427 | 1.00 | 41.01 chnD |
| ATOM | 4533 | C | TYR | D | 66 | 59.208 | 34.841 | 71.690 | 1.00 | 67.07 chnD |
| ATOM | 4534 | O | TYR | D | 66 | 59.197 | 33.806 | 71.019 | 1.00 | 69.05 chnD |
| ATOM | 4535 | N | LYS | D | 67 | 58.135 | 35.323 | 72.315 | 1.00 | 73.81 chnD |
| ATOM | 4536 | CA | LYS | D | 67 | 56.822 | 34.686 | 72.246 | 1.00 | 79.11 chnD |
| ATOM | 4537 | CB | LYS | D | 67 | 56.561 | 33.833 | 73.488 | 1.00 | 81.84 chnD |
| ATOM | 4538 | CG | LYS | D | 67 | 57.481 | 32.655 | 73.728 | 1.00 | 85.83 chnD |
| ATOM | 4539 | CD | LYS | D | 67 | 57.164 | 32.063 | 75.108 | 1.00 | 90.36 chnD |
| ATOM | 4540 | CE | LYS | D | 67 | 58.088 | 30.914 | 75.495 | 1.00 | 93.06 chnD |
| ATOM | 4541 | NZ | LYS | D | 67 | 57.842 | 30.447 | 76.889 | 1.00 | 94.47 chnD |
| ATOM | 4542 | C | LYS | D | 67 | 55.734 | 35.748 | 72.195 | 1.00 | 81.61 chnD |
| ATOM | 4543 | O | LYS | D | 67 | 55.905 | 36.851 | 72.716 | 1.00 | 80.64 chnD |
| ATOM | 4544 | N | CYS | D | 68 | 54.600 | 35.394 | 71.601 | 1.00 | 86.64 chnD |
| ATOM | 4545 | CA | CYS | D | 68 | 53.468 | 36.305 | 71.514 | 1.00 | 93.32 chnD |
| ATOM | 4546 | C | CYS | D | 68 | 52.197 | 35.596 | 71.967 | 1.00 | 95.87 chnD |
| ATOM | 4547 | O | CYS | D | 68 | 52.019 | 34.402 | 71.726 | 1.00 | 95.69 chnD |
| ATOM | 4548 | CB | CYS | D | 68 | 53.312 | 36.851 | 70.094 | 1.00 | 95.78 chnD |
| ATOM | 4549 | SG | CYS | D | 68 | 52.604 | 35.706 | 68.866 | 1.00 | 100.42 chnD |
| ATOM | 4550 | N | GLN | D | 69 | 51.328 | 36.337 | 72.647 | 1.00 | 100.05 chnD |
| ATOM | 4551 | CA | GLN | D | 69 | 50.076 | 35.784 | 73.157 | 1.00 | 104.85 chnD |
| ATOM | 4552 | CB | GLN | D | 69 | 50.133 | 35.677 | 74.690 | 1.00 | 106.93 chnD |
| ATOM | 4553 | CG | GLN | D | 69 | 49.027 | 34.831 | 75.329 | 1.00 | 110.02 chnD |
| ATOM | 4554 | CD | GLN | D | 69 | 49.146 | 34.741 | 76.854 | 1.00 | 110.42 chnD |
| ATOM | 4555 | OE1 | GLN | D | 69 | 50.239 | 34.564 | 77.400 | 1.00 | 110.53 chnD |
| ATOM | 4556 | NE2 | GLN | D | 69 | 48.012 | 34.853 | 77.545 | 1.00 | 111.83 chnD |
| ATOM | 4557 | C | GLN | D | 69 | 48.879 | 36.637 | 72.739 | 1.00 | 105.86 chnD |
| ATOM | 4558 | O | GLN | D | 69 | 48.902 | 37.867 | 72.852 | 1.00 | 105.76 chnD |
| ATOM | 4559 | N | HIS | D | 70 | 47.846 | 35.974 | 72.231 | 1.00 | 107.18 chnD |
| ATOM | 4560 | CA | HIS | D | 70 | 46.631 | 36.658 | 71.807 | 1.00 | 108.58 chnD |
| ATOM | 4561 | CB | HIS | D | 70 | 46.207 | 36.178 | 70.408 | 1.00 | 108.35 chnD |
| ATOM | 4562 | CG | HIS | D | 70 | 46.751 | 37.011 | 69.283 | 1.00 | 107.62 chnD |
| ATOM | 4563 | CD2 | HIS | D | 70 | 46.870 | 36.746 | 67.960 | 1.00 | 106.39 chnD |
| ATOM | 4564 | ND1 | HIS | D | 70 | 47.214 | 38.297 | 69.460 | 1.00 | 107.50 chnD |
| ATOM | 4565 | CE1 | HIS | D | 70 | 47.592 | 38.791 | 68.293 | 1.00 | 107.04 chnD |
| ATOM | 4566 | NE2 | HIS | D | 70 | 47.394 | 37.872 | 67.368 | 1.00 | 107.22 chnD |
| ATOM | 4567 | C | HIS | D | 70 | 45.513 | 36.414 | 72.832 | 1.00 | 109.42 chnD |
| ATOM | 4568 | O | HIS | D | 70 | 45.301 | 37.222 | 73.746 | 1.00 | 108.82 chnD |
| ATOM | 4569 | N | GLN | D | 71 | 44.797 | 35.305 | 72.666 | 1.00 | 111.21 chnD |
| ATOM | 4570 | CA | GLN | D | 71 | 43.717 | 34.930 | 73.577 | 1.00 | 112.11 chnD |
| ATOM | 4571 | CB | GLN | D | 71 | 42.613 | 34.151 | 72.836 | 1.00 | 113.83 chnD |
| ATOM | 4572 | CG | GLN | D | 71 | 41.918 | 34.890 | 71.678 | 1.00 | 115.13 chnD |
| ATOM | 4573 | CD | GLN | D | 71 | 40.860 | 34.026 | 70.965 | 1.00 | 115.59 chnD |
| ATOM | 4574 | OE1 | GLN | D | 71 | 41.187 | 33.018 | 70.317 | 1.00 | 114.99 chnD |
| ATOM | 4575 | NE2 | GLN | D | 71 | 39.588 | 34.425 | 71.080 | 1.00 | 116.03 chnD |
| ATOM | 4576 | C | GLN | D | 71 | 44.323 | 34.019 | 74.639 | 1.00 | 110.78 chnD |
| ATOM | 4577 | O | GLN | D | 71 | 45.087 | 33.100 | 74.312 | 1.00 | 110.14 chnD |
| ATOM | 4578 | N | GLN | D | 72 | 44.004 | 34.277 | 75.907 | 1.00 | 110.19 chnD |
| ATOM | 4579 | CA | GLN | D | 72 | 44.508 | 33.436 | 76.995 | 1.00 | 111.16 chnD |
| ATOM | 4580 | CB | GLN | D | 72 | 43.967 | 33.882 | 78.356 | 1.00 | 112.26 chnD |
| ATOM | 4581 | CG | GLN | D | 72 | 43.765 | 35.369 | 78.550 | 1.00 | 114.12 chnD |
| ATOM | 4582 | CD | GLN | D | 72 | 42.829 | 35.659 | 79.722 | 1.00 | 115.15 chnD |
| ATOM | 4583 | OE1 | GLN | D | 72 | 41.609 | 35.452 | 79.626 | 1.00 | 114.56 chnD |
| ATOM | 4584 | NE2 | GLN | D | 72 | 43.398 | 36.115 | 80.844 | 1.00 | 115.26 chnD |
| ATOM | 4585 | C | GLN | D | 72 | 43.988 | 32.019 | 76.738 | 1.00 | 111.97 chnD |
| ATOM | 4586 | O | GLN | D | 72 | 42.784 | 31.816 | 76.560 | 1.00 | 112.10 chnD |
| ATOM | 4587 | N | VAL | D | 73 | 44.918 | 31.070 | 76.685 | 1.00 | 113.09 chnD |
| ATOM | 4588 | CA | VAL | D | 73 | 44.673 | 29.639 | 76.461 | 1.00 | 115.40 chnD |
| ATOM | 4589 | CB | VAL | D | 73 | 43.647 | 29.322 | 75.291 | 1.00 | 115.86 chnD |
| ATOM | 4590 | CG1 | VAL | D | 73 | 44.055 | 28.031 | 74.529 | 1.00 | 115.86 chnD |
| ATOM | 4591 | CG2 | VAL | D | 73 | 42.228 | 29.111 | 75.863 | 1.00 | 114.50 chnD |
| ATOM | 4592 | C | VAL | D | 73 | 46.046 | 29.077 | 76.119 | 1.00 | 115.47 chnD |
| ATOM | 4593 | O | VAL | D | 73 | 46.542 | 28.175 | 76.820 | 1.00 | 115.29 chnD |
| ATOM | 4594 | N | ASN | D | 74 | 46.651 | 29.617 | 75.050 | 1.00 | 115.94 chnD |
| ATOM | 4595 | CA | ASN | D | 74 | 47.984 | 29.185 | 74.640 | 1.00 | 116.68 chnD |
| ATOM | 4596 | CB | ASN | D | 74 | 47.919 | 27.950 | 73.730 | 1.00 | 118.53 chnD |
| ATOM | 4597 | CG | ASN | D | 74 | 47.499 | 26.678 | 74.478 | 1.00 | 119.50 chnD |
| ATOM | 4598 | OD1 | ASN | D | 74 | 47.976 | 26.394 | 75.583 | 1.00 | 119.70 chnD |
| ATOM | 4599 | ND2 | ASN | D | 74 | 46.603 | 25.907 | 73.868 | 1.00 | 119.67 chnD |
| ATOM | 4600 | C | ASN | D | 74 | 48.851 | 30.268 | 73.997 | 1.00 | 115.33 chnD |
| ATOM | 4601 | O | ASN | D | 74 | 48.364 | 31.152 | 73.280 | 1.00 | 115.46 chnD |
| ATOM | 4602 | N | GLU | D | 75 | 50.144 | 30.192 | 74.302 | 1.00 | 112.75 chnD |
| ATOM | 4603 | CA | GLU | D | 75 | 51.143 | 31.115 | 73.782 | 1.00 | 110.01 chnD |
| ATOM | 4604 | CB | GLU | D | 75 | 52.279 | 31.289 | 74.800 | 1.00 | 109.92 chnD |
| ATOM | 4605 | CG | GLU | D | 75 | 51.838 | 31.753 | 76.183 | 1.00 | 109.01 chnD |
| ATOM | 4606 | CD | GLU | D | 75 | 53.002 | 31.878 | 77.153 | 1.00 | 107.87 chnD |
| ATOM | 4607 | OE1 | GLU | D | 75 | 53.663 | 30.847 | 77.425 | 1.00 | 107.77 chnD |
| ATOM | 4608 | OE2 | GLU | D | 75 | 53.250 | 33.006 | 77.640 | 1.00 | 106.53 chnD |
| ATOM | 4609 | C | GLU | D | 75 | 51.711 | 30.510 | 72.504 | 1.00 | 109.00 chnD |
| ATOM | 4610 | O | GLU | D | 75 | 51.479 | 29.331 | 72.203 | 1.00 | 109.44 chnD |

-continued

| | | | | | | | | | | |
|---|---|---|---|---|---|---|---|---|---|---|
| ATOM | 4611 | N | SER | D | 76 | 52.469 | 31.314 | 71.765 | 1.00 | 106.58 chnD |
| ATOM | 4612 | CA | SER | D | 76 | 53.094 | 30.863 | 70.525 | 1.00 | 104.50 chnD |
| ATOM | 4613 | CB | SER | D | 76 | 53.430 | 32.065 | 69.642 | 1.00 | 104.53 chnD |
| ATOM | 4614 | OG | SER | D | 76 | 54.359 | 32.921 | 70.287 | 1.00 | 104.33 chnD |
| ATOM | 4615 | C | SER | D | 76 | 54.378 | 30.083 | 70.813 | 1.00 | 103.25 chnD |
| ATOM | 4616 | O | SER | D | 76 | 54.898 | 30.105 | 71.935 | 1.00 | 102.42 chnD |
| ATOM | 4617 | N | GLU | D | 77 | 54.879 | 29.377 | 69.806 | 1.00 | 102.50 chnD |
| ATOM | 4618 | CA | GLU | D | 77 | 56.119 | 28.638 | 69.969 | 1.00 | 102.19 chnD |
| ATOM | 4619 | CB | GLU | D | 77 | 56.330 | 27.672 | 68.806 | 1.00 | 105.98 chnD |
| ATOM | 4620 | CG | GLU | D | 77 | 55.349 | 26.512 | 68.789 | 1.00 | 109.72 chnD |
| ATOM | 4621 | CD | GLU | D | 77 | 55.421 | 25.674 | 70.055 | 1.00 | 111.66 chnD |
| ATOM | 4622 | OE1 | GLU | D | 77 | 56.396 | 24.907 | 70.213 | 1.00 | 113.18 chnD |
| ATOM | 4623 | OE2 | GLU | D | 77 | 54.503 | 25.788 | 70.896 | 1.00 | 113.12 chnD |
| ATOM | 4624 | C | GLU | D | 77 | 57.257 | 29.652 | 70.039 | 1.00 | 99.06 chnD |
| ATOM | 4625 | O | GLU | D | 77 | 57.196 | 30.716 | 69.422 | 1.00 | 99.03 chnD |
| ATOM | 4626 | N | PRO | D | 78 | 58.287 | 29.355 | 70.835 | 1.00 | 95.36 chnD |
| ATOM | 4627 | CD | PRO | D | 78 | 58.379 | 28.194 | 71.732 | 1.00 | 95.44 chnD |
| ATOM | 4628 | CA | PRO | D | 78 | 59.446 | 30.233 | 71.003 | 1.00 | 92.10 chnD |
| ATOM | 4629 | CB | PRO | D | 78 | 60.281 | 29.496 | 72.050 | 1.00 | 94.12 chnD |
| ATOM | 4630 | CG | PRO | D | 78 | 59.260 | 28.728 | 72.827 | 1.00 | 95.30 chnD |
| ATOM | 4631 | C | PRO | D | 78 | 60.244 | 30.424 | 69.718 | 1.00 | 88.82 chnD |
| ATOM | 4632 | O | PRO | D | 78 | 60.471 | 29.475 | 68.959 | 1.00 | 88.76 chnD |
| ATOM | 4633 | N | VAL | D | 79 | 60.636 | 31.670 | 69.474 | 1.00 | 82.83 chnD |
| ATOM | 4634 | CA | VAL | D | 79 | 61.433 | 32.020 | 68.313 | 1.00 | 80.10 chnD |
| ATOM | 4635 | CB | VAL | D | 79 | 60.699 | 33.020 | 67.400 | 1.00 | 79.21 chnD |
| ATOM | 4636 | CG1 | VAL | D | 79 | 61.581 | 33.416 | 66.232 | 1.00 | 81.17 chnD |
| ATOM | 4637 | CG2 | VAL | D | 79 | 59.424 | 32.395 | 66.883 | 1.00 | 81.03 chnD |
| ATOM | 4638 | C | VAL | D | 79 | 62.700 | 32.645 | 68.872 | 1.00 | 78.60 chnD |
| ATOM | 4639 | O | VAL | D | 79 | 62.643 | 33.617 | 69.627 | 1.00 | 79.17 chnD |
| ATOM | 4640 | N | TYR | D | 80 | 63.839 | 32.053 | 68.539 | 1.00 | 77.16 chnD |
| ATOM | 4641 | CA | TYR | D | 80 | 65.115 | 32.545 | 69.032 | 1.00 | 76.76 chnD |
| ATOM | 4642 | CB | TYR | D | 80 | 65.998 | 31.365 | 69.443 | 1.00 | 83.13 chnD |
| ATOM | 4643 | CG | TYR | D | 80 | 65.353 | 30.479 | 70.492 | 1.00 | 88.39 chnD |
| ATOM | 4644 | CD1 | TYR | D | 80 | 64.648 | 29.329 | 70.125 | 1.00 | 89.38 chnD |
| ATOM | 4645 | CE1 | TYR | D | 80 | 64.039 | 28.519 | 71.082 | 1.00 | 90.42 chnD |
| ATOM | 4646 | CD2 | TYR | D | 80 | 65.434 | 30.799 | 71.850 | 1.00 | 89.93 chnD |
| ATOM | 4647 | CE2 | TYR | D | 80 | 64.828 | 29.997 | 72.816 | 1.00 | 91.31 chnD |
| ATOM | 4648 | CZ | TYR | D | 80 | 64.132 | 28.858 | 72.426 | 1.00 | 91.14 chnD |
| ATOM | 4649 | OH | TYR | D | 80 | 63.533 | 28.054 | 73.374 | 1.00 | 92.19 chnD |
| ATOM | 4650 | C | TYR | D | 80 | 65.835 | 33.457 | 68.044 | 1.00 | 73.02 chnD |
| ATOM | 4651 | O | TYR | D | 80 | 65.996 | 33.127 | 66.873 | 1.00 | 74.59 chnD |
| ATOM | 4652 | N | LEU | D | 81 | 66.230 | 34.624 | 68.536 | 1.00 | 66.32 chnD |
| ATOM | 4653 | CA | LEU | D | 81 | 66.930 | 35.625 | 67.751 | 1.00 | 59.32 chnD |
| ATOM | 4654 | CB | LEU | D | 81 | 66.187 | 36.952 | 67.851 | 1.00 | 57.21 chnD |
| ATOM | 4655 | CG | LEU | D | 81 | 66.852 | 38.190 | 67.261 | 1.00 | 56.33 chnD |
| ATOM | 4656 | CD1 | LEU | D | 81 | 66.908 | 38.084 | 65.752 | 1.00 | 57.97 chnD |
| ATOM | 4657 | CD2 | LEU | D | 81 | 66.068 | 39.418 | 67.667 | 1.00 | 57.81 chnD |
| ATOM | 4658 | C | LEU | D | 81 | 68.318 | 35.784 | 68.334 | 1.00 | 58.40 chnD |
| ATOM | 4659 | O | LEU | D | 81 | 68.478 | 35.804 | 69.547 | 1.00 | 59.05 chnD |
| ATOM | 4660 | N | GLU | D | 82 | 69.324 | 35.907 | 67.478 | 1.00 | 57.13 chnD |
| ATOM | 4661 | CA | GLU | D | 82 | 70.691 | 36.070 | 67.957 | 1.00 | 55.42 chnD |
| ATOM | 4662 | CB | GLU | D | 82 | 71.440 | 34.744 | 67.856 | 1.00 | 59.72 chnD |
| ATOM | 4663 | CG | GLU | D | 82 | 72.757 | 34.710 | 68.619 | 1.00 | 68.62 chnD |
| ATOM | 4664 | CD | GLU | D | 82 | 73.408 | 33.328 | 68.623 | 1.00 | 72.75 chnD |
| ATOM | 4665 | OE1 | GLU | D | 82 | 72.954 | 32.431 | 67.868 | 1.00 | 74.67 chnD |
| ATOM | 4666 | OE2 | GLU | D | 82 | 74.380 | 33.141 | 69.391 | 1.00 | 75.80 chnD |
| ATOM | 4667 | C | GLU | D | 82 | 71.435 | 37.178 | 67.214 | 1.00 | 51.31 chnD |
| ATOM | 4668 | O | GLU | D | 82 | 71.493 | 37.189 | 65.987 | 1.00 | 50.03 chnD |
| ATOM | 4669 | N | VAL | D | 83 | 71.977 | 38.121 | 67.978 | 1.00 | 45.77 chnD |
| ATOM | 4670 | CA | VAL | D | 83 | 72.712 | 39.255 | 67.430 | 1.00 | 43.52 chnD |
| ATOM | 4671 | CB | VAL | D | 83 | 72.416 | 40.524 | 68.223 | 1.00 | 41.28 chnD |
| ATOM | 4672 | CG1 | VAL | D | 83 | 73.228 | 41.689 | 67.686 | 1.00 | 41.30 chnD |
| ATOM | 4673 | CG2 | VAL | D | 83 | 70.940 | 40.831 | 68.168 | 1.00 | 37.94 chnD |
| ATOM | 4674 | C | VAL | D | 83 | 74.222 | 39.036 | 67.427 | 1.00 | 45.31 chnD |
| ATOM | 4675 | O | VAL | D | 83 | 74.831 | 38.843 | 68.486 | 1.00 | 49.18 chnD |
| ATOM | 4676 | N | PHE | D | 84 | 74.822 | 39.114 | 66.237 | 1.00 | 41.57 chnD |
| ATOM | 4677 | CA | PHE | D | 84 | 76.255 | 38.914 | 66.077 | 1.00 | 36.72 chnD |
| ATOM | 4678 | CB | PHE | D | 84 | 76.525 | 37.892 | 64.987 | 1.00 | 37.12 chnD |
| ATOM | 4679 | CG | PHE | D | 84 | 75.987 | 36.532 | 65.277 | 1.00 | 37.17 chnD |
| ATOM | 4680 | CD1 | PHE | D | 84 | 74.660 | 36.229 | 65.021 | 1.00 | 37.65 chnD |
| ATOM | 4681 | CD2 | PHE | D | 84 | 76.819 | 35.533 | 65.752 | 1.00 | 35.92 chnD |
| ATOM | 4682 | CE1 | PHE | D | 84 | 74.177 | 34.948 | 65.224 | 1.00 | 38.60 chnD |
| ATOM | 4683 | CE2 | PHE | D | 84 | 76.341 | 34.253 | 65.956 | 1.00 | 38.62 chnD |
| ATOM | 4684 | CZ | PHE | D | 84 | 75.021 | 33.961 | 65.693 | 1.00 | 38.25 chnD |
| ATOM | 4685 | C | PHE | D | 84 | 76.981 | 40.186 | 65.703 | 1.00 | 36.30 chnD |
| ATOM | 4686 | O | PHE | D | 84 | 76.365 | 41.205 | 65.398 | 1.00 | 31.82 chnD |
| ATOM | 4687 | N | SER | D | 85 | 78.305 | 40.107 | 65.735 | 1.00 | 38.92 chnD |
| ATOM | 4688 | CA | SER | D | 85 | 79.157 | 41.224 | 65.359 | 1.00 | 44.87 chnD |
| ATOM | 4689 | CB | SER | D | 85 | 79.418 | 42.134 | 66.540 | 1.00 | 44.30 chnD |

-continued

| ATOM | 4690 | OG | SER | D | 85 | 80.181 | 43.245 | 66.107 | 1.00 | 50.34 | chnD |
|------|------|-----|-----|---|----|--------|--------|--------|------|-------|------|
| ATOM | 4691 | C | SER | D | 85 | 80.479 | 40.700 | 64.798 | 1.00 | 47.41 | chnD |
| ATOM | 4692 | O | SER | D | 85 | 81.536 | 40.810 | 65.429 | 1.00 | 45.43 | chnD |
| ATOM | 4693 | N | ASP | D | 86 | 80.382 | 40.093 | 63.617 | 1.00 | 50.67 | chnD |
| ATOM | 4694 | CA | ASP | D | 86 | 81.511 | 39.509 | 62.908 | 1.00 | 49.33 | chnD |
| ATOM | 4695 | CB | ASP | D | 86 | 81.267 | 37.999 | 62.785 | 1.00 | 53.30 | chnD |
| ATOM | 4696 | CG | ASP | D | 86 | 82.555 | 37.192 | 62.713 | 1.00 | 59.07 | chnD |
| ATOM | 4697 | OD1 | ASP | D | 86 | 83.323 | 37.333 | 61.725 | 1.00 | 62.05 | chnD |
| ATOM | 4698 | OD2 | ASP | D | 86 | 82.791 | 36.392 | 63.646 | 1.00 | 61.73 | chnD |
| ATOM | 4699 | C | ASP | D | 86 | 81.565 | 40.178 | 61.521 | 1.00 | 47.44 | chnD |
| ATOM | 4700 | O | ASP | D | 86 | 80.806 | 41.110 | 61.256 | 1.00 | 45.33 | chnD |
| ATOM | 4701 | N | TRP | D | 87 | 82.485 | 39.736 | 60.664 | 1.00 | 45.61 | chnD |
| ATOM | 4702 | CA | TRP | D | 87 | 82.618 | 40.281 | 59.304 | 1.00 | 40.49 | chnD |
| ATOM | 4703 | CB | TRP | D | 87 | 84.036 | 40.075 | 58.765 | 1.00 | 40.50 | chnD |
| ATOM | 4704 | CG | TRP | D | 87 | 84.996 | 41.189 | 59.104 | 1.00 | 40.21 | chnD |
| ATOM | 4705 | CD2 | TRP | D | 87 | 85.041 | 42.477 | 58.508 | 1.00 | 37.53 | chnD |
| ATOM | 4706 | CE2 | TRP | D | 87 | 86.113 | 43.175 | 59.100 | 1.00 | 37.72 | chnD |
| ATOM | 4707 | CE3 | TRP | D | 87 | 84.285 | 43.109 | 57.523 | 1.00 | 36.43 | chnD |
| ATOM | 4708 | CD1 | TRP | D | 87 | 86.011 | 41.156 | 60.017 | 1.00 | 40.56 | chnD |
| ATOM | 4709 | NE1 | TRP | D | 87 | 86.689 | 42.345 | 60.021 | 1.00 | 38.07 | chnD |
| ATOM | 4710 | CZ2 | TRP | D | 87 | 86.444 | 44.471 | 58.743 | 1.00 | 37.70 | chnD |
| ATOM | 4711 | CZ3 | TRP | D | 87 | 84.612 | 44.398 | 57.166 | 1.00 | 39.88 | chnD |
| ATOM | 4712 | CH2 | TRP | D | 87 | 85.686 | 45.068 | 57.774 | 1.00 | 39.44 | chnD |
| ATOM | 4713 | C | TRP | D | 87 | 81.613 | 39.619 | 58.376 | 1.00 | 38.51 | chnD |
| ATOM | 4714 | O | TRP | D | 87 | 81.013 | 40.266 | 57.520 | 1.00 | 34.05 | chnD |
| ATOM | 4715 | N | LEU | D | 88 | 81.439 | 38.319 | 58.549 | 1.00 | 36.28 | chnD |
| ATOM | 4716 | CA | LEU | D | 88 | 80.486 | 37.589 | 57.740 | 1.00 | 39.62 | chnD |
| ATOM | 4717 | CB | LEU | D | 88 | 81.201 | 36.655 | 56.779 | 1.00 | 40.47 | chnD |
| ATOM | 4718 | CG | LEU | D | 88 | 81.988 | 37.293 | 55.644 | 1.00 | 40.99 | chnD |
| ATOM | 4719 | CD1 | LEU | D | 88 | 82.546 | 36.192 | 54.772 | 1.00 | 40.45 | chnD |
| ATOM | 4720 | CD2 | LEU | D | 88 | 81.084 | 38.192 | 54.838 | 1.00 | 41.45 | chnD |
| ATOM | 4721 | C | LEU | D | 88 | 79.565 | 36.791 | 58.645 | 1.00 | 41.00 | chnD |
| ATOM | 4722 | O | LEU | D | 88 | 80.011 | 36.215 | 59.635 | 1.00 | 46.72 | chnD |
| ATOM | 4723 | N | LEU | D | 89 | 78.282 | 36.756 | 58.300 | 1.00 | 37.22 | chnD |
| ATOM | 4724 | CA | LEU | D | 89 | 77.308 | 36.023 | 59.083 | 1.00 | 35.66 | chnD |
| ATOM | 4725 | CB | LEU | D | 89 | 76.415 | 36.998 | 59.836 | 1.00 | 36.80 | chnD |
| ATOM | 4726 | CG | LEU | D | 89 | 75.227 | 36.443 | 60.620 | 1.00 | 36.88 | chnD |
| ATOM | 4727 | CD1 | LEU | D | 89 | 75.680 | 35.420 | 61.629 | 1.00 | 36.75 | chnD |
| ATOM | 4728 | CD2 | LEU | D | 89 | 74.527 | 37.587 | 61.316 | 1.00 | 38.26 | chnD |
| ATOM | 4729 | C | LEU | D | 89 | 76.460 | 35.156 | 58.183 | 1.00 | 36.93 | chnD |
| ATOM | 4730 | O | LEU | D | 89 | 75.827 | 35.665 | 57.266 | 1.00 | 34.15 | chnD |
| ATOM | 4731 | N | LEU | D | 90 | 76.474 | 33.847 | 58.424 | 1.00 | 38.25 | chnD |
| ATOM | 4732 | CA | LEU | D | 90 | 75.677 | 32.928 | 57.624 | 1.00 | 39.62 | chnD |
| ATOM | 4733 | CB | LEU | D | 90 | 76.209 | 31.501 | 57.711 | 1.00 | 38.90 | chnD |
| ATOM | 4734 | CG | LEU | D | 90 | 75.384 | 30.507 | 56.887 | 1.00 | 40.50 | chnD |
| ATOM | 4735 | CD1 | LEU | D | 90 | 75.529 | 30.804 | 55.409 | 1.00 | 42.38 | chnD |
| ATOM | 4736 | CD2 | LEU | D | 90 | 75.824 | 29.104 | 57.175 | 1.00 | 40.57 | chnD |
| ATOM | 4737 | C | LEU | D | 90 | 74.257 | 32.960 | 58.144 | 1.00 | 40.85 | chnD |
| ATOM | 4738 | O | LEU | D | 90 | 73.995 | 32.550 | 59.271 | 1.00 | 44.96 | chnD |
| ATOM | 4739 | N | GLN | D | 91 | 73.343 | 33.449 | 57.321 | 1.00 | 39.44 | chnD |
| ATOM | 4740 | CA | GLN | D | 91 | 71.959 | 33.544 | 57.718 | 1.00 | 40.20 | chnD |
| ATOM | 4741 | CB | GLN | D | 91 | 71.400 | 34.903 | 57.299 | 1.00 | 39.30 | chnD |
| ATOM | 4742 | CG | GLN | D | 91 | 72.162 | 36.069 | 57.909 | 1.00 | 42.25 | chnD |
| ATOM | 4743 | CD | GLN | D | 91 | 71.569 | 37.419 | 57.584 | 1.00 | 43.81 | chnD |
| ATOM | 4744 | OE1 | GLN | D | 91 | 71.741 | 37.937 | 56.486 | 1.00 | 47.99 | chnD |
| ATOM | 4745 | NE2 | GLN | D | 91 | 70.891 | 38.010 | 58.551 | 1.00 | 43.49 | chnD |
| ATOM | 4746 | C | GLN | D | 91 | 71.190 | 32.401 | 57.092 | 1.00 | 43.17 | chnD |
| ATOM | 4747 | O | GLN | D | 91 | 71.547 | 31.931 | 56.018 | 1.00 | 42.46 | chnD |
| ATOM | 4748 | N | ALA | D | 92 | 70.179 | 31.911 | 57.807 | 1.00 | 46.90 | chnD |
| ATOM | 4749 | CA | ALA | D | 92 | 69.338 | 30.813 | 57.337 | 1.00 | 47.92 | chnD |
| ATOM | 4750 | CB | ALA | D | 92 | 69.678 | 29.528 | 58.067 | 1.00 | 44.71 | chnD |
| ATOM | 4751 | C | ALA | D | 92 | 67.862 | 31.140 | 57.526 | 1.00 | 50.93 | chnD |
| ATOM | 4752 | O | ALA | D | 92 | 67.465 | 31.751 | 58.525 | 1.00 | 51.76 | chnD |
| ATOM | 4753 | N | SER | D | 93 | 67.059 | 30.746 | 56.541 | 1.00 | 53.59 | chnD |
| ATOM | 4754 | CA | SER | D | 93 | 65.618 | 30.962 | 56.563 | 1.00 | 56.09 | chnD |
| ATOM | 4755 | CB | SER | D | 93 | 64.998 | 30.421 | 55.275 | 1.00 | 56.28 | chnD |
| ATOM | 4756 | OG | SER | D | 93 | 65.310 | 29.041 | 55.116 | 1.00 | 54.33 | chnD |
| ATOM | 4757 | C | SER | D | 93 | 65.039 | 30.216 | 57.757 | 1.00 | 58.62 | chnD |
| ATOM | 4758 | O | SER | D | 93 | 64.061 | 30.647 | 58.363 | 1.00 | 63.67 | chnD |
| ATOM | 4759 | N | ALA | D | 94 | 65.662 | 29.089 | 58.078 | 1.00 | 58.66 | chnD |
| ATOM | 4760 | CA | ALA | D | 94 | 65.262 | 28.241 | 59.187 | 1.00 | 59.01 | chnD |
| ATOM | 4761 | CB | ALA | D | 94 | 63.986 | 27.492 | 58.839 | 1.00 | 60.58 | chnD |
| ATOM | 4762 | C | ALA | D | 94 | 66.422 | 27.269 | 59.436 | 1.00 | 59.89 | chnD |
| ATOM | 4763 | O | ALA | D | 94 | 67.113 | 26.857 | 58.508 | 1.00 | 60.38 | chnD |
| ATOM | 4764 | N | GLU | D | 95 | 66.623 | 26.882 | 60.686 | 1.00 | 62.15 | chnD |
| ATOM | 4765 | CA | GLU | D | 95 | 67.736 | 26.002 | 61.045 | 1.00 | 64.62 | chnD |
| ATOM | 4766 | CB | GLU | D | 95 | 68.475 | 26.616 | 62.230 | 1.00 | 62.28 | chnD |
| ATOM | 4767 | CG | GLU | D | 95 | 67.957 | 28.018 | 62.560 | 1.00 | 63.18 | chnD |
| ATOM | 4768 | CD | GLU | D | 95 | 69.056 | 28.987 | 62.871 | 1.00 | 65.02 | chnD |

-continued

| ATOM | 4769 | OE1 | GLU | D | 95 | 69.227 | 29.952 | 62.095 | 1.00 | 64.72 | chnD |
|------|------|-----|-----|---|-----|--------|--------|--------|------|-------|------|
| ATOM | 4770 | OE2 | GLU | D | 95 | 69.745 | 28.784 | 63.897 | 1.00 | 70.83 | chnD |
| ATOM | 4771 | C | GLU | D | 95 | 67.283 | 24.573 | 61.339 | 1.00 | 67.33 | chnD |
| ATOM | 4772 | O | GLU | D | 95 | 68.102 | 23.664 | 61.559 | 1.00 | 66.76 | chnD |
| ATOM | 4773 | N | VAL | D | 96 | 65.961 | 24.411 | 61.383 | 1.00 | 71.01 | chnD |
| ATOM | 4774 | CA | VAL | D | 96 | 65.300 | 23.124 | 61.595 | 1.00 | 73.79 | chnD |
| ATOM | 4775 | CB | VAL | D | 96 | 64.636 | 23.009 | 63.004 | 1.00 | 74.71 | chnD |
| ATOM | 4776 | CG1 | VAL | D | 96 | 64.314 | 21.557 | 63.305 | 1.00 | 75.09 | chnD |
| ATOM | 4777 | CG2 | VAL | D | 96 | 65.546 | 23.579 | 64.093 | 1.00 | 73.57 | chnD |
| ATOM | 4778 | C | VAL | D | 96 | 64.228 | 23.133 | 60.491 | 1.00 | 75.95 | chnD |
| ATOM | 4779 | O | VAL | D | 96 | 63.172 | 23.769 | 60.616 | 1.00 | 72.51 | chnD |
| ATOM | 4780 | N | VAL | D | 97 | 64.569 | 22.505 | 59.371 | 1.00 | 78.69 | chnD |
| ATOM | 4781 | CA | VAL | D | 97 | 63.694 | 22.453 | 58.210 | 1.00 | 82.61 | chnD |
| ATOM | 4782 | CB | VAL | D | 97 | 64.488 | 22.804 | 56.932 | 1.00 | 82.48 | chnD |
| ATOM | 4783 | CG1 | VAL | D | 97 | 63.566 | 22.909 | 55.735 | 1.00 | 82.98 | chnD |
| ATOM | 4784 | CG2 | VAL | D | 97 | 65.242 | 24.098 | 57.132 | 1.00 | 83.47 | chnD |
| ATOM | 4785 | C | VAL | D | 97 | 63.025 | 21.095 | 58.019 | 1.00 | 84.05 | chnD |
| ATOM | 4786 | O | VAL | D | 97 | 63.648 | 20.042 | 58.185 | 1.00 | 83.27 | chnD |
| ATOM | 4787 | N | MET | D | 98 | 61.748 | 21.133 | 57.657 | 1.00 | 85.63 | chnD |
| ATOM | 4788 | CA | MET | D | 98 | 60.984 | 19.921 | 57.423 | 1.00 | 87.74 | chnD |
| ATOM | 4789 | CB | MET | D | 98 | 59.504 | 20.200 | 57.666 | 1.00 | 91.12 | chnD |
| ATOM | 4790 | CG | MET | D | 98 | 58.863 | 19.265 | 58.672 | 1.00 | 93.97 | chnD |
| ATOM | 4791 | SD | MET | D | 98 | 57.419 | 20.022 | 59.454 | 1.00 | 98.49 | chnD |
| ATOM | 4792 | CE | MET | D | 98 | 57.925 | 19.982 | 61.192 | 1.00 | 96.59 | chnD |
| ATOM | 4793 | C | MET | D | 98 | 61.224 | 19.447 | 55.990 | 1.00 | 87.81 | chnD |
| ATOM | 4794 | O | MET | D | 98 | 61.250 | 20.252 | 55.055 | 1.00 | 86.72 | chnD |
| ATOM | 4795 | N | GLU | D | 99 | 61.410 | 18.139 | 55.829 | 1.00 | 88.12 | chnD |
| ATOM | 4796 | CA | GLU | D | 99 | 61.669 | 17.537 | 54.518 | 1.00 | 88.70 | chnD |
| ATOM | 4797 | CB | GLU | D | 99 | 61.781 | 16.006 | 54.649 | 1.00 | 92.66 | chnD |
| ATOM | 4798 | CG | GLU | D | 99 | 62.160 | 15.260 | 53.351 | 1.00 | 96.89 | chnD |
| ATOM | 4799 | CD | GLU | D | 99 | 62.587 | 13.802 | 53.586 | 1.00 | 98.22 | chnD |
| ATOM | 4800 | OE1 | GLU | D | 99 | 61.720 | 12.955 | 53.919 | 1.00 | 99.37 | chnD |
| ATOM | 4801 | OE2 | GLU | D | 99 | 63.796 | 13.505 | 53.429 | 1.00 | 97.98 | chnD |
| ATOM | 4802 | C | GLU | D | 99 | 60.614 | 17.908 | 53.477 | 1.00 | 85.78 | chnD |
| ATOM | 4803 | O | GLU | D | 99 | 59.445 | 17.537 | 53.606 | 1.00 | 84.66 | chnD |
| ATOM | 4804 | N | GLY | D | 100 | 61.023 | 18.671 | 52.469 | 1.00 | 82.38 | chnD |
| ATOM | 4805 | CA | GLY | D | 100 | 60.091 | 19.053 | 51.430 | 1.00 | 81.41 | chnD |
| ATOM | 4806 | C | GLY | D | 100 | 59.971 | 20.547 | 51.218 | 1.00 | 80.51 | chnD |
| ATOM | 4807 | O | GLY | D | 100 | 59.657 | 20.991 | 50.109 | 1.00 | 81.64 | chnD |
| ATOM | 4808 | N | GLN | D | 101 | 60.196 | 21.328 | 52.271 | 1.00 | 78.82 | chnD |
| ATOM | 4809 | CA | GLN | D | 101 | 60.104 | 22.784 | 52.153 | 1.00 | 80.35 | chnD |
| ATOM | 4810 | CB | GLN | D | 101 | 59.519 | 23.393 | 53.434 | 1.00 | 84.00 | chnD |
| ATOM | 4811 | CG | GLN | D | 101 | 60.361 | 23.160 | 54.677 | 1.00 | 90.69 | chnD |
| ATOM | 4812 | CD | GLN | D | 101 | 59.708 | 23.679 | 55.960 | 1.00 | 93.02 | chnD |
| ATOM | 4813 | OE1 | GLN | D | 101 | 58.475 | 23.684 | 56.096 | 1.00 | 94.34 | chnD |
| ATOM | 4814 | NE2 | GLN | D | 101 | 60.540 | 24.103 | 56.916 | 1.00 | 95.27 | chnD |
| ATOM | 4815 | C | GLN | D | 101 | 61.451 | 23.437 | 51.787 | 1.00 | 77.60 | chnD |
| ATOM | 4816 | O | GLN | D | 101 | 62.508 | 22.801 | 51.857 | 1.00 | 73.32 | chnD |
| ATOM | 4817 | N | PRO | D | 102 | 61.420 | 24.709 | 51.346 | 1.00 | 75.43 | chnD |
| ATOM | 4818 | CD | PRO | D | 102 | 60.240 | 25.536 | 51.019 | 1.00 | 75.61 | chnD |
| ATOM | 4819 | CA | PRO | D | 102 | 62.658 | 25.398 | 50.973 | 1.00 | 71.85 | chnD |
| ATOM | 4820 | CB | PRO | D | 102 | 62.145 | 26.622 | 50.210 | 1.00 | 73.54 | chnD |
| ATOM | 4821 | CG | PRO | D | 102 | 60.837 | 26.915 | 50.884 | 1.00 | 73.90 | chnD |
| ATOM | 4822 | C | PRO | D | 102 | 63.561 | 25.797 | 52.130 | 1.00 | 68.22 | chnD |
| ATOM | 4823 | O | PRO | D | 102 | 63.106 | 25.975 | 53.260 | 1.00 | 67.14 | chnD |
| ATOM | 4824 | N | LEU | D | 103 | 64.849 | 25.922 | 51.818 | 1.00 | 64.86 | chnD |
| ATOM | 4825 | CA | LEU | D | 103 | 65.884 | 26.326 | 52.762 | 1.00 | 61.25 | chnD |
| ATOM | 4826 | CB | LEU | D | 103 | 66.758 | 25.130 | 53.139 | 1.00 | 57.61 | chnD |
| ATOM | 4827 | CG | LEU | D | 103 | 67.957 | 25.436 | 54.034 | 1.00 | 56.40 | chnD |
| ATOM | 4828 | CD1 | LEU | D | 103 | 67.521 | 26.204 | 55.275 | 1.00 | 56.47 | chnD |
| ATOM | 4829 | CD2 | LEU | D | 103 | 68.641 | 24.138 | 54.413 | 1.00 | 55.17 | chnD |
| ATOM | 4830 | C | LEU | D | 103 | 66.738 | 27.403 | 52.088 | 1.00 | 60.12 | chnD |
| ATOM | 4831 | O | LEU | D | 103 | 67.283 | 27.186 | 51.008 | 1.00 | 58.20 | chnD |
| ATOM | 4832 | N | PHE | D | 104 | 66.845 | 28.566 | 52.721 | 1.00 | 57.99 | chnD |
| ATOM | 4833 | CA | PHE | D | 104 | 67.623 | 29.659 | 52.158 | 1.00 | 56.74 | chnD |
| ATOM | 4834 | CB | PHE | D | 104 | 66.725 | 30.873 | 51.914 | 1.00 | 62.91 | chnD |
| ATOM | 4835 | CG | PHE | D | 104 | 65.571 | 30.602 | 50.994 | 1.00 | 68.08 | chnD |
| ATOM | 4836 | CD1 | PHE | D | 104 | 64.279 | 30.459 | 51.500 | 1.00 | 69.75 | chnD |
| ATOM | 4837 | CD2 | PHE | D | 104 | 65.771 | 30.495 | 49.619 | 1.00 | 70.89 | chnD |
| ATOM | 4838 | CE1 | PHE | D | 104 | 63.198 | 30.214 | 50.644 | 1.00 | 71.76 | chnD |
| ATOM | 4839 | CE2 | PHE | D | 104 | 64.698 | 30.251 | 48.752 | 1.00 | 74.04 | chnD |
| ATOM | 4840 | CZ | PHE | D | 104 | 63.410 | 30.110 | 49.265 | 1.00 | 73.31 | chnD |
| ATOM | 4841 | C | PHE | D | 104 | 68.789 | 30.058 | 53.055 | 1.00 | 52.63 | chnD |
| ATOM | 4842 | O | PHE | D | 104 | 68.618 | 30.278 | 54.252 | 1.00 | 49.86 | chnD |
| ATOM | 4843 | N | LEU | D | 105 | 69.981 | 30.114 | 52.473 | 1.00 | 48.65 | chnD |
| ATOM | 4844 | CA | LEU | D | 105 | 71.175 | 30.512 | 53.205 | 1.00 | 44.20 | chnD |
| ATOM | 4845 | CB | LEU | D | 105 | 72.210 | 29.403 | 53.214 | 1.00 | 43.16 | chnD |
| ATOM | 4846 | CG | LEU | D | 105 | 71.744 | 28.071 | 53.777 | 1.00 | 42.26 | chnD |
| ATOM | 4847 | CD1 | LEU | D | 105 | 72.932 | 27.150 | 53.920 | 1.00 | 44.84 | chnD |

-continued

| | | | | | | | | | | |
|---|---|---|---|---|---|---|---|---|---|---|
| ATOM | 4848 | CD2 | LEU | D | 105 | 71.110 | 28.298 | 55.114 | 1.00 | 42.23 | chnD |
| ATOM | 4849 | C | LEU | D | 105 | 71.745 | 31.741 | 52.535 | 1.00 | 42.13 | chnD |
| ATOM | 4850 | O | LEU | D | 105 | 71.723 | 31.850 | 51.316 | 1.00 | 42.48 | chnD |
| ATOM | 4851 | N | ARG | D | 106 | 72.306 | 32.634 | 53.334 | 1.00 | 39.13 | chnD |
| ATOM | 4852 | CA | ARG | D | 106 | 72.837 | 33.888 | 52.834 | 1.00 | 40.30 | chnD |
| ATOM | 4853 | CB | ARG | D | 106 | 71.774 | 34.965 | 53.066 | 1.00 | 40.40 | chnD |
| ATOM | 4854 | CG | ARG | D | 106 | 72.176 | 36.378 | 52.747 | 1.00 | 43.42 | chnD |
| ATOM | 4855 | CD | ARG | D | 106 | 71.088 | 37.350 | 53.185 | 1.00 | 42.88 | chnD |
| ATOM | 4856 | NE | ARG | D | 106 | 71.464 | 38.730 | 52.893 | 1.00 | 46.09 | chnD |
| ATOM | 4857 | CZ | ARG | D | 106 | 71.066 | 39.789 | 53.591 | 1.00 | 46.27 | chnD |
| ATOM | 4858 | NH1 | ARG | D | 106 | 70.266 | 39.631 | 54.636 | 1.00 | 46.19 | chnD |
| ATOM | 4859 | NH2 | ARG | D | 106 | 71.480 | 41.007 | 53.245 | 1.00 | 45.94 | chnD |
| ATOM | 4860 | C | ARG | D | 106 | 74.131 | 34.246 | 53.558 | 1.00 | 39.58 | chnD |
| ATOM | 4861 | O | ARG | D | 106 | 74.164 | 34.307 | 54.788 | 1.00 | 41.68 | chnD |
| ATOM | 4862 | N | CYS | D | 107 | 75.200 | 34.466 | 52.797 | 1.00 | 37.93 | chnD |
| ATOM | 4863 | CA | CYS | D | 107 | 76.486 | 34.813 | 53.384 | 1.00 | 37.04 | chnD |
| ATOM | 4864 | C | CYS | D | 107 | 76.545 | 36.317 | 53.509 | 1.00 | 35.83 | chnD |
| ATOM | 4865 | O | CYS | D | 107 | 77.192 | 36.979 | 52.706 | 1.00 | 36.80 | chnD |
| ATOM | 4866 | CB | CYS | D | 107 | 77.611 | 34.304 | 52.502 | 1.00 | 35.87 | chnD |
| ATOM | 4867 | SG | CYS | D | 107 | 79.258 | 34.423 | 53.244 | 1.00 | 39.78 | chnD |
| ATOM | 4868 | N | HIS | D | 108 | 75.856 | 36.825 | 54.534 | 1.00 | 35.87 | chnD |
| ATOM | 4869 | CA | HIS | D | 108 | 75.719 | 38.254 | 54.848 | 1.00 | 39.74 | chnD |
| ATOM | 4870 | CB | HIS | D | 108 | 74.632 | 38.421 | 55.906 | 1.00 | 40.99 | chnD |
| ATOM | 4871 | CG | HIS | D | 108 | 74.195 | 39.832 | 56.109 | 1.00 | 43.57 | chnD |
| ATOM | 4872 | CD2 | HIS | D | 108 | 73.777 | 40.484 | 57.217 | 1.00 | 45.47 | chnD |
| ATOM | 4873 | ND1 | HIS | D | 108 | 74.151 | 40.747 | 55.082 | 1.00 | 46.26 | chnD |
| ATOM | 4874 | CE1 | HIS | D | 108 | 73.723 | 41.907 | 55.550 | 1.00 | 49.79 | chnD |
| ATOM | 4875 | NE2 | HIS | D | 108 | 73.489 | 41.774 | 56.843 | 1.00 | 49.38 | chnD |
| ATOM | 4876 | C | HIS | D | 108 | 76.976 | 38.980 | 55.313 | 1.00 | 40.52 | chnD |
| ATOM | 4877 | O | HIS | D | 108 | 77.668 | 38.531 | 56.225 | 1.00 | 41.78 | chnD |
| ATOM | 4878 | N | GLY | D | 109 | 77.228 | 40.141 | 54.719 | 1.00 | 40.11 | chnD |
| ATOM | 4879 | CA | GLY | D | 109 | 78.397 | 40.917 | 55.089 | 1.00 | 38.74 | chnD |
| ATOM | 4880 | C | GLY | D | 109 | 78.048 | 42.052 | 56.031 | 1.00 | 41.34 | chnD |
| ATOM | 4881 | O | GLY | D | 109 | 76.952 | 42.614 | 55.965 | 1.00 | 40.76 | chnD |
| ATOM | 4882 | N | TRP | D | 110 | 78.969 | 42.383 | 56.926 | 1.00 | 40.42 | chnD |
| ATOM | 4883 | CA | TRP | D | 110 | 78.756 | 43.466 | 57.877 | 1.00 | 40.70 | chnD |
| ATOM | 4884 | CB | TRP | D | 110 | 80.016 | 43.676 | 58.700 | 1.00 | 42.23 | chnD |
| ATOM | 4885 | CG | TRP | D | 110 | 79.947 | 44.794 | 59.640 | 1.00 | 43.38 | chnD |
| ATOM | 4886 | CD2 | TRP | D | 110 | 79.367 | 44.781 | 60.941 | 1.00 | 45.86 | chnD |
| ATOM | 4887 | CE2 | TRP | D | 110 | 79.582 | 46.051 | 61.505 | 1.00 | 46.43 | chnD |
| ATOM | 4888 | CE3 | TRP | D | 110 | 78.687 | 43.816 | 61.689 | 1.00 | 47.93 | chnD |
| ATOM | 4889 | CD1 | TRP | D | 110 | 80.466 | 46.033 | 59.463 | 1.00 | 44.90 | chnD |
| ATOM | 4890 | NE1 | TRP | D | 110 | 80.257 | 46.799 | 60.581 | 1.00 | 47.60 | chnD |
| ATOM | 4891 | CZ2 | TRP | D | 110 | 79.144 | 46.386 | 62.783 | 1.00 | 48.66 | chnD |
| ATOM | 4892 | CZ3 | TRP | D | 110 | 78.251 | 44.147 | 62.963 | 1.00 | 50.52 | chnD |
| ATOM | 4893 | CH2 | TRP | D | 110 | 78.482 | 45.425 | 63.497 | 1.00 | 49.79 | chnD |
| ATOM | 4894 | C | TRP | D | 110 | 78.374 | 44.755 | 57.164 | 1.00 | 40.22 | chnD |
| ATOM | 4895 | O | TRP | D | 110 | 79.037 | 45.162 | 56.204 | 1.00 | 39.15 | chnD |
| ATOM | 4896 | N | ARG | D | 111 | 77.284 | 45.370 | 57.623 | 1.00 | 41.92 | chnD |
| ATOM | 4897 | CA | ARG | D | 111 | 76.768 | 46.619 | 57.057 | 1.00 | 43.27 | chnD |
| ATOM | 4898 | CB | ARG | D | 111 | 77.781 | 47.751 | 57.212 | 1.00 | 44.21 | chnD |
| ATOM | 4899 | CG | ARG | D | 111 | 77.951 | 48.242 | 58.608 | 1.00 | 49.03 | chnD |
| ATOM | 4900 | CD | ARG | D | 111 | 78.853 | 49.444 | 58.627 | 1.00 | 52.65 | chnD |
| ATOM | 4901 | NE | ARG | D | 111 | 78.799 | 50.133 | 59.910 | 1.00 | 58.35 | chnD |
| ATOM | 4902 | CZ | ARG | D | 111 | 78.284 | 51.343 | 60.084 | 1.00 | 62.65 | chnD |
| ATOM | 4903 | NH1 | ARG | D | 111 | 77.779 | 52.006 | 59.053 | 1.00 | 66.02 | chnD |
| ATOM | 4904 | NH2 | ARG | D | 111 | 78.259 | 51.882 | 61.293 | 1.00 | 67.13 | chnD |
| ATOM | 4905 | C | ARG | D | 111 | 76.423 | 46.481 | 55.586 | 1.00 | 42.85 | chnD |
| ATOM | 4906 | O | ARG | D | 111 | 76.447 | 47.468 | 54.848 | 1.00 | 42.30 | chnD |
| ATOM | 4907 | N | ASN | D | 112 | 76.125 | 45.254 | 55.163 | 1.00 | 42.67 | chnD |
| ATOM | 4908 | CA | ASN | D | 112 | 75.781 | 44.966 | 53.774 | 1.00 | 44.67 | chnD |
| ATOM | 4909 | CB | ASN | D | 112 | 74.563 | 45.764 | 53.319 | 1.00 | 48.06 | chnD |
| ATOM | 4910 | CG | ASN | D | 112 | 73.296 | 44.974 | 53.425 | 1.00 | 54.54 | chnD |
| ATOM | 4911 | OD1 | ASN | D | 112 | 73.063 | 44.054 | 52.638 | 1.00 | 56.76 | chnD |
| ATOM | 4912 | ND2 | ASN | D | 112 | 72.471 | 45.303 | 54.422 | 1.00 | 58.34 | chnD |
| ATOM | 4913 | C | ASN | D | 112 | 76.907 | 45.199 | 52.791 | 1.00 | 44.43 | chnD |
| ATOM | 4914 | O | ASN | D | 112 | 76.680 | 45.123 | 51.579 | 1.00 | 46.69 | chnD |
| ATOM | 4915 | N | TRP | D | 113 | 78.097 | 45.513 | 53.300 | 1.00 | 39.27 | chnD |
| ATOM | 4916 | CA | TRP | D | 113 | 79.252 | 45.729 | 52.449 | 1.00 | 40.11 | chnD |
| ATOM | 4917 | CB | TRP | D | 113 | 80.484 | 45.869 | 53.319 | 1.00 | 40.10 | chnD |
| ATOM | 4918 | CG | TRP | D | 113 | 80.593 | 47.175 | 53.987 | 1.00 | 42.15 | chnD |
| ATOM | 4919 | CD2 | TRP | D | 113 | 81.441 | 47.496 | 55.088 | 1.00 | 42.65 | chnD |
| ATOM | 4920 | CE2 | TRP | D | 113 | 81.270 | 48.871 | 55.359 | 1.00 | 43.24 | chnD |
| ATOM | 4921 | CE3 | TRP | D | 113 | 82.334 | 46.755 | 55.872 | 1.00 | 41.92 | chnD |
| ATOM | 4922 | CD1 | TRP | D | 113 | 79.951 | 48.328 | 53.646 | 1.00 | 42.71 | chnD |
| ATOM | 4923 | NE1 | TRP | D | 113 | 80.353 | 49.354 | 54.465 | 1.00 | 44.30 | chnD |
| ATOM | 4924 | CZ2 | TRP | D | 113 | 81.958 | 49.523 | 56.381 | 1.00 | 43.23 | chnD |
| ATOM | 4925 | CZ3 | TRP | D | 113 | 83.021 | 47.403 | 56.892 | 1.00 | 43.28 | chnD |
| ATOM | 4926 | CH2 | TRP | D | 113 | 82.828 | 48.776 | 57.135 | 1.00 | 43.36 | chnD |

-continued

| ATOM | 4927 | C | TRP | D | 113 | 79.440 | 44.565 | 51.456 | 1.00 | 45.40 | chnD |
| --- | --- | --- | --- | --- | --- | --- | --- | --- | --- | --- | --- |
| ATOM | 4928 | O | TRP | D | 113 | 79.235 | 43.399 | 51.806 | 1.00 | 49.18 | chnD |
| ATOM | 4929 | N | ASP | D | 114 | 79.831 | 44.885 | 50.222 | 1.00 | 46.70 | chnD |
| ATOM | 4930 | CA | ASP | D | 114 | 80.015 | 43.879 | 49.172 | 1.00 | 44.31 | chnD |
| ATOM | 4931 | CB | ASP | D | 114 | 80.395 | 44.552 | 47.842 | 1.00 | 48.38 | chnD |
| ATOM | 4932 | CG | ASP | D | 114 | 79.263 | 45.401 | 47.257 | 1.00 | 50.12 | chnD |
| ATOM | 4933 | OD1 | ASP | D | 114 | 78.094 | 44.959 | 47.297 | 1.00 | 52.12 | chnD |
| ATOM | 4934 | OD2 | ASP | D | 114 | 79.547 | 46.510 | 46.746 | 1.00 | 51.72 | chnD |
| ATOM | 4935 | C | ASP | D | 114 | 81.028 | 42.793 | 49.511 | 1.00 | 44.33 | chnD |
| ATOM | 4936 | O | ASP | D | 114 | 82.161 | 43.082 | 49.895 | 1.00 | 42.46 | chnD |
| ATOM | 4937 | N | VAL | D | 115 | 80.600 | 41.544 | 49.367 | 1.00 | 42.09 | chnD |
| ATOM | 4938 | CA | VAL | D | 115 | 81.435 | 40.378 | 49.637 | 1.00 | 43.21 | chnD |
| ATOM | 4939 | CB | VAL | D | 115 | 80.691 | 39.366 | 50.533 | 1.00 | 42.81 | chnD |
| ATOM | 4940 | CG1 | VAL | D | 115 | 81.559 | 38.161 | 50.796 | 1.00 | 43.34 | chnD |
| ATOM | 4941 | CG2 | VAL | D | 115 | 80.275 | 40.004 | 51.831 | 1.00 | 43.63 | chnD |
| ATOM | 4942 | C | VAL | D | 115 | 81.704 | 39.684 | 48.309 | 1.00 | 44.85 | chnD |
| ATOM | 4943 | O | VAL | D | 115 | 80.778 | 39.449 | 47.538 | 1.00 | 44.01 | chnD |
| ATOM | 4944 | N | TYR | D | 116 | 82.962 | 39.359 | 48.038 | 1.00 | 45.05 | chnD |
| ATOM | 4945 | CA | TYR | D | 116 | 83.312 | 38.676 | 46.797 | 1.00 | 46.21 | chnD |
| ATOM | 4946 | CB | TYR | D | 116 | 84.301 | 39.510 | 45.977 | 1.00 | 53.47 | chnD |
| ATOM | 4947 | CG | TYR | D | 116 | 83.789 | 40.876 | 45.551 | 1.00 | 58.37 | chnD |
| ATOM | 4948 | CD1 | TYR | D | 116 | 84.459 | 42.037 | 45.922 | 1.00 | 60.42 | chnD |
| ATOM | 4949 | CE1 | TYR | D | 116 | 84.004 | 43.290 | 45.538 | 1.00 | 61.54 | chnD |
| ATOM | 4950 | CD2 | TYR | D | 116 | 82.643 | 41.008 | 44.780 | 1.00 | 59.57 | chnD |
| ATOM | 4951 | CE2 | TYR | D | 116 | 82.179 | 42.263 | 44.393 | 1.00 | 61.48 | chnD |
| ATOM | 4952 | CZ | TYR | D | 116 | 82.868 | 43.396 | 44.780 | 1.00 | 61.75 | chnD |
| ATOM | 4953 | OH | TYR | D | 116 | 82.422 | 44.645 | 44.422 | 1.00 | 64.44 | chnD |
| ATOM | 4954 | C | TYR | D | 116 | 83.910 | 37.306 | 47.101 | 1.00 | 43.56 | chnD |
| ATOM | 4955 | O | TYR | D | 116 | 84.166 | 36.977 | 48.259 | 1.00 | 44.90 | chnD |
| ATOM | 4956 | N | LYS | D | 117 | 84.116 | 36.503 | 46.063 | 1.00 | 41.19 | chnD |
| ATOM | 4957 | CA | LYS | D | 117 | 84.690 | 35.169 | 46.219 | 1.00 | 45.66 | chnD |
| ATOM | 4958 | CB | LYS | D | 117 | 86.182 | 35.261 | 46.580 | 1.00 | 53.14 | chnD |
| ATOM | 4959 | CG | LYS | D | 117 | 87.022 | 36.229 | 45.733 | 1.00 | 57.80 | chnD |
| ATOM | 4960 | CD | LYS | D | 117 | 87.357 | 35.677 | 44.355 | 1.00 | 63.62 | chnD |
| ATOM | 4961 | CE | LYS | D | 117 | 88.403 | 36.530 | 43.636 | 1.00 | 64.23 | chnD |
| ATOM | 4962 | NZ | LYS | D | 117 | 89.725 | 36.554 | 44.335 | 1.00 | 69.54 | chnD |
| ATOM | 4963 | C | LYS | D | 117 | 83.958 | 34.395 | 47.313 | 1.00 | 43.37 | chnD |
| ATOM | 4964 | O | LYS | D | 117 | 84.585 | 33.843 | 48.221 | 1.00 | 43.84 | chnD |
| ATOM | 4965 | N | VAL | D | 118 | 82.631 | 34.396 | 47.243 | 1.00 | 42.04 | chnD |
| ATOM | 4966 | CA | VAL | D | 118 | 81.804 | 33.711 | 48.230 | 1.00 | 42.86 | chnD |
| ATOM | 4967 | CB | VAL | D | 118 | 80.362 | 34.215 | 48.195 | 1.00 | 40.60 | chnD |
| ATOM | 4968 | CG1 | VAL | D | 118 | 79.593 | 33.661 | 49.362 | 1.00 | 43.74 | chnD |
| ATOM | 4969 | CG2 | VAL | D | 118 | 80.333 | 35.722 | 48.207 | 1.00 | 43.88 | chnD |
| ATOM | 4970 | C | VAL | D | 118 | 81.769 | 32.211 | 48.026 | 1.00 | 42.68 | chnD |
| ATOM | 4971 | O | VAL | D | 118 | 81.535 | 31.738 | 46.927 | 1.00 | 45.91 | chnD |
| ATOM | 4972 | N | ILE | D | 119 | 81.992 | 31.463 | 49.096 | 1.00 | 42.06 | chnD |
| ATOM | 4973 | CA | ILE | D | 119 | 81.969 | 30.008 | 49.027 | 1.00 | 42.92 | chnD |
| ATOM | 4974 | CB | ILE | D | 119 | 83.374 | 29.399 | 49.148 | 1.00 | 41.31 | chnD |
| ATOM | 4975 | CG2 | ILE | D | 119 | 83.314 | 27.915 | 48.898 | 1.00 | 37.39 | chnD |
| ATOM | 4976 | CG1 | ILE | D | 119 | 84.323 | 30.033 | 48.146 | 1.00 | 42.31 | chnD |
| ATOM | 4977 | CD1 | ILE | D | 119 | 85.744 | 29.565 | 48.297 | 1.00 | 49.87 | chnD |
| ATOM | 4978 | C | ILE | D | 119 | 81.147 | 29.464 | 50.183 | 1.00 | 44.89 | chnD |
| ATOM | 4979 | O | ILE | D | 119 | 81.384 | 29.825 | 51.332 | 1.00 | 49.98 | chnD |
| ATOM | 4980 | N | TYR | D | 120 | 80.170 | 28.615 | 49.885 | 1.00 | 41.33 | chnD |
| ATOM | 5027 | CB | GLU | D | 125 | 82.367 | 19.387 | 51.369 | 1.00 | 77.92 | chnD |
| ATOM | 5028 | CG | GLU | D | 125 | 83.144 | 18.105 | 51.592 | 1.00 | 88.53 | chnD |
| ATOM | 5029 | CD | GLU | D | 125 | 82.454 | 16.900 | 50.971 | 1.00 | 93.03 | chnD |
| ATOM | 5030 | OE1 | GLU | D | 125 | 81.773 | 16.154 | 51.714 | 1.00 | 97.09 | chnD |
| ATOM | 5031 | OE2 | GLU | D | 125 | 82.581 | 16.709 | 49.740 | 1.00 | 95.70 | chnD |
| ATOM | 5032 | C | GLU | D | 125 | 82.449 | 21.853 | 51.248 | 1.00 | 64.90 | chnD |
| ATOM | 5033 | O | GLU | D | 125 | 81.330 | 22.247 | 51.571 | 1.00 | 63.59 | chnD |
| ATOM | 5034 | N | ALA | D | 126 | 83.190 | 22.442 | 50.317 | 1.00 | 59.69 | chnD |
| ATOM | 5035 | CA | ALA | D | 126 | 82.731 | 23.618 | 49.587 | 1.00 | 58.23 | chnD |
| ATOM | 5036 | CB | ALA | D | 126 | 83.915 | 24.362 | 48.997 | 1.00 | 59.58 | chnD |
| ATOM | 5037 | C | ALA | D | 126 | 81.815 | 23.149 | 48.475 | 1.00 | 56.77 | chnD |
| ATOM | 5038 | O | ALA | D | 126 | 82.247 | 22.413 | 47.596 | 1.00 | 56.12 | chnD |
| ATOM | 5039 | N | LEU | D | 127 | 80.556 | 23.567 | 48.504 | 1.00 | 57.34 | chnD |
| ATOM | 5040 | CA | LEU | D | 127 | 79.626 | 23.134 | 47.473 | 1.00 | 60.61 | chnD |
| ATOM | 5041 | CB | LEU | D | 127 | 78.394 | 22.452 | 48.073 | 1.00 | 62.06 | chnD |
| ATOM | 5042 | CG | LEU | D | 127 | 77.626 | 23.107 | 49.208 | 1.00 | 62.47 | chnD |
| ATOM | 5043 | CD1 | LEU | D | 127 | 76.249 | 22.488 | 49.281 | 1.00 | 65.44 | chnD |
| ATOM | 5044 | CD2 | LEU | D | 127 | 78.365 | 22.912 | 50.513 | 1.00 | 64.51 | chnD |
| ATOM | 5045 | C | LEU | D | 127 | 79.215 | 24.152 | 46.423 | 1.00 | 60.79 | chnD |
| ATOM | 5046 | O | LEU | D | 127 | 78.623 | 23.779 | 45.414 | 1.00 | 64.76 | chnD |
| ATOM | 5047 | N | LYS | D | 128 | 79.521 | 25.426 | 46.645 | 1.00 | 61.02 | chnD |
| ATOM | 5048 | CA | LYS | D | 128 | 79.196 | 26.470 | 45.671 | 1.00 | 61.91 | chnD |
| ATOM | 5049 | CB | LYS | D | 128 | 77.716 | 26.844 | 45.735 | 1.00 | 65.16 | chnD |
| ATOM | 5050 | CG | LYS | D | 128 | 76.857 | 25.966 | 44.834 | 1.00 | 71.74 | chnD |
| ATOM | 5051 | CD | LYS | D | 128 | 75.378 | 26.246 | 44.981 | 1.00 | 74.92 | chnD |

-continued

| | | | | | | | | | | |
|---|---|---|---|---|---|---|---|---|---|---|
| ATOM | 5052 | CE | LYS | D | 128 | 74.556 | 25.305 | 44.103 | 1.00 | 77.65 | chnD |
| ATOM | 5053 | NZ | LYS | D | 128 | 74.705 | 23.871 | 44.503 | 1.00 | 79.29 | chnD |
| ATOM | 5054 | C | LYS | D | 128 | 80.083 | 27.709 | 45.756 | 1.00 | 60.81 | chnD |
| ATOM | 5055 | O | LYS | D | 128 | 80.441 | 28.153 | 46.842 | 1.00 | 62.76 | chnD |
| ATOM | 5056 | N | TYR | D | 129 | 80.409 | 28.270 | 44.592 | 1.00 | 60.79 | chnD |
| ATOM | 5057 | CA | TYR | D | 129 | 81.279 | 29.442 | 44.483 | 1.00 | 60.39 | chnD |
| ATOM | 5058 | CB | TYR | D | 129 | 82.646 | 28.996 | 43.986 | 1.00 | 59.55 | chnD |
| ATOM | 5059 | CG | TYR | D | 129 | 83.674 | 30.086 | 43.864 | 1.00 | 60.74 | chnD |
| ATOM | 5060 | CD1 | TYR | D | 129 | 84.747 | 30.132 | 44.736 | 1.00 | 62.74 | chnD |
| ATOM | 5061 | CE1 | TYR | D | 129 | 85.754 | 31.068 | 44.594 | 1.00 | 63.78 | chnD |
| ATOM | 5062 | CD2 | TYR | D | 129 | 83.623 | 31.024 | 42.835 | 1.00 | 61.88 | chnD |
| ATOM | 5063 | CE2 | TYR | D | 129 | 84.629 | 31.973 | 42.680 | 1.00 | 64.79 | chnD |
| ATOM | 5064 | CZ | TYR | D | 129 | 85.696 | 31.979 | 43.566 | 1.00 | 65.04 | chnD |
| ATOM | 5065 | OH | TYR | D | 129 | 86.745 | 32.851 | 43.411 | 1.00 | 67.30 | chnD |
| ATOM | 5066 | C | TYR | D | 129 | 80.748 | 30.505 | 43.527 | 1.00 | 60.89 | chnD |
| ATOM | 5067 | O | TYR | D | 129 | 80.466 | 30.218 | 42.363 | 1.00 | 64.32 | chnD |
| ATOM | 5068 | N | TRP | D | 130 | 80.736 | 31.751 | 43.997 | 1.00 | 62.00 | chnD |
| ATOM | 5069 | CA | TRP | D | 130 | 80.273 | 32.904 | 43.217 | 1.00 | 63.57 | chnD |
| ATOM | 5070 | CB | TRP | D | 130 | 78.831 | 33.263 | 43.595 | 1.00 | 65.38 | chnD |
| ATOM | 5071 | CG | TRP | D | 130 | 77.782 | 32.355 | 43.030 | 1.00 | 68.22 | chnD |
| ATOM | 5072 | CD2 | TRP | D | 130 | 76.942 | 31.463 | 43.763 | 1.00 | 68.38 | chnD |
| ATOM | 5073 | CE2 | TRP | D | 130 | 76.086 | 30.837 | 42.835 | 1.00 | 70.75 | chnD |
| ATOM | 5074 | CE3 | TRP | D | 130 | 76.827 | 31.133 | 45.118 | 1.00 | 68.95 | chnD |
| ATOM | 5075 | CD1 | TRP | D | 130 | 77.414 | 32.237 | 41.717 | 1.00 | 70.65 | chnD |
| ATOM | 5076 | NE1 | TRP | D | 130 | 76.394 | 31.327 | 41.593 | 1.00 | 71.89 | chnD |
| ATOM | 5077 | CZ2 | TRP | D | 130 | 75.128 | 29.899 | 43.219 | 1.00 | 72.04 | chnD |
| ATOM | 5078 | CZ3 | TRP | D | 130 | 75.876 | 30.203 | 45.501 | 1.00 | 69.66 | chnD |
| ATOM | 5079 | CH2 | TRP | D | 130 | 75.037 | 29.597 | 44.555 | 1.00 | 71.31 | chnD |
| ATOM | 5080 | C | TRP | D | 130 | 81.152 | 34.139 | 43.440 | 1.00 | 63.36 | chnD |
| ATOM | 5081 | O | TRP | D | 130 | 81.337 | 34.564 | 44.577 | 1.00 | 66.96 | chnD |
| ATOM | 5082 | N | TYR | D | 131 | 81.670 | 34.728 | 42.362 | 1.00 | 64.47 | chnD |
| ATOM | 5083 | CA | TYR | D | 131 | 82.504 | 35.929 | 42.466 | 1.00 | 66.79 | chnD |
| ATOM | 5084 | CB | TYR | D | 131 | 82.949 | 36.400 | 41.072 | 1.00 | 68.99 | chnD |
| ATOM | 5085 | CG | TYR | D | 131 | 83.655 | 37.740 | 41.076 | 1.00 | 71.26 | chnD |
| ATOM | 5086 | CD1 | TYR | D | 131 | 85.031 | 37.821 | 41.258 | 1.00 | 72.11 | chnD |
| ATOM | 5087 | CE1 | TYR | D | 131 | 85.674 | 39.059 | 41.341 | 1.00 | 74.47 | chnD |
| ATOM | 5088 | CD2 | TYR | D | 131 | 82.932 | 38.936 | 40.964 | 1.00 | 72.09 | chnD |
| ATOM | 5089 | CE2 | TYR | D | 131 | 83.562 | 40.176 | 41.044 | 1.00 | 72.41 | chnD |
| ATOM | 5090 | CZ | TYR | D | 131 | 84.934 | 40.233 | 41.238 | 1.00 | 74.04 | chnD |
| ATOM | 5091 | OH | TYR | D | 131 | 85.565 | 41.455 | 41.362 | 1.00 | 75.07 | chnD |
| ATOM | 5092 | C | TYR | D | 131 | 81.737 | 37.044 | 43.192 | 1.00 | 66.28 | chnD |
| ATOM | 5093 | O | TYR | D | 131 | 82.219 | 37.595 | 44.173 | 1.00 | 66.03 | chnD |
| ATOM | 5094 | N | GLU | D | 132 | 80.557 | 37.380 | 42.678 | 1.00 | 66.71 | chnD |
| ATOM | 5095 | CA | GLU | D | 132 | 79.679 | 38.397 | 43.261 | 1.00 | 68.76 | chnD |
| ATOM | 5096 | CB | GLU | D | 132 | 78.797 | 39.019 | 42.173 | 1.00 | 71.88 | chnD |
| ATOM | 5097 | CG | GLU | D | 132 | 79.515 | 39.891 | 41.147 | 1.00 | 74.96 | chnD |
| ATOM | 5098 | CD | GLU | D | 132 | 79.462 | 41.376 | 41.479 | 1.00 | 76.71 | chnD |
| ATOM | 5099 | OE1 | GLU | D | 132 | 80.402 | 42.096 | 41.087 | 1.00 | 78.63 | chnD |
| ATOM | 5100 | OE2 | GLU | D | 132 | 78.481 | 41.832 | 42.108 | 1.00 | 78.79 | chnD |
| ATOM | 5101 | C | GLU | D | 132 | 78.773 | 37.677 | 44.259 | 1.00 | 69.40 | chnD |
| ATOM | 5102 | O | GLU | D | 132 | 78.228 | 36.616 | 43.937 | 1.00 | 68.99 | chnD |
| ATOM | 5103 | N | ASN | D | 133 | 78.564 | 38.270 | 45.434 | 1.00 | 68.43 | chnD |
| ATOM | 5104 | CA | ASN | D | 133 | 77.729 | 37.646 | 46.461 | 1.00 | 67.33 | chnD |
| ATOM | 5105 | CB | ASN | D | 133 | 77.535 | 38.573 | 47.668 | 1.00 | 69.23 | chnD |
| ATOM | 5106 | CG | ASN | D | 133 | 76.868 | 37.868 | 48.865 | 1.00 | 69.87 | chnD |
| ATOM | 5107 | OD1 | ASN | D | 133 | 76.421 | 36.720 | 48.771 | 1.00 | 67.54 | chnD |
| ATOM | 5108 | ND2 | ASN | D | 133 | 76.807 | 38.566 | 49.996 | 1.00 | 71.16 | chnD |
| ATOM | 5109 | C | ASN | D | 133 | 76.377 | 37.210 | 45.915 | 1.00 | 65.90 | chnD |
| ATOM | 5110 | O | ASN | D | 133 | 75.591 | 38.025 | 45.432 | 1.00 | 66.54 | chnD |
| ATOM | 5111 | N | HIS | D | 134 | 76.140 | 35.904 | 45.984 | 1.00 | 65.44 | chnD |
| ATOM | 5112 | CA | HIS | D | 134 | 74.909 | 35.289 | 45.515 | 1.00 | 66.24 | chnD |
| ATOM | 5113 | CB | HIS | D | 134 | 75.175 | 34.517 | 44.214 | 1.00 | 73.15 | chnD |
| ATOM | 5114 | CG | HIS | D | 134 | 73.945 | 33.919 | 43.591 | 1.00 | 79.64 | chnD |
| ATOM | 5115 | CD2 | HIS | D | 134 | 72.939 | 34.485 | 42.881 | 1.00 | 81.17 | chnD |
| ATOM | 5116 | ND1 | HIS | D | 134 | 73.655 | 32.573 | 43.658 | 1.00 | 81.55 | chnD |
| ATOM | 5117 | CE1 | HIS | D | 134 | 72.523 | 32.333 | 43.016 | 1.00 | 82.97 | chnD |
| ATOM | 5118 | NE2 | HIS | D | 134 | 72.070 | 33.476 | 42.536 | 1.00 | 83.86 | chnD |
| ATOM | 5119 | C | HIS | D | 134 | 74.400 | 34.352 | 46.604 | 1.00 | 63.45 | chnD |
| ATOM | 5120 | O | HIS | D | 134 | 75.164 | 33.615 | 47.211 | 1.00 | 61.68 | chnD |
| ATOM | 5121 | N | ASN | D | 135 | 73.105 | 34.432 | 46.873 | 1.00 | 63.99 | chnD |
| ATOM | 5122 | CA | ASN | D | 135 | 72.437 | 33.611 | 47.877 | 1.00 | 65.34 | chnD |
| ATOM | 5123 | CB | ASN | D | 135 | 70.999 | 34.105 | 48.028 | 1.00 | 69.74 | chnD |
| ATOM | 5124 | CG | ASN | D | 135 | 70.744 | 34.754 | 49.352 | 1.00 | 71.24 | chnD |
| ATOM | 5125 | OD1 | ASN | D | 135 | 71.079 | 35.915 | 49.569 | 1.00 | 73.12 | chnD |
| ATOM | 5126 | ND2 | ASN | D | 135 | 70.126 | 34.012 | 50.251 | 1.00 | 77.39 | chnD |
| ATOM | 5127 | C | ASN | D | 135 | 72.396 | 32.152 | 47.428 | 1.00 | 65.50 | chnD |
| ATOM | 5128 | O | ASN | D | 135 | 72.377 | 31.871 | 46.227 | 1.00 | 69.64 | chnD |
| ATOM | 5129 | N | ILE | D | 136 | 72.391 | 31.223 | 48.378 | 1.00 | 61.84 | chnD |
| ATOM | 5130 | CA | ILE | D | 136 | 72.300 | 29.803 | 48.040 | 1.00 | 59.87 | chnD |

-continued

| | | | | | | | | | | |
|---|---|---|---|---|---|---|---|---|---|---|
| ATOM | 5131 | CB | ILE | D | 136 | 73.362 | 28.966 | 48.763 | 1.00 | 57.55 | chnD |
| ATOM | 5132 | CG2 | ILE | D | 136 | 73.184 | 29.048 | 50.230 | 1.00 | 58.92 | chnD |
| ATOM | 5133 | CG1 | ILE | D | 136 | 73.270 | 27.510 | 48.346 | 1.00 | 56.80 | chnD |
| ATOM | 5134 | CD1 | ILE | D | 136 | 74.329 | 26.648 | 48.987 | 1.00 | 57.04 | chnD |
| ATOM | 5135 | C | ILE | D | 136 | 70.888 | 29.355 | 48.416 | 1.00 | 61.07 | chnD |
| ATOM | 5136 | O | ILE | D | 136 | 70.390 | 29.683 | 49.492 | 1.00 | 60.06 | chnD |
| ATOM | 5137 | N | SER | D | 137 | 70.224 | 28.646 | 47.509 | 1.00 | 65.52 | chnD |
| ATOM | 5138 | CA | SER | D | 137 | 68.853 | 28.213 | 47.748 | 1.00 | 68.92 | chnD |
| ATOM | 5139 | CB | SER | D | 137 | 67.902 | 29.057 | 46.897 | 1.00 | 68.78 | chnD |
| ATOM | 5140 | OG | SER | D | 137 | 66.580 | 28.556 | 46.973 | 1.00 | 73.08 | chnD |
| ATOM | 5141 | C | SER | D | 137 | 68.581 | 26.732 | 47.495 | 1.00 | 70.53 | chnD |
| ATOM | 5142 | O | SER | D | 137 | 68.724 | 26.242 | 46.370 | 1.00 | 71.20 | chnD |
| ATOM | 5143 | N | ILE | D | 138 | 68.160 | 26.035 | 48.548 | 1.00 | 71.87 | chnD |
| ATOM | 5144 | CA | ILE | D | 138 | 67.832 | 24.617 | 48.460 | 1.00 | 73.18 | chnD |
| ATOM | 5145 | CB | ILE | D | 138 | 68.282 | 23.857 | 49.719 | 1.00 | 71.88 | chnD |
| ATOM | 5146 | CG2 | ILE | D | 138 | 67.842 | 22.410 | 49.640 | 1.00 | 71.22 | chnD |
| ATOM | 5147 | CG1 | ILE | D | 138 | 69.804 | 23.924 | 49.850 | 1.00 | 72.39 | chnD |
| ATOM | 5148 | CD1 | ILE | D | 138 | 70.355 | 23.205 | 51.070 | 1.00 | 74.42 | chnD |
| ATOM | 5149 | C | ILE | D | 138 | 66.322 | 24.494 | 48.296 | 1.00 | 76.40 | chnD |
| ATOM | 5150 | O | ILE | D | 138 | 65.577 | 24.606 | 49.269 | 1.00 | 78.68 | chnD |
| ATOM | 5151 | N | THR | D | 139 | 65.884 | 24.269 | 47.059 | 1.00 | 80.57 | chnD |
| ATOM | 5152 | CA | THR | D | 139 | 64.456 | 24.155 | 46.726 | 1.00 | 84.35 | chnD |
| ATOM | 5153 | CB | THR | D | 139 | 64.235 | 23.927 | 45.198 | 1.00 | 86.02 | chnD |
| ATOM | 5154 | OG1 | THR | D | 139 | 64.944 | 22.750 | 44.773 | 1.00 | 86.96 | chnD |
| ATOM | 5155 | CG2 | THR | D | 139 | 64.716 | 25.151 | 44.390 | 1.00 | 86.47 | chnD |
| ATOM | 5156 | C | THR | D | 139 | 63.684 | 23.087 | 47.502 | 1.00 | 83.46 | chnD |
| ATOM | 5157 | O | THR | D | 139 | 62.682 | 23.388 | 48.152 | 1.00 | 83.14 | chnD |
| ATOM | 5158 | N | ASN | D | 140 | 64.138 | 21.842 | 47.420 | 1.00 | 81.90 | chnD |
| ATOM | 5159 | CA | ASN | D | 140 | 63.480 | 20.748 | 48.124 | 1.00 | 79.89 | chnD |
| ATOM | 5160 | CB | ASN | D | 140 | 63.134 | 19.634 | 47.133 | 1.00 | 82.12 | chnD |
| ATOM | 5161 | CG | ASN | D | 140 | 62.295 | 18.528 | 47.758 | 1.00 | 82.72 | chnD |
| ATOM | 5162 | OD1 | ASN | D | 140 | 62.001 | 18.550 | 48.962 | 1.00 | 83.99 | chnD |
| ATOM | 5163 | ND2 | ASN | D | 140 | 61.910 | 17.555 | 46.930 | 1.00 | 80.79 | chnD |
| ATOM | 5164 | C | ASN | D | 140 | 64.417 | 20.227 | 49.211 | 1.00 | 78.57 | chnD |
| ATOM | 5165 | O | ASN | D | 140 | 65.343 | 19.452 | 48.929 | 1.00 | 77.72 | chnD |
| ATOM | 5166 | N | ALA | D | 141 | 64.180 | 20.648 | 50.450 | 1.00 | 74.62 | chnD |
| ATOM | 5167 | CA | ALA | D | 141 | 65.036 | 20.227 | 51.555 | 1.00 | 74.33 | chnD |
| ATOM | 5168 | CB | ALA | D | 141 | 64.695 | 20.989 | 52.813 | 1.00 | 73.81 | chnD |
| ATOM | 5169 | C | ALA | D | 141 | 65.004 | 18.724 | 51.813 | 1.00 | 74.78 | chnD |
| ATOM | 5170 | O | ALA | D | 141 | 63.937 | 18.121 | 51.966 | 1.00 | 74.99 | chnD |
| ATOM | 5171 | N | THR | D | 142 | 66.190 | 18.131 | 51.863 | 1.00 | 75.17 | chnD |
| ATOM | 5172 | CA | THR | D | 142 | 66.339 | 16.700 | 52.087 | 1.00 | 76.01 | chnD |
| ATOM | 5173 | CB | THR | D | 142 | 67.094 | 16.046 | 50.902 | 1.00 | 76.98 | chnD |
| ATOM | 5174 | OG1 | THR | D | 142 | 66.366 | 16.288 | 49.688 | 1.00 | 78.65 | chnD |
| ATOM | 5175 | CG2 | THR | D | 142 | 67.266 | 14.533 | 51.111 | 1.00 | 76.34 | chnD |
| ATOM | 5176 | C | THR | D | 142 | 67.118 | 16.473 | 53.371 | 1.00 | 74.65 | chnD |
| ATOM | 5177 | O | THR | D | 142 | 67.876 | 17.340 | 53.798 | 1.00 | 72.62 | chnD |
| ATOM | 5178 | N | VAL | D | 143 | 66.905 | 15.317 | 53.994 | 1.00 | 76.12 | chnD |
| ATOM | 5179 | CA | VAL | D | 143 | 67.593 | 14.967 | 55.234 | 1.00 | 79.91 | chnD |
| ATOM | 5180 | CB | VAL | D | 143 | 67.095 | 13.590 | 55.791 | 1.00 | 81.70 | chnD |
| ATOM | 5181 | CG1 | VAL | D | 143 | 67.384 | 12.463 | 54.799 | 1.00 | 83.08 | chnD |
| ATOM | 5182 | CG2 | VAL | D | 143 | 67.732 | 13.289 | 57.152 | 1.00 | 83.29 | chnD |
| ATOM | 5183 | C | VAL | D | 143 | 69.106 | 14.944 | 54.992 | 1.00 | 80.33 | chnD |
| ATOM | 5184 | O | VAL | D | 143 | 69.909 | 15.103 | 55.920 | 1.00 | 79.18 | chnD |
| ATOM | 5185 | N | GLU | D | 144 | 69.485 | 14.764 | 53.730 | 1.00 | 82.40 | chnD |
| ATOM | 5186 | CA | GLU | D | 144 | 70.893 | 14.740 | 53.351 | 1.00 | 84.64 | chnD |
| ATOM | 5187 | CB | GLU | D | 144 | 71.044 | 14.300 | 51.895 | 1.00 | 90.21 | chnD |
| ATOM | 5188 | CG | GLU | D | 144 | 70.590 | 12.863 | 51.613 | 1.00 | 99.47 | chnD |
| ATOM | 5189 | CD | GLU | D | 144 | 70.616 | 12.523 | 50.117 | 1.00 | 103.69 | chnD |
| ATOM | 5190 | OE1 | GLU | D | 144 | 71.731 | 12.405 | 49.540 | 1.00 | 105.57 | chnD |
| ATOM | 5191 | OE2 | GLU | D | 144 | 69.518 | 12.384 | 49.520 | 1.00 | 106.30 | chnD |
| ATOM | 5192 | C | GLU | D | 144 | 71.480 | 16.134 | 53.521 | 1.00 | 81.65 | chnD |
| ATOM | 5193 | O | GLU | D | 144 | 72.654 | 16.289 | 53.866 | 1.00 | 81.30 | chnD |
| ATOM | 5194 | N | ASP | D | 145 | 70.639 | 17.141 | 53.296 | 1.00 | 76.78 | chnD |
| ATOM | 5195 | CA | ASP | D | 145 | 71.038 | 18.537 | 53.421 | 1.00 | 72.19 | chnD |
| ATOM | 5196 | CB | ASP | D | 145 | 69.955 | 19.449 | 52.842 | 1.00 | 73.78 | chnD |
| ATOM | 5197 | CG | ASP | D | 145 | 69.811 | 19.298 | 51.340 | 1.00 | 75.73 | chnD |
| ATOM | 5198 | OD1 | ASP | D | 145 | 70.850 | 19.137 | 50.657 | 1.00 | 76.16 | chnD |
| ATOM | 5199 | OD2 | ASP | D | 145 | 68.664 | 19.343 | 50.841 | 1.00 | 76.53 | chnD |
| ATOM | 5200 | C | ASP | D | 145 | 71.377 | 18.966 | 54.847 | 1.00 | 69.39 | chnD |
| ATOM | 5201 | O | ASP | D | 145 | 71.739 | 20.116 | 55.075 | 1.00 | 67.04 | chnD |
| ATOM | 5202 | N | SER | D | 146 | 71.263 | 18.041 | 55.799 | 1.00 | 68.69 | chnD |
| ATOM | 5203 | CA | SER | D | 146 | 71.576 | 18.334 | 57.198 | 1.00 | 69.39 | chnD |
| ATOM | 5204 | CB | SER | D | 146 | 70.957 | 17.279 | 58.121 | 1.00 | 69.99 | chnD |
| ATOM | 5205 | OG | SER | D | 146 | 69.543 | 17.246 | 57.980 | 1.00 | 71.10 | chnD |
| ATOM | 5206 | C | SER | D | 146 | 73.086 | 18.371 | 57.410 | 1.00 | 68.75 | chnD |
| ATOM | 5207 | O | SER | D | 146 | 73.828 | 17.601 | 56.798 | 1.00 | 69.55 | chnD |
| ATOM | 5208 | N | GLY | D | 147 | 73.536 | 19.272 | 58.276 | 1.00 | 67.62 | chnD |
| ATOM | 5209 | CA | GLY | D | 147 | 74.954 | 19.387 | 58.549 | 1.00 | 65.94 | chnD |

-continued

| ATOM | 5210 | C | GLY | D | 147 | 75.334 | 20.790 | 58.964 | 1.00 | 65.75 | chnD |
| ATOM | 5211 | O | GLY | D | 147 | 74.475 | 21.673 | 59.036 | 1.00 | 66.48 | chnD |
| ATOM | 5212 | N | THR | D | 148 | 76.620 | 20.997 | 59.241 | 1.00 | 63.24 | chnD |
| ATOM | 5213 | CA | THR | D | 148 | 77.115 | 22.309 | 59.654 | 1.00 | 62.34 | chnD |
| ATOM | 5214 | CB | THR | D | 148 | 78.296 | 22.203 | 60.675 | 1.00 | 63.80 | chnD |
| ATOM | 5215 | OG1 | THR | D | 148 | 79.524 | 21.941 | 59.989 | 1.00 | 70.59 | chnD |
| ATOM | 5216 | CG2 | THR | D | 148 | 78.059 | 21.065 | 61.657 | 1.00 | 65.50 | chnD |
| ATOM | 5217 | C | THR | D | 148 | 77.545 | 23.121 | 58.433 | 1.00 | 58.99 | chnD |
| ATOM | 5218 | O | THR | D | 148 | 78.426 | 22.717 | 57.676 | 1.00 | 58.19 | chnD |
| ATOM | 5219 | N | TYR | D | 149 | 76.883 | 24.249 | 58.224 | 1.00 | 55.46 | chnD |
| ATOM | 5220 | CA | TYR | D | 149 | 77.194 | 25.115 | 57.099 | 1.00 | 52.31 | chnD |
| ATOM | 5221 | CB | TYR | D | 149 | 75.912 | 25.569 | 56.415 | 1.00 | 52.81 | chnD |
| ATOM | 5222 | CG | TYR | D | 149 | 75.165 | 24.513 | 55.645 | 1.00 | 55.28 | chnD |
| ATOM | 5223 | CD1 | TYR | D | 149 | 74.330 | 23.602 | 56.292 | 1.00 | 56.22 | chnD |
| ATOM | 5224 | CE1 | TYR | D | 149 | 73.568 | 22.690 | 55.568 | 1.00 | 59.16 | chnD |
| ATOM | 5225 | CD2 | TYR | D | 149 | 75.227 | 24.479 | 54.255 | 1.00 | 56.13 | chnD |
| ATOM | 5226 | CE2 | TYR | D | 149 | 74.471 | 23.576 | 53.523 | 1.00 | 59.43 | chnD |
| ATOM | 5227 | CZ | TYR | D | 149 | 73.643 | 22.686 | 54.181 | 1.00 | 60.32 | chnD |
| ATOM | 5228 | OH | TYR | D | 149 | 72.886 | 21.808 | 53.438 | 1.00 | 63.03 | chnD |
| ATOM | 5229 | C | TYR | D | 149 | 77.945 | 26.362 | 57.531 | 1.00 | 51.25 | chnD |
| ATOM | 5230 | O | TYR | D | 149 | 77.789 | 26.837 | 58.655 | 1.00 | 52.49 | chnD |
| ATOM | 5231 | N | TYR | D | 150 | 78.762 | 26.885 | 56.626 | 1.00 | 46.69 | chnD |
| ATOM | 5232 | CA | TYR | D | 150 | 79.500 | 28.122 | 56.865 | 1.00 | 45.57 | chnD |
| ATOM | 5233 | CB | TYR | D | 150 | 80.643 | 27.938 | 57.871 | 1.00 | 48.04 | chnD |
| ATOM | 5234 | CG | TYR | D | 150 | 81.843 | 27.190 | 57.371 | 1.00 | 50.57 | chnD |
| ATOM | 5235 | CD1 | TYR | D | 150 | 82.941 | 27.873 | 56.863 | 1.00 | 50.53 | chnD |
| ATOM | 5236 | CE1 | TYR | D | 150 | 84.068 | 27.195 | 56.429 | 1.00 | 53.67 | chnD |
| ATOM | 5237 | CD2 | TYR | D | 150 | 81.898 | 25.803 | 57.435 | 1.00 | 53.93 | chnD |
| ATOM | 5238 | CE2 | TYR | D | 150 | 83.022 | 25.112 | 57.009 | 1.00 | 56.50 | chnD |
| ATOM | 5239 | CZ | TYR | D | 150 | 84.105 | 25.815 | 56.504 | 1.00 | 55.45 | chnD |
| ATOM | 5240 | OH | TYR | D | 150 | 85.219 | 25.138 | 56.059 | 1.00 | 55.99 | chnD |
| ATOM | 5241 | C | TYR | D | 150 | 79.984 | 28.663 | 55.526 | 1.00 | 44.06 | chnD |
| ATOM | 5242 | O | TYR | D | 150 | 79.947 | 27.954 | 54.528 | 1.00 | 45.65 | chnD |
| ATOM | 5243 | N | CYS | D | 151 | 80.390 | 29.925 | 55.492 | 1.00 | 40.47 | chnD |
| ATOM | 5244 | CA | CYS | D | 151 | 80.836 | 30.529 | 54.248 | 1.00 | 37.53 | chnD |
| ATOM | 5245 | C | CYS | D | 151 | 82.055 | 31.389 | 54.437 | 1.00 | 36.68 | chnD |
| ATOM | 5246 | O | CYS | D | 151 | 82.310 | 31.866 | 55.529 | 1.00 | 38.84 | chnD |
| ATOM | 5247 | CB | CYS | D | 151 | 79.727 | 31.399 | 53.650 | 1.00 | 38.52 | chnD |
| ATOM | 5248 | SG | CYS | D | 151 | 79.359 | 32.910 | 54.605 | 1.00 | 45.05 | chnD |
| ATOM | 5249 | N | THR | D | 152 | 82.803 | 31.584 | 53.355 | 1.00 | 34.26 | chnD |
| ATOM | 5250 | CA | THR | D | 152 | 83.993 | 32.427 | 53.360 | 1.00 | 35.47 | chnD |
| ATOM | 5251 | CB | THR | D | 152 | 85.257 | 31.633 | 53.043 | 1.00 | 34.92 | chnD |
| ATOM | 5252 | OG1 | THR | D | 152 | 85.137 | 31.036 | 51.751 | 1.00 | 38.18 | chnD |
| ATOM | 5253 | CG2 | THR | D | 152 | 85.471 | 30.554 | 54.072 | 1.00 | 39.97 | chnD |
| ATOM | 5254 | C | THR | D | 152 | 83.815 | 33.496 | 52.292 | 1.00 | 35.34 | chnD |
| ATOM | 5255 | O | THR | D | 152 | 83.199 | 33.253 | 51.266 | 1.00 | 37.09 | chnD |
| ATOM | 5256 | N | GLY | D | 153 | 84.350 | 34.680 | 52.528 | 1.00 | 37.55 | chnD |
| ATOM | 5257 | CA | GLY | D | 153 | 84.198 | 35.725 | 51.544 | 1.00 | 37.51 | chnD |
| ATOM | 5258 | C | GLY | D | 153 | 85.338 | 36.707 | 51.575 | 1.00 | 39.69 | chnD |
| ATOM | 5259 | O | GLY | D | 153 | 86.282 | 36.568 | 52.356 | 1.00 | 40.79 | chnD |
| ATOM | 5260 | N | LYS | D | 154 | 85.250 | 37.699 | 50.706 | 1.00 | 39.53 | chnD |
| ATOM | 5261 | CA | LYS | D | 154 | 86.269 | 38.720 | 50.619 | 1.00 | 43.09 | chnD |
| ATOM | 5262 | CB | LYS | D | 154 | 86.974 | 38.621 | 49.244 | 1.00 | 48.34 | chnD |
| ATOM | 5263 | CG | LYS | D | 154 | 88.505 | 38.911 | 49.204 | 1.00 | 52.52 | chnD |
| ATOM | 5264 | CD | LYS | D | 154 | 89.031 | 39.258 | 47.773 | 1.00 | 54.54 | chnD |
| ATOM | 5265 | CE | LYS | D | 154 | 88.515 | 40.643 | 47.253 | 1.00 | 57.71 | chnD |
| ATOM | 5266 | NZ | LYS | D | 154 | 88.793 | 40.961 | 45.807 | 1.00 | 52.12 | chnD |
| ATOM | 5267 | C | LYS | D | 154 | 85.531 | 40.061 | 50.804 | 1.00 | 43.96 | chnD |
| ATOM | 5268 | O | LYS | D | 154 | 84.762 | 40.502 | 49.940 | 1.00 | 43.26 | chnD |
| ATOM | 5269 | N | VAL | D | 155 | 85.634 | 40.624 | 52.002 | 1.00 | 44.79 | chnD |
| ATOM | 5270 | CA | VAL | D | 155 | 85.005 | 41.913 | 52.277 | 1.00 | 42.98 | chnD |
| ATOM | 5271 | CB | VAL | D | 155 | 84.415 | 41.994 | 53.688 | 1.00 | 40.47 | chnD |
| ATOM | 5272 | CG1 | VAL | D | 155 | 83.691 | 43.307 | 53.871 | 1.00 | 36.96 | chnD |
| ATOM | 5273 | CG2 | VAL | D | 155 | 83.454 | 40.851 | 53.902 | 1.00 | 39.08 | chnD |
| ATOM | 5274 | C | VAL | D | 155 | 86.149 | 42.894 | 52.075 | 1.00 | 45.02 | chnD |
| ATOM | 5275 | O | VAL | D | 155 | 87.228 | 42.735 | 52.648 | 1.00 | 42.42 | chnD |
| ATOM | 5276 | N | TRP | D | 156 | 85.902 | 43.893 | 51.233 | 1.00 | 47.81 | chnD |
| ATOM | 5277 | CA | TRP | D | 156 | 86.918 | 44.861 | 50.835 | 1.00 | 48.47 | chnD |
| ATOM | 5278 | CB | TRP | D | 156 | 87.445 | 45.687 | 52.016 | 1.00 | 44.14 | chnD |
| ATOM | 5279 | CG | TRP | D | 156 | 86.340 | 46.610 | 52.515 | 1.00 | 43.81 | chnD |
| ATOM | 5280 | CD2 | TRP | D | 156 | 85.685 | 47.660 | 51.773 | 1.00 | 41.00 | chnD |
| ATOM | 5281 | CE2 | TRP | D | 156 | 84.570 | 48.078 | 52.531 | 1.00 | 39.69 | chnD |
| ATOM | 5282 | CE3 | TRP | D | 156 | 85.917 | 48.263 | 50.530 | 1.00 | 40.58 | chnD |
| ATOM | 5283 | CD1 | TRP | D | 156 | 85.629 | 46.479 | 53.673 | 1.00 | 43.99 | chnD |
| ATOM | 5284 | NE1 | TRP | D | 156 | 84.559 | 47.347 | 53.686 | 1.00 | 40.62 | chnD |
| ATOM | 5285 | CZ2 | TRP | D | 156 | 83.700 | 49.067 | 52.092 | 1.00 | 37.67 | chnD |
| ATOM | 5286 | CZ3 | TRP | D | 156 | 85.049 | 49.246 | 50.094 | 1.00 | 37.52 | chnD |
| ATOM | 5287 | CH2 | TRP | D | 156 | 83.953 | 49.634 | 50.870 | 1.00 | 39.14 | chnD |
| ATOM | 5288 | C | TRP | D | 156 | 87.952 | 43.994 | 50.115 | 1.00 | 52.25 | chnD |

-continued

| | | | | | | | | | | |
|---|---|---|---|---|---|---|---|---|---|---|
| ATOM | 5289 | O | TRP | D | 156 | 87.573 | 43.258 | 49.189 | 1.00 | 57.82 | chnD |
| ATOM | 5290 | N | GLN | D | 157 | 89.218 | 44.003 | 50.499 | 1.00 | 50.95 | chnD |
| ATOM | 5291 | CA | GLN | D | 157 | 90.127 | 43.132 | 49.761 | 1.00 | 53.98 | chnD |
| ATOM | 5292 | CB | GLN | D | 157 | 91.307 | 43.922 | 49.178 | 1.00 | 59.09 | chnD |
| ATOM | 5293 | CG | GLN | D | 157 | 90.944 | 45.169 | 48.367 | 1.00 | 63.10 | chnD |
| ATOM | 5294 | CD | GLN | D | 157 | 90.453 | 44.888 | 46.962 | 1.00 | 62.23 | chnD |
| ATOM | 5295 | OE1 | GLN | D | 157 | 91.236 | 44.872 | 46.018 | 1.00 | 64.63 | chnD |
| ATOM | 5296 | NE2 | GLN | D | 157 | 89.147 | 44.724 | 46.808 | 1.00 | 63.60 | chnD |
| ATOM | 5297 | C | GLN | D | 157 | 90.637 | 42.006 | 50.640 | 1.00 | 52.97 | chnD |
| ATOM | 5298 | O | GLN | D | 157 | 91.433 | 41.189 | 50.199 | 1.00 | 55.84 | chnD |
| ATOM | 5299 | N | LEU | D | 158 | 90.128 | 41.931 | 51.864 | 1.00 | 51.61 | chnD |
| ATOM | 5300 | CA | LEU | D | 158 | 90.574 | 40.925 | 52.819 | 1.00 | 51.78 | chnD |
| ATOM | 5301 | CB | LEU | D | 158 | 90.802 | 41.587 | 54.174 | 1.00 | 56.14 | chnD |
| ATOM | 5302 | CG | LEU | D | 158 | 91.700 | 42.825 | 54.093 | 1.00 | 58.84 | chnD |
| ATOM | 5303 | CD1 | LEU | D | 158 | 91.553 | 43.700 | 55.314 | 1.00 | 61.27 | chnD |
| ATOM | 5304 | CD2 | LEU | D | 158 | 93.138 | 42.397 | 53.901 | 1.00 | 62.61 | chnD |
| ATOM | 5305 | C | LEU | D | 158 | 89.663 | 39.711 | 52.952 | 1.00 | 51.03 | chnD |
| ATOM | 5306 | O | LEU | D | 158 | 88.471 | 39.781 | 52.645 | 1.00 | 48.08 | chnD |
| ATOM | 5307 | N | ASP | D | 159 | 90.254 | 38.603 | 53.408 | 1.00 | 53.46 | chnD |
| ATOM | 5308 | CA | ASP | D | 159 | 89.569 | 37.316 | 53.590 | 1.00 | 56.31 | chnD |
| ATOM | 5309 | CB | ASP | D | 159 | 90.526 | 36.161 | 53.270 | 1.00 | 60.54 | chnD |
| ATOM | 5310 | CG | ASP | D | 159 | 90.910 | 36.089 | 51.803 | 1.00 | 62.96 | chnD |
| ATOM | 5311 | OD1 | ASP | D | 159 | 90.004 | 36.028 | 50.939 | 1.00 | 64.96 | chnD |
| ATOM | 5312 | OD2 | ASP | D | 159 | 92.128 | 36.055 | 51.522 | 1.00 | 62.59 | chnD |
| ATOM | 5313 | C | ASP | D | 159 | 88.998 | 37.083 | 54.991 | 1.00 | 56.04 | chnD |
| ATOM | 5314 | O | ASP | D | 159 | 89.691 | 37.281 | 55.999 | 1.00 | 57.31 | chnD |
| ATOM | 5315 | N | TYR | D | 160 | 87.770 | 36.562 | 55.041 | 1.00 | 52.33 | chnD |
| ATOM | 5316 | CA | TYR | D | 160 | 87.086 | 36.290 | 56.307 | 1.00 | 50.29 | chnD |
| ATOM | 5317 | CB | TYR | D | 160 | 86.194 | 37.478 | 56.695 | 1.00 | 49.06 | chnD |
| ATOM | 5318 | CG | TYR | D | 160 | 86.928 | 38.787 | 56.862 | 1.00 | 48.42 | chnD |
| ATOM | 5319 | CD1 | TYR | D | 160 | 86.688 | 39.851 | 56.002 | 1.00 | 48.73 | chnD |
| ATOM | 5320 | CE1 | TYR | D | 160 | 87.372 | 41.051 | 56.130 | 1.00 | 48.58 | chnD |
| ATOM | 5321 | CD2 | TYR | D | 160 | 87.873 | 38.954 | 57.862 | 1.00 | 49.22 | chnD |
| ATOM | 5322 | CE2 | TYR | D | 160 | 88.563 | 40.144 | 58.004 | 1.00 | 50.55 | chnD |
| ATOM | 5323 | CZ | TYR | D | 160 | 88.312 | 41.192 | 57.137 | 1.00 | 50.63 | chnD |
| ATOM | 5324 | OH | TYR | D | 160 | 89.001 | 42.377 | 57.283 | 1.00 | 51.03 | chnD |
| ATOM | 5325 | C | TYR | D | 160 | 86.244 | 35.016 | 56.264 | 1.00 | 50.33 | chnD |
| ATOM | 5326 | O | TYR | D | 160 | 85.830 | 34.566 | 55.203 | 1.00 | 48.17 | chnD |
| ATOM | 5327 | N | GLU | D | 161 | 86.000 | 34.443 | 57.435 | 1.00 | 53.12 | chnD |
| ATOM | 5328 | CA | GLU | D | 161 | 85.201 | 33.230 | 57.551 | 1.00 | 53.93 | chnD |
| ATOM | 5329 | CB | GLU | D | 161 | 86.074 | 32.061 | 58.029 | 1.00 | 57.71 | chnD |
| ATOM | 5330 | CG | GLU | D | 161 | 85.411 | 30.698 | 57.896 | 1.00 | 63.75 | chnD |
| ATOM | 5331 | CD | GLU | D | 161 | 86.282 | 29.559 | 58.404 | 1.00 | 67.10 | chnD |
| ATOM | 5332 | OE1 | GLU | D | 161 | 85.751 | 28.676 | 59.130 | 1.00 | 71.09 | chnD |
| ATOM | 5333 | OE2 | GLU | D | 161 | 87.493 | 29.552 | 58.079 | 1.00 | 67.95 | chnD |
| ATOM | 5334 | C | GLU | D | 161 | 84.059 | 33.483 | 58.545 | 1.00 | 54.10 | chnD |
| ATOM | 5335 | O | GLU | D | 161 | 84.206 | 34.271 | 59.482 | 1.00 | 54.87 | chnD |
| ATOM | 5336 | N | SER | D | 162 | 82.915 | 32.843 | 58.314 | 1.00 | 53.23 | chnD |
| ATOM | 5337 | CA | SER | D | 162 | 81.754 | 33.000 | 59.180 | 1.00 | 52.22 | chnD |
| ATOM | 5338 | CB | SER | D | 162 | 80.466 | 33.062 | 58.361 | 1.00 | 51.69 | chnD |
| ATOM | 5339 | OG | SER | D | 162 | 80.139 | 31.795 | 57.824 | 1.00 | 49.37 | chnD |
| ATOM | 5340 | C | SER | D | 162 | 81.634 | 31.869 | 60.179 | 1.00 | 53.48 | chnD |
| ATOM | 5341 | O | SER | D | 162 | 82.152 | 30.777 | 59.969 | 1.00 | 53.47 | chnD |
| ATOM | 5342 | N | GLU | D | 163 | 80.927 | 32.144 | 61.263 | 1.00 | 57.05 | chnD |
| ATOM | 5343 | CA | GLU | D | 163 | 80.710 | 31.160 | 62.296 | 1.00 | 59.60 | chnD |
| ATOM | 5344 | CB | GLU | D | 163 | 79.946 | 31.798 | 63.449 | 1.00 | 68.59 | chnD |
| ATOM | 5345 | CG | GLU | D | 163 | 80.741 | 32.825 | 64.242 | 1.00 | 77.36 | chnD |
| ATOM | 5346 | CD | GLU | D | 163 | 81.868 | 32.187 | 65.032 | 1.00 | 80.47 | chnD |
| ATOM | 5347 | OE1 | GLU | D | 163 | 81.569 | 31.433 | 65.988 | 1.00 | 82.94 | chnD |
| ATOM | 5348 | OE2 | GLU | D | 163 | 83.047 | 32.426 | 64.689 | 1.00 | 82.90 | chnD |
| ATOM | 5349 | C | GLU | D | 163 | 79.866 | 30.075 | 61.681 | 1.00 | 55.90 | chnD |
| ATOM | 5350 | O | GLU | D | 163 | 79.007 | 30.361 | 60.866 | 1.00 | 57.20 | chnD |
| ATOM | 5351 | N | PRO | D | 164 | 80.137 | 28.812 | 62.016 | 1.00 | 52.82 | chnD |
| ATOM | 5352 | CD | PRO | D | 164 | 81.244 | 28.363 | 62.870 | 1.00 | 53.24 | chnD |
| ATOM | 5353 | CA | PRO | D | 164 | 79.388 | 27.667 | 61.494 | 1.00 | 52.68 | chnD |
| ATOM | 5354 | CB | PRO | D | 164 | 80.189 | 26.481 | 62.012 | 1.00 | 53.03 | chnD |
| ATOM | 5355 | CG | PRO | D | 164 | 80.772 | 27.004 | 63.288 | 1.00 | 53.39 | chnD |
| ATOM | 5356 | C | PRO | D | 164 | 77.968 | 27.656 | 62.039 | 1.00 | 53.14 | chnD |
| ATOM | 5357 | O | PRO | D | 164 | 77.714 | 28.207 | 63.106 | 1.00 | 54.95 | chnD |
| ATOM | 5358 | N | LEU | D | 165 | 77.051 | 27.023 | 61.315 | 1.00 | 51.81 | chnD |
| ATOM | 5359 | CA | LEU | D | 165 | 75.659 | 26.963 | 61.736 | 1.00 | 54.17 | chnD |
| ATOM | 5360 | CB | LEU | D | 165 | 74.840 | 28.005 | 60.976 | 1.00 | 52.48 | chnD |
| ATOM | 5361 | CG | LEU | D | 165 | 73.348 | 28.108 | 61.286 | 1.00 | 53.36 | chnD |
| ATOM | 5362 | CD1 | LEU | D | 165 | 73.153 | 28.422 | 62.762 | 1.00 | 55.86 | chnD |
| ATOM | 5363 | CD2 | LEU | D | 165 | 72.717 | 29.181 | 60.418 | 1.00 | 51.49 | chnD |
| ATOM | 5364 | C | LEU | D | 165 | 75.049 | 25.586 | 61.520 | 1.00 | 56.69 | chnD |
| ATOM | 5365 | O | LEU | D | 165 | 75.010 | 25.089 | 60.395 | 1.00 | 57.83 | chnD |
| ATOM | 5366 | N | ASN | D | 166 | 74.550 | 24.986 | 62.601 | 1.00 | 62.77 | chnD |
| ATOM | 5367 | CA | ASN | D | 166 | 73.916 | 23.663 | 62.544 | 1.00 | 66.00 | chnD |

-continued

| ATOM | 5368 | CB | ASN | D | 166 | 73.768 | 23.055 | 63.947 | 1.00 | 73.01 | chnD |
|---|---|---|---|---|---|---|---|---|---|---|---|
| ATOM | 5369 | CG | ASN | D | 166 | 75.061 | 22.456 | 64.481 | 1.00 | 79.48 | chnD |
| ATOM | 5370 | OD1 | ASN | D | 166 | 75.953 | 22.095 | 63.711 | 1.00 | 81.72 | chnD |
| ATOM | 5371 | ND2 | ASN | D | 166 | 75.152 | 22.336 | 65.806 | 1.00 | 83.71 | chnD |
| ATOM | 5372 | C | ASN | D | 166 | 72.533 | 23.717 | 61.905 | 1.00 | 64.72 | chnD |
| ATOM | 5373 | O | ASN | D | 166 | 71.611 | 24.343 | 62.432 | 1.00 | 65.71 | chnD |
| ATOM | 5374 | N | ILE | D | 167 | 72.390 | 23.055 | 60.768 | 1.00 | 63.27 | chnD |
| ATOM | 5375 | CA | ILE | D | 167 | 71.116 | 23.015 | 60.073 | 1.00 | 65.56 | chnD |
| ATOM | 5376 | CB | ILE | D | 167 | 71.223 | 23.618 | 58.662 | 1.00 | 64.30 | chnD |
| ATOM | 5377 | CG2 | ILE | D | 167 | 70.036 | 23.198 | 57.807 | 1.00 | 63.18 | chnD |
| ATOM | 5378 | CG1 | ILE | D | 167 | 71.300 | 25.141 | 58.768 | 1.00 | 65.60 | chnD |
| ATOM | 5379 | CD1 | ILE | D | 167 | 71.218 | 25.848 | 57.444 | 1.00 | 68.72 | chnD |
| ATOM | 5380 | C | ILE | D | 167 | 70.637 | 21.573 | 59.997 | 1.00 | 67.47 | chnD |
| ATOM | 5381 | O | ILE | D | 167 | 71.331 | 20.698 | 59.475 | 1.00 | 66.04 | chnD |
| ATOM | 5382 | N | THR | D | 168 | 69.448 | 21.326 | 60.535 | 1.00 | 71.17 | chnD |
| ATOM | 5383 | CA | THR | D | 168 | 68.891 | 19.981 | 60.538 | 1.00 | 72.90 | chnD |
| ATOM | 5384 | CB | THR | D | 168 | 68.634 | 19.486 | 61.976 | 1.00 | 72.90 | chnD |
| ATOM | 5385 | OG1 | THR | D | 168 | 69.829 | 19.635 | 62.754 | 1.00 | 72.00 | chnD |
| ATOM | 5386 | CG2 | THR | D | 168 | 68.239 | 18.018 | 61.970 | 1.00 | 72.11 | chnD |
| ATOM | 5387 | C | THR | D | 168 | 67.596 | 19.899 | 59.742 | 1.00 | 75.20 | chnD |
| ATOM | 5388 | O | THR | D | 168 | 66.735 | 20.779 | 59.840 | 1.00 | 71.49 | chnD |
| ATOM | 5389 | N | VAL | D | 169 | 67.488 | 18.842 | 58.937 | 1.00 | 78.84 | chnD |
| ATOM | 5390 | CA | VAL | D | 169 | 66.315 | 18.597 | 58.106 | 1.00 | 84.11 | chnD |
| ATOM | 5391 | CB | VAL | D | 169 | 66.673 | 18.517 | 56.601 | 1.00 | 82.35 | chnD |
| ATOM | 5392 | CG1 | VAL | D | 169 | 65.407 | 18.398 | 55.767 | 1.00 | 81.69 | chnD |
| ATOM | 5393 | CG2 | VAL | D | 169 | 67.461 | 19.734 | 56.172 | 1.00 | 82.34 | chnD |
| ATOM | 5394 | C | VAL | D | 169 | 65.679 | 17.271 | 58.514 | 1.00 | 89.08 | chnD |
| ATOM | 5395 | O | VAL | D | 169 | 66.215 | 16.199 | 58.213 | 1.00 | 89.87 | chnD |
| ATOM | 5396 | N | ILE | D | 170 | 64.549 | 17.361 | 59.217 | 1.00 | 95.47 | chnD |
| ATOM | 5397 | CA | ILE | D | 170 | 63.794 | 16.189 | 59.684 | 1.00 | 98.47 | chnD |
| ATOM | 5398 | CB | ILE | D | 170 | 63.078 | 16.494 | 61.022 | 1.00 | 98.39 | chnD |
| ATOM | 5399 | CG2 | ILE | D | 170 | 64.089 | 16.593 | 62.153 | 1.00 | 98.48 | chnD |
| ATOM | 5400 | CG1 | ILE | D | 170 | 62.254 | 17.782 | 60.892 | 1.00 | 98.36 | chnD |
| ATOM | 5401 | CD1 | ILE | D | 170 | 61.470 | 18.147 | 62.134 | 1.00 | 101.65 | chnD |
| ATOM | 5402 | C | ILE | D | 170 | 62.728 | 15.799 | 58.654 | 1.00 | 100.52 | chnD |
| ATOM | 5403 | O | ILE | D | 170 | 62.731 | 16.296 | 57.524 | 1.00 | 100.58 | chnD |
| ATOM | 5404 | N | LYS | D | 171 | 61.828 | 14.897 | 59.038 | 1.00 | 103.88 | chnD |
| ATOM | 5405 | CA | LYS | D | 171 | 60.744 | 14.484 | 58.146 | 1.00 | 107.19 | chnD |
| ATOM | 5406 | CB | LYS | D | 171 | 60.425 | 13.001 | 58.329 | 1.00 | 108.67 | chnD |
| ATOM | 5407 | CG | LYS | D | 171 | 59.220 | 12.534 | 57.513 | 1.00 | 110.59 | chnD |
| ATOM | 5408 | CD | LYS | D | 171 | 59.194 | 11.022 | 57.393 | 1.00 | 112.62 | chnD |
| ATOM | 5409 | CE | LYS | D | 171 | 60.455 | 10.517 | 56.693 | 1.00 | 113.60 | chnD |
| ATOM | 5410 | NZ | LYS | D | 171 | 60.487 | 9.033 | 56.605 | 1.00 | 115.81 | chnD |
| ATOM | 5411 | C | LYS | D | 171 | 59.470 | 15.322 | 58.358 | 1.00 | 107.00 | chnD |
| ATOM | 5412 | O | LYS | D | 171 | 59.317 | 16.025 | 59.367 | 1.00 | 106.71 | chnD |
| ATOM | 5413 | N | VAL | W | 1 | 115.080 | 14.055 | 32.553 | 1.00 | 94.51 | chnW |
| ATOM | 5414 | CA | VAL | W | 1 | 114.675 | 15.113 | 33.476 | 1.00 | 93.35 | chnW |
| ATOM | 5415 | CB | VAL | W | 1 | 113.978 | 14.535 | 34.727 | 1.00 | 94.27 | chnW |
| ATOM | 5416 | CG1 | VAL | W | 1 | 113.231 | 15.637 | 35.460 | 1.00 | 95.57 | chnW |
| ATOM | 5417 | CG2 | VAL | W | 1 | 113.034 | 13.395 | 34.341 | 1.00 | 95.69 | chnW |
| ATOM | 5418 | C | VAL | W | 1 | 115.900 | 15.892 | 33.934 | 1.00 | 91.68 | chnW |
| ATOM | 5419 | O | VAL | W | 1 | 116.719 | 15.375 | 34.696 | 1.00 | 93.52 | chnW |
| ATOM | 5420 | N | GLN | W | 2 | 116.025 | 17.128 | 33.462 | 1.00 | 89.07 | chnW |
| ATOM | 5421 | CA | GLN | W | 2 | 117.153 | 17.986 | 33.820 | 1.00 | 86.20 | chnW |
| ATOM | 5422 | CB | GLN | W | 2 | 117.411 | 18.992 | 32.687 | 1.00 | 88.19 | chnW |
| ATOM | 5423 | CG | GLN | W | 2 | 118.435 | 20.090 | 32.995 | 1.00 | 91.71 | chnW |
| ATOM | 5424 | CD | GLN | W | 2 | 119.863 | 19.592 | 32.988 | 1.00 | 93.54 | chnW |
| ATOM | 5425 | OE1 | GLN | W | 2 | 120.606 | 19.837 | 32.039 | 1.00 | 95.24 | chnW |
| ATOM | 5426 | NE2 | GLN | W | 2 | 120.261 | 18.894 | 34.050 | 1.00 | 94.21 | chnW |
| ATOM | 5427 | C | GLN | W | 2 | 116.931 | 18.725 | 35.153 | 1.00 | 83.30 | chnW |
| ATOM | 5428 | O | GLN | W | 2 | 115.895 | 19.373 | 35.343 | 1.00 | 84.09 | chnW |
| ATOM | 5429 | N | CYS | W | 3 | 117.906 | 18.618 | 36.062 | 1.00 | 75.09 | chnW |
| ATOM | 5430 | CA | CYS | W | 3 | 117.854 | 19.277 | 37.373 | 1.00 | 68.70 | chnW |
| ATOM | 5431 | C | CYS | W | 3 | 119.039 | 20.241 | 37.544 | 1.00 | 65.35 | chnW |
| ATOM | 5432 | O | CYS | W | 3 | 120.090 | 20.040 | 36.943 | 1.00 | 65.97 | chnW |
| ATOM | 5433 | CB | CYS | W | 3 | 117.872 | 18.229 | 38.486 | 1.00 | 67.08 | chnW |
| ATOM | 5434 | SG | CYS | W | 3 | 116.522 | 17.024 | 38.352 | 1.00 | 65.01 | chnW |
| ATOM | 5435 | N | PRO | W | 4 | 118.877 | 21.310 | 38.353 | 1.00 | 62.24 | chnW |
| ATOM | 5436 | CD | PRO | W | 4 | 117.643 | 21.729 | 39.039 | 1.00 | 60.16 | chnW |
| ATOM | 5437 | CA | PRO | W | 4 | 119.946 | 22.291 | 38.587 | 1.00 | 61.76 | chnW |
| ATOM | 5438 | CB | PRO | W | 4 | 119.325 | 23.218 | 39.629 | 1.00 | 60.02 | chnW |
| ATOM | 5439 | CG | PRO | W | 4 | 117.896 | 23.196 | 39.283 | 1.00 | 59.43 | chnW |
| ATOM | 5440 | C | PRO | W | 4 | 121.231 | 21.654 | 39.120 | 1.00 | 62.65 | chnW |
| ATOM | 5441 | O | PRO | W | 4 | 121.247 | 20.470 | 39.462 | 1.00 | 62.29 | chnW |
| ATOM | 5442 | N | HIS | W | 5 | 122.306 | 22.436 | 39.191 | 1.00 | 64.67 | chnW |
| ATOM | 5443 | CA | HIS | W | 5 | 123.575 | 21.916 | 39.690 | 1.00 | 66.82 | chnW |
| ATOM | 5444 | CB | HIS | W | 5 | 124.722 | 22.915 | 39.461 | 1.00 | 78.01 | chnW |
| ATOM | 5445 | CG | HIS | W | 5 | 125.193 | 23.005 | 38.039 | 1.00 | 87.59 | chnW |
| ATOM | 5446 | CD2 | HIS | W | 5 | 125.019 | 22.170 | 36.981 | 1.00 | 90.47 | chnW |

-continued

| | | | | | | | | | | |
|---|---|---|---|---|---|---|---|---|---|---|
| ATOM | 5447 | ND1 | HIS | W | 5 | 125.939 | 24.065 | 37.567 | 1.00 | 91.21 chnW |
| ATOM | 5448 | CE1 | HIS | W | 5 | 126.203 | 23.885 | 36.282 | 1.00 | 92.25 chnW |
| ATOM | 5449 | NE2 | HIS | W | 5 | 125.656 | 22.742 | 35.904 | 1.00 | 93.01 chnW |
| ATOM | 5450 | C | HIS | W | 5 | 123.491 | 21.580 | 41.176 | 1.00 | 62.83 chnW |
| ATOM | 5451 | O | HIS | W | 5 | 123.741 | 20.444 | 41.578 | 1.00 | 59.39 chnW |
| ATOM | 5452 | N | PHE | W | 6 | 123.067 | 22.557 | 41.975 | 1.00 | 58.56 chnW |
| ATOM | 5453 | CA | PHE | W | 6 | 122.982 | 22.403 | 43.426 | 1.00 | 55.99 chnW |
| ATOM | 5454 | CB | PHE | W | 6 | 122.309 | 23.624 | 44.074 | 1.00 | 56.14 chnW |
| ATOM | 5455 | CG | PHE | W | 6 | 120.817 | 23.707 | 43.849 | 1.00 | 52.93 chnW |
| ATOM | 5456 | CD1 | PHE | W | 6 | 120.292 | 24.567 | 42.892 | 1.00 | 52.08 chnW |
| ATOM | 5457 | CD2 | PHE | W | 6 | 119.940 | 22.950 | 44.616 | 1.00 | 51.40 chnW |
| ATOM | 5458 | CE1 | PHE | W | 6 | 118.917 | 24.668 | 42.707 | 1.00 | 51.13 chnW |
| ATOM | 5459 | CE2 | PHE | W | 6 | 118.572 | 23.046 | 44.436 | 1.00 | 50.82 chnW |
| ATOM | 5460 | CZ | PHE | W | 6 | 118.060 | 23.904 | 43.483 | 1.00 | 50.57 chnW |
| ATOM | 5461 | C | PHE | W | 6 | 122.354 | 21.119 | 43.944 | 1.00 | 55.25 chnW |
| ATOM | 5462 | O | PHE | W | 6 | 122.597 | 20.727 | 45.084 | 1.00 | 56.53 chnW |
| ATOM | 5463 | N | CYS | W | 7 | 121.535 | 20.467 | 43.127 | 1.00 | 54.81 chnW |
| ATOM | 5464 | CA | CYS | W | 7 | 120.908 | 19.228 | 43.564 | 1.00 | 57.39 chnW |
| ATOM | 5465 | C | CYS | W | 7 | 121.983 | 18.198 | 43.887 | 1.00 | 61.62 chnW |
| ATOM | 5466 | O | CYS | W | 7 | 121.802 | 17.346 | 44.753 | 1.00 | 64.36 chnW |
| ATOM | 5467 | CB | CYS | W | 7 | 119.992 | 18.668 | 42.477 | 1.00 | 53.31 chnW |
| ATOM | 5468 | SG | CYS | W | 7 | 118.592 | 19.712 | 41.972 | 1.00 | 45.89 chnW |
| ATOM | 5469 | N | TYR | W | 8 | 123.114 | 18.306 | 43.197 | 1.00 | 66.72 chnW |
| ATOM | 5470 | CA | TYR | W | 8 | 124.226 | 17.376 | 43.370 | 1.00 | 72.10 chnW |
| ATOM | 5471 | CB | TYR | W | 8 | 124.663 | 16.842 | 41.997 | 1.00 | 73.82 chnW |
| ATOM | 5472 | CG | TYR | W | 8 | 123.506 | 16.457 | 41.091 | 1.00 | 74.97 chnW |
| ATOM | 5473 | CD1 | TYR | W | 8 | 123.191 | 17.219 | 39.969 | 1.00 | 74.54 chnW |
| ATOM | 5474 | CE1 | TYR | W | 8 | 122.112 | 16.892 | 39.157 | 1.00 | 74.71 chnW |
| ATOM | 5475 | CD2 | TYR | W | 8 | 122.711 | 15.353 | 41.375 | 1.00 | 75.38 chnW |
| ATOM | 5476 | CE2 | TYR | W | 8 | 121.630 | 15.022 | 40.567 | 1.00 | 75.13 chnW |
| ATOM | 5477 | CZ | TYR | W | 8 | 121.337 | 15.796 | 39.463 | 1.00 | 74.46 chnW |
| ATOM | 5478 | OH | TYR | W | 8 | 120.260 | 15.478 | 38.674 | 1.00 | 75.40 chnW |
| ATOM | 5479 | C | TYR | W | 8 | 125.411 | 18.023 | 44.094 | 1.00 | 73.63 chnW |
| ATOM | 5480 | O | TYR | W | 8 | 126.086 | 17.377 | 44.898 | 1.00 | 75.65 chnW |
| ATOM | 5481 | N | GLU | W | 9 | 125.642 | 19.302 | 43.808 | 1.00 | 76.71 chnW |
| ATOM | 5482 | CA | GLU | W | 9 | 126.726 | 20.073 | 44.410 | 1.00 | 80.22 chnW |
| ATOM | 5483 | CB | GLU | W | 9 | 126.659 | 21.530 | 43.930 | 1.00 | 83.97 chnW |
| ATOM | 5484 | CG | GLU | W | 9 | 126.731 | 21.737 | 42.425 | 1.00 | 89.32 chnW |
| ATOM | 5485 | CD | GLU | W | 9 | 128.099 | 21.424 | 41.845 | 1.00 | 92.49 chnW |
| ATOM | 5486 | OE1 | GLU | W | 9 | 129.113 | 21.785 | 42.490 | 1.00 | 95.37 chnW |
| ATOM | 5487 | OE2 | GLU | W | 9 | 128.161 | 20.821 | 40.743 | 1.00 | 94.26 chnW |
| ATOM | 5488 | C | GLU | W | 9 | 126.703 | 20.077 | 45.946 | 1.00 | 80.19 chnW |
| ATOM | 5489 | O | GLU | W | 9 | 127.664 | 19.665 | 46.593 | 1.00 | 79.62 chnW |
| ATOM | 5490 | N | LEU | W | 10 | 125.602 | 20.564 | 46.513 | 1.00 | 81.09 chnW |
| ATOM | 5491 | CA | LEU | W | 10 | 125.424 | 20.674 | 47.960 | 1.00 | 83.69 chnW |
| ATOM | 5492 | CB | LEU | W | 10 | 124.087 | 21.347 | 48.272 | 1.00 | 84.53 chnW |
| ATOM | 5493 | CG | LEU | W | 10 | 123.992 | 22.874 | 48.175 | 1.00 | 85.13 chnW |
| ATOM | 5494 | CD1 | LEU | W | 10 | 124.686 | 23.428 | 46.925 | 1.00 | 83.50 chnW |
| ATOM | 5495 | CD2 | LEU | W | 10 | 122.520 | 23.251 | 48.211 | 1.00 | 85.74 chnW |
| ATOM | 5496 | C | LEU | W | 10 | 125.524 | 19.376 | 48.740 | 1.00 | 83.72 chnW |
| ATOM | 5497 | O | LEU | W | 10 | 125.490 | 18.291 | 48.163 | 1.00 | 81.72 chnW |
| ATOM | 5498 | N | ASP | W | 11 | 125.638 | 19.504 | 50.061 | 1.00 | 86.86 chnW |
| ATOM | 5499 | CA | ASP | W | 11 | 125.744 | 18.347 | 50.944 | 1.00 | 89.82 chnW |
| ATOM | 5500 | CB | ASP | W | 11 | 126.052 | 18.783 | 52.381 | 0.00 | 91.19 chnW |
| ATOM | 5501 | CG | ASP | W | 11 | 127.419 | 19.435 | 52.519 | 0.00 | 92.15 chnW |
| ATOM | 5502 | OD1 | ASP | W | 11 | 127.547 | 20.369 | 53.336 | 0.00 | 92.62 chnW |
| ATOM | 5503 | OD2 | ASP | W | 11 | 128.367 | 19.012 | 51.822 | 0.00 | 92.96 chnW |
| ATOM | 5504 | C | ASP | W | 11 | 124.449 | 17.544 | 50.909 | 1.00 | 90.70 chnW |
| ATOM | 5505 | O | ASP | W | 11 | 124.424 | 16.413 | 50.417 | 1.00 | 92.41 chnW |
| ATOM | 5506 | N | TYR | W | 12 | 123.375 | 18.145 | 51.415 | 1.00 | 90.20 chnW |
| ATOM | 5507 | CA | TYR | W | 12 | 122.059 | 17.507 | 51.442 | 1.00 | 87.77 chnW |
| ATOM | 5508 | CB | TYR | W | 12 | 121.184 | 18.196 | 52.494 | 1.00 | 92.07 chnW |
| ATOM | 5509 | CG | TYR | W | 12 | 119.824 | 17.569 | 52.713 | 1.00 | 96.85 chnW |
| ATOM | 5510 | CD1 | TYR | W | 12 | 119.702 | 16.253 | 53.164 | 1.00 | 99.17 chnW |
| ATOM | 5511 | CE1 | TYR | W | 12 | 118.444 | 15.682 | 53.404 | 1.00 | 101.45 chnW |
| ATOM | 5512 | CD2 | TYR | W | 12 | 118.658 | 18.302 | 52.503 | 1.00 | 99.02 chnW |
| ATOM | 5513 | CE2 | TYR | W | 12 | 117.400 | 17.742 | 52.739 | 1.00 | 101.65 chnW |
| ATOM | 5514 | CZ | TYR | W | 12 | 117.300 | 16.434 | 53.189 | 1.00 | 101.61 chnW |
| ATOM | 5515 | OH | TYR | W | 12 | 116.059 | 15.882 | 53.418 | 1.00 | 102.16 chnW |
| ATOM | 5516 | C | TYR | W | 12 | 121.411 | 17.599 | 50.054 | 1.00 | 83.85 chnW |
| ATOM | 5517 | O | TYR | W | 12 | 121.746 | 18.485 | 49.255 | 1.00 | 84.49 chnW |
| ATOM | 5518 | N | GLU | W | 13 | 120.523 | 16.658 | 49.753 | 1.00 | 77.41 chnW |
| ATOM | 5519 | CA | GLU | W | 13 | 119.839 | 16.648 | 48.467 | 1.00 | 72.28 chnW |
| ATOM | 5520 | CB | GLU | W | 13 | 119.834 | 15.229 | 47.887 | 1.00 | 74.49 chnW |
| ATOM | 5521 | CG | GLU | W | 13 | 121.227 | 14.657 | 47.618 | 1.00 | 78.85 chnW |
| ATOM | 5522 | CD | GLU | W | 13 | 121.212 | 13.282 | 46.946 | 1.00 | 79.28 chnW |
| ATOM | 5523 | OE1 | GLU | W | 13 | 122.116 | 13.013 | 46.127 | 1.00 | 79.18 chnW |
| ATOM | 5524 | OE2 | GLU | W | 13 | 120.312 | 12.464 | 47.236 | 1.00 | 80.89 chnW |
| ATOM | 5525 | C | GLU | W | 13 | 118.409 | 17.179 | 48.628 | 1.00 | 67.77 chnW |

-continued

| | | | | | | | | | | |
|---|---|---|---|---|---|---|---|---|---|---|
| ATOM | 5526 | O | GLU | W | 13 | 117.499 | 16.433 | 48.988 | 1.00 | 68.90 | chnW |
| ATOM | 5527 | N | LEU | W | 14 | 118.209 | 18.472 | 48.389 | 1.00 | 59.56 | chnW |
| ATOM | 5528 | CA | LEU | W | 14 | 116.873 | 19.035 | 48.535 | 1.00 | 57.57 | chnW |
| ATOM | 5529 | CB | LEU | W | 14 | 116.901 | 20.491 | 49.020 | 1.00 | 57.11 | chnW |
| ATOM | 5530 | CG | LEU | W | 14 | 118.138 | 21.381 | 49.020 | 1.00 | 55.68 | chnW |
| ATOM | 5531 | CD1 | LEU | W | 14 | 118.915 | 21.155 | 50.291 | 1.00 | 54.41 | chnW |
| ATOM | 5532 | CD2 | LEU | W | 14 | 118.982 | 21.133 | 47.782 | 1.00 | 57.16 | chnW |
| ATOM | 5533 | C | LEU | W | 14 | 115.975 | 18.925 | 47.311 | 1.00 | 55.97 | chnW |
| ATOM | 5534 | O | LEU | W | 14 | 114.832 | 19.386 | 47.349 | 1.00 | 53.61 | chnW |
| ATOM | 5535 | N | CYS | W | 15 | 116.483 | 18.325 | 46.233 | 1.00 | 52.87 | chnW |
| ATOM | 5536 | CA | CYS | W | 15 | 115.712 | 18.160 | 44.998 | 1.00 | 49.40 | chnW |
| ATOM | 5537 | C | CYS | W | 15 | 114.910 | 16.870 | 45.015 | 1.00 | 50.61 | chnW |
| ATOM | 5538 | O | CYS | W | 15 | 115.154 | 16.004 | 45.842 | 1.00 | 51.04 | chnW |
| ATOM | 5539 | CB | CYS | W | 15 | 116.639 | 18.206 | 43.790 | 1.00 | 46.84 | chnW |
| ATOM | 5540 | SG | CYS | W | 15 | 117.436 | 19.825 | 43.635 | 1.00 | 48.23 | chnW |
| ATOM | 5541 | N | PRO | W | 16 | 113.915 | 16.739 | 44.123 | 1.00 | 52.48 | chnW |
| ATOM | 5542 | CD | PRO | W | 16 | 113.428 | 17.759 | 43.183 | 1.00 | 54.26 | chnW |
| ATOM | 5543 | CA | PRO | W | 16 | 113.074 | 15.541 | 44.047 | 1.00 | 55.32 | chnW |
| ATOM | 5544 | CB | PRO | W | 16 | 112.089 | 15.890 | 42.933 | 1.00 | 54.39 | chnW |
| ATOM | 5545 | CG | PRO | W | 16 | 111.999 | 17.354 | 43.001 | 1.00 | 53.52 | chnW |
| ATOM | 5546 | C | PRO | W | 16 | 113.840 | 14.264 | 43.703 | 1.00 | 58.35 | chnW |
| ATOM | 5547 | O | PRO | W | 16 | 114.956 | 14.313 | 43.176 | 1.00 | 61.54 | chnW |
| ATOM | 5548 | N | ASP | W | 17 | 113.202 | 13.125 | 43.967 | 1.00 | 59.56 | chnW |
| ATOM | 5549 | CA | ASP | W | 17 | 113.779 | 11.812 | 43.696 | 1.00 | 60.22 | chnW |
| ATOM | 5550 | CB | ASP | W | 17 | 112.841 | 10.711 | 44.212 | 1.00 | 62.81 | chnW |
| ATOM | 5551 | CG | ASP | W | 17 | 112.662 | 10.752 | 45.725 | 1.00 | 65.21 | chnW |
| ATOM | 5552 | OD1 | ASP | W | 17 | 112.153 | 9.763 | 46.292 | 1.00 | 65.68 | chnW |
| ATOM | 5553 | OD2 | ASP | W | 17 | 113.022 | 11.771 | 46.355 | 1.00 | 67.95 | chnW |
| ATOM | 5554 | C | ASP | W | 17 | 114.081 | 11.615 | 42.209 | 1.00 | 59.44 | chnW |
| ATOM | 5555 | O | ASP | W | 17 | 115.100 | 11.034 | 41.847 | 1.00 | 60.28 | chnW |
| ATOM | 5556 | N | VAL | W | 18 | 113.224 | 12.162 | 41.358 | 1.00 | 58.99 | chnW |
| ATOM | 5557 | CA | VAL | W | 18 | 113.386 | 12.066 | 39.916 | 1.00 | 62.77 | chnW |
| ATOM | 5558 | CB | VAL | W | 18 | 112.265 | 12.846 | 39.190 | 1.00 | 63.13 | chnW |
| ATOM | 5559 | CG1 | VAL | W | 18 | 112.458 | 14.338 | 39.363 | 1.00 | 65.01 | chnW |
| ATOM | 5560 | CG2 | VAL | W | 18 | 112.221 | 12.473 | 37.713 | 1.00 | 67.70 | chnW |
| ATOM | 5561 | C | VAL | W | 18 | 114.750 | 12.586 | 39.442 | 1.00 | 63.71 | chnW |
| ATOM | 5562 | O | VAL | W | 18 | 115.160 | 12.335 | 38.307 | 1.00 | 63.56 | chnW |
| ATOM | 5563 | N | CYS | W | 19 | 115.447 | 13.314 | 40.314 | 1.00 | 66.33 | chnW |
| ATOM | 5564 | CA | CYS | W | 19 | 116.760 | 13.868 | 39.983 | 1.00 | 70.52 | chnW |
| ATOM | 5565 | C | CYS | W | 19 | 117.914 | 12.930 | 40.308 | 1.00 | 73.64 | chnW |
| ATOM | 5566 | O | CYS | W | 19 | 118.989 | 13.049 | 39.723 | 1.00 | 76.25 | chnW |
| ATOM | 5567 | CB | CYS | W | 19 | 117.011 | 15.180 | 40.737 | 1.00 | 67.81 | chnW |
| ATOM | 5568 | SG | CYS | W | 19 | 115.989 | 16.606 | 40.268 | 1.00 | 68.74 | chnW |
| ATOM | 5569 | N | TYR | W | 20 | 117.692 | 12.006 | 41.240 | 1.00 | 77.14 | chnW |
| ATOM | 5570 | CA | TYR | W | 20 | 118.744 | 11.094 | 41.683 | 1.00 | 82.36 | chnW |
| ATOM | 5571 | CB | TYR | W | 20 | 118.796 | 11.112 | 43.215 | 1.00 | 80.18 | chnW |
| ATOM | 5572 | CG | TYR | W | 20 | 118.858 | 12.524 | 43.776 | 1.00 | 80.15 | chnW |
| ATOM | 5573 | CD1 | TYR | W | 20 | 117.904 | 12.984 | 44.685 | 1.00 | 79.53 | chnW |
| ATOM | 5574 | CE1 | TYR | W | 20 | 117.947 | 14.292 | 45.173 | 1.00 | 76.67 | chnW |
| ATOM | 5575 | CD2 | TYR | W | 20 | 119.859 | 13.414 | 43.371 | 1.00 | 79.72 | chnW |
| ATOM | 5576 | CE2 | TYR | W | 20 | 119.906 | 14.718 | 43.856 | 1.00 | 76.34 | chnW |
| ATOM | 5577 | CZ | TYR | W | 20 | 118.951 | 15.145 | 44.751 | 1.00 | 75.16 | chnW |
| ATOM | 5578 | OH | TYR | W | 20 | 119.009 | 16.424 | 45.234 | 1.00 | 72.97 | chnW |
| ATOM | 5579 | C | TYR | W | 20 | 118.692 | 9.663 | 41.140 | 1.00 | 87.31 | chnw |
| ATOM | 5580 | O | TYR | W | 20 | 117.633 | 9.172 | 40.743 | 1.00 | 87.00 | chnW |
| ATOM | 5581 | N | VAL | W | 21 | 119.856 | 9.009 | 41.116 | 1.00 | 93.60 | chnW |
| ATOM | 5582 | CA | VAL | W | 21 | 119.990 | 7.635 | 40.615 | 1.00 | 97.44 | chnW |
| ATOM | 5583 | CB | VAL | W | 21 | 119.151 | 6.614 | 41.457 | 1.00 | 98.99 | chnW |
| ATOM | 5584 | CG1 | VAL | W | 21 | 119.160 | 5.232 | 40.792 | 1.00 | 98.74 | chnW |
| ATOM | 5585 | CG2 | VAL | W | 21 | 119.701 | 6.511 | 42.889 | 1.00 | 98.96 | chnW |
| ATOM | 5586 | C | VAL | W | 21 | 119.573 | 7.540 | 39.145 | 1.00 | 97.86 | chnW |
| ATOM | 5587 | O | VAL | W | 21 | 120.415 | 7.554 | 38.247 | 1.00 | 99.08 | chnW |
| ATOM | 5588 | N | VAL | X | 1 | 85.675 | 61.255 | 35.258 | 1.00 | 98.28 | chnX |
| ATOM | 5589 | CA | VAL | X | 1 | 86.088 | 60.144 | 36.115 | 1.00 | 96.34 | chnX |
| ATOM | 5590 | CB | VAL | X | 1 | 87.141 | 60.581 | 37.184 | 1.00 | 96.67 | chnX |
| ATOM | 5591 | CG1 | VAL | X | 1 | 88.521 | 60.702 | 36.564 | 1.00 | 97.01 | chnX |
| ATOM | 5592 | CG2 | VAL | X | 1 | 86.731 | 61.908 | 37.820 | 1.00 | 96.19 | chnX |
| ATOM | 5593 | C | VAL | X | 1 | 84.903 | 59.529 | 36.846 | 1.00 | 94.21 | chnX |
| ATOM | 5594 | O | VAL | X | 1 | 84.221 | 60.202 | 37.623 | 1.00 | 94.02 | chnX |
| ATOM | 5595 | N | GLN | X | 2 | 84.633 | 58.260 | 36.565 | 1.00 | 91.16 | chnX |
| ATOM | 5596 | CA | GLN | X | 2 | 83.547 | 57.566 | 37.243 | 1.00 | 88.11 | chnX |
| ATOM | 5597 | CB | GLN | X | 2 | 82.721 | 56.720 | 36.266 | 1.00 | 90.98 | chnX |
| ATOM | 5598 | CG | GLN | X | 2 | 83.536 | 55.675 | 35.508 | 1.00 | 95.35 | chnX |
| ATOM | 5599 | CD | GLN | X | 2 | 82.675 | 54.702 | 34.722 | 1.00 | 97.37 | chnX |
| ATOM | 5600 | OE1 | GLN | X | 2 | 82.921 | 54.454 | 33.538 | 1.00 | 96.99 | chnX |
| ATOM | 5601 | NE2 | GLN | X | 2 | 81.665 | 54.134 | 35.382 | 1.00 | 98.04 | chnX |
| ATOM | 5602 | C | GLN | X | 2 | 84.162 | 56.678 | 38.324 | 1.00 | 83.64 | chnX |
| ATOM | 5603 | O | GLN | X | 2 | 85.140 | 55.962 | 38.081 | 1.00 | 83.14 | chnX |
| ATOM | 5604 | N | CYS | X | 3 | 83.649 | 56.812 | 39.542 | 1.00 | 76.50 | chnX |

-continued

| ATOM | 5605 | CA | CYS | X | 3 | 84.115 | 56.014 | 40.666 | 1.00 | 69.85 | chnX |
| ATOM | 5606 | C | CYS | X | 3 | 83.016 | 55.012 | 40.947 | 1.00 | 65.88 | chnX |
| ATOM | 5607 | O | CYS | X | 3 | 81.866 | 55.221 | 40.565 | 1.00 | 66.33 | chnX |
| ATOM | 5608 | CB | CYS | X | 3 | 84.329 | 56.895 | 41.889 | 1.00 | 70.01 | chnX |
| ATOM | 5609 | SG | CYS | X | 3 | 85.472 | 58.266 | 41.585 | 1.00 | 70.14 | chnX |
| ATOM | 5610 | N | PRO | X | 4 | 83.353 | 53.897 | 41.596 | 1.00 | 61.31 | chnX |
| ATOM | 5611 | CD | PRO | X | 4 | 84.677 | 53.505 | 42.093 | 1.00 | 59.15 | chnX |
| ATOM | 5612 | CA | PRO | X | 4 | 82.352 | 52.877 | 41.911 | 1.00 | 61.51 | chnX |
| ATOM | 5613 | CB | PRO | X | 4 | 83.178 | 51.797 | 42.603 | 1.00 | 59.80 | chnX |
| ATOM | 5614 | CG | PRO | X | 4 | 84.313 | 52.574 | 43.192 | 1.00 | 60.30 | chnX |
| ATOM | 5615 | C | PRO | X | 4 | 81.230 | 53.407 | 42.807 | 1.00 | 62.02 | chnX |
| ATOM | 5616 | O | PRO | X | 4 | 81.430 | 54.348 | 43.583 | 1.00 | 62.26 | chnX |
| ATOM | 5617 | N | HIS | X | 5 | 80.054 | 52.799 | 42.683 | 1.00 | 63.72 | chnX |
| ATOM | 5618 | CA | HIS | X | 5 | 78.881 | 53.189 | 43.454 | 1.00 | 67.05 | chnX |
| ATOM | 5619 | CB | HIS | X | 5 | 77.790 | 52.129 | 43.316 | 1.00 | 78.38 | chnX |
| ATOM | 5620 | CG | HIS | X | 5 | 77.074 | 52.156 | 42.000 | 1.00 | 87.15 | chnX |
| ATOM | 5621 | CD2 | HIS | X | 5 | 75.808 | 52.525 | 41.684 | 1.00 | 89.39 | chnX |
| ATOM | 5622 | ND1 | HIS | X | 5 | 77.653 | 51.723 | 40.826 | 1.00 | 91.19 | chnX |
| ATOM | 5623 | CE1 | HIS | X | 5 | 76.772 | 51.818 | 39.842 | 1.00 | 92.83 | chnX |
| ATOM | 5624 | NE2 | HIS | X | 5 | 75.646 | 52.301 | 40.337 | 1.00 | 92.34 | chnX |
| ATOM | 5625 | C | HIS | X | 5 | 79.121 | 53.462 | 44.941 | 1.00 | 63.10 | chnX |
| ATOM | 5626 | O | HIS | X | 5 | 78.750 | 54.523 | 45.447 | 1.00 | 63.21 | chnX |
| ATOM | 5627 | N | PHE | X | 6 | 79.759 | 52.527 | 45.638 | 1.00 | 57.04 | chnX |
| ATOM | 5628 | CA | PHE | X | 6 | 79.996 | 52.696 | 47.068 | 1.00 | 54.15 | chnX |
| ATOM | 5629 | CB | PHE | X | 6 | 80.688 | 51.469 | 47.647 | 1.00 | 52.45 | chnX |
| ATOM | 5630 | CG | PHE | X | 6 | 82.124 | 51.321 | 47.225 | 1.00 | 50.98 | chnX |
| ATOM | 5631 | CD1 | PHE | X | 6 | 82.481 | 50.387 | 46.256 | 1.00 | 51.54 | chnX |
| ATOM | 5632 | CD2 | PHE | X | 6 | 83.126 | 52.079 | 47.826 | 1.00 | 48.52 | chnX |
| ATOM | 5633 | CE1 | PHE | X | 6 | 83.809 | 50.209 | 45.897 | 1.00 | 51.97 | chnX |
| ATOM | 5634 | CE2 | PHE | X | 6 | 84.454 | 51.910 | 47.473 | 1.00 | 48.38 | chnX |
| ATOM | 5635 | CZ | PHE | X | 6 | 84.799 | 50.974 | 46.509 | 1.00 | 49.95 | chnX |
| ATOM | 5636 | C | PHE | X | 6 | 80.766 | 53.949 | 47.472 | 1.00 | 54.46 | chnX |
| ATOM | 5637 | O | PHE | X | 6 | 80.972 | 54.196 | 48.658 | 1.00 | 56.39 | chnX |
| ATOM | 5638 | N | CYS | X | 7 | 81.222 | 54.725 | 46.499 | 1.00 | 55.74 | chnX |
| ATOM | 5639 | CA | CYS | X | 7 | 81.970 | 55.934 | 46.815 | 1.00 | 59.07 | chnX |
| ATOM | 5640 | C | CYS | X | 7 | 81.105 | 57.012 | 47.434 | 1.00 | 64.26 | chnX |
| ATOM | 5641 | O | CYS | X | 7 | 81.552 | 57.740 | 48.317 | 1.00 | 67.62 | chnX |
| ATOM | 5642 | CB | CYS | X | 7 | 82.649 | 56.494 | 45.569 | 1.00 | 55.67 | chnX |
| ATOM | 5643 | SG | CYS | X | 7 | 84.061 | 55.513 | 44.992 | 1.00 | 51.47 | chnX |
| ATOM | 5644 | N | TYR | X | 8 | 79.863 | 57.103 | 46.974 | 1.00 | 69.31 | chnX |
| ATOM | 5645 | CA | TYR | X | 8 | 78.940 | 58.123 | 47.459 | 1.00 | 74.52 | chnX |
| ATOM | 5646 | CB | TYR | X | 8 | 78.378 | 58.918 | 46.279 | 1.00 | 77.03 | chnX |
| ATOM | 5647 | CG | TYR | X | 8 | 79.367 | 59.135 | 45.157 | 1.00 | 79.26 | chnX |
| ATOM | 5648 | CD1 | TYR | X | 8 | 79.488 | 58.207 | 44.121 | 1.00 | 79.26 | chnX |
| ATOM | 5649 | CE1 | TYR | X | 8 | 80.407 | 58.389 | 43.097 | 1.00 | 81.18 | chnX |
| ATOM | 5650 | CD2 | TYR | X | 8 | 80.191 | 60.257 | 45.139 | 1.00 | 80.42 | chnX |
| ATOM | 5651 | CE2 | TYR | X | 8 | 81.115 | 60.452 | 44.121 | 1.00 | 82.07 | chnX |
| ATOM | 5652 | CZ | TYR | X | 8 | 81.221 | 59.515 | 43.102 | 1.00 | 82.56 | chnX |
| ATOM | 5653 | OH | TYR | X | 8 | 82.146 | 59.706 | 42.097 | 1.00 | 84.83 | chnX |
| ATOM | 5654 | C | TYR | X | 8 | 77.782 | 57.521 | 48.238 | 1.00 | 76.47 | chnX |
| ATOM | 5655 | O | TYR | X | 8 | 77.304 | 58.111 | 49.208 | 1.00 | 80.08 | chnX |
| ATOM | 5656 | N | GLU | X | 9 | 77.330 | 56.348 | 47.799 | 1.00 | 77.66 | chnX |
| ATOM | 5657 | CA | GLU | X | 9 | 76.209 | 55.660 | 48.426 | 1.00 | 77.84 | chnX |
| ATOM | 5658 | CB | GLU | X | 9 | 75.600 | 54.654 | 47.449 | 1.00 | 80.87 | chnX |
| ATOM | 5659 | CG | GLU | X | 9 | 74.909 | 55.319 | 46.257 | 1.00 | 87.43 | chnX |
| ATOM | 5660 | CD | GLU | X | 9 | 74.421 | 54.324 | 45.219 | 1.00 | 90.07 | chnX |
| ATOM | 5661 | OE1 | GLU | X | 9 | 73.513 | 53.523 | 45.538 | 1.00 | 93.12 | chnX |
| ATOM | 5662 | OE2 | GLU | X | 9 | 74.945 | 54.351 | 44.083 | 1.00 | 92.11 | chnX |
| ATOM | 5663 | C | GLU | X | 9 | 76.579 | 54.977 | 49.721 | 1.00 | 76.15 | chnX |
| ATOM | 5664 | O | GLU | X | 9 | 76.032 | 53.929 | 50.049 | 1.00 | 76.33 | chnX |
| ATOM | 5665 | N | LEU | X | 10 | 77.491 | 55.592 | 50.466 | 1.00 | 76.33 | chnX |
| ATOM | 5666 | CA | LEU | X | 10 | 77.951 | 55.056 | 51.740 | 1.00 | 78.66 | chnX |
| ATOM | 5667 | CB | LEU | X | 10 | 79.273 | 54.296 | 51.559 | 1.00 | 80.54 | chnX |
| ATOM | 5668 | CG | LEU | X | 10 | 79.330 | 52.798 | 51.905 | 1.00 | 81.14 | chnX |
| ATOM | 5669 | CD1 | LEU | X | 10 | 78.332 | 52.007 | 51.087 | 1.00 | 83.72 | chnX |
| ATOM | 5670 | CD2 | LEU | X | 10 | 80.730 | 52.262 | 51.660 | 1.00 | 81.03 | chnX |
| ATOM | 5671 | C | LEU | X | 10 | 78.133 | 56.185 | 52.747 | 1.00 | 80.06 | chnX |
| ATOM | 5672 | O | LEU | X | 10 | 78.332 | 57.347 | 52.370 | 1.00 | 77.96 | chnX |
| ATOM | 5673 | N | ASP | X | 11 | 78.064 | 55.821 | 54.026 | 1.00 | 83.14 | chnX |
| ATOM | 5674 | CA | ASP | X | 11 | 78.207 | 56.753 | 55.147 | 1.00 | 86.12 | chnX |
| ATOM | 5675 | CB | ASP | X | 11 | 78.252 | 55.977 | 56.463 | 1.00 | 88.84 | chnX |
| ATOM | 5676 | CG | ASP | X | 11 | 77.246 | 54.837 | 56.508 | 1.00 | 90.59 | chnX |
| ATOM | 5677 | OD1 | ASP | X | 11 | 76.221 | 54.985 | 57.212 | 1.00 | 89.12 | chnX |
| ATOM | 5678 | OD2 | ASP | X | 11 | 77.494 | 53.793 | 55.846 | 1.00 | 92.08 | chnX |
| ATOM | 5679 | C | ASP | X | 11 | 79.486 | 57.567 | 55.007 | 1.00 | 86.19 | chnX |
| ATOM | 5680 | O | ASP | X | 11 | 79.444 | 58.780 | 54.785 | 1.00 | 86.21 | chnX |
| ATOM | 5681 | N | TYR | X | 12 | 80.619 | 56.881 | 55.136 | 1.00 | 86.05 | chnX |
| ATOM | 5682 | CA | TYR | X | 12 | 81.926 | 57.514 | 55.009 | 1.00 | 86.70 | chnX |
| ATOM | 5683 | CB | TYR | X | 12 | 82.936 | 56.846 | 55.950 | 1.00 | 92.23 | chnX |

-continued

| | | | | | | | | | |
|---|---|---|---|---|---|---|---|---|---|
| ATOM | 5684 | CG | TYR | X | 12 | 84.304 | 57.505 | 55.946 | 1.00 | 98.60 | chnX |
| ATOM | 5685 | CD1 | TYR | X | 12 | 84.435 | 58.892 | 55.790 | 1.00 | 101.05 | chnX |
| ATOM | 5686 | CE1 | TYR | X | 12 | 85.699 | 59.500 | 55.732 | 1.00 | 104.37 | chnX |
| ATOM | 5687 | CD2 | TYR | X | 12 | 85.470 | 56.741 | 56.056 | 1.00 | 100.30 | chnX |
| ATOM | 5688 | CE2 | TYR | X | 12 | 86.739 | 57.337 | 56.004 | 1.00 | 102.33 | chnX |
| ATOM | 5689 | CZ | TYR | X | 12 | 86.848 | 58.715 | 55.837 | 1.00 | 104.27 | chnX |
| ATOM | 5690 | OH | TYR | X | 12 | 88.092 | 59.309 | 55.745 | 1.00 | 103.38 | chnX |
| ATOM | 5691 | C | TYR | X | 12 | 82.434 | 57.471 | 53.560 | 1.00 | 82.88 | chnX |
| ATOM | 5692 | O | TYR | X | 12 | 82.131 | 56.537 | 52.808 | 1.00 | 83.94 | chnX |
| ATOM | 5693 | N | GLU | X | 13 | 83.169 | 58.511 | 53.170 | 1.00 | 76.08 | chnX |
| ATOM | 5694 | CA | GLU | X | 13 | 83.735 | 58.602 | 51.832 | 1.00 | 70.17 | chnX |
| ATOM | 5695 | CB | GLU | X | 13 | 83.897 | 60.070 | 51.445 | 1.00 | 73.98 | chnX |
| ATOM | 5696 | CG | GLU | X | 13 | 82.588 | 60.863 | 51.404 | 1.00 | 77.31 | chnX |
| ATOM | 5697 | CD | GLU | X | 13 | 82.748 | 62.260 | 50.789 | 1.00 | 80.13 | chnX |
| ATOM | 5698 | OE1 | GLU | X | 13 | 81.794 | 62.737 | 50.131 | 1.00 | 80.41 | chnX |
| ATOM | 5699 | OE2 | GLU | X | 13 | 83.824 | 62.881 | 50.957 | 1.00 | 81.05 | chnX |
| ATOM | 5700 | C | GLU | X | 13 | 85.090 | 57.883 | 51.811 | 1.00 | 66.65 | chnX |
| ATOM | 5701 | O | GLU | X | 13 | 86.072 | 58.380 | 52.371 | 1.00 | 63.34 | chnX |
| ATOM | 5702 | N | LEU | X | 14 | 85.130 | 56.712 | 51.172 | 1.00 | 60.02 | chnX |
| ATOM | 5703 | CA | LEU | X | 14 | 86.350 | 55.900 | 51.099 | 1.00 | 56.61 | chnX |
| ATOM | 5704 | CB | LEU | X | 14 | 86.010 | 54.410 | 51.234 | 1.00 | 54.38 | chnX |
| ATOM | 5705 | CG | LEU | X | 14 | 85.878 | 53.782 | 52.623 | 1.00 | 52.30 | chnX |
| ATOM | 5706 | CD1 | LEU | X | 14 | 84.839 | 54.506 | 53.424 | 1.00 | 54.36 | chnX |
| ATOM | 5707 | CD2 | LEU | X | 14 | 85.509 | 52.322 | 52.498 | 1.00 | 51.36 | chnX |
| ATOM | 5708 | C | LEU | X | 14 | 87.219 | 56.098 | 49.861 | 1.00 | 55.78 | chnX |
| ATOM | 5709 | O | LEU | X | 14 | 88.383 | 55.698 | 49.851 | 1.00 | 57.39 | chnX |
| ATOM | 5710 | N | CYS | X | 15 | 86.647 | 56.707 | 48.827 | 1.00 | 52.81 | chnX |
| ATOM | 5711 | CA | CYS | X | 15 | 87.332 | 56.953 | 47.561 | 1.00 | 50.60 | chnX |
| ATOM | 5712 | C | CYS | X | 15 | 88.174 | 58.228 | 47.521 | 1.00 | 52.01 | chnX |
| ATOM | 5713 | O | CYS | X | 15 | 88.049 | 59.093 | 48.394 | 1.00 | 54.67 | chnX |
| ATOM | 5714 | CB | CYS | X | 15 | 86.293 | 56.962 | 46.454 | 1.00 | 47.00 | chnX |
| ATOM | 5715 | SG | CYS | X | 15 | 85.270 | 55.486 | 46.611 | 1.00 | 46.89 | chnX |
| ATOM | 5716 | N | PRO | X | 16 | 89.057 | 58.355 | 46.509 | 1.00 | 52.89 | chnX |
| ATOM | 5717 | CD | PRO | X | 16 | 89.352 | 57.313 | 45.515 | 1.00 | 53.52 | chnX |
| ATOM | 5718 | CA | PRO | X | 16 | 89.949 | 59.503 | 46.308 | 1.00 | 55.36 | chnX |
| ATOM | 5719 | CB | PRO | X | 16 | 90.688 | 59.133 | 45.029 | 1.00 | 55.11 | chnX |
| ATOM | 5720 | CG | PRO | X | 16 | 90.740 | 57.674 | 45.092 | 1.00 | 53.44 | chnX |
| ATOM | 5721 | C | PRO | X | 16 | 89.232 | 60.840 | 46.155 | 1.00 | 59.82 | chnX |
| ATOM | 5722 | O | PRO | X | 16 | 88.052 | 60.887 | 45.802 | 1.00 | 61.34 | chnX |
| ATOM | 5723 | N | ASP | X | 17 | 89.977 | 61.924 | 46.363 | 1.00 | 61.48 | chnX |
| ATOM | 5724 | CA | ASP | X | 17 | 89.421 | 63.273 | 46.277 | 1.00 | 62.33 | chnX |
| ATOM | 5725 | CB | ASP | X | 17 | 90.456 | 64.323 | 46.706 | 1.00 | 64.02 | chnX |
| ATOM | 5726 | CG | ASP | X | 17 | 90.483 | 64.526 | 48.219 | 1.00 | 67.72 | chnX |
| ATOM | 5727 | OD1 | ASP | X | 17 | 91.530 | 64.270 | 48.853 | 1.00 | 69.84 | chnX |
| ATOM | 5728 | OD2 | ASP | X | 17 | 89.446 | 64.932 | 48.786 | 1.00 | 70.02 | chnX |
| ATOM | 5729 | C | ASP | X | 17 | 88.788 | 63.645 | 44.941 | 1.00 | 61.34 | chnX |
| ATOM | 5730 | O | ASP | X | 17 | 87.845 | 64.437 | 44.895 | 1.00 | 61.76 | chnX |
| ATOM | 5731 | N | VAL | X | 18 | 89.248 | 63.018 | 43.867 | 1.00 | 59.72 | chnX |
| ATOM | 5732 | CA | VAL | X | 18 | 88.714 | 63.317 | 42.552 | 1.00 | 62.41 | chnX |
| ATOM | 5733 | CB | VAL | X | 18 | 89.659 | 62.809 | 41.448 | 1.00 | 61.75 | chnX |
| ATOM | 5734 | CG1 | VAL | X | 18 | 89.599 | 61.303 | 41.345 | 1.00 | 62.43 | chnX |
| ATOM | 5735 | CG2 | VAL | X | 18 | 89.344 | 63.494 | 40.120 | 1.00 | 65.90 | chnX |
| ATOM | 5736 | C | VAL | X | 18 | 87.273 | 62.828 | 42.332 | 1.00 | 63.70 | chnX |
| ATOM | 5737 | O | VAL | X | 18 | 86.623 | 63.236 | 41.370 | 1.00 | 64.90 | chnX |
| ATOM | 5738 | N | CYS | X | 19 | 86.754 | 62.004 | 43.241 | 1.00 | 65.96 | chnX |
| ATOM | 5739 | CA | CYS | X | 19 | 85.378 | 61.498 | 43.108 | 1.00 | 70.00 | chnX |
| ATOM | 5740 | C | CYS | X | 19 | 84.352 | 62.490 | 43.642 | 1.00 | 71.39 | chnX |
| ATOM | 5741 | O | CYS | X | 19 | 83.203 | 62.522 | 43.193 | 1.00 | 70.79 | chnX |
| ATOM | 5742 | CB | CYS | X | 19 | 85.173 | 60.191 | 43.896 | 1.00 | 68.72 | chnX |
| ATOM | 5743 | SG | CYS | X | 19 | 86.171 | 58.748 | 43.427 | 1.00 | 70.19 | chnX |
| ATOM | 5744 | N | TYR | X | 20 | 84.784 | 63.282 | 44.619 | 1.00 | 75.02 | chnX |
| ATOM | 5745 | CA | TYR | X | 20 | 83.921 | 64.235 | 45.298 | 1.00 | 81.32 | chnX |
| ATOM | 5746 | CB | TYR | X | 20 | 84.218 | 64.154 | 46.791 | 1.00 | 78.89 | chnX |
| ATOM | 5747 | CG | TYR | X | 20 | 84.160 | 62.727 | 47.293 | 1.00 | 77.61 | chnX |
| ATOM | 5748 | CD1 | TYR | X | 20 | 85.256 | 62.135 | 47.915 | 1.00 | 77.01 | chnX |
| ATOM | 5749 | CE1 | TYR | X | 20 | 85.209 | 60.812 | 48.328 | 1.00 | 74.97 | chnX |
| ATOM | 5750 | CD2 | TYR | X | 20 | 83.014 | 61.951 | 47.103 | 1.00 | 75.65 | chnX |
| ATOM | 5751 | CE2 | TYR | X | 20 | 82.962 | 60.632 | 47.512 | 1.00 | 71.99 | chnX |
| ATOM | 5752 | CZ | TYR | X | 20 | 84.056 | 60.071 | 48.120 | 1.00 | 72.41 | chnX |
| ATOM | 5753 | OH | TYR | X | 20 | 83.987 | 58.766 | 48.526 | 1.00 | 71.81 | chnX |
| ATOM | 5754 | C | TYR | X | 20 | 83.928 | 65.684 | 44.811 | 1.00 | 87.07 | chnX |
| ATOM | 5755 | O | TYR | X | 20 | 82.973 | 66.431 | 45.071 | 1.00 | 89.84 | chnX |
| ATOM | 5756 | N | VAL | X | 21 | 84.998 | 66.078 | 44.118 | 1.00 | 92.60 | chnX |
| ATOM | 5757 | CA | VAL | X | 21 | 85.141 | 67.433 | 43.572 | 1.00 | 95.58 | chnX |
| ATOM | 5758 | CB | VAL | X | 21 | 84.161 | 67.656 | 42.380 | 1.00 | 95.93 | chnX |
| ATOM | 5759 | CG1 | VAL | X | 21 | 84.307 | 69.073 | 41.818 | 1.00 | 96.26 | chnX |
| ATOM | 5760 | CG2 | VAL | X | 21 | 84.412 | 66.614 | 41.284 | 1.00 | 96.90 | chnX |
| ATOM | 5761 | C | VAL | X | 21 | 84.929 | 68.532 | 44.622 | 1.00 | 96.69 | chnX |
| ATOM | 5762 | O | VAL | X | 21 | 85.630 | 68.592 | 45.636 | 1.00 | 96.82 | chnX |

-continued

| | | | | | | | | | | |
|---|---|---|---|---|---|---|---|---|---|---|
| ATOM | 5763 | N | VAL | Y | 1 | 113.734 | 36.637 | 61.333 | 1.00 | 98.96 chnY |
| ATOM | 5764 | CA | VAL | Y | 1 | 114.176 | 35.244 | 61.393 | 1.00 | 99.13 chnY |
| ATOM | 5765 | CB | VAL | Y | 1 | 113.359 | 34.422 | 62.444 | 1.00 | 100.09 chnY |
| ATOM | 5766 | CG1 | VAL | Y | 1 | 113.961 | 33.025 | 62.602 | 1.00 | 100.50 chnY |
| ATOM | 5767 | CG2 | VAL | Y | 1 | 113.320 | 35.150 | 63.794 | 1.00 | 99.37 chnY |
| ATOM | 5768 | C | VAL | Y | 1 | 114.053 | 34.588 | 60.012 | 1.00 | 97.45 chnY |
| ATOM | 5769 | O | VAL | Y | 1 | 114.977 | 34.690 | 59.197 | 1.00 | 96.98 chnY |
| ATOM | 5770 | N | GLN | Y | 2 | 112.918 | 33.916 | 59.775 | 1.00 | 95.54 chnY |
| ATOM | 5771 | CA | GLN | Y | 2 | 112.603 | 33.227 | 58.511 | 1.00 | 91.88 chnY |
| ATOM | 5772 | CB | GLN | Y | 2 | 112.321 | 34.259 | 57.416 | 1.00 | 96.07 chnY |
| ATOM | 5773 | CG | GLN | Y | 2 | 111.020 | 35.006 | 57.633 | 1.00 | 98.38 chnY |
| ATOM | 5774 | CD | GLN | Y | 2 | 109.835 | 34.061 | 57.701 | 1.00 | 100.03 chnY |
| ATOM | 5775 | OE1 | GLN | Y | 2 | 109.328 | 33.601 | 56.666 | 1.00 | 100.20 chnY |
| ATOM | 5776 | NE2 | GLN | Y | 2 | 109.402 | 33.739 | 58.923 | 1.00 | 99.39. chnY |
| ATOM | 5777 | C | GLN | Y | 2 | 113.611 | 32.179 | 58.013 | 1.00 | 86.67 chnY |
| ATOM | 5778 | O | GLN | Y | 2 | 114.724 | 32.523 | 57.599 | 1.00 | 85.92 chnY |
| ATOM | 5779 | N | CYS | Y | 3 | 113.206 | 30.910 | 58.012 | 1.00 | 76.13 chnY |
| ATOM | 5780 | CA | CYS | Y | 3 | 114.105 | 29.852 | 57.574 | 1.00 | 68.87 chnY |
| ATOM | 5781 | C | CYS | Y | 3 | 113.405 | 28.751 | 56.810 | 1.00 | 65.99 chnY |
| ATOM | 5782 | O | CYS | Y | 3 | 112.395 | 28.225 | 57.264 | 1.00 | 69.38 chnY |
| ATOM | 5783 | CB | CYS | Y | 3 | 114.854 | 29.272 | 58.772 | 1.00 | 65.59 chnY |
| ATOM | 5784 | SG | CYS | Y | 3 | 115.926 | 30.494 | 59.594 | 1.00 | 63.51 chnY |
| ATOM | 5785 | N | PRO | Y | 4 | 113.940 | 28.386 | 55.629 | 1.00 | 61.93 chnY |
| ATOM | 5786 | CD | PRO | Y | 4 | 115.195 | 28.881 | 55.049 | 1.00 | 60.14 chnY |
| ATOM | 5787 | CA | PRO | Y | 4 | 113.378 | 27.340 | 54.778 | 1.00 | 59.78 chnY |
| ATOM | 5788 | CB | PRO | Y | 4 | 114.388 | 27.242 | 53.640 | 1.00 | 57.96 chnY |
| ATOM | 5789 | CG | PRO | Y | 4 | 115.634 | 27.708 | 54.242 | 1.00 | 58.38 chnY |
| ATOM | 5790 | C | PRO | Y | 4 | 113.227 | 26.040 | 55.541 | 1.00 | 59.51 chnY |
| ATOM | 5791 | O | PRO | Y | 4 | 114.049 | 25.698 | 56.388 | 1.00 | 56.72 chnY |
| ATOM | 5792 | N | HIS | Y | 5 | 112.174 | 25.310 | 55.205 | 1.00 | 63.44 chnY |
| ATOM | 5793 | CA | HIS | Y | 5 | 111.815 | 24.066 | 55.872 | 1.00 | 66.12 chnY |
| ATOM | 5794 | CB | HIS | Y | 5 | 110.455 | 23.602 | 55.344 | 1.00 | 77.21 chnY |
| ATOM | 5795 | CG | HIS | Y | 5 | 109.427 | 24.700 | 55.313 | 1.00 | 86.84 chnY |
| ATOM | 5796 | CD2 | HIS | Y | 5 | 108.295 | 24.886 | 56.040 | 1.00 | 89.60 chnY |
| ATOM | 5797 | ND1 | HIS | Y | 5 | 109.546 | 25.807 | 54.499 | 1.00 | 89.42 chnY |
| ATOM | 5798 | CE1 | HIS | Y | 5 | 108.536 | 26.634 | 54.729 | 1.00 | 90.82 chnY |
| ATOM | 5799 | NE2 | HIS | Y | 5 | 107.765 | 26.097 | 55.658 | 1.00 | 91.44 chnY |
| ATOM | 5800 | C | HIS | Y | 5 | 112.818 | 22.915 | 55.952 | 1.00 | 60.28 chnY |
| ATOM | 5801 | O | HIS | Y | 5 | 112.695 | 22.065 | 56.833 | 1.00 | 60.24 chnY |
| ATOM | 5802 | N | PHE | Y | 6 | 113.816 | 22.902 | 55.069 | 1.00 | 53.89 chnY |
| ATOM | 5803 | CA | PHE | Y | 6 | 114.824 | 21.842 | 55.067 | 1.00 | 49.61 chnY |
| ATOM | 5804 | CB | PHE | Y | 6 | 115.565 | 21.737 | 53.721 | 1.00 | 49.27 chnY |
| ATOM | 5805 | CG | PHE | Y | 6 | 116.485 | 22.898 | 53.417 | 1.00 | 48.00 chnY |
| ATOM | 5806 | CD1 | PHE | Y | 6 | 116.076 | 23.923 | 52.569 | 1.00 | 48.44 chnY |
| ATOM | 5807 | CD2 | PHE | Y | 6 | 117.765 | 22.950 | 53.946 | 1.00 | 47.16 chnY |
| ATOM | 5808 | CE1 | PHE | Y | 6 | 116.926 | 24.972 | 52.253 | 1.00 | 47.55 chnY |
| ATOM | 5809 | CE2 | PHE | Y | 6 | 118.621 | 23.998 | 53.635 | 1.00 | 47.49 chnY |
| ATOM | 5810 | CZ | PHE | Y | 6 | 118.201 | 25.010 | 52.788 | 1.00 | 46.69 chnY |
| ATOM | 5811 | C | PHE | Y | 6 | 115.820 | 22.078 | 56.162 | 1.00 | 50.82 chnY |
| ATOM | 5812 | O | PHE | Y | 6 | 116.612 | 21.205 | 56.476 | 1.00 | 52.75 chnY |
| ATOM | 5813 | N | CYS | Y | 7 | 115.814 | 23.286 | 56.704 | 1.00 | 51.93 chnY |
| ATOM | 5814 | CA | CYS | Y | 7 | 116.731 | 23.638 | 57.775 | 1.00 | 57.03 chnY |
| ATOM | 5815 | C | CYS | Y | 7 | 116.537 | 22.731 | 58.978 | 1.00 | 60.84 chnY |
| ATOM | 5816 | O | CYS | Y | 7 | 117.475 | 22.116 | 59.480 | 1.00 | 60.96 chnY |
| ATOM | 5817 | CB | CYS | Y | 7 | 116.510 | 25.090 | 58.184 | 1.00 | 54.38 chnY |
| ATOM | 5818 | SG | CYS | Y | 7 | 117.291 | 26.244 | 57.031 | 1.00 | 49.01 chnY |
| ATOM | 5819 | N | TYR | Y | 8 | 115.286 | 22.626 | 59.397 | 1.00 | 65.89 chnY |
| ATOM | 5820 | CA | TYR | Y | 8 | 114.914 | 21.820 | 60.536 | 1.00 | 70.72 chnY |
| ATOM | 5821 | CB | TYR | Y | 8 | 113.592 | 22.340 | 61.077 | 1.00 | 71.13 chnY |
| ATOM | 5822 | CG | TYR | Y | 8 | 113.627 | 23.837 | 61.284 | 1.00 | 73.35 chnY |
| ATOM | 5823 | CD1 | TYR | Y | 8 | 112.639 | 24.663 | 60.757 | 1.00 | 75.24 chnY |
| ATOM | 5824 | CE1 | TYR | Y | 8 | 112.696 | 26.049 | 60.930 | 1.00 | 76.52 chnY |
| ATOM | 5825 | CD2 | TYR | Y | 8 | 114.669 | 24.432 | 61.989 | 1.00 | 73.94 chnY |
| ATOM | 5826 | CE2 | TYR | Y | 8 | 114.734 | 25.811 | 62.164 | 1.00 | 75.25 chnY |
| ATOM | 5827 | CZ | TYR | Y | 8 | 113.749 | 26.608 | 61.634 | 1.00 | 75.51 chnY |
| ATOM | 5828 | OH | TYR | Y | 8 | 113.823 | 27.966 | 61.797 | 1.00 | 77.49 chnY |
| ATOM | 5829 | C | TYR | Y | 8 | 114.858 | 20.334 | 60.203 | 1.00 | 72.49 chnY |
| ATOM | 5830 | O | TYR | Y | 8 | 114.801 | 19.504 | 61.103 | 1.00 | 75.18 chnY |
| ATOM | 5831 | N | GLU | Y | 9 | 114.889 | 20.005 | 58.910 | 1.00 | 76.61 chnY |
| ATOM | 5832 | CA | GLU | Y | 9 | 114.876 | 18.607 | 58.449 | 1.00 | 79.62 chnY |
| ATOM | 5833 | CB | GLU | Y | 9 | 114.515 | 18.500 | 56.951 | 1.00 | 80.61 chnY |
| ATOM | 5834 | CG | GLU | Y | 9 | 113.035 | 18.792 | 56.609 | 1.00 | 83.80 chnY |
| ATOM | 5835 | CD | GLU | Y | 9 | 112.717 | 18.709 | 55.108 | 1.00 | 83.76 chnY |
| ATOM | 5836 | OE1 | GLU | Y | 9 | 112.137 | 19.666 | 54.557 | 1.00 | 85.39 chnY |
| ATOM | 5837 | OE2 | GLU | Y | 9 | 113.031 | 17.684 | 54.473 | 1.00 | 85.22 chnY |
| ATOM | 5838 | C | GLU | Y | 9 | 116.268 | 18.030 | 58.705 | 1.00 | 80.65 chnY |
| ATOM | 5839 | O | GLU | Y | 9 | 117.151 | 18.750 | 59.186 | 1.00 | 83.15 chnY |
| ATOM | 5840 | N | LEU | Y | 10 | 116.482 | 16.765 | 58.341 | 1.00 | 80.98 chnY |
| ATOM | 5841 | CA | LEU | Y | 10 | 117.764 | 16.078 | 58.576 | 1.00 | 83.64 chnY |

-continued

| | | | | | | | | | | |
|---|---|---|---|---|---|---|---|---|---|---|
| ATOM | 5842 | CB | LEU | Y | 10 | 118.844 | 16.465 | 57.540 | 1.00 | 83.55 chnY |
| ATOM | 5843 | CG | LEU | Y | 10 | 119.255 | 17.888 | 57.134 | 1.00 | 83.64 chnY |
| ATOM | 5844 | CD1 | LEU | Y | 10 | 120.649 | 17.866 | 56.528 | 1.00 | 84.43 chnY |
| ATOM | 5845 | CD2 | LEU | Y | 10 | 118.262 | 18.462 | 56.139 | 1.00 | 84.43 chnY |
| ATOM | 5846 | C | LEU | Y | 10 | 118.305 | 16.191 | 60.020 | 1.00 | 85.19 chnY |
| ATOM | 5847 | O | LEU | Y | 10 | 117.769 | 16.926 | 60.853 | 1.00 | 84.15 chnY |
| ATOM | 5848 | N | ASP | Y | 11 | 119.345 | 15.428 | 60.327 | 1.00 | 87.46 chnY |
| ATOM | 5849 | CA | ASP | Y | 11 | 119.912 | 15.439 | 61.673 | 1.00 | 91.24 chnY |
| ATOM | 5850 | CB | ASP | Y | 11 | 120.231 | 14.002 | 62.118 | 1.00 | 94.39 chnY |
| ATOM | 5851 | CG | ASP | Y | 11 | 118.981 | 13.145 | 62.319 | 1.00 | 97.24 chnY |
| ATOM | 5852 | OD1 | ASP | Y | 11 | 117.967 | 13.357 | 61.612 | 1.00 | 98.08 chnY |
| ATOM | 5853 | OD2 | ASP | Y | 11 | 119.023 | 12.242 | 63.186 | 1.00 | 98.16 chnY |
| ATOM | 5854 | C | ASP | Y | 11 | 121.174 | 16.295 | 61.762 | 1.00 | 92.97 chnY |
| ATOM | 5855 | O | ASP | Y | 11 | 122.274 | 15.756 | 61.916 | 1.00 | 96.12 chnY |
| ATOM | 5856 | N | TYR | Y | 12 | 121.013 | 17.619 | 61.709 | 1.00 | 92.85 chnY |
| ATOM | 5857 | CA | TYR | Y | 12 | 122.152 | 18.547 | 61.759 | 1.00 | 89.94 chnY |
| ATOM | 5858 | CB | TYR | Y | 12 | 123.158 | 18.176 | 60.641 | 1.00 | 93.97 chnY |
| ATOM | 5859 | CG | TYR | Y | 12 | 124.402 | 19.036 | 60.567 | 1.00 | 97.26 chnY |
| ATOM | 5860 | CD1 | TYR | Y | 12 | 125.303 | 19.096 | 61.631 | 1.00 | 98.54 chnY |
| ATOM | 5861 | CE1 | TYR | Y | 12 | 126.437 | 19.926 | 61.576 | 1.00 | 101.26 chnY |
| ATOM | 5862 | CD2 | TYR | Y | 12 | 124.662 | 19.818 | 59.440 | 1.00 | 99.36 chnY |
| ATOM | 5863 | CE2 | TYR | Y | 12 | 125.787 | 20.649 | 59.374 | 1.00 | 101.53 chnY |
| ATOM | 5864 | CZ | TYR | Y | 12 | 126.670 | 20.703 | 60.445 | 1.00 | 101.97 chnY |
| ATOM | 5865 | OH | TYR | Y | 12 | 127.765 | 21.549 | 60.395 | 1.00 | 102.20 chnY |
| ATOM | 5866 | C | TYR | Y | 12 | 121.684 | 20.003 | 61.589 | 1.00 | 85.61 chnY |
| ATOM | 5867 | O | TYR | Y | 12 | 120.644 | 20.263 | 60.989 | 1.00 | 85.77 chnY |
| ATOM | 5868 | N | GLU | Y | 13 | 122.426 | 20.949 | 62.150 | 1.00 | 78.96 chnY |
| ATOM | 5869 | CA | GLU | Y | 13 | 122.067 | 22.354 | 62.005 | 1.00 | 75.15 chnY |
| ATOM | 5870 | CB | GLU | Y | 13 | 122.353 | 23.119 | 63.294 | 1.00 | 77.88 chnY |
| ATOM | 5871 | CG | GLU | Y | 13 | 121.392 | 22.779 | 64.418 | 1.00 | 80.62 chnY |
| ATOM | 5872 | CD | GLU | Y | 13 | 121.826 | 23.357 | 65.748 | 1.00 | 82.64 chnY |
| ATOM | 5873 | OE1 | GLU | Y | 13 | 121.669 | 24.582 | 65.956 | 1.00 | 83.96 chnY |
| ATOM | 5874 | OE2 | GLU | Y | 13 | 122.334 | 22.578 | 66.586 | 1.00 | 84.67 chnY |
| ATOM | 5875 | C | GLU | Y | 13 | 122.819 | 22.948 | 60.811 | 1.00 | 72.31 chnY |
| ATOM | 5876 | O | GLU | Y | 13 | 123.813 | 23.670 | 60.951 | 1.00 | 71.75 chnY |
| ATOM | 5877 | N | LEU | Y | 14 | 122.326 | 22.603 | 59.629 | 1.00 | 66.99 chnY |
| ATOM | 5878 | CA | LEU | Y | 14 | 122.886 | 23.029 | 58.351 | 1.00 | 59.19 chnY |
| ATOM | 5879 | CB | LEU | Y | 14 | 122.071 | 22.372 | 57.238 | 1.00 | 59.42 chnY |
| ATOM | 5880 | CG | LEU | Y | 14 | 122.755 | 21.896 | 55.960 | 1.00 | 61.78 chnY |
| ATOM | 5881 | CD1 | LEU | Y | 14 | 123.844 | 20.894 | 56.292 | 1.00 | 63.54 chnY |
| ATOM | 5882 | CD2 | LEU | Y | 14 | 121.715 | 21.259 | 55.044 | 1.00 | 62.99 chnY |
| ATOM | 5883 | C | LEU | Y | 14 | 122.863 | 24.548 | 58.176 | 1.00 | 55.75 chnY |
| ATOM | 5884 | O | LEU | Y | 14 | 123.857 | 25.163 | 57.801 | 1.00 | 51.84 chnY |
| ATOM | 5885 | N | CYS | Y | 15 | 121.712 | 25.132 | 58.473 | 1.00 | 52.26 chnY |
| ATOM | 5886 | CA | CYS | Y | 15 | 121.473 | 26.565 | 58.354 | 1.00 | 50.50 chnY |
| ATOM | 5887 | C | CYS | Y | 15 | 122.074 | 27.389 | 59.499 | 1.00 | 52.37 chnY |
| ATOM | 5888 | O | CYS | Y | 15 | 122.610 | 26.831 | 60.454 | 1.00 | 55.67 chnY |
| ATOM | 5889 | CB | CYS | Y | 15 | 119.970 | 26.773 | 58.274 | 1.00 | 47.19 chnY |
| ATOM | 5890 | SG | CYS | Y | 15 | 119.209 | 25.616 | 57.105 | 1.00 | 46.27 chnY |
| ATOM | 5891 | N | PRO | Y | 16 | 121.987 | 28.729 | 59.418 | 1.00 | 52.84 chnY |
| ATOM | 5892 | CD | PRO | Y | 16 | 121.418 | 29.506 | 58.307 | 1.00 | 53.56 chnY |
| ATOM | 5893 | CA | PRO | Y | 16 | 122.518 | 29.641 | 60.435 | 1.00 | 55.85 chnY |
| ATOM | 5894 | CB | PRO | Y | 16 | 122.065 | 31.005 | 59.931 | 1.00 | 53.81 chnY |
| ATOM | 5895 | CG | PRO | Y | 16 | 122.068 | 30.845 | 58.493 | 1.00 | 53.40 chnY |
| ATOM | 5896 | C | PRO | Y | 16 | 121.977 | 29.405 | 61.836 | 1.00 | 59.28 chnY |
| ATOM | 5897 | O | PRO | Y | 16 | 120.957 | 28.744 | 62.013 | 1.00 | 61.91 chnY |
| ATOM | 5898 | N | ASP | Y | 17 | 122.661 | 29.974 | 62.826 | 1.00 | 62.02 chnY |
| ATOM | 5899 | CA | ASP | Y | 17 | 122.252 | 29.853 | 64.212 | 1.00 | 62.49 chnY |
| ATOM | 5900 | CB | ASP | Y | 17 | 123.281 | 30.511 | 65.137 | 1.00 | 63.76 chnY |
| ATOM | 5901 | CG | ASP | Y | 17 | 124.576 | 29.721 | 65.238 | 1.00 | 66.64 chnY |
| ATOM | 5902 | OD1 | ASP | Y | 17 | 125.518 | 30.214 | 65.893 | 1.00 | 66.41 chnY |
| ATOM | 5903 | OD2 | ASP | Y | 17 | 124.658 | 28.607 | 64.678 | 1.00 | 69.61 chnY |
| ATOM | 5904 | C | ASP | Y | 17 | 120.898 | 30.525 | 64.382 | 1.00 | 63.23 chnY |
| ATOM | 5905 | O | ASP | Y | 17 | 120.005 | 29.964 | 65.013 | 1.00 | 65.09 chnY |
| ATOM | 5906 | N | VAL | Y | 18 | 120.727 | 31.687 | 63.748 | 1.00 | 63.74 chnY |
| ATOM | 5907 | CA | VAL | Y | 18 | 119.483 | 32.456 | 63.840 | 1.00 | 65.86 chnY |
| ATOM | 5908 | CB | VAL | Y | 18 | 119.435 | 33.611 | 62.811 | 1.00 | 66.35 chnY |
| ATOM | 5909 | CG1 | VAL | Y | 18 | 119.573 | 33.074 | 61.408 | 1.00 | 67.53 chnY |
| ATOM | 5910 | CG2 | VAL | Y | 18 | 118.132 | 34.394 | 62.951 | 1.00 | 66.64 chnY |
| ATOM | 5911 | C | VAL | Y | 18 | 118.227 | 31.613 | 63.688 | 1.00 | 65.72 chnY |
| ATOM | 5912 | O | VAL | Y | 18 | 117.222 | 31.865 | 64.348 | 1.00 | 65.01 chnY |
| ATOM | 5913 | N | CYS | Y | 19 | 118.296 | 30.600 | 62.836 | 1.00 | 67.19 chnY |
| ATOM | 5914 | CA | CYS | Y | 19 | 117.154 | 29.734 | 62.613 | 1.00 | 68.95 chnY |
| ATOM | 5915 | C | CYS | Y | 19 | 116.775 | 28.997 | 63.878 | 1.00 | 72.18 chnY |
| ATOM | 5916 | O | CYS | Y | 19 | 115.738 | 29.290 | 64.469 | 1.00 | 76.64 chnY |
| ATOM | 5917 | CB | CYS | Y | 19 | 117.438 | 28.736 | 61.494 | 1.00 | 65.50 chnY |
| ATOM | 5918 | SG | CYS | Y | 19 | 117.667 | 29.515 | 59.873 | 1.00 | 62.36 chnY |
| ATOM | 5919 | N | TYR | Y | 20 | 117.662 | 28.106 | 64.323 | 1.00 | 76.19 chnY |
| ATOM | 5920 | CA | TYR | Y | 20 | 117.461 | 27.265 | 65.510 | 1.00 | 79.82 chnY |

-continued

| | | | | | | | | | | |
|---|---|---|---|---|---|---|---|---|---|---|
| ATOM | 5921 | CB | TYR | Y | 20 | 118.523 | 26.165 | 65.528 | 1.00 | 77.27 chnY |
| ATOM | 5922 | CG | TYR | Y | 20 | 118.745 | 25.536 | 64.172 | 1.00 | 76.58 chnY |
| ATOM | 5923 | CD1 | TYR | Y | 20 | 119.777 | 25.970 | 63.347 | 1.00 | 75.82 chnY |
| ATOM | 5924 | CE1 | TYR | Y | 20 | 119.974 | 25.420 | 62.082 | 1.00 | 74.30 chnY |
| ATOM | 5925 | CD2 | TYR | Y | 20 | 117.911 | 24.530 | 63.701 | 1.00 | 78.15 chnY |
| ATOM | 5926 | CE2 | TYR | Y | 20 | 118.100 | 23.973 | 62.432 | 1.00 | 76.67 chnY |
| ATOM | 5927 | CZ | TYR | Y | 20 | 119.133 | 24.426 | 61.631 | 1.00 | 74.66 chnY |
| ATOM | 5928 | OH | TYR | Y | 20 | 119.320 | 23.896 | 60.377 | 1.00 | 72.62 chnY |
| ATOM | 5929 | C | TYR | Y | 20 | 117.404 | 27.973 | 66.883 | 1.00 | 83.29 chnY |
| ATOM | 5930 | O | TYR | Y | 20 | 117.438 | 27.314 | 67.933 | 1.00 | 82.32 chnY |
| ATOM | 5931 | N | VAL | Y | 21 | 117.308 | 29.306 | 66.857 | 1.00 | 88.53 chnY |
| ATOM | 5932 | CA | VAL | Y | 21 | 117.223 | 30.149 | 68.057 | 1.00 | 93.46 chnY |
| ATOM | 5933 | CB | VAL | Y | 21 | 115.757 | 30.241 | 68.577 | 1.00 | 95.06 chnY |
| ATOM | 5934 | CG1 | VAL | Y | 21 | 115.683 | 31.121 | 69.820 | 1.00 | 96.53 chnY |
| ATOM | 5935 | CG2 | VAL | Y | 21 | 114.839 | 30.809 | 67.479 | 1.00 | 95.65 chnY |
| ATOM | 5936 | C | VAL | Y | 21 | 118.151 | 29.711 | 69.190 | 1.00 | 95.62 chnY |
| ATOM | 5937 | O | VAL | Y | 21 | 119.301 | 30.153 | 69.268 | 1.00 | 99.57 chnY |
| ATOM | 5938 | N | VAL | Z | 1 | 92.373 | 38.930 | 63.723 | 1.00 | 99.87 chnZ |
| ATOM | 5939 | CA | VAL | Z | 1 | 92.529 | 39.269 | 62.309 | 1.00 | 99.36 chnZ |
| ATOM | 5940 | CB | VAL | Z | 1 | 91.363 | 38.655 | 61.457 | 1.00 | 100.56 chnZ |
| ATOM | 5941 | CG1 | VAL | Z | 1 | 89.993 | 39.187 | 61.927 | 1.00 | 98.89 chnZ |
| ATOM | 5942 | CG2 | VAL | Z | 1 | 91.586 | 38.924 | 59.962 | 1.00 | 100.42 chnZ |
| ATOM | 5943 | C | VAL | Z | 1 | 92.587 | 40.791 | 62.104 | 1.00 | 98.27 chnZ |
| ATOM | 5944 | O | VAL | Z | 1 | 91.808 | 41.527 | 62.721 | 1.00 | 98.49 chnZ |
| ATOM | 5945 | N | GLN | Z | 2 | 93.520 | 41.260 | 61.265 | 1.00 | 95.66 chnZ |
| ATOM | 5946 | CA | GLN | Z | 2 | 93.644 | 42.704 | 60.988 | 1.00 | 91.85 chnZ |
| ATOM | 5947 | CB | GLN | Z | 2 | 95.043 | 43.077 | 60.444 | 1.00 | 91.90 chnZ |
| ATOM | 5948 | CG | GLN | Z | 2 | 95.338 | 42.689 | 58.990 | 1.00 | 93.64 chnZ |
| ATOM | 5949 | CD | GLN | Z | 2 | 95.409 | 41.179 | 58.756 | 1.00 | 94.97 chnZ |
| ATOM | 5950 | OE1 | GLN | Z | 2 | 95.596 | 40.397 | 59.694 | 1.00 | 94.88 chnZ |
| ATOM | 5951 | NE2 | GLN | Z | 2 | 95.259 | 40.767 | 57.495 | 1.00 | 94.92 chnZ |
| ATOM | 5952 | C | GLN | Z | 2 | 92.514 | 43.215 | 60.063 | 1.00 | 87.45 chnZ |
| ATOM | 5953 | O | GLN | Z | 2 | 91.942 | 42.461 | 59.260 | 1.00 | 86.24 chnZ |
| ATOM | 5954 | N | CYS | Z | 3 | 92.177 | 44.492 | 60.208 | 1.00 | 78.66 chnZ |
| ATOM | 5955 | CA | CYS | Z | 3 | 91.095 | 45.080 | 59.432 | 1.00 | 71.31 chnZ |
| ATOM | 5956 | C | CYS | Z | 3 | 91.547 | 46.272 | 58.602 | 1.00 | 65.50 chnZ |
| ATOM | 5957 | O | CYS | Z | 3 | 92.569 | 46.893 | 58.895 | 1.00 | 66.80 chnZ |
| ATOM | 5958 | CB | CYS | Z | 3 | 89.977 | 45.503 | 60.383 | 1.00 | 70.38 chnZ |
| ATOM | 5959 | SG | CYS | Z | 3 | 89.447 | 44.180 | 61.520 | 1.00 | 71.62 chnZ |
| ATOM | 5960 | N | PRO | Z | 4 | 90.792 | 46.606 | 57.542 | 1.00 | 58.28 chnZ |
| ATOM | 5961 | CD | PRO | Z | 4 | 89.548 | 45.987 | 57.058 | 1.00 | 55.31 chnZ |
| ATOM | 5962 | CA | PRO | Z | 4 | 91.163 | 47.741 | 56.701 | 1.00 | 56.56 chnZ |
| ATOM | 5963 | CB | PRO | Z | 4 | 89.989 | 47.838 | 55.724 | 1.00 | 54.14 chnZ |
| ATOM | 5964 | CG | PRO | Z | 4 | 88.870 | 47.143 | 56.425 | 1.00 | 52.85 chnZ |
| ATOM | 5965 | C | PRO | Z | 4 | 91.327 | 48.994 | 57.543 | 1.00 | 57.99 chnZ |
| ATOM | 5966 | O | PRO | Z | 4 | 90.520 | 49.262 | 58.422 | 1.00 | 57.99 chnZ |
| ATOM | 5967 | N | HIS | Z | 5 | 92.401 | 49.734 | 57.291 | 1.00 | 61.46 chnZ |
| ATOM | 5968 | CA | HIS | Z | 5 | 92.714 | 50.955 | 58.032 | 1.00 | 62.21 chnZ |
| ATOM | 5969 | CB | HIS | Z | 5 | 93.926 | 51.655 | 57.399 | 1.00 | 73.22 chnZ |
| ATOM | 5970 | CG | HIS | Z | 5 | 94.331 | 52.920 | 58.098 | 1.00 | 83.55 chnZ |
| ATOM | 5971 | CD2 | HIS | Z | 5 | 94.869 | 54.069 | 57.616 | 1.00 | 86.65 chnZ |
| ATOM | 5972 | ND1 | HIS | Z | 5 | 94.168 | 53.110 | 59.448 | 1.00 | 87.08 chnZ |
| ATOM | 5973 | CE1 | HIS | Z | 5 | 94.582 | 54.325 | 59.777 | 1.00 | 88.25 chnZ |
| ATOM | 5974 | NE2 | HIS | Z | 5 | 95.010 | 54.924 | 58.683 | 1.00 | 88.35 chnZ |
| ATOM | 5975 | C | HIS | Z | 5 | 91.556 | 51.937 | 58.198 | 1.00 | 56.98 chnZ |
| ATOM | 5976 | O | HIS | Z | 5 | 91.455 | 52.608 | 59.214 | 1.00 | 55.09 chnZ |
| ATOM | 5977 | N | PHE | Z | 6 | 90.655 | 51.993 | 57.227 | 1.00 | 52.03 chnZ |
| ATOM | 5978 | CA | PHE | Z | 6 | 89.537 | 52.920 | 57.320 | 1.00 | 50.09 chnZ |
| ATOM | 5979 | CB | PHE | Z | 6 | 88.733 | 52.972 | 56.008 | 1.00 | 50.04 chnZ |
| ATOM | 5980 | CG | PHE | Z | 6 | 87.694 | 51.910 | 55.882 | 1.00 | 50.48 chnZ |
| ATOM | 5981 | CD1 | PHE | Z | 6 | 88.031 | 50.631 | 55.478 | 1.00 | 51.53 chnZ |
| ATOM | 5982 | CD2 | PHE | Z | 6 | 86.371 | 52.196 | 56.153 | 1.00 | 50.88 chnZ |
| ATOM | 5983 | CE1 | PHE | Z | 6 | 87.058 | 49.652 | 55.346 | 1.00 | 51.92 chnZ |
| ATOM | 5984 | CE2 | PHE | Z | 6 | 85.396 | 51.222 | 56.024 | 1.00 | 51.88 chnZ |
| ATOM | 5985 | CZ | PHE | Z | 6 | 85.742 | 49.947 | 55.619 | 1.00 | 51.00 chnZ |
| ATOM | 5986 | C | PHE | Z | 6 | 88.645 | 52.660 | 58.535 | 1.00 | 51.13 chnZ |
| ATOM | 5987 | O | PHE | Z | 6 | 87.788 | 53.474 | 58.863 | 1.00 | 52.03 chnZ |
| ATOM | 5988 | N | CYS | Z | 7 | 88.836 | 51.527 | 59.202 | 1.00 | 52.99 chnZ |
| ATOM | 5989 | CA | CYS | Z | 7 | 88.059 | 51.229 | 60.399 | 1.00 | 56.57 chnZ |
| ATOM | 5990 | C | CYS | Z | 7 | 88.584 | 52.121 | 61.519 | 1.00 | 61.62 chnZ |
| ATOM | 5991 | O | CYS | Z | 7 | 87.836 | 52.841 | 62.188 | 1.00 | 64.43 chnZ |
| ATOM | 5992 | CB | CYS | Z | 7 | 88.277 | 49.790 | 60.837 | 1.00 | 51.30 chnZ |
| ATOM | 5993 | SG | CYS | Z | 7 | 87.685 | 48.555 | 59.674 | 1.00 | 51.01 chnZ |
| ATOM | 5994 | N | TYR | Z | 8 | 89.897 | 52.049 | 61.704 | 1.00 | 66.30 chnZ |
| ATOM | 5995 | CA | TYR | Z | 8 | 90.589 | 52.789 | 62.733 | 1.00 | 70.29 chnZ |
| ATOM | 5996 | CB | TYR | Z | 8 | 91.990 | 52.218 | 62.914 | 1.00 | 72.04 chnZ |
| ATOM | 5997 | CG | TYR | Z | 8 | 91.998 | 50.721 | 63.116 | 1.00 | 75.36 chnZ |
| ATOM | 5998 | CD1 | TYR | Z | 8 | 92.967 | 49.926 | 62.515 | 1.00 | 78.41 chnZ |
| ATOM | 5999 | CE1 | TYR | Z | 8 | 92.968 | 48.545 | 62.684 | 1.00 | 81.56 chnZ |

-continued

| | | | | | | | | | | |
|---|---|---|---|---|---|---|---|---|---|---|
| ATOM | 6000 | CD2 | TYR | Z | 8 | 91.027 | 50.099 | 63.896 | 1.00 | 76.87 | chnZ |
| ATOM | 6001 | CE2 | TYR | Z | 8 | 91.017 | 48.721 | 64.071 | 1.00 | 79.67 | chnZ |
| ATOM | 6002 | CZ | TYR | Z | 8 | 91.991 | 47.949 | 63.462 | 1.00 | 81.53 | chnZ |
| ATOM | 6003 | OH | TYR | Z | 8 | 91.993 | 46.582 | 63.620 | 1.00 | 83.38 | chnZ |
| ATOM | 6004 | C | TYR | Z | 8 | 90.645 | 54.278 | 62.466 | 1.00 | 72.88 | chnZ |
| ATOM | 6005 | O | TYR | Z | 8 | 90.746 | 55.066 | 63.400 | 1.00 | 77.83 | chnZ |
| ATOM | 6006 | N | GLU | Z | 9 | 90.599 | 54.685 | 61.206 | 1.00 | 76.05 | chnZ |
| ATOM | 6007 | CA | GLU | Z | 9 | 90.637 | 56.112 | 60.936 | 1.00 | 80.20 | chnZ |
| ATOM | 6008 | CB | GLU | Z | 9 | 91.306 | 56.434 | 59.588 | 1.00 | 82.37 | chnZ |
| ATOM | 6009 | CG | GLU | Z | 9 | 90.638 | 55.873 | 58.330 | 1.00 | 83.77 | chnZ |
| ATOM | 6010 | CD | GLU | Z | 9 | 91.365 | 56.282 | 57.048 | 1.00 | 83.88 | chnZ |
| ATOM | 6011 | OE1 | GLU | Z | 9 | 92.380 | 55.643 | 56.695 | 1.00 | 82.89 | chnZ |
| ATOM | 6012 | OE2 | GLU | Z | 9 | 90.921 | 57.247 | 56.392 | 1.00 | 84.69 | chnZ |
| ATOM | 6013 | C | GLU | Z | 9 | 89.232 | 56.682 | 61.023 | 1.00 | 82.30 | chnZ |
| ATOM | 6014 | O | GLU | Z | 9 | 88.268 | 56.043 | 60.595 | 1.00 | 84.29 | chnZ |
| ATOM | 6015 | N | LEU | Z | 10 | 89.129 | 57.855 | 61.645 | 1.00 | 84.70 | chnZ |
| ATOM | 6016 | CA | LEU | Z | 10 | 87.864 | 58.575 | 61.846 | 1.00 | 88.30 | chnZ |
| ATOM | 6017 | CB | LEU | Z | 10 | 86.985 | 58.543 | 60.577 | 1.00 | 87.73 | chnZ |
| ATOM | 6018 | CG | LEU | Z | 10 | 87.353 | 59.524 | 59.443 | 1.00 | 90.10 | chnZ |
| ATOM | 6019 | CD1 | LEU | Z | 10 | 87.094 | 60.978 | 59.862 | 1.00 | 87.63 | chnZ |
| ATOM | 6020 | CD2 | LEU | Z | 10 | 88.811 | 59.347 | 59.014 | 1.00 | 89.44 | chnZ |
| ATOM | 6021 | C | LEU | Z | 10 | 87.055 | 58.155 | 63.085 | 1.00 | 88.57 | chnZ |
| ATOM | 6022 | O | LEU | Z | 10 | 87.193 | 57.039 | 63.595 | 1.00 | 87.06 | chnZ |
| ATOM | 6023 | N | ASP | Z | 11 | 86.241 | 59.088 | 63.578 | 1.00 | 90.48 | chnZ |
| ATOM | 6024 | CA | ASP | Z | 11 | 85.393 | 58.876 | 64.752 | 1.00 | 92.15 | chnZ |
| ATOM | 6025 | CB | ASP | Z | 11 | 84.658 | 60.170 | 65.124 | 1.00 | 94.93 | chnZ |
| ATOM | 6026 | CG | ASP | Z | 11 | 85.577 | 61.390 | 65.140 | 1.00 | 98.22 | chnZ |
| ATOM | 6027 | OD1 | ASP | Z | 11 | 85.165 | 62.442 | 64.593 | 1.00 | 98.57 | chnZ |
| ATOM | 6028 | OD2 | ASP | Z | 11 | 86.703 | 61.299 | 65.694 | 1.00 | 100.33 | chnZ |
| ATOM | 6029 | C | ASP | Z | 11 | 84.364 | 57.788 | 64.474 | 1.00 | 92.75 | chnZ |
| ATOM | 6030 | O | ASP | Z | 11 | 83.932 | 57.614 | 63.324 | 1.00 | 92.64 | chnZ |
| ATOM | 6031 | N | TYR | Z | 12 | 83.958 | 57.092 | 65.540 | 1.00 | 92.43 | chnZ |
| ATOM | 6032 | CA | TYR | Z | 12 | 82.985 | 55.994 | 65.493 | 1.00 | 90.79 | chnZ |
| ATOM | 6033 | CB | TYR | Z | 12 | 81.759 | 56.364 | 64.633 | 1.00 | 94.25 | chnZ |
| ATOM | 6034 | CG | TYR | Z | 12 | 80.575 | 55.428 | 64.783 | 1.00 | 99.01 | chnZ |
| ATOM | 6035 | CD1 | TYR | Z | 12 | 80.300 | 54.803 | 66.008 | 1.00 | 101.39 | chnZ |
| ATOM | 6036 | CE1 | TYR | Z | 12 | 79.202 | 53.928 | 66.161 | 1.00 | 103.48 | chnZ |
| ATOM | 6037 | CD2 | TYR | Z | 12 | 79.726 | 55.160 | 63.704 | 1.00 | 101.04 | chnZ |
| ATOM | 6038 | CE2 | TYR | Z | 12 | 78.622 | 54.283 | 63.844 | 1.00 | 103.58 | chnZ |
| ATOM | 6039 | CZ | TYR | Z | 12 | 78.368 | 53.669 | 65.077 | 1.00 | 103.70 | chnZ |
| ATOM | 6040 | OH | TYR | Z | 12 | 77.300 | 52.797 | 65.225 | 1.00 | 101.32 | chnZ |
| ATOM | 6041 | C | TYR | Z | 12 | 83.627 | 54.694 | 64.995 | 1.00 | 87.44 | chnZ |
| ATOM | 6042 | O | TYR | Z | 12 | 84.551 | 54.711 | 64.179 | 1.00 | 86.29 | chnZ |
| ATOM | 6043 | N | GLU | Z | 13 | 83.156 | 53.572 | 65.531 | 1.00 | 82.29 | chnZ |
| ATOM | 6044 | CA | GLU | Z | 13 | 83.664 | 52.254 | 65.157 | 1.00 | 77.19 | chnZ |
| ATOM | 6045 | CB | GLU | Z | 13 | 83.791 | 51.382 | 66.408 | 1.00 | 78.56 | chnZ |
| ATOM | 6046 | CG | GLU | Z | 13 | 84.604 | 52.010 | 67.534 | 1.00 | 80.73 | chnZ |
| ATOM | 6047 | CD | GLU | Z | 13 | 84.867 | 51.047 | 68.690 | 1.00 | 82.00 | chnZ |
| ATOM | 6048 | OE1 | GLU | Z | 13 | 84.074 | 50.097 | 68.886 | 1.00 | 83.53 | chnZ |
| ATOM | 6049 | OE2 | GLU | Z | 13 | 85.876 | 51.239 | 69.404 | 1.00 | 82.21 | chnZ |
| ATOM | 6050 | C | GLU | Z | 13 | 82.716 | 51.586 | 64.149 | 1.00 | 72.79 | chnZ |
| ATOM | 6051 | O | GLU | Z | 13 | 81.920 | 50.716 | 64.525 | 1.00 | 70.95 | chnZ |
| ATOM | 6052 | N | LEU | Z | 14 | 82.841 | 51.954 | 62.870 | 1.00 | 64.77 | chnZ |
| ATOM | 6053 | CA | LEU | Z | 14 | 81.965 | 51.415 | 61.825 | 1.00 | 58.62 | chnZ |
| ATOM | 6054 | CB | LEU | Z | 14 | 81.924 | 52.329 | 60.588 | 1.00 | 57.19 | chnZ |
| ATOM | 6055 | CG | LEU | Z | 14 | 83.148 | 52.531 | 59.697 | 1.00 | 56.73 | chnZ |
| ATOM | 6056 | CD1 | LEU | Z | 14 | 82.813 | 53.537 | 58.609 | 1.00 | 56.68 | chnZ |
| ATOM | 6057 | CD2 | LEU | Z | 14 | 84.336 | 53.014 | 60.515 | 1.00 | 58.23 | chnZ |
| ATOM | 6058 | C | LEU | Z | 14 | 82.168 | 49.956 | 61.426 | 1.00 | 56.30 | chnZ |
| ATOM | 6059 | O | LEU | Z | 14 | 81.239 | 49.307 | 60.950 | 1.00 | 54.48 | chnZ |
| ATOM | 6060 | N | CYS | Z | 15 | 83.367 | 49.429 | 61.619 | 1.00 | 52.04 | chnZ |
| ATOM | 6061 | CA | CYS | Z | 15 | 83.602 | 48.032 | 61.290 | 1.00 | 52.42 | chnZ |
| ATOM | 6062 | C | CYS | Z | 15 | 83.138 | 47.199 | 62.488 | 1.00 | 53.08 | chnZ |
| ATOM | 6063 | O | CYS | Z | 15 | 82.813 | 47.763 | 63.533 | 1.00 | 53.00 | chnZ |
| ATOM | 6064 | CB | CYS | Z | 15 | 85.082 | 47.820 | 61.004 | 1.00 | 50.45 | chnZ |
| ATOM | 6065 | SG | CYS | Z | 15 | 85.687 | 48.864 | 59.641 | 1.00 | 46.19 | chnZ |
| ATOM | 6066 | N | PRO | Z | 16 | 83.015 | 45.867 | 62.334 | 1.00 | 53.72 | chnZ |
| ATOM | 6067 | CD | PRO | Z | 16 | 83.258 | 45.044 | 61.140 | 1.00 | 54.50 | chnZ |
| ATOM | 6068 | CA | PRO | Z | 16 | 82.578 | 45.028 | 63.458 | 1.00 | 56.68 | chnZ |
| ATOM | 6069 | CB | PRO | Z | 16 | 82.574 | 43.619 | 62.859 | 1.00 | 55.50 | chnZ |
| ATOM | 6070 | CG | PRO | Z | 16 | 83.568 | 43.710 | 61.746 | 1.00 | 54.17 | chnZ |
| ATOM | 6071 | C | PRO | Z | 16 | 83.559 | 45.149 | 64.620 | 1.00 | 59.05 | chnZ |
| ATOM | 6072 | O | PRO | Z | 16 | 84.753 | 45.346 | 64.404 | 1.00 | 61.40 | chnZ |
| ATOM | 6073 | N | ASP | Z | 17 | 83.060 | 45.031 | 65.847 | 1.00 | 61.88 | chnZ |
| ATOM | 6074 | CA | ASP | Z | 17 | 83.910 | 45.173 | 67.022 | 1.00 | 63.66 | chnZ |
| ATOM | 6075 | CB | ASP | Z | 17 | 83.070 | 45.443 | 68.282 | 1.00 | 66.45 | chnZ |
| ATOM | 6076 | CG | ASP | Z | 17 | 81.927 | 44.461 | 68.459 | 1.00 | 66.88 | chnZ |
| ATOM | 6077 | OD1 | ASP | Z | 17 | 82.201 | 43.256 | 68.670 | 1.00 | 66.98 | chnZ |
| ATOM | 6078 | OD2 | ASP | Z | 17 | 80.755 | 44.908 | 68.407 | 1.00 | 66.89 | chnZ |

-continued

| ATOM | 6079 | C | ASP | Z | 17 | 84.990 | 44.111 | 67.265 | 1.00 | 61.43 | chnZ |
|---|---|---|---|---|---|---|---|---|---|---|---|
| ATOM | 6080 | O | ASP | Z | 17 | 85.544 | 44.008 | 68.358 | 1.00 | 60.20 | chnZ |
| ATOM | 6081 | N | VAL | Z | 18 | 85.302 | 43.337 | 66.236 | 1.00 | 60.89 | chnZ |
| ATOM | 6082 | CA | VAL | Z | 18 | 86.356 | 42.336 | 66.334 | 1.00 | 64.08 | chnZ |
| ATOM | 6083 | CB | VAL | Z | 18 | 86.107 | 41.163 | 65.362 | 1.00 | 63.86 | chnZ |
| ATOM | 6084 | CG1 | VAL | Z | 18 | 86.109 | 41.668 | 63.931 | 1.00 | 65.66 | chnZ |
| ATOM | 6085 | CG2 | VAL | Z | 18 | 87.158 | 40.069 | 65.553 | 1.00 | 65.81 | chnZ |
| ATOM | 6086 | C | VAL | Z | 18 | 87.666 | 43.038 | 65.954 | 1.00 | 64.60 | chnZ |
| ATOM | 6087 | O | VAL | Z | 18 | 88.765 | 42.532 | 66.185 | 1.00 | 62.57 | chnZ |
| ATOM | 6088 | N | CYS | Z | 19 | 87.523 | 44.217 | 65.362 | 1.00 | 67.18 | chnZ |
| ATOM | 6089 | CA | CYS | Z | 19 | 88.657 | 45.016 | 64.928 | 1.00 | 69.67 | chnZ |
| ATOM | 6090 | C | CYS | Z | 19 | 89.125 | 45.924 | 66.045 | 1.00 | 70.86 | chnZ |
| ATOM | 6091 | O | CYS | Z | 19 | 90.155 | 46.586 | 65.926 | 1.00 | 68.65 | chnZ |
| ATOM | 6092 | CB | CYS | Z | 19 | 88.264 | 45.864 | 63.717 | 1.00 | 69.59 | chnZ |
| ATOM | 6093 | SG | CYS | Z | 19 | 87.712 | 44.894 | 62.279 | 1.00 | 70.95 | chnZ |
| ATOM | 6094 | N | TYR | Z | 20 | 88.352 | 45.969 | 67.123 | 1.00 | 73.51 | chnZ |
| ATOM | 6095 | CA | TYR | Z | 20 | 88.694 | 46.814 | 68.256 | 1.00 | 79.00 | chnZ |
| ATOM | 6096 | CB | TYR | Z | 20 | 87.627 | 47.888 | 68.445 | 1.00 | 76.84 | chnZ |
| ATOM | 6097 | CG | TYR | Z | 20 | 87.297 | 48.638 | 67.180 | 1.00 | 76.23 | chnZ |
| ATOM | 6098 | CD1 | TYR | Z | 20 | 86.316 | 48.174 | 66.307 | 1.00 | 75.63 | chnZ |
| ATOM | 6099 | CE1 | TYR | Z | 20 | 85.991 | 48.877 | 65.141 | 1.00 | 75.02 | chnZ |
| ATOM | 6100 | CD2 | TYR | Z | 20 | 87.950 | 49.821 | 66.860 | 1.00 | 78.52 | chnZ |
| ATOM | 6101 | CE2 | TYR | Z | 20 | 87.629 | 50.532 | 65.696 | 1.00 | 77.89 | chnZ |
| ATOM | 6102 | CZ | TYR | Z | 20 | 86.650 | 50.055 | 64.846 | 1.00 | 75.09 | chnZ |
| ATOM | 6103 | OH | TYR | Z | 20 | 86.325 | 50.766 | 63.718 | 1.00 | 73.22 | chnZ |
| ATOM | 6104 | C | TYR | Z | 20 | 88.862 | 45.988 | 69.532 | 1.00 | 82.69 | chnZ |
| ATOM | 6105 | O | TYR | Z | 20 | 87.904 | 45.776 | 70.280 | 1.00 | 85.88 | chnZ |
| ATOM | 6106 | N | VAL | Z | 21 | 90.085 | 45.502 | 69.745 | 1.00 | 87.08 | chnZ |
| ATOM | 6107 | CA | VAL | Z | 21 | 90.461 | 44.689 | 70.904 | 1.00 | 88.78 | chnZ |
| ATOM | 6108 | CB | VAL | Z | 21 | 90.659 | 45.559 | 72.181 | 1.00 | 90.28 | chnZ |
| ATOM | 6109 | CG1 | VAL | Z | 21 | 89.316 | 45.939 | 72.820 | 1.00 | 90.38 | chnZ |
| ATOM | 6110 | CG2 | VAL | Z | 21 | 91.557 | 44.832 | 73.172 | 1.00 | 92.01 | chnZ |
| ATOM | 6111 | C | VAL | Z | 21 | 89.508 | 43.531 | 71.192 | 1.00 | 88.20 | chnZ |
| ATOM | 6112 | O | VAL | Z | 21 | 89.415 | 42.587 | 70.409 | 1.00 | 87.48 | chnZ |
| ATOM | 6113 | C1 | NAG | A | 221 | 104.837 | 20.694 | 58.989 | 1.00 | 74.97 | chnA |
| ATOM | 6114 | C2 | NAG | A | 221 | 105.545 | 21.910 | 58.456 | 1.00 | 78.66 | chnA |
| ATOM | 6115 | N2 | NAG | A | 221 | 105.598 | 21.850 | 57.010 | 1.00 | 81.85 | chnA |
| ATOM | 6116 | C7 | NAG | A | 221 | 104.870 | 22.690 | 56.279 | 1.00 | 84.75 | chnA |
| ATOM | 6117 | O7 | NAG | A | 221 | 104.118 | 23.542 | 56.772 | 1.00 | 85.40 | chnA |
| ATOM | 6118 | C8 | NAG | A | 221 | 104.989 | 22.555 | 54.768 | 1.00 | 84.21 | chnA |
| ATOM | 6119 | C3 | NAG | A | 221 | 106.938 | 21.922 | 59.034 | 1.00 | 79.60 | chnA |
| ATOM | 6120 | O3 | NAG | A | 221 | 107.624 | 23.091 | 58.623 | 1.00 | 80.44 | chnA |
| ATOM | 6121 | C4 | NAG | A | 221 | 106.921 | 21.864 | 60.554 | 1.00 | 79.99 | chnA |
| ATOM | 6122 | O4 | NAG | A | 221 | 108.256 | 21.521 | 60.959 | 1.00 | 82.13 | chnA |
| ATOM | 6123 | C5 | NAG | A | 221 | 105.942 | 20.792 | 61.092 | 1.00 | 80.28 | chnA |
| ATOM | 6124 | O5 | NAG | A | 221 | 104.680 | 20.836 | 60.397 | 1.00 | 77.40 | chnA |
| ATOM | 6125 | C6 | NAG | A | 221 | 105.626 | 20.997 | 62.568 | 1.00 | 81.34 | chnA |
| ATOM | 6126 | O6 | NAG | A | 221 | 105.332 | 19.770 | 63.223 | 1.00 | 85.16 | chnA |
| ATOM | 6127 | C1 | NAG | A | 222 | 108.779 | 22.063 | 62.118 | 1.00 | 81.55 | chnA |
| ATOM | 6128 | C2 | NAG | A | 222 | 110.233 | 21.648 | 62.231 | 1.00 | 84.63 | chnA |
| ATOM | 6129 | N2 | NAG | A | 222 | 110.389 | 20.203 | 62.117 | 1.00 | 85.54 | chnA |
| ATOM | 6130 | C7 | NAG | A | 222 | 109.726 | 19.369 | 62.915 | 1.00 | 86.21 | chnA |
| ATOM | 6131 | O7 | NAG | A | 222 | 108.958 | 19.750 | 63.802 | 1.00 | 87.09 | chnA |
| ATOM | 6132 | C8 | NAG | A | 222 | 109.963 | 17.879 | 62.698 | 1.00 | 86.86 | chnA |
| ATOM | 6133 | C3 | NAG | A | 222 | 110.766 | 22.179 | 63.548 | 1.00 | 83.32 | chnA |
| ATOM | 6134 | O3 | NAG | A | 222 | 112.134 | 21.823 | 63.709 | 1.00 | 87.25 | chnA |
| ATOM | 6135 | C4 | NAG | A | 222 | 110.621 | 23.701 | 63.623 | 1.00 | 81.15 | chnA |
| ATOM | 6136 | O4 | NAG | A | 222 | 110.898 | 24.054 | 65.000 | 1.00 | 82.73 | chnA |
| ATOM | 6137 | C5 | NAG | A | 222 | 109.182 | 24.149 | 63.211 | 1.00 | 77.17 | chnA |
| ATOM | 6138 | O5 | NAG | A | 222 | 108.720 | 23.479 | 62.016 | 1.00 | 77.46 | chnA |
| ATOM | 6139 | C6 | NAG | A | 222 | 109.103 | 25.621 | 62.877 | 1.00 | 75.27 | chnA |
| ATOM | 6140 | O6 | NAG | A | 222 | 109.236 | 25.832 | 61.477 | 1.00 | 68.33 | chnA |
| ATOM | 6141 | C1 | NAG | A | 223 | 111.157 | 25.352 | 65.446 | 1.00 | 84.37 | chnA |
| ATOM | 6142 | C2 | NAG | A | 223 | 112.576 | 25.502 | 66.019 | 1.00 | 83.30 | chnA |
| ATOM | 6143 | N2 | NAG | A | 223 | 112.791 | 24.519 | 67.073 | 1.00 | 86.95 | chnA |
| ATOM | 6144 | C7 | NAG | A | 223 | 113.853 | 23.714 | 67.064 | 1.00 | 87.45 | chnA |
| ATOM | 6145 | O7 | NAG | A | 223 | 114.723 | 23.756 | 66.198 | 1.00 | 87.23 | chnA |
| ATOM | 6146 | C8 | NAG | A | 223 | 113.974 | 22.719 | 68.211 | 1.00 | 87.85 | chnA |
| ATOM | 6147 | C3 | NAG | A | 223 | 112.707 | 26.918 | 66.591 | 1.00 | 82.99 | chnA |
| ATOM | 6148 | O3 | NAG | A | 223 | 114.039 | 27.138 | 67.016 | 1.00 | 78.80 | chnA |
| ATOM | 6149 | C4 | NAG | A | 223 | 112.317 | 27.957 | 65.534 | 1.00 | 83.62 | chnA |
| ATOM | 6150 | O4 | NAG | A | 223 | 112.324 | 29.268 | 66.091 | 1.00 | 84.36 | chnA |
| ATOM | 6151 | C5 | NAG | A | 223 | 110.931 | 27.639 | 64.976 | 1.00 | 85.52 | chnA |
| ATOM | 6152 | O5 | NAG | A | 223 | 110.929 | 26.309 | 64.422 | 1.00 | 83.48 | chnA |
| ATOM | 6153 | C6 | NAG | A | 223 | 110.485 | 28.599 | 63.891 | 1.00 | 88.38 | chnA |
| ATOM | 6154 | O6 | NAG | A | 223 | 110.798 | 28.097 | 62.597 | 1.00 | 95.74 | chnA |
| ATOM | 6155 | C1 | NAG | A | 242 | 98.938 | 2.347 | 52.468 | 1.00 | 54.85 | chnA |
| ATOM | 6156 | C2 | NAG | A | 242 | 100.434 | 2.107 | 52.628 | 1.00 | 52.42 | chnA |
| ATOM | 6157 | N2 | NAG | A | 242 | 100.867 | 2.564 | 53.931 | 1.00 | 55.43 | chnA |

-continued

| | | | | | | | | | | |
|---|---|---|---|---|---|---|---|---|---|---|
| ATOM | 6158 | C7 | NAG | A | 242 | 100.850 | 1.741 | 54.971 | 1.00 | 57.53 | chnA |
| ATOM | 6159 | O7 | NAG | A | 242 | 100.461 | 0.585 | 54.896 | 1.00 | 61.74 | chnA |
| ATOM | 6160 | C8 | NAG | A | 242 | 101.319 | 2.296 | 56.300 | 1.00 | 61.25 | chnA |
| ATOM | 6161 | C3 | NAG | A | 242 | 101.192 | 2.858 | 51.548 | 1.00 | 52.15 | chnA |
| ATOM | 6162 | O3 | NAG | A | 242 | 102.572 | 2.558 | 51.638 | 1.00 | 53.00 | chnA |
| ATOM | 6163 | C4 | NAG | A | 242 | 100.676 | 2.461 | 50.183 | 1.00 | 53.31 | chnA |
| ATOM | 6164 | O4 | NAG | A | 242 | 101.297 | 3.286 | 49.190 | 1.00 | 56.08 | chnA |
| ATOM | 6165 | C5 | NAG | A | 242 | 99.168 | 2.667 | 50.122 | 1.00 | 53.75 | chnA |
| ATOM | 6166 | O5 | NAG | A | 242 | 98.522 | 1.928 | 51.171 | 1.00 | 55.08 | chnA |
| ATOM | 6167 | C6 | NAG | A | 242 | 98.579 | 2.184 | 48.810 | 1.00 | 54.79 | chnA |
| ATOM | 6168 | O6 | NAG | A | 242 | 97.317 | 2.786 | 48.557 | 1.00 | 58.20 | chnA |
| ATOM | 6169 | C1 | NAG | A | 243 | 102.419 | 2.815 | 48.533 | 1.00 | 58.57 | chnA |
| ATOM | 6170 | C2 | NAG | A | 243 | 102.631 | 3.707 | 47.302 | 1.00 | 60.54 | chnA |
| ATOM | 6171 | N2 | NAG | A | 243 | 101.628 | 3.426 | 46.302 | 1.00 | 63.23 | chnA |
| ATOM | 6172 | C7 | NAG | A | 243 | 100.854 | 4.406 | 45.857 | 1.00 | 63.26 | chnA |
| ATOM | 6173 | O7 | NAG | A | 243 | 100.937 | 5.560 | 46.270 | 1.00 | 64.40 | chnA |
| ATOM | 6174 | C8 | NAG | A | 243 | 99.820 | 4.045 | 44.806 | 1.00 | 65.57 | chnA |
| ATOM | 6175 | C3 | NAG | A | 243 | 104.003 | 3.565 | 46.681 | 1.00 | 63.32 | chnA |
| ATOM | 6176 | O3 | NAG | A | 243 | 104.148 | 4.558 | 45.671 | 1.00 | 63.50 | chnA |
| ATOM | 6177 | C4 | NAG | A | 243 | 104.952 | 3.828 | 47.803 | 1.00 | 65.68 | chnA |
| ATOM | 6178 | O4 | NAG | A | 243 | 106.316 | 4.024 | 47.373 | 1.00 | 74.58 | chnA |
| ATOM | 6179 | C5 | NAG | A | 243 | 104.799 | 2.753 | 48.851 | 1.00 | 62.40 | chnA |
| ATOM | 6180 | O5 | NAG | A | 243 | 103.507 | 2.908 | 49.459 | 1.00 | 56.82 | chnA |
| ATOM | 6181 | C6 | NAG | A | 243 | 105.826 | 2.873 | 49.962 | 1.00 | 62.01 | chnA |
| ATOM | 6182 | O6 | NAG | A | 243 | 105.511 | 2.012 | 51.049 | 1.00 | 63.53 | chnA |
| ATOM | 6183 | C1 | MAN | A | 244 | 107.035 | 3.129 | 46.598 | 1.00 | 78.56 | chnA |
| ATOM | 6184 | C2 | MAN | A | 244 | 107.544 | 3.915 | 45.340 | 1.00 | 81.00 | chnA |
| ATOM | 6185 | O2 | MAN | A | 244 | 107.584 | 5.315 | 45.596 | 1.00 | 82.23 | chnA |
| ATOM | 6186 | C3 | MAN | A | 244 | 108.903 | 3.482 | 44.791 | 1.00 | 82.31 | chnA |
| ATOM | 6187 | O3 | MAN | A | 244 | 109.426 | 4.488 | 43.894 | 1.00 | 76.18 | chnA |
| ATOM | 6188 | C4 | MAN | A | 244 | 109.874 | 3.266 | 45.930 | 1.00 | 85.25 | chnA |
| ATOM | 6189 | O4 | MAN | A | 244 | 111.164 | 2.853 | 45.415 | 1.00 | 91.39 | chnA |
| ATOM | 6190 | C5 | MAN | A | 244 | 109.278 | 2.188 | 46.818 | 1.00 | 85.58 | chnA |
| ATOM | 6191 | O5 | MAN | A | 244 | 108.101 | 2.692 | 47.468 | 1.00 | 81.53 | chnA |
| ATOM | 6192 | C6 | MAN | A | 244 | 110.241 | 1.775 | 47.928 | 1.00 | 86.65 | chnA |
| ATOM | 6193 | O6 | MAN | A | 244 | 111.100 | 2.848 | 48.302 | 1.00 | 90.07 | chnA |
| ATOM | 6194 | C1 | MAN | A | 245 | 111.394 | 1.480 | 45.321 | 0.50 | 92.12 | chnA |
| ATOM | 6195 | C2 | MAN | A | 245 | 111.989 | 1.115 | 43.960 | 0.50 | 93.24 | chnA |
| ATOM | 6196 | O2 | MAN | A | 245 | 113.257 | 1.746 | 43.806 | 0.50 | 93.81 | chnA |
| ATOM | 6197 | C3 | MAN | A | 245 | 112.155 | −0.403 | 43.905 | 0.50 | 92.61 | chnA |
| ATOM | 6198 | O3 | MAN | A | 245 | 112.752 | −0.783 | 42.672 | 0.50 | 92.37 | chnA |
| ATOM | 6199 | C4 | MAN | A | 245 | 113.027 | −0.870 | 45.076 | 0.50 | 91.65 | chnA |
| ATOM | 6200 | O4 | MAN | A | 245 | 113.050 | −2.290 | 45.114 | 0.50 | 91.40 | chnA |
| ATOM | 6201 | C5 | MAN | A | 245 | 112.487 | −0.337 | 46.411 | 0.50 | 90.84 | chnA |
| ATOM | 6202 | O5 | MAN | A | 245 | 112.306 | 1.095 | 46.353 | 0.50 | 92.02 | chnA |
| ATOM | 6203 | C6 | MAN | A | 245 | 113.429 | −0.617 | 47.565 | 0.50 | 88.80 | chnA |
| ATOM | 6204 | O6 | MAN | A | 245 | 113.934 | 0.588 | 48.122 | 0.50 | 85.95 | chnA |
| ATOM | 6205 | C1 | MAN | A | 246 | 110.016 | 3.959 | 42.735 | 0.50 | 68.36 | chnA |
| ATOM | 6206 | C2 | MAN | A | 246 | 108.952 | 3.524 | 41.726 | 0.50 | 65.21 | chnA |
| ATOM | 6207 | O2 | MAN | A | 246 | 108.238 | 4.658 | 41.253 | 0.50 | 61.90 | chnA |
| ATOM | 6208 | C3 | MAN | A | 246 | 109.637 | 2.827 | 40.557 | 0.50 | 63.28 | chnA |
| ATOM | 6209 | O3 | MAN | A | 246 | 108.669 | 2.484 | 39.573 | 0.50 | 62.86 | chnA |
| ATOM | 6210 | C4 | MAN | A | 246 | 110.704 | 3.750 | 39.950 | 0.50 | 62.81 | chnA |
| ATOM | 6211 | O4 | MAN | A | 246 | 111.436 | 3.048 | 38.951 | 0.50 | 62.22 | chnA |
| ATOM | 6212 | C5 | MAN | A | 246 | 111.668 | 4.250 | 41.036 | 0.50 | 62.32 | chnA |
| ATOM | 6213 | O5 | MAN | A | 246 | 110.928 | 4.849 | 42.117 | 0.50 | 65.51 | chnA |
| ATOM | 6214 | C6 | MAN | A | 246 | 112.655 | 5.289 | 40.526 | 0.50 | 60.49 | chnA |
| ATOM | 6215 | O6 | MAN | A | 246 | 112.868 | 6.322 | 41.480 | 0.50 | 57.65 | chnA |
| ATOM | 6216 | C1 | NAG | A | 340 | 75.624 | 25.928 | 36.889 | 0.25 | 55.15 | chnA |
| ATOM | 6217 | C2 | NAG | A | 340 | 74.631 | 26.489 | 35.852 | 0.25 | 52.24 | chnA |
| ATOM | 6218 | N2 | NAG | A | 340 | 75.200 | 26.405 | 34.519 | 0.25 | 50.58 | chnA |
| ATOM | 6219 | C7 | NAG | A | 340 | 74.620 | 25.658 | 33.583 | 0.25 | 49.60 | chnA |
| ATOM | 6220 | O7 | NAG | A | 340 | 73.599 | 24.997 | 33.787 | 0.25 | 49.19 | chnA |
| ATOM | 6221 | C8 | NAG | A | 340 | 75.280 | 25.628 | 32.212 | 0.25 | 48.04 | chnA |
| ATOM | 6222 | C3 | NAG | A | 340 | 74.248 | 27.948 | 36.144 | 0.25 | 50.35 | chnA |
| ATOM | 6223 | O3 | NAG | A | 340 | 73.146 | 28.323 | 35.330 | 0.25 | 49.55 | chnA |
| ATOM | 6224 | C4 | NAG | A | 340 | 73.876 | 28.128 | 37.613 | 0.25 | 50.42 | chnA |
| ATOM | 6225 | O4 | NAG | A | 340 | 73.664 | 29.505 | 37.895 | 0.25 | 48.42 | chnA |
| ATOM | 6226 | C5 | NAG | A | 340 | 75.008 | 27.588 | 38.471 | 0.25 | 50.86 | chnA |
| ATOM | 6227 | O5 | NAG | A | 340 | 75.167 | 26.181 | 38.220 | 0.25 | 53.46 | chnA |
| ATOM | 6228 | C6 | NAG | A | 340 | 74.787 | 27.766 | 39.958 | 0.25 | 50.96 | chnA |
| ATOM | 6229 | O6 | NAG | A | 340 | 76.017 | 28.008 | 40.626 | 0.25 | 49.48 | chhA |
| ATOM | 6230 | C1 | NAG | A | 366 | 92.994 | 8.151 | 33.357 | 1.00 | 78.46 | chnA |
| ATOM | 6231 | C2 | NAG | A | 366 | 93.394 | 6.715 | 33.689 | 1.00 | 80.63 | chnA |
| ATOM | 6232 | N2 | NAG | A | 366 | 94.442 | 6.714 | 34.697 | 1.00 | 82.01 | chnA |
| ATOM | 6233 | C7 | NAG | A | 366 | 94.263 | 6.064 | 35.847 | 1.00 | 84.71 | chnA |
| ATOM | 6234 | O7 | NAG | A | 366 | 93.217 | 5.474 | 36.127 | 1.00 | 86.39 | chnA |
| ATOM | 6235 | C8 | NAG | A | 366 | 95.405 | 6.088 | 36.851 | 1.00 | 85.73 | chnA |
| ATOM | 6236 | C3 | NAG | A | 366 | 93.897 | 5.974 | 32.446 | 1.00 | 79.76 | chnA |

-continued

| | | | | | | | | | | |
|---|---|---|---|---|---|---|---|---|---|---|
| ATOM | 6237 | O3 | NAG | A | 366 | 94.002 | 4.583 | 32.741 | 1.00 | 84.12 | chnA |
| ATOM | 6238 | C4 | NAG | A | 366 | 92.963 | 6.169 | 31.243 | 1.00 | 76.32 | chnA |
| ATOM | 6239 | O4 | NAG | A | 366 | 93.612 | 5.675 | 30.049 | 1.00 | 71.31 | chnA |
| ATOM | 6240 | C5 | NAG | A | 366 | 92.603 | 7.650 | 31.059 | 1.00 | 75.34 | chnA |
| ATOM | 6241 | O5 | NAG | A | 366 | 92.053 | 8.179 | 32.279 | 1.00 | 75.65 | chnA |
| ATOM | 6242 | C6 | NAG | A | 366 | 91.568 | 7.886 | 29.963 | 1.00 | 75.21 | chnA |
| ATOM | 6243 | O6 | NAG | A | 366 | 90.511 | 6.932 | 30.017 | 1.00 | 77.26 | chnA |
| ATOM | 6244 | C1 | NAG | A | 367 | 93.171 | 4.440 | 29.597 | 0.25 | 64.04 | chnA |
| ATOM | 6245 | C2 | NAG | A | 367 | 93.539 | 4.260 | 28.133 | 0.25 | 60.90 | chnA |
| ATOM | 6246 | N2 | NAG | A | 367 | 92.922 | 5.303 | 27.336 | 0.25 | 58.09 | chnA |
| ATOM | 6247 | C7 | NAG | A | 367 | 93.603 | 6.404 | 27.025 | 0.25 | 56.08 | chnA |
| ATOM | 6248 | O7 | NAG | A | 367 | 94.764 | 6.603 | 27.385 | 0.25 | 54.29 | chnA |
| ATOM | 6249 | C8 | NAG | A | 367 | 92.883 | 7.447 | 26.187 | 0.25 | 54.61 | chnA |
| ATOM | 6250 | C3 | NAG | A | 367 | 93.062 | 2.890 | 27.664 | 0.25 | 59.34 | chnA |
| ATOM | 6251 | O3 | NAG | A | 367 | 93.494 | 2.667 | 26.330 | 0.25 | 58.15 | chnA |
| ATOM | 6252 | C4 | NAG | A | 367 | 93.620 | 1.797 | 28.573 | 0.25 | 59.07 | chnA |
| ATOM | 6253 | O4 | NAG | A | 367 | 93.033 | 0.530 | 28.215 | 0.25 | 58.42 | chnA |
| ATOM | 6254 | C5 | NAG | A | 367 | 93.309 | 2.105 | 30.039 | 0.25 | 59.48 | chnA |
| ATOM | 6255 | O5 | NAG | A | 367 | 93.792 | 3.418 | 30.381 | 0.25 | 62.18 | chnA |
| ATOM | 6256 | C6 | NAG | A | 367 | 93.976 | 1.122 | 30.985 | 0.25 | 59.23 | chnA |
| ATOM | 6257 | O6 | NAG | A | 367 | 93.691 | 1.432 | 32.342 | 0.25 | 58.60 | chnA |
| ATOM | 6258 | C1 | MAN | A | 368 | 93.902 | −0.536 | 28.029 | 0.25 | 56.62 | chnA |
| ATOM | 6259 | C2 | MAN | A | 368 | 93.109 | −1.844 | 27.969 | 0.25 | 55.97 | chnA |
| ATOM | 6260 | O2 | MAN | A | 368 | 92.120 | −1.763 | 26.950 | 0.25 | 55.47 | chnA |
| ATOM | 6261 | C3 | MAN | A | 368 | 94.052 | −3.012 | 27.684 | 0.25 | 54.70 | chnA |
| ATOM | 6262 | O3 | MAN | A | 368 | 93.304 | −4.210 | 27.524 | 0.25 | 55.37 | chnA |
| ATOM | 6263 | C4 | MAN | A | 368 | 94.854 | −2.730 | 26.417 | 0.25 | 54.41 | chnA |
| ATOM | 6264 | O4 | MAN | A | 368 | 95.814 | −3.757 | 26.217 | 0.25 | 52.58 | chnA |
| ATOM | 6265 | C5 | MAN | A | 368 | 95.564 | −1.380 | 26.534 | 0.25 | 54.80 | chnA |
| ATOM | 6266 | O5 | MAN | A | 368 | 94.607 | −0.332 | 26.799 | 0.25 | 55.98 | chnA |
| ATOM | 6267 | C6 | MAN | A | 368 | 96.291 | −1.007 | 25.258 | 0.25 | 54.68 | chnA |
| ATOM | 6268 | O6 | MAN | A | 368 | 95.418 | −1.051 | 24.140 | 0.25 | 54.59 | chnA |
| ATOM | 6269 | C1 | NAG | B | 221 | 100.288 | 53.819 | 59.600 | 1.00 | 74.88 | chnB |
| ATOM | 6270 | C2 | NAG | B | 221 | 99.516 | 52.561 | 59.238 | 1.00 | 77.24 | chnB |
| ATOM | 6271 | N2 | NAG | B | 221 | 99.070 | 52.620 | 57.857 | 1.00 | 79.86 | chnB |
| ATOM | 6272 | C7 | NAG | B | 221 | 99.385 | 51.642 | 57.010 | 1.00 | 80.11 | chnB |
| ATOM | 6273 | O7 | NAG | B | 221 | 100.071 | 50.664 | 57.331 | 1.00 | 79.21 | chnB |
| ATOM | 6274 | C8 | NAG | B | 221 | 98.874 | 51.781 | 55.584 | 1.00 | 79.29 | chnB |
| ATOM | 6275 | C3 | NAG | B | 221 | 98.315 | 52.403 | 60.170 | 1.00 | 76.37 | chnB |
| ATOM | 6276 | O3 | NAG | B | 221 | 97.686 | 51.146 | 59.938 | 1.00 | 81.49 | chnB |
| ATOM | 6277 | C4 | NAG | B | 221 | 98.721 | 52.484 | 61.637 | 1.00 | 73.15 | chnB |
| ATOM | 6278 | O4 | NAG | B | 221 | 97.526 | 52.656 | 62.428 | 1.00 | 64.13 | chnB |
| ATOM | 6279 | C5 | NAG | B | 221 | 99.671 | 53.662 | 61.897 | 1.00 | 76.26 | chnB |
| ATOM | 6280 | O5 | NAG | B | 221 | 100.753 | 53.681 | 60.940 | 1.00 | 76.25 | chnB |
| ATOM | 6281 | C6 | NAG | B | 221 | 100.310 | 53.580 | 63.278 | 1.00 | 78.92 | chnB |
| ATOM | 6282 | O6 | NAG | B | 221 | 99.693 | 54.473 | 64.200 | 1.00 | 82.26 | chnB |
| ATOM | 6283 | C1 | NAG | B | 222 | 97.257 | 51.703 | 63.395 | 0.50 | 54.97 | chnB |
| ATOM | 6284 | C2 | NAG | B | 222 | 96.105 | 52.173 | 64.250 | 0.50 | 52.12 | chnB |
| ATOM | 6285 | N2 | NAG | B | 222 | 96.413 | 53.438 | 64.891 | 0.50 | 50.48 | chnB |
| ATOM | 6286 | C7 | NAG | B | 222 | 96.099 | 54.591 | 64.305 | 0.50 | 49.78 | chnB |
| ATOM | 6287 | O7 | NAG | B | 222 | 95.589 | 54.667 | 63.184 | 0.50 | 47.66 | chnB |
| ATOM | 6288 | C8 | NAG | B | 222 | 96.447 | 55.857 | 65.064 | 0.50 | 49.52 | chnB |
| ATOM | 6289 | C3 | NAG | B | 222 | 95.788 | 51.131 | 65.305 | 0.50 | 49.94 | chnB |
| ATOM | 6290 | O3 | NAG | B | 222 | 94.614 | 51.544 | 65.984 | 0.50 | 51.88 | chnB |
| ATOM | 6291 | C4 | NAG | B | 222 | 95.573 | 49.738 | 64.676 | 0.50 | 49.13 | chnB |
| ATOM | 6292 | O4 | NAG | B | 222 | 95.597 | 48.719 | 65.708 | 0.50 | 48.54 | chnB |
| ATOM | 6293 | C5 | NAG | B | 222 | 96.677 | 49.415 | 63.662 | 0.50 | 49.47 | chnB |
| ATOM | 6294 | O5 | NAG | B | 222 | 96.868 | 50.502 | 62.738 | 0.50 | 52.17 | chnB |
| ATOM | 6295 | C6 | NAG | B | 222 | 96.360 | 48.179 | 62.839 | 0.50 | 49.67 | chnB |
| ATOM | 6296 | O6 | NAG | B | 222 | 96.004 | 48.513 | 61.505 | 0.50 | 48.67 | chnB |
| ATOM | 6297 | C1 | NAG | B | 223 | 94.436 | 48.477 | 66.433 | 0.50 | 48.32 | chnB |
| ATOM | 6298 | C2 | NAG | B | 223 | 94.649 | 47.286 | 67.363 | 0.50 | 47.88 | chnB |
| ATOM | 6299 | N2 | NAG | B | 223 | 94.936 | 46.085 | 66.586 | 0.50 | 48.37 | chnB |
| ATOM | 6300 | C7 | NAG | B | 223 | 94.136 | 45.013 | 66.564 | 0.50 | 48.87 | chnB |
| ATOM | 6301 | O7 | NAG | B | 223 | 93.076 | 44.923 | 67.188 | 0.50 | 47.76 | chnB |
| ATOM | 6302 | C8 | NAG | B | 223 | 94.597 | 43.850 | 65.695 | 0.50 | 47.04 | chnB |
| ATOM | 6303 | C3 | NAG | B | 223 | 93.437 | 47.098 | 68.282 | 0.50 | 49.02 | chnB |
| ATOM | 6304 | O3 | NAG | B | 223 | 93.762 | 46.148 | 69.287 | 0.50 | 51.89 | chnB |
| ATOM | 6305 | C4 | NAG | B | 223 | 93.046 | 48.412 | 68.957 | 0.50 | 49.70 | chnB |
| ATOM | 6306 | O4 | NAG | B | 223 | 91.806 | 48.259 | 69.635 | 0.50 | 51.13 | chnB |
| ATOM | 6307 | C5 | NAG | B | 223 | 92.929 | 49.525 | 67.930 | 0.50 | 49.90 | chnB |
| ATOM | 6308 | O5 | NAG | B | 223 | 94.161 | 49.636 | 67.213 | 0.50 | 49.16 | chnB |
| ATOM | 6309 | C6 | NAG | B | 223 | 92.651 | 50.880 | 68.556 | 0.50 | 50.09 | chnB |
| ATOM | 6310 | O6 | NAG | B | 223 | 93.558 | 51.153 | 69.614 | 0.50 | 52.47 | chnB |
| ATOM | 6311 | C1 | NAG | B | 242 | 105.573 | 72.499 | 52.534 | 1.00 | 62.10 | chnB |
| ATOM | 6312 | C2 | NAG | B | 242 | 104.138 | 72.694 | 52.959 | 1.00 | 61.93 | chnB |
| ATOM | 6313 | N2 | NAG | B | 242 | 103.941 | 72.193 | 54.298 | 1.00 | 65.54 | chnB |
| ATOM | 6314 | C7 | NAG | B | 242 | 103.738 | 73.045 | 55.296 | 1.00 | 68.14 | chnB |
| ATOM | 6315 | O7 | NAG | B | 242 | 103.727 | 74.264 | 55.142 | 1.00 | 70.95 | chnB |

-continued

| | | | | | | | | | | |
|---|---|---|---|---|---|---|---|---|---|---|
| ATOM | 6316 | C8 | NAG | B | 242 | 103.534 | 72.453 | 56.679 | 1.00 | 70.05 | chnB |
| ATOM | 6317 | C3 | NAG | B | 242 | 103.226 | 71.961 | 52.003 | 1.00 | 62.68 | chnB |
| ATOM | 6318 | O3 | NAG | B | 242 | 101.881 | 72.214 | 52.366 | 1.00 | 62.04 | chnB |
| ATOM | 6319 | C4 | NAG | B | 242 | 103.469 | 72.426 | 50.573 | 1.00 | 62.80 | chnB |
| ATOM | 6320 | O4 | NAG | B | 242 | 102.759 | 71.556 | 49.672 | 1.00 | 63.56 | chnB |
| ATOM | 6321 | C5 | NAG | B | 242 | 104.967 | 72.389 | 50.227 | 1.00 | 64.02 | chnB |
| ATOM | 6322 | O5 | NAG | B | 242 | 105.749 | 73.072 | 51.237 | 1.00 | 62.86 | chnB |
| ATOM | 6323 | C6 | NAG | B | 242 | 105.266 | 73.069 | 48.892 | 1.00 | 65.40 | chnB |
| ATOM | 6324 | O6 | NAG | B | 242 | 105.930 | 72.193 | 47.986 | 1.00 | 67.31 | chnB |
| ATOM | 6325 | C1 | NAG | B | 243 | 101.525 | 71.968 | 49.194 | 1.00 | 67.38 | chnB |
| ATOM | 6326 | C2 | NAG | B | 243 | 101.125 | 71.043 | 48.026 | 1.00 | 70.71 | chnB |
| ATOM | 6327 | N2 | NAG | B | 243 | 102.003 | 71.242 | 46.889 | 1.00 | 75.15 | chnB |
| ATOM | 6328 | C7 | NAG | B | 243 | 102.456 | 70.193 | 46.205 | 1.00 | 77.65 | chnB |
| ATOM | 6329 | O7 | NAG | B | 243 | 102.171 | 69.026 | 46.492 | 1.00 | 78.31 | chnB |
| ATOM | 6330 | C8 | NAG | B | 243 | 103.367 | 70.480 | 45.020 | 1.00 | 78.24 | chnB |
| ATOM | 6331 | C3 | NAG | B | 243 | 99.670 | 71.252 | 47.610 | 1.00 | 69.36 | chnB |
| ATOM | 6332 | O3 | NAG | B | 243 | 99.324 | 70.329 | 46.584 | 1.00 | 72.59 | chnB |
| ATOM | 6333 | C4 | NAG | B | 243 | 98.902 | 70.966 | 48.867 | 1.00 | 68.23 | chnB |
| ATOM | 6334 | O4 | NAG | B | 243 | 97.488 | 70.725 | 48.667 | 1.00 | 66.25 | chnB |
| ATOM | 6335 | C5 | NAG | B | 243 | 99.212 | 72.050 | 49.886 | 1.00 | 68.10 | chnB |
| ATOM | 6336 | O5 | NAG | B | 243 | 100.590 | 71.889 | 50.289 | 1.00 | 66.27 | chnB |
| ATOM | 6337 | C6 | NAG | B | 243 | 98.346 | 71.971 | 51.144 | 1.00 | 69.93 | chnB |
| ATOM | 6338 | O6 | NAG | B | 243 | 98.797 | 72.859 | 52.160 | 1.00 | 68.90 | chnB |
| ATOM | 6339 | C1 | MAN | B | 244 | 96.601 | 71.612 | 48.090 | 0.25 | 57.50 | chnB |
| ATOM | 6340 | C2 | MAN | B | 244 | 96.047 | 70.933 | 46.814 | 0.25 | 54.69 | chnB |
| ATOM | 6341 | O2 | MAN | B | 244 | 95.871 | 69.542 | 47.041 | 0.25 | 52.85 | chnB |
| ATOM | 6342 | C3 | MAN | B | 244 | 94.727 | 71.529 | 46.329 | 0.25 | 52.02 | chnB |
| ATOM | 6343 | O3 | MAN | B | 244 | 94.175 | 70.707 | 45.281 | 0.25 | 48.06 | chnB |
| ATOM | 6344 | C4 | MAN | B | 244 | 93.754 | 71.582 | 47.487 | 0.25 | 53.14 | chnB |
| ATOM | 6345 | O4 | MAN | B | 244 | 92.498 | 72.148 | 47.056 | 0.25 | 53.04 | chnB |
| ATOM | 6346 | C5 | MAN | B | 244 | 94.377 | 72.428 | 48.584 | 0.25 | 53.92 | chnB |
| ATOM | 6347 | O5 | MAN | B | 244 | 95.566 | 71.788 | 49.075 | 0.25 | 56.28 | chnB |
| ATOM | 6348 | C6 | MAN | B | 244 | 93.447 | 72.582 | 49.770 | 0.25 | 53.10 | chnB |
| ATOM | 6349 | O6 | MAN | B | 244 | 92.757 | 71.370 | 50.037 | 0.25 | 50.89 | chnB |
| ATOM | 6350 | C1 | MAN | B | 245 | 92.391 | 73.530 | 47.116 | 0.25 | 53.16 | chnB |
| ATOM | 6351 | C2 | MAN | B | 245 | 91.807 | 74.079 | 45.818 | 0.25 | 52.67 | chnB |
| ATOM | 6352 | O2 | MAN | B | 245 | 90.517 | 73.522 | 45.596 | 0.25 | 52.72 | chnB |
| ATOM | 6353 | C3 | MAN | B | 245 | 91.710 | 75.601 | 45.925 | 0.25 | 52.01 | chnB |
| ATOM | 6354 | O3 | MAN | B | 245 | 91.075 | 76.132 | 44.770 | 0.25 | 51.29 | chnB |
| ATOM | 6355 | C4 | MAN | B | 245 | 90.924 | 75.998 | 47.174 | 0.25 | 51.22 | chnB |
| ATOM | 6356 | O4 | MAN | B | 245 | 91.003 | 77.404 | 47.350 | 0.25 | 50.06 | chnB |
| ATOM | 6357 | C5 | MAN | B | 245 | 91.481 | 75.298 | 48.418 | 0.25 | 51.63 | chnB |
| ATOM | 6358 | O5 | MAN | B | 245 | 91.538 | 73.873 | 48.210 | 0.25 | 52.51 | chnB |
| ATOM | 6359 | C6 | MAN | B | 245 | 90.632 | 75.536 | 49.654 | 0.25 | 51.90 | chnB |
| ATOM | 6360 | O6 | MAN | B | 245 | 89.304 | 75.070 | 49.466 | 0.25 | 50.57 | chnB |
| ATOM | 6361 | C1 | MAN | B | 246 | 94.671 | 70.947 | 43.997 | 0.25 | 45.00 | chnB |
| ATOM | 6362 | C2 | MAN | B | 246 | 95.999 | 70.220 | 43.813 | 0.25 | 43.99 | chnB |
| ATOM | 6363 | O2 | MAN | B | 246 | 95.801 | 68.818 | 43.951 | 0.25 | 43.63 | chnB |
| ATOM | 6364 | C3 | MAN | B | 246 | 96.564 | 70.527 | 42.430 | 0.25 | 42.95 | chnB |
| ATOM | 6365 | O3 | MAN | B | 246 | 97.754 | 69.778 | 42.225 | 0.25 | 42.70 | chnB |
| ATOM | 6366 | C4 | MAN | B | 246 | 95.537 | 70.171 | 41.355 | 0.25 | 42.08 | chnB |
| ATOM | 6367 | O4 | MAN | B | 246 | 96.007 | 70.600 | 40.085 | 0.25 | 40.52 | chnB |
| ATOM | 6368 | C5 | MAN | B | 246 | 94.189 | 70.834 | 41.647 | 0.25 | 42.14 | chnB |
| ATOM | 6369 | O5 | MAN | B | 246 | 93.760 | 70.536 | 42.990 | 0.25 | 43.15 | chnB |
| ATOM | 6370 | C6 | MAN | B | 246 | 93.098 | 70.338 | 40.716 | 0.25 | 41.20 | chnB |
| ATOM | 6371 | O6 | MAN | B | 246 | 92.848 | 68.952 | 40.907 | 0.25 | 39.59 | chnB |
| ATOM | 6372 | C1 | NAG | B | 340 | 125.412 | 48.656 | 33.093 | 0.50 | 75.90 | chnB |
| ATOM | 6373 | C2 | NAG | B | 340 | 126.296 | 48.033 | 32.018 | 0.50 | 74.88 | chnB |
| ATOM | 6374 | N2 | NAG | B | 340 | 125.817 | 48.401 | 30.700 | 0.50 | 74.93 | chnB |
| ATOM | 6375 | C7 | NAG | B | 340 | 126.684 | 48.722 | 29.744 | 0.50 | 74.40 | chnB |
| ATOM | 6376 | O7 | NAG | B | 340 | 127.905 | 48.735 | 29.921 | 0.50 | 73.58 | chnB |
| ATOM | 6377 | C8 | NAG | B | 340 | 126.108 | 49.091 | 28.383 | 0.50 | 73.71 | chnB |
| ATOM | 6378 | C3 | NAG | B | 340 | 126.311 | 46.513 | 32.159 | 0.50 | 74.80 | chnB |
| ATOM | 6379 | O3 | NAG | B | 340 | 127.258 | 45.964 | 31.252 | 0.50 | 73.57 | chnB |
| ATOM | 6380 | C4 | NAG | B | 340 | 126.684 | 46.126 | 33.590 | 0.50 | 75.15 | chnB |
| ATOM | 6381 | O4 | NAG | B | 340 | 126.560 | 44.720 | 33.757 | 0.50 | 75.44 | chnB |
| ATOM | 6382 | C5 | NAG | B | 340 | 125.780 | 46.841 | 34.590 | 0.50 | 75.93 | chnB |
| ATOM | 6383 | O5 | NAG | B | 340 | 125.863 | 48.266 | 34.393 | 0.50 | 76.21 | chnB |
| ATOM | 6384 | C6 | NAG | B | 340 | 126.199 | 46.557 | 36.021 | 0.50 | 76.57 | chnB |
| ATOM | 6385 | O6 | NAG | B | 340 | 125.255 | 47.065 | 36.951 | 0.50 | 77.14 | chnB |
| ATOM | 6386 | C1 | NAG | B | 366 | 107.869 | 67.077 | 32.994 | 0.75 | 82.06 | chnB |
| ATOM | 6387 | C2 | NAG | B | 366 | 107.106 | 68.051 | 33.896 | 0.75 | 83.67 | chnB |
| ATOM | 6388 | N2 | NAG | B | 366 | 106.441 | 67.310 | 34.951 | 0.75 | 89.56 | chnB |
| ATOM | 6389 | C7 | NAG | B | 366 | 106.533 | 67.719 | 36.214 | 0.75 | 92.91 | chnB |
| ATOM | 6390 | O7 | NAG | B | 366 | 107.164 | 68.728 | 36.549 | 0.75 | 94.15 | chnB |
| ATOM | 6391 | C8 | NAG | B | 366 | 105.810 | 66.885 | 37.268 | 0.75 | 94.28 | chnB |
| ATOM | 6392 | C3 | NAG | B | 366 | 106.069 | 68.845 | 33.105 | 0.75 | 82.16 | chnB |
| ATOM | 6393 | O3 | NAG | B | 366 | 105.482 | 69.827 | 33.952 | 0.75 | 80.92 | chnB |
| ATOM | 6394 | C4 | NAG | B | 366 | 106.760 | 69.514 | 31.923 | 0.75 | 79.60 | chnB |

-continued

| | | | | | | | | | |
|---|---|---|---|---|---|---|---|---|---|
| ATOM | 6395 | O4 | NAG | B | 366 | 105.811 | 70.263 | 31.137 | 0.75 | 75.05 | chnB |
| ATOM | 6396 | C5 | NAG | B | 366 | 107.453 | 68.450 | 31.067 | 0.75 | 79.07 | chnB |
| ATOM | 6397 | O5 | NAG | B | 366 | 108.437 | 67.749 | 31.861 | 0.75 | 79.90 | chnB |
| ATOM | 6398 | C6 | NAG | B | 366 | 108.190 | 69.054 | 29.886 | 0.75 | 77.46 | chnB |
| ATOM | 6399 | O6 | NAG | B | 366 | 107.561 | 68.720 | 28.660 | 0.75 | 74.17 | chnB |
| ATOM | 6400 | C1 | NAG | B | 367 | 105.838 | 71.630 | 31.366 | 0.25 | 72.18 | chnB |
| ATOM | 6401 | C2 | NAG | B | 367 | 105.254 | 72.381 | 30.177 | 0.25 | 70.66 | chnB |
| ATOM | 6402 | N2 | NAG | B | 367 | 106.066 | 72.138 | 28.997 | 0.25 | 68.34 | chnB |
| ATOM | 6403 | C7 | NAG | B | 367 | 107.321 | 72.580 | 28.935 | 0.25 | 66.78 | chnB |
| ATOM | 6404 | O7 | NAG | B | 367 | 107.861 | 73.209 | 29.847 | 0.25 | 65.31 | chnB |
| ATOM | 6405 | C8 | NAG | B | 367 | 108.097 | 72.280 | 27.663 | 0.25 | 65.22 | chnB |
| ATOM | 6406 | C3 | NAG | B | 367 | 105.205 | 73.882 | 30.477 | 0.25 | 70.69 | chnB |
| ATOM | 6407 | O3 | NAG | B | 367 | 104.487 | 74.548 | 29.448 | 0.25 | 70.59 | chnB |
| ATOM | 6408 | C4 | NAG | B | 367 | 104.531 | 74.153 | 31.826 | 0.25 | 71.02 | chnB |
| ATOM | 6409 | O4 | NAG | B | 367 | 104.696 | 75.539 | 32.178 | 0.25 | 71.46 | chnB |
| ATOM | 6410 | C5 | NAG | B | 367 | 105.152 | 73.284 | 32.916 | 0.25 | 71.19 | chnB |
| ATOM | 6411 | O5 | NAG | B | 367 | 105.075 | 71.901 | 32.539 | 0.25 | 71.77 | chnB |
| ATOM | 6412 | C6 | NAG | B | 367 | 104.454 | 73.423 | 34.256 | 0.25 | 70.71 | chnB |
| ATOM | 6413 | O6 | NAG | B | 367 | 105.143 | 72.707 | 35.271 | 0.25 | 68.86 | chnB |
| ATOM | 6414 | C1 | MAN | B | 368 | 103.559 | 76.208 | 32.600 | 0.25 | 71.63 | chnB |
| ATOM | 6415 | C2 | MAN | B | 368 | 103.965 | 77.493 | 33.329 | 0.25 | 72.05 | chnB |
| ATOM | 6416 | O2 | MAN | B | 368 | 104.825 | 78.267 | 32.502 | 0.25 | 72.20 | chnB |
| ATOM | 6417 | C3 | MAN | B | 368 | 102.723 | 78.307 | 33.687 | 0.25 | 71.98 | chnB |
| ATOM | 6418 | O3 | MAN | B | 368 | 103.107 | 79.542 | 34.275 | 0.25 | 72.18 | chnB |
| ATOM | 6419 | C4 | MAN | B | 368 | 101.906 | 78.564 | 32.425 | 0.25 | 71.45 | chnB |
| ATOM | 6420 | O4 | MAN | B | 368 | 100.715 | 79.265 | 32.757 | 0.25 | 70.49 | chnB |
| ATOM | 6421 | C5 | MAN | B | 368 | 101.564 | 77.228 | 31.767 | 0.25 | 70.93 | chnB |
| ATOM | 6422 | O5 | MAN | B | 368 | 102.775 | 76.517 | 31.441 | 0.25 | 71.26 | chnB |
| ATOM | 6423 | C6 | MAN | B | 368 | 100.777 | 77.387 | 30.479 | 0.25 | 70.25 | chnB |
| ATOM | 6424 | O6 | MAN | B | 368 | 101.613 | 77.806 | 29.410 | 0.25 | 69.63 | chnB |
| ATOM | 6425 | C1 | NAG | C | 221 | 137.535 | 23.832 | 55.793 | 1.00 | 91.36 | chnC |
| ATOM | 6426 | C2 | NAG | C | 221 | 136.232 | 23.602 | 55.056 | 1.00 | 94.07 | chnC |
| ATOM | 6427 | N2 | NAG | C | 221 | 135.359 | 24.752 | 55.191 | 1.00 | 96.44 | chnC |
| ATOM | 6428 | C7 | NAG | C | 221 | 134.696 | 25.199 | 54.1427 | 1.00 | 98.15 | chnC |
| ATOM | 6429 | O7 | NAG | C | 221 | 134.763 | 24.660 | 53.015 | 1.00 | 98.52 | chnC |
| ATOM | 6430 | C8 | NAG | C | 221 | 133.802 | 26.415 | 54.326 | 1.00 | 98.54 | chnC |
| ATOM | 6431 | C3 | NAG | C | 221 | 135.583 | 22.345 | 55.621 | 1.00 | 95.33 | chnC |
| ATOM | 6432 | O3 | NAG | C | 221 | 134.392 | 22.060 | 54.895 | 1.00 | 94.84 | chnC |
| ATOM | 6433 | C4 | NAG | C | 221 | 136.564 | 21.156 | 55.510 | 1.00 | 95.88 | chnC |
| ATOM | 6434 | O4 | NAG | C | 221 | 136.047 | 20.022 | 56.245 | 1.00 | 95.53 | chnC |
| ATOM | 6435 | C5 | NAG | C | 221 | 137.972 | 21.509 | 56.048 | 1.00 | 95.43 | chnC |
| ATOM | 6436 | O5 | NAG | C | 221 | 138.432 | 22.764 | 55.506 | 1.00 | 93.99 | chnC |
| ATOM | 6437 | C6 | NAG | C | 221 | 139.026 | 20.471 | 55.681 | 1.00 | 95.77 | chnC |
| ATOM | 6438 | O6 | NAG | C | 221 | 140.342 | 21.013 | 55.767 | 1.00 | 95.06 | chnC |
| ATOM | 6439 | C1 | NAG | C | 222 | 134.730 | 19.659 | 55.994 | 0.50 | 94.07 | chnC |
| ATOM | 6440 | C2 | NAG | C | 222 | 134.673 | 18.201 | 55.539 | 0.50 | 94.10 | chnC |
| ATOM | 6441 | N2 | NAG | C | 222 | 135.352 | 18.055 | 54.264 | 0.50 | 94.41 | chnC |
| ATOM | 6442 | C7 | NAG | C | 222 | 136.262 | 17.102 | 54.093 | 0.50 | 94.26 | chnC |
| ATOM | 6443 | O7 | NAG | C | 222 | 136.591 | 16.315 | 54.983 | 0.50 | 94.42 | chnC |
| ATOM | 6444 | C8 | NAG | C | 222 | 136.917 | 17.020 | 52.725 | 0.50 | 93.68 | chnC |
| ATOM | 6445 | C3 | NAG | C | 222 | 133.226 | 17.736 | 55.392 | 0.50 | 93.52 | chnC |
| ATOM | 6446 | O3 | NAG | C | 222 | 133.202 | 16.332 | 55.164 | 0.50 | 93.12 | chnC |
| ATOM | 6447 | C4 | NAG | C | 222 | 132.420 | 18.059 | 56.647 | 0.50 | 93.90 | chnC |
| ATOM | 6448 | O4 | NAG | C | 222 | 131.043 | 17.806 | 56.405 | 0.50 | 94.31 | chnC |
| ATOM | 6449 | C5 | NAG | C | 222 | 132.601 | 19.522 | 57.046 | 0.50 | 93.99 | chnC |
| ATOM | 6450 | O5 | NAG | C | 222 | 133.997 | 19.823 | 57.206 | 0.50 | 93.79 | chnC |
| ATOM | 6451 | C6 | NAG | C | 222 | 131.928 | 19.840 | 58.370 | 0.50 | 94.63 | chnC |
| ATOM | 6452 | O6 | NAG | C | 222 | 132.200 | 18.839 | 59.343 | 0.50 | 93.82 | chnC |
| ATOM | 6453 | C1 | NAG | C | 242 | 139.180 | 36.905 | 71.285 | 1.00 | 54.14 | chnC |
| ATOM | 6454 | C2 | NAG | C | 242 | 138.267 | 35.833 | 71.827 | 1.00 | 49.81 | chnC |
| ATOM | 6455 | N2 | NAG | C | 242 | 138.806 | 34.514 | 71.585 | 1.00 | 48.25 | chnC |
| ATOM | 6456 | C7 | NAG | C | 242 | 139.669 | 33.970 | 72.431 | 1.00 | 49.62 | chnC |
| ATOM | 6457 | O7 | NAG | C | 242 | 140.130 | 34.561 | 73.408 | 1.00 | 51.34 | chnC |
| ATOM | 6458 | C8 | NAG | C | 242 | 140.143 | 32.570 | 72.096 | 1.00 | 49.61 | chnC |
| ATOM | 6459 | C3 | NAG | C | 242 | 136.930 | 35.952 | 71.146 | 1.00 | 53.07 | chnC |
| ATOM | 6460 | O3 | NAG | C | 242 | 136.072 | 34.946 | 71.646 | 1.00 | 53.77 | chnC |
| ATOM | 6461 | C4 | NAG | C | 242 | 136.343 | 37.335 | 71.398 | 1.00 | 57.32 | chnC |
| ATOM | 6462 | O4 | NAG | C | 242 | 135.123 | 37.493 | 70.641 | 1.00 | 65.07 | chnC |
| ATOM | 6463 | C5 | NAG | C | 242 | 137.348 | 38.403 | 70.961 | 1.00 | 56.70 | chnC |
| ATOM | 6464 | O5 | NAG | C | 242 | 138.628 | 38.189 | 71.595 | 1.00 | 54.69 | chnC |
| ATOM | 6465 | C6 | NAG | C | 242 | 136.884 | 39.802 | 71.324 | 1.00 | 56.87 | chnC |
| ATOM | 6466 | O6 | NAG | C | 242 | 137.968 | 40.716 | 71.375 | 1.00 | 60.85 | chnC |
| ATOM | 6467 | C1 | NAG | C | 243 | 133.912 | 37.241 | 71.276 | 1.00 | 71.78 | chnC |
| ATOM | 6468 | C2 | NAG | C | 243 | 132.766 | 37.587 | 70.299 | 1.00 | 76.24 | chnC |
| ATOM | 6469 | N2 | NAG | C | 243 | 132.687 | 39.014 | 70.056 | 1.00 | 77.81 | chnC |
| ATOM | 6470 | C7 | NAG | C | 243 | 133.063 | 39.503 | 68.874 | 1.00 | 80.85 | chnC |
| ATOM | 6471 | O7 | NAG | C | 243 | 133.497 | 38.792 | 67.953 | 1.00 | 80.66 | chnC |
| ATOM | 6472 | C8 | NAG | C | 243 | 132.949 | 41.010 | 68.678 | 1.00 | 81.09 | chnC |
| ATOM | 6473 | C3 | NAG | C | 243 | 131.418 | 37.034 | 70.774 | 1.00 | 78.15 | chnC |

-continued

| ATOM | 6474 | O3 | NAG | C | 243 | 130.414 | 37.311 | 69.807 | 1.00 | 81.45 | chnC |
|---|---|---|---|---|---|---|---|---|---|---|---|
| ATOM | 6475 | C4 | NAG | C | 243 | 131.704 | 35.565 | 70.858 | 1.00 | 79.13 | chnC |
| ATOM | 6476 | O4 | NAG | C | 243 | 130.564 | 34.689 | 70.875 | 1.00 | 85.43 | chnC |
| ATOM | 6477 | C5 | NAG | C | 243 | 132.617 | 35.344 | 72.017 | 1.00 | 76.03 | chnC |
| ATOM | 6478 | O5 | NAG | C | 243 | 133.908 | 35.843 | 71.641 | 1.00 | 73.62 | chnC |
| ATOM | 6479 | C6 | NAG | C | 243 | 132.759 | 33.872 | 72.363 | 1.00 | 74.91 | chnC |
| ATOM | 6480 | O6 | NAG | C | 243 | 134.116 | 33.452 | 72.361 | 1.00 | 74.34 | chnC |
| ATOM | 6481 | C1 | MAN | C | 244 | 129.362 | 34.955 | 71.498 | 1.00 | 91.72 | chnC |
| ATOM | 6482 | C2 | MAN | C | 244 | 128.340 | 35.376 | 70.414 | 1.00 | 95.61 | chnC |
| ATOM | 6483 | O2 | MAN | C | 244 | 128.467 | 34.539 | 69.274 | 1.00 | 100.77 | chnC |
| ATOM | 6484 | C3 | MAN | C | 244 | 126.892 | 35.320 | 70.892 | 1.00 | 97.64 | chnC |
| ATOM | 6485 | O3 | MAN | C | 244 | 125.999 | 35.477 | 69.760 | 1.00 | 102.68 | chnC |
| ATOM | 6486 | C4 | MAN | C | 244 | 126.611 | 33.978 | 71.551 | 1.00 | 95.58 | chnC |
| ATOM | 6487 | O4 | MAN | C | 244 | 125.298 | 34.022 | 72.161 | 1.00 | 96.12 | chnC |
| ATOM | 6488 | C5 | MAN | C | 244 | 127.673 | 33.661 | 72.621 | 1.00 | 93.56 | chnC |
| ATOM | 6489 | O5 | MAN | C | 244 | 128.989 | 33.696 | 72.058 | 1.00 | 90.93 | chnC |
| ATOM | 6490 | C6 | MAN | C | 244 | 127.510 | 32.257 | 73.184 | 1.00 | 92.69 | chnC |
| ATOM | 6491 | O6 | MAN | C | 244 | 127.425 | 31.291 | 72.140 | 1.00 | 91.14 | chnC |
| ATOM | 6492 | C1 | MAN | C | 245 | 125.273 | 34.300 | 73.526 | 0.50 | 93.19 | chnC |
| ATOM | 6493 | C2 | MAN | C | 245 | 123.988 | 35.022 | 73.928 | 0.50 | 92.40 | chnC |
| ATOM | 6494 | O2 | MAN | C | 245 | 122.856 | 34.210 | 73.636 | 0.50 | 91.93 | chnC |
| ATOM | 6495 | C3 | MAN | C | 245 | 124.050 | 35.318 | 75.431 | 0.50 | 91.13 | chnC |
| ATOM | 6496 | O3 | MAN | C | 245 | 122.811 | 35.865 | 75.862 | 0.50 | 90.73 | chnC |
| ATOM | 6497 | C4 | MAN | C | 245 | 124.366 | 34.043 | 76.238 | 0.50 | 90.02 | chnC |
| ATOM | 6498 | O4 | MAN | C | 245 | 124.656 | 34.394 | 77.585 | 0.50 | 89.29 | chnC |
| ATOM | 6499 | C5 | MAN | C | 245 | 125.566 | 33.288 | 75.646 | 0.50 | 89.38 | chnC |
| ATOM | 6500 | O5 | MAN | C | 245 | 125.370 | 33.071 | 74.242 | 0.50 | 91.79 | chnC |
| ATOM | 6501 | C6 | MAN | C | 245 | 125.784 | 31.923 | 76.270 | 0.50 | 87.79 | chnC |
| ATOM | 6502 | O6 | MAN | C | 245 | 126.315 | 31.003 | 75.322 | 0.50 | 84.42 | chnC |
| ATOM | 6503 | C1 | MAN | C | 246 | 125.470 | 36.766 | 69.545 | 1.00 | 106.48 | chnC |
| ATOM | 6504 | C2 | MAN | C | 246 | 126.282 | 37.502 | 68.476 | 1.00 | 106.64 | chnC |
| ATOM | 6505 | O2 | MAN | C | 246 | 126.133 | 36.842 | 67.224 | 1.00 | 107.90 | chnC |
| ATOM | 6506 | C3 | MAN | C | 246 | 125.780 | 38.942 | 68.364 | 1.00 | 106.57 | chnC |
| ATOM | 6507 | O3 | MAN | C | 246 | 126.457 | 39.604 | 67.302 | 1.00 | 103.85 | chnC |
| ATOM | 6508 | C4 | MAN | C | 246 | 124.262 | 38.979 | 68.107 | 1.00 | 107.95 | chnC |
| ATOM | 6509 | O4 | MAN | C | 246 | 123.798 | 40.320 | 68.261 | 1.00 | 108.89 | chnC |
| ATOM | 6510 | C5 | MAN | C | 246 | 123.475 | 38.055 | 69.072 | 1.00 | 108.33 | chnC |
| ATOM | 6511 | O5 | MAN | C | 246 | 124.093 | 36.744 | 69.158 | 1.00 | 108.03 | chnC |
| ATOM | 6512 | C6 | MAN | C | 246 | 122.007 | 37.836 | 68.666 | 1.00 | 107.56 | chnC |
| ATOM | 6513 | O6 | MAN | C | 246 | 121.688 | 38.433 | 67.408 | 1.00 | 103.55 | chnC |
| ATOM | 6514 | C1 | NAG | C | 340 | 142.986 | 57.399 | 41.172 | 0.25 | 74.75 | chnC |
| ATOM | 6515 | C2 | NAG | C | 340 | 143.087 | 58.456 | 40.074 | 0.25 | 73.02 | chnC |
| ATOM | 6516 | N2 | NAG | C | 340 | 141.885 | 59.269 | 40.060 | 0.25 | 72.17 | chnC |
| ATOM | 6517 | C7 | NAG | C | 340 | 141.970 | 60.595 | 39.998 | 0.25 | 71.34 | chnC |
| ATOM | 6518 | O7 | NAG | C | 340 | 143.041 | 61.200 | 39.942 | 0.25 | 70.97 | chnC |
| ATOM | 6519 | C8 | NAG | C | 340 | 140.661 | 61.367 | 39.988 | 0.25 | 71.58 | chnC |
| ATOM | 6520 | C3 | NAG | C | 340 | 143.282 | 57.779 | 38.717 | 0.25 | 72.34 | chnC |
| ATOM | 6521 | O3 | NAG | C | 340 | 143.506 | 58.765 | 37.719 | 0.25 | 71.77 | chnC |
| ATOM | 6522 | C4 | NAG | C | 340 | 144.474 | 56.819 | 38.773 | 0.25 | 72.15 | chnC |
| ATOM | 6523 | O4 | NAG | C | 340 | 144.555 | 56.083 | 37.559 | 0.25 | 71.67 | chnC |
| ATOM | 6524 | C5 | NAG | C | 340 | 144.316 | 55.853 | 39.947 | 0.25 | 72.27 | chnC |
| ATOM | 6525 | O5 | NAG | C | 340 | 144.165 | 56.589 | 41.174 | 0.25 | 73.81 | chnC |
| ATOM | 6526 | C6 | NAG | C | 340 | 145.503 | 54.927 | 40.125 | 0.25 | 71.63 | chnC |
| ATOM | 6527 | O6 | NAG | C | 340 | 145.154 | 53.790 | 40.903 | 0.25 | 70.35 | chnC |
| ATOM | 6528 | C1 | NAG | C | 366 | 130.258 | 52.182 | 62.615 | 0.75 | 78.87 | chnC |
| ATOM | 6529 | C2 | NAG | C | 366 | 130.147 | 53.664 | 62.881 | 0.75 | 79.49 | chnC |
| ATOM | 6530 | N2 | NAG | C | 366 | 131.482 | 54.219 | 63.012 | 0.75 | 76.56 | chnC |
| ATOM | 6531 | C7 | NAG | C | 366 | 131.709 | 55.492 | 62.719 | 0.75 | 75.51 | chnC |
| ATOM | 6532 | O7 | NAG | C | 366 | 130.818 | 56.265 | 62.365 | 0.75 | 74.51 | chnC |
| ATOM | 6533 | C8 | NAG | C | 366 | 133.136 | 55.993 | 62.871 | 0.75 | 73.90 | chnC |
| ATOM | 6534 | C3 | NAG | C | 366 | 129.345 | 53.876 | 64.160 | 0.75 | 81.20 | chnC |
| ATOM | 6535 | O3 | NAG | C | 366 | 129.152 | 55.271 | 64.369 | 0.75 | 83.36 | chnC |
| ATOM | 6536 | C4 | NAG | C | 366 | 127.989 | 53.168 | 64.016 | 0.75 | 81.52 | chnC |
| ATOM | 6537 | O4 | NAG | C | 366 | 127.200 | 53.301 | 65.229 | 0.75 | 79.86 | chnC |
| ATOM | 6538 | C5 | NAG | C | 366 | 128.183 | 51.681 | 63.640 | 0.75 | 81.62 | chnC |
| ATOM | 6539 | O5 | NAG | C | 366 | 128.981 | 51.577 | 62.436 | 0.75 | 80.65 | chnC |
| ATOM | 6540 | C6 | NAG | C | 366 | 126.872 | 50.953 | 63.376 | 0.75 | 81.69 | chnC |
| ATOM | 6541 | O6 | NAG | C | 366 | 125.842 | 51.856 | 62.994 | 0.75 | 81.67 | chnC |
| ATOM | 6542 | C1 | NAG | C | 367 | 127.813 | 53.078 | 66.457 | 0.25 | 76.23 | chnC |
| ATOM | 6543 | C2 | NAG | C | 367 | 127.426 | 54.210 | 67.431 | 0.25 | 75.28 | chnC |
| ATOM | 6544 | N2 | NAG | C | 367 | 128.046 | 55.458 | 67.020 | 0.25 | 75.63 | chnC |
| ATOM | 6545 | C7 | NAG | C | 367 | 127.378 | 56.606 | 67.117 | 0.25 | 76.02 | chnC |
| ATOM | 6546 | O7 | NAG | C | 367 | 126.224 | 56.679 | 67.546 | 0.25 | 76.50 | chnC |
| ATOM | 6547 | C8 | NAG | C | 367 | 128.095 | 57.869 | 66.670 | 0.25 | 75.52 | chnC |
| ATOM | 6548 | C3 | NAG | C | 367 | 127.849 | 53.885 | 68.869 | 0.25 | 73.83 | chnC |
| ATOM | 6549 | O3 | NAG | C | 367 | 127.339 | 54.871 | 69.758 | 0.25 | 73.79 | chnC |
| ATOM | 6550 | C4 | NAG | C | 367 | 127.318 | 52.513 | 69.261 | 0.25 | 73.47 | chnC |
| ATOM | 6551 | O4 | NAG | C | 367 | 127.757 | 52.170 | 70.594 | 0.25 | 70.49 | chnC |
| ATOM | 6552 | C5 | NAG | C | 367 | 127.842 | 51.499 | 68.253 | 0.25 | 74.05 | chnC |

-continued

| | | | | | | | | | | |
|---|---|---|---|---|---|---|---|---|---|---|
| ATOM | 6553 | O5 | NAG | C | 367 | 127.337 | 51.816 | 66.941 | 0.25 | 75.29 | chnC |
| ATOM | 6554 | C6 | NAG | C | 367 | 127.426 | 50.076 | 68.568 | 0.25 | 74.57 | chnC |
| ATOM | 6555 | O6 | NAG | C | 367 | 128.561 | 49.233 | 68.711 | 0.25 | 75.06 | chnC |
| ATOM | 6556 | C1 | MAN | C | 368 | 126.763 | 51.863 | 71.516 | 0.25 | 68.72 | chnC |
| ATOM | 6557 | C2 | MAN | C | 368 | 127.392 | 51.331 | 72.804 | 0.25 | 67.74 | chnC |
| ATOM | 6558 | O2 | MAN | C | 368 | 128.324 | 52.279 | 73.309 | 0.25 | 67.31 | chnC |
| ATOM | 6559 | C3 | MAN | C | 368 | 126.298 | 51.065 | 73.843 | 0.25 | 67.40 | chnC |
| ATOM | 6560 | O3 | MAN | C | 368 | 126.878 | 50.656 | 75.075 | 0.25 | 66.88 | chnC |
| ATOM | 6561 | C4 | MAN | C | 368 | 125.471 | 52.328 | 74.056 | 0.25 | 66.95 | chnC |
| ATOM | 6562 | O4 | MAN | C | 368 | 124.394 | 52.051 | 74.938 | 0.25 | 66.06 | chnC |
| ATOM | 6563 | C5 | MAN | C | 368 | 124.930 | 52.827 | 72.713 | 0.25 | 66.84 | chnC |
| ATOM | 6564 | O5 | MAN | C | 368 | 126.018 | 53.057 | 71.790 | 0.25 | 67.80 | chnC |
| ATOM | 6565 | C6 | MAN | C | 368 | 124.159 | 54.133 | 72.836 | 0.25 | 66.85 | chnC |
| ATOM | 6566 | O6 | MAN | C | 368 | 124.624 | 54.916 | 73.927 | 0.25 | 66.21 | chnC |
| ATOM | 6567 | C1 | NAG | D | 221 | 67.506 | 50.400 | 60.960 | 1.00 | 82.37 | chnD |
| ATOM | 6568 | C2 | NAG | D | 221 | 68.345 | 50.687 | 59.712 | 1.00 | 85.59 | chnD |
| ATOM | 6569 | N2 | NAG | D | 221 | 69.157 | 49.525 | 59.381 | 1.00 | 88.03 | chnD |
| ATOM | 6570 | C7 | NAG | D | 221 | 68.749 | 48.658 | 58.453 | 1.00 | 90.62 | chnD |
| ATOM | 6571 | O7 | NAG | D | 221 | 67.684 | 48.780 | 57.836 | 1.00 | 92.98 | chnD |
| ATOM | 6572 | C8 | NAG | D | 221 | 69.656 | 47.467 | 58.168 | 1.00 | 89.30 | chnD |
| ATOM | 6573 | C3 | NAG | D | 221 | 69.258 | 51.909 | 59.929 | 1.00 | 86.36 | chnD |
| ATOM | 6574 | O3 | NAG | D | 221 | 69.772 | 52.324 | 58.667 | 1.00 | 84.68 | chnD |
| ATOM | 6575 | C4 | NAG | D | 221 | 68.513 | 53.093 | 60.586 | 1.00 | 86.20 | chnD |
| ATOM | 6576 | O4 | NAG | D | 221 | 69.461 | 54.057 | 61.104 | 1.00 | 87.53 | chnD |
| ATOM | 6577 | C5 | NAG | D | 221 | 67.627 | 52.634 | 61.748 | 1.00 | 83.94 | chnD |
| ATOM | 6578 | O5 | NAG | D | 221 | 66.765 | 51.559 | 61.338 | 1.00 | 83.46 | chnD |
| ATOM | 6579 | C6 | NAG | D | 221 | 66.731 | 53.751 | 62.245 | 1.00 | 82.58 | chnD |
| ATOM | 6580 | O6 | NAG | D | 221 | 67.407 | 54.570 | 63.190 | 1.00 | 80.58 | chnD |
| ATOM | 6581 | C1 | NAG | D | 222 | 70.550 | 54.433 | 60.325 | 0.50 | 86.84 | chnD |
| ATOM | 6582 | C2 | NAG | D | 222 | 70.219 | 55.732 | 59.565 | 0.50 | 86.80 | chnD |
| ATOM | 6583 | N2 | NAG | D | 222 | 69.208 | 55.482 | 58.553 | 0.50 | 87.74 | chnD |
| ATOM | 6584 | C7 | NAG | D | 222 | 68.306 | 56.418 | 58.266 | 0.50 | 88.51 | chnD |
| ATOM | 6585 | O7 | NAG | D | 222 | 68.270 | 57.512 | 58.836 | 0.50 | 88.22 | chnD |
| ATOM | 6586 | C8 | NAG | D | 222 | 67.281 | 56.087 | 57.189 | 0.50 | 87.64 | chnD |
| ATOM | 6587 | C3 | NAG | D | 222 | 71.467 | 56.315 | 58.898 | 0.50 | 86.22 | chnD |
| ATOM | 6588 | O3 | NAG | D | 222 | 71.166 | 57.580 | 58.329 | 0.50 | 85.67 | chnD |
| ATOM | 6589 | C4 | NAG | D | 222 | 72.563 | 56.475 | 59.933 | 0.50 | 86.24 | chnD |
| ATOM | 6590 | O4 | NAG | D | 222 | 73.741 | 56.980 | 59.320 | 0.50 | 86.59 | chnD |
| ATOM | 6637 | C3 | MAN | D | 245 | 83.180 | 39.887 | 78.645 | 0.25 | 69.49 | chnD |
| ATOM | 6638 | O3 | MAN | D | 245 | 84.494 | 39.407 | 78.893 | 0.25 | 68.54 | chnD |
| ATOM | 6639 | C4 | MAN | D | 245 | 82.909 | 41.130 | 79.493 | 0.25 | 68.75 | chnD |
| ATOM | 6640 | O4 | MAN | D | 245 | 82.929 | 40.778 | 80.868 | 0.25 | 68.80 | chnD |
| ATOM | 6641 | C5 | MAN | D | 245 | 81.546 | 41.733 | 79.139 | 0.25 | 68.07 | chnD |
| ATOM | 6642 | O5 | MAN | D | 245 | 81.472 | 41.998 | 77.725 | 0.25 | 69.39 | chnD |
| ATOM | 6643 | C6 | MAN | D | 245 | 81.271 | 43.042 | 79.859 | 0.25 | 67.20 | chnD |
| ATOM | 6644 | O6 | MAN | D | 245 | 81.694 | 44.161 | 79.091 | 0.25 | 64.83 | chnD |
| ATOM | 6645 | C1 | MAN | D | 246 | 81.437 | 37.733 | 73.421 | 0.25 | 66.77 | chnD |
| ATOM | 6646 | C2 | MAN | D | 246 | 80.357 | 37.073 | 72.573 | 0.25 | 65.05 | chnD |
| ATOM | 6647 | O2 | MAN | D | 246 | 80.330 | 37.672 | 71.286 | 0.25 | 63.49 | chnD |
| ATOM | 6648 | C3 | MAN | D | 246 | 80.663 | 35.590 | 72.445 | 0.25 | 63.67 | chnD |
| ATOM | 6649 | O3 | MAN | D | 246 | 79.691 | 34.973 | 71.616 | 0.25 | 63.19 | chnD |
| ATOM | 6650 | C4 | MAN | D | 246 | 82.056 | 35.403 | 71.845 | 0.25 | 63.48 | chnD |
| ATOM | 6651 | O4 | MAN | D | 246 | 82.383 | 34.020 | 71.821 | 0.25 | 62.15 | chnD |
| ATOM | 6652 | C5 | MAN | D | 246 | 83.094 | 36.170 | 72.676 | 0.25 | 63.23 | chnD |
| ATOM | 6653 | O5 | MAN | D | 246 | 82.705 | 37.553 | 72.808 | 0.25 | 65.03 | chnD |
| ATOM | 6654 | C6 | MAN | D | 246 | 84.481 | 36.148 | 72.060 | 0.25 | 62.72 | chnD |
| ATOM | 6655 | O6 | MAN | D | 246 | 84.672 | 37.238 | 71.171 | 0.25 | 61.05 | chnD |
| ATOM | 6656 | C1 | NAG | D | 340 | 60.856 | 16.630 | 47.315 | 0.25 | 75.36 | chnD |
| ATOM | 6657 | C2 | NAG | D | 340 | 60.746 | 15.505 | 46.287 | 0.25 | 73.19 | chnD |
| ATOM | 6658 | N2 | NAG | D | 340 | 62.017 | 14.817 | 46.162 | 0.25 | 70.68 | chnD |
| ATOM | 6659 | C7 | NAG | D | 340 | 62.077 | 13.493 | 46.280 | 0.25 | 69.58 | chnD |
| ATOM | 6660 | O7 | NAG | D | 340 | 61.087 | 12.792 | 46.490 | 0.25 | 68.45 | chnD |
| ATOM | 6661 | C8 | NAG | D | 340 | 63.446 | 12.846 | 46.138 | 0.25 | 68.94 | chnD |
| ATOM | 6662 | C3 | NAG | D | 340 | 60.325 | 16.085 | 44.937 | 0.25 | 72.10 | chnD |
| ATOM | 6663 | O3 | NAG | D | 340 | 60.126 | 15.033 | 44.003 | 0.25 | 72.32 | chnD |
| ATOM | 6664 | C4 | NAG | D | 340 | 59.035 | 16.890 | 45.096 | 0.25 | 71.85 | chnD |
| ATOM | 6665 | O4 | NAG | D | 340 | 58.718 | 17.532 | 43.870 | 0.25 | 70.22 | chnD |
| ATOM | 6666 | C5 | NAG | D | 340 | 59.212 | 17.939 | 46.193 | 0.25 | 72.48 | chnD |
| ATOM | 6667 | O5 | NAG | D | 340 | 59.599 | 17.306 | 47.427 | 0.25 | 74.43 | chnD |
| ATOM | 6668 | C6 | NAG | D | 340 | 57.951 | 18.729 | 46.475 | 0.25 | 71.88 | chnD |
| ATOM | 6669 | O6 | NAG | D | 340 | 58.240 | 19.899 | 47.228 | 0.25 | 71.18 | chnD |
| ATOM | 6670 | C1 | NAG | D | 366 | 76.451 | 22.157 | 66.441 | 0.75 | 86.33 | chnD |
| ATOM | 6671 | C2 | NAG | D | 366 | 76.799 | 23.359 | 67.340 | 0.75 | 86.84 | chnD |
| ATOM | 6672 | N2 | NAG | D | 366 | 76.806 | 24.584 | 66.557 | 0.75 | 85.80 | chnD |
| ATOM | 6673 | C7 | NAG | D | 366 | 75.847 | 25.493 | 66.723 | 0.75 | 85.23 | chnD |
| ATOM | 6674 | O7 | NAG | D | 366 | 74.923 | 25.357 | 67.529 | 0.75 | 85.18 | chnD |
| ATOM | 6675 | C8 | NAG | D | 366 | 75.924 | 26.746 | 65.866 | 0.75 | 83.44 | chnD |
| ATOM | 6676 | C3 | NAG | D | 366 | 78.174 | 23.141 | 67.993 | 0.75 | 87.51 | chnD |
| ATOM | 6677 | O3 | NAG | D | 366 | 78.465 | 24.207 | 68.892 | 0.75 | 88.18 | chnD |

-continued

| | | | | | | | | | | |
|---|---|---|---|---|---|---|---|---|---|---|
| ATOM | 6678 | C4 | NAG | D | 366 | 78.162 | 21.801 | 68.737 | 0.75 | 86.64 chnD |
| ATOM | 6679 | O4 | NAG | D | 366 | 79.446 | 21.533 | 69.346 | 0.75 | 84.11 chnD |
| ATOM | 6680 | C5 | NAG | D | 366 | 77.802 | 20.688 | 67.752 | 0.75 | 86.77 chnD |
| ATOM | 6681 | O5 | NAG | D | 366 | 76.493 | 20.937 | 67.197 | 0.75 | 86.44 chnD |
| ATOM | 6682 | C6 | NAG | D | 366 | 77.792 | 19.288 | 68.355 | 0.75 | 87.93 chnD |
| ATOM | 6683 | O6 | NAG | D | 366 | 77.232 | 19.271 | 69.663 | 0.75 | 88.68 chnD |
| ATOM | 6684 | C1 | NAG | D | 367 | 79.408 | 21.329 | 70.721 | 0.25 | 79.19 chnD |
| ATOM | 6685 | C2 | NAG | D | 367 | 80.447 | 20.289 | 71.142 | 0.25 | 77.71 chnD |
| ATOM | 6686 | N2 | NAG | D | 367 | 80.162 | 19.018 | 70.502 | 0.25 | 75.61 chnD |
| ATOM | 6687 | C7 | NAG | D | 367 | 80.975 | 18.541 | 69.565 | 0.25 | 74.84 chnD |
| ATOM | 6688 | O7 | NAG | D | 367 | 81.990 | 19.130 | 69.192 | 0.25 | 74.52 chnD |
| ATOM | 6689 | C8 | NAG | D | 367 | 80.604 | 17.204 | 68.944 | 0.25 | 73.93 chnD |
| ATOM | 6690 | C3 | NAG | D | 367 | 80.409 | 20.125 | 72.664 | 0.25 | 76.79 chnD |
| ATOM | 6691 | O3 | NAG | D | 367 | 81.456 | 19.261 | 73.081 | 0.25 | 76.97 chnD |
| ATOM | 6692 | C4 | NAG | D | 367 | 80.559 | 21.481 | 73.359 | 0.25 | 76.64 chnD |
| ATOM | 6693 | O4 | NAG | D | 367 | 80.343 | 21.320 | 74.777 | 0.25 | 75.96 chnD |
| ATOM | 6694 | C5 | NAG | D | 367 | 79.540 | 22.477 | 72.798 | 0.25 | 76.76 chnD |
| ATOM | 6695 | O5 | NAG | D | 367 | 79.674 | 22.574 | 71.369 | 0.25 | 77.88 chnD |
| ATOM | 6696 | C6 | NAG | D | 367 | 79.716 | 23.875 | 73.356 | 0.25 | 76.42 chnD |
| ATOM | 6697 | O6 | NAG | D | 367 | 78.532 | 24.643 | 73.200 | 0.25 | 75.92 chnD |
| ATOM | 6698 | C1 | MAN | D | 368 | 81.144 | 22.073 | 75.623 | 0.25 | 75.18 chnD |
| ATOM | 6699 | C2 | MAN | D | 368 | 80.490 | 22.164 | 77.004 | 0.25 | 74.57 chnD |
| ATOM | 6700 | O2 | MAN | D | 368 | 80.212 | 20.859 | 77.492 | 0.25 | 74.96 chnD |
| ATOM | 6701 | C3 | MAN | D | 368 | 81.412 | 22.894 | 77.979 | 0.25 | 74.46 chnD |
| ATOM | 6702 | O3 | MAN | D | 368 | 80.850 | 22.869 | 79.284 | 0.25 | 72.78 chnD |
| ATOM | 6703 | C4 | MAN | D | 368 | 82.781 | 22.222 | 77.995 | 0.25 | 74.56 chnD |
| ATOM | 6704 | O4 | MAN | D | 368 | 83.671 | 22.961 | 78.821 | 0.25 | 74.66 chnD |
| ATOM | 6705 | C5 | MAN | D | 368 | 83.334 | 22.148 | 76.571 | 0.25 | 75.33 chnD |
| ATOM | 6706 | O5 | MAN | D | 368 | 82.417 | 21.426 | 75.722 | 0.25 | 75.00 chnD |
| ATOM | 6707 | C6 | MAN | D | 368 | 84.670 | 21.432 | 76.500 | 0.25 | 74.88 chnD |
| ATOM | 6708 | O6 | MAN | D | 368 | 84.615 | 20.172 | 77.155 | 0.25 | 75.04 chnD |
| ATOM | 6709 | S | SO4 | A | 401 | 112.111 | 24.704 | 51.443 | 0.50 | 118.73 chnA |
| ATOM | 6710 | O1 | SO4 | A | 401 | 112.194 | 25.983 | 52.168 | 0.00 | 117.71 chnA |
| ATOM | 6711 | O2 | SO4 | A | 401 | 112.822 | 23.645 | 52.199 | 0.50 | 117.04 chnA |
| ATOM | 6712 | O3 | SO4 | A | 401 | 110.691 | 24.332 | 51.305 | 0.00 | 117.88 chnA |
| ATOM | 6713 | O4 | SO4 | A | 401 | 112.722 | 24.857 | 50.110 | 0.00 | 117.64 chnA |
| ATOM | 6714 | S | SO4 | B | 402 | 91.393 | 51.271 | 53.911 | 0.50 | 27.89 chnB |
| ATOM | 6715 | O1 | SO4 | B | 402 | 91.604 | 52.544 | 54.624 | 0.00 | 27.73 chnB |
| ATOM | 6716 | O2 | SO4 | B | 402 | 91.413 | 50.161 | 54.865 | 0.00 | 27.62 chnB |
| ATOM | 6717 | O3 | SO4 | B | 402 | 90.102 | 51.300 | 53.197 | 0.00 | 27.86 chnB |
| ATOM | 6718 | O4 | SO4 | B | 402 | 92.484 | 51.078 | 52.939 | 0.00 | 27.95 chn |

The invention provides novel compounds which bind to the high affinity receptor for immunoglobulin E (IgE) designated FcεRI and methods for identifying and preparing such compounds. In particular aspects, the invention provides to the treatment of disorders mediated by IgE utilizing the novel compounds of the invention. The invention also provides compositions, such as pharmaceutical compositions, comprising the novel compounds, as well as for their use in research, diagnostic, therapeutic, and prophylactic methods.

What is claimed is:

1. A peptide which competes with IgE134 (SEQ ID NOS:155, 171) for binding the high affinity IgE receptor (FcεRI) in an in vitro assay and having the formula:

$(Xaa)_x$-Cys-Pro-$Xaa_1$-$Xaa_2$-Cys-Tyr-$(Xaa)_y$-$Xaa_3$-Cys-Pro-$Xaa_4$-$Xaa_5$-Cys-$Xaa_6$-$(Xaa)_z$ (SEQ ID NO: 596)

wherein Xaa is an amino acid and x is 0, 1 or 2; y is between 3 and 10 and z is 0, 1 or 3.

2. The peptide of claim 1 wherein y is 3.

3. The peptide of claim 1 wherein y is 4.

4. The peptide of claim 1 wherein y is 5.

5. The peptide of any of claims 1–4 wherein x is 0.

6. The peptide of any of claims 1–4 wherein z is 0.

7. The peptide of claim 1 having the following general formula:

$(Xaa)_x$-Cys-Pro-$Xaa_1$-$Xaa_2$-Cys-Tyr-$(Xaa)_y$-$Xaa_3$-Cys-Pro-$Xaa_4$-$Xaa_5$-Cys-Tyr-$(Xaa)_z$ (SEQ ID NO:603)

wherein x is 0, 1 or 2, y is 3, 4 or 5, and z is 0, 1 or 3.

8. The peptide of claim 7 having the following general formula:

$(Xaa)_x$-Cys-Pro-$Xaa_1$-$Xaa_2$-Cys-Tyr-$(Xaa)_y$-$Xaa_3$-Cys-Pro-Asp-$Xaa_5$-Cys-Tyr-$(Xaa)_z$ (SEQ ID NO:604).

9. The peptide of claim 8 wherein $Xaa_2$ and $Xaa_3$ are large hydrophobic amino acids.

10. The peptide of claim 8 wherein $Xaa_2$ is Phe and $Xaa_3$ is Leu.

11. The peptide of claim 1 having the sequence of: VQCPHFCYELDYELCPDVCYV-$nh_2$ (IGE134, SEQ ID NO:171).

12. A fusion protein comprising the peptide of claim 1.

13. A method of inhibiting the binding of an IgE to the high affinity IgE receptor (FcεRI) comprising the step of:

a) contacting FcεRI with a composition comprising the peptide of claim 1 under conditions which allow binding of the peptide to FcεRI to occur; and b) determining the amount of IgE binding to FcεRI in the presence of and absence of the peptide, wherein a lower level of IgE binding in the presence of the compound relative to its absence is indicative of inhibition.

14. A method of inhibiting the binding of an IgE to the high affinity IgE receptor comprising contacting the FcεRI with a peptide which comprises the following amino acid sequence wherein Xaa is an amino acid:

$(Xaa)_x$-Cys-Pro-$Xaa_1$-$Xaa_2$-Cys-Tyr-$(Xaa)_y$-$Xaa_3$-Cys-Pro-$Xaa_4$-$Xaa_5$-Cys-$Xaa_6$-$(Xaa)_z$ (SEQ ID NO:596)

and wherein Xaa is an amino acid and x is 0, 1 or 2; y is between 3 and 10 and z is 0, 1 or 3.

15. A method of inhibiting the activation of the high affinity IgE receptor (FcεRI) comprising contacting FcεRI with a composition which comprises a peptide having the following amino acid sequence wherein Xaa is an amino acid:

(Xaa)$_x$—Cys-Pro-Xaa$_1$-Xaa$_2$-Cys-Tyr-(Xaa)$_y$-Xaa$_3$-Cys-Pro-Xaa$_4$-Xaa$_5$-Cys-Xaa$_6$-(Xaa)$_z$ (SEQ ID NO:596)

and wherein Xaa is an amino acid and x is 0, 1 or 2; y is between 3 and 10 and z is 0, 1 or 3.

16. The method of claim 15 wherein the contacting occurs in vivo.

17. The method of claim 15 wherein the contacting occurs in vitro.

18. A method of treating a IgE mediated disease or disorder in a host in need thereof comprising administering to the host a therapeutically effective amount of a peptide of claim 1.

19. A pharmaceutical composition comprising a peptide of claim 1 and a pharmaceutically acceptable carrier.

20. The composition of claim 19 which is suitable for inhalation.

21. The composition of claim 19 which is dry powder.

22. The composition of claim 20 which is a liquid.

23. A peptide having the structural coordinates of Table 8.

24. A peptide which competes with IGE134 (SEQ ID NOS:155, 171) for binding the high affinity IgE receptor (FcεRI) in an in vitro assay and having the formula:

(Xaa)$_x$-Cys-Pro-Xaa$_1$-Xaa$_2$-Cys-Tyr-(Xaa7)$_w$-Xaa$_3$-Cys-Pro-Xaa$_4$-Xaa$_5$-Cys-Xaa$_6$-(Xaa)$_z$ (SEQ ID NO:596)

wherein Xaa$_{1-6}$ are natural amino acids, Xaa7 is a non-natural amino acid and x is 0, 1 or 2; w is 1–10, inclusive, and z is 0, 1 or 3.

* * * * *

SEQUENCE LISTING

```
<160> NUMBER OF SEQ ID NOS: 606

<210> SEQ ID NO 1
<211> LENGTH: 18
<212> TYPE: PRT
<213> ORGANISM: Artificial Sequence
<220> FEATURE:
<223> OTHER INFORMATION: clone g8a.37 shown in Table 1

<400> SEQUENCE: 1

Met Gly Thr Leu Cys Leu Glu Gly Pro Glu Gly Trp Phe Cys Ile
  1               5                  10                  15

Glu Ser Ala

<210> SEQ ID NO 2
<211> LENGTH: 18
<212> TYPE: PRT
```

-continued

```
<213> ORGANISM: Artificial Sequence
<220> FEATURE:
<223> OTHER INFORMATION: clone g8a.18 shown in Table 1

<400> SEQUENCE: 2

Gln Glu Trp Thr Cys Val Glu Gly Pro Arg Gly Trp Glu Cys Ile
  1               5                  10                  15

Ala Val Leu

<210> SEQ ID NO 3
<211> LENGTH: 18
<212> TYPE: PRT
<213> ORGANISM: Artificial Sequence
<220> FEATURE:
<223> OTHER INFORMATION: clone g8a.19 shown in Table 1

<400> SEQUENCE: 3

Asp Gly Ser Leu Cys Phe Glu Gly Pro Trp Gly Asp Ile Cys Gln
  1               5                  10                  15

Ser Asp Gly

<210> SEQ ID NO 4
<211> LENGTH: 18
<212> TYPE: PRT
<213> ORGANISM: Artificial Sequence
<220> FEATURE:
<223> OTHER INFORMATION: clone g8a.20 shown in Table 1

<400> SEQUENCE: 4

Thr Gly Glu Ala Cys Val Glu Gly Pro Gly Ala Trp Val Cys Cys
  1               5                  10                  15

Leu Glu Pro

<210> SEQ ID NO 5
<211> LENGTH: 14
<212> TYPE: PRT
<213> ORGANISM: Artificial Sequence
<220> FEATURE:
<223> OTHER INFORMATION: clone g8b3 shown in Table 2

<400> SEQUENCE: 5

Gly Thr Asp Val Cys Val Glu Gly Pro Trp Gly Glu Val Cys
                  5                  10

<210> SEQ ID NO 6
<211> LENGTH: 18
<212> TYPE: PRT
<213> ORGANISM: Artificial Sequence
<220> FEATURE:
<223> OTHER INFORMATION: clone g8b.22 shown in Table 2

<400> SEQUENCE: 6

Asn Tyr Glu Glu Cys Val Met Gly Pro Asp Gly Val Trp Cys Leu
  1               5                  10                  15

Ile Pro Thr

<210> SEQ ID NO 7
<211> LENGTH: 17
<212> TYPE: PRT
<213> ORGANISM: Artificial Sequence
<220> FEATURE:
<223> OTHER INFORMATION: clone g8b.23 shown in Table 2

<400> SEQUENCE: 7
```

-continued

```
Gly Arg Pro Ser Cys Ile Glu Gly Pro Ser Gly Leu Trp Cys Leu
  1               5                  10                  15

Ile Glu

<210> SEQ ID NO 8
<211> LENGTH: 18
<212> TYPE: PRT
<213> ORGANISM: Artificial Sequence
<220> FEATURE:
<223> OTHER INFORMATION: clone g8b.11 shown in Table 2

<400> SEQUENCE: 8

Glu Ile Gln Glu Cys Thr Glu Gly Pro Trp Gly Trp Phe Cys Val
  1               5                  10                  15

Gly Ser Gly

<210> SEQ ID NO 9
<211> LENGTH: 18
<212> TYPE: PRT
<213> ORGANISM: Artificial Sequence
<220> FEATURE:
<223> OTHER INFORMATION: clone g8b.35 shown in Table 2

<400> SEQUENCE: 9

Ala Glu Ala Thr Cys Thr Glu Gly Pro Trp Gly Trp Val Cys Met
  1               5                  10                  15

Ala Ala Asp

<210> SEQ ID NO 10
<211> LENGTH: 4
<212> TYPE: PRT
<213> ORGANISM: Artificial Sequence
<220> FEATURE:
<223> OTHER INFORMATION: N-terminal sequence of clone g3 sequence shown
      in Table 3

<400> SEQUENCE: 10

Asn Leu Pro Arg

<210> SEQ ID NO 11
<211> LENGTH: 4
<212> TYPE: PRT
<213> ORGANISM: Artificial Sequence
<220> FEATURE:
<223> OTHER INFORMATION: N-terminal sequence of clone g3 sequence shown
      in Table 3

<400> SEQUENCE: 11

Asn Leu Pro Thr

<210> SEQ ID NO 12
<211> LENGTH: 4
<212> TYPE: PRT
<213> ORGANISM: Artificial Sequence
<220> FEATURE:
<223> OTHER INFORMATION: N-terminal sequence of clone g3 sequence shown
      in Table 3

<400> SEQUENCE: 12

Asn Met Pro Thr

<210> SEQ ID NO 13
<211> LENGTH: 4
<212> TYPE: PRT
<213> ORGANISM: Artificial Sequence
```

```
<220> FEATURE:
<223> OTHER INFORMATION: N-terminal sequence of clone g3 sequence shown
      in Table 3

<400> SEQUENCE: 13

Ala Met Ala Gln

<210> SEQ ID NO 14
<211> LENGTH: 4
<212> TYPE: PRT
<213> ORGANISM: Artificial Sequence
<220> FEATURE:
<223> OTHER INFORMATION: N-terminal sequence of clone g3 sequence shown
      in Table 3

<400> SEQUENCE: 14

Gly Arg Ala Gln

<210> SEQ ID NO 15
<211> LENGTH: 4
<212> TYPE: PRT
<213> ORGANISM: Artificial Sequence
<220> FEATURE:
<223> OTHER INFORMATION: N-terminal sequence of clone g3 sequence shown
      in Table 3

<400> SEQUENCE: 15

Asp Leu Pro Ala

<210> SEQ ID NO 16
<211> LENGTH: 4
<212> TYPE: PRT
<213> ORGANISM: Artificial Sequence
<220> FEATURE:
<223> OTHER INFORMATION: N-terminal sequence of clone g3 sequence shown
      in Table 3

<400> SEQUENCE: 16

Gly Arg Thr Glu

<210> SEQ ID NO 17
<211> LENGTH: 18
<212> TYPE: PRT
<213> ORGANISM: Artificial Sequence
<220> FEATURE:
<223> OTHER INFORMATION: formula for Group 2 peptides isolated in
      Example 1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
```

```
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid

<400> SEQUENCE: 17

Xaa Xaa Xaa Xaa Cys Xaa Xaa Gly Pro Xaa Xaa Xaa Xaa Cys Xaa
 1               5                  10                  15

Xaa Xaa Xaa

<210> SEQ ID NO 18
<211> LENGTH: 18
<212> TYPE: PRT
<213> ORGANISM: Artificial Sequence
<220> FEATURE:
<223> OTHER INFORMATION: clone g3b.1 shown in Table 3

<400> SEQUENCE: 18

Asn Leu Pro Arg Cys Thr Glu Gly Pro Trp Gly Trp Val Cys Met
 1               5                  10                  15

Ala Ala Asp

<210> SEQ ID NO 19
<211> LENGTH: 18
<212> TYPE: PRT
<213> ORGANISM: Artificial Sequence
<220> FEATURE:
<223> OTHER INFORMATION: clone g3b.3 shown in Table 3

<400> SEQUENCE: 19

Asn Leu Pro Thr Cys Thr Glu Gly Pro Trp Gly Trp Val Cys Met
 1               5                  10                  15

Ala Ala Asp

<210> SEQ ID NO 20
<211> LENGTH: 18
<212> TYPE: PRT
<213> ORGANISM: Artificial Sequence
<220> FEATURE:
<223> OTHER INFORMATION: clone g3b.5 shown in Table 3

<400> SEQUENCE: 20
```

Val Met Pro Thr Cys Thr Glu Gly Pro Trp Gly Trp Val Cys Met
 1               5                  10                  15

Ala Ala Asp

<210> SEQ ID NO 21
<211> LENGTH: 18
<212> TYPE: PRT
<213> ORGANISM: Artificial Sequence
<220> FEATURE:
<223> OTHER INFORMATION: clone g3b.4 shown in Table 3

<400> SEQUENCE: 21

Ala Met Ala Gln Cys Thr Glu Gly Pro Trp Gly Trp Val Cys Met
 1               5                  10                  15

Ala Ala Asp

<210> SEQ ID NO 22
<211> LENGTH: 18
<212> TYPE: PRT
<213> ORGANISM: Artificial Sequence
<220> FEATURE:
<223> OTHER INFORMATION: clone g3b.6 shown in Table 3

<400> SEQUENCE: 22

Gly Arg Ala Gln Cys Thr Glu Gly Pro Trp Gly Trp Val Cys Met
 1               5                  10                  15

Ala Ala Asp

<210> SEQ ID NO 23
<211> LENGTH: 18
<212> TYPE: PRT
<213> ORGANISM: Artificial Sequence
<220> FEATURE:
<223> OTHER INFORMATION: clone g3b.7 shown in Table 3

<400> SEQUENCE: 23

Asp Leu Pro Ala Cys Thr Glu Gly Pro Trp Gly Trp Val Cys Met
 1               5                  10                  15

Ala Ala Asp

<210> SEQ ID NO 24
<211> LENGTH: 18
<212> TYPE: PRT
<213> ORGANISM: Artificial Sequence
<220> FEATURE:
<223> OTHER INFORMATION: clone g3b.8 shown in Table 3

<400> SEQUENCE: 24

Gly Arg Thr Glu Cys Thr Glu Gly Pro Trp Gly Trp Val Cys Met
 1               5                  10                  15

Ala Ala Asp

<210> SEQ ID NO 25
<211> LENGTH: 17
<212> TYPE: PRT
<213> ORGANISM: Artificial Sequence
<220> FEATURE:
<223> OTHER INFORMATION: clone g3c.29 shown in Table 4

<400> SEQUENCE: 25

Asn Leu Pro Arg Cys Thr Glu Gly Pro Trp Gly Trp Val Cys Met
 1               5                  10                  15

Ala Ala

<210> SEQ ID NO 26
<211> LENGTH: 16
<212> TYPE: PRT
<213> ORGANISM: Artificial Sequence
<220> FEATURE:
<223> OTHER INFORMATION: clone g3c.31 shown in Table 4

<400> SEQUENCE: 26

Asn Leu Pro Arg Cys Thr Glu Gly Pro Trp Gly Trp Val Cys Met
 1               5                  10                  15

Ala

<210> SEQ ID NO 27
<211> LENGTH: 15
<212> TYPE: PRT
<213> ORGANISM: Artificial Sequence
<220> FEATURE:
<223> OTHER INFORMATION: clone g3c.34 shown in Table 4

<400> SEQUENCE: 27

Asn Leu Pro Arg Cys Thr Glu Gly Pro Trp Gly Trp Val Cys Met
 1               5                  10                  15

<210> SEQ ID NO 28
<211> LENGTH: 18
<212> TYPE: PRT
<213> ORGANISM: Artificial Sequence
<220> FEATURE:
<223> OTHER INFORMATION: clone g3c.42 shown in Table 4

<400> SEQUENCE: 28

Asn Leu Pro Arg Cys Thr Glu Gly Pro Trp Gly Trp Val Cys Met
 1               5                  10                  15

Ala Ala Asp

<210> SEQ ID NO 29
<211> LENGTH: 17
<212> TYPE: PRT
<213> ORGANISM: Artificial Sequence
<220> FEATURE:
<223> OTHER INFORMATION: clone g3c.1 shown in Table 4

<400> SEQUENCE: 29

Leu Pro Arg Cys Thr Glu Gly Pro Trp Gly Trp Val Cys Met Ala
 1               5                  10                  15

Ala Asp

<210> SEQ ID NO 30
<211> LENGTH: 15
<212> TYPE: PRT
<213> ORGANISM: Artificial Sequence
<220> FEATURE:
<223> OTHER INFORMATION: clone g3c.17 shown in Table 4

<400> SEQUENCE: 30

Arg Cys Thr Glu Gly Pro Trp Gly Trp Val Cys Met Ala Ala Asp
 1               5                  10                  15

<210> SEQ ID NO 31
<211> LENGTH: 14
<212> TYPE: PRT
<213> ORGANISM: Artificial Sequence
<220> FEATURE:

<223> OTHER INFORMATION: clone g3c.21 shown in Table 4

<400> SEQUENCE: 31

Cys Thr Glu Gly Pro Trp Gly Trp Val Cys Met Ala Ala Asp
                5                   10

<210> SEQ ID NO 32
<211> LENGTH: 18
<212> TYPE: PRT
<213> ORGANISM: Artificial Sequence
<220> FEATURE:
<223> OTHER INFORMATION: variant of SEQ ID NO:28 shown in Table 5.
      IgE031
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 18
<223> OTHER INFORMATION: C-terminal amidation

<400> SEQUENCE: 32

Asn Leu Pro Arg Cys Thr Glu Gly Pro Trp Gly Trp Val Cys Met
 1               5                   10                  15

Ala Asp Asp

<210> SEQ ID NO 33
<211> LENGTH: 18
<212> TYPE: PRT
<213> ORGANISM: Artificial Sequence
<220> FEATURE:
<223> OTHER INFORMATION: variant of SEQ ID NO:28 shown in Table 5.
      IgE032
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 18
<223> OTHER INFORMATION: C-terminal amidation

<400> SEQUENCE: 33

Asn Leu Pro Arg Cys Thr Glu Gly Pro Lys Gly Trp Val Cys Met
 1               5                   10                  15

Ala Asp Asp

<210> SEQ ID NO 34
<211> LENGTH: 18
<212> TYPE: PRT
<213> ORGANISM: Artificial Sequence
<220> FEATURE:
<223> OTHER INFORMATION: variant of SEQ ID NO:28 shown in Table 5.
      IgE042
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 18
<223> OTHER INFORMATION: C-terminal amidation

<400> SEQUENCE: 34

Asn Leu Pro Arg Cys Thr Glu Gly Pro Trp Gly Trp Val Cys Met
 1               5                   10                  15

Ala Ala Asp

-continued

```
<210> SEQ ID NO 35
<211> LENGTH: 18
<212> TYPE: PRT
<213> ORGANISM: Artificial Sequence
<220> FEATURE:
<223> OTHER INFORMATION: IgE receptor binding peptide shown in Table 5.
      IgE043
<220> FEATURE:
<221> NAME/KEY: MOD_RES
<222> LOCATION: 18
<223> OTHER INFORMATION: C-terminal amidation

<400> SEQUENCE: 35

Asn Leu Pro Arg Cys Thr Glu Gly Pro Trp Gly Trp Val Cys Met
  1               5                  10                  15

Ala Ala Asp

<210> SEQ ID NO 36
<211> LENGTH: 11
<212> TYPE: PRT
<213> ORGANISM: Artificial Sequence
<220> FEATURE:
<223> OTHER INFORMATION: IgE receptor binding peptide shown in Table 5.
      IgE044
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 11
<223> OTHER INFORMATION: C-terminal amidation

<400> SEQUENCE: 36

Cys Leu Glu Gly Pro Trp Gly Trp Phe Cys Ile
                  5                  10

<210> SEQ ID NO 37
<211> LENGTH: 11
<212> TYPE: PRT
<213> ORGANISM: Artificial Sequence
<220> FEATURE:
<223> OTHER INFORMATION: IgE receptor binding peptide shown in Table 5.
      IgE045
<220> FEATURE:
<221> NAME/KEY: MOD_RES
<222> LOCATION: 11
<223> OTHER INFORMATION: C-terminal amidation

<400> SEQUENCE: 37

Cys Leu Glu Gly Pro Trp Gly Trp Phe Cys Ile
                  5                  10

<210> SEQ ID NO 38
<211> LENGTH: 11
<212> TYPE: PRT
<213> ORGANISM: Artificial Sequence
<220> FEATURE:
<223> OTHER INFORMATION: IgE receptor binding peptide shown in Table 5.
      IgE046
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 11
<223> OTHER INFORMATION: C-terminal amidation

<400> SEQUENCE: 38
```

Cys Thr Glu Gly Pro Trp Gly Trp Phe Cys Ile
                 5                  10

<210> SEQ ID NO 39
<211> LENGTH: 11
<212> TYPE: PRT
<213> ORGANISM: Artificial Sequence
<220> FEATURE:
<223> OTHER INFORMATION: IgE receptor binding peptide of Table 5. IgE047
<220> FEATURE:
<221> NAME/KEY: MOD_RES
<222> LOCATION: 11
<223> OTHER INFORMATION: C-terminal amidation

<400> SEQUENCE: 39

Cys Thr Glu Gly Pro Trp Gly Trp Phe Cys Ile
                 5                  10

<210> SEQ ID NO 40
<211> LENGTH: 18
<212> TYPE: PRT
<213> ORGANISM: Artificial Sequence
<220> FEATURE:
<223> OTHER INFORMATION: IgE receptor binding peptide of Table 5. IgE50
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 18
<223> OTHER INFORMATION: C-terminal amidation

<400> SEQUENCE: 40

Asn Leu Pro Arg Cys Thr Glu Gly Pro Asn Gly Trp Val Cys Met
 1               5                  10                  15

Ala Ala Asp

<210> SEQ ID NO 41
<211> LENGTH: 18
<212> TYPE: PRT
<213> ORGANISM: Artificial Sequence
<220> FEATURE:
<223> OTHER INFORMATION: IgE receptor binding peptide of Table 5. IgE051
<220> FEATURE:
<221> NAME/KEY: MOD_RES
<222> LOCATION: 18
<223> OTHER INFORMATION: C-terminal amidation

<400> SEQUENCE: 41

Asn Leu Pro Arg Cys Thr Glu Gly Pro Asn Gly Trp Val Cys Met
 1               5                  10                  15

Ala Ala Asp

<210> SEQ ID NO 42
<211> LENGTH: 11
<212> TYPE: PRT
<213> ORGANISM: Artificial Sequence
<220> FEATURE:
<223> OTHER INFORMATION: IgE receptor binding peptide of Table 5. IgE055
<220> FEATURE:
<221> NAME/KEY: MOD_RES
<222> LOCATION: 11
<223> OTHER INFORMATION: C-terminal amidation

<400> SEQUENCE: 42

Cys Thr Glu Gly Pro Trp Gly Trp Val Cys Ile
                 5                  10

```
<210> SEQ ID NO 43
<211> LENGTH: 11
<212> TYPE: PRT
<213> ORGANISM: Artificial Sequence
<220> FEATURE:
<223> OTHER INFORMATION: IgE receptor binding peptide of Table 5. IgE056
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 11
<223> OTHER INFORMATION: C-terminal amidation

<400> SEQUENCE: 43

Cys Thr Glu Gly Pro Trp Gly Trp Val Cys Ile
                5

Ala Ala Asp

<210> SEQ ID NO 47
<211> LENGTH: 17
<212> TYPE: PRT
<213> ORGANISM: Artificial Sequence
<220> FEATURE:
<223> OTHER INFORMATION: IgE receptor binding peptide of Table 5. IgE060
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 17
<223> OTHER INFORMATION: C-terminal amidation

<400> SEQUENCE: 47

Asn Leu Pro Cys Thr Ala Gly Pro Trp Gly Trp Val Cys Met Ala
 1               5                  10                  15

Ala Asp

<210> SEQ ID NO 48
<211> LENGTH: 15
<212> TYPE: PRT
<213> ORGANISM: Artificial Sequence
<220> FEATURE:
<223> OTHER INFORMATION: Ige receptor binding peptide of Table 5. IgE062

<400> SEQUENCE: 48

Asn Leu Pro Arg Cys Thr Glu Gly Pro Trp Gly Trp Val Cys Met
 1               5                  10                  15

<210> SEQ ID NO 49
<211> LENGTH: 15
<212> TYPE: PRT
<213> ORGANISM: Artificial Sequence
<220> FEATURE:
<223> OTHER INFORMATION: IgE receptor binding peptide of Table 5. IgE063
<220> FEATURE:
<221> NAME/KEY: MOD_RES
<222> LOCATION: 1
<223> OTHER INFORMATION: N-terminal acetylation

<400> SEQUENCE: 49

Asn Leu Pro Arg Cys Thr Glu Gly Pro Trp Gly Trp Val Cys Met
 1               5                  10                  15

<210> SEQ ID NO 50
<211> LENGTH: 14
<212> TYPE: PRT
<213> ORGANISM: Artificial Sequence
<220> FEATURE:
<223> OTHER INFORMATION: IgE receptor binding peptide of Table 5. IgE068
<220> FEATURE:
<221> NAME/KEY: MOD_RES
<222> LOCATION: 14
<223> OTHER INFORMATION: C-terminal amidation

<400> SEQUENCE: 50

Leu Pro Arg Cys Thr Glu Gly Pro Trp Gly Trp Val Cys Met
                 5                  10

<210> SEQ ID NO 51
<211> LENGTH: 13
<212> TYPE: PRT
<213> ORGANISM: Artificial Sequence
<220> FEATURE:

```
<223> OTHER INFORMATION: IgE receptor binding peptide of Table 5. IgE069
<220> FEATURE:
<221> NAME/KEY: MOD_RES
<222> LOCATION: 13

<210> SEQ ID NO 57
<211> LENGTH: 15
<212> TYPE: PRT
<213> ORGANISM: Artificial Sequence
<220> FEATURE:
<223> OTHER INFORMATION: IgE receptor binding peptide of Table 5. IgE075

<400> SEQUENCE: 57

Asn Leu Pro Arg Cys Thr Glu Gly Pro Trp Gly Trp Val Cys Ile

```
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 11
<223> OTHER INFORMATION: C-terminal amidation

<400> SEQUENCE: 62

Cys Leu Glu Gly Pro Trp Gly Trp Val Cys Ile
                 5                  10

<210> SEQ ID NO 63
<211> LENGTH: 14
<212> TYPE: PRT
<213> ORGANISM: Artificial Sequence
<220> FEATURE:
<223> OTHER INFORMATION: IgE receptor binding peptide of

```
<211> LENGTH: 15
<212> TYPE: PRT
<213> ORGANISM: Artificial Sequence
<220> FEATURE:
<223> OTHER INFORMATION: IgE receptor binding peptide of Table 5. IgE087
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 9
<223> OTHER INFORMATION: unusual amino acid residue N-methyl glycine.
<220> FEATURE:
<221> NAME/KEY: MOD_RES
<222> LOCATION: 15
<223> OTHER INFORMATION: C-terminal amidation

<400> SEQUENCE: 66

Asn Leu Pro Arg Cys Thr Glu Gly Xaa Trp Gly Trp Val Cys Met
 1               5

-continued

```
Asn Leu Pro Arg Cys Thr Glu Gly Pro Trp Gly Trp Val Cys
                5                   10

<210> SEQ ID NO 70
<211> LENGTH: 15
<212> TYPE: PRT
<213> ORGANISM: Artificial Sequence
<220> FEATURE:
<223> OTHER INFORMATION: IgE receptor binding peptide of Table 5. IgE095
<220> FEATURE:
<221> NAME/KEY: SITE
<222> LOCATION: 9
<223> OTHER INFORMATION: unusual amino acid L-pipecolic acid
<220> FEATURE:
<221> NAME/KEY: MOD_RES
<222> LOCATION: 15
<223> OTHER INFORMATION: N-terminal acetylation

<400> SEQUENCE: 70

Asn Leu Pro Arg Cys Thr Glu Gly Xaa Trp Gly Trp Val Cys Met
 1               5

-continued

```
<222> LOCATION: 9
<223> OTHER INFORMATION: unusual amino acid D-pipecolic acid
<220> FEATURE:
<221> NAME/KEY: MOD_RES
<222> LOCATION: 15
<223> OTHER INFORMATION: C-terminal amidation

<400> SEQUENCE: 73

Asn Leu Pro Arg Cys Thr Glu Gly Xaa Trp Gly Trp Val Cys Met
 1               5                  10                  15

<210> SEQ ID NO 74
<211> LENGTH: 15
<212> TYPE: PRT
<213> ORGANISM: Artificial Sequence
<220> FEATURE:
<223> OTHER INFORMATION: IgE receptor binding peptide of Table 5. IgE099
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 9
<223> OTHER INFORMATION: unusual amino acid D-pipecolic acid

<400> SEQUENCE: 74

Asn Leu Pro Arg Cys Thr Glu Gly Xaa Trp Gly Trp Val Cys Met
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: IgE receptor binding peptide of Table 5. IgE100
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 9
<223> OTHER INFORMATION: unusual amino acid octahydroindole

<400> SEQUENCE: 75

Asn Leu Pro Arg Cys Thr Glu Gly Xaa Trp Gly Trp Val Cys Met
 1               5                  10                  15

<210> SEQ ID NO 76
<211> LENGTH: 15
<212> TYPE: PRT
<213> ORGANISM: Artificial Sequence
<220> FEATURE:
<223> OTHER INFORMATION: IgE receptor binding peptide of
<210> SEQ ID NO 77 (implicit continuation)
<213> ORGANISM: Artificial Sequence
<220> FEATURE:
<223> OTHER INFORMATION: IgE receptor binding peptide of Table 5. IgE102
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 9
<223> OTHER INFORMATION: unusual amino acid benzoxyproline

<400> SEQUENCE: 77

Asn Leu Pro Arg Cys Thr Glu Gly Xaa Trp Gly Trp Val Cys Met
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: IgE receptor binding peptide of Table 5. IgE103
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 10
<223> OTHER INFORMATION: unusual amino acid 2-naphthyl-2-alanine

<400> SEQUENCE: 78

Asn Leu Pro Arg Cys Thr Glu Gly Pro Xaa Gly Trp Val Cys Met
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: IgE receptor binding peptide of Table 5. IgE104
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 14
<223> OTHER INFORMATION: unusual amino acid residue D-Cysteine

<400> SEQUENCE: 79

Asn Leu Pro Arg Cys Thr Glu Gly Pro Trp Gly Trp Val Cys Met
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: IgE receptor binding peptide of Table 5. IgE105
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 11
<223> OTHER INFORMATION: unusual amino acid residue D-alanine

<400> SEQUENCE: 80

Asn Leu Pro Arg Cys Thr Glu Gly Pro Trp Ala Trp Val Cys Met
1 5 10 15

```
<210> SEQ ID NO 81
<211> LENGTH: 15
<212> TYPE: PRT
<213> ORGANISM: Artificial Sequence
<220> FEATURE:
<223> OTHER INFORMATION: IgE receptor binding peptide of Table 5. IgE106
<220> FEATURE:
<221> NAME/KEY: MOD_RES
<222> LOCATION: 1
<223> OTHER INFORMATION: N-terminal acetylation

<400> SEQUENCE: 81

Asn Leu Pro Arg Cys Thr Glu Gly Pro Val Gly Trp Val Cys Met
 1               5                  10                  15

<210> SEQ ID NO 82
<211> LENGTH: 14
<212> TYPE: PRT
<213> ORGANISM: Artificial Sequence
<220> FEATURE:
<223> OTHER INFORMATION: IgE receptor binding peptide of Table 5. IgE107
<220> FEATURE:
<221> NAME/KEY: MOD_RES
<222> LOCATION: 1
<223> OTHER INFORMATION: N-terminal acetylation

<400> SEQUENCE: 82

Asn Leu Pro Cys Thr Glu Gly Pro Trp Gly Trp Val Cys Met
                 5                  10

<210> SEQ ID NO 83
<211> LENGTH: 15
<212> TYPE: PRT
<213> ORGANISM: Artificial Sequence
<220> FEATURE:
<223> OTHER INFORMATION: IgE receptor binding peptide of Table 5. IgE108
<220> FEATURE:
<221> NAME/KEY: MOD_RES
<222> LOCATION: 1
<223> OTHER INFORMATION: N-terminal acetylation

<400> SEQUENCE: 83

Asn Leu Pro Arg Cys Thr Glu Gly Pro Trp Gly Trp Val Cys Met
 1               5                  10                  15

<210> SEQ ID NO 84
<211> LENGTH: 15
<212> TYPE: PRT
<213> ORGANISM: Artificial Sequence
<220> FEATURE:
<223> OTHER INFORMATION: IgE receptor binding peptide of Table 5. IgE109
<220> FEATURE:
<221> NAME/KEY: MOD_RES
<222> LOCATION: 1
<223> OTHER INFORMATION: N-terminal acetylation

<400> SEQUENCE: 84

Asn Leu Pro Arg Cys Thr Glu Gly Pro Trp Gly Leu Val Cys Met
 1               5                  10                  15

<210> SEQ ID NO 85
<211> LENGTH: 15
<212> TYPE: PRT
<213> ORGANISM: Artificial Sequence
<220> FEATURE:
<223> OTHER INFORMATION: IgE receptor binding peptide of Table 5. IgE114
<220> FEATURE:
<221> NAME/KEY: MOD_RES
<222> LOCATION: 1
```

```
<223> OTHER INFORMATION: N-terminal acetylation
<220> FEATURE:
<221> NAME/KEY: SITE
<222> LOCATION: 11
<223> OTHER INFORMATION: unusual amino acid residue D-glutamic acid

<400> SEQUENCE: 85

Asn Leu Pro Arg Cys Thr Glu Gly Pro Trp Glu Trp Val Cys Met
 1               5                  10                  15

<210> SEQ ID NO 86
<211> LENGTH: 15
<212> TYPE: PRT
<213> ORGANISM: Artificial Sequence
<220> FEATURE:
<223> OTHER INFORMATION: IgE receptor binding peptide of Table 5. IgE115
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 9
<223> OTHER INFORMATION: unusual amino acid residue thioproline

<400> SEQUENCE: 86

Asn Leu Pro Arg Cys Thr Glu Gly Xaa Trp Gly Trp Val Cys Met
 1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: IgE receptor binding peptide of Table 5. IgE116
<220> FEATURE:
<221> NAME/KEY: MOD_RES
<222> LOCATION: 1
<223> OTHER INFORMATION: N-terminal acetylation

<400> SEQUENCE: 87

Asn Leu Pro Arg Trp Thr Cys Gly Pro Trp Gly Cys Val Glu Met
 1               5                  10                  15

<210> SEQ ID NO 88
<211> LENGTH: 18
<212> TYPE: PRT
<213> ORGANISM: Artificial Sequence
<220> FEATURE:
<223> OTHER INFORMATION: IgE receptor binding peptide of Table 5. IgE118
<220> FEATURE:
<221> NAME/KEY: MOD_RES
<222> LOCATION: 1
<223> OTHER INFORMATION: N-terminal acetylation

<400> SEQUENCE: 88

Asn Leu Cys Thr Leu Thr Glu Gly Pro Trp Gly Trp Val Leu Thr
 1               5                  10                  15

Cys Ala Asp

<210> SEQ ID NO 89
<211> LENGTH: 16
<212> TYPE: PRT
<213> ORGANISM: Artificial Sequence
<220> FEATURE:
<223> OTHER INFORMATION: IgE receptor binding peptide of Table 5. IgE125
<220> FEATURE:
<221> NAME/KEY: MOD_RES
<222> LOCATION: 1
<223> OTHER INFORMATION: N-terminal acetylation
```

```
<400> SEQUENCE: 89

Asn Leu Pro Arg Cys Thr Glu Gly Pro Ala Trp Gly Trp Val Cys
 1               5                  10                  15

Met

<210> SEQ ID NO 90
<211> LENGTH: 15
<212> TYPE: PRT
<213> ORGANISM: Artificial Sequence
<220> FEATURE:
<223> OTHER INFORMATION: IgE receptor binding peptide of Table 5. IgE133
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 15
<223> OTHER INFORMATION: unusual amino acid homoserine lactone

<400> SEQUENCE: 90

Asn Leu Pro Arg Cys Thr Glu Gly Pro Trp Gly Trp Val

```
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid

<400> SEQUENCE: 93

Ser Gly Thr Ala Cys Xaa Xaa Gly Pro Xaa Xaa Xaa Xaa Cys Ser
 1               5                  10                  15

Leu Ala Gly Ser Pro
             20

<210> SEQ ID NO 94
<211> LENGTH: 20
<212> TYPE: PRT
<213> ORGANISM: Artificial Sequence
<220> FEATURE:
<223> OTHER INFORMATION: generic formula of Group 4 peptides of Example
      1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 15
<223> OTHER INFORMATION: unknown amino acid
```

```
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid

<400> SEQUENCE: 94

Xaa Xaa Xaa Xaa Xaa Xaa Xaa Cys Xaa Xaa Xaa Xaa Cys Xaa Xaa
 1               5                  10                  15

Xaa Xaa Xaa Xaa Xaa
             20

<210> SEQ ID NO 95
<211> LENGTH: 20
<212> TYPE: PRT
<213> ORGANISM: Artificial Sequence
<220> FEATURE:
<223> OTHER INFORMATION: generic formula of Group 4 peptides of Example
      1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
```

```
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid

<400> SEQUENCE: 95

Xaa Xaa Xaa Xaa Xaa Xaa Xaa Cys Xaa Xaa Xaa Xaa Xaa Cys Xaa
 1               5                  10                  15

Xaa Xaa Xaa Xaa Xaa
                20

<210> SEQ ID NO 96
<211> LENGTH: 20
<212> TYPE: PRT
<213> ORGANISM: Artificial Sequence
<220> FEATURE:
<223> OTHER INFORMATION: generic formula of Group 4 peptides of Example
      1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
```

```
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid

<400> SEQUENCE: 96

Xaa Xaa Xaa Xaa Xaa Xaa Cys Xaa Xaa Xaa Xaa Xaa Xaa Cys Xaa
 1               5                  10                  15

Xaa Xaa Xaa Xaa Xaa
            20

<210> SEQ ID NO 97
<211> LENGTH: 20
<212> TYPE: PRT
<213> ORGANISM: Artificial Sequence
<220> FEATURE:
<223> OTHER INFORMATION: generic formula of Group 4 peptides of Example
      1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
```

```
<222> LOCATION: 6
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid

<400> SEQUENCE: 97

Xaa Xaa Xaa Xaa Xaa Xaa Cys Xaa Xaa Xaa Xaa Xaa Xaa Xaa Cys
  1               5                  10                  15

Xaa Xaa Xaa Xaa Xaa
            20

<210> SEQ ID NO 98
<211> LENGTH: 20
<212> TYPE: PRT
<213> ORGANISM: Artificial Sequence
<220> FEATURE:
<223> OTHER INFORMATION: generic formula of Group 4 peptides of Example
      1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
```

```
-continued

<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid

<400> SEQUENCE: 98

Xaa Xaa Xaa Xaa Xaa Cys Xaa Xaa Xaa Xaa Xaa Xaa Xaa Xaa Cys
 1               5                  10                  15

Xaa Xaa Xaa Xaa Xaa
                20

<210> SEQ ID NO 99
<211> LENGTH: 20
<212> TYPE: PRT
<213> ORGANISM: Artificial Sequence
<220> FEATURE:
<223> OTHER INFORMATION: generic formula of Group 4 peptides of Example
      1
<220> FEATURE:
<221> NAME/KEY: unsure
```

-continued

```
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid

<400> SEQUENCE: 99

Xaa Xaa Xaa Xaa Xaa Cys Xaa Xaa Xaa Xaa Xaa Xaa Xaa Xaa Xaa
 1               5                  10                  15

Cys Xaa Xaa Xaa Xaa
             20
```

```
<210> SEQ ID NO 100
<211> LENGTH: 20
<212> TYPE: PRT
<213> ORGANISM: Artificial Sequence
<220> FEATURE:
<223> OTHER INFORMATION: generic formula of Group 4 peptides of Example
      1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
```

<223> OTHER INFORMATION: unknown amino acid

<400> SEQUENCE: 100

Xaa Xaa Xaa Xaa Cys Xaa Xaa Xaa Xaa Xaa Xaa Xaa Xaa Xaa Xaa
 1               5                  10                  15

Cys Xaa Xaa Xaa Xaa
                20

<210> SEQ ID NO 101
<211> LENGTH: 20
<212> TYPE: PRT
<213> ORGANISM: Artificial Sequence
<220> FEATURE:
<223> OTHER INFORMATION: generic formula of Group 3 peptides of Example
      1
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:

-continued

<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid

<400> SEQUENCE: 101

Xaa Xaa Xaa Xaa Xaa Xaa Xaa Xaa Xaa Xaa Xaa Xaa Xaa Xaa Xaa
1 5 10 15

Xaa Xaa Xaa Xaa Xaa
20

<210> SEQ ID NO 102
<211> LENGTH: 8
<212> TYPE: PRT
<213> ORGANISM: Artificial Sequence
<220> FEATURE:
<223> OTHER INFORMATION: generic formula for IgE receptor binding peptide of Example 7
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid

<400> SEQUENCE: 102

Xaa Xaa Xaa Xaa Xaa Xaa Xaa Xaa
5

<210> SEQ ID NO 103
<211> LENGTH: 8
<212> TYPE: PRT
<213> ORGANISM: Artificial Sequence

```
<220> FEATURE:
<223> OTHER INFORMATION: generic formula for IgE receptor binding
      peptide of Example 7
<220> FEATURE:
<221> NAME/KEY: unsure
<222> L

```
<213> ORGANISM: Artificial Sequence
<220> FEATURE:
<223> OTHER INFORMATION: generic formula for IgE receptor binding
      peptide of Example 7
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid

<400> SEQUENCE: 105

```
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid

<400> SEQUENCE: 106

Xaa Xaa Cys Xaa Xaa Xaa Xaa Xaa Cys Xaa Xaa
                 5                  10

<210> SEQ ID NO 107
<211> LENGTH: 12
<212> TYPE: PRT
<213> ORGANISM: Artificial Sequence
<220> FEATURE:
<223> OTHER INFORMATION: generic formula for IgE receptor binding
      peptide of Example 7
<220>

<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid

<400> SEQUENCE: 108

```
Xaa Xaa Cys Xaa Xaa Xaa Xaa Xaa Xaa Xaa Cys Xaa Xaa
                 5                  10
```

<210> SEQ ID NO 109
<211> LENGTH: 14
<212> TYPE: PRT
<213> ORGANISM: Artificial Sequence
<220> FEATURE:
<223> OTHER INFORMATION: generic formula for IgE receptor binding peptide of Example 7
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:

```
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid

<400> SEQUENCE: 109

Xaa Xaa Cys Xaa Xaa Xaa Xaa Xaa Xaa Xaa Xaa Cys Xaa Xaa
                 5                   10

<210> SEQ ID NO 110
<211> LENGTH: 15
<212> TYPE: PRT
<213> ORGANISM: Artificial Sequence
<220> FEATURE:
<223> OTHER INFORMATION: generic formula for IgE receptor binding
      peptide of Example 7
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
```

-continued

<222> LOCATION: 12
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 15
<223> OTHER INFORMATION: unknown amino acid

<400> SEQUENCE: 110

Xaa Xaa Cys Xaa Xaa Xaa Xaa Xaa Xaa Xaa Xaa Xaa Cys Xaa Xaa
1 5 10 15

<210> SEQ ID NO 111
<211> LENGTH: 16
<212> TYPE: PRT
<213> ORGANISM: Artificial Sequence
<220> FEATURE:
<223> OTHER INFORMATION: generic formula for IgE receptor binding peptide of Example 7
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:
<221> NAME/KEY: unsure
<222> LOCATION: 16

-continued

```
<223> OTHER INFORMATION: unknown amino acid

<400> SEQUENCE: 111

Xaa Xaa Cys Xaa Xaa Xaa Xaa Xaa Xaa Xaa Xaa Xaa Xaa Cys Xaa
 1               5                  10                  15

Xaa

<210> SEQ ID NO 112
<211> LENGTH: 27
<212> TYPE: PRT
<213> ORGANISM: Artificial Sequence
<220> FEATURE:
<223> OTHER INFORMATION: generic formula for IgE receptor binding
      peptide of Example 7
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
```

-continued

<222> LOCATION: 21
<223> OTHER INFORMATION: unknown amino acid
<220> FEATURE:
<221> NAME/KEY: unsure
<222> LOCATION: 22
<223> OTHER INFORMATION: unknown amino acid
<220> FEATURE:
<221> NAME/KEY: unsure
<222> LOCATION: 23
<223> OTHER INFORMATION: unknown amino acid
<220> FEATURE:
<221> NAME/KEY: unsure
<222> LOCATION: 24
<223> OTHER INFORMATION: unknown amino acid
<220> FEATURE:
<221> NAME/KEY: unsure
<222> LOCATION: 25
<223> OTHER INFORMATION: unknown amino acid
<220> FEATURE:
<221> NAME/KEY: unsure
<222> LOCATION: 26
<223> OTHER INFORMATION: unknown amino acid

<400> SEQUENCE: 112

```
Cys Xaa Xaa Xaa Xaa Xaa Xaa Cys Xaa Xaa Xaa Xaa Xaa Xaa Cys
  1               5                  10                  15

Cys Xaa Xaa Xaa Cys Xaa Xaa Xaa Xaa Xaa Xaa Cys
                 20                  25
```

<210> SEQ ID NO 113
<211> LENGTH: 13
<212> TYPE: PRT
<213> ORGANISM: Artificial Sequence
<220> FEATURE:
<223> OTHER INFORMATION: generic formula for IgE receptor binding peptide of Example 7
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid

<400> SEQUENCE: 113

```
Cys Cys Xaa Xaa Xaa Cys Xaa Xaa Xaa Xaa Xaa Xaa Cys
```

-continued

```
<210> SEQ ID NO 114
<211> LENGTH: 19
<212> TYPE: PRT
<213> ORGANISM: Artificial Sequence
<220> FEATURE:
<223> OTHER INFORMATION: generic formula for IgE receptor binding
      peptide of Example 7
<220> FEATURE:
<221> NAME/KEY: unsure
<222> LOCATION: 3
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 11
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 15
<223> OTHER INFORMATION: unknown amino acid
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid

<400> SEQUENCE: 114

Cys Cys Xaa Xaa Xaa Xaa Xaa Cys Xaa Xaa Xaa Xaa Cys Xaa Xaa
 1               5                  10                  15

Xaa Xaa Cys Cys

<210> SEQ ID NO 115
<211> LENGTH: 21
<212> TYPE: PRT
<213> ORGANISM: Artificial Sequence
<220> FEATURE:
<223> OTHER INFORMATION: generic formula for IgE receptor binding
      peptide of Example 7
<220> FEATURE:
```

-continued

```
<221> NAME/KEY: unsure
<222> LOCATION: 2
<223> OTHER INFORMATION: unknown amino acid
<220> FEATURE:
<221> NAME/KEY: unsure
<222> LOCATION: 4
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 7
<223> OTHER INFORMATION: unknown amino acid
<220> FEATURE:
<221> NAME/KEY: unsure
<222> LOCATION: 8
<223> OTHER INFORMATION: unknown amino acid
<220> FEATURE:
<221> NAME/KEY: unsure
<222> LOCATION: 9
<223> OTHER INFORMATION: unknown amino acid
<220> FEATURE:
<221> NAME/KEY: unsure
<222> LOCATION: 10
<223> OTHER INFORMATION: unknown amino acid
<220> FEATURE:
<221> NAME/KEY: unsure
<222> LOCATION: 12
<223> OTHER INFORMATION: unknown amino acid
<220> FEATURE:
<221> NAME/KEY: unsure
<222> LOCATION: 13
<223> OTHER INFORMATION: unknown amino acid
<220> FEATURE:
<221> NAME/KEY: unsure
<222> LOCATION: 14
<223> OTHER INFORMATION: unknown amino acid
<220> FEATURE:
<221> NAME/KEY: unsure
<222> LOCATION: 16
<223> OTHER INFORMATION: unknown amino acid
<220> FEATURE:
<221> NAME/KEY: unsure
<222> LOCATION: 17
<223> OTHER INFORMATION: unknown amino acid
<220> FEATURE:
<221> NAME/KEY: unsure
<222> LOCATION: 18
<223> OTHER INFORMATION: unknown amino acid
<220> FEATURE:
<221> NAME/KEY: unsure
<222> LOCATION: 19
<223> OTHER INFORMATION: unknown amino acid
<220> FEATURE:
<221> NAME/KEY: unsure
<222> LOCATION: 20
<223> OTHER INFORMATION: unknown amino acid
<220> FEATURE:
<221> NAME/KEY: unsure
<222> LOCATION: 21
<223> OTHER INFORMATION: unknown amino acid

<400> SEQUENCE: 115

Cys Xaa Cys Xaa Xaa Xaa Xaa Xaa Xaa Xaa Cys Xaa Xaa Xaa Cys
 1               5                  10                  15

Xaa Xaa Xaa Xaa Xaa Xaa
                20

<210> SEQ ID NO 116
<211> LENGTH: 9
```

```
<212> TYPE: PRT
<213> ORGANISM: Artificial Sequence
<220> FEATURE:
<223> OTHER INFORMATION: generic formula for IgE receptor binding
      peptide of Example 7
<220> FEATURE:
<221> NAME/KEY: unsure
<222> LOCATION: 1
<223> OTHER INFORMATION: unknown amino acid
<220> FEATURE:
<221> NAME/KEY: unsure
<222> LOCATION: 2
<223> OTHER INFORMATION: unknown amino acid
<220> FEATURE:
<221> NAME/KEY: unsure
<222> LOCATION: 5
<223> OTHER INFORMATION: unknown amino acid
<220> FEATURE:
<221> NAME/KEY: unsure
<222> LOCATION: 6
<223> OTHER INFORMATION: unknown amino acid
<220> FEATURE:
<221> NAME/KEY: unsure
<222> LOCATION: 9
<223> OTHER INFORMATION: unknown amino acid

<400> SEQUENCE: 116

Xaa Xaa Cys Pro Xaa Xa

```
<223> OTHER INFORMATION: IgE receptor binding peptide identified from
      library 516 in Example 7

<400> SEQUENCE: 120

Ala Ile Cys Pro Ala Leu Cys Tyr Glu
                5

<210> SEQ ID NO 121
<211> LENGTH: 9
<212> TYPE: PRT
<213> ORGANISM: Artificial Sequence
<220> FEATURE:
<223> OTHER INFORMATION: IgE receptor binding peptide identified from
      library 516 in Example 7

<400> SEQUENCE: 121

Ala Glu Cys Pro Ile Met Cys Tyr Ser
                5

<210> SEQ ID NO 122
<211> LENGTH: 9
<212> TYPE: PRT
<213> ORGANISM: Artificial Sequence
<220> FEATURE:
<223> OTHER INFORMATION: IgE receptor binding peptide identified from
      library 516 in Example 7

<400> SEQUENCE: 122

Ser Val Cys Pro Ser Leu Cys Tyr Val
                5

<210> SEQ ID NO 123
<211> LENGTH: 9
<212> TYPE: PRT
<213> ORGANISM: Artificial Sequence
<220> FEATURE:
<223> OTHER INFORMATION: IgE receptor binding peptide identified from
      library 516 in Example 7

<400> SEQUENCE: 123

Ala Leu Cys Pro Glu Val Cys Tyr Val
                5

<210> SEQ ID NO 124
<211> LENGTH: 9
<212> TYPE: PRT
<213> ORGANISM: Artificial Sequence
<220> FEATURE:
<223> OTHER INFORMATION: IgE receptor binding peptide identified in
      Example 7. IgE035
<220> FEATURE:
<221> NAME/KEY: MOD_RES
<222> LOCATION: 9
<223> OTHER INFORMATION: C-terminal amidation

<400> SEQUENCE: 124

Ala Leu Cys Pro Glu Val Cys Tyr Val
                5

<210> SEQ ID NO 125
<211> LENGTH: 9
<212> TYPE: PRT
<213> ORGANISM: Artificial Sequence
<220> FEATURE:
<223> OTHER INFORMATION: IgE receptor binding peptide identified in
      Example 7. IgE036
<220> FEATURE:
<221> NAME/KEY: MOD_RES
<222> LOCATION: 1
```

```
<223> OTHER INFORMATION: N-terminal acetylation
<220> FEATURE:
<221> NAME/KEY: MOD_RES
<222> LOCATION: 9
<223> OTHER INFORMATION: C-terminal amidation

<400> SEQUENCE: 125

Ala Leu Cys Pro Glu Val Cys Tyr Val
                5

<210> SEQ ID NO 126
<211> LENGTH: 9
<212> TYPE: PRT
<213> ORGANISM: Artificial Sequence
<220> FEATURE:
<223> OTHER INFORMATION: IgE receptor binding peptide identified in
      Example 7. IgE053
<220> FEATURE:
<221> NAME/KEY: MOD_RES
<222> LOCATION: 9
<223> OTHER INFORMATION: C-terminal amidation

<400> SEQUENCE: 126

Leu Asn Cys Ser Gln Pro Cys Gln Arg
                5

<210> SEQ ID NO 127
<211> LENGTH: 9
<212> TYPE: PRT
<213> ORGANISM: Artificial Sequence
<220> FEATURE:
<223> OTHER INFORMATION: IgE receptor binding peptide identified in
      Example 7. IgE054
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 9
<223> OTHER INFORMATION: C-terminal amidation

<400> SEQUENCE: 127

Leu Asn Cys Ser Gln Pro Cys Gln Arg
                5

<210> SEQ ID NO 128
<211> LENGTH: 9
<212> TYPE: PRT
<213> ORGANISM: Artificial Sequence
<220> FEATURE:
<223> OTHER INFORMATION: IgE receptor binding peptide identified in
      Example 7. IgE037
<220> FEATURE:
<221> NAME/KEY: MOD_RES
<222> LOCATION: 9
<223> OTHER INFORMATION: C-terminal amidation

<400> SEQUENCE: 128

Ala Leu Cys Pro Ala Val Cys Tyr Val
                5

<210> SEQ ID NO 129
<211> LENGTH: 9
<212> TYPE: PRT
<213> ORGANISM: Artificial Sequence
<220> FEATURE:
<223> OTHER INFORMATION: IgE receptor binding peptide identified in
      Example 7. IgE038
<220> FEATURE:
<221> NAME/KEY: MOD_RES
```

```
<222> LOCATION: 1
<223> OTHER INFORMATION: N-terminal acetylation
<220> FEATURE:
<221> NAME/KEY: MOD_RES
<222> LOCATION: 9
<223> OTHER INFORMATION: C-terminal amidation

<400> SEQUENCE: 129

Ala Leu Cys Pro Ala Val Cys Tyr Val
                5

<210> SEQ ID NO 130
<211> LENGTH: 21
<212> TYPE: PRT
<213> ORGANISM: Artificial Sequence
<220> FEATURE:
<223> OTHER INFORMATION: IgE receptor binding peptide described in
      Example 8. IgE083

<400> SEQUENCE: 130

Ala Leu Cys Pro Ala Val Cys Tyr Val Gly Gly Lys Ala Leu Cys
  1               5                  10                  15

Pro Asp Val Cys Tyr Val
            20

<210> SEQ ID NO 131
<211> LENGTH: 21
<212> TYPE: PRT
<213> ORGANISM: Artificial Sequence
<220> FEATURE:
<223> OTHER INFORMATION: IgE receptor binding peptide described in
      Example 8. IgE120

<400> SEQUENCE: 131

Ile Val Cys Pro Arg Leu Cys Tyr Val Gly Gly Lys Ala Leu Cys
  1               5                  10                  15

Pro Asp Val Cys Tyr Val
            20

<210> SEQ ID NO 132
<211> LENGTH: 21
<212> TYPE: PRT
<213> ORGANISM: Artificial Sequence
<220> FEATURE:
<223> OTHER INFORMATION: IgE receptor binding peptide described in
      Example 8. IgE122

<400> SEQUENCE: 132

Val Gln Cys Pro His Phe Cys Tyr Val Gly Gly Lys Ala Leu Cys
  1               5                  10                  15

Pro Asp Val Cys Tyr Val
            20

<210> SEQ ID NO 133
<211> LENGTH: 14
<212> TYPE: PRT
<213> ORGANISM: Artificial Sequence
<220> FEATURE:
<223> OTHER INFORMATION: linker connecting IgE120 to g3p phage sequence

<400> SEQUENCE: 133

Gly Gly Gly Ser Gly Gly Gly Ser Gly Ser Gly Asp Tyr
                5                  10

<210> SEQ ID NO 134
<211> LENGTH: 21
```

```
<212> TYPE: PRT
<213> ORGANISM: Artificial Sequence
<220> FEATURE:
<223> OTHER INFORMATION: alanine scan variant of IgE120 shown in Table 7

<400> SEQUENCE: 134

Ala Ala Cys Pro Ala Leu Cys Tyr Val Gly Gly Lys Ala Leu Cys
 1               5                  10                  15

Pro Asp Val Cys Tyr Val
            20

<210> SEQ ID NO 135
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 135

Ile Val Cys Ala Arg Leu Cys Tyr Val Gly Gly Lys Ala Leu Cys
 1               5                  10                  15

Pro Asp Val Cys Tyr Val
            20

<210> SEQ ID NO 136
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 136

Ile Val Cys Pro Arg Leu Cys Tyr Val Gly Gly Lys Ala Leu Cys
 1               5                  10                  15

Ala Asp Val Cys Tyr Val
            20

<210> SEQ ID NO 137
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 137

Ile Val Cys Pro Arg Ala Cys Tyr Val Gly Gly Lys Ala Leu Cys
 1               5                  10                  15

Pro Asp Val Cys Tyr Val
            20

<210> SEQ ID NO 138
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 138

Ile Val Cys Pro Arg Ala Cys Tyr Val Gly Gly Lys Ala Leu Cys
 1               5                  10                  15

Pro Asp Ala Cys Tyr Val
            20

<210> SEQ ID NO 139
```

```
-continued

<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 139

Ile Val Cys Pro Arg Leu Cys Tyr Ala Gly Gly Lys Ala Leu Cys
 1               5                  10                  15

Pro Asp Val Cys Tyr Val
                20

<210> SEQ ID NO 140
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 140

Ile Val Cys Pro Arg Leu Cys Tyr Val Gly Gly Lys Ala Leu Cys
 1               5                  10                  15

Pro Asp Val Cys Tyr Ala
                20

<210> SEQ ID NO 141
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 141

Ile Val Cys Pro Arg Leu Cys Tyr Ala Gly Gly Lys Ala Leu Cys
 1               5                  10                  15

Pro Asp Val Cys Tyr Ala
                20

<210> SEQ ID NO 142
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 142

Ile Val Cys Pro Arg Leu Cys Ala Val Gly Gly Lys Ala Leu Cys
 1               5                  10                  15

Pro Asp Val Cys Tyr Val
                20

<210> SEQ ID NO 143
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 143

Ile Val Cys Pro Arg Leu Cys Tyr Val Gly Gly Lys Ala Leu Cys
 1               5                  10                  15

Pro Asp Val Cys Ala Val
                20
```

-continued

```
<210> SEQ ID NO 144
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 144

Ile Val Cys Pro Arg Leu Cys Tyr Val Gly Gly Ala Ala Leu Cys
 1               5                  10                  15

Pro Asp Val Cys Tyr Val
            20

<210> SEQ ID NO 145
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 145

Ile Val Cys Pro Arg Leu Cys Tyr Val Gly Gly Lys Ala Leu Cys
 1               5                  10                  15

Pro Ala Val Cys Tyr Val
            20

<210> SEQ ID NO 146
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 146

Ile Val Cys Pro Arg Leu Cys Tyr Val Gly Gly Lys Ala Ala Cys
 1               5                  10                  15

Pro Ala Val Cys Tyr Ala
            20

<210> SEQ ID NO 147
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 147

Ile Val Cys Pro Arg Ala Cys Tyr Val Gly Gly Lys Ala Ala Cys
 1               5                  10                  15

Pro Asp Val Cys Tyr Val
            20

<210> SEQ ID NO 148
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 148

Ile Val Cys Pro Arg Leu Cys Tyr Val Gly Gly Lys Ala Ala Cys
 1               5                  10                  15

Pro Asp Val Cys Tyr Val
            20
```

<210> SEQ ID NO 149
<211> LENGTH: 21
<212> TYPE: PRT
<213> ORGANISM: Artificial Sequence
<220> FEATURE:
<223> OTHER INFORMATION: alanine scan variant of IgE120 shown in Table 7

<400> SEQUENCE: 149

Ile Val Cys Pro Arg Leu Cys Tyr Val Gly Gly Lys Ala Leu Cys
 1               5                  10                  15

Pro Asp Ala Cys Tyr Val
                20

<210> SEQ ID NO 150
<211> LENGTH: 20
<212> TYPE: PRT
<213> ORGANISM: Artificial Sequence
<220> FEATURE:
<223> OTHER INFORMATION: alanine scan variant of IgE120 shown in Table 7

<400> SEQUENCE: 150

Val Cys Pro Arg Leu Cys Tyr Val Gly Gly Lys Ala Leu Cys Pro
 1               5                  10                  15

Asp Val Cys Tyr Val
                20

<210> SEQ ID NO 151
<211> LENGTH: 19
<212> TYPE: PRT
<213> ORGANISM: Artificial Sequence
<220> FEATURE:
<223> OTHER INFORMATION: alanine scan variant of IgE120 shown in Table 7

<400> SEQUENCE: 151

Cys Pro Arg Leu Cys Tyr Val Gly Gly Lys Ala Leu Cys Pro Asp
 1               5                  10                  15

Val Cys Tyr Val

<210> SEQ ID NO 152
<211> LENGTH: 19
<212> TYPE: PRT
<213> ORGANISM: Artificial Sequence
<220> FEATURE:
<223> OTHER INFORMATION: alanine scan variant of IgE120 shown in Table 7

<400> SEQUENCE: 152

Ile Val Cys Pro Arg Leu Cys Tyr Val Gly Gly Lys Ala Leu Cys
 1               5                  10                  15

Pro Asp Val Cys

<210> SEQ ID NO 153
<211> LENGTH: 21
<212> TYPE: PRT
<213> ORGANISM: Artificial Sequence
<220> FEATURE:
<223> OTHER INFORMATION: IgE120 variant described in Example 8

<400> SEQUENCE: 153

Ile Val Cys Pro Arg Leu Cys Tyr Glu Leu Asp Tyr Glu Leu Cys
 1               5                  10                  15

Pro Asp Val Cys Tyr Val
                20

```
<210> SEQ ID NO 154
<211> LENGTH: 5
<212> TYPE: PRT
<213> ORGANISM: Artificial Sequence
<220> FEATURE:
<223> OTHER INFORMATION: linker sequence identified in Examples 8-9

<400> SEQUENCE: 154

Glu Leu Asp Tyr Glu
                 5

<210> SEQ ID NO 155
<211> LENGTH: 21
<212> TYPE: PRT
<213> ORGANISM: Artificial Sequence
<220> FEATURE:
<223> OTHER INFORMATION: IgE receptor binding peptide identified in
      Example 10. IgE134

<400> SEQUENCE: 155

Val Gln Cys Pro His Phe Cys Tyr Glu Leu Asp Tyr Glu Leu Cys
 1               5                  10                  15

Pro Asp Val Cys Tyr Val
                20

<210> SEQ ID NO 156
<211> LENGTH: 21
<212> TYPE: PRT
<213> ORGANISM: Artificial Sequence
<220> FEATURE:
<223> OTHER INFORMATION: amide variant of SEQ ID NO:134. IgE083
<220> FEATURE:
<221> NAME/KEY: MOD_RES
<222> LOCATION: 21
<223> OTHER INFORMATION: C-terminal amidation

<400> SEQUENCE: 156

Ala Leu Cys Pro Ala Val Cys Tyr Val Gly Gly Lys Ala Leu Cys
 1               5                  10                  15

Pro Asp Val Cys Tyr Val
                20

<210> SEQ ID NO 157
<211> LENGTH: 9
<212> TYPE: PRT
<213> ORGANISM: Artificial Sequence
<220> FEATURE:
<223> OTHER INFORMATION: antiparallel sequence of  IgE089

<400> SEQUENCE: 157

Val Tyr Cys Val Ala Pro Cys Leu Ala
 1               5

<210> SEQ ID NO 158
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE119
<220> FEATURE:
<221> NAME/KEY: MOD_RES
<222> LOCATION: 21
<223> OTHER INFORMATION: C-terminal amidation

<400> SEQUENCE: 158

Asn Gly Cys Pro Gly Trp Cys Tyr Val Gly Gly Lys Ala Leu Cys
 1               5                  10                  15
```

Pro Asp Val Cys Tyr Val
            20

<210> SEQ ID NO 159
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE120
<220> FEATURE:
<221> NAME/KEY: MOD_RES
<222> LOCATION: 21
<223> OTHER INFORMATION: C-terminal amidation

<400> SEQUENCE: 159

Ile Val Cys Pro Arg Leu Cys Tyr Val Gly Gly Lys Ala Leu Cys
 1               5                  10                  15

Pro Asp Val Cys Tyr Val
            20

<210> SEQ ID NO 160
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE121
<220> FEATURE:
<221> NAME/KEY: MOD_RES
<222> LOCATION: 21
<223> OTHER INFORMATION: C-terminal amidation

<400> SEQUENCE: 160

Val Val Cys Pro Asn Met Cys Tyr Val Gly Gly Lys Ala Leu Cys
 1               5                  10                  15

Pro Asp Val Cys Tyr Val
            20

<210> SEQ ID NO 161
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE122
<220> FEATURE:
<221> NAME/KEY: MOD_RES
<222> LOCATION: 21
<223> OTHER INFORMATION: C-terminal amidation

<400> SEQUENCE: 161

Val Gln Cys Pro His Phe Cys Tyr Val Gly Gly Lys Ala Leu Cys
 1               5                  10                  15

Pro Asp Val Cys Tyr Val
            20

<210> SEQ ID NO 162
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE123
<220> FEATURE:
<221> NAME/KEY: MOD_RES
<222> LOCATION: 21
<223> OTHER INFORMATION: C-terminal admidation

```
<400> SEQUENCE: 162

Val Lys Cys Pro Ser Leu Cys Tyr Val Gly Gly Lys Ala Leu Cys
 1               5                  10                  15

Pro Asp Val Cys Tyr Val
                20

<210> SEQ ID NO 163
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE124
<220> FEATURE:
<221> NAME/KEY: MOD_RES
<222> LOCATION: 21
<223> OTHER INFORMATION: C-terminal amidation

<400> SEQUENCE: 163

Val Pro Cys Pro Glu Leu Cys Tyr Val Gly Gly Lys Ala Leu Cys
 1               5                  10                  15

Pro Asp Val Cys Tyr Val
                20

<210> SEQ ID NO 164
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE126
<220> FEATURE:
<221> NAME/KEY: MOD_RES
<222> LOCATION: 21
<223> OTHER INFORMATION: C-terminal amidation

<400> SEQUENCE: 164

Val Thr Cys Pro Arg Trp Cys Tyr Val Gly Gly Lys Ala Leu Cys
 1               5                  10                  15

Pro Asp Val Cys Tyr Val
                20

<210> SEQ ID NO 165
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE127
<220> FEATURE:
<221> NAME/KEY: MOD_RES
<222> LOCATION: 21
<223> OTHER INFORMATION: C-terminal amidation

<400> SEQUENCE: 165

Ile Val Cys Ala Arg Leu Cys Tyr Val Gly Gly Lys Ala Leu Cys
 1               5                  10                  15

Pro Asp Val Cys Tyr Val
                20

<210> SEQ ID NO 166
<211> LENGTH: 21
<212> TYPE: PRT
<213> ORGANISM: Artificial Sequence
<220> FEATURE:
<223> OTHER INFORMATION: IgE receptor binding peptide of Example 12,
```

```
          Table 9. IgE128
<220> FEATURE:
<221> NAME/KEY: MOD_RES
<222> LOCATION: 21
<223> OTHER INFORMATION: C-terminal amidation

<400> SEQUENCE: 166

Lys Ser Cys Pro Leu Trp Cys Tyr Val Gly Gly Lys Ala Leu Cys
  1               5                  10                  15

Pro Asp Val Cys Tyr Val
                20

<210> SEQ ID NO 167
<211> LENGTH: 9
<212> TYPE: PRT
<213> ORGANISM: Artificial Sequence
<220> FEATURE:
<223> OTHER INFORMATION: IgE receptor binding peptide of Example 12,
      Table 9. IgE129
<220> FEATURE:
<221> NAME/KEY: MOD_RES
<222> LOCATION: 9
<223> OTHER INFORMATION: C-terminal amidation

<400> SEQUENCE: 167

Val Gln Cys Pro His Phe Cys Tyr Val
  1               5

<210> SEQ ID NO 168
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE130
<220> FEATURE:
<221> NAME/KEY: MOD_RES
<222> LOCATION: 21
<223> OTHER INFORMATION: C-terminal amidation

<400> SEQUENCE: 168

Ala Leu Cys Pro Asp Val Cys Tyr Val Gly Gly Lys Val Gln Cys
  1               5                  10                  15

Pro His Phe Cys Tyr Val
                20

<210> SEQ ID NO 169
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE131
<220> FEATURE:
<221> NAME/KEY: MOD_RES
<222> LOCATION: 21
<223> OTHER INFORMATION: C-terminal amidation

<400> SEQUENCE: 169

Val Gln Cys Pro His Phe Cys Tyr Val Gly Gly Lys Val Gln Cys
  1               5                  10                  15

Pro His Phe Cys Tyr Val
                20

<210> SEQ ID NO 170
<211> LENGTH: 23
<212> TYPE: PRT
<213> ORGANISM: Artificial Sequence
```

```
<220> FEATURE:
<223> OTHER INFORMATION: IgE receptor binding peptide of Example 12,
      Table 9. IgE132

<400> SEQUENCE: 170

Val Gln Cys Pro His Phe Cys Tyr Val Gly Gly His Ala Leu Cys
  1               5                  10                  15

Pro Asp Val Cys Tyr Val Gly Arg
                20

<210> SEQ ID NO 171
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE134
<220> FEATURE:
<221> NAME/KEY: MOD_RES
<222> LOCATION: 21
<223> OTHER INFORMATION: C-terminal amidation

<400> SEQUENCE: 171

Val Gln Cys Pro His Phe Cys Tyr Glu Leu Asp Tyr Glu Leu Cys
  1               5                  10                  15

Pro Asp Val Cys Tyr Val
                20

<210> SEQ ID NO 172
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE135
<220> FEATURE:
<221> NAME/KEY: MOD_RES
<222> LOCATION: 21
<223> OTHER INFORMATION: C-terminal amidation

<400> SEQUENCE: 172

Val Gln Cys Pro His Phe Cys Tyr Phe Gly Gly Ala Glu Leu Cys
  1               5                  10                  15

Pro Asp Val Cys Tyr Val
                20

<210> SEQ ID NO 173
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE136
<220> FEATURE:
<221> NAME/KEY: MOD_RES
<222> LOCATION: 21
<223> OTHER INFORMATION: C-terminal amidation

<400> SEQUENCE: 173

Val Gln Cys Pro His Phe Cys Tyr Phe Gly Gly Ala Glu Leu Cys
  1               5                  10                  15

Pro Gly Val Cys Tyr Val
                20

<210> SEQ ID NO 174
<211> LENGTH: 21
<212> TYPE: PRT
```

```
<213> ORGANISM: Artificial Sequence
<220> FEATURE:
<223> OTHER INFORMATION: IgE receptor binding peptide of Example 12,
      Table 9. IgE141
<220> FEATURE:
<221> NAME/KEY: MOD_RES
<222> LOCATION: 21
<223> OTHER INFORMATION: C-terminal amidation

<400> SEQUENCE: 174

Ile Val Cys Pro Arg Leu Cys Tyr Glu Leu Asp Tyr Glu Leu Cys
 1               5                  10                  15

Pro Asp Val Cys Tyr Val
                20

<210> SEQ ID NO 175
<211> LENGTH: 23
<212> TYPE: PRT
<213> ORGANISM: Artificial Sequence
<220> FEATURE:
<223> OTHER INFORMATION: IgE receptor binding peptide of Example 12,
      Table 9. IgE142

<400> SEQUENCE: 175

Val Gln Cys Ala His Phe Cys Tyr Val Gly Gly His Ala Leu Cys
 1               5                  10                  15

Pro Asp Val Cys Tyr Val Gly Arg
                20

<210> SEQ ID NO 176
<211> LENGTH: 23
<212> TYPE: PRT
<213> ORGANISM: Artificial Sequence
<220> FEATURE:
<223> OTHER INFORMATION: IgE receptor binding peptide of Example 12,
      Table 9. IgE143

<400> SEQUENCE: 176

Val Gln Cys Pro His Phe Cys Tyr Val Gly Gly His Ala Leu Cys
 1               5                  10                  15

Ala Asp Val Cys Tyr Val Gly Arg
                20

<210> SEQ ID NO 177
<211> LENGTH: 23
<212> TYPE: PRT
<213> ORGANISM: Artificial Sequence
<220> FEATURE:
<223> OTHER INFORMATION: IgE receptor binding peptide of Example 12,
      Table 9. IgE144

<400> SEQUENCE: 177

Val Gln Cys Ala His Phe Cys Tyr Val Gly Gly His Ala Leu Cys
 1               5                  10                  15

Ala Asp Val Cys Tyr Val Gly Arg
                20

<210> SEQ ID NO 178
<211> LENGTH: 23
<212> TYPE: PRT
<213> ORGANISM: Artificial Sequence
<220> FEATURE:
<223> OTHER INFORMATION: IgE receptor binding peptide of Example 12,
      Table 9. IgE145

<400> SEQUENCE: 178
```

```
Val Gln Cys Pro Asp Phe Cys Tyr Val Gly Gly His Ala Leu Cys
  1               5                  10                 15

Pro Asp Val Cys Tyr Val Gly Arg
                20
```

<210> SEQ ID NO 179
<211> LENGTH: 20
<212> TYPE: PRT
<213> ORGANISM: Artificial Sequence
<220> FEATURE:
<223> OTHER INFORMATION: IgE receptor binding peptide of Example 12,
      Table 9. IgE146
<220> FEATURE:
<221> NAME/KEY: MOD_RES
<222> LOCATION: 20
<223> OTHER INFORMATION: C-terminal amidation

<400> SEQUENCE: 179

```
Val Gln Cys Pro His Phe Cys Tyr Val Gly Glu Ala Leu Cys Pro
  1               5                  10                 15

Asp Val Cys Tyr Val
                20
```

<210> SEQ ID NO 180
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE147
<220> FEATURE:
<221> NAME/KEY: MOD_RES
<222> LOCATION: 21
<223> OTHER INFORMATION: C-terminal amidation

<400> SEQUENCE: 180

```
Val Gln Cys Pro His Phe Cys Tyr Val Gly Gly Lys Ala Leu Cys
  1               5                  10                 15

Pro Asp Lys Cys Tyr Val
                20
```

<210> SEQ ID NO 181
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE148
<220> FEATURE:
<221> NAME/KEY: MOD_RES
<222> LOCATION: 21
<223> OTHER INFORMATION: C-terminal amidation

<400> SEQUENCE: 181

```
Val Gln Cys Pro His Phe Cys Tyr Val Gly Gly Lys Ala Leu Cys
  1               5                  10                 15

Pro Asp Lys Cys Tyr Thr
                20
```

<210> SEQ ID NO 182
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE149
<220> FEATURE:
<221> NAME/KEY: MOD_RES

```
<222> LOCATION: 21
<223> OTHER INFORMATION: C-terminal amidation

<400> SEQUENCE: 182

Val Gln Cys Pro His Phe Cys Tyr Val Gly Gly Lys Ala Leu Cys
 1               5                  10                  15

Pro Asp Pro Cys Tyr Val
                20

<210> SEQ ID NO 183
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE150
<220> FEATURE:
<221> NAME/KEY: MOD_RES
<222> LOCATION: 21
<223> OTHER INFORMATION: C-terminal amidation

<400> SEQUENCE: 183

Val Gln Cys Pro His Phe Cys Tyr Val Gly Gly Lys Ala Leu Cys
 1               5                  10                  15

Pro Asp Val Cys Asp Val
                20

<210> SEQ ID NO 184
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE151

<400> SEQUENCE: 184

Val Gln Cys Pro His Phe Cys Tyr Phe Gly Gly Ala Glu Leu Cys
 1               5                  10                  15

Pro Asp Val Cys Tyr Val
                20

<210> SEQ ID NO 185
<211> LENGTH: 20
<212> TYPE: PRT
<213> ORGANISM: Artificial Sequence
<220> FEATURE:
<223> OTHER INFORMATION: IgE receptor binding peptide of Example 12,
      Table 9. IgE152

<400> SEQUENCE: 185

Val Gln Cys Pro His Phe Cys Tyr Phe Gly Ala Glu Leu Cys Pro
 1               5                  10                  15

Asp Val Cys Tyr Val
                20

<210> SEQ ID NO 186
<211> LENGTH: 20
<212> TYPE: PRT
<213> ORGANISM: Artificial Sequence
<220> FEATURE:
<223> OTHER INFORMATION: IgE receptor binding peptide of Example 12,
      Table 9. IgE153
<220> FEATURE:
<221> NAME/KEY: MOD_RES
<222> LOCATION: 20
<223> OTHER INFORMATION: C-terminal amidation
```

```
<400> SEQUENCE: 186

Val Gln Cys Pro His Phe Cys Tyr Glu Leu Asp Tyr Glu Leu Cys
  1               5                  10                  15

Pro Asp Val Cys Tyr
             20

<210> SEQ ID NO 187
<211> LENGTH: 18
<212> TYPE: PRT
<213> ORGANISM: Artificial Sequence
<220> FEATURE:
<223> OTHER INFORMATION: IgE receptor binding peptide of Example 12,
      Table 9. IgE155
<220> FEATURE:
<221> NAME/KEY: MOD_RES
<222> LOCATION: 18
<223> OTHER INFORMATION: C-terminal amidation

<400> SEQUENCE: 187

Cys Pro His Phe Cys Tyr Glu Leu Asp Tyr Glu Leu Cys Pro Asp
  1               5                  10                  15

Val Cys Tyr

<210> SEQ ID NO 188
<211> LENGTH: 23
<212> TYPE: PRT
<213> ORGANISM: Artificial Sequence
<220> FEATURE:
<223> OTHER INFORMATION: IgE receptor binding peptide of Example 12,
      Table 9. IgE156

<400> SEQUENCE: 188

Val Gln Cys Pro His Phe Cys Tyr Glu Leu Asp Tyr Glu Leu Cys
  1               5                  10                  15

Pro Asp Val Cys Tyr Val Gly Arg
             20

<210> SEQ ID NO 189
<211> LENGTH: 19
<212> TYPE: PRT
<213> ORGANISM: Artificial Sequence
<220> FEATURE:
<223> OTHER INFORMATION: IgE receptor binding peptide of Example 12,
      Table 9. IgE157
<220> FEATURE:
<221> NAME/KEY: MOD_RES
<222> LOCATION: 19
<223> OTHER INFORMATION: C-terminal amidation

<400> SEQUENCE: 189

Gln Cys Pro His Phe Cys Tyr Glu Leu Asp Tyr Glu Leu Cys Pro
  1               5                  10                  15

Asp Val Cys Tyr

<210> SEQ ID NO 190
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE158
<220> FEATURE:
<221> NAME/KEY: SITE
<222> LOCATION: 16
<223> OTHER INFORMATION: unusual amino acid residue N-methyl alanine
<220> FEATURE:
<221> NAME/KEY: MOD_RES
```

```
<222> LOCATION: 21
<223> OTHER INFORMATION: C-terminal amidation

<400> SEQUENCE: 190

Val Gln Cys Pro His Phe Cys Tyr Phe Gly Gly Ala Glu Leu Cys
  1               5                  10                  15

Xaa Asp Val Cys Tyr Val
                20

<210> SEQ ID NO 191
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE159
<220> FEATURE:
<221> NAME/KEY: SITE
<222> LOCATION: 4
<223> OTHER INFORMATION: unusual amino acid residue N-methyl alanine
<220> FEATURE:
<221> NAME/KEY: MOD_RES
<222> LOCATION: 21
<223> OTHER INFORMATION: C-terminal amidation

<400> SEQUENCE: 191

Val Gln Cys Xaa His Phe Cys Tyr Phe Gly Gly Ala Glu Leu Cys
  1               5                  10                  15

Pro Asp Val Cys Tyr Val
                20

<210> SEQ ID NO 192
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE160
<220> FEATURE:
<221> NAME/KEY: SITE
<222> LOCATION: 4
<223> OTHER INFORMATION: unusual amino acid residue N-methyl alanine
<220> FEATURE:
<221> NAME/KEY: SITE
<222> LOCATION: 16
<223> OTHER INFORMATION: unusual amino acid residue N-methyl alanine
<220> FEATURE:
<221> NAME/KEY: MOD_RES
<222> LOCATION: 21
<223> OTHER INFORMATION: C-terminal amidation

<400> SEQUENCE: 192

Val Gln Cys Xaa His Phe Cys Tyr Phe Gly Gly Ala Glu Leu Cys
  1               5                  10                  15

Xaa Asp Val Cys Tyr Val
                20

<210> SEQ ID NO 193
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE161-1
<220> FEATURE:
<221> NAME/KEY: SITE
<222> LOCATION: 16
<223> OTHER INFORMATION: unusual amino acid D-pipecolic acid
<220> FEATURE:
<221> NAME/KEY: MOD_RES
```

```
<222> LOCATION: 21
<223> OTHER INFORMATION: C-terminal amidation

<400> SEQUENCE: 193

Val Gln Cys Pro His Phe Cys Tyr Phe Gly Gly Ala Glu Leu Cys
 1               5                  10                  15

Xaa Asp Val Cys Tyr Val
                20

<210> SEQ ID NO 194
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE161-2. residue 16 is Xaa
<220> FEATURE:
<221> NAME/KEY: SITE
<222> LOCATION: 16
<223> OTHER INFORMATION: unusual amino acid L-pipecolic acid
<220> FEATURE:
<221> NAME/KEY: MOD_RES
<222> LOCATION: 21
<223> OTHER INFORMATION: C-terminal amidation

<400> SEQUENCE: 194

Val Gln Cys Pro His Phe Cys Tyr Phe Gly Gly Ala Glu Leu Cys
 1               5                  10                  15

Xaa Asp Val Cys Tyr Val
                20

<210> SEQ ID NO 195
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE162-1
<220> FEATURE:
<221> NAME/KEY: SITE
<222> LOCATION: 4
<223> OTHER INFORMATION: unusual amino acid residue D-pipecolic acid
<220> FEATURE:
<221> NAME/KEY: MOD_RES
<222> LOCATION: 21
<223> OTHER INFORMATION: C-terminal amidation

<400> SEQUENCE: 195

Val Gln Cys Xaa His Phe Cys Tyr Phe Gly Gly Ala Glu Leu Cys
 1               5                  10                  15

Pro Asp Val Cys Tyr Val
                20

<210> SEQ ID NO 196
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE162-2. residue 4 is Xaa
<220> FEATURE:
<221> NAME/KEY: SITE
<222> LOCATION: 4
<223> OTHER INFORMATION: unusual amino acid residue L-pipecolic acid
<220> FEATURE:
<221> NAME/KEY: MOD_RES
<222> LOCATION: 21
<223> OTHER INFORMATION: C-terminal amidation

<400> SEQUENCE: 196
```

-continued

Val Gln Cys Xaa His Phe Cys Tyr Phe Gly Gly Ala Glu Leu Cys
 1               5                   10                  15

Pro Asp Val Cys Tyr Val
                20

<210> SEQ ID NO 197
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE164
<220> FEATURE:
<221> NAME/KEY: SITE
<222> LOCATION: 15
<223> OTHER INFORMATION: unusual amino acid residue homocysteine
<220> FEATURE:
<221> NAME/KEY: MOD_RES
<222> LOCATION: 21
<223> OTHER INFORMATION: C-terminal amidation

<400> SEQUENCE: 197

Val Gln Cys Pro His Phe Cys Tyr Phe Gly Gly Ala Glu Leu Xaa
 1               5                   10                  15

Pro Asp Val Cys Tyr Val
                20

<210> SEQ ID NO 198
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE165
<220> FEATURE:
<221> NAME/KEY: SITE
<222> LOCATION: 19
<223> OTHER INFORMATION: unusual amino acid residue homocysteine
<220> FEATURE:
<221> NAME/KEY: MOD_RES
<222> LOCATION: 21
<223> OTHER INFORMATION: C-terminal amidation

<400> SEQUENCE: 198

Val Gln Cys Pro His Phe Cys Tyr Phe Gly Gly Ala Glu Leu Cys
 1               5                   10                  15

Pro Asp Val Xaa Tyr Val
                20

<210> SEQ ID NO 199
<211> LENGTH: 21
<212> TYPE: PRT
<213> ORGANISM: Artificial Sequence
<220> FEATURE:
<223> OTHER INFORMATION: IgE receptor binding peptide of Example 12,
      Table 9. IgE166
<220> FEATURE:
<221> NAME/KEY: SITE
<222> LOCATION: 7
<223> OTHER INFORMATION: unusual amino acid residue homocysteine
<220> FEATURE:
<221> NAME/KEY: MOD_RES
<222> LOCATION: 21
<223> OTHER INFORMATION: C-terminal amidation

<400> SEQUENCE: 199

Val Gln Cys Pro His Phe Xaa Tyr Phe Gly Gly Ala Glu Leu Cys
 1               5                   10                  15

```
Pro Asp Val Cys Tyr Val
                20

<210> SEQ ID NO 200
<211> LENGTH: 20
<212> TYPE: PRT
<213> ORGANISM: Artificial Sequence
<220> FEATURE:
<223> OTHER INFORMATION: IgE receptor binding peptide of Example 12,
      Table 9. IgE 167
<220> FEATURE:
<221> NAME/KEY: MOD_RES
<222> LOCATION: 20
<223> OTHER INFORMATION: C-terminal amidation

<400> SEQUENCE: 200

Val Gln Cys Pro His Phe Cys Tyr Phe Gly Ala Glu Leu Cys Pro
  1               5                  10                  15

Asp Val Cys Tyr Val
                20

<210> SEQ ID NO 201
<211> LENGTH: 20
<212> TYPE: PRT
<213> ORGANISM: Artificial Sequence
<220> FEATURE:
<223> OTHER INFORMATION: IgE receptor binding peptide of Example 12,
      Table 9. IgE168
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 20
<223> OTHER INFORMATION: C-terminal amidation

<400> SEQUENCE: 201

Val Gln Cys Pro His Phe Cys Tyr Phe Gly Ala Glu Leu Cys Pro
  1               5                  10                  15

Asp Val Cys Tyr Val
                20

<210> SEQ ID NO 202
<211> LENGTH: 20
<212> TYPE: PRT
<213> ORGANISM: Artificial Sequence
<220> FEATURE:
<223> OTHER INFORMATION: IgE receptor binding peptide of Example 12,
      Table 9. IgE169
<220> FEATURE:
<221> NAME/KEY: MOD_RES
<222> LOCATION: 20
<223> OTHER INFORMATION: C-terminal amidation

<400> SEQUENCE: 202

Val Gln Cys Pro His Phe Cys Tyr Phe Gly Ala Glu Leu Cys Pro
  1               5                  10                  15

Ala Val Cys Tyr Val
                20

<210> SEQ ID NO 203
<211> LENGTH: 17
<212> TYPE: PRT
<213> ORGANISM: Artificial Sequence
<220> FEATURE:
<223> OTHER INFORMATION: IgE receptor binding protein of Example 12,
      Table 9. IgE170
<220> FEATURE:
```

```
<221> NAME/KEY: MOD_RES
<222> LOCATION: 17
<223> OTHER INFORMATION: C-terminal amidation

<400> SEQUENCE: 203

Cys Pro His Phe Cys Tyr Phe Gly Ala Glu Leu Cys Pro Asp Val
 1               5                  10                  15

Cys Tyr

<210> SEQ ID NO 204
<211> LENGTH: 17
<212> TYPE: PRT
<213> ORGANISM: Artificial Sequence
<220> FEATURE:
<223> OTHER INFORMATION: IgE receptor binding protein of Example 12,
      Table 9. IgE171
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 17
<223> OTHER INFORMATION: C-terminal amidation

<400> SEQUENCE: 204

Cys Pro His Phe Cys Tyr Phe Gly Ala Glu Leu Cys Pro Asp Val
 1               5                  10                  15

Cys Tyr

<210> SEQ ID NO 205
<211> LENGTH: 21
<212> TYPE: PRT
<213> ORGANISM: Artificial Sequence
<220> FEATURE:
<223> OTHER INFORMATION: IgE receptor binding protein of Example 12,
      Table 9. IgE173
<220> FEATURE:
<221> NAME/KEY: MOD_RES
<222> LOCATION: 21
<223> OTHER INFORMATION: C-terminal amidation

<400> SEQUENCE: 205

Val Gln Cys Pro His Phe Cys Tyr Glu Leu Asp Tyr Glu Leu Cys
 1               5                  10                  15

Pro Asp Lys Cys Tyr Thr
                20

<210> SEQ ID NO 206
<211> LENGTH: 21
<212> TYPE: PRT
<213> ORGANISM: Artificial Sequence
<220> FEATURE:
<223> OTHER INFORMATION: IgE receptor binding protein of Example 12,
      Table 9. IgE174
<220> FEATURE:
<221> NAME/KEY: MOD_RES
<222> LOCATION: 21
<223> OTHER INFORMATION: C-terminal amidation

<400> SEQUENCE: 206

Val Gln Cys Pro His Phe Cys Tyr Glu Leu Asp Tyr Glu Leu Cys
 1               5                  10                  15

Pro Trp Lys Cys Tyr Thr
                20

<210> SEQ ID NO 207
```

```
<211> LENGTH: 21
<212> TYPE: PRT
<213> ORGANISM: Artificial Sequence
<220> FEATURE:
<223> OTHER INFORMATION: IgE receptor binding protein of Example 12,
      Table 9. IgE175
<220> FEATURE:
<221> NAME/KEY: MOD_RES
<222> LOCATION: 21
<223> OTHER INFORMATION: C-terminal amidation

<400> SEQUENCE: 207

<223> OTHER INFORMATION: linker sequence of IgE135

<400> SEQUENCE: 212

Phe Gly Gly Ala Glu
 1               5

<210> SEQ ID NO 213
<211> LENGTH: 4
<212> TYPE: PRT
<213> ORGANISM: Artificial Sequence
<220> FEATURE:
<223> OTHER INFORMATION: linker sequence of IgE152

<400> SEQUENCE: 213

Phe Gly Ala Glu

<210> SEQ ID NO 214
<211> LENGTH: 15
<212> TYPE: PRT
<213> ORGANISM: Artificial Sequence
<220> FEATURE:
<223> OTHER INFORMATION: IgE receptor binding polypeptide of Table 5
<220> FEATURE:
<221> NAME/KEY: MOD_RES
<222> LOCATION: 1
<223> OTHER INFORMATION: N-terminal acetylation

<400> SEQUENCE: 214

Asn Leu Pro Arg Cys Ala Glu Gly Pro Trp Gly Trp Val Cys Met
 1               5                  10                  15

<210> SEQ ID NO 215
<211> LENGTH: 15
<212> TYPE: PRT
<213> ORGANISM: Artificial Sequence
<220> FEATURE:
<223> OTHER INFORMATION: IgE receptor binding polypeptide of Table 5
<220> FEATURE:
<221> NAME/KEY: MOD_RES
<222> LOCATION: 1
<223> OTHER INFORMATION: N-terminal acetylation

<400> SEQUENCE: 215

Asn Leu Pro Arg Cys Thr Glu Gly Pro Trp Gly Trp Ala Cys Met
 1               5                  10                  15

<210> SEQ ID NO 216
<211> LENGTH: 19
<212> TYPE: PRT
<213> ORGANISM: Artificial Sequence
<220> FEATURE:
<223> OTHER INFORMATION: IgE receptor binding peptide shown in Example
      12, Table 9. IgE154
<220> FEATURE:
<221> NAME/KEY: MOD_RES
<222> LOCATION: 19
<223> OTHER INFORMATION: C-terminal amidation

<400> SEQUENCE: 216

Gln Cys Pro His Phe Cys Pro Glu Leu Asp Tyr Glu Leu Cys Pro
 1               5                  10                  15
Cys Val Cys Tyr

<210> SEQ ID NO 217
<211> LENGTH: 21
<212> TYPE: PRT
<213> ORGANISM: Artificial Sequence
<220> FEATURE:

```
<223> OTHER INFORMATION: IgE receptor binding peptide shown in Example
      12, Table 9. IgE179
<220> FEATURE:
<221> NAME/KEY: MOD_RES
<222> LOCATION: 1
<223> OTHER INFORMATION: N-terminal acetylation
<220> FEATURE:
<221> NAME/KEY: MOD_RES
<222> LOCATION: 21
<223> OTHER INFORMATION: C-terminal amidation

<400> SEQUENCE: 217

Val Gln Cys Pro His Phe Cys Tyr Glu Leu Asp Tyr Glu Leu Cys
 1               5                  10                  15

Pro Asp Val Cys Tyr Val
                20

<210> SEQ ID NO 218
<211> LENGTH: 21
<212> TYPE: PRT
<213> ORGANISM: Artificial Sequence
<220> FEATURE:
<223> OTHER INFORMATION: IgE receptor binding peptide shown in Example
      12, Table 9. IgE182
<220> FEATURE:
<221> NAME/KEY: MOD_RES
<222> LOCATION: 21
<223> OTHER INFORMATION: C-terminal amidation

<400> SEQUENCE: 218

Val Gln Cys Pro His Phe Cys Tyr Glu Leu Phe Ser Arg Leu Cys
 1               5                  10                  15

Pro Asp Val Cys Tyr Val
                20

<210> SEQ ID NO 219
<211> LENGTH: 20
<212> TYPE: PRT
<213> ORGANISM: Artificial Sequence
<220> FEATURE:
<223> OTHER INFORMATION: IgE receptor binding peptide shown in Example
      12, Table 9. IgE183
<220> FEATURE:
<221> NAME/KEY: MOD_RES
<222> LOCATION: 20
<223> OTHER INFORMATION: C-terminal amidation

<400> SEQUENCE: 219

Val Gln Cys Pro His Phe Cys Tyr Asp Ala Ser Arg Leu Cys Pro
 1               5                  10                  15

Asp Val Cys Tyr Val
                20

<210> SEQ ID NO 220
<211> LENGTH: 19
<212> TYPE: PRT
<213> ORGANISM: Artificial Sequence
<220> FEATURE:
<223> OTHER INFORMATION: IgE receptor binding peptide shown in Example
      12, Table 9. IgE184

<400> SEQUENCE: 220

Val Gln Cys Pro His Phe Cys Tyr Asp Tyr Glu Leu Cys Pro Asp
 1               5                  10                  15

Val Cys Tyr Val

<210> SEQ ID NO 221
```

```
<211> LENGTH: 19
<212> TYPE: PRT
<213> ORGANISM: Artificial Sequence
<220> FEATURE:
<223> OTHER INFORMATION: IgE receptor binding peptide shown in Example
      12, Table 9. IgE185
<220> FEATURE:
<221> NAME/KEY: MOD_RES
<222> LOCATION: 19
<223> OTHER INFORMATION: C-terminal amidation

<400> SEQUENCE: 221

Val Gln Cys Pro His Phe Cys Tyr Ala Glu Pro Leu Cys Pro Asp
 1               5                  10                  15

Val Cys Tyr Val

<210> SEQ ID NO 222
<211> LENGTH: 20
<212> TYPE: PRT
<213> ORGANISM: Artificial Sequence
<220> FEATURE:
<223> OTHER INFORMATION: IgE receptor binding peptide shown in Example
      12, Table 9. IgE186
<220> FEATURE:
<221> NAME/KEY: SITE
<222> LOCATION: 11
<223> OTHER INFORMATION: unusual amino acid residue amino-valeric acid
<220> FEATURE:
<221> NAME/KEY: MOD_RES
<222> LOCATION: 20
<223> OTHER INFORMATION: C-terminal amidation

<400> SEQUENCE: 222

Val Gln Cys Pro His Phe Cys Tyr Glu Leu Xaa Glu Leu Cys Pro
 1               5                  10                  15

Asp Val Cys Tyr Val
                 20

<210> SEQ ID NO 223
<211> LENGTH: 19
<212> TYPE: PRT
<213> ORGANISM: Artificial Sequence
<220> FEATURE:
<223> OTHER INFORMATION: IgE receptor binding peptide shown in Example
      12, Table 9. IgE187
<220> FEATURE:
<221> NAME/KEY: SITE
<222> LOCATION: 10
<223> OTHER INFORMATION: unusual amino acid residue amino-valeric acid
<220> FEATURE:
<221> NAME/KEY: MOD_RES
<222> LOCATION: 19
<223> OTHER INFORMATION: C-terminal amidation

<400> SEQUENCE: 223

Val Gln Cys Pro His Phe Cys Tyr Glu Xaa Glu Leu Cys Pro Asp
 1               5                  10                  15

Val Cys Tyr Val

<210> SEQ ID NO 224
<211> LENGTH: 24
<212> TYPE: PRT
<213> ORGANISM: Artificial Sequence
<220> FEATURE:
<223> OTHER INFORMATION: IgE receptor binding peptide shown in Example
      12, Table 9. IgE188
<220> FEATURE:
<221> NAME/KEY: MOD_RES
<222> LOCATION: 24
<223> OTHER INFORMATION: C-terminal amidation
```

```
<400> SEQUENCE: 224

Val Gln Cys Pro His Phe Cys Tyr Glu Leu Asp Tyr Glu Ala Asp
 1               5                  10                  15

Arg Leu Cys Pro Asp Val Cys Tyr Val
                20

<210> SEQ ID NO 225
<211> LENGTH: 26
<212> TYPE: PRT
<213> ORGANISM: Artificial Sequence
<220> FEATURE:
<223> OTHER INFORMATION: IgE receptor binding peptide shown in Example
      12, Table 9. IgE189
<220> FEATURE:
<221> NAME/KEY: MOD_RES
<222> LOCATION: 26
<223> OTHER INFORMATION: C-terminal amidation

<400> SEQUENCE: 225

Val Gln Cys Pro His Phe Cys Tyr Glu Leu Asp Tyr Glu Ala Gly
 1               5                  10                  15

Asp Glu Arg Leu Cys Pro Asp Val Cys Tyr Val
                20                  25

<210> SEQ ID NO 226
<211> LENGTH: 21
<212> TYPE: PRT
<213> ORGANISM: Artificial Sequence
<220> FEATURE:
<223> OTHER INFORMATION: IgE receptor binding peptide shown in Example
      12, Table 9. IgE190
<220> FEATURE:
<221> NAME/KEY: MOD_RES
<222> LOCATION: 21
<223> OTHER INFORMATION: C-terminal amidation

<400> SEQUENCE: 226

Val Gln Cys Pro Asp Phe Cys Tyr Glu Leu Asp Tyr Glu Leu Cys
 1               5                  10                  15

Pro Asp Val Cys Tyr Val
                20

<210> SEQ ID NO 227
<211> LENGTH: 21
<212> TYPE: PRT
<213> ORGANISM: Artificial Sequence
<220> FEATURE:
<223> OTHER INFORMATION: IgE receptor binding peptide shown in Example
      12, Table 9. IgE191
<220> FEATURE:
<221> NAME/KEY: MOD_RES
<222> LOCATION: 21
<223> OTHER INFORMATION: C-terminal amidation

<400> SEQUENCE: 227

Val Gln Cys Pro Asp Phe Cys Tyr Phe Gly Gly Ala Glu Leu Cys
 1               5                  10                  15

Pro Asp Val Cys Tyr Val
                20

<210> SEQ ID NO 228
<211> LENGTH: 20
<212> TYPE: PRT
<213> ORGANISM: Artificial Sequence
<220> FEATURE:
<223> OTHER INFORMATION: IgE receptor binding peptide shown in Example
```

-continued

12, Table 9. IgE196
<220> FEATURE:
<221> NAME/KEY: MOD_RES
<222> LOCATION: 20
<223> OTHER INFORMATION: C-terminal amidation

<400> SEQUENCE: 228

Val Gln Cys Pro His Phe Cys Tyr Asp Ala Ser Glu Leu Cys Pro
 1               5                  10                  15

Asp Val Cys Tyr Val
                20

<210> SEQ ID NO 229
<211> LENGTH: 20
<212> TYPE: PRT
<213> ORGANISM: Artificial Sequence
<220> FEATURE:
<223> OTHER INFORMATION: IgE receptor binding peptide shown in Example
      12, Table 9. IgE197
<220> FEATURE:
<221> NAME/KEY: MOD_RES
<222> LOCATION: 20
<223> OTHER INFORMATION: C-terminal amidation

<400> SEQUENCE: 229

Val Gln Cys Pro Asp Phe Cys Tyr Asp Ala Ser Arg Leu Cys Pro
 1               5                  10                  15

Asp Val Cys Tyr Val
                20

<210> SEQ ID NO 230
<211> LENGTH: 17
<212> TYPE: PRT
<213> ORGANISM: Artificial Sequence
<220> FEATURE:
<223> OTHER INFORMATION: IgE receptor binding peptide shown in Example
      12, Table 9. IgE198
<220> FEATURE:
<221> NAME/KEY: MOD_RES
<222> LOCATION: 1
<223> OTHER INFORMATION: N-terminal acetylation
<220> FEATURE:
<221> NAME/KEY: SITE
<222> LOCATION: 9
<223> OTHER INFORMATION: unusual amino acid residue amino-valeric acid
<220> FEATURE:
<221> NAME/KEY: MOD_RES
<222> LOCATION: 17
<223> OTHER INFORMATION: C-terminal amidation

<400> SEQUENCE: 230

Val Gln Cys Pro His Phe Cys Tyr Xaa Leu Cys Pro Asp Val Cys
 1               5                  10                  15

Tyr Val

<210> SEQ ID NO 231
<211> LENGTH: 17
<212> TYPE: PRT
<213> ORGANISM: Artificial Sequence
<220> FEATURE:
<223> OTHER INFORMATION: IgE receptor binding peptide shown in Example
      12, Table 9.  IgE199
<220> FEATURE:
<221> NAME/KEY: SITE
<222> LOCATION: 9
<223> OTHER INFORMATION: unusual amino acid residue amino-valeric acid
<220> FEATURE:
<221> NAME/KEY: MOD_RES
<222> LOCATION: 17
<223> OTHER INFORMATION: C-terminal amidation -continued

```
<400> SEQUENCE: 231

Val Gln Cys Pro Asp Phe Cys Tyr Xaa Leu Cys Pro Asp Val Cys
 1               5                  10                  15

Tyr Val

<210> SEQ ID NO 232
<211> LENGTH: 17
<212> TYPE: PRT
<213> ORGANISM: Artificial Sequence
<220> FEATURE:
<223> OTHER INFORMATION: IgE receptor binding peptide shown in Example
      12, Table 9. IgE200
<220> FEATURE:
<221> NAME/KEY: SITE
<222> LOCATION: 9
<223> OTHER INFORMATION: unusual amino acid residue amino-valeric acid
<220> FEATURE:
<221> NAME/KEY: MOD_RES
<222> LOCATION: 17
<223> OTHER INFORMATION: C-terminal amidation

<400> SEQUENCE: 232

Val Gln Cys Pro Lys Phe Cys Tyr Xaa Leu Cys Pro Asp Val Cys
 1               5                  10                  15

Tyr Val

<210> SEQ ID NO 233
<211> LENGTH: 17
<212> TYPE: PRT
<213> ORGANISM: Artificial Sequence
<220> FEATURE:
<223> OTHER INFORMATION: IgE receptor binding peptide shown in Example
      12, Table 9. IgE201
<220> FEATURE:
<221> NAME/KEY: SITE
<222> LOCATION: 9
<223> OTHER INFORMATION: unusual amino acid residue amino-valeric acid
<220> FEATURE:
<221> NAME/KEY: MOD_RES
<222> LOCATION: 17
<223> OTHER INFORMATION: C-terminal amidation

<400> SEQUENCE: 233

Val Gln Cys Pro Asp Phe Cys Tyr Xaa Leu Cys Pro Asp Gln Cys
 1               5                  10                  15

Tyr Val

<210> SEQ ID NO 234
<211> LENGTH: 16
<212> TYPE: PRT
<213> ORGANISM: Artificial Sequence
<220> FEATURE:
<223> OTHER INFORMATION: IgE receptor binding peptide shown in Example
      12, Table 9. IgE202
<220> FEATURE:
<221> NAME/KEY: SITE
<222> LOCATION: 9
<223> OTHER INFORMATION: unusual amino acid residue amino-valeric acid
<220> FEATURE:
<221> NAME/KEY: MOD_RES
<222> LOCATION: 16
<223> OTHER INFORMATION: C-terminal amidation

<400> SEQUENCE: 234

Val Gln Cys Pro Asp Phe Cys Tyr Xaa Cys Pro Asp Val Cys Tyr
 1               5                  10                  15

Val
```

<210> SEQ ID NO 235
<211> LENGTH: 17
<212> TYPE: PRT
<213> ORGANISM: Artificial Sequence
<220> FEATURE:
<223> OTHER INFORMATION: IgE receptor binding peptide shown in Example
     12, Table 9. IgE203
<220> FEATURE:
<221> NAME/KEY: SITE
<222> LOCATION: 10
<223> OTHER INFORMATION: unusual amino acid residue amino-valeric acid
<220> FEATURE:
<221> NAME/KEY: MOD_RES
<222> LOCATION: 17
<223> OTHER INFORMATION: C-terminal amidation

<400> SEQUENCE: 235

Val Gln Cys Pro Lys Phe Cys Tyr Glu Xaa Cys Pro Asp Val Cys
 1               5                  10                  15

Tyr Val

<210> SEQ ID NO 236
<211> LENGTH: 21
<212> TYPE: PRT
<213> ORGANISM: Artificial Sequence
<220> FEATURE:
<223> OTHER INFORMATION: sequence is synthesized

<400> SEQUENCE: 236

Ile Val Cys Pro Arg Leu Cys Tyr Val Gly Gly Lys Ala Leu Cys
 1               5                  10                  15

Pro Asp Val Cys Tyr Val
                20

<210> SEQ ID NO 237
<211> LENGTH: 21
<212> TYPE: PRT
<213> ORGANISM: Artificial Sequence
<220> FEATURE:
<223> OTHER INFORMATION: sequence is synthesized

<400> SEQUENCE: 237

Val Gln Cys Pro His Phe Cys Tyr Val Gly Gly Lys Ala Leu Cys
 1               5                  10                  15

Pro Asp Val Cys Tyr Val
                20

<210> SEQ ID NO 238
<211> LENGTH: 21
<212> TYPE: PRT
<213> ORGANISM: Artificial Sequence
<220> FEATURE:
<223> OTHER INFORMATION: sequence is synthesized

<400> SEQUENCE: 238

Thr Asp Cys Pro Ala Phe Cys Tyr Val Gly Gly Lys Ala Leu Cys
 1               5                  10                  15

Pro Asp Val Cys Tyr Val
                20

<210> SEQ ID NO 239
<211> LENGTH: 21
<212> TYPE: PRT
<213> ORGANISM: Artificial Sequence
<220> FEATURE:

<223> OTHER INFORMATION: sequence is synthesized

<400> SEQUENCE: 239

Lys Ser Cys Pro Leu Trp Cys Tyr Val Gly Gly Lys Ala Leu Cys
 1               5                  10                  15

Pro Asp Val Cys Tyr Val
            20

<210> SEQ ID NO 240
<211> LENGTH: 21
<212> TYPE: PRT
<213> ORGANISM: Artificial Sequence
<220> FEATURE:
<223> OTHER INFORMATION: sequence is synthesized

<400> SEQUENCE: 240

Arg Val Cys Pro Thr Trp Cys Tyr Val Gly Gly Lys Ala Leu Cys
 1               5                  10                  15

Pro Asp Val Cys Tyr Val
            20

<210> SEQ ID NO 241
<211> LENGTH: 21
<212> TYPE: PRT
<213> ORGANISM: Artificial Sequence
<220> FEATURE:
<223> OTHER INFORMATION: sequence is synthesized

<400> SEQUENCE: 241

Asn Arg Cys Pro Gly Trp Cys Tyr Val Gly Gly Lys Ala Leu Cys
 1               5                  10                  15

Pro Asp Val Cys Tyr Val
            20

<210> SEQ ID NO 242
<211> LENGTH: 21
<212> TYPE: PRT
<213> ORGANISM: Artificial Sequence
<220> FEATURE:
<223> OTHER INFORMATION: sequence is synthesized

<400> SEQUENCE: 242

Val Val Cys Pro Asn Met Cys Tyr Val Gly Gly Lys Ala Leu Cys
 1               5                  10                  15

Pro Asp Val Cys Tyr Val
            20

<210> SEQ ID NO 243
<211> LENGTH: 21
<212> TYPE: PRT
<213> ORGANISM: Artificial Sequence
<220> FEATURE:
<223> OTHER INFORMATION: sequence is synthesized

<400> SEQUENCE: 243

Lys Leu Cys Pro Ser Trp Cys Tyr Val Gly Gly Lys Ala Leu Cys
 1               5                  10                  15

Pro Asp Val Cys Tyr Val
            20

<210> SEQ ID NO 244
<211> LENGTH: 21
<212> TYPE: PRT
<213> ORGANISM: Artificial Sequence

```
<220> FEATURE:
<223> OTHER INFORMATION: sequence is synthesized

<400> SEQUENCE: 244

Leu Pro Cys Pro Met Trp Cys Tyr Val Gly Gly Lys Ala Leu Cys
 1               5                   10                  15

Pro Asp Val Cys Tyr Val
                20

<210> SEQ ID NO 245
<211> LENGTH: 21
<212> TYPE: PRT
<213> ORGANISM: Artificial Sequence
<220> FEATURE:
<223> OTHER INFORMATION: sequence is synthesized

<400> SEQUENCE: 245

Met Met Cys Pro Arg Trp Cys Tyr Val Gly Gly Lys Ala Leu Cys
 1               5                   10                  15

Pro Asp Val Cys Tyr Val
                20

<210> SEQ ID NO 246
<211> LENGTH: 21
<212> TYPE: PRT
<213> ORGANISM: Artificial Sequence
<220> FEATURE:
<223> OTHER INFORMATION: sequence is synthesized

<400> SEQUENCE: 246

Asn Gly Cys Pro Gly Trp Cys Tyr Val Gly Gly Lys Ala Leu Cys
 1               5                   10                  15

Pro Asp Val Cys Tyr Val
                20

<210> SEQ ID NO 247
<211> LENGTH: 21
<212> TYPE: PRT
<213> ORGANISM: Artificial Sequence
<220> FEATURE:
<223> OTHER INFORMATION: sequence is synthesized

<400> SEQUENCE: 247

Ser Lys Cys Pro Phe Met Cys Tyr Val Gly Gly Lys Ala Leu Cys
 1               5                   10                  15

Pro Asp Val Cys Tyr Val
                20

<210> SEQ ID NO 248
<211> LENGTH: 21
<212> TYPE: PRT
<213> ORGANISM: Artificial Sequence
<220> FEATURE:
<223> OTHER INFORMATION: sequence is synthesized

<400> SEQUENCE: 248

Val Gln Cys Pro Arg Leu Cys Tyr Val Gly Gly Lys Ala Leu Cys
 1               5                   10                  15

Pro Asp Val Cys Tyr Val
                20

<210> SEQ ID NO 249
<211> LENGTH: 21
<212> TYPE: PRT
```

<213> ORGANISM: Artificial Sequence
<220> FEATURE:
<223> OTHER INFORMATION: sequence is synthesized

<400> SEQUENCE: 249

Ala Ala Cys Pro Phe Trp Cys Tyr Val Gly Gly Lys Ala Leu Cys
 1               5                  10                  15

Pro Asp Val Cys Tyr Val
                20

<210> SEQ ID NO 250
<211> LENGTH: 21
<212> TYPE: PRT
<213> ORGANISM: Artificial Sequence
<220> FEATURE:
<223> OTHER INFORMATION: sequence is synthesized

<400> SEQUENCE: 250

Gly Gly Cys Pro Asp Trp Cys Tyr Val Gly Gly Lys Ala Leu Cys
 1               5                  10                  15

Pro Asp Val Cys Tyr Val
                20

<210> SEQ ID NO 251
<211> LENGTH: 21
<212> TYPE: PRT
<213> ORGANISM: Artificial Sequence
<220> FEATURE:
<223> OTHER INFORMATION: sequence is synthesized

<400> SEQUENCE: 251

Gly Gly Cys Pro Ser Trp Cys Tyr Val Gly Gly Lys Ala Leu Cys
 1               5                  10                  15

Pro Asp Val Cys Tyr Val
                20

<210> SEQ ID NO 252
<211> LENGTH: 21
<212> TYPE: PRT
<213> ORGANISM: Artificial Sequence
<220> FEATURE:
<223> OTHER INFORMATION: sequence is synthesized

<400> SEQUENCE: 252

Gly His Cys Pro Gly Met Cys Tyr Val Gly Gly Lys Ala Leu Cys
 1               5                  10                  15

Pro Asp Val Cys Tyr Val
                20

<210> SEQ ID NO 253
<211> LENGTH: 21
<212> TYPE: PRT
<213> ORGANISM: Artificial Sequence
<220> FEATURE:
<223> OTHER INFORMATION: sequence is synthesized

<400> SEQUENCE: 253

Ile Arg Cys Pro Gln Leu Cys Tyr Val Gly Gly Lys Ala Leu Cys
 1               5                  10                  15

Pro Asp Val Cys Tyr Val
                20

<210> SEQ ID NO 254
<211> LENGTH: 21

-continued

```
<212> TYPE: PRT
<213> ORGANISM: Artificial Sequence
<220> FEATURE:
<223> OTHER INFORMATION: sequence is synthesized

<400> SEQUENCE: 254

Lys Ser Cys Pro Pro Gln Cys Tyr Val Gly Gly Lys Ala Leu Cys
 1               5                  10                  15

Pro Asp Val Cys Tyr Val
            20

<210> SEQ ID NO 255
<211> LENGTH: 21
<212> TYPE: PRT
<213> ORGANISM: Artificial Sequence
<220> FEATURE:
<223> OTHER INFORMATION: sequence is synthesized

<400> SEQUENCE: 255

Leu Leu Cys Pro Trp Leu Cys Tyr Val Gly Gly Lys Ala Leu Cys
 1               5                  10                  15

Pro Asp Val Cys Tyr Val
            20

<210> SEQ ID NO 256
<211> LENGTH: 21
<212> TYPE: PRT
<213> ORGANISM: Artificial Sequence
<220> FEATURE:
<223> OTHER INFORMATION: sequence is synthesized

<400> SEQUENCE: 256

Leu Val Cys Pro Arg Met Cys Tyr Val Gly Gly Lys Ala Leu Cys
 1               5                  10                  15

Pro Asp Val Cys Tyr Val
            20

<210> SEQ ID NO 257
<211> LENGTH: 21
<212> TYPE: PRT
<213> ORGANISM: Artificial Sequence
<220> FEATURE:
<223> OTHER INFORMATION: sequence is synthesized

<400> SEQUENCE: 257

Met Met Cys Pro Ser Met Cys Tyr Val Gly Gly Lys Ala Leu Cys
 1               5                  10                  15

Pro Asp Val Cys Tyr Val
            20

<210> SEQ ID NO 258
<211> LENGTH: 21
<212> TYPE: PRT
<213> ORGANISM: Artificial Sequence
<220> FEATURE:
<223> OTHER INFORMATION: sequence is synthesized

<400> SEQUENCE: 258

Met Arg Cys Pro Thr Leu Cys Tyr Val Gly Gly Lys Ala Leu Cys
 1               5                  10                  15

Pro Asp Val Cys Tyr Val
            20

<210> SEQ ID NO 259
```

```
<211> LENGTH: 21
<212> TYPE: PRT
<213> ORGANISM: Artificial Sequence
<220> FEATURE:
<223> OTHER INFORMATION: sequence is synthesized

<400> SEQUENCE: 259

Arg Glu Cys Pro Leu Leu Cys Tyr Val Gly Gly Lys Ala Leu Cys
 1               5                  10                  15

Pro Asp Val Cys Tyr Val
            20

<210> SEQ ID NO 260
<211> LENGTH: 21
<212> TYPE: PRT
<213> ORGANISM: Artificial Sequence
<220> FEATURE:
<223> OTHER INFORMATION: sequence is synthesized

<400> SEQUENCE: 260

Arg Thr Cys Pro Pro Leu Cys Tyr Val Gly Gly Lys Ala Leu Cys
 1               5                  10                  15

Pro Asp Val Cys Tyr Val
            20

<210> SEQ ID NO 261
<211> LENGTH: 21
<212> TYPE: PRT
<213> ORGANISM: Artificial Sequence
<220> FEATURE:
<223> OTHER INFORMATION: sequence is synthesized

<400> SEQUENCE: 261

Arg Val Cys Pro Gln Met Cys Tyr Val Gly Gly Lys Ala Leu Cys
 1               5                  10                  15

Pro Asp Val Cys Tyr Val
            20

<210> SEQ ID NO 262
<211> LENGTH: 21
<212> TYPE: PRT
<213> ORGANISM: Artificial Sequence
<220> FEATURE:
<223> OTHER INFORMATION: sequence is synthesized

<400> SEQUENCE: 262

Ser Ala Cys Pro Ser Phe Cys Tyr Val Gly Gly Lys Ala Leu Cys
 1               5                  10                  15

Pro Asp Val Cys Tyr Val
            20

<210> SEQ ID NO 263
<211> LENGTH: 21
<212> TYPE: PRT
<213> ORGANISM: Artificial Sequence
<220> FEATURE:
<223> OTHER INFORMATION: sequence is synthesized

<400> SEQUENCE: 263

Ser Lys Cys Pro Phe Phe Cys Tyr Val Gly Gly Lys Ala Leu Cys
 1               5                  10                  15

Pro Asp Val Cys Tyr Val
            20
```

```
<210> SEQ ID NO 264
<211> LENGTH: 21
<212> TYPE: PRT
<213> ORGANISM: Artificial Sequence
<220> FEATURE:
<223> OTHER INFORMATION: sequence is synthesized

<400> SEQUENCE: 264

Ser Lys Cys Pro Phe Gly Cys Tyr Val Gly Gly Lys Ala Leu Cys
 1               5                  10                  15

Pro Asp Val Cys Tyr Val
            20

<210> SEQ ID NO 265
<211> LENGTH: 21
<212> TYPE: PRT
<213> ORGANISM: Artificial Sequence
<220> FEATURE:
<223> OTHER INFORMATION: sequence is synthesized

<400> SEQUENCE: 265

Ser Lys Cys Pro Trp Leu Cys Tyr Val Gly Gly Lys Ala Leu Cys
 1               5                  10                  15

Pro Asp Val Cys Tyr Val
            20

<210> SEQ ID NO 266
<211> LENGTH: 21
<212> TYPE: PRT
<213> ORGANISM: Artificial Sequence
<220> FEATURE:
<223> OTHER INFORMATION: sequence is synthesized

<400> SEQUENCE: 266

Ser Pro Cys Pro Ala Leu Cys Tyr Val Gly Gly Lys Ala Leu Cys
 1               5                  10                  15

Pro Asp Val Cys Tyr Val
            20

<210> SEQ ID NO 267
<211> LENGTH: 21
<212> TYPE: PRT
<213> ORGANISM: Artificial Sequence
<220> FEATURE:
<223> OTHER INFORMATION: sequence is synthesized

<400> SEQUENCE: 267

Ser Pro Cys Pro Arg Leu Cys Tyr Val Gly Gly Lys Ala Leu Cys
 1               5                  10                  15

Pro Asp Val Cys Tyr Val
            20

<210> SEQ ID NO 268
<211> LENGTH: 21
<212> TYPE: PRT
<213> ORGANISM: Artificial Sequence
<220> FEATURE:
<223> OTHER INFORMATION: sequence is synthesized

<400> SEQUENCE: 268

Thr Leu Cys Pro Gly Leu Cys Tyr Val Gly Gly Lys Ala Leu Cys
 1               5                  10                  15

Pro Asp Val Cys Tyr Val
            20
```

```
<210> SEQ ID NO 269
<211> LENGTH: 21
<212> TYPE: PRT
<213> ORGANISM: Artificial Sequence
<220> FEATURE:
<223> OTHER INFORMATION: sequence is synthesized

<400> SEQUENCE: 269

Val Ala Cys Pro Ala Leu Cys Tyr Val Gly Gly Lys Ala Leu Cys
 1               5                  10                  15

Pro Asp Val Cys Tyr Val
            20

<210> SEQ ID NO 270
<211> LENGTH: 21
<212> TYPE: PRT
<213> ORGANISM: Artificial Sequence
<220> FEATURE:
<223> OTHER INFORMATION: sequence is synthesized

<400> SEQUENCE: 270

Val Ala Cys Pro Phe Leu Cys Tyr Val Gly Gly Lys Ala Leu Cys
 1               5                  10                  15

Pro Asp Val Cys Tyr Val
            20

<210> SEQ ID NO 271
<211> LENGTH: 21
<212> TYPE: PRT
<213> ORGANISM: Artificial Sequence
<220> FEATURE:
<223> OTHER INFORMATION: sequence is synthesized

<400> SEQUENCE: 271

Val Ala Cys Pro Arg Leu Cys Tyr Val Gly Gly Lys Ala Leu Cys
 1               5                  10                  15

Pro Asp Val Cys Tyr Val
            20

<210> SEQ ID NO 272
<211> LENGTH: 21
<212> TYPE: PRT
<213> ORGANISM: Artificial Sequence
<220> FEATURE:
<223> OTHER INFORMATION: sequence is synthesized

<400> SEQUENCE: 272

Val Ala Cys Pro Ser Leu Cys Tyr Val Gly Gly Lys Ala Leu Cys
 1               5                  10                  15

Pro Asp Val Cys Tyr Val
            20

<210> SEQ ID NO 273
<211> LENGTH: 21
<212> TYPE: PRT
<213> ORGANISM: Artificial Sequence
<220> FEATURE:
<223> OTHER INFORMATION: sequence is synthesized

<400> SEQUENCE: 273

Val Leu Cys Pro Arg Phe Cys Tyr Val Gly Gly Lys Ala Leu Cys
 1               5                  10                  15

Pro Asp Val Cys Tyr Val
            20
```

<210> SEQ ID NO 274
<211> LENGTH: 21
<212> TYPE: PRT
<213> ORGANISM: Artificial Sequence
<220> FEATURE:
<223> OTHER INFORMATION: sequence is synthesized

<400> SEQUENCE: 274

Val Leu Cys Pro Ser Phe Cys Tyr Val Gly Gly Lys Ala Leu Cys
 1               5                  10                  15

Pro Asp Val Cys Tyr Val
                20

<210> SEQ ID NO 275
<211> LENGTH: 21
<212> TYPE: PRT
<213> ORGANISM: Artificial Sequence
<220> FEATURE:
<223> OTHER INFORMATION: sequence is synthesized

<400> SEQUENCE: 275

Val Met Cys Pro Thr Leu Cys Tyr Val Gly Gly Lys Ala Leu Cys
 1               5                  10                  15

Pro Asp Val Cys Tyr Val
                20

<210> SEQ ID NO 276
<211> LENGTH: 21
<212> TYPE: PRT
<213> ORGANISM: Artificial Sequence
<220> FEATURE:
<223> OTHER INFORMATION: sequence is synthesized

<400> SEQUENCE: 276

Val Pro Cys Pro Glu Leu Cys Tyr Val Gly Gly Lys Ala Leu Cys
 1               5                  10                  15

Pro Asp Val Cys Tyr Val
                20

<210> SEQ ID NO 277
<211> LENGTH: 21
<212> TYPE: PRT
<213> ORGANISM: Artificial Sequence
<220> FEATURE:
<223> OTHER INFORMATION: sequence is synthesized

<400> SEQUENCE: 277

Val Gln Cys Pro Arg Phe Cys Tyr Val Gly Gly Lys Ala Leu Cys
 1               5                  10                  15

Pro Asp Val Cys Tyr Val
                20

<210> SEQ ID NO 278
<211> LENGTH: 21
<212> TYPE: PRT
<213> ORGANISM: Artificial Sequence
<220> FEATURE:
<223> OTHER INFORMATION: sequence is synthesized

<400> SEQUENCE: 278

Val Arg Cys Pro His Met Cys Tyr Val Gly Gly Lys Ala Leu Cys
 1               5                  10                  15

Pro Asp Val Cys Tyr Val

-continued

```
<210> SEQ ID NO 279
<211> LENGTH: 21
<212> TYPE: PRT
<213> ORGANISM: Artificial Sequence
<220> FEATURE:
<223> OTHER INFORMATION: sequence is synthesized

<400> SEQUENCE: 279

Val Ser Cys Pro Arg Leu Cys Tyr Val Gly Gly Lys Ala Leu Cys
 1               5                  10                  15

Pro Asp Val Cys Tyr Val
            20

<210> SEQ ID NO 280
<211> LENGTH: 21
<212> TYPE: PRT
<213> ORGANISM: Artificial Sequence
<220> FEATURE:
<223> OTHER INFORMATION: sequence is synthesized

<400> SEQUENCE: 280

Ser Lys Cys Pro Trp Leu Cys Tyr Val Gly Gly Lys Ala Leu Cys
 1               5                  10                  15

Pro Asp Val Cys Tyr Val
            20

<210> SEQ ID NO 281
<211> LENGTH: 21
<212> TYPE: PRT
<213> ORGANISM: Artificial Sequence
<220> FEATURE:
<223> OTHER INFORMATION: sequence is synthesized

<400> SEQUENCE: 281

Ile Val Cys Pro Arg Leu Cys Tyr Val Gly Gly Lys Ala Leu Cys
 1               5                  10                  15

Pro Asp Val Cys Tyr Val
            20

<210> SEQ ID NO 282
<211> LENGTH: 21
<212> TYPE: PRT
<213> ORGANISM: Artificial Sequence
<220> FEATURE:
<223> OTHER INFORMATION: sequence is synthesized

<400> SEQUENCE: 282

Val Gln Cys Pro His Phe Cys Tyr Val Gly Gly Lys Ala Leu Cys
 1               5                  10                  15

Pro Asp Val Cys Tyr Val
            20

<210> SEQ ID NO 283
<211> LENGTH: 21
<212> TYPE: PRT
<213> ORGANISM: Artificial Sequence
<220> FEATURE:
<223> OTHER INFORMATION: sequence is synthesized

<400> SEQUENCE: 283

Leu Trp Cys Pro Arg Ile Cys Tyr Val Gly Gly Lys Ala Leu Cys
 1               5                  10                  15
```

-continued

```
Pro Asp Val Cys Tyr Val
            20

<210> SEQ ID NO 284
<211> LENGTH: 21
<212> TYPE: PRT
<213> ORGANISM: Artificial Sequence
<220> FEATURE:
<223> OTHER INFORMATION: sequence is synthesized

<400> SEQUENCE: 284

Met Met Cys Pro Arg Trp Cys Tyr Val Gly Gly Lys Ala Leu Cys
 1               5                  10                  15

Pro Asp Val Cys Tyr Val
            20

<210> SEQ ID NO 285
<211> LENGTH: 21
<212> TYPE: PRT
<213> ORGANISM: Artificial Sequence
<220> FEATURE:
<223> OTHER INFORMATION: sequence is synthesized

<400> SEQUENCE: 285

Arg Trp Cys Pro Arg Phe Cys Tyr Val Gly Gly Lys Ala Leu Cys
 1               5                  10                  15

Pro Asp Val Cys Tyr Val
            20

<210> SEQ ID NO 286
<211> LENGTH: 21
<212> TYPE: PRT
<213> ORGANISM: Artificial Sequence
<220> FEATURE:
<223> OTHER INFORMATION: sequence is synthesized

<400> SEQUENCE: 286

Val Lys Cys Pro Ser Leu Cys Tyr Val Gly Gly Lys Ala Leu Cys
 1               5                  10                  15

Pro Asp Val Cys Tyr Val
            20

<210> SEQ ID NO 287
<211> LENGTH: 21
<212> TYPE: PRT
<213> ORGANISM: Artificial Sequence
<220> FEATURE:
<223> OTHER INFORMATION: sequence is synthesized

<400> SEQUENCE: 287

Val Thr Cys Pro Arg Trp Cys Tyr Val Gly Gly Lys Ala Leu Cys
 1               5                  10                  15

Pro Asp Val Cys Tyr Val
            20

<210> SEQ ID NO 288
<211> LENGTH: 21
<212> TYPE: PRT
<213> ORGANISM: Artificial Sequence
<220> FEATURE:
<223> OTHER INFORMATION: sequence is synthesized

<400> SEQUENCE: 288

Ala Leu Cys Pro Ala Val Cys Tyr Val Gly Gly Lys Ala Leu Cys
 1               5                  10                  15
```

Pro Asp Val Cys Tyr Val
            20

<210> SEQ ID NO 289
<211> LENGTH: 21
<212> TYPE: PRT
<213> ORGANISM: Artificial Sequence
<220> FEATURE:
<223> OTHER INFORMATION: sequence is synthesized

<400> SEQUENCE: 289

Ala Leu Cys Pro Ala Val Cys Tyr Val Gly Gly Lys Ala Leu Cys
 1               5                  10                  15

Pro Asp Val Cys Tyr Val
            20

<210> SEQ ID NO 290
<211> LENGTH: 21
<212> TYPE: PRT
<213> ORGANISM: Artificial Sequence
<220> FEATURE:
<223> OTHER INFORMATION: sequence is synthesized

<400> SEQUENCE: 290

Ile Val Cys Pro Arg Leu Cys Tyr Val Gly Gly Lys Ala Leu Cys
 1               5                  10                  15

Pro Asp Val Cys Tyr Val
            20

<210> SEQ ID NO 291
<211> LENGTH: 21
<212> TYPE: PRT
<213> ORGANISM: Artificial Sequence
<220> FEATURE:
<223> OTHER INFORMATION: sequence is synthesized

<400> SEQUENCE: 291

Ile Val Cys Pro Arg Leu Cys Tyr Val Gly Gly Lys Ala Leu Cys
 1               5                  10                  15

Pro Asp Val Cys Tyr Val
            20

<210> SEQ ID NO 292
<211> LENGTH: 21
<212> TYPE: PRT
<213> ORGANISM: Artificial Sequence
<220> FEATURE:
<223> OTHER INFORMATION: sequence is synthesized

<400> SEQUENCE: 292

Ile Val Cys Pro Arg Leu Cys Tyr Ala Ser Leu Gln Gly Leu Cys
 1               5                  10                  15

Pro Asp Val Cys Tyr Val
            20

<210> SEQ ID NO 293
<211> LENGTH: 21
<212> TYPE: PRT
<213> ORGANISM: Artificial Sequence
<220> FEATURE:
<223> OTHER INFORMATION: sequence is synthesized

<400> SEQUENCE: 293

Ile Val Cys Pro Arg Leu Cys Tyr Glu Glu Leu Phe Glu Leu Cys

```
                1               5                  10                  15
Pro Asp Val Cys Tyr Val
                20

<210> SEQ ID NO 294
<211> LENGTH: 21
<212> TYPE: PRT
<213> ORGANISM: Artificial Sequence
<220> FEATURE:
<223> OTHER INFORMATION: sequence is synthesized

<400> SEQUENCE: 294

Ile Val Cys Pro Arg Leu Cys Tyr Glu Phe Ala Glu Gly Leu Cys
 1               5                  10                  15
Pro Asp Val Cys Tyr Val
                20

<210> SEQ ID NO 295
<211> LENGTH: 21
<212> TYPE: PRT
<213> ORGANISM: Artificial Sequence
<220> FEATURE:
<223> OTHER INFORMATION: sequence is synthesized

<400> SEQUENCE: 295

Ile Val Cys Pro Arg Leu Cys Tyr Glu Gly Gly Trp Asp Leu Cys
 1               5                  10                  15
Pro Asp Val Cys Tyr Val
                20

<210> SEQ ID NO 296
<211> LENGTH: 21
<212> TYPE: PRT
<213> ORGANISM: Artificial Sequence
<220> FEATURE:
<223> OTHER INFORMATION: sequence is synthesized

<400> SEQUENCE: 296

Ile Val Cys Pro Arg Leu Cys Tyr Glu Pro Ser Lys Leu Leu Cys
 1               5                  10                  15
Pro Asp Val Cys Tyr Val
                20

<210> SEQ ID NO 297
<211> LENGTH: 21
<212> TYPE: PRT
<213> ORGANISM: Artificial Sequence
<220> FEATURE:
<223> OTHER INFORMATION: sequence is synthesized

<400> SEQUENCE: 297

Ile Val Cys Pro Arg Leu Cys Tyr Gly Glu Gly Ala Gly Leu Cys
 1               5                  10                  15
Pro Asp Val Cys Tyr Val
                20

<210> SEQ ID NO 298
<211> LENGTH: 21
<212> TYPE: PRT
<213> ORGANISM: Artificial Sequence
<220> FEATURE:
<223> OTHER INFORMATION: sequence is synthesized

<400> SEQUENCE: 298
```

```
Ile Val Cys Pro Arg Leu Cys Tyr Gly Phe Met Asp Gly Leu Cys
 1               5                  10                  15

Pro Asp Val Cys Tyr Val
                 20

<210> SEQ ID NO 299
<211> LENGTH: 21
<212> TYPE: PRT
<213> ORGANISM: Artificial Sequence
<220> FEATURE:
<223> OTHER INFORMATION: sequence is synthesized

<400> SEQUENCE: 299

Ile Val Cys Pro Arg Leu Cys Tyr Gly Ser Tyr Trp Val Leu Cys
 1               5                  10                  15

Pro Asp Val Cys Tyr Val
                 20

<210> SEQ ID NO 300
<211> LENGTH: 21
<212> TYPE: PRT
<213> ORGANISM: Artificial Sequence
<220> FEATURE:
<223> OTHER INFORMATION: sequence is synthesized

<400> SEQUENCE: 300

Ile Val Cys Pro Arg Leu Cys Tyr Gly Val Ser Leu Ser Leu Cys
 1               5                  10                  15

Pro Asp Val Cys Tyr Val
                 20

<210> SEQ ID NO 301
<211> LENGTH: 21
<212> TYPE: PRT
<213> ORGANISM: Artificial Sequence
<220> FEATURE:
<223> OTHER INFORMATION: sequence is synthesized

<400> SEQUENCE: 301

Ile Val Cys Pro Arg Leu Cys Tyr Ile Trp Ala Pro Ser Leu Cys
 1               5                  10                  15

Pro Asp Val Cys Tyr Val
                 20

<210> SEQ ID NO 302
<211> LENGTH: 21
<212> TYPE: PRT
<213> ORGANISM: Artificial Sequence
<220> FEATURE:
<223> OTHER INFORMATION: sequence is synthesized

<400> SEQUENCE: 302

Ile Val Cys Pro Arg Leu Cys Tyr Lys Gly Val Glu Arg Leu Cys
 1               5                  10                  15

Pro Asp Val Cys Tyr Val
                 20

<210> SEQ ID NO 303
<211> LENGTH: 21
<212> TYPE: PRT
<213> ORGANISM: Artificial Sequence
<220> FEATURE:
<223> OTHER INFORMATION: sequence is synthesized

<400> SEQUENCE: 303
```

```
Ile Val Cys Pro Arg Leu Cys Tyr Leu Ser Gly Glu Gln Leu Cys
 1               5                  10                  15

Pro Asp Val Cys Tyr Val
                20
```

<210> SEQ ID NO 304
<211> LENGTH: 21
<212> TYPE: PRT
<213> ORGANISM: Artificial Sequence
<220> FEATURE:
<223> OTHER INFORMATION: sequence is synthesized

<400> SEQUENCE: 304

```
Ile Val Cys Pro Arg Leu Cys Tyr Leu Trp Phe Asp Ser Leu Cys
 1               5                  10                  15

Pro Asp Val Cys Tyr Val
                20
```

<210> SEQ ID NO 305
<211> LENGTH: 21
<212> TYPE: PRT
<213> ORGANISM: Artificial Sequence
<220> FEATURE:
<223> OTHER INFORMATION: sequence is synthesized

<400> SEQUENCE: 305

```
Ile Val Cys Pro Arg Leu Cys Tyr Met Phe Ser Ser Ser Leu Cys
 1               5                  10                  15

Pro Asp Val Cys Tyr Val
                20
```

<210> SEQ ID NO 306
<211> LENGTH: 21
<212> TYPE: PRT
<213> ORGANISM: Artificial Sequence
<220> FEATURE:
<223> OTHER INFORMATION: sequence is synthesized

<400> SEQUENCE: 306

```
Ile Val Cys Pro Arg Leu Cys Tyr Asn Asp Asp Val Glu Leu Cys
 1               5                  10                  15

Pro Asp Val Cys Tyr Val
                20
```

<210> SEQ ID NO 307
<211> LENGTH: 21
<212> TYPE: PRT
<213> ORGANISM: Artificial Sequence
<220> FEATURE:
<223> OTHER INFORMATION: sequence is synthesized

<400> SEQUENCE: 307

```
Ile Val Cys Pro Arg Leu Cys Tyr Val Ser Met Val Gly Leu Cys
 1               5                  10                  15

Pro Asp Val Cys Tyr Val
                20
```

<210> SEQ ID NO 308
<211> LENGTH: 21
<212> TYPE: PRT
<213> ORGANISM: Artificial Sequence
<220> FEATURE:
<223> OTHER INFORMATION: sequence is synthesized

```
<400> SEQUENCE: 308

Ile Val Cys Pro Arg Leu Cys Tyr Trp Glu Gly Asp Thr Leu Cys
 1               5                  10                  15

Pro Asp Val Cys Tyr Val
                20

<210> SEQ ID NO 309
<211> LENGTH: 21
<212> TYPE: PRT
<213> ORGANISM: Artificial Sequence
<220> FEATURE:
<223> OTHER INFORMATION: sequence is synthesized

<400> SEQUENCE: 309

Ile Val Cys Pro Arg Leu Cys Tyr Trp Phe Gly Ser Ala Leu Cys
 1               5                  10                  15

Pro Asp Val Cys Tyr Val
                20

<210> SEQ ID NO 310
<211> LENGTH: 21
<212> TYPE: PRT
<213> ORGANISM: Artificial Sequence
<220> FEATURE:
<223> OTHER INFORMATION: sequence is synthesized

<400> SEQUENCE: 310

Ile Val Cys Pro Arg Leu Cys Tyr Trp Phe Pro Gly Gln Leu Cys
 1               5                  10                  15

Pro Asp Val Cys Tyr Val
                20

<210> SEQ ID NO 311
<211> LENGTH: 21
<212> TYPE: PRT
<213> ORGANISM: Artificial Sequence
<220> FEATURE:
<223> OTHER INFORMATION: sequence is synthesized

<400> SEQUENCE: 311

Ile Val Cys Pro Arg Leu Cys Tyr Tyr Ala Phe Asp Ala Leu Cys
 1               5                  10                  15

Pro Asp Val Cys Tyr Val
                20

<210> SEQ ID NO 312
<211> LENGTH: 21
<212> TYPE: PRT
<213> ORGANISM: Artificial Sequence
<220> FEATURE:
<223> OTHER INFORMATION: sequence is synthesized

<400> SEQUENCE: 312

Ile Val Cys Pro Arg Leu Cys Tyr Glu Leu Asp Tyr Glu Leu Cys
 1               5                  10                  15

Pro Asp Val Cys Tyr Val
                20

<210> SEQ ID NO 313
<211> LENGTH: 21
<212> TYPE: PRT
<213> ORGANISM: Artificial Sequence
<220> FEATURE:
<223> OTHER INFORMATION: sequence is synthesized
```

```
<400> SEQUENCE: 313

Ile Val Cys Pro Arg Leu Cys Tyr Ser Asp Leu Arg Gly Leu Cys
  1               5                  10                  15

Pro Asp Val Cys Tyr Val
                20

<210> SEQ ID NO 314
<211> LENGTH: 21
<212> TYPE: PRT
<213> ORGANISM: Artificial Sequence
<220> FEATURE:
<223> OTHER INFORMATION: sequence is synthesized

<400> SEQUENCE: 314

Ile Val Cys Pro Arg Leu Cys Tyr Ser Asp Gln Arg Gly Leu Cys
  1               5                  10                  15

Pro Asp Val Cys Tyr Val
                20

<210> SEQ ID NO 315
<211> LENGTH: 21
<212> TYPE: PRT
<213> ORGANISM: Artificial Sequence
<220> FEATURE:
<223> OTHER INFORMATION: sequence is synthesized

<400> SEQUENCE: 315

Ile Val Cys Pro Arg Leu Cys Tyr Phe Val Pro Trp Gln Leu Cys
  1               5                  10                  15

Pro Asp Val Cys Tyr Val
                20

<210> SEQ ID NO 316
<211> LENGTH: 21
<212> TYPE: PRT
<213> ORGANISM: Artificial Sequence
<220> FEATURE:
<223> OTHER INFORMATION: sequence is synthesized

<400> SEQUENCE: 316

Ile Val Cys Pro Arg Leu Cys Tyr Val Asp Leu Gln Gly Leu Cys
  1               5                  10                  15

Pro Asp Val Cys Tyr Val
                20

<210> SEQ ID NO 317
<211> LENGTH: 21
<212> TYPE: PRT
<213> ORGANISM: Artificial Sequence
<220> FEATURE:
<223> OTHER INFORMATION: sequence is synthesized

<400> SEQUENCE: 317

Ile Val Cys Pro Arg Leu Cys Tyr Val Glu Leu Ala Gly Leu Cys
  1               5                  10                  15

Pro Asp Val Cys Tyr Val
                20

<210> SEQ ID NO 318
<211> LENGTH: 21
<212> TYPE: PRT
<213> ORGANISM: Artificial Sequence
<220> FEATURE:
```

<223> OTHER INFORMATION: sequence is synthesized

<400> SEQUENCE: 318

Ile Val Cys Pro Arg Leu Cys Tyr Ala Trp Gly Gly Phe Leu Cys
1               5                   10                  15

Pro Asp Val Cys Tyr Val
            20

<210> SEQ ID NO 319
<211> LENGTH: 21
<212> TYPE: PRT
<213> ORGANISM: Artificial Sequence
<220> FEATURE:
<223> OTHER INFORMATION: sequence is synthesized

<400> SEQUENCE: 319

Ile Val Cys Pro Arg Leu Cys Tyr Asp Gly Ser Val Gly Leu Cys
1               5                   10                  15

Pro Asp Val Cys Tyr Val
            20

<210> SEQ ID NO 320
<211> LENGTH: 21
<212> TYPE: PRT
<213> ORGANISM: Artificial Sequence
<220> FEATURE:
<223> OTHER INFORMATION: sequence is synthesized

<400> SEQUENCE: 320

Ile Val Cys Pro Arg Leu Cys Tyr Asp Ser Glu Glu Glu Leu Cys
1               5                   10                  15

Pro Asp Val Cys Tyr Val
            20

<210> SEQ ID NO 321
<211> LENGTH: 21
<212> TYPE: PRT
<213> ORGANISM: Artificial Sequence
<220> FEATURE:
<223> OTHER INFORMATION: sequence is synthesized

<400> SEQUENCE: 321

Ile Val Cys Pro Arg Leu Cys Tyr Glu Gly Ala Trp Asp Leu Cys
1               5                   10                  15

Pro Asp Val Cys Tyr Val
            20

<210> SEQ ID NO 322
<211> LENGTH: 21
<212> TYPE: PRT
<213> ORGANISM: Artificial Sequence
<220> FEATURE:
<223> OTHER INFORMATION: sequence is synthesized

<400> SEQUENCE: 322

Ile Val Cys Pro Arg Leu Cys Tyr Glu Gly Pro Glu Pro Leu Cys
1               5                   10                  15

Pro Asp Val Cys Tyr Val
            20

<210> SEQ ID NO 323
<211> LENGTH: 21
<212> TYPE: PRT
<213> ORGANISM: Artificial Sequence

```
<220> FEATURE:
<223> OTHER INFORMATION: sequence is synthesized

<400> SEQUENCE: 323

Ile Val Cys Pro Arg Leu Cys Tyr Phe Glu Leu Asp Arg Leu Cys
 1               5                  10                  15

Pro Asp Val Cys Tyr Val
                20

<210> SEQ ID NO 324
<211> LENGTH: 21
<212> TYPE: PRT
<213> ORGANISM: Artificial Sequence
<220> FEATURE:
<223> OTHER INFORMATION: sequence is synthesized

<400> SEQUENCE: 324

Ile Val Cys Pro Arg Leu Cys Tyr Gly Gly Ile Val Gly Leu Cys
 1               5                  10                  15

Pro Asp Val Cys Tyr Val
                20

<210> SEQ ID NO 325
<211> LENGTH: 21
<212> TYPE: PRT
<213> ORGANISM: Artificial Sequence
<220> FEATURE:
<223> OTHER INFORMATION: sequence is synthesized

<400> SEQUENCE: 325

Ile Val Cys Pro Arg Leu Cys Tyr Leu Gly Ser Ile Glu Leu Cys
 1               5                  10                  15

Pro Asp Val Cys Tyr Val
                20

<210> SEQ ID NO 326
<211> LENGTH: 21
<212> TYPE: PRT
<213> ORGANISM: Artificial Sequence
<220> FEATURE:
<223> OTHER INFORMATION: sequence is synthesized

<400> SEQUENCE: 326

Ile Val Cys Pro Arg Leu Cys Tyr Leu Ser Gly Glu Pro Leu Cys
 1               5                  10                  15

Pro Asp Val Cys Tyr Val
                20

<210> SEQ ID NO 327
<211> LENGTH: 21
<212> TYPE: PRT
<213> ORGANISM: Artificial Sequence
<220> FEATURE:
<223> OTHER INFORMATION: sequence is synthesized

<400> SEQUENCE: 327

Ile Val Cys Pro Arg Leu Cys Tyr Leu Tyr Gly Pro Gly Leu Cys
 1               5                  10                  15

Pro Asp Val Cys Tyr Val
                20

<210> SEQ ID NO 328
<211> LENGTH: 21
<212> TYPE: PRT
```

```
<213> ORGANISM: Artificial Sequence
<220> FEATURE:
<223> OTHER INFORMATION: sequence is synthesized

<400> SEQUENCE: 328

Ile Val Cys Pro Arg Leu Cys Tyr Met Gly Asp Ser Glu Leu Cys
 1               5                  10                  15

Pro Asp Val Cys Tyr Val
                20

<210> SEQ ID NO 329
<211> LENGTH: 21
<212> TYPE: PRT
<213> ORGANISM: Artificial Sequence
<220> FEATURE:
<223> OTHER INFORMATION: sequence is synthesized

<400> SEQUENCE: 329

Ile Val Cys Pro Arg Leu Cys Tyr Met Ser Asp Leu Phe Leu Cys
 1               5                  10                  15

Pro Asp Val Cys Tyr Val
                20

<210> SEQ ID NO 330
<211> LENGTH: 21
<212> TYPE: PRT
<213> ORGANISM: Artificial Sequence
<220> FEATURE:
<223> OTHER INFORMATION: sequence is synthesized

<400> SEQUENCE: 330

Ile Val Cys Pro Arg Leu Cys Tyr Asn Asp Leu Gln Gly Leu Cys
 1               5                  10                  15

Pro Asp Val Cys Tyr Val
                20

<210> SEQ ID NO 331
<211> LENGTH: 21
<212> TYPE: PRT
<213> ORGANISM: Artificial Sequence
<220> FEATURE:
<223> OTHER INFORMATION: sequence is synthesized

<400> SEQUENCE: 331

Ile Val Cys Pro Arg Leu Cys Tyr Ser Gly Leu Trp Gly Leu Cys
 1               5                  10                  15

Pro Asp Val Cys Tyr Val
                20

<210> SEQ ID NO 332
<211> LENGTH: 21
<212> TYPE: PRT
<213> ORGANISM: Artificial Sequence
<220> FEATURE:
<223> OTHER INFORMATION: sequence is synthesized

<400> SEQUENCE: 332

Ile Val Cys Pro Arg Leu Cys Tyr Thr Thr Leu Ser Gly Leu Cys
 1               5                  10                  15

Pro Asp Val Cys Tyr Val
                20

<210> SEQ ID NO 333
<211> LENGTH: 21
```

```
<212> TYPE: PRT
<213> ORGANISM: Artificial Sequence
<220> FEATURE:
<223> OTHER INFORMATION: sequence is synthesized

<400> SEQUENCE: 333

Ile Val Cys Pro Arg Leu Cys Tyr Val Gly Ser Leu Asp Leu Cys
 1               5                  10                  15

Pro Asp Val Cys Tyr Val
            20

<210> SEQ ID NO 334
<211> LENGTH: 21
<212> TYPE: PRT
<213> ORGANISM: Artificial Sequence
<220> FEATURE:
<223> OTHER INFORMATION: sequence is synthesized

<400> SEQUENCE: 334

Ile Val Cys Pro Arg Leu Cys Tyr Trp Gly Ser His Gly Leu Cys
 1               5                  10                  15

Pro Asp Val Cys Tyr Val
            20

<210> SEQ ID NO 335
<211> LENGTH: 21
<212> TYPE: PRT
<213> ORGANISM: Artificial Sequence
<220> FEATURE:
<223> OTHER INFORMATION: sequence is synthesized

<400> SEQUENCE: 335

Ile Val Cys Pro Arg Leu Cys Tyr Trp Ser Gly Thr Leu Leu Cys
 1               5                  10                  15

Pro Asp Val Cys Tyr Val
            20

<210> SEQ ID NO 336
<211> LENGTH: 21
<212> TYPE: PRT
<213> ORGANISM: Artificial Sequence
<220> FEATURE:
<223> OTHER INFORMATION: sequence is synthesized

<400> SEQUENCE: 336

Ile Val Cys Pro Arg Leu Cys Tyr Tyr Gly Ala Ala Gly Leu Cys
 1               5                  10                  15

Pro Asp Val Cys Tyr Val
            20

<210> SEQ ID NO 337
<211> LENGTH: 21
<212> TYPE: PRT
<213> ORGANISM: Artificial Sequence
<220> FEATURE:
<223> OTHER INFORMATION: sequence is synthesized

<400> SEQUENCE: 337

Ile Val Cys Pro Arg Leu Cys Tyr Trp Tyr Pro Ser Leu Leu Cys
 1               5                  10                  15

Pro Asp Val Cys Tyr Val
            20

<210> SEQ ID NO 338
```

```
<211> LENGTH: 21
<212> TYPE: PRT
<213> ORGANISM: Artificial Sequence
<220> FEATURE:
<223> OTHER INFORMATION: sequence is synthesized

<400> SEQUENCE: 338

Val Gln Cys Pro Pro Phe Cys Tyr Cys Gly Gly Pro Glu Leu Cys
 1               5                  10                  15

Pro Asp Ser Cys Tyr Gly
                20

<210> SEQ ID NO 339
<211> LENGTH: 21
<212> TYPE: PRT
<213> ORGANISM: Artificial Sequence
<220> FEATURE:
<223> OTHER INFORMATION: sequence is synthesized

<400> SEQUENCE: 339

Val Gln Cys Pro Asp Phe Cys Tyr Val Cys Gly Asp Ala Phe Cys
 1               5                  10                  15

Pro Asp Val Cys Tyr Val
                20

<210> SEQ ID NO 340
<211> LENGTH: 21
<212> TYPE: PRT
<213> ORGANISM: Artificial Sequence
<220> FEATURE:
<223> OTHER INFORMATION: sequence is synthesized

<400> SEQUENCE: 340

Val Lys Cys Pro Arg Phe Cys Tyr Asp Gly Gly Thr Ala Leu Cys
 1               5                  10                  15

Pro Asp Val Cys Tyr Val
                20

<210> SEQ ID NO 341
<211> LENGTH: 21
<212> TYPE: PRT
<213> ORGANISM: Artificial Sequence
<220> FEATURE:
<223> OTHER INFORMATION: sequence is synthesized

<400> SEQUENCE: 341

Val Pro Cys Pro His Phe Cys Tyr Asp Gly Asp Lys Glu Leu Cys
 1               5                  10                  15

Pro Glu Val Cys His Val
                20

<210> SEQ ID NO 342
<211> LENGTH: 21
<212> TYPE: PRT
<213> ORGANISM: Artificial Sequence
<220> FEATURE:
<223> OTHER INFORMATION: sequence is synthesized

<400> SEQUENCE: 342

Val Gln Cys Pro His Phe Cys Tyr Tyr Gly Gly Lys Glu Leu Cys
 1               5                  10                  15

Pro Asp Val Cys Tyr Val
                20
```

```
<210> SEQ ID NO 343
<211> LENGTH: 21
<212> TYPE: PRT
<213> ORGANISM: Artificial Sequence
<220> FEATURE:
<223> OTHER INFORMATION: sequence is synthesized

<400> SEQUENCE: 343

Gly Gln Cys Pro Gln Trp Cys Tyr Leu Gly Cys His Glu Leu Cys
 1               5                  10                  15

Pro Asp Val Cys Tyr Val
            20

<210> SEQ ID NO 344
<211> LENGTH: 21
<212> TYPE: PRT
<213> ORGANISM: Artificial Sequence
<220> FEATURE:
<223> OTHER INFORMATION: sequence is synthesized

<400> SEQUENCE: 344

Val Gln Cys Pro Leu Phe Cys Tyr Glu Thr Gly Glu Gly Leu Cys
 1               5                  10                  15

Pro Asp Val Cys Tyr Val
            20

<210> SEQ ID NO 345
<211> LENGTH: 21
<212> TYPE: PRT
<213> ORGANISM: Artificial Sequence
<220> FEATURE:
<223> OTHER INFORMATION: sequence is synthesized

<400> SEQUENCE: 345

Val Gln Cys Pro Asp Phe Cys Tyr Cys Gly Gly Asn Ser Leu Cys
 1               5                  10                  15

Pro Asp Val Cys Tyr Val
            20

<210> SEQ ID NO 346
<211> LENGTH: 21
<212> TYPE: PRT
<213> ORGANISM: Artificial Sequence
<220> FEATURE:
<223> OTHER INFORMATION: sequence is synthesized

<400> SEQUENCE: 346

Val Gln Cys Pro Ser Phe Cys Tyr Asp Gly Gly Lys Ala Ile Cys
 1               5                  10                  15

Pro Asp Val Cys Tyr Val
            20

<210> SEQ ID NO 347
<211> LENGTH: 21
<212> TYPE: PRT
<213> ORGANISM: Artificial Sequence
<220> FEATURE:
<223> OTHER INFORMATION: sequence is synthesized

<400> SEQUENCE: 347

Val Gln Cys Pro His Phe Cys Tyr Ile Gly Val Arg Gly Leu Cys
 1               5                  10                  15

Pro Asp Val Cys Tyr Val
            20
```

```
<210> SEQ ID NO 348
<211> LENGTH: 21
<212> TYPE: PRT
<213> ORGANISM: Artificial Sequence
<220> FEATURE:
<223> OTHER INFORMATION: sequence is synthesized

<400> SEQUENCE: 348

Val Lys Cys Pro His Phe Cys Tyr Phe Gly Pro Thr Ser Leu Cys
 1               5                  10                  15

Pro Asp Val Cys Tyr Lys
                20

<210> SEQ ID NO 349
<211> LENGTH: 21
<212> TYPE: PRT
<213> ORGANISM: Artificial Sequence
<220> FEATURE:
<223> OTHER INFORMATION: sequence is synthesized

<400> SEQUENCE: 349

Val Gln Cys Pro His Phe Cys Tyr Arg Gly Asp Glu Ala Leu Cys
 1               5                  10                  15

Pro Asp Val Cys Tyr Val
                20

<210> SEQ ID NO 350
<211> LENGTH: 21
<212> TYPE: PRT
<213> ORGANISM: Artificial Sequence
<220> FEATURE:
<223> OTHER INFORMATION: sequence is synthesized

<400> SEQUENCE: 350

Val Gln Cys Pro Gln Phe Cys Tyr Cys Gly Gly Asn Glu Leu Cys
 1               5                  10                  15

Pro Asp Val Cys Tyr Val
                20

<210> SEQ ID NO 351
<211> LENGTH: 21
<212> TYPE: PRT
<213> ORGANISM: Artificial Sequence
<220> FEATURE:
<223> OTHER INFORMATION: sequence is synthesized

<400> SEQUENCE: 351

Val Gln Cys Pro Gln Phe Cys Tyr Val Gly Gly Cys Glu Val Cys
 1               5                  10                  15

Pro Asp Ile Cys Thr Ser
                20

<210> SEQ ID NO 352
<211> LENGTH: 21
<212> TYPE: PRT
<213> ORGANISM: Artificial Sequence
<220> FEATURE:
<223> OTHER INFORMATION: sequence is synthesized

<400> SEQUENCE: 352

Val Pro Cys Pro Ser Phe Cys Tyr Val Gly Cys Asn Glu Leu Cys
 1               5                  10                  15

Pro Asp Val Cys Tyr Val
                20
```

```
<210> SEQ ID NO 353
<211> LENGTH: 21
<212> TYPE: PRT
<213> ORGANISM: Artificial Sequence
<220> FEATURE:
<223> OTHER INFORMATION: sequence is synthesized

<400> SEQUENCE: 353

Ile Gln Cys Pro Ser Phe Cys Tyr Val Glu Cys Asn Gly Ile Cys
 1               5                  10                  15

Pro Asp Val Cys Tyr Phe
             20

<210> SEQ ID NO 354
<211> LENGTH: 21
<212> TYPE: PRT
<213> ORGANISM: Artificial Sequence
<220> FEATURE:
<223> OTHER INFORMATION: sequence is synthesized

<400> SEQUENCE: 354

Val Gln Cys Pro His Phe Cys Tyr Val Gly Asp Lys Ser Leu Cys
 1               5                  10                  15

Pro Asp Val Cys Tyr Val
             20

<210> SEQ ID NO 355
<211> LENGTH: 21
<212> TYPE: PRT
<213> ORGANISM: Artificial Sequence
<220> FEATURE:
<223> OTHER INFORMATION: sequence is synthesized

<400> SEQUENCE: 355

Val Arg Cys Pro Ser Leu Cys Tyr Phe Leu Gly Thr Ser Leu Cys
 1               5                  10                  15

Pro Asp Gln Cys Tyr Val
             20

<210> SEQ ID NO 356
<211> LENGTH: 21
<212> TYPE: PRT
<213> ORGANISM: Artificial Sequence
<220> FEATURE:
<223> OTHER INFORMATION: sequence is synthesized

<400> SEQUENCE: 356

Val Gln Cys Pro Tyr Phe Cys Tyr Ala Gly Gly Lys Ser Leu Cys
 1               5                  10                  15

Pro Asp Val Cys Tyr Val
             20

<210> SEQ ID NO 357
<211> LENGTH: 21
<212> TYPE: PRT
<213> ORGANISM: Artificial Sequence
<220> FEATURE:
<223> OTHER INFORMATION: sequence is synthesized

<400> SEQUENCE: 357

Val Lys Cys Pro His Phe Cys Tyr Phe Gly Gly Lys Glu Leu Cys
 1               5                  10                  15

Pro Gly Val Cys Tyr Ala
```

```
<210> SEQ ID NO 358
<211> LENGTH: 21
<212> TYPE: PRT
<213> ORGANISM: Artificial Sequence
<220> FEATURE:
<223> OTHER INFORMATION: sequence is synthesized

<400> SEQUENCE: 358

Val Arg Cys Pro His Phe Cys Tyr Val Gly Cys Asp Thr Leu Cys
 1               5                  10                  15

Pro Asp Val Cys Tyr Val
            20

<210> SEQ ID NO 359
<211> LENGTH: 21
<212> TYPE: PRT
<213> ORGANISM: Artificial Sequence
<220> FEATURE:
<223> OTHER INFORMATION: sequence is synthesized

<400> SEQUENCE: 359

Ile Val Cys Pro Arg Leu Cys Tyr Val Gly Gly Lys His Phe Cys
 1               5                  10                  15

Pro Ser Arg Cys Tyr Val
            20

<210> SEQ ID NO 360
<211> LENGTH: 21
<212> TYPE: PRT
<213> ORGANISM: Artificial Sequence
<220> FEATURE:
<223> OTHER INFORMATION: sequence is synthesized

<400> SEQUENCE: 360

Ile Val Cys Pro Arg Leu Cys Tyr Val Gly Gly Lys Gln Phe Cys
 1               5                  10                  15

Pro Gly Val Cys Tyr Val
            20

<210> SEQ ID NO 361
<211> LENGTH: 21
<212> TYPE: PRT
<213> ORGANISM: Artificial Sequence
<220> FEATURE:
<223> OTHER INFORMATION: sequence is synthesized

<400> SEQUENCE: 361

Ile Val Cys Pro Arg Leu Cys Tyr Val Gly Gly Lys Gly Leu Cys
 1               5                  10                  15

Pro Asp Lys Cys Tyr Val
            20

<210> SEQ ID NO 362
<211> LENGTH: 21
<212> TYPE: PRT
<213> ORGANISM: Artificial Sequence
<220> FEATURE:
<223> OTHER INFORMATION: sequence is synthesized

<400> SEQUENCE: 362

Ile Val Cys Pro Arg Leu Cys Tyr Val Gly Gly Lys Leu Leu Cys
 1               5                  10                  15
```

```
Pro Asp Lys Cys Tyr Val
            20

<210> SEQ ID NO 363
<211> LENGTH: 21
<212> TYPE: PRT
<213> ORGANISM: Artificial Sequence
<220> FEATURE:
<223> OTHER INFORMATION: sequence is synthesized

<400> SEQUENCE: 363

Ile Val Cys Pro Arg Leu Cys Tyr Val Gly Gly Lys Ala Trp Cys
  1               5                  10                  15

Pro Ala Leu Cys Tyr Val
            20

<210> SEQ ID NO 364
<211> LENGTH: 21
<212> TYPE: PRT
<213> ORGANISM: Artificial Sequence
<220> FEATURE:
<223> OTHER INFORMATION: sequence is synthesized

<400> SEQUENCE: 364

Ile Val Cys Pro Arg Leu Cys Tyr Val Gly Gly Lys Ala Trp Cys
  1               5                  10                  15

Pro His Phe Cys Tyr Val
            20

<210> SEQ ID NO 365
<211> LENGTH: 21
<212> TYPE: PRT
<213> ORGANISM: Artificial Sequence
<220> FEATURE:
<223> OTHER INFORMATION: sequence is synthesized

<400> SEQUENCE: 365

Ile Val Cys Pro Arg Leu Cys Tyr Val Gly Gly Lys Ala Trp Cys
  1               5                  10                  15

Pro Ser Phe Cys Tyr Val
            20

<210> SEQ ID NO 366
<211> LENGTH: 21
<212> TYPE: PRT
<213> ORGANISM: Artificial Sequence
<220> FEATURE:
<223> OTHER INFORMATION: sequence is synthesized

<400> SEQUENCE: 366

Ile Val Cys Pro Arg Leu Cys Tyr Val Gly Gly Lys Ala Trp Cys
  1               5                  10                  15

Pro Ser Ser Cys Tyr Val
            20

<210> SEQ ID NO 367
<211> LENGTH: 21
<212> TYPE: PRT
<213> ORGANISM: Artificial Sequence
<220> FEATURE:
<223> OTHER INFORMATION: sequence is synthesized

<400> SEQUENCE: 367

Ile Val Cys Pro Arg Leu Cys Tyr Val Gly Gly Lys Asp Trp Cys
  1               5                  10                  15
```

Pro Gly Leu Cys Tyr Val
            20

<210> SEQ ID NO 368
<211> LENGTH: 21
<212> TYPE: PRT
<213> ORGANISM: Artificial Sequence
<220> FEATURE:
<223> OTHER INFORMATION: sequence is synthesized

<400> SEQUENCE: 368

Ile Val Cys Pro Arg Leu Cys Tyr Val Gly Gly Lys His Trp Cys
 1               5                  10                  15
Pro Phe Leu Cys Tyr Val
            20

<210> SEQ ID NO 369
<211> LENGTH: 21
<212> TYPE: PRT
<213> ORGANISM: Artificial Sequence
<220> FEATURE:
<223> OTHER INFORMATION: sequence is synthesized

<400> SEQUENCE: 369

Ile Val Cys Pro Arg Leu Cys Tyr Val Gly Gly Lys His Trp Cys
 1               5                  10                  15
Pro Asn Met Cys Tyr Val
            20

<210> SEQ ID NO 370
<211> LENGTH: 21
<212> TYPE: PRT
<213> ORGANISM: Artificial Sequence
<220> FEATURE:
<223> OTHER INFORMATION: sequence is synthesized

<400> SEQUENCE: 370

Ile Val Cys Pro Arg Leu Cys Tyr Val Gly Gly Lys His Trp Cys
 1               5                  10                  15
Pro Ser Val Cys Tyr Val
            20

<210> SEQ ID NO 371
<211> LENGTH: 21
<212> TYPE: PRT
<213> ORGANISM: Artificial Sequence
<220> FEATURE:
<223> OTHER INFORMATION: sequence is synthesized

<400> SEQUENCE: 371

Ile Val Cys Pro Arg Leu Cys Tyr Val Gly Gly Lys His Trp Cys
 1               5                  10                  15
Pro Trp Ser Cys Tyr Val
            20

<210> SEQ ID NO 372
<211> LENGTH: 21
<212> TYPE: PRT
<213> ORGANISM: Artificial Sequence
<220> FEATURE:
<223> OTHER INFORMATION: sequence is synthesized

<400> SEQUENCE: 372

Ile Val Cys Pro Arg Leu Cys Tyr Val Gly Gly Lys Leu Trp Cys

```
                1               5                  10                  15

Pro Ser Phe Cys Tyr Val
                20

<210> SEQ ID NO 373
<211> LENGTH: 21
<212> TYPE: PRT
<213> ORGANISM: Artificial Sequence
<220> FEATURE:
<223> OTHER INFORMATION: sequence is synthesized

<400> SEQUENCE: 373

Ile Val Cys Pro Arg Leu Cys Tyr Val Gly Gly Lys Pro Trp Cys
 1               5                  10                  15

Pro Ser Met Cys Tyr Val
                20

<210> SEQ ID NO 374
<211> LENGTH: 21
<212> TYPE: PRT
<213> ORGANISM: Artificial Sequence
<220> FEATURE:
<223> OTHER INFORMATION: sequence is synthesized

<400> SEQUENCE: 374

Ile Val Cys Pro Arg Leu Cys Tyr Val Gly Gly Lys Gln Trp Cys
 1               5                  10                  15

Pro Ala Ile Cys Tyr Val
                20

<210> SEQ ID NO 375
<211> LENGTH: 21
<212> TYPE: PRT
<213> ORGANISM: Artificial Sequence
<220> FEATURE:
<223> OTHER INFORMATION: sequence is synthesized

<400> SEQUENCE: 375

Ile Val Cys Pro Arg Leu Cys Tyr Val Gly Gly Lys Thr Trp Cys
 1               5                  10                  15

Pro Gly Phe Cys Tyr Val
                20

<210> SEQ ID NO 376
<211> LENGTH: 21
<212> TYPE: PRT
<213> ORGANISM: Artificial Sequence
<220> FEATURE:
<223> OTHER INFORMATION: sequence is synthesized

<400> SEQUENCE: 376

Ile Val Cys Pro Arg Leu Cys Tyr Val Gly Gly Lys Thr Trp Cys
 1               5                  10                  15

Pro Ser Trp Cys Tyr Val
                20

<210> SEQ ID NO 377
<211> LENGTH: 21
<212> TYPE: PRT
<213> ORGANISM: Artificial Sequence
<220> FEATURE:
<223> OTHER INFORMATION: sequence is synthesized

<400> SEQUENCE: 377
```

```
Ile Val Cys Pro Arg Leu Cys Tyr Val Gly Gly Lys Trp Trp Cys
 1               5                  10                  15

Pro Gln Met Cys Tyr Val
                20
```

<210> SEQ ID NO 378
<211> LENGTH: 21
<212> TYPE: PRT
<213> ORGANISM: Artificial Sequence
<220> FEATURE:
<223> OTHER INFORMATION: sequence is synthesized

<400> SEQUENCE: 378

```
Val Gln Cys Pro His Phe Cys Tyr Val Gly Gly Lys Arg Glu Cys
 1               5                  10                  15

Pro Asp Lys Cys Tyr Val
                20
```

<210> SEQ ID NO 379
<211> LENGTH: 21
<212> TYPE: PRT
<213> ORGANISM: Artificial Sequence
<220> FEATURE:
<223> OTHER INFORMATION: sequence is synthesized

<400> SEQUENCE: 379

```
Val Gln Cys Pro His Phe Cys Tyr Val Gly Gly Lys Thr Asp Cys
 1               5                  10                  15

Pro Asp Ser Cys Tyr Val
                20
```

<210> SEQ ID NO 380
<211> LENGTH: 21
<212> TYPE: PRT
<213> ORGANISM: Artificial Sequence
<220> FEATURE:
<223> OTHER INFORMATION: sequence is synthesized

<400> SEQUENCE: 380

```
Val Gln Cys Pro His Phe Cys Tyr Val Gly Gly Lys Arg Glu Cys
 1               5                  10                  15

Pro Asp Arg Cys Tyr Val
                20
```

<210> SEQ ID NO 381
<211> LENGTH: 21
<212> TYPE: PRT
<213> ORGANISM: Artificial Sequence
<220> FEATURE:
<223> OTHER INFORMATION: sequence is synthesized

<400> SEQUENCE: 381

```
Val Gln Cys Pro His Phe Cys Tyr Val Gly Gly Lys Gly Leu Cys
 1               5                  10                  15

Pro Asp Ile Cys Tyr Val
                20
```

<210> SEQ ID NO 382
<211> LENGTH: 21
<212> TYPE: PRT
<213> ORGANISM: Artificial Sequence
<220> FEATURE:
<223> OTHER INFORMATION: sequence is synthesized

<400> SEQUENCE: 382

Val Gln Cys Pro His Phe Cys Tyr Val Gly Gly Lys Gln Leu Cys
1               5                   10                  15

Pro Asp Gly Cys Tyr Val
            20

<210> SEQ ID NO 383
<211> LENGTH: 21
<212> TYPE: PRT
<213> ORGANISM: Artificial Sequence
<220> FEATURE:
<223> OTHER INFORMATION: sequence is synthesized

<400> SEQUENCE: 383

Val Gln Cys Pro His Phe Cys Tyr Val Gly Gly Lys His Pro Cys
1               5                   10                  15

Pro Asp Val Cys Tyr Val
            20

<210> SEQ ID NO 384
<211> LENGTH: 21
<212> TYPE: PRT
<213> ORGANISM: Artificial Sequence
<220> FEATURE:
<223> OTHER INFORMATION: sequence is synthesized

<400> SEQUENCE: 384

Val Gln Cys Pro His Phe Cys Tyr Val Gly Gly Lys Asn Gln Cys
1               5                   10                  15

Pro Asp Lys Cys Tyr Val
            20

<210> SEQ ID NO 385
<211> LENGTH: 21
<212> TYPE: PRT
<213> ORGANISM: Artificial Sequence
<220> FEATURE:
<223> OTHER INFORMATION: sequence is synthesized

<400> SEQUENCE: 385

Val Gln Cys Pro His Phe Cys Tyr Val Gly Gly Lys Gly Val Cys
1               5                   10                  15

Pro Asp Thr Cys Tyr Val
            20

<210> SEQ ID NO 386
<211> LENGTH: 21
<212> TYPE: PRT
<213> ORGANISM: Artificial Sequence
<220> FEATURE:
<223> OTHER INFORMATION: sequence is synthesized

<400> SEQUENCE: 386

Val Gln Cys Pro His Phe Cys Tyr Val Gly Gly Lys Gly Leu Cys
1               5                   10                  15

Pro Asp Thr Cys Tyr Val
            20

<210> SEQ ID NO 387
<211> LENGTH: 21
<212> TYPE: PRT
<213> ORGANISM: Artificial Sequence
<220> FEATURE:
<223> OTHER INFORMATION: sequence is synthesized -continued

```
<400> SEQUENCE: 387

Val Gln Cys Pro His Phe Cys Tyr Val Gly Gly Lys Ser Met Cys
  1               5                  10                  15

Pro Asp Pro Cys Tyr Val
                20

<210> SEQ ID NO 388
<211> LENGTH: 21
<212> TYPE: PRT
<213> ORGANISM: Artificial Sequence
<220> FEATURE:
<223> OTHER INFORMATION: sequence is synthesized

<400> SEQUENCE: 388

Val Gln Cys Pro His Phe Cys Tyr Val Gly Gly Lys Leu Leu Cys
  1               5                  10                  15

Pro Asp Ile Cys Tyr Val
                20

<210> SEQ ID NO 389
<211> LENGTH: 21
<212> TYPE: PRT
<213> ORGANISM: Artificial Sequence
<220> FEATURE:
<223> OTHER INFORMATION: sequence is synthesized

<400> SEQUENCE: 389

Val Gln Cys Pro His Phe Cys Tyr Val Gly Gly Lys Ser Leu Cys
  1               5                  10                  15

Pro Asp Arg Cys Tyr Val
                20

<210> SEQ ID NO 390
<211> LENGTH: 21
<212> TYPE: PRT
<213> ORGANISM: Artificial Sequence
<220> FEATURE:
<223> OTHER INFORMATION: sequence is synthesized

<400> SEQUENCE: 390

Val Gln Cys Pro His Phe Cys Tyr Val Gly Gly Lys Leu Val Cys
  1               5                  10                  15

Pro Asp Ala Cys Tyr Val
                20

<210> SEQ ID NO 391
<211> LENGTH: 21
<212> TYPE: PRT
<213> ORGANISM: Artificial Sequence
<220> FEATURE:
<223> OTHER INFORMATION: sequence is synthesized

<400> SEQUENCE: 391

Val Gln Cys Pro His Phe Cys Tyr Val Gly Gly Lys Ala Leu Cys
  1               5                  10                  15

Pro Asp Lys Cys Tyr Thr
                20

<210> SEQ ID NO 392
<211> LENGTH: 21
<212> TYPE: PRT
<213> ORGANISM: Artificial Sequence
<220> FEATURE:
<223> OTHER INFORMATION: sequence is synthesized
```

```
<400> SEQUENCE: 392

Val Gln Cys Pro His Phe Cys Tyr Val Gly Gly Lys Ala Leu Cys
 1               5                   10                  15

Pro Asp Arg Cys Tyr Ser
                20

<210> SEQ ID NO 393
<211> LENGTH: 21
<212> TYPE: PRT
<213> ORGANISM: Artificial Sequence
<220> FEATURE:
<223> OTHER INFORMATION: sequence is synthesized

<400> SEQUENCE: 393

Val Gln Cys Pro His Phe Cys Tyr Val Gly Gly Lys Ala Leu Cys
 1               5                   10                  15

Pro Asp Val Cys Tyr Arg
                20

<210> SEQ ID NO 394
<211> LENGTH: 21
<212> TYPE: PRT
<213> ORGANISM: Artificial Sequence
<220> FEATURE:
<223> OTHER INFORMATION: sequence is synthesized

<400> SEQUENCE: 394

Val Arg Cys Pro His Phe Cys Tyr Val Gly Gly Lys Ala Leu Cys
 1               5                   10                  15

Pro Asp Val Cys Tyr Val
                20

<210> SEQ ID NO 395
<211> LENGTH: 21
<212> TYPE: PRT
<213> ORGANISM: Artificial Sequence
<220> FEATURE:
<223> OTHER INFORMATION: sequence is synthesized

<400> SEQUENCE: 395

Val Val Cys Pro His Phe Cys Tyr Val Gly Gly Lys Ala Leu Cys
 1               5                   10                  15

Pro Asp Lys Cys Tyr Val
                20

<210> SEQ ID NO 396
<211> LENGTH: 21
<212> TYPE: PRT
<213> ORGANISM: Artificial Sequence
<220> FEATURE:
<223> OTHER INFORMATION: sequence is synthesized

<400> SEQUENCE: 396

Val Glu Cys Pro His Phe Cys Tyr Val Gly Gly Lys Ala Leu Cys
 1               5                   10                  15

Pro Asp Leu Cys Tyr Val
                20

<210> SEQ ID NO 397
<211> LENGTH: 21
<212> TYPE: PRT
<213> ORGANISM: Artificial Sequence
<220> FEATURE:
```

<223> OTHER INFORMATION: sequence is synthesized

<400> SEQUENCE: 397

Val Arg Cys Pro His Phe Cys Tyr Val Gly Gly Lys Ala Leu Cys
 1               5                  10                  15

Pro Asp Val Cys Tyr Val
            20

<210> SEQ ID NO 398
<211> LENGTH: 21
<212> TYPE: PRT
<213> ORGANISM: Artificial Sequence
<220> FEATURE:
<223> OTHER INFORMATION: sequence is synthesized

<400> SEQUENCE: 398

Val Arg Cys Pro His Phe Cys Tyr Val Gly Gly Lys Ala Leu Cys
 1               5                  10                  15

Pro Asp Pro Cys Tyr Val
            20

<210> SEQ ID NO 399
<211> LENGTH: 21
<212> TYPE: PRT
<213> ORGANISM: Artificial Sequence
<220> FEATURE:
<223> OTHER INFORMATION: sequence is synthesized

<400> SEQUENCE: 399

Val Arg Cys Pro His Phe Cys Tyr Val Gly Gly Lys Ala Leu Cys
 1               5                  10                  15

Pro Asp Arg Cys Tyr Val
            20

<210> SEQ ID NO 400
<211> LENGTH: 21
<212> TYPE: PRT
<213> ORGANISM: Artificial Sequence
<220> FEATURE:
<223> OTHER INFORMATION: sequence is synthesized

<400> SEQUENCE: 400

Val Lys Cys Pro His Phe Cys Tyr Val Gly Gly Lys Gly Leu Cys
 1               5                  10                  15

Pro Asp Lys Cys Tyr Val
            20

<210> SEQ ID NO 401
<211> LENGTH: 21
<212> TYPE: PRT
<213> ORGANISM: Artificial Sequence
<220> FEATURE:
<223> OTHER INFORMATION: sequence is synthesized

<400> SEQUENCE: 401

Val Met Cys Pro His Phe Cys Tyr Val Gly Gly Lys Ala Leu Cys
 1               5                  10                  15

Pro Asp Lys Cys Tyr Val
            20

<210> SEQ ID NO 402
<211> LENGTH: 21
<212> TYPE: PRT
<213> ORGANISM: Artificial Sequence

```
<220> FEATURE:
<223> OTHER INFORMATION: sequence is synthesized

<400> SEQUENCE: 402

Val Met Cys Pro His Phe Cys Tyr Val Gly Gly Lys Ala Leu Cys
 1               5                  10                  15

Pro Asp Val Cys Tyr Val
            20

<210> SEQ ID NO 403
<211> LENGTH: 21
<212> TYPE: PRT
<213> ORGANISM: Artificial Sequence
<220> FEATURE:
<223> OTHER INFORMATION: sequence is synthesized

<400> SEQUENCE: 403

Val Arg Cys Pro His Phe Cys Tyr Val Gly Gly Lys Thr Leu Cys
 1               5                  10                  15

Pro Asp Gln Cys Tyr Val
            20

<210> SEQ ID NO 404
<211> LENGTH: 21
<212> TYPE: PRT
<213> ORGANISM: Artificial Sequence
<220> FEATURE:
<223> OTHER INFORMATION: sequence is synthesized

<400> SEQUENCE: 404

Val Val Cys Pro His Phe Cys Tyr Val Gly Gly Lys Ala Leu Cys
 1               5                  10                  15

Pro Asp Val Cys Tyr Val
            20

<210> SEQ ID NO 405
<211> LENGTH: 21
<212> TYPE: PRT
<213> ORGANISM: Artificial Sequence
<220> FEATURE:
<223> OTHER INFORMATION: sequence is synthesized

<400> SEQUENCE: 405

Val Gln Cys Pro His Phe Cys Phe Val Gly Gly Lys Ala Leu Cys
 1               5                  10                  15

Pro Asp Val Cys Tyr Val
            20

<210> SEQ ID NO 406
<211> LENGTH: 21
<212> TYPE: PRT
<213> ORGANISM: Artificial Sequence
<220> FEATURE:
<223> OTHER INFORMATION: sequence is synthesized

<400> SEQUENCE: 406

Val Gln Cys Pro His Phe Cys Phe Val Gly Asp Lys Ala Leu Cys
 1               5                  10                  15

Pro Asp Val Cys Tyr Val
            20

<210> SEQ ID NO 407
<211> LENGTH: 20
<212> TYPE: PRT
```

```
<213> ORGANISM: Artificial Sequence
<220> FEATURE:
<223> OTHER INFORMATION: sequence is synthesized

<400> SEQUENCE: 407

Val Gln Cys Pro His Phe Cys Phe Val Gly Glu Ala Leu Cys Pro
 1               5                  10                  15

Asp Val Cys Tyr Val
             20

<210> SEQ ID NO 408
<211> LENGTH: 21
<212> TYPE: PRT
<213> ORGANISM: Artificial Sequence
<220> FEATURE:
<223> OTHER INFORMATION: sequence is synthesized

<400> SEQUENCE: 408

Val Gln Cys Pro His Phe Cys Tyr Val Gly Gly Lys Ala Leu Cys
 1               5                  10                  15

Pro Asp Val Cys Asp Val
             20

<210> SEQ ID NO 409
<211> LENGTH: 21
<212> TYPE: PRT
<213> ORGANISM: Artificial Sequence
<220> FEATURE:
<223> OTHER INFORMATION: sequence is synthesized

<400> SEQUENCE: 409

Val Gln Cys Pro His Phe Cys Tyr Val Gly Gly Lys Ala Leu Cys
 1               5                  10                  15

Pro Asp Val Cys Tyr Val
             20

<210> SEQ ID NO 410
<211> LENGTH: 21
<212> TYPE: PRT
<213> ORGANISM: Artificial Sequence
<220> FEATURE:
<223> OTHER INFORMATION: sequence is synthesized

<400> SEQUENCE: 410

Val Gln Cys Pro His Phe Cys Tyr Val Gly Gly Lys Ala Leu Cys
 1               5                  10                  15

Pro Asp Val Cys Tyr Val
             20

<210> SEQ ID NO 411
<211> LENGTH: 21
<212> TYPE: PRT
<213> ORGANISM: Artificial Sequence
<220> FEATURE:
<223> OTHER INFORMATION: sequence is synthesized

<400> SEQUENCE: 411

Val Gln Cys Pro His Phe Cys Tyr Val Gly Gly Lys Ala Leu Cys
 1               5                  10                  15

Pro Asp Val Cys Tyr Val
             20

<210> SEQ ID NO 412
<211> LENGTH: 21
```

```
<212> TYPE: PRT
<213> ORGANISM: Artificial Sequence
<220> FEATURE:
<223> OTHER INFORMATION: sequence is synthesized

<400> SEQUENCE: 412

Val Gln Cys Pro His Phe Cys Tyr Val Gly Gly Lys Ala Leu Cys
 1               5                  10                  15

Pro Asp Val Cys Tyr Val
            20

<210> SEQ ID NO 413
<211> LENGTH: 21
<212> TYPE: PRT
<213> ORGANISM: Artificial Sequence
<220> FEATURE:
<223> OTHER INFORMATION: sequence is synthesized

<400> SEQUENCE: 413

Ile Leu Cys Pro Leu Phe Cys Tyr Glu Leu Asp Tyr Glu Leu Cys
 1               5                  10                  15

Pro Asp Val Cys Tyr Val
            20

<210> SEQ ID NO 414
<211> LENGTH: 21
<212> TYPE: PRT
<213> ORGANISM: Artificial Sequence
<220> FEATURE:
<223> OTHER INFORMATION: sequence is synthesized

<400> SEQUENCE: 414

Gln Ala Cys Pro Leu Phe Cys Tyr Glu Leu Asp Tyr Glu Leu Cys
 1               5                  10                  15

Pro Asp Val Cys Tyr Val
            20

<210> SEQ ID NO 415
<211> LENGTH: 21
<212> TYPE: PRT
<213> ORGANISM: Artificial Sequence
<220> FEATURE:
<223> OTHER INFORMATION: sequence is synthesized

<400> SEQUENCE: 415

Ala Gly Cys Pro Leu Phe Cys Tyr Glu Leu Asp Tyr Glu Leu Cys
 1               5                  10                  15

Pro Asp Val Cys Tyr Val
            20

<210> SEQ ID NO 416
<211> LENGTH: 21
<212> TYPE: PRT
<213> ORGANISM: Artificial Sequence
<220> FEATURE:
<223> OTHER INFORMATION: sequence is synthesized

<400> SEQUENCE: 416

Ala Leu Cys Pro Leu Phe Cys Tyr Glu Leu Asp Tyr Glu Leu Cys
 1               5                  10                  15

Pro Asp Val Cys Tyr Val
            20

<210> SEQ ID NO 417
```

```
<211> LENGTH: 21
<212> TYPE: PRT
<213> ORGANISM: Artificial Sequence
<220> FEATURE:
<223> OTHER INFORMATION: sequence is synthesized

<400> SEQUENCE: 417

Tyr Glu Cys Pro Cys Phe Cys Tyr Glu Leu Asp Tyr Glu Leu Cys
 1               5                  10                  15

Pro Asp Val Cys Tyr Val
            20

<210> SEQ ID NO 418
<211> LENGTH: 21
<212> TYPE: PRT
<213> ORGANISM: Artificial Sequence
<220> FEATURE:
<223> OTHER INFORMATION: sequence is synthesized

<400> SEQUENCE: 418

Lys Leu Cys Pro Leu Phe Cys Tyr Glu Leu Asp Tyr Glu Leu Cys
 1               5                  10                  15

Pro Asp Val Cys Tyr Val
            20

<210> SEQ ID NO 419
<211> LENGTH: 21
<212> TYPE: PRT
<213> ORGANISM: Artificial Sequence
<220> FEATURE:
<223> OTHER INFORMATION: sequence is synthesized

<400> SEQUENCE: 419

Val Gln Cys Pro His Trp Cys Tyr Glu Leu Asp Gly Glu Leu Cys
 1               5                  10                  15

Pro Asp Val Cys Tyr Val
            20

<210> SEQ ID NO 420
<211> LENGTH: 21
<212> TYPE: PRT
<213> ORGANISM: Artificial Sequence
<220> FEATURE:
<223> OTHER INFORMATION: sequence is synthesized

<400> SEQUENCE: 420

Val Gln Cys Pro His Met Cys Tyr Glu Leu Asp Glu Glu Leu Cys
 1               5                  10                  15

Pro Asp Val Cys Tyr Val
            20

<210> SEQ ID NO 421
<211> LENGTH: 21
<212> TYPE: PRT
<213> ORGANISM: Artificial Sequence
<220> FEATURE:
<223> OTHER INFORMATION: sequence is synthesized

<400> SEQUENCE: 421

Val Gln Cys Pro His Leu Cys Tyr Glu Leu Asp Glu Glu Val Cys
 1               5                  10                  15

Pro Asp Val Cys Tyr Val
            20
```

```
<210> SEQ ID NO 422
<211> LENGTH: 21
<212> TYPE: PRT
<213> ORGANISM: Artificial Sequence
<220> FEATURE:
<223> OTHER INFORMATION: sequence is synthesized

<400> SEQUENCE: 422

Val Gln Cys Pro His Leu Cys Tyr Glu Leu Asp Gly Glu Glu Cys
 1               5                  10                  15

Pro Asp Val Cys Tyr Val
                20

<210> SEQ ID NO 423
<211> LENGTH: 21
<212> TYPE: PRT
<213> ORGANISM: Artificial Sequence
<220> FEATURE:
<223> OTHER INFORMATION: sequence is synthesized

<400> SEQUENCE: 423

Val Gln Cys Pro His Leu Cys Tyr Glu Leu Asp Leu Glu Leu Cys
 1               5                  10                  15

Pro Asp Val Cys Tyr Val
                20

<210> SEQ ID NO 424
<211> LENGTH: 21
<212> TYPE: PRT
<213> ORGANISM: Artificial Sequence
<220> FEATURE:
<223> OTHER INFORMATION: sequence is synthesized

<400> SEQUENCE: 424

Val Gln Cys Pro His Leu Cys Tyr Glu Leu Asp Pro Glu Leu Cys
 1               5                  10                  15

Pro Asp Val Cys Tyr Val
                20

<210> SEQ ID NO 425
<211> LENGTH: 21
<212> TYPE: PRT
<213> ORGANISM: Artificial Sequence
<220> FEATURE:
<223> OTHER INFORMATION: sequence is synthesized

<400> SEQUENCE: 425

Val Gln Cys Pro His Leu Cys Tyr Glu Leu Asp Thr Glu Pro Cys
 1               5                  10                  15

Pro Asp Val Cys Tyr Val
                20

<210> SEQ ID NO 426
<211> LENGTH: 21
<212> TYPE: PRT
<213> ORGANISM: Artificial Sequence
<220> FEATURE:
<223> OTHER INFORMATION: sequence is synthesized

<400> SEQUENCE: 426

Val Gln Cys Pro His Ile Cys Tyr Glu Leu Asp Glu Glu Val Cys
 1               5                  10                  15

Pro Asp Val Cys Tyr Val
                20
```

```
<210> SEQ ID NO 427
<211> LENGTH: 21
<212> TYPE: PRT
<213> ORGANISM: Artificial Sequence
<220> FEATURE:
<223> OTHER INFORMATION: sequence is synthesized

<400> SEQUENCE: 427

Val Gln Cys Pro His Phe Cys Tyr Glu Leu Asp Asp Glu Pro Cys
 1               5                  10                  15

Pro Asp Val Cys Tyr Val
            20

<210> SEQ ID NO 428
<211> LENGTH: 21
<212> TYPE: PRT
<213> ORGANISM: Artificial Sequence
<220> FEATURE:
<223> OTHER INFORMATION: sequence is synthesized

<400> SEQUENCE: 428

Val Gln Cys Pro His Phe Cys Tyr Glu Leu Asp Gly Glu Gln Cys
 1               5                  10                  15

Pro Asp Val Cys Tyr Val
            20

<210> SEQ ID NO 429
<211> LENGTH: 21
<212> TYPE: PRT
<213> ORGANISM: Artificial Sequence
<220> FEATURE:
<223> OTHER INFORMATION: sequence is synthesized

<400> SEQUENCE: 429

Val Gln Cys Pro His Phe Cys Tyr Glu Leu Asp Leu Glu Leu Cys
 1               5                  10                  15

Pro Asp Val Cys Tyr Val
            20

<210> SEQ ID NO 430
<211> LENGTH: 21
<212> TYPE: PRT
<213> ORGANISM: Artificial Sequence
<220> FEATURE:
<223> OTHER INFORMATION: sequence is synthesized

<400> SEQUENCE: 430

Val Gln Cys Pro His Phe Cys Tyr Glu Leu Asp Arg Glu Pro Cys
 1               5                  10                  15

Pro Asp Val Cys Tyr Val
            20

<210> SEQ ID NO 431
<211> LENGTH: 21
<212> TYPE: PRT
<213> ORGANISM: Artificial Sequence
<220> FEATURE:
<223> OTHER INFORMATION: sequence is synthesized

<400> SEQUENCE: 431

Val Gln Cys Pro His Phe Cys Tyr Glu Leu Asp Ser Glu Met Cys
 1               5                  10                  15

Pro Asp Val Cys Tyr Val
            20
```

```
<210> SEQ ID NO 432
<211> LENGTH: 21
<212> TYPE: PRT
<213> ORGANISM: Artificial Sequence
<220> FEATURE:
<223> OTHER INFORMATION: sequence is synthesized

<400> SEQUENCE: 432

Val Gln Cys Pro His Phe Cys Tyr Glu Leu Asp Ser Glu Val Cys
 1               5                  10                  15

Pro Asp Val Cys Tyr Val
            20

<210> SEQ ID NO 433
<211> LENGTH: 21
<212> TYPE: PRT
<213> ORGANISM: Artificial Sequence
<220> FEATURE:
<223> OTHER INFORMATION: sequence is synthesized

<400> SEQUENCE: 433

Val Gln Cys Pro His Phe Cys Tyr Glu Leu Asp Tyr Glu Leu Cys
 1               5                  10                  15

Pro Asp Val Cys Tyr Val
            20

<210> SEQ ID NO 434
<211> LENGTH: 21
<212> TYPE: PRT
<213> ORGANISM: Artificial Sequence
<220> FEATURE:
<223> OTHER INFORMATION: sequence is synthesized

<400> SEQUENCE: 434

Val Gln Cys Pro His Phe Cys Tyr Ser Gly Gly Tyr Glu Leu Cys
 1               5                  10                  15

Pro Asp Val Cys Tyr Val
            20

<210> SEQ ID NO 435
<211> LENGTH: 21
<212> TYPE: PRT
<213> ORGANISM: Artificial Sequence
<220> FEATURE:
<223> OTHER INFORMATION: sequence is synthesized

<400> SEQUENCE: 435

Val Gln Cys Pro His Phe Cys Tyr Cys Ala Gly Tyr Glu Leu Cys
 1               5                  10                  15

Pro Asp Val Cys Tyr Val
            20

<210> SEQ ID NO 436
<211> LENGTH: 21
<212> TYPE: PRT
<213> ORGANISM: Artificial Sequence
<220> FEATURE:
<223> OTHER INFORMATION: sequence is synthesized

<400> SEQUENCE: 436

Val Gln Cys Pro His Phe Cys Tyr Cys Phe Gln Tyr Glu Leu Cys
 1               5                  10                  15

Pro Asp Val Cys Tyr Val
```

<210> SEQ ID NO 437
<211> LENGTH: 21
<212> TYPE: PRT
<213> ORGANISM: Artificial Sequence
<220> FEATURE:
<223> OTHER INFORMATION: sequence is synthesized

<400> SEQUENCE: 437

Val Gln Cys Pro His Phe Cys Tyr Cys Gly Asp Tyr Glu Leu Cys
 1               5                  10                  15

Pro Asp Val Cys Tyr Val
            20

<210> SEQ ID NO 438
<211> LENGTH: 21
<212> TYPE: PRT
<213> ORGANISM: Artificial Sequence
<220> FEATURE:
<223> OTHER INFORMATION: sequence is synthesized

<400> SEQUENCE: 438

Val Gln Cys Pro His Phe Cys Tyr Cys Pro Gly Tyr Glu Leu Cys
 1               5                  10                  15

Pro Asp Val Cys Tyr Val
            20

<210> SEQ ID NO 439
<211> LENGTH: 21
<212> TYPE: PRT
<213> ORGANISM: Artificial Sequence
<220> FEATURE:
<223> OTHER INFORMATION: sequence is synthesized

<400> SEQUENCE: 439

Val Gln Cys Pro His Phe Cys Tyr Phe Gly Asp Tyr Glu Leu Cys
 1               5                  10                  15

Pro Asp Val Cys Tyr Val
            20

<210> SEQ ID NO 440
<211> LENGTH: 21
<212> TYPE: PRT
<213> ORGANISM: Artificial Sequence
<220> FEATURE:
<223> OTHER INFORMATION: sequence is synthesized

<400> SEQUENCE: 440

Val Gln Cys Pro His Phe Cys Tyr Phe Gln Gln Tyr Glu Leu Cys
 1               5                  10                  15

Pro Asp Val Cys Tyr Val
            20

<210> SEQ ID NO 441
<211> LENGTH: 21
<212> TYPE: PRT
<213> ORGANISM: Sequence Listing

<400> SEQUENCE: 441

Val Gln Cys Pro His Phe Cys Tyr Gly Trp Thr Tyr Glu Leu Cys
 1               5                  10                  15

Pro Asp Val Cys Tyr Val
            20

<210> SEQ ID NO 442
<211> LENGTH: 21
<212> TYPE: PRT
<213> ORGANISM: Artificial Sequence
<220> FEATURE:
<223> OTHER INFORMATION: sequence is synthesized

<400> SEQUENCE: 442

Val Gln Cys Pro His Phe Cys Tyr Gly Trp Thr Tyr Glu Leu Cys
1               5                   10                  15

Pro Asp Val Cys Tyr Val
            20

<210> SEQ ID NO 443
<211> LENGTH: 21
<212> TYPE: PRT
<213> ORGANISM: Artificial Sequence
<220> FEATURE:
<223> OTHER INFORMATION: sequence is synthesized

<400> SEQUENCE: 443

Val Gln Cys Pro His Phe Cys Tyr Arg Leu Gly Tyr Glu Leu Cys
1               5                   10                  15

Pro Asp Val Cys Tyr Val
            20

<210> SEQ ID NO 444
<211> LENGTH: 21
<212> TYPE: PRT
<213> ORGANISM: Artificial Sequence
<220> FEATURE:
<223> OTHER INFORMATION: sequence is synthesized

<400> SEQUENCE: 444

Val Gln Cys Pro His Phe Cys Tyr Arg Trp Gly Tyr Glu Leu Cys
1               5                   10                  15

Pro Asp Val Cys Tyr Val
            20

<210> SEQ ID NO 445
<211> LENGTH: 21
<212> TYPE: PRT
<213> ORGANISM: Artificial Sequence
<220> FEATURE:
<223> OTHER INFORMATION: sequence is synthesized

<400> SEQUENCE: 445

Val Gln Cys Pro His Phe Cys Tyr Ser Gly Ala Tyr Glu Leu Cys
1               5                   10                  15

Pro Asp Val Cys Tyr Val
            20

<210> SEQ ID NO 446
<211> LENGTH: 21
<212> TYPE: PRT
<213> ORGANISM: Artificial Sequence
<220> FEATURE:
<223> OTHER INFORMATION: sequence is synthesized

<400> SEQUENCE: 446

Val Gln Cys Pro His Phe Cys Tyr Val Gly Cys Tyr Glu Leu Cys
1               5                   10                  15

Pro Asp Val Cys Tyr Val

-continued

<210> SEQ ID NO 447
<211> LENGTH: 21
<212> TYPE: PRT
<213> ORGANISM: Artificial Sequence
<220> FEATURE:
<223> OTHER INFORMATION: sequence is synthesized

<400> SEQUENCE: 447

Val Gln Cys Pro His Phe Cys Tyr Glu Leu Cys Glu Arg Leu Cys
 1               5                  10                  15

Pro Asp Val Cys Tyr Val
            20

<210> SEQ ID NO 448
<211> LENGTH: 21
<212> TYPE: PRT
<213> ORGANISM: Artificial Sequence
<220> FEATURE:
<223> OTHER INFORMATION: sequence is synthesized

<400> SEQUENCE: 448

Val Gln Cys Pro His Phe Cys Tyr Glu Leu Ala Asp Pro Leu Cys
 1               5                  10                  15

Pro Asp Val Cys Tyr Val
            20

<210> SEQ ID NO 449
<211> LENGTH: 21
<212> TYPE: PRT
<213> ORGANISM: Artificial Sequence
<220> FEATURE:
<223> OTHER INFORMATION: sequence is synthesized

<400> SEQUENCE: 449

Val Gln Cys Pro His Phe Cys Tyr Glu Leu Ala Leu Thr Leu Cys
 1               5                  10                  15

Pro Asp Val Cys Tyr Val
            20

<210> SEQ ID NO 450
<211> LENGTH: 21
<212> TYPE: PRT
<213> ORGANISM: Artificial Sequence
<220> FEATURE:
<223> OTHER INFORMATION: sequence is synthesized

<400> SEQUENCE: 450

Val Gln Cys Pro His Phe Cys Tyr Glu Leu Asp Ser Gly Leu Cys
 1               5                  10                  15

Pro Asp Val Cys Tyr Val
            20

<210> SEQ ID NO 451
<211> LENGTH: 21
<212> TYPE: PRT
<213> ORGANISM: Artificial Sequence
<220> FEATURE:
<223> OTHER INFORMATION: sequence is synthesized

<400> SEQUENCE: 451

Val Gln Cys Pro His Phe Cys Tyr Glu Leu Glu Ala Gly Leu Cys
 1               5                  10                  15

-continued

Pro Asp Val Cys Tyr Val
            20

<210> SEQ ID NO 452
<211> LENGTH: 21
<212> TYPE: PRT
<213> ORGANISM: Artificial Sequence
<220> FEATURE:
<223> OTHER INFORMATION: sequence is synthesized

<400> SEQUENCE: 452

Val Gln Cys Pro His Phe Cys Tyr Glu Leu Glu Leu Gln Leu Cys
1               5                   10                  15

Pro Asp Val Cys Tyr Val
            20

<210> SEQ ID NO 453
<211> LENGTH: 21
<212> TYPE: PRT
<213> ORGANISM: Artificial Sequence
<220> FEATURE:
<223> OTHER INFORMATION: sequence is synthesized

<400> SEQUENCE: 453

Val Gln Cys Pro His Phe Cys Tyr Glu Leu Glu Val Lys Leu Cys
1               5                   10                  15

Pro Asp Val Cys Tyr Val
            20

<210> SEQ ID NO 454
<211> LENGTH: 21
<212> TYPE: PRT
<213> ORGANISM: Artificial Sequence
<220> FEATURE:
<223> OTHER INFORMATION: sequence is synthesized

<400> SEQUENCE: 454

Val Gln Cys Pro His Phe Cys Tyr Glu Leu Gly Cys Asn Leu Cys
1               5                   10                  15

Pro Asp Val Cys Tyr Val
            20

<210> SEQ ID NO 455
<211> LENGTH: 21
<212> TYPE: PRT
<213> ORGANISM: Artificial Sequence
<220> FEATURE:
<223> OTHER INFORMATION: sequence is synthesized

<400> SEQUENCE: 455

Val Gln Cys Pro His Phe Cys Tyr Glu Leu Pro Asp Lys Leu Cys
1               5                   10                  15

Pro Asp Val Cys Tyr Val
            20

<210> SEQ ID NO 456
<211> LENGTH: 21
<212> TYPE: PRT
<213> ORGANISM: Artificial Sequence
<220> FEATURE:
<223> OTHER INFORMATION: sequence is synthesized

<400> SEQUENCE: 456

Val Gln Cys Pro His Phe Cys Tyr Glu Leu Pro Glu Gln Leu Cys
1               5                   10                  15

-continued

```
Pro Asp Val Cys Tyr Val
            20

<210> SEQ ID NO 457
<211> LENGTH: 21
<212> TYPE: PRT
<213> ORGANISM: Artificial Sequence
<220> FEATURE:
<223> OTHER INFORMATION: sequence is synthesized

<400> SEQUENCE: 457

Val Gln Cys Pro His Phe Cys Tyr Glu Leu Pro Gly Glu Leu Cys
 1               5                  10                  15

Pro Asp Val Cys Tyr Val
            20

<210> SEQ ID NO 458
<211> LENGTH: 21
<212> TYPE: PRT
<213> ORGANISM: Artificial Sequence
<220> FEATURE:
<223> OTHER INFORMATION: sequence is synthesized

<400> SEQUENCE: 458

Val Gln Cys Pro His Phe Cys Tyr Glu Leu Pro Gln Ala Leu Cys
 1               5                  10                  15

Pro Asp Val Cys Tyr Val
            20

<210> SEQ ID NO 459
<211> LENGTH: 21
<212> TYPE: PRT
<213> ORGANISM: Artificial Sequence
<220> FEATURE:
<223> OTHER INFORMATION: sequence is synthesized

<400> SEQUENCE: 459

Val Gln Cys Pro His Phe Cys Tyr Glu Leu Gln Ala Asn Leu Cys
 1               5                  10                  15

Pro Asp Val Cys Tyr Val
            20

<210> SEQ ID NO 460
<211> LENGTH: 21
<212> TYPE: PRT
<213> ORGANISM: Artificial Sequence
<220> FEATURE:
<223> OTHER INFORMATION: sequence is synthesized

<400> SEQUENCE: 460

Val Gln Cys Pro His Phe Cys Tyr Glu Leu Ser Lys Ser Leu Cys
 1               5                  10                  15

Pro Asp Val Cys Tyr Val
            20

<210> SEQ ID NO 461
<211> LENGTH: 21
<212> TYPE: PRT
<213> ORGANISM: Artificial Sequence
<220> FEATURE:
<223> OTHER INFORMATION: sequence is synthesized

<400> SEQUENCE: 461

Val Gln Cys Pro His Phe Cys Tyr Glu Leu Ser Ser Arg Leu Cys
```

Pro Asp Val Cys Tyr Val
            20

<210> SEQ ID NO 462
<211> LENGTH: 21
<212> TYPE: PRT
<213> ORGANISM: Artificial Sequence
<220> FEATURE:
<223> OTHER INFORMATION: sequence is synthesized

<400> SEQUENCE: 462

Val Gln Cys Pro His Phe Cys Tyr Glu Leu Val Leu Gly Leu Cys
 1               5                  10                  15

Pro Asp Val Cys Tyr Val
            20

<210> SEQ ID NO 463
<211> LENGTH: 21
<212> TYPE: PRT
<213> ORGANISM: Artificial Sequence
<220> FEATURE:
<223> OTHER INFORMATION: sequence is synthesized

<400> SEQUENCE: 463

Val Gln Cys Pro His Phe Cys Tyr Glu Leu Asp Tyr Glu Leu Cys
 1               5                  10                  15

Pro Asp Val Cys Tyr Val
            20

<210> SEQ ID NO 464
<211> LENGTH: 21
<212> TYPE: PRT
<213> ORGANISM: Artificial Sequence
<220> FEATURE:
<223> OTHER INFORMATION: sequence is synthesized

<400> SEQUENCE: 464

Val Gln Cys Pro His Phe Cys Tyr Glu Leu Asp Tyr Glu Leu Cys
 1               5                  10                  15

Pro Asp Val Cys Asp Val
            20

<210> SEQ ID NO 465
<211> LENGTH: 21
<212> TYPE: PRT
<213> ORGANISM: Artificial Sequence
<220> FEATURE:
<223> OTHER INFORMATION: sequence is synthesized

<400> SEQUENCE: 465

Val Gln Cys Pro His Phe Cys Tyr Glu Leu Asp Tyr Glu Leu Cys
 1               5                  10                  15

Pro Asp Val Cys His Val
            20

<210> SEQ ID NO 466
<211> LENGTH: 21
<212> TYPE: PRT
<213> ORGANISM: Artificial Sequence
<220> FEATURE:
<223> OTHER INFORMATION: sequence is synthesized

<400> SEQUENCE: 466

Val Gln Cys Pro His Phe Cys Tyr Glu Leu Asp Tyr Glu Leu Cys
 1               5                  10                  15

Pro Asp Val Cys Asp Val
            20

<210> SEQ ID NO 467
<211> LENGTH: 21
<212> TYPE: PRT
<213> ORGANISM: Artificial Sequence
<220> FEATURE:
<223> OTHER INFORMATION: sequence is synthesized

<400> SEQUENCE: 467

Val Gln Cys Pro His Phe Cys Ala Glu Leu Asp Tyr Glu Leu Cys
 1               5                  10                  15

Pro Asp Val Cys Ala Val
            20

<210> SEQ ID NO 468
<211> LENGTH: 21
<212> TYPE: PRT
<213> ORGANISM: Artificial Sequence
<220> FEATURE:
<223> OTHER INFORMATION: sequence is synthesized

<400> SEQUENCE: 468

Val Gln Cys Pro His Phe Cys Tyr Glu Leu Asp Tyr Glu Leu Cys
 1               5                  10                  15

Pro Asp Val Cys Gly Val
            20

<210> SEQ ID NO 469
<211> LENGTH: 21
<212> TYPE: PRT
<213> ORGANISM: Artificial Sequence
<220> FEATURE:
<223> OTHER INFORMATION: sequence is synthesized

<400> SEQUENCE: 469

Val Gln Cys Pro His Phe Cys Tyr Glu Leu Asp Tyr Glu Leu Cys
 1               5                  10                  15

Pro Asp Val Cys Ser Val
            20

<210> SEQ ID NO 470
<211> LENGTH: 21
<212> TYPE: PRT
<213> ORGANISM: Artificial Sequence
<220> FEATURE:
<223> OTHER INFORMATION: sequence is synthesized

<400> SEQUENCE: 470

Ile Leu Cys Pro Leu Phe Cys Tyr Glu Leu Asp Tyr Glu Leu Cys
 1               5                  10                  15

Pro Asp Val Cys Tyr Val
            20

<210> SEQ ID NO 471
<211> LENGTH: 21
<212> TYPE: PRT
<213> ORGANISM: Artificial Sequence
<220> FEATURE:
<223> OTHER INFORMATION: sequence is synthesized

<400> SEQUENCE: 471

Gln Ala Cys Pro Leu Phe Cys Tyr Glu Leu Asp Tyr Glu Leu Cys
 1               5                  10                  15

Pro Asp Val Cys Tyr Val
            20

<210> SEQ ID NO 472
<211> LENGTH: 21
<212> TYPE: PRT
<213> ORGANISM: Artificial Sequence
<220> FEATURE:
<223> OTHER INFORMATION: sequence is synthesized

<400> SEQUENCE: 472

Ala Gly Cys Pro Leu Phe Cys Tyr Glu Leu Asp Tyr Glu Leu Cys
 1               5                  10                  15

Pro Asp Val Cys Tyr Val
            20

<210> SEQ ID NO 473
<211> LENGTH: 21
<212> TYPE: PRT
<213> ORGANISM: Artificial Sequence
<220> FEATURE:
<223> OTHER INFORMATION: sequence is synthesized

<400> SEQUENCE: 473

Thr Arg Cys Pro Leu Phe Cys Tyr Glu Leu Asp Tyr Glu Leu Cys
 1               5                  10                  15

Pro Asp Val Cys Tyr Val
            20

<210> SEQ ID NO 474
<211> LENGTH: 21
<212> TYPE: PRT
<213> ORGANISM: Artificial Sequence
<220> FEATURE:
<223> OTHER INFORMATION: sequence is synthesized

<400> SEQUENCE: 474

Ile Leu Cys Pro Cys Phe Cys Tyr Glu Leu Asp Tyr Glu Leu Cys
 1               5                  10                  15

Pro Asp Val Cys Tyr Val
            20

<210> SEQ ID NO 475
<211> LENGTH: 21
<212> TYPE: PRT
<213> ORGANISM: Artificial Sequence
<220> FEATURE:
<223> OTHER INFORMATION: sequence is synthesized

<400> SEQUENCE: 475

Lys Ser Cys Pro Cys Phe Cys Tyr Glu Leu Asp Tyr Glu Leu Cys
 1               5                  10                  15

Pro Asp Val Cys Tyr Val
            20

<210> SEQ ID NO 476
<211> LENGTH: 21
<212> TYPE: PRT
<213> ORGANISM: Artificial Sequence
<220> FEATURE:
<223> OTHER INFORMATION: sequence is synthesized -continued

```
<400> SEQUENCE: 476

Leu Asp Cys Pro Cys Phe Cys Tyr Glu Leu Asp Tyr Glu Leu Cys
 1               5                  10                  15

Pro Asp Val Cys Tyr Val
             20

<210> SEQ ID NO 477
<211> LENGTH: 21
<212> TYPE: PRT
<213> ORGANISM: Artificial Sequence
<220> FEATURE:
<223> OTHER INFORMATION: sequence is synthesized

<400> SEQUENCE: 477

Ser Thr Cys Pro Cys Phe Cys Tyr Glu Leu Asp Tyr Glu Leu Cys
 1               5                  10                  15

Pro Asp Val Cys Tyr Val
             20

<210> SEQ ID NO 478
<211> LENGTH: 21
<212> TYPE: PRT
<213> ORGANISM: Artificial Sequence
<220> FEATURE:
<223> OTHER INFORMATION: sequence is synthesized

<400> SEQUENCE: 478

Val Lys Cys Pro Cys Phe Cys Tyr Glu Leu Asp Tyr Glu Leu Cys
 1               5                  10                  15

Pro Asp Val Cys Tyr Val
             20

<210> SEQ ID NO 479
<211> LENGTH: 21
<212> TYPE: PRT
<213> ORGANISM: Artificial Sequence
<220> FEATURE:
<223> OTHER INFORMATION: sequence is synthesized

<400> SEQUENCE: 479

Tyr Thr Cys Pro Cys Phe Cys Tyr Glu Leu Asp Tyr Glu Leu Cys
 1               5                  10                  15

Pro Asp Val Cys Tyr Val
             20

<210> SEQ ID NO 480
<211> LENGTH: 21
<212> TYPE: PRT
<213> ORGANISM: Artificial Sequence
<220> FEATURE:
<223> OTHER INFORMATION: sequence is synthesized

<400> SEQUENCE: 480

Ala Leu Cys Pro Leu Phe Cys Tyr Glu Leu Asp Tyr Glu Leu Cys
 1               5                  10                  15

Pro Asp Val Cys Tyr Val
             20

<210> SEQ ID NO 481
<211> LENGTH: 21
<212> TYPE: PRT
<213> ORGANISM: Artificial Sequence
<220> FEATURE:
<223> OTHER INFORMATION: sequence is synthesized
```

```
<400> SEQUENCE: 481

Lys Glu Cys Pro Leu Phe Cys Tyr Glu Leu Asp Tyr Glu Leu Cys
 1               5                  10                  15

Pro Asp Val Cys Tyr Val
                20

<210> SEQ ID NO 482
<211> LENGTH: 21
<212> TYPE: PRT
<213> ORGANISM: Artificial Sequence
<220> FEATURE:
<223> OTHER INFORMATION: sequence is synthesized

<400> SEQUENCE: 482

Leu Pro Cys Pro Leu Phe Cys Tyr Glu Leu Asp Tyr Glu Leu Cys
 1               5                  10                  15

Pro Asp Val Cys Tyr Val
                20

<210> SEQ ID NO 483
<211> LENGTH: 21
<212> TYPE: PRT
<213> ORGANISM: Artificial Sequence
<220> FEATURE:
<223> OTHER INFORMATION: sequence is synthesized

<400> SEQUENCE: 483

Ser Ala Cys Pro Ser Phe Cys Tyr Glu Leu Asp Tyr Glu Leu Cys
 1               5                  10                  15

Pro Asp Val Cys Tyr Val
                20

<210> SEQ ID NO 484
<211> LENGTH: 21
<212> TYPE: PRT
<213> ORGANISM: Artificial Sequence
<220> FEATURE:
<223> OTHER INFORMATION: sequence is synthesized

<400> SEQUENCE: 484

Ile Leu Cys Pro Val Phe Cys Tyr Glu Leu Asp Tyr Glu Leu Cys
 1               5                  10                  15

Pro Asp Val Cys Tyr Val
                20

<210> SEQ ID NO 485
<211> LENGTH: 21
<212> TYPE: PRT
<213> ORGANISM: Artificial Sequence
<220> FEATURE:
<223> OTHER INFORMATION: sequence is synthesized

<400> SEQUENCE: 485

Val Gln Cys Pro His Phe Cys Tyr Glu Leu Asp Leu Glu Leu Cys
 1               5                  10                  15

Pro Asp Val Cys Tyr Val
                20

<210> SEQ ID NO 486
<211> LENGTH: 21
<212> TYPE: PRT
<213> ORGANISM: Artificial Sequence
<220> FEATURE:
```

```
<223> OTHER INFORMATION: sequence is synthesized

<400> SEQUENCE: 486

Val Gln Cys Pro His Phe Cys Tyr Glu Leu Asp Asp Glu Ile Cys
 1               5                  10                  15

Pro Asp Val Cys Tyr Val
            20

<210> SEQ ID NO 487
<211> LENGTH: 21
<212> TYPE: PRT
<213> ORGANISM: Artificial Sequence
<220> FEATURE:
<223> OTHER INFORMATION: sequence is synthesized

<400> SEQUENCE: 487

Val Gln Cys Pro His Phe Cys Tyr Glu Leu Asp Asp Glu Val Cys
 1               5                  10                  15

Pro Asp Val Cys Tyr Val
            20

<210> SEQ ID NO 488
<211> LENGTH: 21
<212> TYPE: PRT
<213> ORGANISM: Artificial Sequence
<220> FEATURE:
<223> OTHER INFORMATION: sequence is synthesized

<400> SEQUENCE: 488

Val Gln Cys Pro His Phe Cys Tyr Glu Leu Asp Glu Glu Glu Cys
 1               5                  10                  15

Pro Asp Val Cys Tyr Val
            20

<210> SEQ ID NO 489
<211> LENGTH: 21
<212> TYPE: PRT
<213> ORGANISM: Artificial Sequence
<220> FEATURE:
<223> OTHER INFORMATION: sequence is synthesized

<400> SEQUENCE: 489

Val Gln Cys Pro His Phe Cys Tyr Glu Leu Asp Gly Glu Ile Cys
 1               5                  10                  15

Pro Asp Val Cys Tyr Val
            20

<210> SEQ ID NO 490
<211> LENGTH: 21
<212> TYPE: PRT
<213> ORGANISM: Artificial Sequence
<220> FEATURE:
<223> OTHER INFORMATION: sequence is synthesized

<400> SEQUENCE: 490

Val Gln Cys Pro His Phe Cys Tyr Glu Leu Asp Gly Glu Leu Cys
 1               5                  10                  15

Pro Asp Val Cys Tyr Val
            20

<210> SEQ ID NO 491
<211> LENGTH: 21
<212> TYPE: PRT
<213> ORGANISM: Artificial Sequence
```

<220> FEATURE:
<223> OTHER INFORMATION: sequence is synthesized

<400> SEQUENCE: 491

Val Gln Cys Pro His Phe Cys Tyr Glu Leu Asp Gly Glu Pro Cys
1               5                   10                  15

Pro Asp Val Cys Tyr Val
            20

<210> SEQ ID NO 492
<211> LENGTH: 21
<212> TYPE: PRT
<213> ORGANISM: Artificial Sequence
<220> FEATURE:
<223> OTHER INFORMATION: sequence is synthesized

<400> SEQUENCE: 492

Val Gln Cys Pro His Phe Cys Tyr Glu Leu Asp Gln Glu Val Cys
1               5                   10                  15

Pro Asp Val Cys Tyr Val
            20

<210> SEQ ID NO 493
<211> LENGTH: 21
<212> TYPE: PRT
<213> ORGANISM: Artificial Sequence
<220> FEATURE:
<223> OTHER INFORMATION: sequence is synthesized

<400> SEQUENCE: 493

Val Gln Cys Pro His Phe Cys Tyr Glu Leu Asp Arg Glu Ile Cys
1               5                   10                  15

Pro Asp Val Cys Tyr Val
            20

<210> SEQ ID NO 494
<211> LENGTH: 21
<212> TYPE: PRT
<213> ORGANISM: Artificial Sequence
<220> FEATURE:
<223> OTHER INFORMATION: sequence is synthesized

<400> SEQUENCE: 494

Val Gln Cys Pro His Phe Cys Tyr Glu Leu Asp Arg Glu Leu Cys
1               5                   10                  15

Pro Asp Val Cys Tyr Val
            20

<210> SEQ ID NO 495
<211> LENGTH: 21
<212> TYPE: PRT
<213> ORGANISM: Artificial Sequence
<220> FEATURE:
<223> OTHER INFORMATION: sequence is synthesized

<400> SEQUENCE: 495

Val Gln Cys Pro His Phe Cys Tyr Glu Leu Asp Arg Glu Met Cys
1               5                   10                  15

Pro Asp Val Cys Tyr Val
            20

<210> SEQ ID NO 496
<211> LENGTH: 21
<212> TYPE: PRT

```
<213> ORGANISM: Artificial Sequence
<220> FEATURE:
<223> OTHER INFORMATION: sequence is synthesized

<400> SEQUENCE: 496

Val Gln Cys Pro His Ile Cys Tyr Glu Leu Asp Glu Glu Val Cys
 1               5                  10                  15

Pro Asp Val Cys Tyr Val
                20

<210> SEQ ID NO 497
<211> LENGTH: 21
<212> TYPE: PRT
<213> ORGANISM: Artificial Sequence
<220> FEATURE:
<223> OTHER INFORMATION: sequence is synthesized

<400> SEQUENCE: 497

Val Gln Cys Pro His Leu Cys Tyr Glu Leu Asp Arg Glu Leu Cys
 1               5                  10                  15

Pro Asp Val Cys Tyr Val
                20

<210> SEQ ID NO 498
<211> LENGTH: 21
<212> TYPE: PRT
<213> ORGANISM: Artificial Sequence
<220> FEATURE:
<223> OTHER INFORMATION: sequence is synthesized

<400> SEQUENCE: 498

Val Gln Cys Pro His Met Cys Tyr Glu Leu Asp Asp Glu Pro Cys
 1               5                  10                  15

Pro Asp Val Cys Tyr Val
                20

<210> SEQ ID NO 499
<211> LENGTH: 21
<212> TYPE: PRT
<213> ORGANISM: Artificial Sequence
<220> FEATURE:
<223> OTHER INFORMATION: sequence is synthesized

<400> SEQUENCE: 499

Val Gln Cys Pro His Phe Cys Tyr Ser Gly Gly Tyr Glu Leu Cys
 1               5                  10                  15

Pro Asp Val Cys Tyr Val
                20

<210> SEQ ID NO 500
<211> LENGTH: 21
<212> TYPE: PRT
<213> ORGANISM: Artificial Sequence
<220> FEATURE:
<223> OTHER INFORMATION: sequence is synthesized

<400> SEQUENCE: 500

Val Gln Cys Pro His Phe Cys Tyr Cys Gly Val Tyr Glu Leu Cys
 1               5                  10                  15

Pro Asp Val Cys Tyr Val
                20

<210> SEQ ID NO 501
<211> LENGTH: 21
```

<212> TYPE: PRT
<213> ORGANISM: Artificial Sequence
<220> FEATURE:
<223> OTHER INFORMATION: sequence is synthesized

<400> SEQUENCE: 501

Val Gln Cys Pro His Phe Cys Tyr Ala Gly Cys Tyr Glu Leu Cys
 1               5                  10                  15

Pro Asp Val Cys Tyr Val
            20

<210> SEQ ID NO 502
<211> LENGTH: 21
<212> TYPE: PRT
<213> ORGANISM: Artificial Sequence
<220> FEATURE:
<223> OTHER INFORMATION: sequence is synthesized

<400> SEQUENCE: 502

Val Gln Cys Pro His Phe Cys Tyr Ala Leu Pro Tyr Glu Leu Cys
 1               5                  10                  15

Pro Asp Val Cys Tyr Val
            20

<210> SEQ ID NO 503
<211> LENGTH: 21
<212> TYPE: PRT
<213> ORGANISM: Artificial Sequence
<220> FEATURE:
<223> OTHER INFORMATION: sequence is synthesized

<400> SEQUENCE: 503

Val Gln Cys Pro His Phe Cys Tyr Cys Gly Asp Tyr Glu Leu Cys
 1               5                  10                  15

Pro Asp Val Cys Tyr Val
            20

<210> SEQ ID NO 504
<211> LENGTH: 21
<212> TYPE: PRT
<213> ORGANISM: Artificial Sequence
<220> FEATURE:
<223> OTHER INFORMATION: sequence is synthesized

<400> SEQUENCE: 504

Val Gln Cys Pro His Phe Cys Tyr Cys Gly Glu Tyr Glu Leu Cys
 1               5                  10                  15

Pro Asp Val Cys Tyr Val
            20

<210> SEQ ID NO 505
<211> LENGTH: 21
<212> TYPE: PRT
<213> ORGANISM: Artificial Sequence
<220> FEATURE:
<223> OTHER INFORMATION: sequence is synthesized

<400> SEQUENCE: 505

Val Gln Cys Pro His Phe Cys Tyr Cys Ser Ala Tyr Glu Leu Cys
 1               5                  10                  15

Pro Asp Val Cys Tyr Val
            20

<210> SEQ ID NO 506

```
<211> LENGTH: 21
<212> TYPE: PRT
<213> ORGANISM: Artificial Sequence
<220> FEATURE:
<223> OTHER INFORMATION: sequence is synthesized

<400> SEQUENCE: 506

Val Gln Cys Pro His Phe Cys Tyr Phe Leu Thr Tyr Glu Leu Cys
 1               5                  10                  15

Pro Asp Val Cys Tyr Val
            20

<210> SEQ ID NO 507
<211> LENGTH: 21
<212> TYPE: PRT
<213> ORGANISM: Artificial Sequence
<220> FEATURE:
<223> OTHER INFORMATION: sequence is synthesized

<400> SEQUENCE: 507

Val Gln Cys Pro His Phe Cys Tyr Gly Thr Ser Tyr Glu Leu Cys
 1               5                  10                  15

Pro Asp Val Cys Tyr Val
            20

<210> SEQ ID NO 508
<211> LENGTH: 21
<212> TYPE: PRT
<213> ORGANISM: Artificial Sequence
<220> FEATURE:
<223> OTHER INFORMATION: sequence is synthesized

<400> SEQUENCE: 508

Val Gln Cys Pro His Phe Cys Tyr Glu Leu Gly Val Val Leu Cys
 1               5                  10                  15

Pro Asp Val Cys Tyr Val
            20

<210> SEQ ID NO 509
<211> LENGTH: 21
<212> TYPE: PRT
<213> ORGANISM: Artificial Sequence
<220> FEATURE:
<223> OTHER INFORMATION: sequence is synthesized

<400> SEQUENCE: 509

Val Gln Cys Pro His Phe Cys Tyr Glu Leu Gly Cys His Leu Cys
 1               5                  10                  15

Pro Asp Val Cys Tyr Val
            20

<210> SEQ ID NO 510
<211> LENGTH: 21
<212> TYPE: PRT
<213> ORGANISM: Artificial Sequence
<220> FEATURE:
<223> OTHER INFORMATION: sequence is synthesized

<400> SEQUENCE: 510

Val Gln Cys Pro His Phe Cys Tyr Glu Leu Phe Ser Arg Leu Cys
 1               5                  10                  15

Pro Asp Val Cys Tyr Val
            20
```

```
<210> SEQ ID NO 511
<211> LENGTH: 21
<212> TYPE: PRT
<213> ORGANISM: Artificial Sequence
<220> FEATURE:
<223> OTHER INFORMATION: sequence is synthesized

<400> SEQUENCE: 511

Val Gln Cys Pro His Phe Cys Tyr Glu Leu Phe Ser Arg Leu Cys
 1               5                  10                  15

Pro Asp Val Cys Tyr Val
            20

<210> SEQ ID NO 512
<211> LENGTH: 21
<212> TYPE: PRT
<213> ORGANISM: Artificial Sequence
<220> FEATURE:
<223> OTHER INFORMATION: sequence is synthesized

<400> SEQUENCE: 512

Val Gln Cys Pro His Phe Cys Tyr Glu Leu Gly Asp Gln Leu Cys
 1               5                  10                  15

Pro Asp Val Cys Tyr Val
            20

<210> SEQ ID NO 513
<211> LENGTH: 21
<212> TYPE: PRT
<213> ORGANISM: Artificial Sequence
<220> FEATURE:
<223> OTHER INFORMATION: sequence is synthesized

<400> SEQUENCE: 513

Val Gln Cys Pro His Phe Cys Tyr Glu Leu Gly Val Ala Leu Cys
 1               5                  10                  15

Pro Asp Val Cys Tyr Val
            20

<210> SEQ ID NO 514
<211> LENGTH: 21
<212> TYPE: PRT
<213> ORGANISM: Artificial Sequence
<220> FEATURE:
<223> OTHER INFORMATION: sequence is synthesized

<400> SEQUENCE: 514

Val Gln Cys Pro His Phe Cys Tyr Glu Leu Met Gln Arg Leu Cys
 1               5                  10                  15

Pro Asp Val Cys Tyr Val
            20

<210> SEQ ID NO 515
<211> LENGTH: 21
<212> TYPE: PRT
<213> ORGANISM: Artificial Sequence
<220> FEATURE:
<223> OTHER INFORMATION: sequence is synthesized

<400> SEQUENCE: 515

Val Gln Cys Pro His Phe Cys Tyr Glu Leu Asn Glu Asp Leu Cys
 1               5                  10                  15

Pro Asp Val Cys Tyr Val
            20
```

```
<210> SEQ ID NO 516
<211> LENGTH: 21
<212> TYPE: PRT
<213> ORGANISM: Artificial Sequence
<220> FEATURE:
<223> OTHER INFORMATION: sequence is synthesized

<400> SEQUENCE: 516

Val Gln Cys Pro His Phe Cys Tyr Glu Leu Pro Thr Val Leu Cys
 1               5                  10                  15

Pro Asp Val Cys Tyr Val
            20

<210> SEQ ID NO 517
<211> LENGTH: 21
<212> TYPE: PRT
<213> ORGANISM: Artificial Sequence
<220> FEATURE:
<223> OTHER INFORMATION: sequence is synthesized

<400> SEQUENCE: 517

Val Gln Cys Pro His Phe Cys Tyr Glu Leu Asp Tyr Glu Leu Cys
 1               5                  10                  15

Pro Asp Val Cys Asp Val
            20

<210> SEQ ID NO 518
<211> LENGTH: 21
<212> TYPE: PRT
<213> ORGANISM: Artificial Sequence
<220> FEATURE:
<223> OTHER INFORMATION: sequence is synthesized

<400> SEQUENCE: 518

Val Gln Cys Pro His Phe Cys Tyr Glu Leu Asp Tyr Glu Leu Cys
 1               5                  10                  15

Pro Asp Val Cys Tyr Val
            20

<210> SEQ ID NO 519
<211> LENGTH: 21
<212> TYPE: PRT
<213> ORGANISM: Artificial Sequence
<220> FEATURE:
<223> OTHER INFORMATION: sequence is synthesized

<400> SEQUENCE: 519

Val Gln Cys Pro His Phe Cys Tyr Glu Leu Asp Tyr Glu Leu Cys
 1               5                  10                  15

Pro Asp Lys Cys Tyr Val
            20

<210> SEQ ID NO 520
<211> LENGTH: 21
<212> TYPE: PRT
<213> ORGANISM: Artificial Sequence
<220> FEATURE:
<223> OTHER INFORMATION: sequence is synthesized

<400> SEQUENCE: 520

Val Gln Cys Pro His Phe Cys Tyr Glu Leu Asp Tyr Glu Leu Cys
 1               5                  10                  15

Pro Asp Ala Cys Tyr Val
            20
```

```
<210> SEQ ID NO 521
<211> LENGTH: 21
<212> TYPE: PRT
<213> ORGANISM: Artificial Sequence
<220> FEATURE:
<223> OTHER INFORMATION: sequence is synthesized

<400> SEQUENCE: 521

Val Gln Cys Pro His Phe Cys Tyr Glu Leu Asp Tyr Glu Leu Cys
  1               5                  10                  15

Pro Asp Ala Cys Tyr Val
            20

<210> SEQ ID NO 522
<211> LENGTH: 21
<212> TYPE: PRT
<213> ORGANISM: Artificial Sequence
<220> FEATURE:
<223> OTHER INFORMATION: sequence is synthesized

<400> SEQUENCE: 522

Val Gln Cys Pro His Phe Cys Tyr Glu Leu Asp Tyr Glu Leu Cys
  1               5                  10                  15

Pro Asp Pro Cys Tyr Val
            20

<210> SEQ ID NO 523
<211> LENGTH: 21
<212> TYPE: PRT
<213> ORGANISM: Artificial Sequence
<220> FEATURE:
<223> OTHER INFORMATION: sequence is synthesized

<400> SEQUENCE: 523

Val Gln Cys Pro His Phe Cys Tyr Glu Leu Asp Tyr Glu Leu Cys
  1               5                  10                  15

Pro Asp Arg Cys Tyr Val
            20

<210> SEQ ID NO 524
<211> LENGTH: 21
<212> TYPE: PRT
<213> ORGANISM: Artificial Sequence
<220> FEATURE:
<223> OTHER INFORMATION: sequence is synthesized

<400> SEQUENCE: 524

Val Gln Cys Pro His Phe Cys Tyr Glu Leu Asp Tyr Glu Leu Cys
  1               5                  10                  15

Glu Asp Arg Cys Tyr Val
            20

<210> SEQ ID NO 525
<211> LENGTH: 21
<212> TYPE: PRT
<213> ORGANISM: Artificial Sequence
<220> FEATURE:
<223> OTHER INFORMATION: sequence is synthesized

<400> SEQUENCE: 525

Val Gln Cys Pro His Phe Cys Tyr Glu Leu Asp Tyr Glu Leu Cys
  1               5                  10                  15

Pro Asp Ser Cys Tyr Val
```

```
                    20

<210> SEQ ID NO 526
<211> LENGTH: 21
<212> TYPE: PRT
<213> ORGANISM: Artificial Sequence
<220> FEATURE:
<223> OTHER INFORMATION: sequence is synthesized

<400> SEQUENCE: 526

Val Gln Cys Pro His Phe Cys Tyr Glu Leu Asp Tyr Glu Leu Cys
 1               5                  10                  15

Pro Gly Val Cys Tyr Val
            20

<210> SEQ ID NO 527
<211> LENGTH: 21
<212> TYPE: PRT
<213> ORGANISM: Artificial Sequence
<220> FEATURE:
<223> OTHER INFORMATION: sequence is synthesized

<400> SEQUENCE: 527

Val Gln Cys Pro His Phe Cys Tyr Glu Leu Asp Tyr Glu Leu Cys
 1               5                  10                  15

Pro Arg Val Cys Tyr Val
            20

<210> SEQ ID NO 528
<211> LENGTH: 21
<212> TYPE: PRT
<213> ORGANISM: Artificial Sequence
<220> FEATURE:
<223> OTHER INFORMATION: sequence is synthesized

<400> SEQUENCE: 528

Val Gln Cys Pro His Phe Cys Tyr Glu Leu Asp Tyr Glu Leu Cys
 1               5                  10                  15

Pro Ala Val Cys Tyr Val
            20

<210> SEQ ID NO 529
<211> LENGTH: 21
<212> TYPE: PRT
<213> ORGANISM: Artificial Sequence
<220> FEATURE:
<223> OTHER INFORMATION: sequence is synthesized

<400> SEQUENCE: 529

Val Gln Cys Pro His Phe Cys Tyr Glu Leu Asp Tyr Glu Leu Cys
 1               5                  10                  15

Pro Trp Val Cys Tyr Val
            20

<210> SEQ ID NO 530
<211> LENGTH: 21
<212> TYPE: PRT
<213> ORGANISM: Artificial Sequence
<220> FEATURE:
<223> OTHER INFORMATION: sequence is synthesized

<400> SEQUENCE: 530

Val Gln Cys Pro His Phe Cys Tyr Glu Leu Asp Tyr Glu Leu Cys
 1               5                  10                  15
```

Pro Asp Val Cys Tyr Gly
            20

<210> SEQ ID NO 531
<211> LENGTH: 21
<212> TYPE: PRT
<213> ORGANISM: Artificial Sequence
<220> FEATURE:
<223> OTHER INFORMATION: sequence is synthesized

<400> SEQUENCE: 531

Val Gln Cys Pro His Phe Cys Tyr Glu Leu Asp Tyr Glu Leu Cys
 1               5                  10                  15

Pro Asp Lys Cys Tyr Ala
            20

<210> SEQ ID NO 532
<211> LENGTH: 21
<212> TYPE: PRT
<213> ORGANISM: Artificial Sequence
<220> FEATURE:
<223> OTHER INFORMATION: sequence is synthesized

<400> SEQUENCE: 532

Val Gln Cys Pro His Phe Cys Tyr Glu Leu Asp Tyr Glu Leu Cys
 1               5                  10                  15

Pro Asp Leu Cys Tyr Gly
            20

<210> SEQ ID NO 533
<211> LENGTH: 21
<212> TYPE: PRT
<213> ORGANISM: Artificial Sequence
<220> FEATURE:
<223> OTHER INFORMATION: sequence is synthesized

<400> SEQUENCE: 533

Val Gln Cys Pro His Phe Cys Tyr Glu Leu Asp Tyr Glu Leu Cys
 1               5                  10                  15

Pro Asp Met Cys Tyr Thr
            20

<210> SEQ ID NO 534
<211> LENGTH: 21
<212> TYPE: PRT
<213> ORGANISM: Artificial Sequence
<220> FEATURE:
<223> OTHER INFORMATION: sequence is synthesized

<400> SEQUENCE: 534

Val Gln Cys Pro His Phe Cys Tyr Glu Leu Asp Tyr Glu Leu Cys
 1               5                  10                  15

Pro Asp Arg Cys Tyr Ser
            20

<210> SEQ ID NO 535
<211> LENGTH: 21
<212> TYPE: PRT
<213> ORGANISM: Artificial Sequence
<220> FEATURE:
<223> OTHER INFORMATION: sequence is synthesized

<400> SEQUENCE: 535

Val Gln Cys Pro His Phe Cys Tyr Glu Leu Asp Tyr Glu Leu Cys
 1               5                  10                  15

Pro Asp Ser Cys Tyr Gly
            20

<210> SEQ ID NO 536
<211> LENGTH: 21
<212> TYPE: PRT
<213> ORGANISM: Artificial Sequence
<220> FEATURE:
<223> OTHER INFORMATION: sequence is synthesized

<400> SEQUENCE: 536

Val Gln Cys Pro His Phe Cys Tyr Glu Leu Asp Tyr Glu Leu Cys
 1               5                  10                  15

Pro Asp Thr Cys Tyr Gly
            20

<210> SEQ ID NO 537
<211> LENGTH: 21
<212> TYPE: PRT
<213> ORGANISM: Artificial Sequence
<220> FEATURE:
<223> OTHER INFORMATION: sequence is synthesized

<400> SEQUENCE: 537

Val Gln Cys Pro His Phe Cys Tyr Glu Leu Asp Tyr Glu Leu Cys
 1               5                  10                  15

Pro Asp Val Cys Tyr Cys
            20

<210> SEQ ID NO 538
<211> LENGTH: 21
<212> TYPE: PRT
<213> ORGANISM: Artificial Sequence
<220> FEATURE:
<223> OTHER INFORMATION: sequence is synthesized

<400> SEQUENCE: 538

Val Gln Cys Pro His Phe Cys Tyr Glu Leu Asp Tyr Glu Leu Cys
 1               5                  10                  15

Pro Asp Val Cys Tyr Leu
            20

<210> SEQ ID NO 539
<211> LENGTH: 21
<212> TYPE: PRT
<213> ORGANISM: Artificial Sequence
<220> FEATURE:
<223> OTHER INFORMATION: sequence is synthesized

<400> SEQUENCE: 539

Val Gln Cys Pro His Phe Cys Tyr Glu Leu Asp Tyr Glu Leu Cys
 1               5                  10                  15

Pro Asp Val Cys Tyr Asn
            20

<210> SEQ ID NO 540
<211> LENGTH: 21
<212> TYPE: PRT
<213> ORGANISM: Artificial Sequence
<220> FEATURE:
<223> OTHER INFORMATION: sequence is synthesized

<400> SEQUENCE: 540

Val Gln Cys Pro His Phe Cys Tyr Glu Leu Asp Tyr Glu Leu Cys

```
                1               5              10              15

Pro Asp Val Cys Tyr Val
                20

<210> SEQ ID NO 541
<211> LENGTH: 24
<212> TYPE: PRT
<213> ORGANISM: Artificial Sequence
<220> FEATURE:
<223> OTHER INFORMATION: sequence is synthesized

<400> SEQUENCE: 541

Val Gln Cys Pro His Phe Cys Tyr Glu Leu Asp Tyr Glu Arg Glu
  1               5              10              15

Thr Leu Cys Pro Asp Val Cys Tyr Val
                20

<210> SEQ ID NO 542
<211> LENGTH: 24
<212> TYPE: PRT
<213> ORGANISM: Artificial Sequence
<220> FEATURE:
<223> OTHER INFORMATION: sequence is synthesized

<400> SEQUENCE: 542

Val Gln Cys Pro His Phe Cys Tyr Glu Leu Asp Tyr Glu Lys Glu
  1               5              10              15

His Leu Cys Pro Asp Val Cys Tyr Val
                20

<210> SEQ ID NO 543
<211> LENGTH: 24
<212> TYPE: PRT
<213> ORGANISM: Artificial Sequence
<220> FEATURE:
<223> OTHER INFORMATION: sequence is synthesized

<400> SEQUENCE: 543

Val Gln Cys Pro His Phe Cys Tyr Glu Leu Asp Tyr Glu Arg Glu
  1               5              10              15

Gly Leu Cys Pro Asp Val Cys Tyr Val
                20

<210> SEQ ID NO 544
<211> LENGTH: 24
<212> TYPE: PRT
<213> ORGANISM: Artificial Sequence
<220> FEATURE:
<223> OTHER INFORMATION: sequence is synthesized

<400> SEQUENCE: 544

Val Gln Cys Pro His Phe Cys Tyr Glu Leu Asp Tyr Glu Ser Glu
  1               5              10              15

Ser Leu Cys Pro Asp Val Cys Tyr Val
                20

<210> SEQ ID NO 545
<211> LENGTH: 24
<212> TYPE: PRT
<213> ORGANISM: Artificial Sequence
<220> FEATURE:
<223> OTHER INFORMATION: sequence is synthesized

<400> SEQUENCE: 545
```

-continued

```
Val Gln Cys Pro His Phe Cys Tyr Glu Leu Asp Tyr Glu Ala Asp
  1               5                  10                  15

Arg Leu Cys Pro Asp Val Cys Tyr Val
                20

<210> SEQ ID NO 546
<211> LENGTH: 24
<212> TYPE: PRT
<213> ORGANISM: Artificial Sequence
<220> FEATURE:
<223> OTHER INFORMATION: sequence is synthesized

<400> SEQUENCE: 546

Val Gln Cys Pro His Phe Cys Tyr Glu Leu Asp Tyr Glu Glu Val
  1               5                  10                  15

Trp Leu Cys Pro Asp Val Cys Tyr Val
                20

<210> SEQ ID NO 547
<211> LENGTH: 24
<212> TYPE: PRT
<213> ORGANISM: Artificial Sequence
<220> FEATURE:
<223> OTHER INFORMATION: sequence is synthesized

<400> SEQUENCE: 547

Val Gln Cys Pro His Phe Cys Tyr Glu Leu Asp Tyr Glu Gly Arg
  1               5                  10                  15

Pro Leu Cys Pro Asp Val Cys Tyr Val
                20

<210> SEQ ID NO 548
<211> LENGTH: 24
<212> TYPE: PRT
<213> ORGANISM: Artificial Sequence
<220> FEATURE:
<223> OTHER INFORMATION: sequence is synthesized

<400> SEQUENCE: 548

Val Gln Cys Pro His Phe Cys Tyr Glu Leu Asp Tyr Glu Leu Thr
  1               5                  10                  15

Gly Leu Cys Pro Asp Val Cys Tyr Val
                20

<210> SEQ ID NO 549
<211> LENGTH: 24
<212> TYPE: PRT
<213> ORGANISM: Artificial Sequence
<220> FEATURE:
<223> OTHER INFORMATION: sequence is synthesized

<400> SEQUENCE: 549

Val Gln Cys Pro His Phe Cys Tyr Glu Leu Asp Tyr Glu Met Leu
  1               5                  10                  15

Gly Leu Cys Pro Asp Val Cys Tyr Val
                20

<210> SEQ ID NO 550
<211> LENGTH: 24
<212> TYPE: PRT
<213> ORGANISM: Artificial Sequence
<220> FEATURE:
<223> OTHER INFORMATION: sequence is synthesized

<400> SEQUENCE: 550
```

```
Val Gln Cys Pro His Phe Cys Tyr Glu Leu Asp Tyr Glu Gly Gly
 1               5                  10                  15

Gly Leu Cys Pro Asp Val Cys Tyr Val
                20
```

<210> SEQ ID NO 551
<211> LENGTH: 26
<212> TYPE: PRT
<213> ORGANISM: Artificial Sequence
<220> FEATURE:
<223> OTHER INFORMATION: sequence is synthesized

<400> SEQUENCE: 551

```
Val Gln Cys Pro His Phe Cys Tyr Glu Leu Asp Tyr Glu Met Asp
 1               5                  10                  15

Gly Gln Leu Leu Cys Pro Asp Val Cys Tyr Val
                20                  25
```

<210> SEQ ID NO 552
<211> LENGTH: 26
<212> TYPE: PRT
<213> ORGANISM: Artificial Sequence
<220> FEATURE:
<223> OTHER INFORMATION: sequence is synthesized

<400> SEQUENCE: 552

```
Val Gln Cys Pro His Phe Cys Tyr Glu Leu Asp Tyr Glu Pro Gly
 1               5                  10                  15

Lys Leu Lys Leu Cys Pro Asp Val Cys Tyr Val
                20                  25
```

<210> SEQ ID NO 553
<211> LENGTH: 26
<212> TYPE: PRT
<213> ORGANISM: Artificial Sequence
<220> FEATURE:
<223> OTHER INFORMATION: sequence is synthesized

<400> SEQUENCE: 553

```
Val Gln Cys Pro His Phe Cys Tyr Glu Leu Asp Tyr Glu Ala Gly
 1               5                  10                  15

Asp Glu Arg Leu Cys Pro Asp Val Cys Tyr Val
                20                  25
```

<210> SEQ ID NO 554
<211> LENGTH: 26
<212> TYPE: PRT
<213> ORGANISM: Artificial Sequence
<220> FEATURE:
<223> OTHER INFORMATION: sequence is synthesized

<400> SEQUENCE: 554

```
Val Gln Cys Pro His Phe Cys Tyr Glu Leu Asp Tyr Glu Pro Asp
 1               5                  10                  15

Ser Val Gly Leu Cys Pro Asp Val Cys Tyr Val
                20                  25
```

<210> SEQ ID NO 555
<211> LENGTH: 26
<212> TYPE: PRT
<213> ORGANISM: Artificial Sequence
<220> FEATURE:
<223> OTHER INFORMATION: sequence is synthesized

```
<400> SEQUENCE: 555

Val Gln Cys Pro His Phe Cys Tyr Glu Leu Asp Tyr Glu Val Glu
  1               5                  10                  15

Asp Ala Pro Leu Cys Pro Asp Val Cys Tyr Val
             20                  25

<210> SEQ ID NO 556
<211> LENGTH: 20
<212> TYPE: PRT
<213> ORGANISM: Artificial Sequence
<220> FEATURE:
<223> OTHER INFORMATION: sequence is synthesized

<400> SEQUENCE: 556

Val Gln Cys Pro His Phe Cys Tyr Gly Ala Leu Glu Leu Cys Pro
  1               5                  10                  15

Asp Val Cys Tyr Val
             20

<210> SEQ ID NO 557
<211> LENGTH: 20
<212> TYPE: PRT
<213> ORGANISM: Artificial Sequence
<220> FEATURE:
<223> OTHER INFORMATION: sequence is synthesized

<400> SEQUENCE: 557

Val Gln Cys Pro His Phe Cys Tyr Val His Met Glu Leu Cys Pro
  1               5                  10                  15

Asp Val Cys Tyr Val
             20

<210> SEQ ID NO 558
<211> LENGTH: 20
<212> TYPE: PRT
<213> ORGANISM: Artificial Sequence
<220> FEATURE:
<223> OTHER INFORMATION: sequence is synthesized

<400> SEQUENCE: 558

Val Gln Cys Pro His Phe Cys Tyr Leu Val Met Glu Leu Cys Pro
  1               5                  10                  15

Asp Val Cys Tyr Val
             20

<210> SEQ ID NO 559
<211> LENGTH: 20
<212> TYPE: PRT
<213> ORGANISM: Artificial Sequence
<220> FEATURE:
<223> OTHER INFORMATION: sequence is synthesized

<400> SEQUENCE: 559

Val Gln Cys Pro His Phe Cys Tyr Leu Glu Cys Gly Leu Cys Pro
  1               5                  10                  15

Asp Val Cys Tyr Val
             20

<210> SEQ ID NO 560
<211> LENGTH: 20
<212> TYPE: PRT
<213> ORGANISM: Artificial Sequence
<220> FEATURE:
<223> OTHER INFORMATION: sequence is synthesized
```

```
<400> SEQUENCE: 560

Val Gln Cys Pro His Phe Cys Tyr Gly Cys Arg Leu Leu Cys Pro
 1               5                  10                  15

Asp Val Cys Tyr Val
                20

<210> SEQ ID NO 561
<211> LENGTH: 20
<212> TYPE: PRT
<213> ORGANISM: Artificial Sequence
<220> FEATURE:
<223> OTHER INFORMATION: sequence is synthesized

<400> SEQUENCE: 561

Val Gln Cys Pro His Phe Cys Tyr Lys Asp Arg Asn Leu Cys Pro
 1               5                  10                  15

Asp Val Cys Tyr Val
                20

<210> SEQ ID NO 562
<211> LENGTH: 20
<212> TYPE: PRT
<213> ORGANISM: Artificial Sequence
<220> FEATURE:
<223> OTHER INFORMATION: sequence is synthesized

<400> SEQUENCE: 562

Val Gln Cys Pro His Phe Cys Tyr Asp Ala Ser Arg Leu Cys Pro
 1               5                  10                  15

Asp Val Cys Tyr Val
                20

<210> SEQ ID NO 563
<211> LENGTH: 19
<212> TYPE: PRT
<213> ORGANISM: Artificial Sequence
<220> FEATURE:
<223> OTHER INFORMATION: sequence is synthesized

<400> SEQUENCE: 563

Val Gln Cys Pro His Phe Cys Tyr Val Glu Glu Leu Cys Pro Asp
 1               5                  10                  15

Val Cys Tyr Val

<210> SEQ ID NO 564
<211> LENGTH: 19
<212> TYPE: PRT
<213> ORGANISM: Artificial Sequence
<220> FEATURE:
<223> OTHER INFORMATION: sequence is synthesized

<400> SEQUENCE: 564

Val Gln Cys Pro His Phe Cys Tyr Met Gly Glu Leu Cys Pro Asp
 1               5                  10                  15

Val Cys Tyr Val

<210> SEQ ID NO 565
<211> LENGTH: 19
<212> TYPE: PRT
<213> ORGANISM: Artificial Sequence
<220> FEATURE:
<223> OTHER INFORMATION: sequence is synthesized
```

-continued

```
<400> SEQUENCE: 565

Val Gln Cys Pro His Phe Cys Tyr Ser Gly Glu Leu Cys Pro Asp
1               5                   10                  15

Val Cys Tyr Val

<210> SEQ ID NO 566
<211> LENGTH: 19
<212> TYPE: PRT
<213> ORGANISM: Artificial Sequence
<220> FEATURE:
<223> OTHER INFORMATION: sequence is synthesized

<400> SEQUENCE: 566

Val Gln Cys Pro His Phe Cys Tyr Phe Ser Glu Leu Cys Pro Asp
1               5                   10                  15

Val Cys Tyr Val

<210> SEQ ID NO 567
<211> LENGTH: 19
<212> TYPE: PRT
<213> ORGANISM: Artificial Sequence
<220> FEATURE:
<223> OTHER INFORMATION: sequence is synthesized

<400> SEQUENCE: 567

Val Gln Cys Pro His Phe Cys Tyr Ala Glu Pro Leu Cys Pro Asp
1               5                   10                  15

Val Cys Tyr Val

<210> SEQ ID NO 568
<211> LENGTH: 19
<212> TYPE: PRT
<213> ORGANISM: Artificial Sequence
<220> FEATURE:
<223> OTHER INFORMATION: sequence is synthesized

<400> SEQUENCE: 568

Val Gln Cys Pro His Phe Cys Tyr Val Arg Pro Leu Cys Pro Asp
1               5                   10                  15

Val Cys Tyr Val

<210> SEQ ID NO 569
<211> LENGTH: 19
<212> TYPE: PRT
<213> ORGANISM: Artificial Sequence
<220> FEATURE:
<223> OTHER INFORMATION: sequence is synthesized

<400> SEQUENCE: 569

Val Gln Cys Pro His Phe Cys Tyr Leu Thr Arg Leu Cys Pro Asp
1               5                   10                  15

Val Cys Tyr Val

<210> SEQ ID NO 570
<211> LENGTH: 21
<212> TYPE: PRT
<213> ORGANISM: Artificial Sequence
<220> FEATURE:
<223> OTHER INFORMATION: sequence is synthesized

<400> SEQUENCE: 570

Val Gln Cys Pro His Phe Cys Tyr Glu Leu Asp Tyr Glu Leu Cys
1               5                   10                  15
```

Pro Asp Val Cys Tyr Val
            20

<210> SEQ ID NO 571
<211> LENGTH: 21
<212> TYPE: PRT
<213> ORGANISM: Artificial Sequence
<220> FEATURE:
<223> OTHER INFORMATION: sequence is synthesized

<400> SEQUENCE: 571

Val Gln Cys Pro His Phe Cys Tyr Glu Glu Asp Glu Glu Leu Cys
 1               5                  10                  15

Pro Asp Val Cys Tyr Val
            20

<210> SEQ ID NO 572
<211> LENGTH: 21
<212> TYPE: PRT
<213> ORGANISM: Artificial Sequence
<220> FEATURE:
<223> OTHER INFORMATION: sequence is synthesized

<400> SEQUENCE: 572

Val Gln Cys Pro His Phe Cys Ala Glu Leu Asp Tyr Glu Leu Cys
 1               5                  10                  15

Pro Asp Val Cys Tyr Val
            20

<210> SEQ ID NO 573
<211> LENGTH: 21
<212> TYPE: PRT
<213> ORGANISM: Artificial Sequence
<220> FEATURE:
<223> OTHER INFORMATION: sequence is synthesized

<400> SEQUENCE: 573

Val Gln Cys Pro His Phe Cys Tyr Glu Leu Asp Tyr Glu Leu Cys
 1               5                  10                  15

Pro Asp Val Cys Ala Val
            20

<210> SEQ ID NO 574
<211> LENGTH: 21
<212> TYPE: PRT
<213> ORGANISM: Artificial Sequence
<220> FEATURE:
<223> OTHER INFORMATION: sequence is synthesized

<400> SEQUENCE: 574

Val Gln Cys Pro His Phe Cys Tyr Glu Leu Asp Tyr Glu Ala Cys
 1               5                  10                  15

Pro Asp Val Cys Tyr Val
            20

<210> SEQ ID NO 575
<211> LENGTH: 21
<212> TYPE: PRT
<213> ORGANISM: Artificial Sequence
<220> FEATURE:
<223> OTHER INFORMATION: sequence is synthesized

<400> SEQUENCE: 575

Val Gln Cys Pro His Phe Cys Tyr Glu Leu Asp Ala Glu Leu Cys

```
                1               5                  10                 15

Pro Asp Val Cys Tyr Val
                20

<210> SEQ ID NO 576
<211> LENGTH: 21
<212> TYPE: PRT
<213> ORGANISM: Artificial Sequence
<220> FEATURE:
<223> OTHER INFORMATION: sequence is synthesized

<400> SEQUENCE: 576

Val Gln Cys Pro His Phe Cys Tyr Glu Ala Asp Tyr Glu Leu Cys
  1               5                  10                 15

Pro Asp Val Cys Tyr Val
                20

<210> SEQ ID NO 577
<211> LENGTH: 21
<212> TYPE: PRT
<213> ORGANISM: Artificial Sequence
<220> FEATURE:
<223> OTHER INFORMATION: sequence is synthesized

<400> SEQUENCE: 577

Val Gln Cys Pro His Phe Cys Tyr Glu Leu Asp Tyr Glu Leu Cys
  1               5                  10                 15

Pro Asp Val Cys Tyr Ala
                20

<210> SEQ ID NO 578
<211> LENGTH: 21
<212> TYPE: PRT
<213> ORGANISM: Artificial Sequence
<220> FEATURE:
<223> OTHER INFORMATION: sequence is synthesized

<400> SEQUENCE: 578

Val Gln Cys Pro His Phe Cys Tyr Glu Leu Asp Tyr Glu Leu Cys
  1               5                  10                 15

Pro Asp Lys Cys Tyr Val
                20

<210> SEQ ID NO 579
<211> LENGTH: 19
<212> TYPE: PRT
<213> ORGANISM: Artificial Sequence
<220> FEATURE:
<223> OTHER INFORMATION: sequence is synthesized

<400> SEQUENCE: 579

Cys Pro His Phe Cys Tyr Glu Leu Asp Tyr Glu Leu Cys Pro Asp
  1               5                  10                 15

Val Cys Tyr Val

<210> SEQ ID NO 580
<211> LENGTH: 21
<212> TYPE: PRT
<213> ORGANISM: Artificial Sequence
<220> FEATURE:
<223> OTHER INFORMATION: sequence is synthesized

<400> SEQUENCE: 580

Val Gln Cys Pro His Phe Cys Tyr Glu Leu Asp Tyr Glu Ala Cys
```

```
Pro Ala Ala Cys Tyr Ala
            20
```

<210> SEQ ID NO 581
<211> LENGTH: 21
<212> TYPE: PRT
<213> ORGANISM: Artificial Sequence
<220> FEATURE:
<223> OTHER INFORMATION: sequence is synthesized

<400> SEQUENCE: 581

```
Ala Ala Cys Pro Ala Ala Cys Tyr Ala Leu Asp Tyr Glu Leu Cys
  1               5                  10                  15
Pro Asp Val Cys Tyr Val
            20
```

<210> SEQ ID NO 582
<211> LENGTH: 21
<212> TYPE: PRT
<213> ORGANISM: Artificial Sequence
<220> FEATURE:
<223> OTHER INFORMATION: sequence is synthesized

<400> SEQUENCE: 582

```
Val Gln Cys Pro His Phe Cys Tyr Glu Leu Asp Tyr Glu Leu Cys
  1               5                  10                  15
Pro Ala Val Cys Tyr Val
            20
```

<210> SEQ ID NO 583
<211> LENGTH: 21
<212> TYPE: PRT
<213> ORGANISM: Artificial Sequence
<220> FEATURE:
<223> OTHER INFORMATION: sequence is synthesized

<400> SEQUENCE: 583

```
Val Gln Cys Pro His Phe Cys Tyr Glu Leu Ala Tyr Glu Leu Cys
  1               5                  10                  15
Pro Asp Val Cys Tyr Val
            20
```

<210> SEQ ID NO 584
<211> LENGTH: 21
<212> TYPE: PRT
<213> ORGANISM: Artificial Sequence
<220> FEATURE:
<223> OTHER INFORMATION: sequence is synthesized

<400> SEQUENCE: 584

```
Val Gln Cys Pro His Phe Cys Tyr Glu Leu Asp Tyr Ala Leu Cys
  1               5                  10                  15
Pro Asp Val Cys Tyr Val
            20
```

<210> SEQ ID NO 585
<211> LENGTH: 21
<212> TYPE: PRT
<213> ORGANISM: Artificial Sequence
<220> FEATURE:
<223> OTHER INFORMATION: sequence is synthesized

<400> SEQUENCE: 585

```
Val Gln Cys Pro His Phe Cys Tyr Glu Leu Asp Tyr Ala Leu Cys
 1               5                  10                  15

Pro Ala Val Cys Tyr Val
                20

<210> SEQ ID NO 586
<211> LENGTH: 21
<212> TYPE: PRT
<213> ORGANISM: Artificial Sequence
<220> FEATURE:
<223> OTHER INFORMATION: sequence is synthesized

<400> SEQUENCE: 586

Val Gln Cys Pro His Phe Cys Tyr Glu Leu Ala Tyr Ala Leu Cys
 1               5                  10                  15

Pro Ala Val Cys Tyr Val
                20

<210> SEQ ID NO 587
<211> LENGTH: 21
<212> TYPE: PRT
<213> ORGANISM: Artificial Sequence
<220> FEATURE:
<223> OTHER INFORMATION: sequence is synthesized

<400> SEQUENCE: 587

Val Gln Cys Pro His Phe Cys Tyr Ala Leu Asp Tyr Ala Leu Cys
 1               5                  10                  15

Pro Ala Val Cys Tyr Val
                20

<210> SEQ ID NO 588
<211> LENGTH: 21
<212> TYPE: PRT
<213> ORGANISM: Artificial Sequence
<220> FEATURE:
<223> OTHER INFORMATION: sequence is synthesized

<400> SEQUENCE: 588

Val Gln Cys Pro His Phe Cys Tyr Ala Ala Ala Ala Ala Leu Cys
 1               5                  10                  15

Pro Asp Val Cys Tyr Val
                20

<210> SEQ ID NO 589
<211> LENGTH: 21
<212> TYPE: PRT
<213> ORGANISM: Artificial Sequence
<220> FEATURE:
<223> OTHER INFORMATION: sequence is synthesized

<400> SEQUENCE: 589

Val Gln Cys Pro His Phe Cys Tyr Ala Leu Ala Tyr Ala Leu Cys
 1               5                  10                  15

Pro Ala Val Cys Tyr Val
                20

<210> SEQ ID NO 590
<211> LENGTH: 21
<212> TYPE: PRT
<213> ORGANISM: Artificial Sequence
<220> FEATURE:
<223> OTHER INFORMATION: sequence is synthesized

<400> SEQUENCE: 590
```

Val Gln Cys Ala His Phe Cys Tyr Glu Leu Asp Tyr Glu Leu Cys
 1               5                  10                  15

Pro Asp Val Cys Tyr Val
                20

<210> SEQ ID NO 591
<211> LENGTH: 21
<212> TYPE: PRT
<213> ORGANISM: Artificial Sequence
<220> FEATURE:
<223> OTHER INFORMATION: sequence is synthesized

<400> SEQUENCE: 591

Val Gln Cys Pro His Phe Cys Tyr Glu Leu Asp Tyr Glu Leu Cys
 1               5                  10                  15

Ala Asp Val Cys Tyr Val
                20

<210> SEQ ID NO 592
<211> LENGTH: 21
<212> TYPE: PRT
<213> ORGANISM: Artificial Sequence
<220> FEATURE:
<223> OTHER INFORMATION: sequence is synthesized

<400> SEQUENCE: 592

Val Gln Cys Pro His Ala Cys Tyr Glu Leu Asp Tyr Glu Ala Cys
 1               5                  10                  15

Pro Asp Val Cys Tyr Val
                20

<210> SEQ ID NO 593
<211> LENGTH: 21
<212> TYPE: PRT
<213> ORGANISM: Artificial Sequence
<220> FEATURE:
<223> OTHER INFORMATION: sequence is synthesized

<400> SEQUENCE: 593

Val Gln Cys Pro His Phe Ala Tyr Glu Leu Asp Tyr Glu Leu Ala
 1               5                  10                  15

Pro Asp Val Cys Tyr Val
                20

<210> SEQ ID NO 594
<211> LENGTH: 21
<212> TYPE: PRT
<213> ORGANISM: Artificial Sequence
<220> FEATURE:
<223> OTHER INFORMATION: sequence is synthesized

<400> SEQUENCE: 594

Val Gln Ala Pro His Phe Cys Tyr Glu Leu Asp Tyr Glu Leu Cys
 1               5                  10                  15

Pro Asp Val Ala Tyr Val
                20

<210> SEQ ID NO 595
<211> LENGTH: 20
<212> TYPE: PRT
<213> ORGANISM: Artificial Sequence
<220> FEATURE:
<223> OTHER INFORMATION: sequence is synthesized -continued

```
<400> SEQUENCE: 595

Val Gln Cys Pro His Phe Cys Tyr Glu Leu Asp Tyr Glu Leu Cys
 1               5                  10                  15

Pro Asp Val Cys Tyr
            20

<210> SEQ ID NO 596
<211> LENGTH: 123
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1-50, 57-66, 74-123
<223> OTHER INFORMATION: amino acid residue can be present or absent
<220> FEATURE:
<221> NAME/KEY: Variable
<222> LOCATION: 53-54, 67, 70, 71, 73
<223> OTHER INFORMATION: can be any amino acid residue

<400> SEQUENCE: 596

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Cys Pro Xaa Xaa Cys Tyr Xaa Xaa Xaa Xaa
            50                  55                  60

Xaa Xaa Xaa Xaa Xaa Xaa Xaa Cys Pro Xaa Xaa Cys Xaa Xaa Xaa
            65                  70                  75

Xaa Xaa Xaa Xaa Xaa Xaa Xaa Xaa Xaa Xaa Xaa Xaa Xaa Xaa Xaa
            80                  85                  90

Xaa Xaa Xaa Xaa Xaa Xaa Xaa Xaa Xaa Xaa Xaa Xaa Xaa Xaa Xaa
            95                 100                 105

Xaa Xaa Xaa Xaa Xaa Xaa Xaa Xaa Xaa Xaa Xaa Xaa Xaa Xaa Xaa
           110                 115                 120

Xaa Xaa Xaa

<210> SEQ ID NO 597
<211> LENGTH: 79
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1-6, 30-79
<223> OTHER INFORMATION: amino acid residue can be present or absent
<220> FEATURE:
<221> NAME/KEY: Variable
<222> LOCATION: 9, 10, 23, 26, 27, 29
<223> OTHER INFORMATION: can be any naturally occurring amino acid
      residue
<220> FEATURE:
<221> NAME/KEY: Variable
<222> LOCATION: 13-22
<223> OTHER INFORMATION: non-naturally occurring residue, present or
      absent

<400> SEQUENCE: 597

Xaa Xaa Xaa Xaa Xaa Xaa Cys Pro Xaa Xaa Cys Tyr Xaa Xaa Xaa
 1               5                  10                  15
```

-continued

```
Xaa Xaa Xaa Xaa Xaa Xaa Xaa Xaa Cys Pro Xaa Xaa Cys Xaa Xaa
                    20                  25                  30

Xaa Xaa Xaa Xaa Xaa Xaa Xaa Xaa Xaa Xaa Xaa Xaa Xaa Xaa Xaa
                    35                  40                  45

Xaa Xaa Xaa Xaa Xaa Xaa Xaa Xaa Xaa Xaa Xaa Xaa Xaa Xaa Xaa
                    50                  55                  60

Xaa Xaa Xaa Xaa Xaa Xaa Xaa Xaa Xaa Xaa Xaa Xaa Xaa Xaa Xaa
                    65                  70                  75

Xaa Xaa Xaa Xaa
```

<210> SEQ ID NO 598
<211> LENGTH: 18
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1-4, 6, 7, 10-13, 15-18
<223> OTHER INFORMATION: can be any naturally occurring amino acid
      residue

<400> SEQUENCE: 598

```
Xaa Xaa Xaa Xaa Cys Xaa Xaa Gly Pro Xaa Xaa Xaa Xaa Cys Xaa
 1               5                  10                  15

Xaa Xaa Xaa
```

<210> SEQ ID NO 599
<211> LENGTH: 22
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 3, 4, 16, 19, 20, 22
<223> OTHER INFORMATION: can be any amino acid residue
<220> FEATURE:
<221> NAME/KEY: Variable
<222> LOCATION: 7-15
<223> OTHER INFORMATION: amino acid residue can be absent or present

<400> SEQUENCE: 599

```
Cys Pro Xaa Xaa Cys Tyr Xaa Xaa Xaa Xaa Xaa Xaa Xaa Xaa Xaa
 1               5                  10                  15

Xaa Cys Pro Xaa Xaa Cys Xaa
                    20
```

<210> SEQ ID NO 600
<211> LENGTH: 116
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1-50, 67-116
<223> OTHER INFORMATION: amino acid residue can be absent or present
<220> FEATURE:
<221> NAME/KEY: Variable
<222> LOCATION: 53, 54, 57-60, 63, 64, 66
<223> OTHER INFORMATION: can be any amino acid residue

<400> SEQUENCE: 600

```
Xaa Xaa Xaa Xaa Xaa Xaa Xaa Xaa Xaa Xaa Xaa Xaa Xaa Xaa Xaa
 1               5                  10                  15
```

```
Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
            35                  40                  45

Xaa Xaa Xaa Xaa Xaa Cys Pro Xaa Xaa Cys Tyr Xaa Xaa Xaa Xaa
            50                  55                      60

Cys Pro Xaa Xaa Cys Xaa Xaa Xaa Xaa Xaa Xaa Xaa Xaa Xaa
            65                  70                  75

Xaa Xaa Xaa Xaa Xaa Xaa Xaa Xaa Xaa Xaa Xaa Xaa Xaa Xaa
            80                  85                  90

Xaa Xaa Xaa Xaa Xaa Xaa Xaa Xaa Xaa Xaa Xaa Xaa Xaa Xaa
            95                  100                 105

Xaa Xaa Xaa Xaa Xaa Xaa Xaa Xaa Xaa Xaa Xaa
            110                 115

<210> SEQ ID NO 601
<211> LENGTH: 117
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1-50, 68-117
<223> OTHER INFORMATION: amino acid residue can be absent or present
<220> FEATURE:
<221> NAME/KEY: Variable
<222> LOCATION: 53, 54, 57-61, 64, 65, 67
<223> OTHER INFORMATION: can be any amino acid residue

<400> SEQUENCE: 601

Xaa Xaa Xaa Xaa Xaa Xaa Xaa Xaa Xaa Xaa Xaa Xaa Xaa Xaa
 1              5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
            35                  40                  45

Xaa Xaa Xaa Xaa Xaa Cys Pro Xaa Xaa Cys Tyr Xaa Xaa Xaa Xaa
            50                  55                      60

Xaa Cys Pro Xaa Xaa Cys Xaa Xaa Xaa Xaa Xaa Xaa Xaa Xaa Xaa
            65                  70                  75

Xaa Xaa Xaa Xaa Xaa Xaa Xaa Xaa Xaa Xaa Xaa Xaa Xaa Xaa
            80                  85                  90

Xaa Xaa Xaa Xaa Xaa Xaa Xaa Xaa Xaa Xaa Xaa Xaa Xaa Xaa
            95                  100                 105

Xaa Xaa Xaa Xaa Xaa Xaa Xaa Xaa Xaa Xaa Xaa Xaa
            110                 115

<210> SEQ ID NO 602
<211> LENGTH: 118
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1-50, 68-118
<223> OTHER INFORMATION: amino acid residue can be absent or present
<220> FEATURE:
<221> NAME/KEY: Variable
<222> LOCATION: 53, 54, 57-62, 65, 66, 68
<223> OTHER INFORMATION: can be any amino acid residue
```

-continued

```
<400> SEQUENCE: 602

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Cys Pro Xaa Xaa Cys Tyr Xaa Xaa Xaa Xaa
                50                  55                  60

Xaa Xaa Cys Pro Xaa Xaa Cys Xaa Xaa Xaa Xaa Xaa Xaa Xaa Xaa
                65                  70                  75

Xaa Xaa Xaa Xaa Xaa Xaa Xaa Xaa Xaa Xaa Xaa Xaa Xaa Xaa Xaa
                80                  85                  90

Xaa Xaa Xaa Xaa Xaa Xaa Xaa Xaa Xaa Xaa Xaa Xaa Xaa Xaa Xaa
                95                 100                 105

Xaa Xaa Xaa Xaa Xaa Xaa Xaa Xaa Xaa Xaa Xaa Xaa
                110                 115

<210> SEQ ID NO 603
<211> LENGTH: 23
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1, 2, 9-13, 21-23
<223> OTHER INFORMATION: amino acid residue can be absent or present
<220> FEATURE:
<221> NAME/KEY: Variable
<222> LOCATION: 5, 6, 14, 17, 18
<223> OTHER INFORMATION: can be any amino acid residue

<400> SEQUENCE: 603

Xaa Xaa Cys Pro Xaa Xaa Cys Tyr Xaa Xaa Xaa Xaa Xaa Xaa Cys
 1               5                  10                  15

Pro Xaa Xaa Cys Tyr Xaa Xaa Xaa
                20

<210> SEQ ID NO 604
<211> LENGTH: 22
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1, 2, 9-13, 21-22
<223> OTHER INFORMATION: amino acid residue can be absent or present
<220> FEATURE:
<221> NAME/KEY: Variable
<222> LOCATION: 5, 6, 14, 18
<223> OTHER INFORMATION: can be any amino acid residue

<400> SEQUENCE: 604

Xaa Xaa Cys Pro Xaa Xaa Cys Tyr Xaa Xaa Xaa Xaa Xaa Xaa Cys
 1               5                  10                  15

Pro Asp Xaa Cys Tyr Xaa Xaa
                20

<210> SEQ ID NO 605
<211> LENGTH: 23
<212> TYPE: PRT
<213> ORGANISM: Artificial sequence
```

```
<220> FEATURE:
<223> OTHER INFORMATION: sequence is synthesized
<220> FEATURE:
<221> NAME/KEY: Variable
<222> LOCATION: 1, 2, 9-13, 21-23
<223> OTHER INFORMATION: amino acid residue can be absent or present
<220> FEATURE:
<221> NAME/KEY: Variable
<222> LOCATION: 5, 17, 18
<223> OTHER INFORMATION: can be any amino acid residue
<220> FEATURE:
<221> NAME/KEY: Site
<222> LOCATION: 6, 14
<223> OTHER INFORMATION: amino acid residue with large hydrophobic side
      chain

<400> SEQUENCE: 605

Xaa Xaa Cys Pro Xaa Xaa Cys Tyr Xaa Xaa Xaa Xaa Xaa Xaa Cys
 1               5                  10                  15

Pro Xaa Xaa Cys Tyr Xaa Xaa Xaa
                20

<210> SEQ ID NO 606
<211> LENGTH: 18
<212> TYPE: PRT
<213> ORGANISM: Artificial sequence
<220> FEATURE:
<223> OTHER INFORMATION: sequence is synthesized
<220> FEATURE:
<221> NAME/KEY: Variable
<222> LOCATION: 1-4, 6, 7, 13, 15-18
<223> OTHER INFORMATION: can be any amino acid residue

<400> SEQUENCE: 606

Xaa Xaa Xaa Xaa Cys Xaa Xaa Gly Pro Trp Gly Trp Xaa Cys Xaa
 1               5                  10                  15

Xaa Xaa Xaa
```